US011612647B2

(12) United States Patent
Ambrosino et al.

(10) Patent No.: US 11,612,647 B2
(45) Date of Patent: Mar. 28, 2023

(54) IMMUNOGENIC COMPOSITIONS

(71) Applicants: University of Maryland, Baltimore, Baltimore, MD (US); Affinivax, Inc., Cambridge, MA (US)

(72) Inventors: Donna Ambrosino, Stuart, FL (US); Teresa J. Broering, Brookline, MA (US); Alan Cross, Chevy Chase, MD (US); Richard Malley, Beverly, MA (US); Francis Michon, Bethesda, MD (US); George Rainer Siber, New York, NY (US); Raphael Simon, Upper Saddle River, NJ (US); Sharon Tennant, Ellicott City, MD (US)

(73) Assignees: University of Maryland, Baltimore, Baltimore, MD (US); Affinivax, Inc., Cambridge, MA (US)

( * ) Notice: Subject to any disclaimer, the term of this patent is extended or adjusted under 35 U.S.C. 154(b) by 0 days.

(21) Appl. No.: 16/625,468

(22) PCT Filed: Jun. 22, 2018

(86) PCT No.: PCT/US2018/038907
§ 371 (c)(1),
(2) Date: Dec. 20, 2019

(87) PCT Pub. No.: WO2018/237221
PCT Pub. Date: Dec. 27, 2018

(65) Prior Publication Data
US 2022/0072118 A1 Mar. 10, 2022

Related U.S. Application Data

(60) Provisional application No. 62/524,315, filed on Jun. 23, 2017, provisional application No. 62/633,807, filed on Feb. 22, 2018.

(51) Int. Cl.
| | |
|---|---|
| *A61K 39/104* | (2006.01) |
| *A61P 31/04* | (2006.01) |
| *A61K 39/02* | (2006.01) |
| *A61K 39/40* | (2006.01) |
| *C07K 14/21* | (2006.01) |
| *C07K 14/26* | (2006.01) |
| *C08B 37/00* | (2006.01) |
| *A61K 39/108* | (2006.01) |
| *A61K 39/00* | (2006.01) |

(52) U.S. Cl.
CPC ........ *A61K 39/104* (2013.01); *A61K 39/0258* (2013.01); *A61K 39/0266* (2013.01); *A61K 39/40* (2013.01); *A61P 31/04* (2018.01); *C07K 14/21* (2013.01); *C07K 14/26* (2013.01); *C08B 37/0003* (2013.01); *A61K 2039/6031* (2013.01); *A61K 2039/6087* (2013.01); *A61K 2039/625* (2013.01); *A61K 2039/70* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,755,381 A | 7/1988 | Cryz |
| 6,287,568 B1 | 9/2001 | Wang et al. |
| 7,588,920 B2 | 9/2009 | Doucette-Stamm et al. |
| 9,499,593 B2 | 11/2016 | Malley et al. |
| 10,017,548 B2 | 7/2018 | Malley et al. |
| 10,766,932 B2 | 9/2020 | Malley et al. |
| 11,013,793 B2 | 5/2021 | Malley et al. |
| 2002/0032323 A1 | 3/2002 | Kunsch et al. |
| 2005/0002948 A1 | 1/2005 | Ryall |
| 2006/0228380 A1 | 10/2006 | Hausdorff et al. |
| 2006/0251675 A1 | 11/2006 | Hagen |
| 2007/0128183 A1 | 6/2007 | Meinke et al. |
| 2008/0032340 A1 | 2/2008 | Ghosh et al. |
| 2008/0112964 A1 | 5/2008 | Kirkham et al. |
| 2009/0054251 A1 | 2/2009 | O'Connor et al. |
| 2009/0148894 A1 | 6/2009 | Broedel et al. |
| 2009/0148897 A1 | 6/2009 | Dai |
| 2009/0285846 A1 | 11/2009 | Tweten |
| 2010/0003266 A1 | 1/2010 | Simon |
| 2010/0020945 A1 | 1/2010 | Li et al. |
| 2010/0022401 A1 | 1/2010 | Nordlund et al. |
| 2010/0166802 A1 | 7/2010 | Caplan et al. |
| 2010/0209450 A1 | 8/2010 | Biemans et al. |
| 2011/0027265 A1 | 2/2011 | Bubeck-Wardenburg et al. |
| 2011/0065660 A1 | 3/2011 | Baron et al. |
| 2013/0115230 A1 | 5/2013 | Simon |
| 2014/0154286 A1 | 6/2014 | Malley et al. |
| 2014/0154287 A1 | 6/2014 | Malley et al. |
| 2015/0374811 A1 | 12/2015 | Malley et al. |
| 2016/0090404 A1 | 3/2016 | Malley et al. |
| 2019/0119335 A1 | 4/2019 | Malley et al. |
| 2020/0407404 A1 | 12/2020 | Malley et al. |
| 2021/0332090 A1 | 10/2021 | Malley et al. |

FOREIGN PATENT DOCUMENTS

| | | |
|---|---|---|
| CN | 1787839 A | 6/2006 |
| CN | 101797381 A | 8/2010 |
| CN | 101951948 A | 1/2011 |
| CN | 103732222 A | 4/2014 |
| CN | 106794237 A | 5/2017 |

(Continued)

OTHER PUBLICATIONS

Buerret et al. Carbohydrate Research vol. 157, pp. 13-25 Dec. 1986.*
Campbell et al. Clinical Infectious Disease 1996; 23:179-181.*
Faezi et al. Int J Mol Cell Med. 2016 Winter; 5(1):37-48.*

(Continued)

*Primary Examiner* — Oluwatosin A Ogunbiyi
(74) *Attorney, Agent, or Firm* — Choate, Hall & Stewart LLP; Rolando Medina; Janet M. Tse

(57) ABSTRACT

Technologies for the prevention and/or treatment of nosocomial infections.

40 Claims, 96 Drawing Sheets

Specification includes a Sequence Listing.

(56) References Cited

FOREIGN PATENT DOCUMENTS

| | | |
|---|---|---|
| EP | 0118831 A2 | 9/1984 |
| EP | 1838345 A2 | 10/2007 |
| JP | H11-502820 A | 3/1999 |
| JP | 2001-505415 A | 4/2001 |
| JP | 2002-504096 A | 2/2002 |
| JP | 2002/539294 A | 11/2002 |
| JP | 2005/500250 A | 1/2005 |
| JP | 2007-504237 A | 3/2007 |
| JP | 2008-509682 A | 4/2008 |
| JP | 2010-517532 A | 5/2010 |
| JP | 2014/514363 A | 6/2014 |
| JP | 2014-517835 A | 7/2014 |
| JP | 6366501 B2 | 8/2018 |
| JP | 6666389 B2 | 3/2020 |
| KR | 20080090411 A | 10/2008 |
| RU | 2164943 C2 | 4/2001 |
| RU | 2006117425 A | 12/2007 |
| RU | 2378008 C2 | 1/2010 |
| RU | 2407749 C2 | 12/2010 |
| WO | WO-1995/021195 A1 | 8/1995 |
| WO | WO-1996/029094 A1 | 9/1996 |
| WO | WO-1998/18930 A2 | 5/1998 |
| WO | WO-98/47530 A2 | 10/1998 |
| WO | WO-00/55210 A1 | 9/2000 |
| WO | WO-2002/064161 A2 | 8/2002 |
| WO | WO-02/077021 A2 | 10/2002 |
| WO | WO-2003/094960 A2 | 11/2003 |
| WO | WO-2004/080490 A2 | 9/2004 |
| WO | WO-2004/092209 A2 | 10/2004 |
| WO | WO-2005/037190 A2 | 4/2005 |
| WO | WO-2005/039501 A2 | 5/2005 |
| WO | WO-2006/017929 A1 | 2/2006 |
| WO | WO-2006/067632 A2 | 6/2006 |
| WO | WO-2006/084467 A1 | 8/2006 |
| WO | WO-2007/026249 A2 | 3/2007 |
| WO | WO-2007/067681 A2 | 6/2007 |
| WO | WO-2007/081583 A2 | 7/2007 |
| WO | WO-2007/150020 A1 | 12/2007 |
| WO | WO-2008/094986 A2 | 8/2008 |
| WO | WO-2008/152448 A2 | 12/2008 |
| WO | WO-2009/016515 A2 | 2/2009 |
| WO | WO-2009/021548 A1 | 2/2009 |
| WO | WO-2009/029831 A1 | 3/2009 |
| WO | WO-2010/053559 A1 | 5/2010 |
| WO | WO-2010/071986 A1 | 7/2010 |
| WO | WO-2010/081875 A1 | 7/2010 |
| WO | WO-2011/008548 A1 | 1/2011 |
| WO | WO-2011/103588 A1 | 8/2011 |
| WO | WO-2011/137354 A2 | 11/2011 |
| WO | WO-2012/155007 A1 | 11/2012 |
| WO | WO-2012/155053 A1 | 11/2012 |
| WO | WO-2014/018904 A1 | 1/2014 |
| WO | WO-2014/124228 A1 | 8/2014 |
| WO | WO-2015158403 A1 * 10/2015 ........... A61K 39/104 | |
| WO | WO-2016/044773 A1 | 3/2016 |
| WO | WO-2017/035154 A1 | 3/2017 |
| WO | WO-2018/183475 A1 | 10/2018 |
| WO | WO-2018/237221 A1 | 12/2018 |

OTHER PUBLICATIONS

Baer, M. et al., An engineered human antibody fab fragment specific for *Pseudomonas aeruginosa* PcrV antigen has potent antibacterial activity, Infect. Immun., 77(3):1083-90 (2009).
Baraniak, A. et al., Molecular characteristics of KPC-producing Enterobacteriaceae at the early stage of their dissemination in Poland, 2008-2009, Antimicrob. Agents Chemother., 55(12):5493-5499 (2011).
Barnea, Y. et al., Efficacy of antibodies against the N-terminal of *Pseudomonas aeruginosa* flagellin for treating infections in a murine burn wound model, Plast. Reconstr. Surg., 117(7):2284-91 (2006).
Barnea, Y. et al., Therapy with anti-flagellin A monoclonal antibody limits *Pseudomonas aeruginosa* invasiveness in a mouse burn wound sepsis model, Burns., 35(3):390-6 (2009).
Baumgartner, J. D., Monoclonal anti-endotoxin antibodies for the treatment of gram-negative bacteremia and septic shock, Eur. J. Clin. Microbiol. Infect. Dis., 9(10):711-6 (1990).
Brisse, S. et al., wzi Gene Sequencing, a Rapid Method for Determination of Capsular Type for Klebsiella Strains, J. Clin. Microbiol., 51(12):4073-4078 (2013).
Burmølle, M. et al., Type 3 fimbriae, encoded by the conjugative plasmid pOLA52, enhance biofilm formation and transfer frequencies in Enterobacteriaceae strains, Microbiology, 154(Pt 1):187-95 (2008).
Campodónico, V. L. et al., Efficacy of a conjugate vaccine containing polymannuronic acid and flagellin against experimental Pseudomonas aeruginosa lung infection in mice, Infect. Immun., 79(8):3455-64 (2011).
Campodónico, V. L. et al., Evaluation of flagella and flagellin of *Pseudomonas aeruginosa* as vaccines, Infect. Immun., 78(2):746-55 (2010).
Chan, C.-H. et al., Identification of protein domains on major pilin MrkA that affects the mechanical properties of Klebsiella pneumoniae type 3 fimbriae, Langmuir, 28(19):7428-35 (2012).
Chen, L. et al., Epidemic *Klebsiella pneumoniae* ST258 is a hybrid strain, mBio, 5(3):e01355-14 (2014).
Chen, L. et al., Multiplex PCR for identification of two capsular types in epidemic KPC-producing Klebsiella pneumoniae sequence Type 258 strains, Antimicrob. Agents Chemother., 58(7):4196-4199 (2014).
Clegg, S. and Gerlach, G. F., Enterobacterial fimbriae, J. Bacteriol. ,169(3):934-938 (1987).
Clements, A., et al. The major surface-associated saccharides of *Klebsiella pneumoniae* contribute to host cell association, PLoS One, 3(11):e3817 (2008).
ClinicalTrials.gov Identifier: NCT01695343, 6 pages (posted on Sep. 27, 2012).
ClinicalTrials.gov Identifier: NCT02255760, 9 pages (posted on Oct. 3, 2014).
Cross, A. S. et al., Role of lipopolysaccharide and capsule in the serum resistance of bacteremic strains of *Escherichia coli*, J. Infect. Dis., 154(3):497-503 (1986).
Cross, A. S. et al., Evaluation of immunotherapeutic approaches for the potential treatment of infections caused by K1-positive *Escherichia coli*, J. Infect. Dis., 147(1):68-76 (1983).
Cross, A. S. et al., The importance of the K1 capsule in invasive infections caused by *Escherichia coli*, J. Infect. Dis., 149(2):184-93 (1984).
Cross, A. et al., Safety and immunogenicity of a polyvalent *Escherichia coli* vaccine in human volunteers, J. Infect. Dis., 170(4):834-40 (1994).
Crowe, B. A. et al., The first clinical trial of immuno's experimental Pseudomonas aeruginosa flagellar vaccines, Antibiot. Chemother., 44:143-56 (1991).
Cryz, S. J. et al., Safety and immunogenicity of *Klebsiella pneumoniae* K1 capsular polysaccharide vaccine in humans, J. Infect. Dis., 151(4):665-671 (1985).
Cryz, S. J. Jr et al., Protection against fatal *Pseudomonas aeruginosa* burn wound sepsis by immunization with lipopolysaccharide and high-molecular-weight polysaccharide, Infect. Immun., 43(3):795-9 (1984).
Cryz, S. J. Jr et al., Seroepidemiology of Klebsiella bacteremic isolates and implications for vaccine development, J. Clin. Microbiol., 23(4):687-90 (1986).
Cryz, S. J. Jr et al., Immunization of noncolonized cystic fibrosis patients against *Pseudomonas aeruginosa*, J. Infect. Dis., 169(5):1159-62 (1994).
Cryz, S. J. Jr et al., Safety and immunogenicity of a polyvalent Klebsiella capsular polysaccharide vaccine in humans, Vaccine, 4(1):15-20 (1986).
Deleo, F. R. et al., Molecular dissection of the evolution of carbapenem-resistant multilocus sequence type 258 *Klebsiella pneumoniae*, Proc. Natl. Acad. Sci. U. S. A., 111(13):4988-4993 (2014).

(56) References Cited

OTHER PUBLICATIONS

Digiandomenico, A. et al., A multifunctional bispecific antibody protects against *Pseudomonas aeruginosa*, Sci. Transl. Med., 6(262):262ra155 (2014).
Digiandomenico, A. et al., Identification of broadly protective human antibodies to *Pseudomonas aeruginosa* exopolysaccharide PsI by phenotypic screening, J. Exp. Med., 209(7):1273-87 (2012).
Digiandomenico, A. et al., Antibacterial monoclonal antibodies: the next generation?, Curr. Opin. Microbiol., 27:78-85 (2015).
Digiandomenico, A. et al., Intranasal immunization with heterologously expressed polysaccharide protects against multiple *Pseudomonas aeruginosa* infections, Proc. Natl. Acad. Sci. U. S. A., 104(11):4624-9 (2007).
Digiandomenico, A. et al., Oral vaccination of BALB/c mice with *Salmonella enterica* serovar Typhimurium expressing *Pseudomonas aeruginosa* O antigen promotes increased survival in an acute fatal pneumonia model, Infect. Immun., 72(12):7012-21 (2004).
Domenico, P. et al., Reduction of capsular polysaccharide production in *Klebsiella pneumoniae* by sodium salicylate, Infect. Immun., 57(12):3778-82 (1989).
Doring, G. et al., A double-blind randomized placebo-controlled phase III study of a Pseudomonas aeruginosa flagella vaccine in cystic fibrosis patients, Proc. Natl. Acad. Sci. U. S. A., 104(26):11020-5 (2007).
Doring, G. et al., A multicenter vaccine trial using the *Pseudomonas aeruginosa* flagella vaccine IMMUNO in patients with cystic fibrosis, Behring. Inst. Mitt., (98):338-44 (1997).
Doring, G. et al., Parenteral application of a *Pseudomonas aeruginosa* flagella vaccine elicits specific anti-flagella antibodies in the airways of healthy individuals, Am. J. Respir. Crit. Care. Med., 151(4):983-5 (1995).
Doring, G. and Pier, G. B., Vaccines and immunotherapy against *Pseudomonas aeruginosa*, Vaccine, 26(8):1011-24 (2008).
Edelman, R. et al., Phase 1 trial of a 24-valent Klebsiella capsular polysaccharide vaccine and an eight-valent Pseudomonas O-polysaccharide conjugate vaccine administered simultaneously, Vaccine, 12(14):1288-94 (1994).
Faezi, S. et al., Passive immunisation against *Pseudomonas aeruginosa* recombinant flagellin in an experimental model of burn wound sepsis, Burns., 37(5):865-72 (2011).
Faezi, S. et al., Protective efficacy of *Pseudomonas aeruginosa* type-A flagellin in the murine burn wound model of infection, APMIS, 122(2):115-27 (2014).
Feldman, M. F. et al., Engineering N-linked protein glycosylation with diverse O antigen lipopolysaccharide structures in *Escherichia coli*, Proc. Natl. Acad. Sci. U. S. A., 102(8):3016-21 (2005).
François, B. et al., Safety and pharmacokinetics of an anti-PcrV PEGylated monoclonal antibody fragment in mechanically ventilated patients colonized with *Pseudomonas aeruginosa*: a randomized, double-blind, placebo-controlled trial, Crit. Care Med., 40(8):2320-6 (2012).
Frank, D. W. et al., Generation and characterization of a protective monoclonal antibody to *Pseudomonas aeruginosa* PcrV. J. Infect. Dis., 186(1):64-73 (2002).
Gerland, G. F. et al., Identification and characterization of the genes encoding the type 3 and type 1 fimbrial adhesins of *Klebsiella pneumoniae*, J. Bacteriol., 171(3):1262-70 (1989).
Giakkoupi, P. et al., An update of the evolving epidemic of blaKPC-2-carrying *Klebsiella pneumoniae* in Greece (Oct. 2009), J. Antimicrob. Chemother., 66(7):1510-1513 (2011).
Giani, T. et al., Epidemic diffusion of KPC carbapenemase-producing *Klebsiella pneumoniae* in Italy: results of the first countrywide survey, May 15 to Jun. 30, 2011, Euro. Surveill., 18(22):20489 (2013).
Gransden, W. R. et al., Bacteremia due to *Escherichia coli*: a study of 861 episodes, Rev. Infect. Dis., 12(6):1008-18 (1990).
Greenberger, M. J. et al., IL-12 gene therapy protects mice in lethal *Klebsiella pneumonia*, J Immunol., 157(7):3006-12 (1996).

Hansen, D. S. et al., *Klebsiella pneumoniae* lipopolysaccharide O typing: revision of prototype strains and O-group distribution among clinical isolates from different sources and countries, J. Clin. Microbiol. 37(1):56-62 (1999).
Holder, I. A. et al., Experimental studies of the pathogenesis of infections due to Pseudomonas aeruginosa: immunization using divalent flagella preparations, J. Trauma., 26(2):118-22 (1986).
Holder, I. A. et al., Flagellar preparations from Pseudomonas aeruginosa: animal protection studies, Infect. Immun., 35(1):276-80 (1982).
Holder, I. A. et al., PcrV immunization enhances survival of burned *Pseudomonas aeruginosa*-infected mice, Infect. Immun., 69(9):5908-10 (2001).
Hornick, D. B. et al., Adherence to respiratory epithelia by recombinant *Escherichia coli* expressing Klebsiella pneumoniae type 3 fimbrial gene products, Infect. Immun., 60(4):1577-88 (1992).
Hu, R. et al., Outer Membrane Protein A (OmpA) Conferred Immunoprotection against Enterobacteriaceae Infection in Mice, Israel Journal of Veterinary Medicine, 68(1):48-55 (2013).
International Search Report for PCT/US2012/037412 (Multiple Antigen Presenting Immunogenic Composition, and Methods and Uses Thereof, filed May 11, 2012), issued by ISA/FIPS, 3 pages (Aug. 23, 2012).
International Search Report for PCT/US2012/037541 (Modified Biotin-Binding Protein, Fusion Proteins Thereof and Applications, filed May 11, 2012), issued by ISA/FIPS, 4 pages (Aug. 30, 2012).
Iqbal, H. M. N. et al., Laccase-assisted grafting of poly(3-hydroxybutyrate) onto the bacterial cellulose as backbone polymer: development and characterization, Carbohydr. Polym., 113:131-137 (2014).
Jones, R. J. et al., A new Pseudomonas vaccine: preliminary trial on human volunteers, J. Hyg. (Lond.), 76(3):429-39 (1976).
Jones, R. J. et al., Low mortality in burned patients in a Pseudomonas vaccine trial, Lancet, 2(8086):401-3 (1978).
Jones, R. J. et al., Controlled trials of a polyvalent pseudomonas vaccine in burns, Lancet, 2(8150):977-82 (1979).
Kaijser, B. and Ahlstedt, S., Protective capacity of antibodies against *Escherichia coli* O and K antigens, Infect. Immun., 17(2):286-9 (1977).
Kelly, R. F. et al., Structures of the O-antigens of Klebsiella serotypes O2 (2a,2e), O2 (2a,2e,2h), and O2 (2a,2f,2g), members of a family of related D-galactan O-antigens in *Klebsiella* spp., J. Endotoxin Res., 2:131-140 (1995).
Knirel, Y. A. et al., Conserved and variable structural features in the lipopolysaccharide of *Pseudomonas aeruginosa*, J. Endotoxin Res., 12(6):324-36 (2006).
Kol, O. et al., Structure of the O-specific polysaccharide chain of *Klebsiella pneumoniae* O1K2 (NCTC 5055) lipopolysaccharide. A complementary elucidation, Carbohydr. Res., 236, 339-344 (1992).
Kreger, B. E. et al., Gram-negative bacteremia. III. Reassessment of etiology, epidemiology and ecology in 612 patients, Am. J. Med., 68(3):332-43 (1980).
Landman, D. et al., Transmission of carbapenem-resistant pathogens in New York City hospitals: progress and frustration, J. Antimicrob. Chemother., 67(6):1427-1431 (2012).
Lang, A. B. et al., Effect of high-affinity anti-Pseudomonas aeruginosa lipopolysaccharide antibodies induced by immunization on the rate of *Pseudomonas aeruginosa* infection in patients with cystic fibrosis, J. Pediatr., 127(5):711-7 (1995).
Langford, D. T. and Hiller, J., Prospective, controlled study of a polyvalent pseudomonas vaccine in cystic fibrosis—three year results, Arch. Dis. Child., 59(12):1131-4 (1984).
Langstraat, J. et al. Type 3 fimbrial shaft (MrkA) of *Klebsiella pneumoniae*, but not the fimbrial adhesin (MrkD), facilitates biofilm formation, Infect. Immun., 69(9):5805-12 (2001).
Ma, L. et al., Analysis of *Pseudomonas aeruginosa* conditional psl variants reveals roles for the psl polysaccharide in adhesion and maintaining biofilm structure post attachment, J. Bacteriol., 188(23):8213-21 (2006).
Mandine, E. et al., Murine monoclonal antibodies to *Klebsiella pneumoniae* protect against lethal endotoxemia and experimental infection with capsulated K. pneumoniae, Infect. Immun., 58(9):2828-33 (1990).

(56) References Cited

OTHER PUBLICATIONS

Mccabe, W. R. et al., *Escherichia coli* in bacteremia: K and O antigens and serum sensitivity of strains from adults and neonates, J. Infect. Dis., 138(1):33-41 (1978).
Meir, A. et al., Crystal structure of rhizavidin: insights into the enigmatic high-affinity interaction of an innate biotin-binding protein dimer, J. Mol Biol., 386(2):379-90 (2009).
Milla, C. E. et al., Anti-PcrV antibody in cystic fibrosis: a novel approach targeting *Pseudomonas aeruginosa* airway infection, Pediatr. Pulmonol., 49(7):650-8 (2014).
Montie, T. C. et al., Motility, virulence, and protection with a flagella vaccine against Pseudomonas aeruginosa infection, Antibiot. Chemother. (1971), 39:233-48 (1987).
Moriel, D. G. et al., Identification of protective and broadly conserved vaccine antigens from the genome of extraintestinal pathogenic *Escherichia coli*, Proc. Natl. Acad. Sci. U. S. A., 107(20):9072-7 (2010).
Murphy, C. N. and Clegg, S., *Klebsiella pneumoniae* and type 3 fimbriae: nosocomial infection, regulation and biofilm formation, Future Microbiol., 7(8):991-1002 (2012).
Navon-Venezia, S. et al., First report on a hyperepidemic clone of KPC-3-producing Klebsiella pneumoniae in Israel genetically related to a strain causing outbreaks in the United States, Antimicrob. Agents Chemother., 53(2):818-820 (2009).
Neely, A. N. et al., Differential effects of two different routes of immunization on protection against gram-negative sepsis by a detoxified *Escherichia coli* J5 lipopolysaccharide group B meningococcal outer membrane protein complex vaccine in a burned mouse model, J. Burn Care Rehabil., 23(5):333-40 (2002).
Nesta, B. et al., FdeC, a novel broadly conserved *Escherichia coli* adhesin eliciting protection against urinary tract infections, mBio, 3(2):e00010-12 (2012).
Pereira, P. S. et al., Update of the molecular epidemiology of KPC-2-producing Klebsiella pneumoniae in Brazil: spread of clonal complex 11 (ST11, ST437 and ST340), J. Antimicrob. Chemother., 68(2):312-316 (2013).
Podschun, R. and Ullmann, U., *Klebsiella* spp. as nosocomial pathogens: epidemiology, taxonomy, typing methods, and pathogenicity factors, Clin. Microbiol. Rev., 11(4):589-603 (1998).
Poolman, J. T. and Wacker, M., Extraintestinal Pathogenic *Escherichia coli*, a Common Human Pathogen: Challenges for Vaccine Development and Progress in the Field, J. Infect. Dis., 213(1):6-13 (2016).
Priebe, G. P. et al., IL-17 is a critical component of vaccine-induced protection against lung infection by lipopolysaccharide-heterologous strains of Pseudomonas aeruginosa, J. Immunol., 181(7):4965-75 (2008).
Qi, Y. et al., ST11, the dominant clone of KPC-producing *Klebsiella pneumoniae* in China, J. Antimicrob. Chemother., 66(2):307-312 (2011).
Robbins, J. B. et al., *Escherichia coli* K1 capsular polysaccharide associated with neonatal meningitis, N. Engl. J. Med., 290(22):1216-20 (1974).
Saha, S. et al., Blocking of the TLR5 activation domain hampers protective potential of flagellin DNA vaccine, J. Immunol., 179(2):1147-54 (2007).
Sawa, T. et al., Active and passive immunization with the Pseudomonas V antigen protects against type III intoxication and lung injury. Nat. Med., 5(4):392-8 (1999).
Schaad, U. B. et al., Safety and immunogenicity of *Pseudomonas aeruginosa* conjugate A vaccine in cystic fibrosis, Lancet, 338(8777):1236-7 (1991).
Schweizer, H. P. Allelic exchange in Pseudomonas aeruginosa using novel ColE1-type vectors and a family of cassettes containing a portable oriT and the counter-selectable Bacillus subtilis sacB marker, Mol. Microbiol., 6(9):1195-204 (1992).
Shime, N. et al., Therapeutic administration of anti-PcrV F(ab')(2) in sepsis associated with Pseudomonas aeruginosa, J. Immunol., 167(10):5880-6 (2001).
Song, W. S. and Yoon, S., Crystal structure of FliC flagellin from *Pseudomonas aeruginosa* and its implication in TLR5 binding and formation of the flagellar filament, Biochem. Biophys. Res. Commun., 444(2):109-15 (2014).
Szijártó, V. et al., Both clades of the epidemic KPC-producing Klebsiella pneumoniae clone ST258 share a modified galactan O-antigen type, International Journal of Medical Microbiology, 306(2):89-98 (2016).
Tarkkanen, A. M. et al., Type V collagen as the target for type-3 fimbriae, enterobacterial adherence organelles, Mol. Microbiol., 4(8):1353-61 (1990).
Tarkkanen, A. M. et al., Binding of the type 3 fimbriae of Klebsiella pneumoniae to human endothelial and urinary bladder cells, Infect. Immun., 65(4):1546-9 (1997).
Tomas, J. M. et al., Surface exposure of the O-antigen in *Klebsiella pneumoniae* O1:K1 serotype strains, Microb. Pathog., 5(2):141-7 (1988).
Trautmann, M. et al., O-Antigen Seroepidemiology of Klebsiella Clinical Isolates and Implications for Immunoprophylaxis of Klebsiella Infections, Clinical and Diagnostic Laboratory Immunology, 4(5):550-555 (1997).
Vinogradov, E. et al., Structures of lipopolysaccharides from Klebsiella pneumoniae. Elucidation of the structure of the linkage region between core and polysaccharide O chain and identification of the residues at the non-reducing termini of the O chains, J. Biol. Chem., 277(28):25070-81 (2002).
Walczak, M. J. et al., Intramolecular donor strand complementation in the *E. coli* type 1 pilus subunit FimA explains the existence of FimA monomers as off-pathway products of pilus assembly that inhibit host cell apoptosis, J. Mol. Biol., 426(3):542-9 (2014).
Wang, Q. et al. Target-Agnostic Identification of Functional Monoclonal Antibodies Against *Klebsiella pneumoniae* Multimeric MrkA Fimbrial Subunit, J. Infect. Dis., 213(11):1800-8 (2016).
Warrener, P. et al., A novel anti-PcrV antibody providing enhanced protection against *Pseudomonas aeruginosa* in multiple animal infection models, Antimicrob. Agents Chemother., 58(8):4384-91 (2014).
Welch, W. D. et al., Relative opsonic and protective activities of antibodies against K1, O and lipid A antigens of *Escherichia coli*, Scand. J. Infect. Dis., 11(4):291-301 (1979).
Westritschnig, K. et al., A randomized, placebo-controlled phase I study assessing the safety and immunogenicity of a *Pseudomonas aeruginosa* hybrid outer membrane protein OprF/I vaccine (IC43) in healthy volunteers, Hum. Vaccin. Immunother., 10(1):170-183 (2014).
Whitfield, C. et al., Structural analysis of the O-antigen side chain polysaccharides in the lipopolysaccharides of Klebsiella serotypes O2(2a), O2(2a,2b), and O2(2a,2c), J. Bacteriol., 174(15):4913-4919 (1992).
Whitfield, C. et al., Expression of two structurally distinct D-galactan O antigens in the lipopolysaccharide of *Klebsiella pneumoniae* serotype O1, J. Bacteriol., 173(4):1420-1431 (1991).
Woodford, N. et al., Multiresistant Gram-negative bacteria: the role of high-risk clones in the dissemination of antibiotic resistance, FEMS Microbiol. Rev., 35(5):736-55 (2011).
Written Opinion for PCT/US2012/037412 (Multiple Antigen Presenting Immunogenic Composition, and Methods and Uses Thereof, filed May 11, 2012), issued by ISA/FIPS, 4 pages (Aug. 23, 2012).
Written Opinion for PCT/US2012/037541 (Modified Biotin-Binding Protein, Fusion Proteins Thereof and Applications, filed May 11, 2012), issued by ISA/FIPS, 3 pages (Aug. 30, 2012).
Wu, W. et al., Th17-stimulating protein vaccines confer protection against Pseudomonas aeruginosa pneumonia, Am. J. Respir. Crit. Care Med., 186(5):420-7 (2012).
Würker, M. et al., Type of fimbriation determines adherence of Klebsiella bacteria to human epithelial cells, Zentralbl. Bakteriol., 274(2):239-45 (1990).
Centers for Disease Control and Prevention. "Preventing pneumococcal disease among infants and young children." Morbidity and Mortality Weekly Report. 49: 1-38 (2000).

(56) References Cited

OTHER PUBLICATIONS

Anttila, M. et al., Avidity of IgG for *Streptococcus pneumoniae* type 6B and 23F polysaccharides in infants primed with pneumococcal conjugates and boosted with polysaccharide or conjugate vaccines, J. Infect. Dis., 177(6):1614-1621 (1998).
Avci, F.Y. et al, A mechanism for glycoconjugate vaccine activation of the adaptive immune system and its implications for vaccine design, Nat. Med., 17(12): 1602-1609 (2011).
Berry, M. A. et al., Effect of Defined Point Mutations in Pneumolysin Gene on the Virulence of *Streptococcus pneumonia*, Infection and Immunity, 63(5):1969-1974 (1995).
Centers for Disease Control and Prevention. "Prevention of pneumococcal disease among infants and children—use of 13-valent pneumococcal conjugate vaccine and 23-valent pneumococcal polysaccharide vaccine." Morbidity and Mortality Weekly Report. 59: 1-24 (2010).
Colino, J. et al., Noncovalent association of protein and capsular polysaccharide on bacteria-sized latex beads as a model for polysaccharide-specific humoral immunity to intact Gram-positive extracellular bacteria, J. Immunol., 191(6): 3254-3263 (2013).
Colino, J. et al, Parameters Underlying Distinct T Cell-Dependent Polysaccharide-Specific IgG Responses to an Intact Gram-Positive Bacterium versus a Soluble Conjugate Vaccine, The Journal of Immunology, 183(3):1559 (2009).
Cortajarena, A.L., et al, A receptor-binding region in *Escherichia coli* alpha-haemolysin, J. Biol. Chem., 278(21):19159-63 (2003).
Dagan, R. et al., Glycoconjugate vaccines and immune interference: A review, Vaccine, 28(34): 5513-5523 (2010).
Daniels, C. C. et al., The Proline-Rich Region of Pneumococcal Surface Proteins A and C Contains Surface-Accessible Epitopes Common to All Pneumococci and Elicits Antibody-Mediated Protection against Sepsis, Infection and Immunity, 78(5):2163-2172 (2010).
Database, UniProt KB/TrEMBL, B3Q265_RHIE6, retrieved Jan. 3, 2021.
Database, UniProt KB/TrEMBL, F2AA21_RHIET, retrieved Jan. 4, 2021.
Database, UniProt KB/TrEMBL, Q8KKW2_RHIEC, retrieved Jan. 4, 2021.
Douce, G. et al., Genetically detoxified mutants of heat-labile toxin from *Escherichia coli* are able to act as oral adjuvants, Infect Immun., 67(9):4400-4406 (1999).
Douce, G. et al., Mutants of *Escherichia coli* heat-labile toxin lacking ADP-ribosyltransferase activity act as non-toxic, mucosal adjuvants, PNAS 92:1644-1648 (1995).
Elgert, K. D., Immunology Understanding the Immune System, John Wiley & Sons, Inc. Hoboken, New Jersey, p. 111 (2009).
Evans, J. T. et al., Enhancement of antigen-specific immunity via the TLR4 ligands MPL adjuvant and Ribi.529, Expert Rev Vaccines, 2(2):219-229 (2003).
Fauvart, M. et al, Genome Sequence of Rhizobium etli CNPAF512, a Nitrogen-Fixing Symbiont Isolated from Bean Root Nodules in Brazil, Journal of Bacteriology, 193(12): 3158-3159 (2011).
Ferreira, D. M. et al., DNA vaccines based on genetically detoxified derivatives of pneumolysin fail to protect mice against challenge with *Streptococcus pneumonia*, FEMS Immunology Med. Microbial 46: 291-297 (2006).
Gaj, T. et al., The AviD-tag, a NeutrAvidin/avidin specific peptide affinity tag for the immobilization and purification of recombinant proteins, Protein Expr. Purif., 56(1):54-61 (2007).
Giuliani, M. M. et al., Mucosal adjuvanticity and immunogenicity of LTR72, a novel mutant of *Escherichia coli* heat-labile enterotoxin with partial knockout of ADP-ribosyltransferase activity, J. Exp. Med., 187(7):1123-1132 (1998).
González, V. et al, The mosaic structure of the symbiotic plasmid of Rhizobium etli CFN42 and its relation to other symbiotic genome compartments, Genome Biol., 4(6): R36 (2003).
Gruber, M.F. et al., Licensing of pneumococcal conjugate vaccines for children and adults: Regulatory perspective from the European Medicines Agency and the U.S. Food and Drug Administration, Pneumococcal Vaccines: The Impact of Conjugate Vaccine, 183-96 (2008).
Grun, C. H. et al, One-step biotinylation procedure for carbohydrates to study carbohydrate-protein interactions, Anal. Biochem., 354(1):54-63 (2006).
Helppolainen, S. H. et al, Bradavidin II from Bradyrhizobium japonicum: a new avidin-like biotin-binding protein, Biochim. Biophys. Acta., 1784(7-8):1002-10 (2008).
Helppolainen, S.H. et al., Rhizavidin from Rhizobium etli: the first natural dimer in the avidin protein family, Biochem J., 405(3): 397-405 (2007).
Hermanson, G. T., Bioconjugate Techniques, Elsevier Science, ProQuest Ebook Central, http://ebookcentral.proquest.com/lib.uspto-ebooks/detail.action?docID=307203, created from uspto-ebooks on Sep. 6, 2017, 570-592 (1996).
Holliger, P. et al., "Diabodies": small bivalent and bi specific antibody fragments, Proc. Natl. Acad, Sci, USA, 90:6444-6448 (1993).
Hsu, T-L. et al, Profiling Carbohydrate-Receptor Interaction with Recombinant Innate Immunity Receptor-Fc Fusion Proteins, J. Biol. Chem., 284(50): 34479-34489 (2009).
Huang, H. et al, Robust stimulation of humoral and cellular immune responses following vaccination with antigen-loaded beta-glucan particles, MBio, 1(3):e00164-10 (2010).
Hytonen, V.P. et al., Efficient production of active chicken avidin using a bacterial signal peptide in *Escherichia coli*, Biochem J., 384(Pt 2): 385-90 (2004).
Insel, R. et al., Response to oligosaccharide-protein conjugate vaccine against Hemophilus influenzae b in two patients with IgG2 deficiency unresponsive to capsular polysaccharide vaccine, N. Engl J. Med., 315:8, p. 499-503 (1986).
International Preliminary Report on Patentability for PCT/US2018/038907, 7 pages (dated Dec. 24, 2019.
Ishizaka, S.T. and Hawkins, L.D., E6020: a synthetic Toll-like receptor 4 agonist as a vaccine adjuvant, Expert Rev. Vaccines, 6(5):773-784 (2007).
Izard, J. W. and Kendall, D. A., Signal peptides: exquisitely designed transport promoters, Mol. Microbiol. 13(5):765-73 (1994).
Jin, Z. et al., Conjugates of group A and W135 capsular polysaccharides of neisseria meningitidis bound to recombinant *Staphylococcus aureus* enterotoxin C1: preparation, physicochemical characterization, and immunological properties in mice, Infect Immun, 73(12):7887-7893 (2005).
Kehoe, M. et al., Cloning, Expression, and Mapping of the *Staphylococcus aureus* a-Hemolysin Determinant in *Escherichia coli* K-12, 41(3):1105-1111 (1985).
Kim, K. H. et al., Efficiency of a Pneumococcal Opsonophagocytic Killing Assay Improved by Multiplexing and by Coloring Colonies, Clin. Diagn. Lab. Immunol., 10(4):616-621 (2003).
Kojima, K. et al., Quantitation of IgG subclass antibodies to pneumococcal capsular polysaccharides by ELISA, using Pneumovax-specific antibodies as a reference, Tohoku J. Exp. Med., 161(3):209-215 (1990).
Koskela, M. and Leinonen, M., Comparison of ELISA and RIA for measurement of pneumococcal antibodies before and after vaccination with 14-valent pneumococcal capsular polysaccharide vaccine, J. Clin. Pathol., 34(1):93-98 (1981).
Lees, A. et al, Enhanced immunogenicity of protein-dextran conjugates: I. Rapid stimulation of enhanced antibody responses to poorly immunogenic molecules, Vaccine, 12(13): 1160-1166 (1994).
Martinez, J. E. et al., A flow cytometric opsonophagocytic assay for measurement of functional antibodies elicited after vaccination with the 23-valent pneumococcal polysaccharide vaccine, Clin. Diagn. Lab Immunol., 6(4):581-586 (1999).
Moffitt, K. L. et al., Identification of Protective Pneumococcal Th17 Antigens from the Soluble Fraction of a Killed Whole Cell Vaccine, PLoS One 7(8):e43445 (2012).
Munro, C. S. et al., Assessment of biological activity of immunoglobulin preparations by using opsonized micro-organisms to stimulate neutrophil chemiluminescence, Clin. Exp. Immunol., 61(1):183-188 (1985).
Ojo-Amaize, E. A. et al., A rapid and sensitive chemiluminescence assay for evaluation of functional opsonic activity of Haemophilus influenzae type b-specific antibodies, Clin. Diagn. Lab. Immunol., 2(3):286-290 (1995).

(56) References Cited

OTHER PUBLICATIONS

O'Reilly, M. et al., Inactivation of the alpha-haemolysin gene of *Staphylococcus aureus* 8325-4 by site-directed mutagenesis and studies on the expression of its haemolysins, Microbial Pathogenesis, 1:125-138 (1986).

Paton, P C. et al., Purification and immunogenicity of genetically obtained pneumolysin toxoids and their conjugation to *Streptococcus pneumoniae* type 19F polysaccharide, Infect. Lmmun., 59(7):2297-2304 (1991).

Pneumovax® 23 (prescribing information). Whitehouse Station, NJ: Merck & Co.; May 2015.

Poljak, R. J., Production and structure of diabodies, Structure. 2(12):1121-1123 (1994).

Pollabauer, E. M. et al., The influence of carrier protein on the immunogenicity of simultaneously administered conjugate vaccines in infants, Vaccine, 27(11): 1674-1679 (2009).

Prevnar 13® (prescribing information). New York, NY: Pfizer; Aug. 2017.

Richter, S. S. et al., Changes in pneumococcal serotypes and antimicrobial resistance after introduction of the 13-valent conjugate vaccine in the United States, Antimicrob Agents Chemother., 58(11):6484-6489 (2014).

Romero-Steiner, S. et al., Avidity determinations for Haemophilus influenzae Type b anti-polyribosylribitol phosphate antibodies, Clin. Diagn. Lab. Immunol., 12(9):1029-1035 (2005).

Romero-Steiner, S. et al., Standardization of an opsonophagocytic assay for the measurement of functional antibody activity against *Streptococcus pneumoniae* using differentiated HL-60 cells, Clin. Diagn. Lab. Immunol., 4(4):415-422 (1997).

Rosenberg, I.M., Protein Analysis and Purification, Springer Science + Business Media New York, 153-182 (1996).

Saeland, E. et al., Pneumococcal pneumonia and bacteremia model in mice for the analysis of protective antibodies, Microb. Pathog., 29(2):81-91 (2000).

Sanabria-Valentin, Dissertation, Department of Basic Medical Sciences, NYU, p. 8-9 describing the general structure of LPS (2008).

Sano, T. et al, Methods in Enzymology, Elsevier, 326: 305-307 (2000).

Saunders, F. K. et al., Pneumolysin, the thiol-activated toxin of *Streptococcus pneumoniae*, does not require a thiol group for in vitro activity, Infect. Immun. 57(8):2547-2552 (1989).

Scott, D. et al., Immunogenicity of biotinylated hapten-avidin complexes, Mol. Immunol., 21(11):1055-1060 (1984).

Sen, G. et al., In vivo humoral immune responses to isolated Pneumococcal polysaccharides are dependent on the presence of associated TLR ligands, The Journal of Immunology, 175(5):3084-3091 (2005).

Singh, M. and Srivastava I., Advances in vaccine adjuvants for infectious diseases, Current HIV Research 1(3):309-320 (2003).

Stack, A. M. et al., Minimum protective serum concentrations of pneumococcal anti-capsular antibodies in infant rats, J. Infect. Dis., 177(4):986-990 (1998).

Takakura, Y. et al, Tamavidin, a versatile affinity tag for protein purification and immobilization, J. Biotechnol., 145(4): 317-322 (2010).

Thermo Scientific Avidin-Biotin Technical Handbook, 2009, p. 16-17. Found on the Internet on May 5, 2016 at: https://www.thermofisher.com/content/dam/LifeTech/Images/integration/1601675_AvBi_HB_INTL.pdf.

Wardenburg, J. and Schneewind, O., Vaccine protection against *Staphylococcus aureus* pneumonia, J. Exp. Med., 205(2): 287-94 (2008).

Williams et al., Innate Imprinting by the Modified Heat-Labile Toxin of *Escherichia coli* (LTK63) Provides Generic Protection against Lung Infectious Disease, The Journal of Immunology, 173: 7435-7443 (2004).

Wu, W. et al., Th17-stimulating protein vaccines confer protection against Pseudomonas aeruginosa pneumonia, Am. J. Respir. Crit. Care Med., 186(5):420-427 (2012).

Zhang, F. et al, Design and evaluation of multiple antigen presenting system (MAPS)-based pneumococcal vaccine to prevent invasive disease and carriage, poster presented at the 10th International Symposium on Pneumococci and Pneumococcal Diseases (ISPPD-10), Glasgow, Scotland, Jun. 26-30, 2016.

Zhang, F. et al., Multiple antigen-presenting system (MAPS) to induce comprehensive B- and T-cell immunity, Proc. Natl. Acad. Sci., 110(33):13564-13569 (2013).

International Search Report for PCT/US2018/038907 (Immunogenic Compositions, filed Jun. 22, 2018), issued by ISA/EPO, 6 pages (dated Oct. 11, 2018).

Written Opinion for PCT/US2018/038907 (Immunogenic Compositions, Jun. 22, 2018), issued by ISA/EPO, 8 pages (dated Oct. 11, 2018).

Menzies, B. E. and Kernodle, D. S., Site-Directed Mutagenesis of the Alpha-Toxin Gene of *Staphylococcus aureus*: Role of Histidines in Toxin Activity in Vitro and in a Murine Model, Infection and Immunity, 62(5):1843-1847 (1994).

Reed, S. G. et al., Key roles of adjuvants in modern vaccines, Nature Medicine, 19(12):1597-1608 (2013).

Walker, B. and Bayley, H. et al., Key Residues for Membrane Binding, Oligomerization, and Pore Forming Activity of Staphylococcal a-Hemolysin Identified by Cysteine Scanning Mutagenesis and Targeted Chemical Modification*, The Journal of Biological Chemistry, 270(39):23065-23071 (1995).

* cited by examiner

O1 → 4)-D-GalNAc-(α1 → 4)-D-GlcNAc3NAcA-(β1 → 3)-D-FucNAc-(α1 → 3)-D-QuiNAc-(α1 →

O2 → 4)-D-ManNAc3NAmA-(β1 → 4)-L-Gu1NAc3NAcA-(α1 → 3)-D-FucNAc-(β1 →

O3 → 2)-L-Rha3Ac-(α1 → 6)-DGlcNAc-(α1 → 4)-L-GalNAcA4Ac-(α1 → 3)-D-QuiNAc4NSHb-(β1 →

O4 → 2)-L-Rha-(α1 → 3)-L-FucNAc-(α1 → 3)-L-FucNAc-(α1 → 3)-D-QuiNAc-(α1 →

O5 → 4)-D-ManNAc3NAmA-(β1 → 4)-D-ManNAc3NAcA-(β1 → 3)-D-FucNAc-(α1 →

O6 → 3)-L-Rha-(α1 → 4)-D-GalNAcA3Ac-(α1 → 4)-D-GalNFoA-(α1 → 3)-D-QuiNAc-(α1 →

O10 → 3)-L-Rha2Ac-(α1 → 4)-L-GalNAcA-(α1 → 3)-D-QuiNAc-(α1 →

O11 → 2)-D-Glc-(β1 → 3)-L-FucNAc-(α1 → 3)-D-FucNAc-(β1 →

Figure 1B

|  | SEROTYPE |
|---|---|

```
       D         C         B'        A         B        A"
   -3)-β-Galp-(1-3)-α-Galp-(1 m-β-Galf-(1 3)-α-Galp-(1-3)-β-Galf-(1 n-3)-α-Galp-CP        O1

B'        A         B        A"
       β-Galf-(1 3)-α-Galp-(1-3)-β-Galf-(1 n-3)-α-Galp-CP                                  O1, O2a, O2a,c D(D')      C       B'(B*)      A         B        A"
   -5)-β-Galf-(1-3)-β-GlcNAc-(1 m-β-Galf-(1 3)-α-Galp-(1-3)-β-Galf-(1 n-3)-α-Galp-CP       O2a,c E         D         C         B         A         N         Q
   T 2)α-Man-(1-2)-α-Man-(1-2)-α-Man-(1-3)-α-Man-(1-3)-α-Man-(1 n-3)-α-Man-(1-3)-α-Man-CP  O3

T        B'        A         B        A"
   α-Kdo-(2-2)-β-Ribf-(1 4)-α-Gal-(1-2)-β-Ribf-(1 n-4)-α-Gal-(1-CP                         O4

T         C         B         A        N         Q
   Me-3)-α-Man-(1 3)-β-Man-(1-2)-α-Man-(1-2)-α-Man-(1 n-3)-α-Man-(1-3)-α-Man-(1-CP         O5

T         A'        B         A
   β-Kdo-(2-3)-α-Rha-(1 3)-β-GlcNAc-(1-4)-α-Rha-(1 n-(1-CP                                 O12

F         L         M
   -3)-β-GlcNAc-(1-5)-α-Kdo-(2-6)-anhMan                                  CP (COMMON PART)
                  P-(1-4)
   a, P=H
   b, P=α-Hep
```

Figure 1D

☐ OPS
⊖ RHIVAVIDIN FUSION PROTEIN
△ BIOTIN-PEG3-AMINE

MAPS WITH NATIVE OPS

SEQUENCE LISTING

```
<160> NUMBER OF SEQ ID NOS: 36

<210> SEQ ID NO 1
<211> LENGTH: 182
<212> TYPE: PRT
<213> ORGANISM: Klebsiella pneumoniae

<400> SEQUENCE: 1

Met Lys Ile Lys Thr Leu Ala Met Ile Val Val Ser Ala Leu Ser Leu
1               5                   10                  15

Ser Ser Thr Ala Ala Leu Ala Asp Thr Thr Val Asn Gly Gly Thr
            20                  25                  30

Val His Phe Lys Gly Glu Val Val Asn Ala Ala Cys Ala Val Asp Ala
            35                  40                  45

Gly Ser Ile Asp Gln Thr Val Gln Leu Gly Gln Val Arg Ser Ala Lys
        50                  55                  60

Leu Ala Thr Ala Gly Ser Thr Ser Ser Ala Val Gly Phe Asn Ile Gln
65                  70                  75                  80

Leu Asp Asp Cys Asp Thr Thr Val Ala Thr Lys Ala Ser Val Ala Phe
                85                  90                  95

Ala Gly Thr Ala Ile Asp Ser Ser Asn Thr Thr Val Leu Ala Leu Gln
            100                 105                 110

Asn Ser Ala Ala Gly Ser Ala Thr Asn Val Gly Val Gln Ile Leu Asp
            115                 120                 125

Asn Thr Gly Thr Pro Leu Ala Leu Asp Gly Ala Thr Phe Ser Ala Ala
            130                 135                 140

Thr Thr Leu Asn Asp Gly Pro Asn Ile Ile Pro Phe Gln Ala Arg Tyr
145                 150                 155                 160

Tyr Ala Thr Gly Ala Ala Thr Ala Gly Ile Ala Asn Ala Asp Ala Thr
                165                 170                 175

Phe Lys Val Gln Tyr Glu
            180

<210> SEQ ID NO 2
<211> LENGTH: 202
<212> TYPE: PRT
<213> ORGANISM: Klebsiella pneumoniae

<400> SEQUENCE: 2

Met Lys Lys Val Leu Leu Ser Ala Ala Met Ala Thr Ala Phe Phe Gly
1               5                   10                  15

Met Thr Ala Ala His Ala Ala Asp Thr Thr Val Gly Gly Gly Gln Val
            20                  25                  30
```

```
Asn Phe Phe Gly Lys Val Thr Asp Val Ser Cys Thr Val Ser Val Asn
            35                  40                  45
Gly Gln Gly Ser Asp Ala Asn Val Tyr Leu Ser Pro Val Thr Leu Thr
 50                  55                  60
Glu Val Lys Ala Ala Ala Asp Thr Tyr Leu Lys Pro Lys Ser Phe
 65                  70                  75                  80
Thr Ile Asp Val Ser Asn Cys Gln Ala Ala Asp Gly Thr Lys Gln Asp
                    85                  90                  95
Asp Val Ser Lys Leu Gly Val Asn Trp Thr Gly Gly Asn Leu Leu Ala
               100                 105                 110
Gly Ala Thr Ser Lys Gln Gln Gly Tyr Leu Ala Asn Thr Glu Ala Ser
               115                 120                 125
Gly Ala Gln Asn Ile Gln Leu Val Leu Ser Thr Asp Asn Ala Thr Ala
 130                 135                 140
Leu Thr Asn Lys Ile Ile Pro Gly Asp Ser Thr Gln Pro Lys Ala Lys
 145                 150                 155                 160
Gly Asp Ala Ser Ala Val Ala Asp Gly Ala Arg Phe Thr Tyr Tyr Val
                 165                 170                 175
Gly Tyr Ala Thr Ser Ala Pro Thr Thr Val Thr Thr Gly Val Val Asn
              180                 185                 190
Ser Tyr Ala Thr Tyr Glu Ile Thr Tyr Gln
              195                 200

<210> SEQ ID NO 3
<211> LENGTH: 206
<212> TYPE: PRT
<213> ORGANISM: Klebsiella pneumoniae

<400> SEQUENCE: 3

Ala Asp Thr Thr Val Gly Gly Gln Val Asn Phe Phe Gly Lys Val
 1               5                  10                  15
Thr Asp Val Ser Cys Thr Val Ser Val Asn Gly Gln Gly Ser Asp Ala
                20                  25                  30
Asn Val Tyr Leu Ser Pro Val Thr Leu Thr Glu Val Lys Ala Ala Ala
                35                  40                  45
Ala Asp Thr Tyr Leu Lys Pro Lys Ser Phe Thr Ile Asp Val Ser Asn
 50                  55                  60
Cys Gln Ala Ala Asp Gly Thr Lys Gln Asp Val Ser Lys Leu Gly
 65                  70                  75                  80
Val Asn Trp Thr Gly Gly Asn Leu Leu Ala Gly Ala Thr Ser Lys Gln
                 85                  90                  95
Gln Gly Tyr Leu Ala Asn Thr Glu Ala Ser Gly Ala Gln Asn Ile Gln
               100                 105                 110
Leu Val Leu Ser Thr Asp Asn Ala Thr Ala Leu Thr Asn Lys Ile Ile
               115                 120                 125
Pro Gly Asp Ser Thr Gln Pro Lys Ala Lys Gly Asp Ala Ser Ala Val
 130                 135                 140
Ala Asp Gly Ala Arg Phe Thr Tyr Tyr Val Gly Tyr Ala Thr Ser Ala
 145                 150                 155                 160
Pro Thr Thr Val Thr Thr Gly Val Val Asn Ser Tyr Ala Thr Tyr Glu
                 165                 170                 175
Ile Thr Tyr Gln Gly Gly Gly Gly Ala Asp Thr Thr Val Gly
                 180                 185                 190
Gly Gly Gln Val Asn Phe Phe Gly Lys Val Thr Asp Val Ser
                 195                 200                 205
```

-continued

```
<210> SEQ ID NO 4
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gln Val Arg Leu Gln Gln Ser Gly Pro Gly Leu Val Lys Pro Ser Glu
1               5                   10                  15

Thr Leu Ser Leu Thr Cys Thr Val Ser Gly Gly Ser Thr Ser Pro Tyr
            20                  25                  30

Phe Trp Ser Trp Leu Arg Gln Pro Pro Gly Lys Gly Leu Glu Trp Ile
        35                  40                  45

Gly Tyr Ile His Ser Asn Gly Thr Asn Tyr Asn Pro Ser Leu Lys
    50                  55                  60

Ser Arg Leu Thr Ile Ser Gly Asp Thr Ser Lys Asn Gln Phe Ser Leu
65                  70                  75                  80

Asn Leu Ser Phe Val Thr Ala Ala Asp Thr Ala Leu Tyr Tyr Cys Ala
                85                  90                  95

Arg Thr Asp Tyr Asp Val Tyr Gly Pro Ala Phe Asp Ile Trp Gly Gln
            100                 105                 110

Gly Thr Met Val Thr Val
        115

<210> SEQ ID NO 5
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105

<210> SEQ ID NO 6
<211> LENGTH: 394
<212> TYPE: PRT
<213> ORGANISM: Pseudomonas aeruginosa
```

<400> SEQUENCE: 6

```
Met Ala Leu Thr Val Asn Thr Asn Ile Ala Ser Leu Asn Thr Gln Arg
1               5                   10                  15

Asn Leu Asn Asn Ser Ser Ala Ser Leu Asn Thr Ser Leu Gln Arg Leu
            20                  25                  30

Ser Thr Gly Ser Arg Ile Asn Ser Ala Lys Asp Asp Ala Ala Gly Leu
        35                  40                  45

Gln Ile Ala Asn Arg Leu Thr Ser Gln Val Asn Gly Leu Asn Val Ala
    50                  55                  60

Thr Lys Asn Ala Asn Asp Gly Ile Ser Leu Ala Gln Thr Ala Glu Gly
65                  70                  75                  80

Ala Leu Gln Gln Ser Thr Asn Ile Leu Gln Arg Met Arg Asp Leu Ser
            85                  90                  95

Leu Gln Ser Ala Asn Gly Ser Asn Ser Asp Ser Glu Arg Thr Ala Leu
        100                 105                 110

Asn Gly Glu Val Lys Gln Leu Gln Lys Glu Leu Asp Arg Ile Ser Asn
    115                 120                 125

Thr Thr Thr Phe Gly Gly Arg Lys Leu Leu Asp Gly Ser Phe Gly Val
130                 135                 140

Ala Ser Phe Gln Val Gly Ser Ala Ala Asn Glu Ile Ile Ser Val Gly
145                 150                 155                 160

Ile Asp Glu Met Ser Ala Glu Ser Leu Asn Gly Thr Tyr Phe Lys Ala
            165                 170                 175

Asp Gly Gly Gly Ala Val Thr Ala Ala Thr Ala Ser Gly Thr Val Asp
        180                 185                 190

Ile Ala Ile Gly Ile Thr Gly Gly Ser Ala Val Asn Val Lys Val Asp
    195                 200                 205

Met Lys Gly Asn Glu Thr Ala Glu Gln Ala Ala Lys Ile Ala Ala
210                 215                 220

Ala Val Asn Asp Ala Asn Val Gly Ile Gly Ala Phe Ser Asp Gly Asp
225                 230                 235                 240

Thr Ile Ser Tyr Val Ser Lys Ala Gly Lys Asp Gly Ser Gly Ala Ile
            245                 250                 255

Thr Ser Ala Val Ser Gly Val Val Ile Ala Asp Thr Gly Ser Thr Gly
        260                 265                 270

Val Gly Thr Ala Ala Gly Val Thr Pro Ser Ala Thr Ala Phe Ala Lys
    275                 280                 285

Thr Asn Asp Thr Val Ala Lys Ile Asp Ile Ser Thr Ala Lys Gly Ala
290                 295                 300

Gln Ser Ala Val Leu Val Ile Asp Glu Ala Ile Lys Gln Ile Asp Ala
305                 310                 315                 320

Gln Arg Ala Asp Leu Gly Ala Val Gln Asn Arg Phe Asp Asn Thr Ile
            325                 330                 335

Asn Asn Leu Lys Asn Ile Gly Glu Asn Val Ser Ala Ala Arg Gly Arg
        340                 345                 350

Ile Glu Asp Thr Asp Phe Ala Ala Glu Thr Ala Asn Leu Thr Lys Asn
    355                 360                 365

Gln Val Leu Gln Gln Ala Gly Thr Ala Ile Leu Ala Gln Ala Asn Gln
370                 375                 380

Leu Pro Gln Ser Val Leu Ser Leu Leu Arg
385                 390
```

```
<210> SEQ ID NO 7
<211> LENGTH: 488
<212> TYPE: PRT
<213> ORGANISM: Pseudomonas aeruginosa

<400> SEQUENCE: 7

Met Ala Leu Thr Val Asn Thr Asn Ile Ala Ser Leu Asn Thr Gln Arg
1               5                   10                  15

Asn Leu Asn Ala Ser Ser Asn Asp Leu Asn Thr Ser Leu Gln Arg Leu
            20                  25                  30

Thr Thr Gly Tyr Arg Ile Asn Ser Ala Lys Asp Asp Ala Ala Gly Leu
        35                  40                  45

Gln Ile Ser Asn Arg Leu Ser Asn Gln Ile Ser Gly Leu Asn Val Ala
    50                  55                  60

Thr Arg Asn Ala Asn Asp Gly Ile Ser Leu Ala Gln Thr Ala Glu Gly
65                  70                  75                  80

Ala Leu Gln Gln Ser Thr Asn Ile Leu Gln Arg Ile Arg Asp Leu Ala
                85                  90                  95

Leu Gln Ser Ala Asn Gly Ser Asn Ser Asp Ala Asp Arg Ala Ala Leu
            100                 105                 110

Gln Lys Glu Val Ala Ala Gln Ala Glu Leu Thr Arg Ile Ser Asp
        115                 120                 125

Thr Thr Thr Phe Gly Gly Arg Lys Leu Leu Asp Gly Ser Phe Gly Thr
130                 135                 140

Thr Ser Phe Gln Val Gly Ser Asn Ala Tyr Glu Thr Ile Asp Ile Ser
145                 150                 155                 160

Leu Gln Asn Ala Ser Ala Ser Ala Ile Gly Ser Tyr Gln Val Gly Ser
                165                 170                 175

Asn Gly Ala Gly Thr Val Ala Ser Val Ala Gly Thr Ala Thr Ala Ser
            180                 185                 190

Gly Ile Ala Ser Gly Thr Val Asn Leu Val Gly Gly Gln Val Lys
        195                 200                 205

Asn Ile Ala Ile Ala Ala Gly Asp Ser Ala Lys Ala Ile Ala Glu Lys
    210                 215                 220

Met Asp Gly Ala Ile Pro Asn Leu Ser Ala Arg Ala Arg Thr Val Phe
225                 230                 235                 240

Thr Ala Asp Val Ser Gly Val Thr Gly Gly Ser Leu Asn Phe Asp Val
                245                 250                 255

Thr Val Gly Ser Asn Thr Val Ser Leu Ala Gly Val Thr Ser Thr Gln
            260                 265                 270

Asp Leu Ala Asp Gln Leu Asn Ser Asn Ser Ser Lys Leu Gly Ile Thr
        275                 280                 285

Ala Ser Ile Asn Asp Lys Gly Val Leu Thr Ile Thr Ser Ala Thr Gly
    290                 295                 300

Glu Asn Val Lys Phe Gly Ala Gln Thr Gly Thr Ala Thr Ala Gly Gln
305                 310                 315                 320

Val Ala Val Lys Val Gln Gly Ser Asp Gly Lys Phe Glu Ala Ala Ala
                325                 330                 335

Lys Asn Val Val Ala Ala Gly Thr Ala Ala Thr Thr Thr Ile Val Thr
            340                 345                 350

Gly Tyr Val Gln Leu Asn Ser Pro Thr Ala Tyr Ser Val Ser Gly Thr
        355                 360                 365

Gly Thr Gln Ala Ser Gln Val Phe Gly Asn Ala Ser Ala Ala Gln Lys
    370                 375                 380
```

```
Ser Ser Val Ala Ser Val Asp Ile Ser Thr Ala Asp Gly Ala Gln Asn
385                 390                 395                 400

Ala Ile Ala Val Val Asp Asn Ala Leu Ala Ala Ile Asp Ala Gln Arg
            405                 410                 415

Ala Asp Leu Gly Ala Val Gln Asn Arg Phe Lys Asn Thr Ile Asp Asn
            420                 425                 430

Leu Thr Asn Ile Ser Glu Asn Ala Thr Asn Ala Arg Ser Arg Ile Lys
            435                 440                 445

Asp Thr Asp Phe Ala Ala Glu Thr Ala Ala Leu Ser Lys Asn Gln Val
            450                 455                 460

Leu Gln Gln Ala Gly Thr Ala Ile Leu Ala Gln Ala Asn Gln Leu Pro
465                 470                 475                 480

Gln Ala Val Leu Ser Leu Leu Arg
                485

<210> SEQ ID NO 8
<211> LENGTH: 294
<212> TYPE: PRT
<213> ORGANISM: Pseudomonas aeruginosa

<400> SEQUENCE: 8

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
            35                  40                  45

Pro Leu Ser Glu Ala Gln Val Leu Lys Ala Leu Ala Trp Leu Leu Ala
50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
            85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
            115                 120                 125

Lys Ala Leu Leu Asp Glu Leu Lys Ala Leu Thr Ala Glu Leu Lys Val
            130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
            165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Leu
            210                 215                 220

Ser Asp Glu Tyr Pro Phe Glu Lys Asp Asn Pro Val Gly Asn Phe
225                 230                 235                 240

Ala Thr Thr Val Ser Asp Arg Ser Arg Pro Leu Asn Asp Lys Val Asn
            245                 250                 255

Glu Lys Thr Thr Leu Leu Asn Asp Thr Ser Ser Arg Tyr Asn Ser Ala
            260                 265                 270
```

Val Glu Ala Leu Asn Arg Phe Ile Gln Lys Tyr Asp Ser Val Leu Arg
            275                 280                 285

Asp Ile Leu Ser Ala Ile
        290

<210> SEQ ID NO 9
<211> LENGTH: 387
<212> TYPE: PRT
<213> ORGANISM: Pseudomonas aeruginosa

<400> SEQUENCE: 9

Met Ala Leu Thr Val Asn Thr Asn Ile Ala Ser Leu Asn Thr Gln Arg
1               5                   10                  15

Asn Leu Asn Asn Ser Ser Ala Ser Leu Asn Thr Ser Leu Gln Arg Leu
            20                  25                  30

Ser Thr Gly Ser Arg Ile Asn Ser Ala Lys Asp Asp Ala Ala Gly Leu
        35                  40                  45

Gln Ile Ala Asn Arg Leu Thr Ser Gln Val Asn Gly Leu Asn Val Ala
    50                  55                  60

Thr Lys Asn Ala Asn Asp Gly Ile Ser Leu Ala Gln Thr Ala Glu Gly
65                  70                  75                  80

Ala Leu Gln Gln Ser Thr Asn Ile Leu Gln Arg Met Arg Asp Leu Ser
                85                  90                  95

Leu Gln Ser Ala Asn Gly Ser Asn Ser Asp Ser Glu Arg Thr Ala Leu
            100                 105                 110

Asn Gly Glu Val Lys Gln Leu Gln Lys Glu Leu Asp Arg Ile Ser Asn
        115                 120                 125

Thr Thr Thr Phe Gly Gly Arg Lys Leu Leu Asp Gly Ser Phe Gly Val
    130                 135                 140

Ala Ser Phe Gln Val Gly Ser Ala Ala Asn Glu Ile Ile Ser Val Gly
145                 150                 155                 160

Ile Asp Glu Met Ser Ala Glu Ser Leu Asn Gly Thr Tyr Phe Thr Ala
                165                 170                 175

Thr Gly Gly Gly Ala Val Thr Ala Ala Thr Ala Ser Gly Thr Val Asp
            180                 185                 190

Ile Ala Ile Gly Ile Thr Gly Gly Ser Ala Val Asn Val Lys Val Asp
        195                 200                 205

Met Lys Gly Asn Glu Thr Ala Glu Gln Ala Ala Lys Ile Ala Ala
    210                 215                 220

Ala Val Asn Asp Ala Asn Val Gly Ile Gly Ala Phe Thr Asp Gly Ala
225                 230                 235                 240

Gln Ile Ser Tyr Val Ser Lys Ala Ser Ala Asp Gly Thr Thr Ser Ala
                245                 250                 255

Val Ser Gly Val Ala Ile Thr Asp Thr Gly Ser Thr Gly Ala Gly Thr
            260                 265                 270

Ala Ala Gly Thr Thr Thr Phe Thr Glu Ala Asn Asp Thr Val Ala Lys
        275                 280                 285

Ile Asp Ile Ser Thr Ala Lys Gly Ala Gln Ser Ala Val Leu Val Ile
    290                 295                 300

Asp Glu Ala Ile Lys Gln Ile Asp Ala Gln Arg Ala Asp Leu Gly Ala
305                 310                 315                 320

Val Gln Asn Arg Phe Asp Asn Thr Ile Asn Asn Leu Lys Asn Ile Gly
                325                 330                 335

Glu Asn Val Ser Ala Ala Arg Gly Arg Ile Glu Asp Thr Asp Phe Ala
            340                 345                 350

```
Ala Glu Thr Ala Asn Leu Thr Lys Asn Gln Val Leu Gln Gln Ala Gly
            355                 360                 365

Thr Ala Ile Leu Ala Gln Ala Asn Gln Leu Pro Gln Ser Val Leu Ser
        370                 375                 380

Leu Leu Arg
385

<210> SEQ ID NO 10
<211> LENGTH: 217
<212> TYPE: PRT
<213> ORGANISM: Pseudomonas aeruginosa

<400> SEQUENCE: 10

Gly Ser Tyr Gln Val Gly Ser Asn Gly Ala Gly Thr Val Ala Ser Val
1               5                   10                  15

Ala Gly Thr Ala Thr Ala Ser Gly Ile Ala Ser Gly Thr Val Asn Leu
            20                  25                  30

Val Gly Gly Gly Gln Val Lys Asn Ile Ala Ile Ala Ala Gly Asp Ser
        35                  40                  45

Ala Lys Ala Ile Ala Glu Lys Met Asp Gly Ala Ile Pro Asn Leu Ser
    50                  55                  60

Ala Arg Ala Arg Thr Val Phe Thr Ala Asp Val Ser Gly Val Thr Gly
65                  70                  75                  80

Gly Ser Leu Asn Phe Asp Val Thr Val Gly Ser Asn Thr Val Ser Leu
                85                  90                  95

Ala Gly Val Thr Ser Thr Gln Asp Leu Ala Asp Gln Leu Asn Ser Asn
            100                 105                 110

Ser Ser Lys Leu Gly Ile Thr Ala Ser Ile Asn Asp Lys Gly Val Leu
        115                 120                 125

Thr Ile Thr Ser Ala Thr Gly Glu Asn Val Lys Phe Gly Ala Gln Thr
    130                 135                 140

Gly Thr Ala Thr Ala Gly Gln Val Ala Val Lys Val Gln Gly Ser Asp
145                 150                 155                 160

Gly Lys Phe Glu Ala Ala Ala Lys Asn Val Val Ala Ala Gly Thr Ala
                165                 170                 175

Ala Thr Thr Thr Ile Val Thr Gly Tyr Val Gln Leu Asn Ser Pro Thr
            180                 185                 190

Ala Tyr Ser Val Ser Gly Thr Gly Thr Gln Ala Ser Gln Val Phe Gly
        195                 200                 205

Asn Ala Ser Ala Ala Gln Lys Ser Ser
    210                 215

<210> SEQ ID NO 11
<211> LENGTH: 123
<212> TYPE: PRT
<213> ORGANISM: Pseudomonas aeruginosa

<400> SEQUENCE: 11

Asn Gly Thr Tyr Phe Lys Ala Asp Gly Gly Ala Val Thr Ala Ala
1               5                   10                  15

Thr Ala Ser Gly Thr Val Asp Ile Ala Ile Gly Ile Thr Gly Gly Ser
            20                  25                  30

Ala Val Asn Val Lys Val Asp Met Lys Gly Asn Glu Thr Ala Glu Gln
        35                  40                  45

Ala Ala Ala Lys Ile Ala Ala Val Asn Asp Ala Asn Val Gly Ile
    50                  55                  60
```

```
Gly Ala Phe Ser Asp Gly Asp Thr Ile Ser Tyr Val Ser Lys Ala Gly
 65                  70                  75                  80

Lys Asp Gly Ser Gly Ala Ile Thr Ser Ala Val Ser Gly Val Val Ile
                 85                  90                  95

Ala Asp Thr Gly Ser Thr Gly Val Gly Thr Ala Ala Gly Val Thr Pro
            100                 105                 110

Ser Ala Thr Ala Phe Ala Lys Thr Asn Asp Thr
        115                 120

<210> SEQ ID NO 12
<211> LENGTH: 116
<212> TYPE: PRT
<213> ORGANISM: Pseudomonas aeruginosa

<400> SEQUENCE: 12

Asn Gly Thr Tyr Phe Thr Ala Thr Gly Gly Ala Val Thr Ala Ala
1               5                   10                  15

Thr Ala Ser Gly Thr Val Asp Ile Ala Ile Gly Ile Thr Gly Gly Ser
            20                  25                  30

Ala Val Asn Val Lys Val Asp Met Lys Gly Asn Glu Thr Ala Glu Gln
        35                  40                  45

Ala Ala Ala Lys Ile Ala Ala Ala Val Asn Asp Ala Asn Val Gly Ile
    50                  55                  60

Gly Ala Phe Thr Asp Gly Ala Gln Ile Ser Tyr Val Ser Lys Ala Ser
65                  70                  75                  80

Ala Asp Gly Thr Thr Ser Ala Val Ser Gly Val Ala Ile Thr Asp Thr
                85                  90                  95

Gly Ser Thr Gly Ala Gly Thr Ala Ala Gly Thr Thr Thr Phe Thr Glu
            100                 105                 110

Ala Asn Asp Thr
        115

<210> SEQ ID NO 13
<211> LENGTH: 179
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Met Ile Ile Thr Ser Leu Tyr Ala Thr Phe Gly Thr Ile Ala Asp Gly
1               5                   10                  15

Arg Arg Thr Ser Gly Gly Lys Thr Met Ile Arg Thr Asn Ala Val Ala
            20                  25                  30

Ala Leu Val Phe Ala Val Ala Thr Ser Ala Leu Ala Phe Asp Ala Ser
        35                  40                  45

Asn Phe Lys Asp Phe Ser Ser Ile Ala Ser Ala Ser Ser Ser Trp Gln
    50                  55                  60

Asn Gln Ser Gly Ser Thr Met Ile Ile Gln Val Asp Ser Phe Gly Asn
65                  70                  75                  80

Val Ser Gly Gln Tyr Val Asn Arg Ala Gln Thr Gly Cys Gln Asn
                85                  90                  95

Ser Pro Tyr Pro Leu Thr Gly Arg Val Asn Gly Thr Phe Ile Ala Phe
            100                 105                 110

Ser Val Gly Trp Asn Asn Ser Thr Glu Asn Cys Asn Ser Ala Thr Gly
        115                 120                 125
```

```
Trp Thr Gly Tyr Ala Gln Val Asn Gly Asn Asn Thr Glu Ile Val Thr
        130                 135                 140

Ser Trp Asn Leu Ala Tyr Glu Gly Ser Gly Pro Ala Ile Glu Gln
145                 150                 155                 160

Gly Gln Asp Thr Phe Gln Tyr Val Pro Thr Thr Glu Asn Lys Ser Leu
                165                 170                 175

Leu Lys Asp

<210> SEQ ID NO 14
<211> LENGTH: 135
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Phe Asp Ala Ser Asn Phe Lys Asp Phe Ser Ser Ile Ala Ser Ala Ser
1               5                   10                  15

Ser Ser Trp Gln Asn Gln Ser Gly Ser Thr Met Ile Ile Gln Val Asp
            20                  25                  30

Ser Phe Gly Asn Val Ser Gly Gln Tyr Val Asn Arg Ala Gln Gly Thr
        35                  40                  45

Gly Cys Gln Asn Ser Pro Tyr Pro Leu Thr Gly Arg Val Asn Gly Thr
    50                  55                  60

Phe Ile Ala Phe Ser Val Gly Trp Asn Ser Thr Glu Asn Cys Asn
65                  70                  75                  80

Ser Ala Thr Gly Trp Thr Gly Tyr Ala Gln Val Asn Gly Asn Asn Thr
                85                  90                  95

Glu Ile Val Thr Ser Trp Asn Leu Ala Tyr Glu Gly Ser Gly Pro
                100                 105                 110

Ala Ile Glu Gln Gly Gln Asp Thr Phe Gln Tyr Val Pro Thr Thr Glu
            115                 120                 125

Asn Lys Ser Leu Leu Lys Asp
        130                 135

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Gly Gly Gly Ser Ser Ser
1               5

<210> SEQ ID NO 16
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 16

Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
            20                  25                  30

Asp Ser Phe Gly Asn Val Ser Gly Gln Tyr Val Asn Arg Ala Gln Gly
        35                  40                  45

Thr Gly Cys Gln Asn Ser Pro Tyr Pro Leu Thr Gly Arg Val Asn Gly
    50                  55                  60

Thr Phe Ile Ala Phe Ser Val Gly Trp Asn Asn Ser Thr Glu Asn Cys
65                  70                  75                  80

Asn Ser Ala Thr Gly Trp Thr Gly Tyr Ala Gln Val Asn Gly Asn Asn
                85                  90                  95

Thr Glu Ile Val Thr Ser Trp Asn Leu Ala Tyr Glu Gly Gly Ser Gly
            100                 105                 110

Pro Ala Ile Glu Gln Gly Gln Asp Thr Phe Gln Tyr Val Pro Thr Thr
        115                 120                 125

Glu Asn Lys Ser Leu Leu Lys Asp Gly Gly Gly Ser Ser Ser Met
    130                 135                 140

Glu Val Arg Asn Leu Asn Ala Ala Arg Glu Leu Phe Leu Asp Glu Leu
145                 150                 155                 160

Leu Ala Ala Ser Ala Pro Ser Ala Glu Gln Glu Leu Leu
                165                 170                 175

Ala Leu Leu Arg Ser Glu Arg Ile Val Leu Ala His Ala Gly Gln Pro
            180                 185                 190

Leu Ser Glu Ala Gln Val Leu Lys Ala Leu Ala Trp Leu Leu Ala Ala
        195                 200                 205

Asn Pro Ser Ala Pro Gly Gln Gly Leu Glu Val Leu Arg Glu Val
    210                 215                 220

Leu Gln Ala Arg Arg Gln Pro Gly Ala Gln Trp Asp Leu Arg Glu Phe
225                 230                 235                 240

Leu Val Ser Ala Tyr Phe Ser Leu His Gly Arg Leu Asp Glu Asp Val
                245                 250                 255

Ile Gly Val Tyr Lys Asp Val Leu Gln Thr Gln Asp Gly Lys Arg Lys
            260                 265                 270

Ala Leu Leu Asp Glu Leu Lys Ala Leu Thr Ala Glu Leu Lys Val Tyr
        275                 280                 285

Ser Val Ile Gln Ser Gln Ile Asn Ala Ala Leu Ser Ala Lys Gln Gly
    290                 295                 300

Ile Arg Ile Asp Ala Gly Gly Ile Asp Leu Val Asp Pro Thr Leu Tyr
305                 310                 315                 320

Gly Tyr Ala Val Gly Asp Pro Arg Trp Lys Ser Pro Glu Tyr Ala
                325                 330                 335

Leu Leu Ser Asn Leu Asp Thr Phe Ser Gly Lys Leu Ser Ile Lys Asp
            340                 345                 350

Phe Leu Ser Gly Ser Pro Lys Gln Ser Gly Glu Leu Lys Gly Leu Ser
        355                 360                 365

Asp Glu Tyr Pro Phe Glu Lys Asp Asn Pro Val Gly Asn Phe Ala
    370                 375                 380

Thr Thr Val Ser Asp Arg Ser Arg Pro Leu Asn Asp Lys Val Asn Glu
385                 390                 395                 400

Lys Thr Thr Leu Leu Asn Asp Thr Ser Ser Arg Tyr Asn Ser Ala Val
                405                 410                 415

```
Glu Ala Leu Asn Arg Phe Ile Gln Lys Tyr Asp Ser Val Leu Arg Asp
                420                 425                 430

Ile Leu Ser Ala Ile Gly Ser Gly His His His His His His
            435                 440                 445

<210> SEQ ID NO 17
<211> LENGTH: 359
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
                20                  25                  30

Asp Ser Phe Gly Asn Val Ser Gly Gln Tyr Val Asn Arg Ala Gln Gly
            35                  40                  45

Thr Gly Cys Gln Asn Ser Pro Tyr Pro Leu Thr Gly Arg Val Asn Gly
50                  55                  60

Thr Phe Ile Ala Phe Ser Val Gly Trp Asn Asn Ser Thr Glu Asn Cys
65                  70                  75                  80

Asn Ser Ala Thr Gly Trp Thr Gly Tyr Ala Gln Val Asn Gly Asn Asn
                85                  90                  95

Thr Glu Ile Val Thr Ser Trp Asn Leu Ala Tyr Glu Gly Ser Gly
            100                 105                 110

Pro Ala Ile Glu Gln Gly Gln Asp Thr Phe Gln Tyr Val Pro Thr Thr
            115                 120                 125

Glu Asn Lys Ser Leu Leu Lys Asp Gly Gly Gly Ser Ser Ser Met
130                 135                 140

Ala Asp Thr Thr Val Gly Gly Gln Val Asn Phe Phe Gly Lys Val
145                 150                 155                 160

Thr Asp Val Ser Cys Thr Val Ser Val Asn Gly Gln Gly Ser Asp Ala
                165                 170                 175

Asn Val Tyr Leu Ser Pro Val Thr Leu Thr Glu Val Lys Ala Ala Ala
            180                 185                 190

Ala Asp Thr Tyr Leu Lys Pro Lys Ser Phe Thr Ile Asp Val Ser Asn
            195                 200                 205

Cys Gln Ala Ala Asp Gly Thr Lys Gln Asp Asp Val Ser Lys Leu Gly
210                 215                 220

Val Asn Trp Thr Gly Gly Asn Leu Leu Ala Gly Ala Thr Ser Lys Gln
225                 230                 235                 240

Gln Gly Tyr Leu Ala Asn Thr Glu Ala Ser Gly Ala Gln Asn Ile Gln
                245                 250                 255

Leu Val Leu Ser Thr Asp Asn Ala Thr Ala Leu Thr Asn Lys Ile Ile
            260                 265                 270

Pro Gly Asp Ser Thr Gln Pro Lys Ala Lys Gly Asp Ala Ser Ala Val
            275                 280                 285

Ala Asp Gly Ala Arg Phe Thr Tyr Tyr Val Gly Tyr Ala Thr Ser Ala
            290                 295                 300

Pro Thr Thr Val Thr Thr Gly Val Val Asn Ser Tyr Ala Thr Tyr Glu
305                 310                 315                 320
```

```
Ile Thr Tyr Gln Gly Gly Gly Gly Gly Ala Asp Thr Thr Val Gly
            325                 330                 335

Gly Gly Gln Val Asn Phe Phe Gly Lys Val Thr Asp Ser Gly Ser
        340                 345                 350

Gly His His His His His His
        355

<210> SEQ ID NO 18
<211> LENGTH: 546
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
            20                  25                  30

Asp Ser Phe Gly Asn Val Ser Gly Gln Tyr Val Asn Arg Ala Gln Gly
        35                  40                  45

Thr Gly Cys Gln Asn Ser Pro Tyr Pro Leu Thr Gly Arg Val Asn Gly
    50                  55                  60

Thr Phe Ile Ala Phe Ser Val Gly Trp Asn Asn Ser Thr Glu Asn Cys
65                  70                  75                  80

Asn Ser Ala Thr Gly Trp Thr Gly Tyr Ala Gln Val Asn Gly Asn Asn
                85                  90                  95

Thr Glu Ile Val Thr Ser Trp Asn Leu Ala Tyr Glu Gly Gly Ser Gly
            100                 105                 110

Pro Ala Ile Glu Gln Gly Gln Asp Thr Phe Gln Tyr Val Pro Thr Thr
        115                 120                 125

Glu Asn Lys Ser Leu Leu Lys Asp Gly Gly Gly Ser Ser Ser Met
    130                 135                 140

Ala Leu Thr Val Asn Thr Asn Ile Ala Ser Leu Asn Thr Gln Arg Asn
145                 150                 155                 160

Leu Asn Asn Ser Ser Ala Ser Leu Asn Thr Ser Leu Gln Arg Leu Ser
                165                 170                 175

Thr Gly Ser Arg Ile Asn Ser Ala Lys Asp Asp Ala Ala Gly Leu Gln
            180                 185                 190

Ile Ala Asn Arg Leu Thr Ser Gln Val Asn Gly Leu Asn Val Ala Thr
        195                 200                 205

Lys Asn Ala Asn Asp Gly Ile Ser Leu Ala Gln Thr Ala Glu Gly Ala
    210                 215                 220

Leu Gln Gln Ser Thr Asn Ile Leu Gln Arg Met Arg Asp Leu Ser Leu
225                 230                 235                 240

Gln Ser Ala Asn Gly Ser Asn Ser Asp Ser Glu Arg Thr Ala Leu Asn
                245                 250                 255

Gly Glu Val Lys Gln Leu Gln Lys Glu Leu Asp Arg Ile Ser Asn Thr
            260                 265                 270

Thr Thr Phe Gly Gly Arg Lys Leu Leu Asp Gly Ser Phe Gly Val Ala
        275                 280                 285

Ser Phe Gln Val Gly Ser Ala Ala Asn Glu Ile Ile Ser Val Gly Ile
    290                 295                 300
```

Asp Glu Met Ser Ala Glu Ser Leu Asn Gly Thr Tyr Phe Lys Ala Asp
305                 310                 315                 320

Gly Gly Gly Ala Val Thr Ala Ala Thr Ala Ser Gly Thr Val Asp Ile
            325                 330                 335

Ala Ile Gly Ile Thr Gly Gly Ser Ala Val Asn Val Lys Val Asp Met
            340                 345                 350

Lys Gly Asn Glu Thr Ala Glu Gln Ala Ala Lys Ile Ala Ala Ala
            355                 360                 365

Val Asn Asp Ala Asn Val Gly Ile Gly Ala Phe Ser Asp Gly Asp Thr
            370                 375                 380

Ile Ser Tyr Val Ser Lys Ala Gly Lys Asp Gly Ser Gly Ala Ile Thr
385                 390                 395                 400

Ser Ala Val Ser Gly Val Val Ile Ala Asp Thr Gly Ser Thr Gly Val
            405                 410                 415

Gly Thr Ala Ala Gly Val Thr Pro Ser Ala Thr Ala Phe Ala Lys Thr
            420                 425                 430

Asn Asp Thr Val Ala Lys Ile Asp Ile Ser Thr Ala Lys Gly Ala Gln
            435                 440                 445

Ser Ala Val Leu Val Ile Asp Glu Ala Ile Lys Gln Ile Asp Ala Gln
            450                 455                 460

Arg Ala Asp Leu Gly Ala Val Gln Asn Arg Phe Asp Asn Thr Ile Asn
465                 470                 475                 480

Asn Leu Lys Asn Ile Gly Glu Asn Val Ser Ala Ala Arg Gly Arg Ile
            485                 490                 495

Glu Asp Thr Asp Phe Ala Ala Glu Thr Ala Asn Leu Thr Lys Asn Gln
            500                 505                 510

Val Leu Gln Gln Ala Gly Thr Ala Ile Leu Ala Gln Ala Asn Gln Leu
            515                 520                 525

Pro Gln Ser Val Leu Ser Leu Leu Arg Gly Ser Gly His His His His
            530                 535                 540

His His
545

<210> SEQ ID NO 19
<211> LENGTH: 539
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
            20                  25                  30

Asp Ser Phe Gly Asn Val Ser Gly Gln Tyr Val Asn Arg Ala Gln Gly
            35                  40                  45

Thr Gly Cys Gln Asn Ser Pro Tyr Pro Leu Thr Gly Arg Val Asn Gly
            50                  55                  60

Thr Phe Ile Ala Phe Ser Val Gly Trp Asn Asn Ser Thr Glu Asn Cys
65                  70                  75                  80

Asn Ser Ala Thr Gly Trp Thr Gly Tyr Ala Gln Val Asn Gly Asn Asn
            85                  90                  95

```
Thr Glu Ile Val Thr Ser Trp Asn Leu Ala Tyr Glu Gly Gly Ser Gly
            100                 105                 110

Pro Ala Ile Glu Gln Gly Gln Asp Thr Phe Gln Tyr Val Pro Thr Thr
        115                 120                 125

Glu Asn Lys Ser Leu Leu Lys Asp Gly Gly Gly Ser Ser Ser Met
130                 135                 140

Ala Leu Thr Val Asn Thr Asn Ile Ala Ser Leu Asn Thr Gln Arg Asn
145                 150                 155                 160

Leu Asn Asn Ser Ser Ala Ser Leu Asn Thr Ser Leu Gln Arg Leu Ser
                165                 170                 175

Thr Gly Ser Arg Ile Asn Ser Ala Lys Asp Asp Ala Ala Gly Leu Gln
            180                 185                 190

Ile Ala Asn Arg Leu Thr Ser Gln Val Asn Gly Leu Asn Val Ala Thr
        195                 200                 205

Lys Asn Ala Asn Asp Gly Ile Ser Leu Ala Gln Thr Ala Glu Gly Ala
210                 215                 220

Leu Gln Gln Ser Thr Asn Ile Leu Gln Arg Met Arg Asp Leu Ser Leu
225                 230                 235                 240

Gln Ser Ala Asn Gly Ser Asn Ser Asp Ser Glu Arg Thr Ala Leu Asn
                245                 250                 255

Gly Glu Val Lys Gln Leu Gln Lys Glu Leu Asp Arg Ile Ser Asn Thr
            260                 265                 270

Thr Thr Phe Gly Gly Arg Lys Leu Leu Asp Gly Ser Phe Gly Val Ala
        275                 280                 285

Ser Phe Gln Val Gly Ser Ala Ala Asn Glu Ile Ile Ser Val Gly Ile
290                 295                 300

Asp Glu Met Ser Ala Glu Ser Leu Asn Gly Thr Tyr Phe Thr Ala Thr
305                 310                 315                 320

Gly Gly Gly Ala Val Thr Ala Ala Thr Ala Ser Gly Thr Val Asp Ile
                325                 330                 335

Ala Ile Gly Ile Thr Gly Gly Ser Ala Val Asn Val Lys Val Asp Met
            340                 345                 350

Lys Gly Asn Glu Thr Ala Glu Gln Ala Ala Ala Lys Ile Ala Ala Ala
        355                 360                 365

Val Asn Asp Ala Asn Val Gly Ile Gly Ala Phe Thr Asp Gly Ala Gln
370                 375                 380

Ile Ser Tyr Val Ser Lys Ala Ser Ala Asp Gly Thr Thr Ser Ala Val
385                 390                 395                 400

Ser Gly Val Ala Ile Thr Asp Thr Gly Ser Thr Gly Ala Gly Thr Ala
                405                 410                 415

Ala Gly Thr Thr Thr Phe Thr Glu Ala Asn Asp Thr Val Ala Lys Ile
            420                 425                 430

Asp Ile Ser Thr Ala Lys Gly Ala Gln Ser Ala Val Leu Val Ile Asp
        435                 440                 445

Glu Ala Ile Lys Gln Ile Asp Ala Gln Arg Ala Asp Leu Gly Ala Val
450                 455                 460

Gln Asn Arg Phe Asp Asn Thr Ile Asn Asn Leu Lys Asn Ile Gly Glu
465                 470                 475                 480

Asn Val Ser Ala Ala Arg Gly Arg Ile Glu Asp Thr Asp Phe Ala Ala
                485                 490                 495

Glu Thr Ala Asn Leu Thr Lys Asn Gln Val Leu Gln Gln Ala Gly Thr
            500                 505                 510
```

```
Ala Ile Leu Ala Gln Ala Asn Gln Leu Pro Gln Ser Val Leu Ser Leu
            515                 520                 525

Leu Arg Gly Ser Gly His His His His His
        530                 535

<210> SEQ ID NO 20
<211> LENGTH: 640
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
            20                  25                  30

Asp Ser Phe Gly Asn Val Ser Gly Gln Tyr Val Asn Arg Ala Gln Gly
        35                  40                  45

Thr Gly Cys Gln Asn Ser Pro Tyr Pro Leu Thr Gly Arg Val Asn Gly
    50                  55                  60

Thr Phe Ile Ala Phe Ser Val Gly Trp Asn Asn Ser Thr Glu Asn Cys
65                  70                  75                  80

Asn Ser Ala Thr Gly Trp Thr Gly Tyr Ala Gln Val Asn Gly Asn Asn
                85                  90                  95

Thr Glu Ile Val Thr Ser Trp Asn Leu Ala Tyr Glu Gly Gly Ser Gly
            100                 105                 110

Pro Ala Ile Glu Gln Gly Gln Asp Thr Phe Gln Tyr Val Pro Thr Thr
        115                 120                 125

Glu Asn Lys Ser Leu Leu Lys Asp Gly Gly Gly Ser Ser Ser Met
130                 135                 140

Ala Leu Thr Val Asn Thr Asn Ile Ala Ser Leu Asn Thr Gln Arg Asn
145                 150                 155                 160

Leu Asn Ala Ser Ser Asn Asp Leu Asn Thr Ser Leu Gln Arg Leu Thr
                165                 170                 175

Thr Gly Tyr Arg Ile Asn Ser Ala Lys Asp Asp Ala Ala Gly Leu Gln
            180                 185                 190

Ile Ser Asn Arg Leu Ser Asn Gln Ile Ser Gly Leu Asn Val Ala Thr
        195                 200                 205

Arg Asn Ala Asn Asp Gly Ile Ser Leu Ala Gln Thr Ala Glu Gly Ala
    210                 215                 220

Leu Gln Gln Ser Thr Asn Ile Leu Gln Arg Ile Arg Asp Leu Ala Leu
225                 230                 235                 240

Gln Ser Ala Asn Gly Ser Asn Ser Asp Ala Asp Arg Ala Ala Leu Gln
                245                 250                 255

Lys Glu Val Ala Ala Gln Gln Ala Glu Leu Thr Arg Ile Ser Asp Thr
            260                 265                 270

Thr Thr Phe Gly Gly Arg Lys Leu Leu Asp Gly Ser Phe Gly Thr Thr
        275                 280                 285

Ser Phe Gln Val Gly Ser Asn Ala Tyr Glu Thr Ile Asp Ile Ser Leu
    290                 295                 300

Gln Asn Ala Ser Ala Ser Ala Ile Gly Ser Tyr Gln Val Gly Ser Asn
305                 310                 315                 320
```

```
Gly Ala Gly Thr Val Ala Ser Val Ala Gly Thr Ala Thr Ala Ser Gly
                325                 330                 335

Ile Ala Ser Gly Thr Val Asn Leu Val Gly Gly Gln Val Lys Asn
            340                 345                 350

Ile Ala Ile Ala Ala Gly Asp Ser Ala Lys Ala Ile Ala Glu Lys Met
            355                 360                 365

Asp Gly Ala Ile Pro Asn Leu Ser Ala Arg Ala Arg Thr Val Phe Thr
            370                 375                 380

Ala Asp Val Ser Gly Val Thr Gly Gly Ser Leu Asn Phe Asp Val Thr
385                 390                 395                 400

Val Gly Ser Asn Thr Val Ser Leu Ala Gly Val Thr Ser Thr Gln Asp
                405                 410                 415

Leu Ala Asp Gln Leu Asn Ser Asn Ser Ser Lys Leu Gly Ile Thr Ala
                420                 425                 430

Ser Ile Asn Asp Lys Gly Val Leu Thr Ile Thr Ser Ala Thr Gly Glu
                435                 440                 445

Asn Val Lys Phe Gly Ala Gln Thr Gly Thr Ala Thr Ala Gly Gln Val
                450                 455                 460

Ala Val Lys Val Gln Gly Ser Asp Gly Lys Phe Glu Ala Ala Ala Lys
465                 470                 475                 480

Asn Val Val Ala Ala Gly Thr Ala Ala Thr Thr Ile Val Thr Gly
                485                 490                 495

Tyr Val Gln Leu Asn Ser Pro Thr Ala Tyr Ser Val Ser Gly Thr Gly
                500                 505                 510

Thr Gln Ala Ser Gln Val Phe Gly Asn Ala Ser Ala Ala Gln Lys Ser
                515                 520                 525

Ser Val Ala Ser Val Asp Ile Ser Thr Ala Asp Gly Ala Gln Asn Ala
                530                 535                 540

Ile Ala Val Val Asp Asn Ala Leu Ala Ala Ile Asp Ala Gln Arg Ala
545                 550                 555                 560

Asp Leu Gly Ala Val Gln Asn Arg Phe Lys Asn Thr Ile Asp Asn Leu
                565                 570                 575

Thr Asn Ile Ser Glu Asn Ala Thr Asn Ala Arg Ser Arg Ile Lys Asp
                580                 585                 590

Thr Asp Phe Ala Ala Glu Thr Ala Ala Leu Ser Lys Asn Gln Val Leu
                595                 600                 605

Gln Gln Ala Gly Thr Ala Ile Leu Ala Gln Ala Asn Gln Leu Pro Gln
                610                 615                 620

Ala Val Leu Ser Leu Leu Arg Gly Ser Gly His His His His His His
625                 630                 635                 640
```

<210> SEQ ID NO 21
<211> LENGTH: 370
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

```
Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
                20                  25                  30
```

Asp Ser Phe Gly Asn Val Ser Gly Gln Tyr Val Asn Arg Ala Gln Gly
            35                  40                  45

Thr Gly Cys Gln Asn Ser Pro Tyr Pro Leu Thr Gly Arg Val Asn Gly
 50                  55                  60

Thr Phe Ile Ala Phe Ser Val Gly Trp Asn Asn Ser Thr Glu Asn Cys
 65                  70                  75                  80

Asn Ser Ala Thr Gly Trp Thr Gly Tyr Ala Gln Val Asn Gly Asn Asn
                 85                  90                  95

Thr Glu Ile Val Thr Ser Trp Asn Leu Ala Tyr Gly Gly Ser Gly
                100                 105                 110

Pro Ala Ile Glu Gln Gly Gln Asp Thr Phe Gln Tyr Val Pro Thr Thr
                115                 120                 125

Glu Asn Lys Ser Leu Leu Lys Asp Gly Gly Gly Ser Ser Ser Met
            130                 135                 140

Gly Ser Tyr Gln Val Gly Ser Asn Gly Ala Gly Thr Val Ala Ser Val
145                 150                 155                 160

Ala Gly Thr Ala Thr Ala Ser Gly Ile Ala Ser Gly Thr Val Asn Leu
                165                 170                 175

Val Gly Gly Gly Gln Val Lys Asn Ile Ala Ile Ala Ala Gly Asp Ser
                180                 185                 190

Ala Lys Ala Ile Ala Glu Lys Met Asp Gly Ala Ile Pro Asn Leu Ser
            195                 200                 205

Ala Arg Ala Arg Thr Val Phe Thr Ala Asp Val Ser Gly Val Thr Gly
            210                 215                 220

Gly Ser Leu Asn Phe Asp Val Thr Val Gly Ser Asn Thr Val Ser Leu
225                 230                 235                 240

Ala Gly Val Thr Ser Thr Gln Asp Leu Ala Asp Gln Leu Asn Ser Asn
                245                 250                 255

Ser Ser Lys Leu Gly Ile Thr Ala Ser Ile Asn Asp Lys Gly Val Leu
            260                 265                 270

Thr Ile Thr Ser Ala Thr Gly Glu Asn Val Lys Phe Gly Ala Gln Thr
            275                 280                 285

Gly Thr Ala Thr Ala Gly Gln Val Ala Val Lys Val Gln Gly Ser Asp
290                 295                 300

Gly Lys Phe Glu Ala Ala Ala Lys Asn Val Val Ala Ala Gly Thr Ala
305                 310                 315                 320

Ala Thr Thr Thr Ile Val Thr Gly Tyr Val Gln Leu Asn Ser Pro Thr
                325                 330                 335

Ala Tyr Ser Val Ser Gly Thr Gly Thr Gln Ala Ser Gln Val Phe Gly
                340                 345                 350

Asn Ala Ser Ala Ala Gln Lys Ser Ser Gly Ser Gly His His His His
            355                 360                 365

His His
    370

<210> SEQ ID NO 22
<211> LENGTH: 269
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

```
<400> SEQUENCE: 22

Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
            20                  25                  30

Asp Ser Phe Gly Asn Val Ser Gly Gln Tyr Val Asn Arg Ala Gln Gly
        35                  40                  45

Thr Gly Cys Gln Asn Ser Pro Tyr Pro Leu Thr Gly Arg Val Asn Gly
    50                  55                  60

Thr Phe Ile Ala Phe Ser Val Gly Trp Asn Asn Ser Thr Glu Asn Cys
65                  70                  75                  80

Asn Ser Ala Thr Gly Trp Thr Gly Tyr Ala Gln Val Asn Gly Asn Asn
                85                  90                  95

Thr Glu Ile Val Thr Ser Trp Asn Leu Ala Tyr Glu Gly Gly Ser Gly
            100                 105                 110

Pro Ala Ile Glu Gln Gly Gln Asp Thr Phe Gln Tyr Val Pro Thr Thr
        115                 120                 125

Glu Asn Lys Ser Leu Leu Lys Asp Gly Gly Gly Ser Ser Ser Met
    130                 135                 140

Asn Gly Thr Tyr Phe Thr Ala Thr Gly Gly Gly Ala Val Thr Ala Ala
145                 150                 155                 160

Thr Ala Ser Gly Thr Val Asp Ile Ala Ile Gly Ile Thr Gly Gly Ser
                165                 170                 175

Ala Val Asn Val Lys Val Asp Met Lys Gly Asn Glu Thr Ala Glu Gln
            180                 185                 190

Ala Ala Ala Lys Ile Ala Ala Val Asn Asp Ala Asn Val Gly Ile
        195                 200                 205

Gly Ala Phe Thr Asp Gly Ala Gln Ile Ser Tyr Val Ser Lys Ala Ser
    210                 215                 220

Ala Asp Gly Thr Thr Ser Ala Val Ser Gly Val Ala Ile Thr Asp Thr
225                 230                 235                 240

Gly Ser Thr Gly Ala Gly Thr Ala Ala Gly Thr Thr Thr Phe Thr Glu
                245                 250                 255

Ala Asn Asp Thr Gly Ser Gly His His His His His
            260                 265

<210> SEQ ID NO 23
<211> LENGTH: 938
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
            20                  25                  30

Asp Ser Phe Gly Asn Val Ser Gly Gln Tyr Val Asn Arg Ala Gln Gly
        35                  40                  45

Thr Gly Cys Gln Asn Ser Pro Tyr Pro Leu Thr Gly Arg Val Asn Gly
    50                  55                  60

Thr Phe Ile Ala Phe Ser Val Gly Trp Asn Asn Ser Thr Glu Asn Cys
65                  70                  75                  80
```

-continued

```
Asn Ser Ala Thr Gly Trp Thr Gly Tyr Ala Gln Val Asn Gly Asn Asn
                 85                  90                  95

Thr Glu Ile Val Thr Ser Trp Asn Leu Ala Tyr Glu Gly Gly Ser Gly
            100                 105                 110

Pro Ala Ile Glu Gln Gly Gln Asp Thr Phe Gln Tyr Val Pro Thr Thr
            115                 120                 125

Glu Asn Lys Ser Leu Leu Lys Asp Gly Gly Gly Ser Ser Ser Met
130                 135                 140

Ala Leu Thr Val Asn Thr Asn Ile Ala Ser Leu Asn Thr Gln Arg Asn
145                 150                 155                 160

Leu Asn Ala Ser Ser Asn Asp Leu Asn Thr Ser Leu Gln Arg Leu Thr
                165                 170                 175

Thr Gly Tyr Arg Ile Asn Ser Ala Lys Asp Asp Ala Ala Gly Leu Gln
            180                 185                 190

Ile Ser Asn Arg Leu Ser Asn Gln Ile Ser Gly Leu Asn Val Ala Thr
            195                 200                 205

Arg Asn Ala Asn Asp Gly Ile Ser Leu Ala Gln Thr Ala Glu Gly Ala
210                 215                 220

Leu Gln Gln Ser Thr Asn Ile Leu Gln Arg Ile Arg Asp Leu Ala Leu
225                 230                 235                 240

Gln Ser Ala Asn Gly Ser Asn Ser Asp Ala Asp Arg Ala Ala Leu Gln
                245                 250                 255

Lys Glu Val Ala Ala Gln Ala Glu Leu Thr Arg Ile Ser Asp Thr
            260                 265                 270

Thr Thr Phe Gly Gly Arg Lys Leu Leu Asp Gly Ser Phe Gly Thr Thr
            275                 280                 285

Ser Phe Gln Val Gly Ser Asn Ala Tyr Glu Thr Ile Asp Ile Ser Leu
            290                 295                 300

Gln Asn Ala Ser Ala Ser Ala Ile Gly Ser Tyr Gln Val Gly Ser Asn
305                 310                 315                 320

Gly Ala Gly Thr Val Ala Ser Val Ala Gly Thr Ala Thr Ala Ser Gly
                325                 330                 335

Ile Ala Ser Gly Thr Val Asn Leu Val Gly Gly Gln Val Lys Asn
            340                 345                 350

Ile Ala Ile Ala Ala Gly Asp Ser Ala Lys Ala Ile Ala Glu Lys Met
            355                 360                 365

Asp Gly Ala Ile Pro Asn Leu Ser Ala Arg Ala Arg Thr Val Phe Thr
370                 375                 380

Ala Asp Val Ser Gly Val Thr Gly Gly Ser Leu Asn Phe Asp Val Thr
385                 390                 395                 400

Val Gly Ser Asn Thr Val Ser Leu Ala Gly Val Thr Ser Thr Gln Asp
                405                 410                 415

Leu Ala Asp Gln Leu Asn Ser Asn Ser Ser Lys Leu Gly Ile Thr Ala
            420                 425                 430

Ser Ile Asn Asp Lys Gly Val Leu Thr Ile Thr Ser Ala Thr Gly Glu
            435                 440                 445

Asn Val Lys Phe Gly Ala Gln Thr Gly Thr Ala Thr Ala Gly Gln Val
            450                 455                 460

Ala Val Lys Val Gln Gly Ser Asp Gly Lys Phe Glu Ala Ala Ala Lys
465                 470                 475                 480

Asn Val Val Ala Ala Gly Thr Ala Ala Thr Thr Thr Ile Val Thr Gly
                485                 490                 495
```

```
Tyr Val Gln Leu Asn Ser Pro Thr Ala Tyr Ser Val Ser Gly Thr Gly
            500                 505                 510

Thr Gln Ala Ser Gln Val Phe Gly Asn Ala Ser Ala Ala Gln Lys Ser
        515                 520                 525

Ser Val Ala Ser Val Asp Ile Ser Thr Ala Asp Gly Ala Gln Asn Ala
    530                 535                 540

Ile Ala Val Val Asp Asn Ala Leu Ala Ala Ile Asp Ala Gln Arg Ala
545                 550                 555                 560

Asp Leu Gly Ala Val Gln Asn Arg Phe Lys Asn Thr Ile Asp Asn Leu
            565                 570                 575

Thr Asn Ile Ser Glu Asn Ala Thr Asn Ala Arg Ser Arg Ile Lys Asp
        580                 585                 590

Thr Asp Phe Ala Ala Glu Thr Ala Ala Leu Ser Lys Asn Gln Val Leu
    595                 600                 605

Gln Gln Ala Gly Thr Ala Ile Leu Ala Gln Ala Asn Gln Leu Pro Gln
610                 615                 620

Ala Val Leu Ser Leu Leu Arg Ala Ala Ala Met Glu Val Arg Asn
625                 630                 635                 640

Leu Asn Ala Ala Arg Glu Leu Phe Leu Asp Glu Leu Leu Ala Ala Ser
            645                 650                 655

Ala Ala Pro Ala Ser Ala Glu Gln Glu Leu Leu Ala Leu Leu Arg
        660                 665                 670

Ser Glu Arg Ile Val Leu Ala His Ala Gly Gln Pro Leu Ser Glu Ala
    675                 680                 685

Gln Val Leu Lys Ala Leu Ala Trp Leu Leu Ala Ala Asn Pro Ser Ala
690                 695                 700

Pro Pro Gly Gln Gly Leu Glu Val Leu Arg Glu Val Leu Gln Ala Arg
705                 710                 715                 720

Arg Gln Pro Gly Ala Gln Trp Asp Leu Arg Glu Phe Leu Val Ser Ala
            725                 730                 735

Tyr Phe Ser Leu His Gly Arg Leu Asp Glu Asp Val Ile Gly Val Tyr
        740                 745                 750

Lys Asp Val Leu Gln Thr Gln Asp Gly Lys Arg Lys Ala Leu Leu Asp
    755                 760                 765

Glu Leu Lys Ala Leu Thr Ala Glu Leu Lys Val Tyr Ser Val Ile Gln
770                 775                 780

Ser Gln Ile Asn Ala Ala Leu Ser Ala Lys Gln Gly Ile Arg Ile Asp
785                 790                 795                 800

Ala Gly Gly Ile Asp Leu Val Asp Pro Thr Leu Tyr Gly Tyr Ala Val
            805                 810                 815

Gly Asp Pro Arg Trp Lys Asp Ser Pro Glu Tyr Ala Leu Leu Ser Asn
        820                 825                 830

Leu Asp Thr Phe Ser Gly Lys Leu Ser Ile Lys Asp Phe Leu Ser Gly
    835                 840                 845

Ser Pro Lys Gln Ser Gly Glu Leu Lys Gly Leu Ser Asp Glu Tyr Pro
850                 855                 860

Phe Glu Lys Asp Asn Asn Pro Val Gly Asn Phe Ala Thr Thr Val Ser
865                 870                 875                 880

Asp Arg Ser Arg Pro Leu Asn Asp Lys Val Asn Glu Lys Thr Thr Leu
            885                 890                 895

Leu Asn Asp Thr Ser Ser Arg Tyr Asn Ser Ala Val Glu Ala Leu Asn
        900                 905                 910
```

Arg Phe Ile Gln Lys Tyr Asp Ser Val Leu Arg Asp Ile Leu Ser Ala
            915                 920                 925

Ile Gly Ser Gly His His His His His
            930                 935

<210> SEQ ID NO 24
<211> LENGTH: 581
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
            20                  25                  30

Asp Ser Phe Gly Asn Val Ser Gly Gln Tyr Val Asn Arg Ala Gln Gly
        35                  40                  45

Thr Gly Cys Gln Asn Ser Pro Tyr Pro Leu Thr Gly Arg Val Asn Gly
    50                  55                  60

Thr Phe Ile Ala Phe Ser Val Gly Trp Asn Asn Ser Thr Glu Asn Cys
65                  70                  75                  80

Asn Ser Ala Thr Gly Trp Thr Gly Tyr Ala Gln Val Asn Gly Asn Asn
                85                  90                  95

Thr Glu Ile Val Thr Ser Trp Asn Leu Ala Tyr Glu Gly Gly Ser Gly
            100                 105                 110

Pro Ala Ile Glu Gln Gly Gln Asp Thr Phe Gln Tyr Val Pro Thr Thr
        115                 120                 125

Glu Asn Lys Ser Leu Leu Lys Asp Gly Gly Gly Ser Ser Ser Met
130                 135                 140

Gly Ser Tyr Gln Val Gly Ser Asn Gly Ala Gly Thr Val Ala Ser Val
145                 150                 155                 160

Ala Gly Thr Ala Thr Ala Ser Gly Ile Ala Ser Gly Thr Val Asn Leu
                165                 170                 175

Val Gly Gly Gln Val Lys Asn Ile Ala Ile Ala Ala Gly Asp Ser
            180                 185                 190

Ala Lys Ala Ile Ala Glu Lys Met Asp Gly Ala Ile Pro Asn Leu Ser
        195                 200                 205

Ala Arg Ala Arg Thr Val Phe Thr Ala Asp Val Ser Gly Val Thr Gly
    210                 215                 220

Gly Ser Leu Asn Phe Asp Val Thr Val Gly Ser Asn Thr Val Ser Leu
225                 230                 235                 240

Ala Gly Val Thr Ser Thr Gln Asp Leu Ala Asp Gln Leu Asn Ser Asn
                245                 250                 255

Ser Ser Lys Leu Gly Ile Thr Ala Ser Ile Asn Asp Lys Gly Val Leu
            260                 265                 270

Thr Ile Thr Ser Ala Thr Gly Glu Asn Val Lys Phe Gly Ala Gln Thr
        275                 280                 285

Gly Thr Ala Thr Ala Gly Gln Val Ala Val Lys Val Gln Gly Ser Asp
    290                 295                 300

Gly Lys Phe Glu Ala Ala Ala Lys Asn Val Val Ala Ala Gly Thr Ala
305                 310                 315                 320

Ala Thr Thr Thr Ile Val Thr Gly Tyr Val Gln Leu Asn Ser Pro Thr
            325                 330                 335

Ala Tyr Ser Val Ser Gly Thr Thr Gln Ala Ser Gln Val Phe Gly
        340                 345                 350

Asn Ala Ser Ala Ala Gln Lys Ser Ser Ala Ala Ala Met Ala Asp
            355                 360                 365

Thr Thr Val Gly Gly Gln Val Asn Phe Phe Gly Lys Val Thr Asp
370                 375                 380

Val Ser Cys Thr Val Ser Val Asn Gly Gln Gly Ser Asp Ala Asn Val
385                 390                 395                 400

Tyr Leu Ser Pro Val Thr Leu Thr Glu Val Lys Ala Ala Ala Asp
            405                 410                 415

Thr Tyr Leu Lys Pro Lys Ser Phe Thr Ile Asp Val Ser Asn Cys Gln
            420                 425                 430

Ala Ala Asp Gly Thr Lys Gln Asp Asp Val Ser Lys Leu Gly Val Asn
            435                 440                 445

Trp Thr Gly Gly Asn Leu Leu Ala Gly Ala Thr Ser Lys Gln Gln Gly
    450                 455                 460

Tyr Leu Ala Asn Thr Glu Ala Ser Gly Ala Gln Asn Ile Gln Leu Val
465                 470                 475                 480

Leu Ser Thr Asp Asn Ala Thr Ala Leu Thr Asn Lys Ile Ile Pro Gly
            485                 490                 495

Asp Ser Thr Gln Pro Lys Ala Lys Gly Asp Ala Ser Ala Val Ala Asp
            500                 505                 510

Gly Ala Arg Phe Thr Tyr Tyr Val Gly Tyr Ala Thr Ser Ala Pro Thr
            515                 520                 525

Thr Val Thr Thr Gly Val Val Asn Ser Tyr Ala Thr Tyr Glu Ile Thr
            530                 535                 540

Tyr Gln Gly Gly Gly Gly Gly Ala Asp Thr Thr Val Gly Gly
545                 550                 555                 560

Gln Val Asn Phe Phe Gly Lys Val Thr Asp Val Ser Gly Ser Gly His
            565                 570                 575

His His His His His
            580

<210> SEQ ID NO 25
<211> LENGTH: 657
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
            20                  25                  30

Asp Ser Phe Gly Asn Val Ser Gly Gln Tyr Val Asn Arg Ala Gln Gly
        35                  40                  45

Thr Gly Cys Gln Asn Ser Pro Tyr Pro Leu Thr Gly Arg Val Asn Gly
    50                  55                  60

Thr Phe Ile Ala Phe Ser Val Gly Trp Asn Asn Ser Thr Glu Asn Cys
65                  70                  75                  80

-continued

```
Asn Ser Ala Thr Gly Trp Thr Gly Tyr Ala Gln Val Asn Gly Asn Asn
             85                  90                  95

Thr Glu Ile Val Thr Ser Trp Asn Leu Ala Tyr Glu Gly Gly Ser Gly
            100                 105                 110

Pro Ala Ile Glu Gln Gly Gln Asp Thr Phe Gln Tyr Val Pro Thr Thr
            115                 120                 125

Glu Asn Lys Ser Leu Leu Lys Asp Gly Gly Gly Ser Ser Ser Met
130                 135                 140

Ala Asp Thr Thr Val Gly Gly Gln Val Asn Phe Phe Gly Lys Val
145                 150                 155                 160

Thr Asp Val Ser Cys Thr Val Ser Val Asn Gly Gln Gly Ser Asp Ala
                165                 170                 175

Asn Val Tyr Leu Ser Pro Val Thr Leu Thr Glu Val Lys Ala Ala Ala
            180                 185                 190

Ala Asp Thr Tyr Leu Lys Pro Lys Ser Phe Thr Ile Asp Val Ser Asn
            195                 200                 205

Cys Gln Ala Ala Asp Gly Thr Lys Gln Asp Val Ser Lys Leu Gly
210                 215                 220

Val Asn Trp Thr Gly Gly Asn Leu Leu Ala Gly Ala Thr Ser Lys Gln
225                 230                 235                 240

Gln Gly Tyr Leu Ala Asn Thr Glu Ala Ser Gly Ala Gln Asn Ile Gln
                245                 250                 255

Leu Val Leu Ser Thr Asp Asn Ala Thr Ala Leu Thr Asn Lys Ile Ile
                260                 265                 270

Pro Gly Asp Ser Thr Gln Pro Lys Ala Lys Gly Asp Ala Ser Ala Val
            275                 280                 285

Ala Asp Gly Ala Arg Phe Thr Tyr Tyr Val Gly Tyr Ala Thr Ser Ala
290                 295                 300

Pro Thr Thr Val Thr Thr Gly Val Val Asn Ser Tyr Ala Thr Tyr Glu
305                 310                 315                 320

Ile Thr Tyr Gln Gly Gly Gly Gly Gly Ala Asp Thr Thr Val Gly
                325                 330                 335

Gly Gly Gln Val Asn Phe Phe Gly Lys Val Thr Asp Val Ser Ala Ala
            340                 345                 350

Ala Ala Met Glu Val Arg Asn Leu Asn Ala Ala Arg Glu Leu Phe Leu
            355                 360                 365

Asp Glu Leu Leu Ala Ala Ser Ala Ala Pro Ala Ser Ala Glu Gln Glu
370                 375                 380

Glu Leu Leu Ala Leu Leu Arg Ser Glu Arg Ile Val Leu Ala His Ala
385                 390                 395                 400

Gly Gln Pro Leu Ser Glu Ala Gln Val Leu Lys Ala Leu Ala Trp Leu
            405                 410                 415

Leu Ala Ala Asn Pro Ser Ala Pro Pro Gly Gln Gly Leu Glu Val Leu
            420                 425                 430

Arg Glu Val Leu Gln Ala Arg Arg Gln Pro Gly Ala Gln Trp Asp Leu
            435                 440                 445

Arg Glu Phe Leu Val Ser Ala Tyr Phe Ser Leu His Gly Arg Leu Asp
            450                 455                 460

Glu Asp Val Ile Gly Val Tyr Lys Asp Val Leu Gln Thr Gln Asp Gly
465                 470                 475                 480

Lys Arg Lys Ala Leu Leu Asp Glu Leu Lys Ala Leu Thr Ala Glu Leu
            485                 490                 495
```

```
Lys Val Tyr Ser Val Ile Gln Ser Gln Ile Asn Ala Ala Leu Ser Ala
                500                 505                 510

Lys Gln Gly Ile Arg Ile Asp Ala Gly Gly Ile Asp Leu Val Asp Pro
            515                 520                 525

Thr Leu Tyr Gly Tyr Ala Val Gly Asp Pro Arg Trp Lys Asp Ser Pro
        530                 535                 540

Glu Tyr Ala Leu Leu Ser Asn Leu Asp Thr Phe Ser Gly Lys Leu Ser
545                 550                 555                 560

Ile Lys Asp Phe Leu Ser Gly Ser Pro Lys Gln Ser Gly Glu Leu Lys
                565                 570                 575

Gly Leu Ser Asp Glu Tyr Pro Phe Glu Lys Asp Asn Asn Pro Val Gly
            580                 585                 590

Asn Phe Ala Thr Thr Val Ser Asp Arg Ser Arg Pro Leu Asn Asp Lys
        595                 600                 605

Val Asn Glu Lys Thr Thr Leu Leu Asn Asp Thr Ser Ser Arg Tyr Asn
    610                 615                 620

Ser Ala Val Glu Ala Leu Asn Arg Phe Ile Gln Lys Tyr Asp Ser Val
625                 630                 635                 640

Leu Arg Asp Ile Leu Ser Ala Ile Gly Ser Gly His His His His His
                645                 650                 655

His

<210> SEQ ID NO 26
<211> LENGTH: 668
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
                20                  25                  30

Asp Ser Phe Gly Asn Val Ser Gly Gln Tyr Val Asn Arg Ala Gln Gly
            35                  40                  45

Thr Gly Cys Gln Asn Ser Pro Tyr Pro Leu Thr Gly Arg Val Asn Gly
        50                  55                  60

Thr Phe Ile Ala Phe Ser Val Gly Trp Asn Asn Ser Thr Glu Asn Cys
65                  70                  75                  80

Asn Ser Ala Thr Gly Trp Thr Gly Tyr Ala Gln Val Asn Gly Asn Asn
                85                  90                  95

Thr Glu Ile Val Thr Ser Trp Asn Leu Ala Tyr Glu Gly Gly Ser Gly
            100                 105                 110

Pro Ala Ile Glu Gln Gly Gln Asp Thr Phe Gln Tyr Val Pro Thr Thr
        115                 120                 125

Glu Asn Lys Ser Leu Leu Lys Asp Gly Gly Gly Ser Ser Ser Met
130                 135                 140

Gly Ser Tyr Gln Val Gly Ser Asn Gly Ala Gly Thr Val Ala Ser Val
145                 150                 155                 160

Ala Gly Thr Ala Thr Ala Ser Gly Ile Ala Ser Gly Thr Val Asn Leu
                165                 170                 175

Val Gly Gly Gly Gln Val Lys Asn Ile Ala Ile Ala Ala Gly Asp Ser
            180                 185                 190
```

```
Ala Lys Ala Ile Ala Glu Lys Met Asp Gly Ala Ile Pro Asn Leu Ser
            195                 200                 205
Ala Arg Ala Arg Thr Val Phe Thr Ala Asp Val Ser Gly Val Thr Gly
210                 215                 220
Gly Ser Leu Asn Phe Asp Val Thr Val Gly Ser Asn Thr Val Ser Leu
225                 230                 235                 240
Ala Gly Val Thr Ser Thr Gln Asp Leu Ala Asp Gln Leu Asn Ser Asn
            245                 250                 255
Ser Ser Lys Leu Gly Ile Thr Ala Ser Ile Asn Asp Lys Gly Val Leu
            260                 265                 270
Thr Ile Thr Ser Ala Thr Gly Glu Asn Val Lys Phe Gly Ala Gln Thr
        275                 280                 285
Gly Thr Ala Thr Ala Gly Gln Val Ala Val Lys Val Gln Gly Ser Asp
290                 295                 300
Gly Lys Phe Glu Ala Ala Lys Asn Val Val Ala Ala Gly Thr Ala
305                 310                 315                 320
Ala Thr Thr Thr Ile Val Thr Gly Tyr Val Gln Leu Asn Ser Pro Thr
                325                 330                 335
Ala Tyr Ser Val Ser Gly Thr Gly Thr Gln Ala Ser Gln Val Phe Gly
            340                 345                 350
Asn Ala Ser Ala Ala Gln Lys Ser Ser Ala Ala Ala Met Glu Val
            355                 360                 365
Arg Asn Leu Asn Ala Ala Arg Glu Leu Phe Leu Asp Glu Leu Leu Ala
370                 375                 380
Ala Ser Ala Ala Pro Ala Ser Ala Glu Gln Glu Leu Leu Ala Leu
385                 390                 395                 400
Leu Arg Ser Glu Arg Ile Val Leu Ala His Ala Gly Gln Pro Leu Ser
                405                 410                 415
Glu Ala Gln Val Leu Lys Ala Leu Ala Trp Leu Leu Ala Ala Asn Pro
            420                 425                 430
Ser Ala Pro Pro Gly Gln Gly Leu Glu Val Leu Arg Glu Val Leu Gln
            435                 440                 445
Ala Arg Arg Gln Pro Gly Ala Gln Trp Asp Leu Arg Glu Phe Leu Val
450                 455                 460
Ser Ala Tyr Phe Ser Leu His Gly Arg Leu Asp Glu Asp Val Ile Gly
465                 470                 475                 480
Val Tyr Lys Asp Val Leu Gln Thr Gln Asp Gly Lys Arg Lys Ala Leu
            485                 490                 495
Leu Asp Glu Leu Lys Ala Leu Thr Ala Glu Leu Lys Val Tyr Ser Val
            500                 505                 510
Ile Gln Ser Gln Ile Asn Ala Ala Leu Ser Ala Lys Gln Gly Ile Arg
            515                 520                 525
Ile Asp Ala Gly Gly Ile Asp Leu Val Asp Pro Thr Leu Tyr Gly Tyr
            530                 535                 540
Ala Val Gly Asp Pro Arg Trp Lys Asp Ser Pro Glu Tyr Ala Leu Leu
545                 550                 555                 560
Ser Asn Leu Asp Thr Phe Ser Gly Lys Leu Ser Ile Lys Asp Phe Leu
                565                 570                 575
Ser Gly Ser Pro Lys Gln Ser Gly Glu Leu Lys Gly Leu Ser Asp Glu
            580                 585                 590
Tyr Pro Phe Glu Lys Asp Asn Asn Pro Val Gly Asn Phe Ala Thr Thr
            595                 600                 605
```

```
Val Ser Asp Arg Ser Arg Pro Leu Asn Asp Lys Val Asn Glu Lys Thr
610                 615                 620

Thr Leu Leu Asn Asp Thr Ser Ser Arg Tyr Asn Ser Ala Val Glu Ala
625                 630                 635                 640

Leu Asn Arg Phe Ile Gln Lys Tyr Asp Ser Val Leu Arg Asp Ile Leu
                645                 650                 655

Ser Ala Ile Gly Ser Gly His His His His His His
                660             665

<210> SEQ ID NO 27
<211> LENGTH: 202
<212> TYPE: PRT
<213> ORGANISM: Klebsiella pneumoniae

<400> SEQUENCE: 27

Met Lys Lys Val Leu Leu Ser Ala Ala Met Ala Thr Ala Phe Phe Gly
1               5                   10                  15

Met Ala Ala Asn Ala Ala Asp Thr Asn Val Gly Gly Gly Gln Val
                20                  25                  30

Asn Phe Phe Gly Lys Val Thr Asp Val Ser Cys Thr Val Ser Val Asn
                35                  40                  45

Gly Gln Gly Ser Asp Ala Asn Val Tyr Leu Ser Pro Val Thr Leu Thr
50                  55                  60

Glu Val Lys Ala Ala Ala Asp Thr Tyr Leu Lys Pro Lys Ser Phe
65                  70                  75                  80

Thr Ile Asp Val Ser Asp Cys Gln Ala Ala Asp Gly Thr Lys Gln Asp
                85                  90                  95

Asp Val Ser Lys Leu Gly Val Asn Trp Thr Gly Gly Asn Leu Leu Ala
                100                 105                 110

Gly Ala Thr Ala Lys Gln Gln Gly Tyr Leu Ala Asn Thr Glu Ala Ala
                115                 120                 125

Gly Ala Gln Asn Ile Gln Leu Val Leu Ser Thr Asp Asn Ala Thr Ala
                130                 135                 140

Leu Thr Asn Lys Ile Ile Pro Gly Asp Ser Thr Gln Pro Lys Ala Ala
145                 150                 155                 160

Gly Asp Ala Ser Ala Val Gln Asp Gly Ala Arg Phe Thr Tyr Tyr Val
                165                 170                 175

Gly Tyr Ala Thr Ser Thr Pro Thr Thr Val Thr Thr Gly Val Val Asn
                180                 185                 190

Ser Tyr Ala Thr Tyr Glu Ile Thr Tyr Gln
                195                 200

<210> SEQ ID NO 28
<211> LENGTH: 202
<212> TYPE: PRT
<213> ORGANISM: Klebsiella pneumoniae

<400> SEQUENCE: 28

Met Lys Lys Val Leu Leu Ser Ala Ala Met Ala Thr Ala Phe Phe Gly
1               5                   10                  15

Met Thr Ala Ala His Ala Ala Asp Thr Asn Val Gly Gly Gly Gln Val
                20                  25                  30

Asn Phe Phe Gly Lys Val Thr Asp Val Ser Cys Thr Val Ser Val Asn
                35                  40                  45

Gly Gln Gly Ser Asp Ala Asn Val Tyr Leu Ser Pro Val Thr Leu Thr
50                  55                  60
```

Glu Val Lys Ala Ala Ala Ala Asp Thr Tyr Leu Lys Pro Lys Ser Phe
65                  70                  75                  80

Thr Ile Asp Val Ser Asn Cys Gln Ala Ala Asp Gly Thr Lys Gln Asp
            85                  90                  95

Asp Val Thr Lys Leu Gly Val Asn Trp Thr Gly Gly Asn Leu Leu Ala
            100                 105                 110

Gly Ala Thr Ser Lys Gln Gln Gly Tyr Leu Ala Asn Thr Glu Ala Ser
            115                 120                 125

Gly Ala Gln Asn Ile Gln Leu Val Leu Ser Thr Asp Asn Ala Thr Ala
        130                 135                 140

Leu Thr Asn Lys Ile Ile Pro Gly Asp Ser Thr Gln Pro Lys Ala Lys
145                 150                 155                 160

Gly Asp Ala Ala Ala Val Ala Asp Gly Ala Arg Phe Thr Tyr Tyr Val
            165                 170                 175

Gly Tyr Ala Thr Ser Ala Pro Thr Thr Val Thr Thr Gly Val Val Asn
            180                 185                 190

Ser Tyr Ala Thr Tyr Glu Ile Thr Tyr Gln
            195                 200

<210> SEQ ID NO 29
<211> LENGTH: 202
<212> TYPE: PRT
<213> ORGANISM: Klebsiella pneumoniae

<400> SEQUENCE: 29

Met Lys Lys Val Leu Leu Ser Ala Ala Met Ala Thr Ala Phe Phe Gly
1               5                   10                  15

Met Thr Ala Ala His Ala Ala Asp Thr Asn Val Gly Gly Gly Gln Val
            20                  25                  30

Asn Phe Phe Gly Lys Val Thr Asp Val Ser Cys Thr Val Ser Val Asn
            35                  40                  45

Gly Gln Gly Ser Asp Ala Asn Val Tyr Leu Ser Pro Val Thr Leu Thr
        50                  55                  60

Glu Val Lys Ala Ala Ala Ala Asp Thr Tyr Leu Lys Pro Lys Ser Phe
65                  70                  75                  80

Thr Ile Asp Val Ser Asn Cys Gln Ala Ala Asp Gly Thr Lys Gln Asp
            85                  90                  95

Asp Val Ser Lys Leu Gly Val Asn Trp Thr Gly Gly Asn Leu Leu Ala
            100                 105                 110

Gly Ala Thr Ser Lys Gln Gln Gly Tyr Leu Ala Asn Thr Glu Ala Ser
            115                 120                 125

Gly Ala Gln Asn Ile Gln Leu Val Leu Ser Thr Asp Asn Ala Thr Ala
        130                 135                 140

Leu Thr Asn Lys Ile Ile Pro Gly Asp Ser Thr Gln Pro Lys Ala Lys
145                 150                 155                 160

Gly Asp Ala Ser Ala Val Ala Asp Gly Ala Arg Phe Thr Tyr Tyr Val
            165                 170                 175

Gly Tyr Ala Thr Ser Ala Pro Thr Thr Val Thr Thr Gly Val Val Asn
            180                 185                 190

Ser Tyr Ala Thr Tyr Glu Ile Thr Tyr Gln
            195                 200

<210> SEQ ID NO 30
<211> LENGTH: 204
<212> TYPE: PRT
<213> ORGANISM: Klebsiella pneumoniae

<400> SEQUENCE: 30

Met Ala Met Lys Lys Val Leu Leu Ser Ala Ala Met Ala Thr Ala Phe
1               5                   10                  15

Phe Gly Met Thr Ala Ala His Ala Ala Asp Thr Asn Val Gly Gly Gly
            20                  25                  30

Gln Val Asn Phe Phe Gly Lys Val Thr Asp Val Ser Cys Thr Val Ser
        35                  40                  45

Val Asn Gly Gln Gly Ser Asp Ala Asn Val Tyr Leu Ser Pro Val Thr
    50                  55                  60

Leu Thr Glu Val Lys Ala Ala Ala Asp Thr Tyr Leu Lys Pro Lys
65                  70                  75                  80

Ser Phe Thr Ile Asp Val Ser Asn Cys Gln Ala Ala Asp Gly Thr Lys
                85                  90                  95

Gln Asp Asp Val Ser Lys Leu Gly Val Asn Trp Thr Gly Gly Asn Leu
            100                 105                 110

Leu Ala Gly Ala Thr Ser Lys Gln Gln Gly Tyr Leu Ala Asn Thr Glu
        115                 120                 125

Ala Ser Gly Ala Gln Asn Ile Gln Leu Val Leu Ser Thr Asp Asn Ala
    130                 135                 140

Thr Ala Leu Thr Asn Lys Ile Ile Pro Gly Asp Ser Thr Gln Pro Lys
145                 150                 155                 160

Ala Lys Gly Asp Ala Ser Ala Val Ala Asp Gly Ala Arg Phe Thr Tyr
                165                 170                 175

Tyr Val Gly Tyr Ala Thr Ser Ala Pro Thr Thr Val Thr Thr Gly Val
            180                 185                 190

Val Asn Ser Tyr Ala Thr Tyr Glu Ile Thr Tyr Gln
        195                 200

<210> SEQ ID NO 31
<211> LENGTH: 202
<212> TYPE: PRT
<213> ORGANISM: Klebsiella pneumoniae

<400> SEQUENCE: 31

Met Lys Lys Val Leu Leu Ser Ala Ala Met Ala Thr Ala Phe Phe Gly
1               5                   10                  15

Met Thr Ala Ala His Ala Ala Asp Thr Thr Val Gly Gly Gly Gln Val
            20                  25                  30

Asn Phe Phe Gly Lys Val Thr Asp Val Ser Cys Thr Val Ser Val Asn
        35                  40                  45

Gly Gln Gly Ser Asp Ala Asn Val Tyr Leu Ser Pro Val Thr Leu Thr
    50                  55                  60

Glu Val Lys Ala Ala Ala Ala Asp Thr Tyr Leu Lys Pro Lys Ser Phe
65                  70                  75                  80

Thr Ile Asp Val Ser Asn Cys Gln Ala Ala Asp Gly Thr Lys Gln Asp
                85                  90                  95

Asp Val Ser Lys Leu Gly Val Asn Trp Thr Gly Gly Asn Leu Leu Ala
            100                 105                 110

Gly Ala Thr Ser Lys Gln Gln Gly Tyr Leu Ala Asn Thr Glu Ala Ser
        115                 120                 125

Gly Ala Gln Asn Ile Gln Leu Val Leu Ser Thr Asp Asn Ala Thr Ala
    130                 135                 140

Leu Thr Asn Lys Ile Ile Pro Gly Asp Ser Thr Gln Pro Lys Ala Lys
145                 150                 155                 160

-continued

Gly Asp Ala Ser Ala Val Ala Asp Gly Ala Arg Phe Thr Tyr Tyr Val
                165                 170                 175

Gly Tyr Ala Thr Ser Ala Pro Thr Thr Val Thr Thr Gly Val Val Asn
            180                 185                 190

Ser Tyr Ala Thr Tyr Glu Ile Thr Tyr Gln
        195                 200

<210> SEQ ID NO 32
<211> LENGTH: 138
<212> TYPE: PRT
<213> ORGANISM: Klebsiella pneumoniae

<400> SEQUENCE: 32

Lys Val Thr Asp Val Ser Cys Thr Val Ser Val Asn Gly Gln Gly Ser
1               5                   10                  15

Asp Ala Asn Val Tyr Leu Ser Pro Val Thr Leu Thr Glu Val Lys Ala
            20                  25                  30

Ala Ala Ala Asp Thr Tyr Leu Lys Pro Lys Ser Phe Thr Ile Asp Val
        35                  40                  45

Ser Asn Cys Gln Ala Ala Asp Gly Thr Lys Gln Asp Asp Val Ser Lys
    50                  55                  60

Leu Gly Val Asn Trp Thr Gly Gly Asn Leu Leu Ala Gly Ala Thr Ser
65                  70                  75                  80

Lys Gln Gln Gly Tyr Leu Ala Asn Thr Glu Ala Ser Gly Ala Gln Asn
                85                  90                  95

Ile Gln Leu Val Leu Ser Thr Asp Asn Ala Thr Ala Leu Thr Asn Lys
            100                 105                 110

Ile Ile Pro Gly Asp Ser Thr Gln Pro Lys Ala Lys Gly Asp Ala Ser
        115                 120                 125

Ala Val Ala Asp Gly Ala Arg Phe Thr Tyr
    130                 135

<210> SEQ ID NO 33
<211> LENGTH: 138
<212> TYPE: PRT
<213> ORGANISM: Klebsiella pneumoniae

<400> SEQUENCE: 33

Lys Val Thr Asp Val Ser Cys Thr Val Ser Val Asn Gly Gln Gly Ser
1               5                   10                  15

Asp Ala Asn Val Tyr Leu Ser Pro Val Thr Leu Thr Glu Val Lys Ala
            20                  25                  30

Ala Ala Ala Asp Thr Tyr Leu Lys Pro Lys Ser Phe Thr Ile Asp Val
        35                  40                  45

Ser Asn Cys Gln Ala Ala Asp Gly Thr Lys Gln Asp Asp Val Ser Lys
    50                  55                  60

Leu Gly Val Asn Trp Thr Gly Gly Asn Leu Leu Ala Gly Ala Thr Ser
65                  70                  75                  80

Lys Gln Gln Gly Tyr Leu Ala Asn Thr Glu Ala Ser Gly Ala Gln Asn
                85                  90                  95

Ile Gln Leu Val Leu Ser Thr Asp Asn Ala Thr Ala Leu Thr Asn Lys
            100                 105                 110

Ile Ile Pro Gly Asp Ser Thr Gln Pro Lys Ala Lys Gly Asp Ala Ser
        115                 120                 125

Ala Val Ala Asp Gly Ala Arg Phe Thr Tyr
    130                 135

```
<210> SEQ ID NO 34
<211> LENGTH: 193
<212> TYPE: PRT
<213> ORGANISM: Klebsiella pneumoniae

<400> SEQUENCE: 34

Met Ala Thr Ala Phe Phe Gly Met Thr Ala His Ala Ala Asp Thr
1               5                   10                  15

Thr Val Gly Gly Gly Gln Val Asn Phe Phe Gly Lys Val Thr Asp Val
            20                  25                  30

Ser Cys Thr Val Ser Val Asn Gly Gln Gly Ser Asp Ala Asn Val Tyr
        35                  40                  45

Leu Ser Pro Val Thr Leu Thr Glu Val Lys Ala Ala Ala Asp Thr
    50                  55                  60

Tyr Leu Lys Pro Lys Ser Phe Thr Ile Asp Val Ser Asn Cys Gln Ala
65                  70                  75                  80

Ala Asp Gly Thr Lys Gln Asp Val Ser Lys Leu Gly Val Asn Trp
                85                  90                  95

Thr Gly Gly Asn Leu Leu Ala Gly Ala Thr Ser Lys Gln Gln Gly Tyr
            100                 105                 110

Leu Ala Asn Thr Glu Ala Ser Gly Ala Gln Asn Ile Gln Leu Val Leu
        115                 120                 125

Ser Thr Asp Asn Ala Thr Ala Leu Thr Asn Lys Ile Ile Pro Gly Asp
130                 135                 140

Ser Thr Gln Pro Lys Ala Lys Gly Asp Ala Ser Ala Val Ala Asp Gly
145                 150                 155                 160

Ala Arg Phe Thr Tyr Tyr Val Gly Tyr Ala Thr Ser Ala Pro Thr Thr
                165                 170                 175

Val Thr Thr Gly Val Val Asn Ser Tyr Ala Thr Tyr Glu Ile Thr Tyr
            180                 185                 190

Gln

<210> SEQ ID NO 35
<211> LENGTH: 204
<212> TYPE: PRT
<213> ORGANISM: Klebsiella pneumoniae

<400> SEQUENCE: 35

Met Ala Met Lys Lys Val Leu Leu Ser Ala Ala Met Ala Thr Ala Phe
1               5                   10                  15

Phe Gly Met Thr Ala Ala His Ala Ala Asp Thr Thr Val Gly Gly Gly
            20                  25                  30

Gln Val Asn Phe Phe Gly Lys Val Thr Asp Val Ser Cys Thr Val Ser
        35                  40                  45

Val Asn Gly Gln Gly Ser Asp Ala Asn Val Tyr Leu Ser Pro Val Thr
    50                  55                  60

Leu Thr Glu Val Lys Ala Ala Ala Ala Asp Thr Tyr Leu Lys Pro Lys
65                  70                  75                  80

Ser Phe Thr Ile Asp Val Ser Asn Cys Gln Ala Ala Asp Gly Thr Lys
                85                  90                  95

Gln Asp Asp Val Ser Lys Leu Gly Val Asn Trp Thr Gly Gly Asn Leu
            100                 105                 110

Leu Ala Gly Ala Thr Ser Lys Gln Gln Gly Tyr Leu Ala Asn Thr Glu
        115                 120                 125

Ala Ser Gly Ala Gln Asn Ile Gln Leu Val Leu Ser Thr Asp Asn Ala
    130                 135                 140
```

-continued

```
Thr Ala Leu Thr Asn Lys Ile Ile Pro Gly Asp Ser Thr Gln Pro Lys
145                 150                 155                 160

Ala Lys Gly Asp Ala Ser Ala Val Ala Asp Gly Ala Arg Phe Thr Tyr
                165                 170                 175

Tyr Val Gly Tyr Ala Thr Ser Ala Pro Thr Thr Val Thr Thr Gly Val
            180                 185                 190

Val Asn Ser Tyr Ala Thr Tyr Glu Ile Thr Tyr Gln
            195                 200

<210> SEQ ID NO 36
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 36

His His His His His His
1               5
```

IMMUNOGENIC COMPOSITIONS

CROSS REFERENCE TO RELATED APPLICATIONS

The present application is a national stage filing under U.S.C. § 371 of PCT International Application No. PCT/US2018/038907 filed Jun. 22, 2018, which claims priority to and the benefit of U.S. Provisional Application No. 62/524,315, filed Jun. 23, 2017, and U.S. Provisional Application No. 62/633,807, filed Feb. 22, 2018, the contents of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Dec. 20, 2019, is named Sequence_Listing.txt and is 97,193 bytes in size.

BACKGROUND

Nosocomial infection, also referred to as hospital acquired infection, is a major problem facing patients today. Surveys conducted in the United States in 183 hospitals (Magill et al., 2014) demonstrated that of 11,282 patients, 452 had one or more health care-associated infections (4.0%; 95% confidence interval, 3.7 to 4.4). Of 504 such infections, the most common types were pneumonia (21.8%), surgical-site infections (21.8%), and gastrointestinal infections (17.1%). *Clostridium difficile* was the most commonly reported pathogen (causing 12.1% of health care-associated infections). Device-associated infections (i.e., central-catheter-associated bloodstream infection, catheter-associated urinary tract infection, and ventilator-associated pneumonia), which have traditionally been the focus of programs to prevent health care-associated infections, accounted for 25.6% of such infections. The authors estimated that there were 648,000 patients with 721,800 health care-associated infections (HAI) in the United States (US) acute care hospitals in 2011.

With the dramatic increase in multidrug resistant (MDR) bacteria, it has become difficult to treat nosocomial infections. Clinicians have had to resort to more toxic and less effective antibiotics. Nevertheless, the Center for Disease Control and Prevention (CDC) estimates that ~23,000 deaths occur yearly from infections caused by MDR bacteria.

Thus, there remains a need for effective technologies for the prevention and/or treatment of such infections.

SUMMARY

The present disclosure addresses the lack of suitable technologies for the prevention and/or treatment of nosocomial infections. Among other things, the present disclosure addresses challenges in providing vaccines with sufficient immunogenicity to achieve immunity and prevention of colonization.

Among other things, the present disclosure provides compositions and methods for prevention and/or treatment of nosocomial infections in patient populations in need thereof.

Among other things, the present invention provides immunogenic compositions comprising, for example, (i) a backbone polymer comprising a polymer and one or more antigenic polysaccharides conjugated to the polymer; and (ii) one or more polypeptide antigens non-covalently complexed with the polymer or the antigenic polysaccharide.

In some embodiments, an immunogenic composition may comprise one or more antigenic polysaccharides conjugated to a polymer with a linker. In some embodiments, an immunogenic composition may comprise one or more antigenic polysaccharides conjugated to a polymer without a linker. In some embodiments, the one or more antigenic polysaccharides are derived from gram-negative bacteria and/or gram-positive bacteria. In some embodiments, the one or more antigenic polysaccharides are derived from *Klebsiella, Pseudomonas*, and/or *E. coli* antigenic polysaccharides.

In some embodiments, one or more of the opsonization potential, or immunogenicity of the one or more antigenic polysaccharides is increased relative to a predetermined level, as measured by ELISA and/or by an antibody functional assay. In some embodiments, one or more of the opsonization potential, or immunogenicity of the one or more antigenic polysaccharides is increased relative to a control composition, as measured by ELISA and/or by an antibody functional assay. In some embodiments, a control composition may comprise an antigenic polysaccharide present in the immunogenic composition and not comprising a backbone polymer present in the immunogenic composition. In some embodiments, a control composition may comprise an antigenic polypeptide present in the immunogenic composition and not comprising a backbone polymer present in the immunogenic composition. In some embodiments, a control composition may comprise an antigenic polypeptide present in the immunogenic composition and/or an antigenic polysaccharide present in the immunogenic composition, and not comprising a polymer present in the immunogenic composition. In some embodiments, a control composition may comprise an antigenic polysaccharide present in the vaccine composition and not comprising a backbone polymer present in the vaccine composition. In some embodiments, a control composition may comprise an antigenic polypeptide present in the vaccine composition and not comprising a backbone polymer present in the vaccine composition. In some embodiments, a control composition may comprise an antigenic polypeptide present in the vaccine composition and/or an antigenic polysaccharide present in the vaccine composition, and not comprising a polymer present in the vaccine composition. In some embodiments, a control composition may comprise an antigenic polysaccharide present in the pharmaceutical composition and not comprising a backbone polymer present in the pharmaceutical composition. In some embodiments, a control composition may comprise an antigenic polypeptide present in the pharmaceutical composition and not comprising a backbone polymer present in the pharmaceutical composition. In some embodiments, a control composition may comprise an antigenic polypeptide present in the pharmaceutical composition and/or an antigenic polysaccharide present in the pharmaceutical composition, and not comprising a polymer present in the pharmaceutical composition.

In some embodiments, one or more of the opsonization potential, or immunogenicity of the one or more antigenic polysaccharides is increased at least 1-fold, 2-fold, 3-fold, 4-fold, or 5-fold relative to a predetermined level, as measured by ELISA and or by an antibody functional assay. In some embodiments, the predetermined level is a preimmune level. In some embodiments, the epitope valency of the one or more antigenic polysaccharides is at least 1-fold, 2-fold, 3-fold, 4-fold, or 5-fold above that of the native polysaccharide.

In some embodiments, one or more polypeptide antigens may be carrier proteins for one or more antigenic polysaccharides. In some embodiments, upon administration to a subject, an immunogenic composition induces antibody production against one or more pathogens in the subject at level greater than a composition comprising an antigenic polysaccharide and not comprising the backbone polymer, as measured by ELISA. In some embodiments, upon administration to a subject, an immunogenic composition induces antibody production against one or more pathogens in the subject at level greater than a composition comprising a polypeptide antigen and not comprising the backbone polymer, as measured by ELISA. In some embodiments, the one or more pathogens are selected from, *Klebsiella, Pseudomonas*, and *E. coli*. In some embodiments, upon administration to a subject, an immunogenic composition elicits an immune response against one or more of *Klebsiella, Pseudomonas*, and *E. coli*.

In some embodiments, a polypeptide antigen is or comprises a bacterial polypeptide, a fungal polypeptide, and/or a viral polypeptide, or combinations thereof. In some embodiments, a polypeptide antigen is or comprises a polypeptide or immunogenic fragment thereof from *Klebsiella, Pseudomonas*, and/or *E. coli*. In some embodiments, a polypeptide antigen is or comprises a polypeptide derived from *Klebsiella, Pseudomonas*, and/or an *E. coli* polypeptide.

In some embodiments, a polymer is or comprises a polysaccharide, a polypeptide, or a synthetic dendrimer. In some embodiments, the polymer is about 50 kDa to about 2000 kDa in size. In some embodiments, a polymer is or comprises a capsular polysaccharide derived from a gram-negative or gram-positive bacteria. In some embodiments, a capsular polysaccharide is or comprises a *Klebsiella* capsular polysaccharide, *Pseudomonas* exopolysaccharide, and/or *Escherichia* capsular polysaccharide. In some embodiments, a polymer is or comprises a *Klebsiella* spp. K19 capsular polysaccharide. In some embodiments, a polymer is or comprises a linear poly-L-lysine, or a dendrimer of L-lysine. In some embodiments, a polymer is or comprises a dendrimer of a synthetic monosaccharide or oligosaccharide.

In some embodiments, one or more polypeptide antigens are non-covalently complexed with a polymer and/or one or more antigenic polysaccharides by formation of at least one complementary affinity-molecule pair comprising (i) a first affinity molecule associated with the polymer or one or more antigenic polysaccharides; and (ii) a complementary affinity molecule associated with one or more polypeptide antigens. In some embodiments, the complementary affinity-molecule pair is selected from the group consisting of: biotin/biotin-binding protein, antibody/antigen, enzyme/substrate, receptor/ligand, metal/metal-binding protein, carbohydrate/carbohydrate binding protein, lipid/lipid-binding protein, and His tag/His tag-binding molecule. In some embodiments, the first affinity molecule is biotin or a derivative thereof. In some embodiments, the complementary affinity molecule is a biotin-binding protein or biotin-binding domain thereof. In some embodiments, the biotin-binding protein is rhizavidin, avidin, streptavidin, bradavidin, tamavidin, lentiavidin, zebavidin, NeutrAvidin, CaptAvidin™, or a combination thereof.

In some embodiments, a first affinity molecule is cross-linked or covalently bonded to the polymer or the one or more antigenic polysaccharides. In some embodiments, the first affinity molecule is cross-linked or covalently bonded to the polymer of the backbone polymer. In some embodiments, the first affinity molecule is cross-linked or covalently bonded to the one or more antigenic polysaccharides. In some embodiments, the first affinity molecule is cross-linked or covalently bonded to the polymer of the backbone polymer and to the one or more antigenic polysaccharides. In some embodiments, the polymer is or comprises poly-L-Lysine. In some embodiments, the one or more antigenic polysaccharides is or comprises a polysaccharide of one or more of *Klebsiella, Pseudomonas*, and *E. coli*.

In some embodiments, the one or more antigenic polysaccharides is or comprises a *K. pneumoniae* OPS of type O1, O2, O3, O5, or a combination thereof. In some embodiments, the one or more antigenic polysaccharides is or comprises a *P. aeruginosa* OPS of type O1, O2, O3, O4, O5, O6, O10, O11, O12, or a combination thereof. In some embodiments, at least one of the antigenic polysaccharides is or comprises the *P. aeruginosa* exopolysaccharide PsL. In some embodiments, the PsL is or comprises at least one epitope that binds to a monoclonal antibody comprising an amino acid sequence having at least 80%, 85%, 90%, 95%, 96%, 97%, 98%, 99%, or 100% identity to the sequence of SEQ ID NO:4 and/or an amino acid sequence having at least 80%, 85%, 90%, 95%, 96%, 97%, 98%, 99%, or 100% identity to the sequence of SEQ ID NO:5.

In some embodiments, at least one polypeptide antigen is or comprises an amino acid sequence having at least 80%, 85%, 90%, 95%, 96%, 97%, 98%, 99%, or 100% identity to the sequence of SEQ ID NO:1 (*K. pneumoniae* Type I fimbrial protein), or an immunogenic fragment thereof. In some embodiments, at least one polypeptide antigen is or comprises an amino acid sequence having at least 80%, 85%, 90%, 95%, 96%, 97%, 98%, 99%, or 100% identity to the sequence of SEQ ID NO:2 (*K. pneumoniae* conserved Type III fimbrial protein MrkA) and/or an amino acid sequence having at least 80%, 85%, 90%, 95%, 96%, 97%, 98%, 99%, or 100% identity to the sequence of SEQ ID NO:3 or an immunogenic fragment thereof. In some embodiments, at least one polypeptide antigen is or comprises a *P. aeruginosa* FliC flagellin subtype A, *P. aeruginosa* FliC flagellin subtype B, or an immunogenic fragment thereof. In some embodiments, at least one polypeptide antigen is or comprises an amino acid sequence having at least 80%, 85%, 90%, 95%, 96%, 97%, 98%, 99%, or 100% identity to the sequence of SEQ ID NO:6 (*P. aeruginosa* FliC flagellin subtype A1), an amino acid sequence having at least 80%, 85%, 90%, 95%, 96%, 97%, 98%, 99%, or 100% identity to the sequence of SEQ ID NO:9 (*P. aeruginosa* FliC flagellin subtype A2), an amino acid sequence having at least 80%, 85%, 90%, 95%, 96%, 97%, 98%, 99%, or 100% identity to the sequence of SEQ ID NO:7 (*P. aeruginosa* FliC flagellin subtype B) or an immunogenic fragment thereof. In some embodiments, at least one polypeptide antigen is or comprises an amino acid sequence having at least 80%, 85%, 90%, 95%, 96%, 97%, 98%, 99%, or 100% identity to the sequence of SEQ ID NO:8 (*P. aeruginosa* PcrV), or an immunogenic fragment thereof.

In some embodiments, an immunogenic composition of the invention is or comprises (a) a backbone polymer comprising (i) a polymer comprising a *Klebsiella* spp. K19 capsular polysaccharide; and (ii) one or more antigenic polysaccharides comprising a polysaccharide of *Klebsiella* or *Pseudomonas* conjugated to the *Klebsiella* spp. K19 capsular polysaccharide; and (b) one or more polypeptide antigens non-covalently complexed with the polymer by formation of at least one complementary affinity-molecule pair comprising (i) a first affinity molecule associated with the polymer; and (ii) a complementary affinity molecule associated with the one or more polypeptide antigens. In some embodiments, the one or more antigenic polysaccharides is or comprises a *K. pneumoniae* OPS of type O1, O2, O3, O5, or a combination thereof. In some embodiments, the one or more antigenic polysaccharides is or comprises a *P. aeruginosa* OPS of type O1, O2, O3, O4, O5, O6, O10, O11, or a combination thereof. In some embodiments, the first affinity molecule is biotin or a derivative thereof and the complementary affinity molecule is or comprises a biotin-binding protein or biotin-binding domain thereof. In some embodiments, the biotin-binding protein is or comprises rhizavidin or a biotin-binding domain thereof. In some embodiments, the one or more polypeptide antigens is or comprises *P. aeruginosa* FliC flagellin subtype B D2 domain lacking the TLR5 binding motif, *P. aeruginosa* PcrV, *K. pneumoniae* MrkA, antigenic fragments thereof, or a combination thereof.

In some embodiments, at least one complementary affinity-molecule pair comprises a fusion protein comprising (i) a biotin-binding protein or biotin-binding domain thereof, (ii) a polypeptide comprising an amino acid sequence having at least 80%, 85%, 90%, 95%, 96%, 97%, 98%, 99%, or 100% identity to the sequence of SEQ ID NO:10 (FlaB flagellin D2 domain lacking the TLR5 binding motif) or an immunogenic fragment thereof, and (iii) a polypeptide comprising an amino acid sequence having at least 80%, 85%, 90%, 95%, 96%, 97%, 98%, 99%, or 100% identity to the sequence of SEQ ID NO:2 or SEQ ID NO:3 (*K. pneumoniae* MrkA) or an immunogenic fragment thereof. In some embodiments, the fusion protein is or comprises a polypeptide comprising an amino acid sequence having at least 80%, 85%, 90%, 95%, 96%, 97%, 98%, 99%, or 100% identity to the sequence of SEQ ID NO:24 (Rhavi-FlaB-Domain2-MrkA-His).

In some embodiments, at least one complementary affinity-molecule pair comprises a fusion protein comprising (i) a biotin-binding protein or biotin-binding domain thereof, (ii) a polypeptide comprising an amino acid sequence having at least 80%, 85%, 90%, 95%, 96%, 97%, 98%, 99%, or 100% identity to the sequence of SEQ ID NO:10 (*P. aeruginosa* FliC flagellin subtype B D2 domain lacking the TLR5 binding motif) or an immunogenic fragment thereof, and (iii) a polypeptide comprising an amino acid sequence having at least 80%, 85%, 90%, 95%, 96%, 97%, 98%, 99%, or 100% identity to the sequence of SEQ ID NO:8 (*P. aeruginosa* PcrV) or an immunogenic fragment thereof. In some embodiments, a fusion protein is or comprises a polypeptide comprising an amino acid sequence having at least 80%, 85%, 90%, 95%, 96%, 97%, 98%, 99%, or 100% identity to the sequence of SEQ ID NO:26 (Rhavi-FlaB-Domain2-PcrV-His).

Among other things, the present invention provides vaccine compositions. In some embodiments a vaccine composition may comprise one or more immunogenic compositions. In some embodiments a vaccine composition may comprise a pharmaceutically acceptable carrier.

In some embodiments, a vaccine composition may comprise one or more of (a) an immunogenic composition comprising a backbone polymer comprising a polymer comprising a biotinylated *Klebsiella* spp. K19 capsular polysaccharide, a KP O1 OPS conjugated to the *Klebsiella* spp. K19 capsular polysaccharide, and a Rhavi-FlaBD2-MrkA fusion protein non-covalently complexed to the biotinylated backbone polymer; (b) an immunogenic composition comprising a backbone polymer comprising a polymer comprising a biotinylated *Klebsiella* spp. K19 capsular polysaccharide, a KP O2 OPS conjugated to the *Klebsiella* spp. K19 capsular polysaccharide, and a Rhavi-FlaBD2-MrkA fusion protein non-covalently complexed to the biotinylated backbone polymer; (c) an immunogenic composition comprising a backbone polymer comprising a polymer comprising a biotinylated *Klebsiella* spp. K19 capsular polysaccharide, a KP O3 OPS conjugated to the *Klebsiella* spp. K19 capsular polysaccharide, and a Rhavi-FlaBD2-MrkA fusion protein non-covalently complexed to the biotinylated backbone polymer; and (d) an immunogenic composition comprising a backbone polymer comprising a polymer comprising a biotinylated *Klebsiella* spp. K19 capsular polysaccharide, a KP O5 OPS conjugated to the *Klebsiella* spp. K19 capsular polysaccharide, and a Rhavi-FlaBD2-MrkA fusion protein non-covalently complexed to the biotinylated backbone polymer.

In some embodiments, a vaccine composition may comprise one or more of (a) an immunogenic composition comprising a backbone polymer comprising a polymer comprising a biotinylated *Klebsiella* spp. K19 capsular polysaccharide, a KP O1 OPS conjugated to the *Klebsiella* spp. K19 capsular polysaccharide, and a Rhavi-FlaBD2-MrkA fusion protein non-covalently complexed to the biotinylated backbone polymer; (b) an immunogenic composition comprising a backbone polymer comprising a polymer comprising a biotinylated *Klebsiella* spp. K19 capsular polysaccharide, a KP O2 OPS conjugated to the *Klebsiella* spp. K19 capsular polysaccharide, and a Rhavi-FlaBD2-PcrV fusion protein non-covalently complexed to the biotinylated backbone polymer; (c) an immunogenic composition comprising a backbone polymer comprising a polymer comprising a biotinylated *Klebsiella* spp. K19 capsular polysaccharide, a KP O3 OPS conjugated to the *Klebsiella* spp. K19 capsular polysaccharide, and a Rhavi-FlaBD2-MrkA fusion protein non-covalently complexed to the biotinylated backbone polymer; and (d) an immunogenic composition comprising a backbone polymer comprising a polymer comprising a biotinylated *Klebsiella* spp. K19 capsular polysaccharide, a KP O5 OPS conjugated to the *Klebsiella* spp. K19 capsular polysaccharide, and a Rhavi-FlaBD2-PcrV fusion protein non-covalently complexed to the biotinylated backbone polymer.

In some embodiments, a vaccine composition may comprise one or more of (a) an immunogenic composition comprising a backbone polymer comprising a polymer comprising a biotinylated *Klebsiella* spp. K19 capsular polysaccharide, a PA O1 OPS conjugated to the *Klebsiella* spp. K19 capsular polysaccharide, and a Rhavi-FlaBD2-MrkA fusion protein non-covalently complexed to the biotinylated backbone polymer; (b) an immunogenic composition comprising a backbone polymer comprising a polymer comprising a biotinylated *Klebsiella* spp. K19 capsular polysaccharide, a PA O2 OPS conjugated to the *Klebsiella* spp. K19 capsular polysaccharide, and a Rhavi-FlaBD2-MrkA fusion protein non-covalently complexed to the biotinylated backbone polymer; (c) an immunogenic composition comprising a backbone polymer comprising a polymer comprising a biotinylated *Klebsiella* spp. K19 capsular polysaccharide, a PA O3 OPS conjugated to the *Klebsiella* spp. K19 capsular polysaccharide, and a Rhavi-FlaBD2-MrkA fusion protein non-covalently complexed to the biotinylated backbone polymer; (d) an immunogenic composition comprising a backbone polymer comprising a polymer comprising a biotinylated *Klebsiella* spp. K19 capsular polysaccharide, a PA O4 OPS conjugated to the *Klebsiella* spp. K19 capsular polysaccharide, and a Rhavi-FlaBD2-MrkA fusion protein non-covalently complexed to the biotinylated backbone polymer; (e) an immunogenic composition comprising a backbone polymer comprising a polymer comprising a biotinylated *Klebsiella* spp. K19 capsular polysaccharide, a PA O5 OPS conjugated to the *Klebsiella* spp. K19 capsular polysaccharide, and a Rhavi-FlaBD2-MrkA fusion protein non-covalently complexed to the biotinylated backbone polymer; (f) an immunogenic composition comprising a backbone polymer comprising a polymer comprising a biotinylated *Klebsiella* spp. K19 capsular polysaccharide, a PA O6 OPS conjugated to the *Klebsiella* spp. K19 capsular polysaccharide, and a Rhavi-FlaBD2-MrkA fusion protein non-covalently complexed to the biotinylated backbone polymer; (g) an immunogenic composition comprising a backbone polymer comprising a polymer comprising a biotinylated *Klebsiella* spp. K19 capsular polysaccharide, a PA O10 OPS conjugated to the *Klebsiella* spp. K19 capsular polysaccharide, and a Rhavi-FlaBD2-MrkA fusion protein non-covalently complexed to the biotinylated backbone polymer; and (h) an immunogenic composition comprising a backbone polymer comprising a polymer comprising a biotinylated *Klebsiella* spp. K19 capsular polysaccharide, a PA O11 OPS conjugated to the *Klebsiella* spp. K19 capsular polysaccharide, and a Rhavi-FlaBD2-MrkA fusion protein non-covalently complexed to the biotinylated backbone polymer.

In some embodiments, a vaccine composition may comprise one or more of (a) an immunogenic composition comprising a backbone polymer comprising a polymer comprising a biotinylated *Klebsiella* spp. K19 capsular polysaccharide, a PA O1 OPS conjugated to the *Klebsiella* spp. K19 capsular polysaccharide, and a Rhavi-FlaBD2-PcrV fusion protein non-covalently complexed to the biotinylated backbone polymer; (b) an immunogenic composition comprising a backbone polymer comprising a polymer comprising a biotinylated *Klebsiella* spp. K19 capsular polysaccharide, a PA O2 OPS conjugated to the *Klebsiella* spp. K19 capsular polysaccharide, and a Rhavi-FlaBD2-PcrV fusion protein non-covalently complexed to the biotinylated backbone polymer; (c) an immunogenic composition comprising a backbone polymer comprising a polymer comprising a biotinylated *Klebsiella* spp. K19 capsular polysaccharide, a PA O3 OPS conjugated to the *Klebsiella* spp. K19 capsular polysaccharide, and a Rhavi-FlaBD2-PcrV fusion protein non-covalently complexed to the biotinylated backbone polymer; (d) an immunogenic composition comprising a backbone polymer comprising a polymer comprising a biotinylated *Klebsiella* spp. K19 capsular polysaccharide, a PA O4 OPS conjugated to the *Klebsiella* spp. K19 capsular polysaccharide, and a Rhavi-FlaBD2-PcrV fusion protein non-covalently complexed to the biotinylated backbone polymer; (e) an immunogenic composition comprising a backbone polymer comprising a polymer comprising a biotinylated *Klebsiella* spp. K19 capsular polysaccharide, a PA O5 OPS conjugated to the *Klebsiella* spp. K19 capsular polysaccharide, and a Rhavi-FlaBD2-MrkA fusion protein non-covalently complexed to the biotinylated backbone polymer; (f) an immunogenic composition comprising a backbone polymer comprising a polymer comprising a biotinylated *Klebsiella* spp. K19 capsular polysaccharide, a PA O6 OPS conjugated to the *Klebsiella* spp. K19 capsular polysaccharide, and a Rhavi-FlaBD2-MrkA fusion protein non-covalently complexed to the biotinylated backbone polymer; (g) an immunogenic composition comprising a backbone polymer comprising a polymer comprising a biotinylated *Klebsiella* spp. K19 capsular polysaccharide, a PA O10 OPS conjugated to the *Klebsiella* spp. K19 capsular polysaccharide, and a Rhavi-FlaBD2-MrkA fusion protein non-covalently complexed to the biotinylated backbone polymer; and (h) an immunogenic composition comprising a backbone polymer comprising a polymer comprising a biotinylated *Klebsiella* spp. K19 capsular polysaccharide, a PA O11 OPS conjugated to the *Klebsiella* spp. K19 capsular polysaccharide, and a Rhavi-FlaBD2-MrkA fusion protein non-covalently complexed to the biotinylated backbone polymer.

In some embodiments, a vaccine composition may comprise one or more of: (a) an immunogenic composition comprising a backbone polymer comprising a polymer comprising a biotinylated *Klebsiella* spp. K19 capsular polysaccharide, a KP O1 OPS conjugated to the *Klebsiella* spp. K19 capsular polysaccharide, and a Rhavi-FlaBD2-MrkA fusion protein non-covalently complexed to the biotinylated backbone polymer; (b) an immunogenic composition comprising a backbone polymer comprising a polymer comprising a biotinylated *Klebsiella* spp. K19 capsular polysaccharide, a KP O2 OPS conjugated to the *Klebsiella* spp. K19 capsular polysaccharide, and a Rhavi-FlaBD2-MrkA fusion protein non-covalently complexed to the biotinylated backbone polymer; (c) an immunogenic composition comprising a backbone polymer comprising a polymer comprising a biotinylated *Klebsiella* spp. K19 capsular polysaccharide, a KP O3 OPS conjugated to the *Klebsiella* spp. K19 capsular polysaccharide, and a Rhavi-FlaBD2-MrkA fusion protein non-covalently complexed to the biotinylated backbone polymer; (d) an immunogenic composition comprising a backbone polymer comprising a polymer comprising a biotinylated *Klebsiella* spp. K19 capsular polysaccharide, a KP O5 OPS conjugated to the *Klebsiella* spp. K19 capsular polysaccharide, and a Rhavi-FlaBD2-MrkA fusion protein non-covalently complexed to the biotinylated backbone polymer; (e) an immunogenic composition comprising a backbone polymer comprising a polymer comprising a biotinylated *Klebsiella* spp. K19 capsular polysaccharide, a PA O1 OPS conjugated to the *Klebsiella* spp. K19 capsular polysaccharide, and a Rhavi-FlaBD2-MrkA fusion protein non-covalently complexed to the biotinylated backbone polymer; (f) an immunogenic composition comprising a backbone polymer comprising a polymer comprising a biotinylated *Klebsiella* spp. K19 capsular polysaccharide, a PA O2 OPS conjugated to the *Klebsiella* spp. K19 capsular polysaccharide, and a Rhavi-FlaBD2-MrkA fusion protein non-covalently complexed to the biotinylated backbone polymer; (g) an immunogenic composition comprising a backbone polymer comprising a polymer comprising a biotinylated *Klebsiella* spp. K19 capsular polysaccharide, a PA O3 OPS conjugated to the *Klebsiella* spp. K19 capsular polysaccharide, and a Rhavi-FlaBD2-MrkA fusion protein non-covalently complexed to the biotinylated backbone polymer; (h) an immunogenic composition comprising a backbone polymer comprising a polymer comprising a biotinylated *Klebsiella* spp. K19 capsular polysaccharide, a PA O4 OPS conjugated to the *Klebsiella* spp. K19 capsular polysaccharide, and a Rhavi-FlaBD2-MrkA fusion protein non-covalently complexed to the biotinylated backbone polymer; (i) an immunogenic composition comprising a backbone polymer comprising a polymer comprising a biotinylated *Klebsiella* spp. K19 capsular polysaccharide, a PA O5 OPS conjugated to the *Klebsiella* spp. K19 capsular polysaccharide, and a Rhavi-FlaBD2-MrkA fusion protein non-covalently complexed to the biotinylated backbone polymer; (j) an immunogenic composition comprising a backbone polymer comprising a polymer comprising a biotinylated *Klebsiella* spp. K19 capsular polysaccharide, a PA O6 OPS conjugated to the *Klebsiella* spp. K19 capsular polysaccharide, and a Rhavi-FlaBD2-MrkA fusion protein non-covalently complexed to the biotinylated backbone polymer; (k) an immunogenic composition comprising a backbone polymer comprising a polymer comprising a biotinylated *Klebsiella* spp. K19 capsular polysaccharide, a PA O10 OPS conjugated to the *Klebsiella* spp. K19 capsular polysaccharide, and a Rhavi-FlaBD2-MrkA fusion protein non-covalently complexed to the biotinylated backbone polymer; and (1) an immunogenic composition comprising a backbone polymer comprising a polymer comprising a biotinylated *Klebsiella* spp. K19 capsular polysaccharide, a PA O11 OPS conjugated to the *Klebsiella* spp. K19 capsular polysaccharide, and a Rhavi-FlaBD2-MrkA fusion protein non-covalently complexed to the biotinylated backbone polymer.

In some embodiments, a vaccine composition may comprise one or more of (a) an immunogenic composition comprising a backbone polymer comprising a polymer comprising a biotinylated *Klebsiella* spp. K19 capsular polysaccharide, a KP O1 OPS conjugated to the *Klebsiella* spp. K19 capsular polysaccharide, and a Rhavi-FlaBD2-MrkA fusion protein non-covalently complexed to the biotinylated backbone polymer; (b) an immunogenic composition comprising a backbone polymer comprising a polymer comprising a biotinylated *Klebsiella* spp. K19 capsular polysaccharide, a KP O2 OPS conjugated to the *Klebsiella* spp. K19 capsular polysaccharide, and a Rhavi-FlaBD2-PcrV fusion protein non-covalently complexed to the biotinylated backbone polymer; (c) an immunogenic composition comprising a backbone polymer comprising a polymer comprising a biotinylated *Klebsiella* spp. K19 capsular polysaccharide, a KP O3 OPS conjugated to the *Klebsiella* spp. K19 capsular polysaccharide, and a Rhavi-FlaBD2-MrkA fusion protein non-covalently complexed to the biotinylated backbone polymer; (d) an immunogenic composition comprising a backbone polymer comprising a polymer comprising a biotinylated *Klebsiella* spp. K19 capsular polysaccharide, a KP O5 OPS conjugated to the *Klebsiella* spp. K19 capsular polysaccharide, and a Rhavi-FlaBD2-PcrV fusion protein non-covalently complexed to the biotinylated backbone polymer; (e) an immunogenic composition comprising a backbone polymer comprising a polymer comprising a biotinylated *Klebsiella* spp. K19 capsular polysaccharide, a PA O1 OPS conjugated to the *Klebsiella* spp. K19 capsular polysaccharide, and a Rhavi-FlaBD2-PcrV fusion protein non-covalently complexed to the biotinylated backbone polymer; (f) an immunogenic composition comprising a backbone polymer comprising a polymer comprising a biotinylated *Klebsiella* spp. K19 capsular polysaccharide, a PA O2 OPS conjugated to the *Klebsiella* spp. K19 capsular polysaccharide, and a Rhavi-FlaBD2-PcrV fusion protein non-covalently complexed to the biotinylated backbone polymer; (g) an immunogenic composition comprising a backbone polymer comprising a polymer comprising a biotinylated *Klebsiella* spp. K19 capsular polysaccharide, a PA O3 OPS conjugated to the *Klebsiella* spp. K19 capsular polysaccharide, and a Rhavi-FlaBD2-PcrV fusion protein non-covalently complexed to the biotinylated backbone polymer; (h) an immunogenic composition comprising a backbone polymer comprising a polymer comprising a biotinylated *Klebsiella* spp. K19 capsular polysaccharide, a PA O4 OPS conjugated to the *Klebsiella* spp. K19 capsular polysaccharide, and a Rhavi-FlaBD2-PcrV fusion protein non-covalently complexed to the biotinylated backbone polymer; (i) an immunogenic composition comprising a backbone polymer comprising a polymer comprising a biotinylated *Klebsiella* spp. K19 capsular polysaccharide, a PA O5 OPS conjugated to the *Klebsiella* spp. K19 capsular polysaccharide, and a Rhavi-FlaBD2-MrkA fusion protein non-covalently complexed to the biotinylated backbone polymer; (j) an immunogenic composition comprising a backbone polymer comprising a polymer comprising a biotinylated *Klebsiella* spp. K19 capsular polysaccharide, a PA O6 OPS conjugated to the *Klebsiella* spp. K19 capsular polysaccharide, and a Rhavi-FlaBD2-MrkA fusion protein non-covalently complexed to the biotinylated backbone polymer; (k) an immunogenic composition comprising a backbone polymer comprising a polymer comprising a biotinylated *Klebsiella* spp. K19 capsular polysaccharide, a PA O10 OPS conjugated to the *Klebsiella* spp. K19 capsular polysaccharide, and a Rhavi-FlaBD2-MrkA fusion protein non-covalently complexed to the biotinylated backbone polymer; and (1) an immunogenic composition comprising a backbone polymer comprising a polymer comprising a biotinylated *Klebsiella* spp. K19 capsular polysaccharide, a PA O11 OPS conjugated to the *Klebsiella* spp. K19 capsular polysaccharide, and a Rhavi-FlaBD2-MrkA fusion protein non-covalently complexed to the biotinylated backbone polymer. In some embodiments, the Rhavi-FlaBD2-MrkA fusion protein is or comprises a polypeptide comprising an amino acid sequence having at least 80%, 85%, 90%, 95%, 96%, 97%, 98%, 99%, or 100% identity to the sequence of SEQ ID NO:24 (Rhavi-FlaB-Domain2-MrkA-His). In some embodiments, the Rhavi-FlaBD2-PcrV fusion protein is or comprises a polypeptide comprising an amino acid sequence having at least 80%, 85%, 90%, 95%, 96%, 97%, 98%, 99%, or 100% identity to the sequence of SEQ ID NO:26 (Rhavi-FlaB-Domain2-PcrV-His).

In some embodiments, the OPS of each immunogenic composition is present in a w/w ratio of about 1:1. In some embodiments, the backbone polymer of each immunogenic composition is present in a w/w ratio of about 1:1. In some embodiments, the combined OPS and CPS of each immunogenic composition is present in a w/w ratio of about 1:1. In some embodiments, the OPS of each immunogenic composition is present at about 1 µg. In some embodiments, the backbone polymer of each immunogenic composition is present at about 1 µg. In some embodiments, the combined OPS and CPS of each immunogenic composition is present at about 1 µg. In some embodiments, the OPS of each immunogenic composition is present at about 5 µg. In some embodiments, the backbone polymer of each immunogenic composition is present at about 5 µg. In some embodiments, the combined OPS and CPS of each immunogenic composition is present at about 5 µg. In some embodiments, the backbone polymer is or comprises a BP-1 backbone. In some embodiments, the backbone polymer is or comprises BP-1.2 backbone. In some embodiments, the backbone polymer is or comprises BP-2a backbone. In some embodiments, the backbone polymer is or comprises BP-2b backbone. In some embodiments, the backbone polymer is or comprises BP-3 backbone.

In some embodiments, one or more polypeptide antigens is or comprises one or more *P. aeruginosa* proteins or variants, and wherein the complementary affinity molecule is or comprises a biotin-binding protein or biotin-binding domain thereof. In some embodiments, at least one of the polypeptide antigens is or comprises an amino acid sequence having at least 80%, 85%, 90%, 95%, 96%, 97%, 98%, 99%, or 100% identity to the sequence of SEQ ID NO:7 (*P. aeruginosa* FlaB flagellin) or an immunogenic fragment thereof. In some embodiments, at least one of the polypeptide antigens is or comprises an amino acid sequence having at least 80%, 85%, 90%, 95%, 96%, 97%, 98%, 99%, or 100% identity to the sequence of SEQ ID NO:6 (*P. aeruginosa* FlaA1 flagellin) or an immunogenic fragment thereof.

In some embodiments, at least one complementary affinity-molecule pair is or comprises a fusion protein comprising a biotin-binding protein or biotin-binding domain thereof and a polypeptide comprising an amino acid sequence having at least 80%, 85%, 90%, 95%, 96%, 97%, 98%, 99%, or 100% identity to the sequence of SEQ ID NO:9 (FlaA2 flagellin) or an immunogenic fragment thereof.

In some embodiments, at least one complementary affinity-molecule pair is or comprises a fusion protein comprising a biotin-binding protein or biotin-binding domain thereof and a polypeptide comprising an amino acid sequence having at least 80%, 85%, 90%, 95%, 96%, 97%, 98%, 99%, or 100% identity to the sequence of SEQ ID NO:10 (FlaB flagellin D2 domain lacking the TLR5 binding motif) or an immunogenic fragment thereof or a polypeptide comprising an amino acid sequence having at least 80%, 85%, 90%, 95%, 96%, 97%, 98%, 99%, or 100% identity to the sequence of SEQ ID NO:11 (FlaA1 flagellin D2 domain lacking the TLR5 binding motif) or an immunogenic fragment thereof or a polypeptide comprising an amino acid sequence having at least 80%, 85%, 90%, 95%, 96%, 97%, 98%, 99%, or 100% identity to the sequence of SEQ ID NO:12 (FlaA2 flagellin D2 domain lacking the TLR5 binding motif) or an immunogenic fragment thereof.

In some embodiments, at least one complementary affinity-molecule pair is or comprises a fusion protein comprising a biotin-binding protein or biotin-binding domain thereof and a polypeptide comprising an amino acid sequence having at least 80%, 85%, 90%, 95%, 96%, 97%, 98%, 99%, or 100% identity to the sequence of SEQ ID NO:10 (FlaB flagellin D2 domain lacking the TLR5 binding motif) or an immunogenic fragment thereof.

In some embodiments, at least one complementary affinity-molecule pair is or comprises a fusion protein comprising a biotin-binding protein or biotin-binding domain thereof and a polypeptide comprising an amino acid sequence having at least 80%, 85%, 90%, 95%, 96%, 97%, 98%, 99%, or 100% identity to the sequence of SEQ ID NO:11 (FlaA1 flagellin D2 domain lacking the TLR5 binding motif) or an immunogenic fragment thereof.

In some embodiments, at least one complementary affinity-molecule pair is or comprises a fusion protein comprising a biotin-binding protein or biotin-binding domain thereof and a polypeptide comprising an amino acid sequence having at least 80%, 85%, 90%, 95%, 96%, 97%, 98%, 99%, or 100% identity to the sequence of SEQ ID NO:12 (FlaA2 flagellin D2 domain lacking the TLR5 binding motif) or an immunogenic fragment thereof.

In some embodiments, at least one complementary affinity-molecule pair is or comprises a fusion protein comprising a biotin-binding protein or biotin-binding domain thereof and a polypeptide comprising an amino acid sequence having at least 80%, 85%, 90%, 95%, 96%, 97%, 98%, 99%, or 100% identity to the sequence of SEQ ID NO:8 (*P. aeruginosa* type III secretion system (TTSS) PcrV) or an immunogenic fragment thereof.

In some embodiments, at least one complementary affinity-molecule pair is or comprises a fusion protein comprising (i) a biotin-binding protein or biotin-binding domain thereof, (ii) a polypeptide comprising an amino acid sequence having at least 80%, 85%, 90%, 95%, 96%, 97%, 98%, 99%, or 100% identity to the sequence of SEQ ID NO:7 (*P. aeruginosa* FliC flagellin subtype B) or an immunogenic fragment thereof, and (iii) a polypeptide comprising an amino acid sequence having at least 80%, 85%, 90%, 95%, 96%, 97%, 98%, 99%, or 100% identity to the sequence of SEQ ID NO:8 (*P. aeruginosa* PcrV) or an immunogenic fragment thereof.

In some embodiments, at least one complementary affinity-molecule pair is or comprises a fusion protein comprising (i) a biotin-binding protein or biotin-binding domain thereof, (ii) a polypeptide comprising an amino acid sequence having at least 80%, 85%, 90%, 95%, 96%, 97%, 98%, 99%, or 100% identity to the sequence of SEQ ID NO:10 (*P. aeruginosa* FliC flagellin subtype B D2 domain lacking the TLR5 binding motif) or an immunogenic fragment thereof, and (iii) a polypeptide comprising an amino acid sequence having at least 80%, 85%, 90%, 95%, 96%, 97%, 98%, 99%, or 100% identity to the sequence of SEQ ID NO:8 (*P. aeruginosa* PcrV) or an immunogenic fragment thereof.

In some embodiments, at least one complementary affinity-molecule pair is or comprises a fusion protein comprising (i) a biotin-binding protein or biotin-binding domain thereof, (ii) a polypeptide comprising an amino acid sequence having at least 80%, 85%, 90%, 95%, 96%, 97%, 98%, 99%, or 100% identity to the sequence of SEQ ID NO:7 (*P. aeruginosa* FliC subtype B flagellin) or an immunogenic fragment thereof, and (iii) a polypeptide comprising an amino acid sequence having at least 80%, 85%, 90%, 95%, 96%, 97%, 98%, 99%, or 100% identity to the sequence of SEQ ID NO:2 or SEQ ID NO:3 (*K. pneumoniae* MrkA) or an immunogenic fragment thereof.

In some embodiments, at least one complementary affinity-molecule pair is or comprises a fusion protein comprising (i) a biotin-binding protein or biotin-binding domain thereof, (ii) a polypeptide comprising an amino acid sequence having at least 80%, 85%, 90%, 95%, 96%, 97%, 98%, 99%, or 100% identity to the sequence of SEQ ID NO:10 (*P. aeruginosa* FliC subtype B flagellin D2 domain lacking the TLR5 binding motif) or an immunogenic fragment thereof, and (iii) a polypeptide comprising an amino acid sequence having at least 80%, 85%, 90%, 95%, 96%, 97%, 98%, 99%, or 100% identity to the sequence of SEQ ID NO:2 or SEQ ID NO:3 (*K. pneumoniae* MrkA) or an immunogenic fragment thereof.

In some embodiments, at least one complementary affinity-molecule pair is or comprises a fusion protein comprising (i) a biotin-binding protein or biotin-binding domain thereof, (ii) a polypeptide comprising an amino acid sequence having at least 80%, 85%, 90%, 95%, 96%, 97%, 98%, 99%, or 100% identity to the sequence of SEQ ID NO:8 (*P. aeruginosa* PcrV) or an immunogenic fragment thereof, and (iii) a polypeptide comprising an amino acid sequence having at least 80%, 85%, 90%, 95%, 96%, 97%, 98%, 99%, or 100% identity to the sequence of SEQ ID NO:2 or SEQ ID NO:3 (*K. pneumoniae* MrkA) or an immunogenic fragment thereof.

In some embodiments, upon administration to a subject, an immunogenic composition elicits antibodies that recognize native MrkA on *K. pneumoniae* expressing MrkA. In some embodiments, upon administration to a subject, a vaccine composition elicits antibodies that recognize native MrkA on *K. pneumoniae* expressing MrkA.

In some embodiments, a pharmaceutical composition comprises one or more immunogenic compositions or vaccine compositions described herein. In some embodiments, a pharmaceutical composition comprises a pharmaceutically acceptable carrier. In some embodiments, a pharmaceutical composition comprises one or more adjuvants. In some embodiments, the adjuvant is selected from the group of aluminum phosphate, aluminum hydroxide, phosphated aluminum hydroxide, TLRs agonists such as the TLR2 saponin (QS21) or porins and TLR4 agonists such as for example monophosphoryl lipidA (MPL) and TLR5 such as flagellins, etc.

In some embodiments, a pharmaceutical composition is formulated for intramuscular, intraperitoneal, intradermal and/or subcutaneous administration. In some embodiments, the pharmaceutical composition is formulated for injection. In some embodiments, upon administration to a subject, a pharmaceutical composition elicits a Th1 and/or Th17 cell response. In some embodiments, upon administration to a subject, a pharmaceutical composition elicits an opsonic/bactericidal response against one or more of *Klebsiella*, *Pseudomonas*, and *E. coli*. In some embodiments, upon administration to a subject, a pharmaceutical composition reduces rate of transmission and/or colonization of the mucosal surfaces by one or more of *Klebsiella, Pseudomonas*, and *E. coli*. In some embodiments, upon administration to a subject, a pharmaceutical composition reduces rate of transmission and/or colonization of the GI tract by one or more of *Klebsiella, Pseudomonas*, and *E. coli*.

Some embodiments provide methods of immunizing a subject against *Klebsiella* infection comprising administering to the subject an effective amount of an immunogenic composition of the invention. Some embodiments provide methods of immunizing a subject against *Klebsiella* infection comprising administering to the subject an effective amount of a vaccine composition of the invention. Some embodiments provide methods of immunizing a subject against *Klebsiella* infection comprising administering to the subject an effective amount of a pharmaceutical composition of the invention.

Some embodiments provide methods of immunizing a subject against *P. aeruginosa* infection comprising administering to the subject an effective amount of an immunogenic composition of the invention. Some embodiments provide methods of immunizing a subject against *P. aeruginosa* infection comprising administering to the subject an effective amount of a vaccine composition of the invention. Some embodiments provide methods of immunizing a subject against *P. aeruginosa* infection comprising administering to the subject an effective amount of a pharmaceutical composition of the invention.

Some embodiments provide methods of immunizing a subject against *E. coli* infection comprising administering to the subject an effective amount of an immunogenic composition of the invention. Some embodiments provide methods of immunizing a subject against *E. coli* infection comprising administering to the subject an effective amount of a vaccine composition of the invention. Some embodiments provide methods of immunizing a subject against *E. coli* infection comprising administering to the subject an effective amount of a pharmaceutical composition of the invention.

In some embodiments, upon administration to a subject, an immunogenic composition elicits an immune response against gram-negative and/or gram-positive bacteria. In some embodiments, upon administration to a subject, a vaccine composition elicits an immune response against gram-negative and/or gram-positive bacteria. In some embodiments, upon administration to a subject, a pharmaceutical composition elicits an immune response against gram-negative and/or gram-positive bacteria. In some embodiments, the gram-negative bacteria are selected from *Klebsiella, Pseudomonas, E. coli*, and a combination thereof. In some embodiments, the immune response is an antibody or B cell response. In some embodiments, the immune response is a CD4+ T cell response, including Th1, Th2, or Th17 response, or a CD8+ T cell response, or CD4+/CD8+ T cell response. In some embodiments, the immune response is an antibody or B cell response; and a T cell response.

Some embodiments provide antibody compositions comprising antibodies raised in a mammal immunized with an immunogenic composition of the invention. Some embodiments provide antibody compositions comprising antibodies raised in a mammal immunized with a vaccine composition of the invention. Some embodiments provide antibody compositions comprising antibodies raised in a mammal immunized with a pharmaceutical composition of the invention. In some embodiments, the antibody composition comprises at least one antibody selected from the group consisting of monoclonal antibodies and anti-idiotype antibodies. In some embodiments, the antibody composition comprises an isolated gamma globulin fraction.

In some embodiments, the invention provides methods of purifying an O-antigen polysaccharide from one or more cellular components of *Klebsiella*, wherein the cellular components include protein and/or nucleic acid, the method comprising steps of: contacting one or more cellular components with an oxidizing reagent to obtain a mixture, wherein the pH of the mixture is between about 3 and 5; separating the O-antigen polysaccharide from the cellular components; and recovering the OPS, wherein the OPS is substantially free of the other cellular components and contains a free aldehyde at its reducing terminal end. In some embodiments, the oxidizing reagent is sodium nitrite, the acid is acetic acid and wherein the reducing terminal end of the OPS is a 2,5-anhydromannose residue containing a free aldehyde.

In some embodiments, the invention provides methods of purifying an O-antigen polysaccharide from one or more cellular components of gram-negative bacteria, wherein the cellular components include protein and/or nucleic acid, the method comprising: contacting one or more cellular components with an acidic reagent to obtain a mixture wherein the pH of the mixture is between about 3 and 5, heating the mixture to between about 80° C. to about 100° C.; separating the O-antigen polysaccharide from the cellular components; and recovering the OPS, wherein the OPS is substantially free of the other cellular components and contains a ketone at its reducing terminal end.

In some embodiments, the invention provides methods of making a backbone polymer comprising at least one non-biotinylated O-antigen polysaccharide, wherein the O-antigen polysaccharide comprises a primary amino group, and at least one biotinylated polysaccharide, the method comprising: chemically linking the O-antigen polysaccharide primary amino group by mixing the O-antigen polysaccharide with a partially oxidized polysaccharide containing aldehyde groups and a biotin containing primary amine to obtain a mixture; and reductively aminating the mixture with a reducing agent to produce a BP-1 polymer backbone, wherein the polysaccharide is biotinylated and the chemically linked O-antigen polysaccharide is not biotinylated. Some embodiments provide for a BP-1 polymer backbone made by the methods disclosed herein.

In some embodiments, the invention provides methods of making a backbone polymer comprising at least one non-biotinylated O-antigen polysaccharide, wherein the 0-antigen polysaccharide comprises a primary amino group, and at least one biotinylated polysaccharide, the method comprising: chemically linking the O-antigen polysaccharide primary amino group by mixing the O-antigen polysaccharide with a polysaccharide biotinylated and oxidized obtained by first treating the carboxylate groups of the polysaccharide with 1-Ethyl-3-(3-dimethylaminopropyl)-carbodiimide N-hydroxysuccinimide (EDC) and N-Hydroxysuccinimide (NETS) and a biotin hydrazide, then treating the polysaccharide with an oxidizing agent; and reductively aminating the mixture with a reducing agent to produce BP-1.2 polymer backbone, wherein the polysaccharide is biotinylated and the chemically linked O-antigen polysaccharide is not biotinylated. In some embodiments, the primary group on the O-antigen polysaccharide is the L-Alanine α-amino group of the outer core OPS of P. aeruginosa or an amino group that has been introduced into the reducing end of the O-antigen polysaccharide by chemically linking a short spacer molecule containing a primary group at each end by reductive amination with a reducing agent. In some embodiments, the oxidizing agent for the oxidation of the polysaccharide is sodium periodate, the short spacer containing di-amine is adipic dihydrazide and the reductive amination reductive agent is sodium cyanoborohydride. Some embodiments provide for a BP-1.2 polymer backbone made by the methods disclosed herein.

In some embodiments, the invention provides methods of making a backbone polymer comprising at least one non-biotinylated O-antigen polysaccharide, wherein the O-antigen polysaccharide comprises a primary amino group, and at least one biotinylated polysaccharide, the method comprising: chemically linking the O-antigen polysaccharide primary amino group by mixing the O-antigen polysaccharide with a polysaccharide biotinylated and CDAP-activated obtained by first treating the carboxylate groups of the polysaccharide with 1-Ethyl-3-(3-dimethylaminopropyl)-carbodiimide N-hydroxysuccinimide (EDC) and N-Hydroxysuccinimide (NETS) and a biotin hydrazide, then activating the biotinylated polysaccharide with CDAP to produce BP-1.3 polymer backbone, wherein the polysaccharide is biotinylated and the chemically linked O-antigen polysaccharide is not biotinylated. In some embodiments, the primary group on the O-antigen polysaccharide is the L-Alanine α-amino group of the outer core OPS of P. aeruginosa or an amino group that has been introduced into the reducing end of the O-antigen polysaccharide by chemically linking a short spacer molecule containing a primary group at each end by reductive amination with a reducing agent. In some embodiments, the short spacer containing di-amine is adipic dihydrazide and the reductive amination reductive agent is sodium cyanoborohydride. Some embodiments provide for a BP-1.3 polymer backbone made by the methods disclosed herein.

In some embodiments, the invention provides methods of making a backbone polymer comprising at least one biotinylated O-antigen polysaccharide and at least one biotinylated polysaccharide, the method comprising: chemically linking the O-antigen polysaccharide containing a primary amine in their core obtained by either linking a short spacer containing a primary amine at each end to an O-antigen polysaccharide by reductive amination to obtain an O-antigen polysaccharide-spacer molecule or using underivatized OPS containing L-alanine α-amino group, mixing the O-antigen polysaccharide containing primary amine with a partially oxidized polysaccharide to obtain a mixture; reductively aminating the mixture to form an OPS backbone; and derivatizing the OPS backbone with CDAP and a biotin containing primary amine, thereby forming a backbone polymer, wherein the polysaccharide and the chemically linked O-antigen polysaccharide are biotinylated. Some embodiments provide for a backbone polymer made by the methods disclosed herein.

In some embodiments, the invention provides methods of making a backbone polymer comprising at least one biotinylated O-antigen polysaccharide and at least one non-biotinylated polysaccharide, the method comprising: biotinylating an O-antigen polysaccharide comprising one or more core KDOs and/or heptose moieties with CDAP and a biotin containing primary amine to obtain a biotinylated OPS mixture; partially oxidizing the biotinylated OPS mixture with sodium periodate to introduce aldehydes into the core KDOs and/or heptose moieties; reductively aminating the biotinylation mixture with adipic acid dihydrazide; mixing the biotinylated and aminated OPS with a partially oxidized polysaccharide to form a mixture; and reductively aminating the mixture; thereby forming a backbone polymer, wherein the polysaccharide is not biotinylated and the chemically linked O-antigen polysaccharide is biotinylated. Some embodiments provide for a backbone polymer made by the methods disclosed herein.

In some embodiments, the invention provides methods of making a backbone polymer comprising at least one biotinylated O-antigen polysaccharide and a PLL polymer, the method comprising: reductively aminating an O-antigen polysaccharide containing terminal aldehydes or alpha KDOs with the ε-NH2 groups of a PLL polymer to produce an OPS PLL polymer; derivatizing the OPS with CDAP to form a derivative mixture; reacting the derivative mixture with a biotin containing primary amine; and treating or not treating the mixture with an acylating reagent to cap the unreacted ε-NH2 groups of the PLL polymer; thereby making a backbone polymer, wherein the capped N-acetylated-PLL backbone or uncapped PLL is not biotinylated and the chemically linked O-antigen polysaccharide is biotinylated. In some embodiments, the acylating agent is acetic anhydride or acetyl chloride. In some embodiments, the reducing agent is sodium cyanoborohydride. Some embodiments provide for a backbone polymer made by the methods disclosed herein.

In some embodiments, the invention provides methods of making a backbone polymer comprising at least one non-biotinylated O-antigen polysaccharide, wherein the O-antigen polysaccharide comprises an azido group at its reducing terminal end, and at least one biotinylated polysaccharide containing alkynes groups, the method comprising: chemically click-linking in the presence of a catalyst the O-antigen polysaccharide containing azido groups at their reducing ends with a biotinylated polysaccharide containing alkynes, thereby forming an OPS backbone polymer, wherein the polysaccharide is biotinylated but the chemically click-linked O-antigen polysaccharide is not biotinylated. Some embodiments provide for a backbone polymer made by the methods disclosed herein.

In some embodiments, the invention provides methods of making a backbone polymer comprising at least one non-biotinylated O-antigen polysaccharide, wherein the O-antigen polysaccharide comprises an aldehyde or ketone group at its reducing terminal end, and at least one biotinylated polysaccharide containing primary amino groups obtained by click-linking in the presence of a catalyst the biotinylated polysaccharide containing alkynes groups with a small MW compound containing an azido at one end and a free amino group at the other end, the method comprising: chemically linking the O-antigen polysaccharide containing aldehyde or ketone groups by mixing the O-antigen polysaccharide with a biotinylated polysaccharide containing primary amino groups and reductively aminating the mixture with a reducing agent, thereby forming a backbone polymer, wherein the polysaccharide is biotinylated but the chemically linked O-antigen polysaccharide is not biotinylated. Some embodiments provide for a backbone polymer made by the methods disclosed herein.

In some embodiments, the invention provides methods of making a backbone polymer comprising at least one biotinylated O-antigen polysaccharide, wherein the biotinylated O-antigen polysaccharide comprises an azide group at its reducing terminal end, and at least one non-biotinylated polysaccharide containing alkynes, the method comprising: chemically click-linking in the presence of a catalyst the biotinylated O-antigen polysaccharide containing azido groups at their reducing ends with a non-biotinylated polysaccharide containing alkynes, thereby forming a backbone polymer, wherein the polysaccharide is non-biotinylated and the chemically click-linked O-antigen polysaccharide is biotinylated. In some embodiments, the catalyst for click-linking the O-antigen polysaccharide and the polysaccharide via the alkyne-azide cycloaddition is copper sulfate. In some embodiments, the alkyne group to derivatize the polysaccharide is selected from the group consisting of 1-Amino-3-butyne, 1-Amino-4-pentyne, DBCO-amine, and Alkyne-PEG4-Amine. In some embodiments, the azide group to derivatize the polysaccharide is selected from the group consisting of Azido-PEG3-Amine, Azido-Propylamine and Azido-Butylamine. Some embodiments provide for a backbone polymer made by the methods disclosed herein.

In some embodiments, a fusion protein is or comprises a biotin-binding domain and a polypeptide that is or comprises an amino acid sequence having at least 80%, 85%, 90%, 95%, 96%, 97%, 98%, 99%, or 100% identity to the sequence of any one of SEQ ID NOs:16 to 26. In some embodiments, a fusion protein is or comprises a biotin-binding domain and a polypeptide which is or comprises an amino acid sequence having at least 80%, 85%, 90%, 95%, 96%, 97%, 98%, 99%, or 100% identity to the sequence of any one of SEQ ID NOs:1-3 or 6-26.

In some embodiments, a method of making a variant MAPS comprises complexing at least one backbone polymer described herein with at least one fusion protein described herein. In some embodiments, the variant MAPS is a BP-1 MAPS, a BP-1.2 MAPS, a BP-1.3 MAPS, a BP-2a MAPS, a BP-2b MAPS, or a BP-3 MAPS.

In some embodiments, a method of assessing the immunogenicity of an immunogenic composition described herein, comprises evaluating, measuring, and/or comparing an immune response using one or more in vitro bioassays including B cell and T cell responses such as antibody levels by ELISA, functional antibody levels by FC, OPK and other functional tests like agglutination, motility, cytotoxicity, Th1/Th17 cells and cytokine levels and in vivo assays in animal models of nosocomial disease (*pneumoniae*, sepsis, burn wounds, GI and surgical site infections), such as bacterial clearance, passive and active protection following challenge with the nosocomial pathogens that are the targets of the immunogenic composition. In some embodiments the immune response is compared to a control composition. In some embodiments, a control composition may comprise an antigenic polysaccharide present in the immunogenic composition and not comprising a backbone polymer present in the immunogenic composition. In some embodiments, a control composition may comprise an antigenic polypeptide present in the immunogenic composition and not comprising a backbone polymer present in the immunogenic composition. In some embodiments, a control composition may comprise an antigenic polypeptide present in the immunogenic composition and/or an antigenic polysaccharide present in the immunogenic composition, and not comprising a polymer present in the immunogenic composition.

In some embodiments, a method of assessing the potency of an immunogenic composition described herein, comprises evaluating, measuring, and/or comparing an immune response using one or more in vitro bioassays including B cell and T cell responses such as antibody levels by ELISA, functional antibody levels by FC, OPK and other functional tests like agglutination, motility, cytotoxicity, Th1/Th17 cells and cytokine levels and in vivo assays in animal models of nosocomial disease (*pneumoniae*, sepsis, burn wounds, GI and surgical site infections), such as bacterial clearance, passive and active protection following challenge with the nosocomial pathogens that are the targets of the immunogenic composition. In some embodiments the immune response is compared to a control composition. In some embodiments, a control composition may comprise an antigenic polysaccharide present in the immunogenic composition and not comprising a backbone polymer present in the immunogenic composition. In some embodiments, a control composition may comprise an antigenic polypeptide present in the immunogenic composition and not comprising a backbone polymer present in the immunogenic composition. In some embodiments, a control composition may comprise an antigenic polypeptide present in the immunogenic composition and/or an antigenic polysaccharide present in the immunogenic composition, and not comprising a polymer present in the immunogenic composition.

In some embodiments, a method of assessing the immunogenicity of an vaccine composition described herein, comprises evaluating, measuring, and/or comparing an immune response using one or more in vitro bioassays including B cell and T cell responses such as antibody levels by ELISA, functional antibody levels by FC, OPK and other functional tests like agglutination, motility, cytotoxicity, Th1/Th17 cells and cytokine levels and in vivo assays in animal models of nosocomial disease (*pneumoniae*, sepsis, burn wounds, GI and surgical site infections), such as bacterial clearance, passive and active protection following challenge with the nosocomial pathogens that are the targets of the vaccine composition. In some embodiments the immune response is compared to a control composition. In some embodiments, a control composition may comprise an antigenic polysaccharide present in the vaccine composition and not comprising a backbone polymer present in the vaccine composition. In some embodiments, a control composition may comprise an antigenic polypeptide present in the vaccine composition and not comprising a backbone polymer present in the vaccine composition. In some embodiments, a control composition may comprise an antigenic polypeptide present in the vaccine composition and/or an antigenic polysaccharide present in the vaccine composition, and not comprising a polymer present in the vaccine composition.

In some embodiments, a method of assessing the potency of an vaccine composition described herein, comprises evaluating, measuring, and/or comparing an immune response using one or more in vitro bioassays including B cell and T cell responses such as antibody levels by ELISA, functional antibody levels by FC, OPK and other functional tests like agglutination, motility, cytotoxicity, Th1/Th17 cells and cytokine levels and in vivo assays in animal models of nosocomial disease (*pneumoniae*, sepsis, burn wounds, GI and surgical site infections), such as bacterial clearance, passive and active protection following challenge with the nosocomial pathogens that are the targets of the vaccine composition. In some embodiments the immune response is compared to a control composition. In some embodiments, a control composition may comprise an antigenic polysaccharide present in the vaccine composition and not comprising a backbone polymer present in the vaccine composition. In some embodiments, a control composition may comprise an antigenic polypeptide present in the vaccine composition and not comprising a backbone polymer present in the vaccine composition. In some embodiments, a control composition may comprise an antigenic polypeptide present in the vaccine composition and/or an antigenic polysaccharide present in the vaccine composition, and not comprising a polymer present in the vaccine composition.

In some embodiments, a method of assessing the immunogenicity of an pharmaceutical composition described herein, comprises evaluating, measuring, and/or comparing an immune response using one or more in vitro bioassays including B cell and T cell responses such as antibody levels by ELISA, functional antibody levels by FC, OPK and other functional tests like agglutination, motility, cytotoxicity, Th1/Th17 cells and cytokine levels and in vivo assays in animal models of nosocomial disease (pneumoniae, sepsis, burn wounds, GI and surgical site infections), such as bacterial clearance, passive and active protection following challenge with the nosocomial pathogens that are the targets of the pharmaceutical composition. In some embodiments the immune response is compared to a control composition. In some embodiments, a control composition may comprise an antigenic polysaccharide present in the pharmaceutical composition and not comprising a backbone polymer present in the pharmaceutical composition. In some embodiments, a control composition may comprise an antigenic polypeptide present in the pharmaceutical composition and not comprising a backbone polymer present in the pharmaceutical composition. In some embodiments, a control composition may comprise an antigenic polypeptide present in the pharmaceutical composition and/or an antigenic polysaccharide present in the pharmaceutical composition, and not comprising a polymer present in the pharmaceutical composition.

In some embodiments, a method of assessing the potency of an pharmaceutical composition described herein, comprises evaluating, measuring, and/or comparing an immune response using one or more in vitro bioassays including B cell and T cell responses such as antibody levels by ELISA, functional antibody levels by FC, OPK and other functional tests like agglutination, motility, cytotoxicity, Th1/Th17 cells and cytokine levels and in vivo assays in animal models of nosocomial disease (pneumoniae, sepsis, burn wounds, GI and surgical site infections), such as bacterial clearance, passive and active protection following challenge with the nosocomial pathogens that are the targets of the pharmaceutical composition. In some embodiments the immune response is compared to a control composition. In some embodiments, a control composition may comprise an antigenic polysaccharide present in the pharmaceutical composition and not comprising a backbone polymer present in the pharmaceutical composition. In some embodiments, a control composition may comprise an antigenic polypeptide present in the pharmaceutical composition and not comprising a backbone polymer present in the pharmaceutical composition. In some embodiments, a control composition may comprise an antigenic polypeptide present in the pharmaceutical composition and/or an antigenic polysaccharide present in the pharmaceutical composition, and not comprising a polymer present in the pharmaceutical composition.

List of Common Abbreviations

ADH: Adipic Dihydrazide; AMR: antimicrobial resistance; AU: arbitrary unit; BB: Backbone; BP: Backbone Polymer; CDAP: 1-cyano-4-dimethylaminopyridinium tetrafluoro borate; CDC: Center for Disease Control and Prevention; CDM: chemically defined media; CF: Cystic Fibrosis; CP: Common Part; CPS: Capsular Polysaccharide; CFU: colony forming units; COPS: Core 0 Polysaccharide; CT: cholera toxin; DNA: deoxyribonucleic acid; DTT: Dithiothreitol; EC: *Escherichia coli*; EDC: 1-Ethyl-3-(3-dimethylaminopropyl)-carbodiimide; ELISA: enzyme linked immunosorbent assay; ELISpot: enzyme linked immunospot; ETEC: enterotoxic *E. coli*; FC: Flow Cytometry; FT; Flow Through; GI: gastrointestinal; GNB: gram-negative bacteria; GNR: gram-negative rod; H-NMR: proton nuclear magnetic resonance; HA: hemagglutination; HK: heat killed; HL-60 cells: human promyelocytic leukemia cells; HPLC: high performance liquid chromatography; IATS: International Antigenic Typing Scheme; ICU: intensive care unit; IEC: Ion Exchange Chromatography; IFN: Interferon; IL: Interleukin; IM: intramuscular; IN: intranasal; IP: intraperitoneal; IV: intravenously; IVIG: intravenous immunoglobulin; Ig: immunoglobulin; KDO: keto acid group; KP: *Klebsiella pneumoniae*; KO: *Klebsiella oxytoca*; LAL: limulus amoebocyte lysate: LPS: Lipopolysaccharide; mAb: monoclonal antibody; MALLS: multiangle laser light scattering; MAPS: multiple antigen presentation system; MDR: multi-drug resistant; MHC: major histocompatibility complex; MW: molecular weight; NAPLL: N-Acetyl Poly-L-Lysine; NaBH$_3$CN: Sodium cyanoborohydride; NaIO$_4$: Sodium metaperiodate; NHS: N-hydroxysuccinimide; NHS: Normal Human Serum; NMR: Nuclear Magnetic Resonance; OD: optical density; OMP: outer membrane protein; OPA: opsonophagocytic assay; OPK: opsonophagocytic OPS: O Polysaccharide; PA: *Pseudomonas aeruginosa*; PCR: polymerase chain reaction; PBS: phosphate buffered solution; PEG: Polyethlene glycol; PMN: Polymorphonuclear leukocytes; PLL: Poly-L-Lysine; PO: perorally; PPG: Polypropylene glycol; PRO-CN: Carrier protein control; PT: Pertussis toxin; RCB: research cell bank; RI: refractive index; RIA: radioimmunoassay; RNA: ribonucleic acid; RPM: rotations per minutes; SBA: serum bactericidal assay; SC: Subcutaneously; SDS: sodium dodecyl sulfate; SDS-PAGE: sodium dodecyl sulfate polyacrylamide gel electrophoresis: SEC: Size Exclusion Chromatography; TFF: Tangential flow filtration; TLR: toll-like receptor; TNF: tumor necrosis factor; TTSS: type three secretion system, UF: Ultrafiltration; US: United States; WFI: Water For Injection.

BRIEF DESCRIPTION OF THE DRAWING

The present teachings described herein will be more fully understood from the following description of various illustrative embodiments, when read together with the accompanying drawings. It should be understood that the drawings described below are for illustration purposes only and are not intended to limit the scope of the present teachings in any way.

FIG. 1B shows the chemical structure of the repeating 0 polysaccharide (OPS) units of several of the different PA core internationally accepted typing standard (IATS) types. FIG. 1D shows the chemical structure of the repeating units of several of the *K. pneumoniae* (KP) OPS with the 2,5 anhydromannose at the reducing end of the CP of the OPS.

FIG. 7B depicts an exemplary schematic of a BP-2a MAPS complex with a rhizavidin fusion protein and an OPS BP-2a.

FIG. 10 upper panel shows an exemplary SEC elution profile on a Superdex-200 column of BP-2a MAPS complexes of the Rhavi-FlaBD2-MrkA fusion protein with K19: KPO2-ADH BP-2a. FIG. 10 lower panel shows a screening by sodium dodecyl sulfate polyacrylamide gel electrophoresis (SDS-PAGE) and total protein stain of the fractions eluting from the SEC column, samples were processed without heat in sodium dodecyl sulfate (SDS) sample buffer with 10 mM Dithiothreitol (DTT) prior to SDS-PAGE to allow MAPS complexes to remain intact.

FIG. 11A depicts an exemplary SDS-PAGE of variant BP-1 MAPS complexes between the rhizavidin fusion protein (PRO-CN) formed separately with PA O10 OPS BP-1 (lanes 4 and 5), PA O1 OPS BP-1 (lanes 6 and 7) and PA O2 OPS BP-1 (lanes 8 and 9).

FIG. 11B depicts an exemplary SDS-PAGE of BP-1 variant MAPS complexes between the rhizavidin-FlaB- PcrV protein (Rhavi-FlaB-PcrV) formed separately with PA O10 OPS BP-1 (lanes 4 and 5), PA O1 OPS BP-1 (lanes 6 and 7) and PA O2 OPS BP-1 (lanes 8 and 9).

FIG. 11C depicts an exemplary SDS-PAGE of BP-1 variant MAPS complexes between the rhizavidin-FlaB-D2-MrkA protein (Rhavi-FlaBD2-MrkA) with PA O10 OPS BP-1 (lanes 4 and 5), PA O1 OPS (lanes 6 and 7) and PA O2 OPS BP-1 (lanes 8 and 9). In FIGS. 11A-11C, Rhizavidin fusion protein alone was run as a control (lanes 1 and 2). Each of the samples was processed with heat (by boiling) (lanes 1, 4, 6 and 8) and without heat (lanes 2, 5, 7 and 9). BP-1 variant MAPS complexes were not disrupted without heat, and the protein in the BP-1 variant MAPS complexes was retained at the very top of the gel. With boiling, BP-1 variant MAPS complexes were disrupted, the protein was released and the protein dimer was also disassociated. A protein molecular weight marker was also included (lane 3) and the molecular weight of standard is indicated to the left of the gel in kDa.

FIG. 13A upper panel: immunoglobulin (IgG) response to PnCPS 19A with PRO-CN; rhizavidin alone (Rhavi); rhizavidin-FlaB-D2 (FlaBD2); rhizavidin-FlaA2-D2 (FlaA2D2); rhizavidin-FlaB-PcrV (FlaB-PcrV); rhizavidin-FlaB-D2-MrkA (FlaBD2-MrkA); rhizavidin-PcrV-MrkA (PcrV-MrkA). FIG. 13A lower panel: PRO-CN; rhizavidin-PcrV (PcrV); rhizavidin-FlaB (FlaB); rhizavidin-FlaA1 (FlaA1); rhizavidin-FlaA2 (FlaA2); rhizavidin-MrkA (MrkA). FIG. 13B upper panel: IgG response to PnCPS 6B with PRO-CN; rhizavidin alone (Rhavi); rhizavidin-FlaB-D2 (FlaBD2); rhizavidin-FlaA2-D2 (FlaA2D2); rhizavidin-FlaB-PcrV (FlaB-PcrV); rhizavidin-FlaB-D2-MrkA (FlaBD2-MrkA); rhizavidin-PcrV-MrkA (PcrV-MrkA). FIG. 13B lower panel: PRO-CN; rhizavidin-PcrV (PcrV); rhizavidin-FlaB (FlaB); rhizavidin-FlaA1 (FlaA1); rhizavidin-FlaA2 (FlaA2); rhizavidin-MrkA (MrkA).

FIG. 19B (lower panel) shows FC total binding events to the same three *Klebsiella* O1 strains of a serum from a rabbit vaccinated with a 2-valent KP O1, O5 OPS BP-1 PRO-CN MAPS. These binding data suggest that the amount of CPS affected OPS exposure possibly influenced by growth conditions.

DEFINITIONS

Figure 1A:
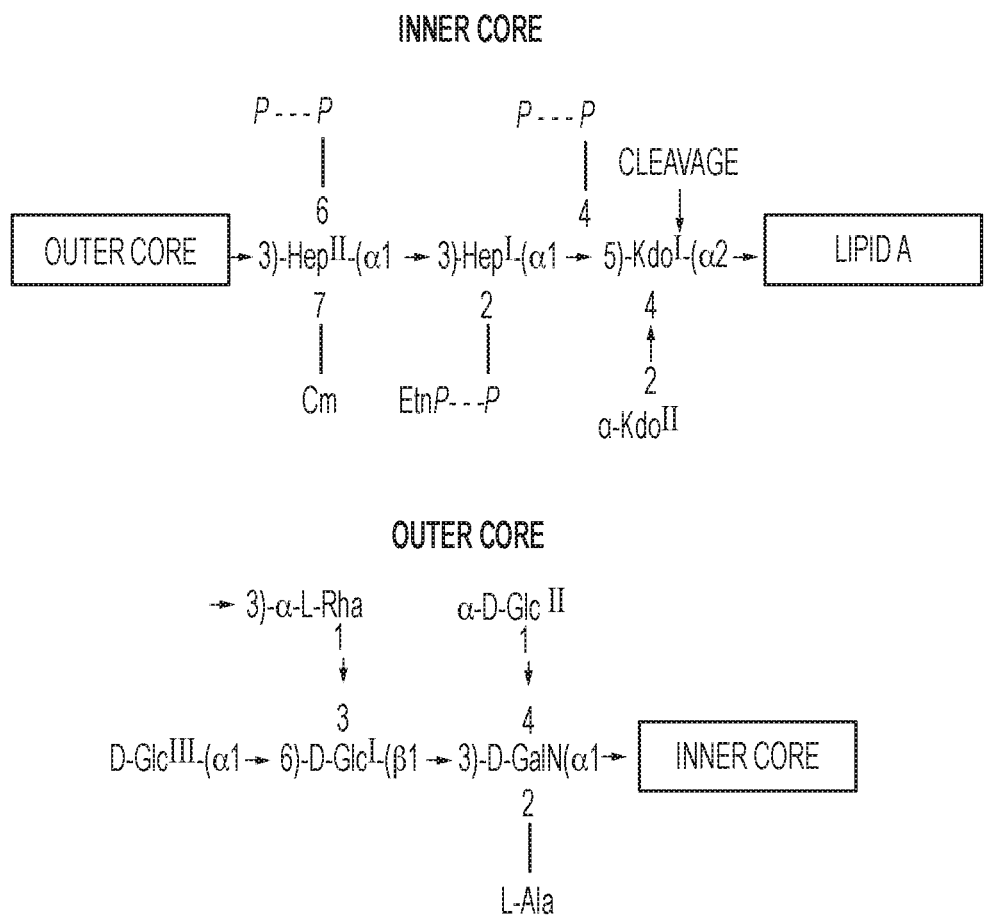
FIG. 1A shows the chemical structure of the inner core (top) and the outer core (bottom) of the lipopolysaccharide from *P. aeruginosa* (PA), an arrow labeled "cleavage" points to the site of cleavage mediated by acetic acid between the "keto acid groups" (KDO) and the lipid A molecule.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastrical, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Amino acid: In its broadest sense, the term "amino acid", as used herein, refers to any compound and/or substance that can be incorporated into a polypeptide chain, e.g., through formation of one or more peptide bonds. In some embodiments, an amino acid has the general structure $H_2N$—$C(H)$(R)—COOH. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kDa tetrameric agents comprised of two identical heavy chain polypeptides (about 50 kDa each) and two identical light chain polypeptides (about 25 kDa each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies) (TandAb®; VI-11-1s; Anticalins®; Nanobodies® minibodies; BiTE® s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., polyethylene glycol, etc.]

Antigen: The term "antigen", as used herein, refers to (i) an agent that elicits an immune response; and/or (ii) an agent that binds to a T cell receptor (e.g., when presented by an MHC molecule) or to an antibody. In some embodiments, an antigen elicits a humoral response (e.g., including production of antigen-specific antibodies); in some embodiments, an elicits a cellular response (e.g., involving T cells whose receptors specifically interact with the antigen). In some embodiments, an antigen elicits a humoral response and a cellular response. In some embodiments, and antigen binds to an antibody and may or may not induce a particular physiological response in an organism. In general, an antigen may be or include any chemical entity such as, for example, a small molecule, a nucleic acid, a polypeptide, a carbohydrate, a lipid, a polymer (in some embodiments other than a biologic polymer (e.g., other than a nucleic acid or amino acid polymer)), etc. In some embodiments, an antigen is or comprises a polypeptide. In some embodiments, an antigen is or comprises a polysaccharide. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is a recombinant antigen.

Associated with: Two entities are "associated" with one another, as that term is used herein, if the presence, level and/or form of one is correlated with that of the other. In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of affinity interactions, hydrogen bonds, van der Waals interaction, hydrophobic interactions, magnetism, and combinations thereof.

Backbone Polymer: As used herein the term "backbone polymer" refers to a polymer to which one or more polysaccharides (e.g., antigenic polysaccharides) is or can be conjugated. In some embodiments, a backbone polymer is a polymer and one or more polysaccharides (e.g., antigenic polysaccharides) conjugated to the polymer.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Carrier protein: As used herein, the term "carrier protein" refers to a protein or peptide that elicits or improves an immune response to a coupled or complexed hapten. In some embodiments, an immune response elicited or improved by a carrier protein is a response to the hapten. In some embodiments, no significant response to the carrier protein itself occurs; in some embodiments, response to the carrier protein may be detected. In some embodiments a carrier protein is complexed with one or more other molecules.

Click Chemistry: As used herein, the term "click chemistry" refers to a rapid and high yielding reaction, e.g., as described by K. B. Sharpless in 2001. In some embodiments, a click chemistry reaction creates byproducts that can be removed without chromatography. In some embodiments, a click chemistry reaction only creates byproducts that can be removed without chromatography. In some embodiments, a click chemistry reaction is stereospecific. In some embodiments, a click chemistry reaction may be conducted using one or more easily removable solvents. In some embodiments, a click chemistry reaction may be conducted using one or more benign solvents. In some embodiments, a click chemistry reaction utilizes a copper-catalyzed azide-alkyne cycloaddition reaction to connect one or more molecular entities. In some embodiments, the one or more molecular entities are not limited by molecular size. In some embodiments, a click chemistry reaction may be bio-orthogonal; e.g., neither the reactants nor their products' functional groups interact with functionalized biomolecules and/or the reaction proceed with ease under mild nontoxic conditions, such as at room temperature and, preferably, in water. In some embodiments, a click chemistry reaction may be the copper-catalyzed Huisgen cycloaddition, azide-alkyne [3+2] dipolar cycloaddition, Staudinger ligation, or azide-phosphine ligation. In some embodiments click chemistry may be used to link two biopolymers together (e.g. two nucleic acids, or a nucleic acid and a protein or a peptide, or two glycopolymers, etc.).

Colonization (e.g., of mucosa or GI tract): As used herein, the term "colonization" refers to the ability of a microbe to establish a niche at an anatomical site, e.g., a mucosal membrane, injury site, organ, etc.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Composition: Those skilled in the art will appreciate that the term "composition", as used herein, may be used to refer to a discrete physical entity that comprises one or more specified components. In general, unless otherwise specified, a composition may be of any form—e.g., gas, gel, liquid, solid, etc.

Derivative: As used herein, the term "derivative" refers to a structural analogue of a reference substance. That is, a "derivative" is a substance that shows significant structural similarity with the reference substance, for example sharing a core or consensus structure, but also differs in certain discrete ways. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, etc.).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Epitope: As used herein, the term "epitope" includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Exopolysaccharide: The term "exopolysaccharide" as used herein refers to natural polymers of high molecular weight composed of sugar residues and secreted by microorganisms into their environment. Exopolysaccharides may be referred to interchangeably as extracellular polysaccharides (EPSs). EPSs establish the functional and structural integrity of biofilms, and are considered the fundamental component that determines the physiochemical properties of a biofilm. EPSs constitute 50% to 90% of a biofilm's total organic matter.

Fragment: A "fragment" of a material or entity as described herein has a structure that includes a discrete portion of the whole, but lacks one or more moieties found in the whole. In some embodiments, a fragment consists of such a discrete portion. In some embodiments, a fragment includes a discrete portion of the whole which discrete portion shares one or more functional characteristics found in the whole. In some embodiments, a fragment consists of such a discrete portion. In some embodiments, a fragment consists of or comprises a characteristic structural element or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may in some embodiments be referred to as the "parent" of the whole.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgap-dna.CMP matrix.

"Improve," "increase", "inhibit" or "reduce": As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

Isolated: As used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced Linker: As used herein, is used to refer to that portion of a multi-element agent that connects different elements to one another. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (Holliger et al., 1993; Poljak, 1994).

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Polysaccharide: The term "ppolysaccharide" as used herein refers to a polymeric carbohydrate molecule composed of long chains of monosaccharide units bound together by glycosidic linkages and on hydrolysis give the constituent monosaccharides or oligosaccharides. Ppolysaccharides range in structure from linear to highly branched. Examples include storage polysaccharides such as starch and glycogen, structural polysaccharides such as cellulose and chitin and microbial polysaccharides, and antigenic polysaccharides found in microorganisms including, but not limited to, OPS, CPS, COPS, and LPS.

Prevent or prevention: As used herein when used in connection with the occurrence of a disease, disorder, and/or condition, prevent or prevention refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof.

Prevention: The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. Prevention may be considered complete when onset of a disease, disorder or condition has been delayed for a predefined period of time.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain l-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Recombinant: As used herein, is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Tumor or subject response may be measured according to a wide variety of criteria, including clinical criteria and objective criteria. Techniques for assessing response include, but are not limited to, clinical examination, positron emission tomography, chest X-ray CT scan, MRI, ultrasound, endoscopy, laparoscopy, presence or level of tumor markers in a sample obtained from a subject, cytology, and/or histology. Many of these techniques attempt to determine the size of a tumor or otherwise determine the total tumor burden. Methods and guidelines for assessing response to treatment are discussed in Therasse et. al. (2000) "New guidelines to evaluate the response to treatment in solid tumors", European Organization for Research and Treatment of Cancer, National Cancer Institute of the United States, National Cancer Institute of Canada. The exact response criteria can be selected in any appropriate manner, provided that when comparing groups of tumors and/or patients, the groups to be compared are assessed based on the same or comparable criteria for determining response rate. One of ordinary skill in the art will be able to select appropriate criteria.

Risk: As will be understood from context, "risk" of a disease, disorder, and/or condition refers to a likelihood that a particular individual will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is 0, 1, 2, 3, 4, 5, 6, 7, 8, 9, 10, or more.

Serotype: As used herein, the term "serotype", also referred to as a serovar, refers to a distinct variation within a species of bacteria or virus or among immune cells of different individuals. These microorganisms, viruses, or cells are classified together based on their cell surface antigens, allowing the epidemiologic classification of organisms to the sub-species level. A group of serovars with common antigens may be referred to as a serogroup or sometimes serocomplex.

Short oligosaccharide: For purposes of the present disclosure, an oligosaccharide is typically considered to be "short" if it has fewer than 4, or certainly fewer than 3, residues in any linear chain.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Susceptible to: An individual who is "susceptible to" a disease, disorder, or condition is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen. In some embodiments a therapeutically effective amount may reference an amount of an immunogenic composition or vaccine which is suitable to elicit an immune response. For example, the "therapeutically effective amount" refers to a nontoxic but sufficient amount that can be an amount to treat, attenuate, or prevent infection and/or disease (e.g., bacterial infection, pneumococcal infection, etc.) in any subject.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Variant: As used herein in the context of molecules, e.g., nucleic acids, proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence and/or one or more differences in chemical moieties (e.g., carbohydrates, lipids, phosphate groups) that are covalently components of the polypeptide or nucleic acid (e.g., that are attached to the polypeptide or nucleic acid backbone). In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid. In some embodiments, a variant polypeptide or nucleic acid lacks one or more of the biological activities of the reference polypeptide or nucleic acid. In some embodiments, a variant polypeptide or nucleic acid shows a reduced level of one or more biological activities as compared to the reference polypeptide or nucleic acid. In some embodiments, a polypeptide or nucleic acid of interest is considered to be a "variant" of a reference polypeptide or nucleic acid if it has an amino acid or nucleotide sequence that is identical to that of the reference but for a small number of sequence alterations at particular positions. Typically, fewer than about 20%, about 15%, about 10%, about 9%, about 8%, about 7%, about 6%, about 5%, about 4%, about 3%, or about 2% of the residues in a variant are substituted, inserted, or deleted, as compared to the reference. In some embodiments, a variant polypeptide or nucleic acid comprises about 10, about 9, about 8, about 7, about 6, about 5, about 4, about 3, about 2, or about 1 substituted residues as compared to a reference. Often, a variant polypeptide or nucleic acid comprises a very small number (e.g., fewer than about 5, about 4, about 3, about 2, or about 1) number of substituted, inserted, or deleted, functional residues (i.e., residues that participate in a particular biological activity) relative to the reference. In some embodiments, a variant polypeptide or nucleic acid comprises not more than about 5, about 4, about 3, about 2, or about 1 addition or deletion, and, in some embodiments, comprises no additions or deletions, as compared to the reference. In some embodiments, a variant polypeptide or nucleic acid comprises fewer than about 25, about 20, about 19, about 18, about 17, about 16, about 15, about 14, about 13, about 10, about 9, about 8, about 7, about 6, and commonly fewer than about 5, about 4, about 3, or about 2 additions or deletions as compared to the reference. In some embodiments, a reference polypeptide or nucleic acid is one found in nature. In some embodiments, a reference polypeptide or nucleic acid is a human polypeptide or nucleic acid.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

DETAILED DESCRIPTION OF CERTAIN EMBODIMENTS

The present disclosure relates, generally, to compositions, system, and methods that include complexed proteins and polysaccharides, e.g., vaccines of complexed proteins and polysaccharides. Such complexes can be used, e.g., to induce and/or increase an immunoprotective response in patients at risk of nosocomial infection.

A nosocomial infection is an infection that is acquired in a hospital or other health care facility at least about 48 hr after admission. To emphasize both hospital and nonhospital settings, nosocomial infection is sometimes instead called a health care-associated infection (HAI or HCAI). In some embodiments, a nosocomial infection may be acquired in hospital, nursing home, rehabilitation facility, outpatient clinic, or other clinical settings. In some embodiments nosocomial infection is spread to the susceptible patient in the clinical setting by various means. In some embodiments, health care staff can spread nosocomial infection, in addition to contaminated equipment, bed linens, or air droplets. In some embodiments, nosocomial infection can originate from the outside environment, another infected patient, staff that may be infected, or in some cases, the source of the nosocomial infection cannot be determined. In some cases, a microorganism causing nosocomial infection originates from the patient's own skin microbiota, becoming opportunistic after surgery or other procedures that compromise the protective skin barrier. Though a patient may have contracted the infection from their own skin, such an infection is still considered nosocomial since it develops in the health care setting.

Antimicrobial Resistance

There is a growing appreciation for the role of vaccines in confronting the problem of antimicrobial resistance (AMR). Vaccines can reduce the prevalence of resistance by reducing the need for antimicrobial use and can reduce its impact by reducing the total number of cases. By reducing the number of pathogens that may be responsible for a particular clinical syndrome, vaccines can permit the use of narrower-spectrum antibiotics for empirical therapy. These effects may be amplified by herd immunity, extending protection to unvaccinated persons in the population. Because much selection for resistance is due to selection on bystander members of the normal flora, vaccination can reduce pressure for resistance even in pathogens not included in the vaccine. Some vaccines have had disproportionate effects on drug-resistant lineages within the target species, a benefit that could be more deliberately exploited in vaccine design (Lipsitch and Siber, 2016). The benefits of vaccines in combating AMR by each of these mechanisms can be amplified by the indirect protection, or herd immunity (Fine, 1993), that results when vaccinated individuals do not themselves become infected or colonized, and hence do not transmit the pathogen to others. In this way, infections, resistant infections, and antimicrobial use can be reduced not only in vaccinated individuals but also in their contacts. Finally, for vaccines against organisms which asymptomatically colonize the nasopharynx, skin, gut, or other sites, there is the theoretical possibility that reducing the density of microbial populations by vaccination reduces the opportunities for genetic exchange of resistance elements (Levin et al., 1979; Levin and Cornejo, 2009).

Vaccines of particular interest are those targeting the most important causes of HAI which are frequently resistant to multiple antibiotics (CDC, 2013; Chang et al., 2015). The most common causes of HAI include multiple resistant gram-negative bacteria; recent publications report isolates from across the globe that have become resistant to the last-resort agents, polymyxin B and colistin (Du et al., 2015: Liu et al., 2016). Resistance to first- and second-line agents is also a problem in gram-positive organisms. Candida species are important causes of mucosal and disseminated infections in immunocompromised patients and as a consequence of antimicrobial therapy (CDC, 2013). The gram-negative E. coli, Pseudomonas, Klebsiella and Acinetobacter species are also becoming increasingly resistant to multiple antibiotics (McGann et al., 2016; Collignon, 2009; Agodi et al., 2011, WHO report, 2014). To address this knowledge gap, the CDC began a three-phase effort in 2009 to develop and conduct a multistate prevalence survey of HAI and use of antimicrobial agents. Prevalence surveys have been used in other countries to describe the scope and magnitude of the problem of such infections. The CDC effort culminated in 2011 in a large-scale survey that estimated the prevalence of HAI in acute care hospitals, determined the distribution of these infections according to infection site and pathogen as seen in Table 1, and generated updated estimates of the national burden of these infections (Magill et al., 2014).

Surveys were conducted in the US in 183 hospitals (Magill et al., 2014). Of 11,282 patients, 452 had 1 or more HAI (4.0%; 95% confidence interval, 3.7 to 4.4). Of 504 such infections, the most common types were pneumonia (21.8%), surgical-site infections (21.8%), and gastrointestinal (GI) infections (17.1%). C. difficile was the most commonly reported pathogen (causing 12.1% of health care-associated infections). Device-associated infections (i.e., central-catheter-associated bloodstream infection, catheter-associated urinary tract infection, and ventilator-associated pneumonia), which have traditionally been the focus of programs to prevent HAI, accounted for 25.6% of such infections. The authors estimated that there were 648,000 patients with 721,800 HAI in US acute care hospitals in 2011. Targeting K. pneumoniae, P. aeruginosa, E. coli, or a combination thereof by vaccination in hospital settings would significantly impact the incidence of most common HAI infections such as pneumonia, surgical-site and urinary tract infections as well as reducing the prevalence of antibiotic resistance as shown in Table 1.

TABLE 1

Multistate Point-Prevalence Survey of HAI: According to Type of Infection (Magill et al., 2014)

| Pathogen | All Sites | Pneumonia | Surgical Site Infections | BSI | UTI | GI Infections |
|---|---|---|---|---|---|---|
| K. pneumoniae | 9.9% | 11.8% | 13.6% | 8% | 23.1%* | 1.2% |
| P. aeruginosa | 7.1% | 12.7%* | 6.4%* | 4% | 10.8%* | 1.2% |
| A. baumannii | 1.6% | 3.6%* | 1.8% | 0% | 0% | 0% |
| E. coli | 9.3% | 2.7% | 12.7%* | 10% | 27.7%* | 1.2% |
| S. aureus | 10.7% | 16.4%* | 15.5%* | 14% | 3.1% | 1.2% |
| C. difficile | 12.1% | 0% | 0% | 0% | 0% | 70.9%* |
| Candida | 6.3% | 3.6% | 2.7% | 22%* | 4.6% | 3.5% |

*Most multiple antibiotic resistant bacteria are in these groups

Immunogenic Complexes

The present disclosure encompasses immunogenic complexes that include backbone polymers, polysaccharides, and polypeptides.

In some embodiments immunogenic complexes are multiple antigen presenting systems (MAPS). Certain MAPS systems have been previously described in WO 2012/155007. In general, an immunogenic complex described herein represents new variant MAPS-type complexes which include (i) a backbone polymer comprising a polymer and one or more polysaccharides (e.g., antigenic polysaccharides) conjugated to the polymer; and (ii) one or more polypeptides (e.g., antigenic polypeptides and/or carrier peptides) non-covalently complexed with the polymer and/or the antigenic polysaccharide. Some exemplary backbone polymers are depicted in the immunogenic complexes shown in FIGS. 7A-7D. In some embodiments, the variant MAPS complex is a BP-1 MAPS. In some embodiments the variant MAPS complex is a BP-1.2 MAPS. In some embodiments, the variant MAPS complex is a BP-2a MAPS. In some embodiments, the variant MAPS complex is a BP-2b MAPS. In some embodiments, the variant MAPS complex is a BP-3 MAPS.

In some embodiments, one or more polypeptide antigens are non-covalently complexed with a backbone polymer, and/or an antigenic polysaccharide conjugated to said polymer, by formation of at least one affinity molecule/complementary affinity molecule pair comprising (i) a first affinity molecule associated with the polymer and/or antigenic polysaccharide; and (ii) a complementary affinity molecule associated with one or more polypeptide antigens. In some embodiments, the one or more polysaccharides are chemically linked to the polymer. In some embodiments, the one or more antigenic polysaccharides are derived from gram-negative bacteria and/or gram-positive bacteria. In some embodiments, one or more microbial antigenic polysaccharides are derived from K. pneumoniae, P. aeruginosa, and E. coli antigenic polysaccharides.

In some embodiments, one or more polypeptides are covalently linked (e.g., fused) to a complementary affinity molecule described herein.

In some embodiments, one or more antigenic polysaccharides are conjugated to a backbone polymer. In some embodiments, one or more antigenic polysaccharides are conjugated to the backbone polymer in a ratio of about 0.01 to about 10 w/w. In some embodiments, one or more antigenic polysaccharides are conjugated to the backbone polymer in a ratio of about 0.01 to about 0.1 w/w. In some embodiments, one or more antigenic polysaccharides are conjugated to the backbone polymer in a ratio of about 0.01 to about 1 w/w. In some embodiments, one or more antigenic polysaccharides are conjugated to the backbone polymer in a ratio of about 0.1 to about 1 w/w. In some embodiments, one or more antigenic polysaccharides are conjugated to the backbone polymer in a ratio of about 0.1 to about 10 w/w. In some embodiments, one or more antigenic polysaccharides are conjugated to the backbone polymer in a ratio of about 1 to about 10 w/w.

In some embodiments, one or more antigenic polysaccharides are derived from one or more pathogens. In some embodiments, one or more antigenic polysaccharides are derived from 1, 2, 3, 4, 5, 6, 7, 8, 9, 10, 11, 12, 13, 14, 15, 16, 17, 18, 19, 20, 21, 22, 23, 24, or 25 serotypes or strains of a pathogen.

In some embodiments, a backbone polymer comprises one or more affinity molecules conjugated to the backbone polymer. In some embodiments, the antigenic polysaccharides comprise one or more affinity molecules conjugated to the antigenic polysaccharides. In some embodiments, the backbone polymer and the antigenic polysaccharides are conjugated to one or more affinity molecules. In some embodiments, the backbone polymer is conjugated to one or more affinity molecules and the antigenic polysaccharides are not conjugated to an affinity molecule. In some embodiments, the backbone polymer is not conjugated to an affinity molecule and the antigenic polysaccharides are conjugated to one or more affinity molecules. In some embodiments, the affinity molecules comprise biotin or biotin derivatives.

In some embodiments, a backbone polymer comprises a plurality of affinity molecules conjugated to the backbone polymer. In some embodiments, the antigenic polysaccharides comprise a plurality of affinity molecules conjugated to the antigenic polysaccharides. In some embodiments, the backbone polymer and the antigenic polysaccharides are conjugated to a plurality of affinity molecules. In some embodiments, the backbone polymer is conjugated to a plurality of affinity molecules and the antigenic polysaccharides are not conjugated to an affinity molecule. In some embodiments, the backbone polymer is not conjugated to an affinity molecule and the antigenic polysaccharides are conjugated to a plurality of affinity molecules. In some embodiments, the affinity molecules comprise biotin or biotin derivatives.

In some embodiments, polysaccharides and/or polypeptides that may be included in immunogenic complexes are recombinantly or synthetically produced. In some embodiments, polysaccharides and/or polypeptides that can be included in immunogenic complexes are isolated and/or derived from natural sources. Exemplary polysaccharides and/or polypeptides are described below.

Klebsiella

The vast majority of Klebsiella infections are associated with hospitalization. As opportunistic pathogens, Klebsiella spp. primarily attack immunocompromised individuals who are hospitalized and suffer from severe underlying diseases such as diabetes mellitus or chronic pulmonary obstruction. Nosocomial Klebsiella infections are caused mainly by K. pneumoniae, the medically most important species of the genus. It is estimated that Klebsiella spp. cause 8% of all nosocomial bacterial infections in the US and in Europe (Podschun and Ullmann, 1998). No great geographical variations in frequency have been noted, except for hypervirulent K1-encapsualted strains that are found predominantly in Asia, and uncommon in Europe and the Western Hemisphere. In the US, Klebsiella accounts for 3 to 7% of all nosocomial bacterial infections, placing them among the eight most important infectious pathogens in hospitals (Horan et al., 1988; Schaberg et al., 1991), and data collected from the United Kingdom (Bergogne-Berezin, 1995) and from Germany (Ullmann, 1986) are remarkably similar to those reported by the CDC. Thus, in some embodiments, an immunogenic complex described herein includes one or more Klebsiella polysaccharides and/or polypeptides.

In some embodiments, an immunogenic complex described herein includes one or more Klebsiella LPS-derived and/or CPS polysaccharides. In some embodiments, LPS-derived polysaccharides are OPS. In some embodiments LPS-derived polysaccharides are COPS. Capsules are produced by almost all Klebsiella strains; they represent the outermost layer of surface structures in contact with the host milieu, and they have been proven to be highly immunogenic and nontoxic (Cryz et al., 1985). A disadvantage of a Klebsiella pneumoniae (KP) CPS vaccine is the great number of capsule (K) antigens (over 80 different antigens). However, in a study of the incidence of the capsule types among bacteremic Klebsiella isolates, it was observed that only 25 serotypes made up 70% of all bacteremic strains (Cryz et al., 1986a). Based on their sero-epidemiological findings, a 24-valent KP CPS vaccine was formulated that subsequently was proven to be safe and immunogenic (Edelman et al., 1994). However, plain polysaccharides are not sufficiently immunogenic on their own to mount and sustain a long and effective memory response and must often be conjugated to proteins to be effective. Developing a 24-valent KP polysaccharide conjugate vaccine is complicated and challenging, as combining 24 glycoconjugates into one vaccine may require balancing the immunogenicity elicited by each component.

Due to their endotoxic properties, LPS are considered important in the pathology of septicemia. Until recently, Klebsiella LPS 0 antigens were generally considered to be masked by the CPS and thus not exposed on the bacterial surface. Several studies, however, demonstrated surface exposure and antibody accessibility of 0 antigens in strains expressing particular capsular serotypes (Tomas et al., 1988). In contrast to the K antigens, only eight 0 types are known, 01 being the most commonly found 0 type in clinical isolates. Four KP Isolates (O1, O2, O3, O5) account for the majority of clinical isolates (Hansen et al., 1999). The administration of monoclonal antibodies (mAbs) to the Klebsiella 01 antigen has been reported to be protective in a mouse model of lethal endotoxemia (Mandine et al., 1990).

In some embodiments, an immunogenic complex described herein includes a Klebsiella type 3 pili protein or polypeptide. Unlike other fimbriae, type 3 pili agglutinate erythrocytes that have been treated with tannin. Although its name, mannose-resistant, Klebsiella-like hemagglutinin (MR/K-HA), implies that this fimbrial type is synthesized only by Klebsiella, later studies demonstrated that type 3 pili occur in many enteric genera (Clegg and Gerlach, 1987). Moreover, type 3 pili apparently are not identical in all genera of enterobacteria, since serological studies showed considerable antigenic diversity (Old and Adegbola, 1985). Originally described as the adhesion organelles of Klebsiella inhabiting plant roots, these pili were later found to be capable of binding to various human cells. Strains of K. pneumoniae expressing type 3 pili adhere to endothelial cells, epithelia of the respiratory tract, and uroepithelial cells (Hornick et al., 1992; Tarkkanen et al., 1997; Würker et al, 1990). In the kidneys, these pili mediate bacterial adhesion to tubular basement membranes, Bowman's capsules, and renal vessels (Tarkkanen et al., 1990). MrkA is a major protein of the type III fimbriae complex and has been implicated in host cell attachment and biofilm formation (Murphy and Clegg, 2012), a strategy bacterial pathogens use to establish infection (Burmolle et al., 2008). MrkA but not adhesin (MrkD) was previously shown to facilitate biofilm formation (Langstraat et al., 2001). MrkA antigen exhibits a high degree of sequence conservation among different KP isolates and is general accessible as an extracellular target (Wang et al., 2016). MrkA from the two most dominant pathogenic isolates, *K. pneumoniae* and *Klebsiella oxytoca*, exhibits 95% homology. In addition, the MrkA homology among representative members of the Enterobacteriaceae family is >90% and so these sequence data suggest a potential opportunity to develop a MrkA-based anti-*K. pneumoniae* and pan-gram-negative bacteria strategy.

*Klebsiella pneumoniae* Polysaccharides

In some embodiments, an immunogenic complex described herein includes one or more *K. pneumoniae* polysaccharides. Besides the CPS (e.g., K antigen) the OPS is another important virulence factor for *K. pneumoniae*. There are at least 9 sub-types of *K. pneumoniae* OPS, each having a different polysaccharide chemical structure. In some embodiments, OPS polysaccharides are included in an immune complex described herein. Each of the serotype designations as used herein is designated according to the World Health Organization (WHO) collaborating Centre for Reference and Research on *Escherichia* and *Klebsiella*.

In some embodiments, an immunogenic complex includes one or more *Klebsiella* polysaccharides that are, or derived from, one or more *K. pneumoniae* serotypes selected from O1 (and d-Gal-III variants), O2 (and d-Gal-III variants), O2ac, O3, O4, O5, O7, O8, and O12. In some embodiments, an immune complex includes *Klebsiella* polysaccharides from or derived from one or more of serotypes O1, O2, O3, and O5, or a combination thereof. In some embodiments, an immune complex includes *Klebsiella* polysaccharides from or derived from each of serotypes O1, O2, O3, and O5.

In some embodiments, an immunogenic complex includes one or more *Klebsiella* polysaccharides that are, or are derived from, an OPS. In some embodiments, the OPS is or is derived from *Klebsiella* of serotype O1, O2, O3, O5, and variants or a combination thereof. In some embodiments, an immune complex includes *Klebsiella* OPS selected from or derived from one or more of serotypes of O1, O2, O3, and O5, or a combination thereof. In some embodiments, an immune complex includes *Klebsiella* OPS from or derived from each of serotypes O1, O2, O3, and O5.

In some embodiments, an immunogenic complex includes one or more *Klebsiella* polysaccharides that are, or are derived from, a CPS. In some embodiments, the CPS is or is derived from *Klebsiella* K1, K2, K10, K16 and K19. In some embodiments, the CPS is or is derived from *Klebsiella* K19.

*Klebsiella pneumoniae* Polypeptides

In some embodiments, an immunogenic complex described herein includes one or more *K. pneumoniae* polypeptides. In some embodiments, a *K. pneumoniae* polypeptide is or is derived from *K. pneumoniae* Type I fimbrial protein or an immunogenic fragment thereof. In some embodiments, a *K. pneumoniae* polypeptide is or comprises a polypeptide of SEQ ID NO:1 published in Gerlach et al., 2012, J Bacteriology or an immunogenic fragment thereof. In some embodiments, a *K. pneumoniae* polypeptide is or comprises a polypeptide having at least 80%, 85%, 90%, 95%, 96%, 97%, 98%, or 99% identity to the sequence of SEQ ID NO:1, or an immunogenic fragment thereof.

*K. pneumoniae* Type I Fimbrial Protein SEQ ID NO:1

MKIKTLAMIVVSALSLSSTAALADTTTVNGGTVHFKGEVVNAACAVDAGS

IDQTVQLGQVRSAKLATAGSTSSAVGFNIQLDDCDTTVATKASVAFAGTA

IDSSNTTVLALQNSAAGSATNVGVQILDNTGTPLALDGATFSAATTLNDG

PNIIPFQARYYATGAATAGIANADATFKVQYE

In some embodiments, a *K. pneumoniae* polypeptide is or is derived from *K. pneumoniae* conserved Type III fimbrial protein MrkA or an immunogenic fragment thereof. In some embodiments, a *K. pneumoniae* polypeptide is or comprises a polypeptide of SEQ ID NO:2 or an immunogenic fragment thereof. In some embodiments, a *K. pneumoniae* polypeptide is or comprises a polypeptide having at least 80%, 85%, 90%, 95%, 96%, 97%, 98%, or 99% identity to the sequence of SEQ ID NO:2, or an immunogenic fragment thereof.

*K. pneumoniae* Conserved Type III Fimbrial Protein MrkA SEQ ID NO:2

MKKVLLSAAMATAFFGMTAAHAADTTVGGGQVNFFGKVTDVSCTVSVNGQ

GSDANVYLSPVTLTEVKAAAADTYLKPKSFTIDVSNCQAADGTKQDDVSK

LGVNWTGGNLLAGATSKQQGYLANTEASGAQNIQLVLSTDNATALTNKII

PGDSTQPKAKGDASAVADGARFTYYVGYATSAPTTVTTGVVNSYATYEIT

YQ

In some embodiments, a *K. pneumoniae* polypeptide is or is derived from *K. pneumoniae* Type III fimbrial protein MrkA or an immunogenic fragment, e.g., a fragment with repeated sequences to provide stabilizing interactions to a MrkA monomer protein. In some embodiments, a *K. pneumoniae* polypeptide is or comprises a polypeptide of SEQ ID NO:3 or an immunogenic fragment thereof. In some embodiments, a *K. pneumoniae* polypeptide is or comprises a polypeptide having at least 80%, 85%, 90%, 95%, 96%, 97%, 98%, or 99% identity to the sequence of SEQ ID NO:3, or an immunogenic fragment thereof.

*K. pneumoniae* Stabilized Type III Fimbrial Protein MrkA SEQ ID NO:3

ADTTVGGGQVNFFGKVTDVSCTVSVNGQGSDANVYLSPVTLTEVKAAAAD

TYLKPKSFTIDVSNCQAADGTKQDDVSKLGVNWTGGNLLAGATSKQQGYL

ANTEASGAQNIQLVLSTDNATALTNKIIPGDSTQPKAKGDASAVADGARF

TYYVGYATSAPTTVTTGVVNSYATYEITYQGGGGGGADTTVGGGQVNFFG

KVTDVS

*Pseudomonas*

*Pseudomonas* is a major cause of HAI infections, particularly in immunocompromised by neutropenia and mechanically ventilated patients, and it is the leading cause of death in cystic fibrosis patients. *Pseudomonas* infection is also implicated in burn injury, eye (e.g., corneal) injury, trauma, etc. Thus, in some embodiments, an immunogenic complex described herein includes one or more *Pseudomonas* polysaccharides and/or polypeptides.

In some embodiments, an immunogenic complex described herein includes a *Pseudomonas* O-antigen. Wellcome Research provided most of the early efforts in developing a vaccine based on this antigen, combining purified extracts containing 16 of the 20 O-antigen serotypes into the PEV-1 vaccine. The results of a total of five phase 1-2 clinical trials were published between 1976 and 1984 (Jones et al., 1976, 1978, 1979, 1980; Langford and Hiller, 1984). Vaccine safety data indicate that it had been well-tolerated. Seroconversion appeared relatively consistent in vaccinated groups of normal volunteers and burn or cystic fibrosis (CF) patients. Vaccination had variable effects on burn wound colonization from little or no effect to significant effect. Blood cultures showed a nearly 10-fold reduction due to vaccination in one study. In each study in burn patients, there was a reduction in death, which varied from 70-100%, although the number of deaths due to P. aeruginosa was not always clear. In the CF study (Langford and Hiller, 1984), there appeared to be neither clinical benefit nor difference in P. aeruginosa colonization with vaccination and there was no correlation between antibody ELISA titers and clinical or bacteriological readouts. The Swiss Serum Institute, Berna Biotech and Crucell developed an octavalent O-antigen-exotoxin A conjugate vaccine (Aerugen), which went through three published phase 1-2 clinical trials (Schaad, et al., 1991; Lang, et al., 1995; Cryz et al., 1994). Their intramuscular (IM)-administered vaccine appeared well-tolerated and seroconversion to all serotypes was deemed significant in all studies. Vaccination resulted in a significant decrease in colonization in the majority of studies and no PA-related deaths were reported in vaccine or placebo groups. In a Crucell 476-patient phase 3 study in CF patients, the vaccine did not meet the desired endpoint or repeat results observed in previous studies.

In some embodiments, an immunogenic complex described herein includes a *Pseudomonas* flagellum or antigenic portion thereof. Early research efficacy studies (Holder et al., 1982; Holder and Naglich, 1986; Montie, et al., 1987) established that either type a or b flagella could provide type-specific protection from death in murine burn models, but that type b flagella appeared to be somewhat more adept at doing so. In preclinical studies, IMMUNO AG (Crowe, et al., 1991) used individual vaccines consisting of a0, a0a1a2, a0a2, a0a3, a0a3a4, and type b flagella to determine that the b antigen appeared to be a better immunogen, providing high rates of protection in an immunocompromised mouse model than the type a preparations. A phase 1 study in the same paper showed that all of these immunogens elicited high titered, long-lasting serum antibodies, as did a single type b immunogen in a follow up phase 2 study (Döring, et al, 1995), which also showed IgG, IgA, and sIgA seroconversion in bronchoalveolar washes. Administration of a combination type a (a0a1a2)+type b flagellar vaccine in CF patients (phase 3) resulted in high titered, long-lasting serum IgG. However, although there was some protective efficacy vs. P. aeruginosa lung infection, the presence of serotypes not associated with the vaccine clouded the interpretation of the outcome (Döring and Dorner, 1997; airing, et al 2007). In a subsequent review, Döring and Pier (2008) suggested that a bivalent flagellar vaccine may not be optimal and that said, data does not appear to exist on a single vaccine that includes type b flagella and all of the type a subtypes.

In some embodiments, an immunogenic complex described herein includes a *Pseudomonas* flagellin or antigenic fragment thereof. Studies on the subunits of flagella, flagellin, have not progressed beyond the research phase. Studies have included purified flagellin (Campodonico, et al., 2010; Faezi, et al., 2013), DNA vaccine with flagellin (Saha, et al., 2007), as well as a flagellin/polymannuronic acid conjugate (Campodonico, et al., 2011). While all of these are immunogenic and protective, they do not appear to reach the levels attained by flagellar preparations. Passive immunization has also been studied with anti-type b serum (Barnea, et al., 2006), mAb anti-type a (Barnea, et al., 2009), and anti-type a serum (Faezi, et al., 2011). All preparations showed reductions in death in the mouse burn model.

In some embodiments, an immunogenic complex described herein includes a *Pseudomonas* PcrV (Type III Secretion) or antigenic fragment thereof. A key virulence factor associated with disease severity is the P. aeruginosa type III secretion system (T3 SS), which injects bacterial toxins directly into the cytoplasm of host cells. The PcrV protein, located at the tip of the T3SS injectisome complex, is required for T3SS function and is a well-validated target in animal models of immunoprophylactic strategies targeting P. aeruginosa. Based on previous groundwork on PcrV, in which active and passive immunization (Sawa, et al., 1999; Holder, et al., 2001; Shime, et al., 2001; Frank, et al., 2002) showed protection in various animal models, KaloBios has developed a "Humaneered, high affinity, PEGylated Fab'" (KB-001), which has been investigated as passive therapy in preclinical (Baer, et al., 2009) and clinical trials (Francois et al., 2012; Milla et al., 2014). While both mouse and "humaneered" mAbs and Fab' fragments thereof proved efficacious in animal studies, a clinical trial with KB-001 showed no significant differences in P. aeruginosa colonization counts, symptoms, or spirometry, and a new-improved version, KB-001A to treat P. aeruginosa infections in cystic fibrosis patients did not meet its primary end points in a phase 2 human clinical trial (ClinTrials.gov, 2014). With respect to its use as an active vaccine until the present disclosure little work has been done with the PcrV protein antigen.

In some embodiments, an immunogenic complex described herein includes a *Pseudomonas* exopolysaccharide. In some embodiments, an immune complex described herein includes a *Pseudomonas* PsL. This exopolysaccharide is important for P. aeruginosa attachment to mammalian cells, and for the formation and maintenance of biofilms produced by nonmucoid and mucoid P. aeruginosa isolates. PsL polysaccharide functions to hold biofilm cells together, hence the critical role of PsL in adhesion (Ma et al., 2006). Functional screens revealed that mAbs to one PsL epitope exhibit superior activity in OPK and cell attachment assays, and confer significant protection in multiple animal models.

Polysaccharide PsL is an antibody-accessible serotype-independent surface feature that is prevalent among both nonmucoid and mucoid clinical isolates (DiGiandomenico et al., 2012). In animals, PsL antibodies mediate OPK in the presence of effector cells and inhibit P. aeruginosa binding to epithelial cells. PsL-putative specific mAb Cam-003 passively protected and reduced bacterial burden in the organs of mice in a dose-dependent manner (DiGiandomenico et al., 2012). Cam-003 mab was also protective against multiple P. aeruginosa serotypes in a mouse pneumonia model. Similar results were obtained in the scratch-injured cornea or burned mouse models, in both cases Cam-003 was effective at diminishing infection. MEDI 3902 is a bispecific antibody targeting the serotype-independent TTSS virulence factor PcrV and persistence factor PsL exopolysaccharide (DiGiandomenico et al., 2014). A phase 1 safety trial with MEDI 3902 for the prevention of pneumonia (Ventilator Associated Pneumonia) caused by *Pseudomonas* has been completed (https://clinicaltrials.gov/NCT02255760). With respect to its use as an active vaccine until the present disclosure little work has been done with the PsL exopolysaccharide antigen.

Pseudomonas aeruginosa Polysaccharides

In some embodiments, an immunogenic complex described herein includes one or more *P. aeruginosa* polysaccharides. There are approximately 20 known serotypes of O-antigen by the IATS method. The O-antigen polysaccharide of the molecule provides a non-toxic potential target for vaccine development. In some embodiments, an immunogenic complex described herein includes one or more *Pseudomonas* OPS, LPS, and/or exopolysaccharides. In some embodiments, LPS-derived polysaccharides are OPS. In some embodiments LPS-derived polysaccharides are COPS.

In some embodiments, an immunogenic complex includes one or more *Pseudomonas* polysaccharides that are, or derived from, one or more *P. aeruginosa* serotypes selected from O1, O2, O3, O4, O5, O6, O7, O8, O9, O10, O11, O12, O13, O14, O15, O16, O17, O18, O19 and O20 (IATS). In some embodiments, an immune complex includes one or more *Pseudomonas* polysaccharides that are, or derived from, one or more *P. aeruginosa* serotypes selected from O1, O2, O3, O4, O5, O6, O10, and O11, or a combination thereof. In some embodiments, an immune complex includes *Pseudomonas* polysaccharides that are, or derived from, each of *P. aeruginosa* serotypes selected from O1, O2, O3, O4, O5, O6, O10, and O11.

In some embodiments, an immunogenic complex includes one or more *Pseudomonas* polysaccharides that are, or derived from an OPS. In some embodiments, the OPS is or is derived from *Pseudomonas* of type O1, O2, O3, O4, O5, O6, O7, O8, O9, O10, O11, O12, O13, O14, O15, O16, O17, O18, O19 and O20, or a combination thereof. In some embodiments, the OPS is or is derived from *Pseudomonas* of type O1, O2, O3, O4, O5, O6, O10, or O11, or a combination thereof. In some embodiments, the OPS is or is derived from each of *Pseudomonas* of type O1, O2, O3, O4, O5, O6, O10, or O11.

In some embodiments, an immunogenic complex includes one or more *Pseudomonas* polysaccharides that are, or derived from a capsular or capsular-like extracellular polysaccharide. In some embodiments, the capsular or capsular-like polysaccharide is or is derived from *Pseudomonas* alginate, Psl, or Pel.

In some embodiments, an immunogenic complex includes one or more *Pseudomonas* polysaccharides that are, or derived from an exopolysaccharide. In some embodiments, the exopolysaccharide is or is derived from PsL. In some embodiments, the PsL comprises at least one epitope that binds to a monoclonal antibody comprising SEQ ID NO:4 and/or SEQ ID NO:5. In some embodiments, a monoclonal antibody that binds to at least one epitope of PsL is or comprises a polypeptide having at least 80%, 85%, 90%, 95%, 96%, 97%, 98%, or 99% identity to the sequence of SEQ ID NO:4, or PsL binding fragment thereof. In some embodiments, a monoclonal antibody that binds to at least one epitope of PsL is or comprises a polypeptide having at least 80%, 85%, 90%, 95%, 96%, 97%, 98%, or 99% identity to the sequence of SEQ ID NO:5, or PsL binding fragment thereof. In some embodiments, a monoclonal antibody that binds to at least one epitope of PsL is or comprises a polypeptide having at least 80%, 85%, 90%, 95%, 96%, 97%, 98%, or 99% identity to the sequence of SEQ ID NO:4, or PsL binding fragment thereof and a polypeptide having at least 80%, 85%, 90%, 95%, 96%, 97%, 98%, or 99% identity to the sequence of SEQ ID NO:5, or PsL binding fragment thereof.

Sequence in PsL Binding Cam-003 mAb SEQ ID NO:4

QVRLQQSGPGLVKPSETLSLTCTVSGGSTSPYFWSWLRQPPGKGLEWIGY

IHSNGGTNYNPSLKSRLTISGDTSKNQFSLNLSFVTAADTALYYCARTDY

DVYGPAFDIWGQGTMVTV

Sequence in PsL Binding Cam-003 mAb SEQ ID NO:5

SSELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVFG

GGTKLTVL

Pseudomonas aeruginosa Polypeptides

In some embodiments, an immunogenic complex described herein includes one or more *P. aeruginosa* polypeptides. In some embodiments, a *P. aeruginosa* polypeptide is or is derived from *P. aeruginosa* FliC flagellin subtype A1 or an immunogenic fragment thereof. In some embodiments, a *P. aeruginosa* polypeptide is or comprises a polypeptide of SEQ ID NO:6 or an immunogenic fragment thereof. In some embodiments, a *P. aeruginosa* polypeptide is or comprises a polypeptide having at least 80%, 85%, 90%, 95%, 96%, 97%, 98%, or 99% identity to the sequence of SEQ ID NO:6, or an immunogenic fragment thereof.

*P. aeruginosa* FliC Flagellin Subtype A1 SEQ ID NO:6

MALTVNTNIASLNTQRNLNNSSASLNTSLQRLSTGSRINSAKDDAAGLQI

ANRLTSQVNGLNVATKNANDGISLAQTAEGALQQSTNILQRMRDLSLQSA

NGSNSDSERTALNGEVKQLQKELDRISNTTTFGGRKLLDGSFGVASFQVG

SAANEIISVGIDEMSAESLNGTYFKADGGGAVTAATASGTVDIAIGITGG

SAVNVKVDMKGNETAEQAAAKIAAAVNDANVGIGAFSDGDTISYVSKAGK

DGSGAITSAVSGVVIADTGSTGVGTAAGVTPSATAFAKTNDTVAKIDIST

AKGAQSAVLVIDEAIKQIDAQRADLGAVQNRFDNTINNLKNIGENVSAAR

GRIEDTDFAAETANLTKNQVLQQAGTAILAQANQLPQSVLSLLR

In some embodiments, a *P. aeruginosa* polypeptide is or is derived from *P. aeruginosa* FliC flagellin subtype B or an immunogenic fragment thereof. In some embodiments, a *P. aeruginosa* polypeptide is or comprises a polypeptide of SEQ ID NO:7 or an immunogenic fragment thereof. In some embodiments, a *P. aeruginosa* polypeptide is or comprises a polypeptide having at least 80%, 85%, 90%, 95%, 96%, 97%, 98%, or 99% identity to the sequence of SEQ ID NO:7, or an immunogenic fragment thereof.

*P. aeruginosa* FliC Flagellin Subtype B SEQ ID NO:7

MALTVNTNIASLNTQRNLNASSNDLNTSLQRLTTGYRINSAKDDAAGLQI

SNRLSNQISGLNVATRNANDGISLAQTAEGALQQSTNILQRIRDLALQSA

NGSNSDADRAALQKEVAAQQAELTRISDTTTFGGRKLLDGSFGTTSFQVG

SNAYETIDISLQNASASAIGSYQVGSNGAGTVASVAGTATASGIASGTVN

LVGGGQVKNIAIAAGDSAKAIAEKMDGAIPNLSARARTVFTADVSGVTGG

SLNFDVTVGSNTVSLAGVTSTQDLADQLNSNSSKLGITASINDKGVLTIT

SATGENVKFGAQTGTATAGQVAVKVQGSDGKFEAAAKNVVAAGTAATTTI

-continued

```
VTGYVQLNSPTAYSVSGTGTQASQVFGNASAAQKSSVASVDISTADGAQN

AIAVVDNALAAIDAQRADLGAVQNRFKNTIDNLTNISENATNARSRIKDT

DFAAETAALSKNQVLQQAGTAILAQANQLPQAVLSLLR
```

In some embodiments, a *P. aeruginosa* polypeptide is or is derived from *P. aeruginosa* FliC flagellin subtype B D2 domain lacking the TLR5 binding motif or an immunogenic fragment thereof. In some embodiments, a *P. aeruginosa* polypeptide is or comprises a polypeptide of SEQ ID NO:10 or an immunogenic fragment thereof. In some embodiments, a *P. aeruginosa* polypeptide is or comprises a polypeptide having at least 80%, 85%, 90%, 95%, 96%, 97%, 98%, or 99% identity to the sequence of SEQ ID NO:10, or an immunogenic fragment thereof.

*P. aeruginosa* FliC Flagellin Subtype B Flagellin D2 Domain Lacking the TLR5 Binding Motif SEQ ID NO:10

```
GSYQVGSNGAGTVASVAGTATASGIASGTVNLVGGGQVKNIAIAAGDSAK

AIAEKMDGAIPNLSARARTVFTADVSGVTGGSLNFDVTVGSNTVSLAGVT

STQDLADQLNSNSSKLGITASINDKGVLTITSATGENVKFGAQTGTATAG

QVAVKVQGSDGKFEAAAKNVVAAGTAATTTIVTGYVQLNSPTAYSVSGTG

TQASQVFGNASAAQKSS
```

In some embodiments, a *P. aeruginosa* polypeptide is or is derived from a *P. aeruginosa* type three secretion system (TTSS) Virulence Factor PcrV or an immunogenic fragment thereof. In some embodiments, a *P. aeruginosa* polypeptide is or comprises a polypeptide of SEQ ID NO:8 or an immunogenic fragment thereof. In some embodiments, a *P. aeruginosa* polypeptide is or comprises a polypeptide having at least 80%, 85%, 90%, 95%, 96%, 97%, 98%, or 99% identity to the sequence of SEQ ID NO:8, or an immunogenic fragment thereof.

*P. aeruginosa* Type Three Secretion System (TTSS) Virulence Factor PcrV SEQ ID NO:8

```
MEVRNLNAARELFLDELLAASAAPASAEQEELLALLRSERIVLAHAGQPL

SEAQVLKALAWLLAANPSAPPGQGLEVLREVLQARRQPGAQWDLREFLVS

AYFSLHGRLDEDVIGVYKDVLQTQDGKRKALLDELKALTAELKVYSVIQS

QINAALSAKQGIRIDAGGIDLVDPTLYGYAVGDPRWKDSPEYALLSNLDT

FSGKLSIKDFLSGSPKQSGELKGLSDEYPFEKDNNPVGNFATTVSDRSRP

LNDKVNEKTTLLNDTSSRYNSAVEALNRFIQKYDSVLRDILSAI
```

*Escherichia coli*

Mortality associated with *E. coli* sepsis is 20%-40% even with optimal antimicrobial therapy and supportive care (Grandsen et al., 1990; Kreger et al., 1980; Rayner and Willcox, 1988; Bryan et al., 1983; Cross et al., 1983). New prophylactic and therapeutic approaches, including adjunctive treatment with antibodies to these and other gram-negative bacteria, are clearly needed. While O-antigen-specific antibodies protect against infection with homologous bacterial strains, investigators considered immunotherapy with such antibodies to be of limited value in view of the serotype diversity of gram-negative bacteria (Baumgartner, 1990). However, epidemiologic surveys of bacterial serotypes associated with extra-intestinal invasive *E. coli* infection reveal that a limited number of O-serogroups account for nearly 60% of the bacteremia cases (Grandsen et al., 1990; Cross et al., 1984; McCabe et al., 1978). Accordingly, there remains a need for effective technologies for prevention and/or treatment of such infections.

Methods of Purifying Polysaccharides

In some embodiments, the disclosure provides methods of purifying one or more polysaccharides described herein from one or more cellular components of bacteria. In some embodiments, methods involve purifying an O-antigen polysaccharide from one or more cellular components of bacteria. In some embodiments, methods involve purifying CPS from one or more cellular components of bacteria.

In some embodiments, the bacteria are gram-negative. In some embodiments *K. pneumoniae*, *P. aeruginosa*, and *E. coli*.

In some embodiments, the cellular components include protein. In some embodiments, the cellular proteins include nucleic acid. In some embodiments, the cellular components include lipids. In some embodiments, the cellular components include polysaccharides. In some embodiments, the cellular components are part of a lysate.

In some embodiments, a method of purifying a polysaccharide from one or more cellular components of bacteria comprises contacting the cellular components with an oxidizing reagent and an acid to obtain a mixture. In some embodiments, the oxidizing agent comprises sodium nitrite. In some embodiments, the acid is acetic acid. In some embodiments, the pH of the mixture is between about 3 and about 5. In some embodiments, the method comprises separating the O-antigen polysaccharide from one or more cellular components in the mixture. In some embodiments, the separated OPS contains a free aldehyde at its reducing terminal end. In some embodiments, the separated OPS contains 2,5-anhydromannose residue containing a free aldehyde at its reducing terminal end. In some embodiments, the method comprises recovering the OPS, wherein the recovered OPS is substantially free of one or more other cellular components. In some embodiments, the recovered OPS contains a free aldehyde at its reducing terminal end. In some embodiments, the recovered OPS contains 2,5-anhydromannose residue containing a free aldehyde at its reducing terminal end.

In some embodiments, a method of purifying a polysaccharide from one or more cellular components of gram-negative bacteria comprises contacting the cellular components with an acidic reagent to obtain a mixture. In some embodiments, the pH of the mixture is between about 3 and about 5. In some embodiments, the method comprises heating the mixture to between about 80° C. to about 135° C. In some embodiments, the method comprises separating the core and O-antigen polysaccharide (COPS) from one or more cellular components in the mixture. In some embodiments, the separated COPS contains a KDO at its reducing terminal end. In some embodiments, the separated COPS contains a ketone within the KDO at its reducing terminal end. In some embodiments, the method comprises recovering the COPS, wherein the recovered COPS is substantially free of one or more other cellular components. In some embodiments, the recovered COPS contains a ketone at its reducing terminal end.

Affinity Molecule Pairs

As described herein, in some embodiments, immune complexes of the disclosure include one or more polypeptides non-covalently complexed with one or more polymers and/or one or more antigenic polysaccharides. In some embodiments, one or more polypeptides are complexed via affinity interaction with one or more polymers and/or one or more antigenic polysaccharides. In some embodiments, immune complexes of the disclosure include one or more polypeptides non-covalently complexed with one or more polymers and/or one or more antigenic polysaccharides using one or more affinity molecule/complementary affinity molecule pairs. In some embodiments, an immune complex includes (i) a first affinity molecule described herein conjugated to one or more polymers and/or conjugated to one or more antigenic polysaccharides, and (ii) a fusion protein that is or comprises a complementary affinity molecule described herein and a polypeptide. Upon association of the first affinity molecule and the complementary affinity molecule, the one or more polypeptides are non-covalently complexed to the one or more polymers and/or one or more antigenic polysaccharides.

In some embodiments, the affinity molecule/complementary affinity molecule pair is selected from one or more of biotin/biotin-binding protein, antibody/antigen, enzyme/substrate, receptor/ligand, metal/metal-binding protein, carbohydrate/carbohydrate binding protein, lipid/lipid-binding protein, and His tag/His tag-binding molecule.

In some embodiments, the first affinity molecule is biotin (or a derivative or fragment thereof), and the complementary affinity molecule is a biotin-binding protein or biotin-binding domain thereof. In some embodiments, the biotin-binding protein is rhizavidin, avidin, streptavidin, bradavidin, tamavidin, lentiavidin, zebavidin, NeutrAvidin, CaptAvidin™, or a biotin-binding fragment thereof, or a combination thereof. In some embodiments, the biotin-binding protein is rhizavidin or a biotin-binding fragment thereof. In some embodiments, biotin-binding protein comprises a polypeptide of SEQ ID NO:13 or a biotin-binding fragment thereof. In some embodiments, biotin-binding protein comprises a polypeptide of SEQ ID NO:14 or a biotin-binding fragment thereof.

Fusion Proteins

In some embodiments, an immune complex described herein includes a fusion protein that is or comprises a complementary affinity molecule described herein, and one or more polypeptides described herein. In some embodiments, such fusion proteins have carrier and/or antigenic properties. In some embodiments, a fusion protein is or comprises a biotin-binding protein, or biotin-binding domain thereof, and a polypeptide.

In some embodiments, the biotin binding protein comprises a polypeptide of SEQ ID NO:13 or a biotin binding fragment thereof. In some embodiments, the polypeptide is or comprises a polypeptide having at least 80%, 85%, 90%, 95%, 96%, 97%, 98%, or 99% identity to the sequence of SEQ ID NO:13, or biotin binding fragment thereof. In some embodiments, the biotin binding protein comprises a polypeptide of SEQ ID NO:14 or a biotin binding fragment thereof. In some embodiments, the polypeptide is or comprises a polypeptide having at least 80%, 85%, 90%, 95%, 96%, 97%, 98%, or 99% identity to the sequence of SEQ ID NO:14, or biotin binding fragment thereof.

In some embodiments a fusion protein comprises a complementary affinity molecule described herein (e.g., a biotin-binding protein described herein) and one or more polypeptides derived from one or more of *K. pneumoniae*, *P. aeruginosa*, and *E. coli*.

In some embodiments, a fusion protein comprises one or more linkers and/or histidine tag. In some embodiments a linker comprises a polypeptide comprising an amino acid sequence of SEQ ID NO:15 (GGGGSSS). In some embodiments, a linker comprises a polypeptide comprising an amino acid sequence having at least 80%, 85%, 90%, 95%, 96%, 97%, 98%, or 99% identity to the sequence of SEQ ID NO:15.

In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:7 (*P. aeruginosa* FlaB flagellin) or an immunogenic fragment thereof. In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:6 (*P. aeruginosa* FlaA1 flagellin) or an immunogenic fragment thereof. In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:9 (*P. aeruginosa* FlaA2 flagellin) or an immunogenic fragment thereof.

In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:10 (*P. aeruginosa* FlaB flagellin D2 domain lacking the TLR5 binding motif) or an immunogenic fragment thereof. In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:11 (*P. aeruginosa* FlaA1 flagellin D2 domain lacking the TLR5 binding motif) or an immunogenic fragment thereof. In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:12 (*P. aeruginosa* FlaA2 flagellin D2 domain lacking the TLR5 binding motif) or an immunogenic fragment thereof. In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:8 (*P. aeruginosa* type III secretion system (TTSS) PcrV) or an immunogenic fragment thereof.

In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:7 (*P. aeruginosa* FliC flagellin subtype B) or an immunogenic fragment thereof and a polypeptide comprising an amino acid sequence having at least 80%, 85%, 90%, 95%, 96%, 97%, 98%, 99%, or 100% identity to the sequence of SEQ ID NO:8 (*P. aeruginosa* PcrV) or an immunogenic fragment thereof. In some embodiments, a fusion protein comprises a polypeptide comprising an amino acid sequence having at least 80%, 85%, 90%, 95%, 96%, 97%, 98%, 99%, or 100% identity to the sequence of SEQ ID NO:23. In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:10 (*P. aeruginosa* FliC flagellin subtype B D2 domain lacking the TLR5 binding motif) or an immunogenic fragment thereof and a polypeptide comprising an amino acid sequence having at least 80%, 85%, 90%, 95%, 96%, 97%, 98%, 99%, or 100% identity to the sequence of SEQ ID NO:8 (*P. aeruginosa* PcrV) or an immunogenic fragment thereof. In some embodiments, a fusion protein comprises a polypeptide comprising an amino acid sequence having at least 80%, 85%, 90%, 95%, 96%, 97%, 98%, 99%, or 100% identity to the sequence of SEQ ID NO:26.

In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:7 (*P. aeruginosa* FliC subtype B flagellin) or an immunogenic fragment thereof and a polypeptide comprising an amino acid sequence having at least 80%, 85%, 90%, 95%, 96%, 97%, 98%, 99%, or 100% identity to the sequence of SEQ ID NO:2 (*K. pneumoniae* conserved MrkA) or an immunogenic fragment thereof.

In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:10 (*P. aeruginosa* FliC subtype B flagellin D2 domain lacking the TLR5 binding motif) or an immunogenic fragment thereof and a polypeptide comprising an amino acid sequence having at least 80%, 85%, 90%, 95%, 96%, 97%, 98%, 99%, or 100% identity to the sequence of SEQ ID NO:3 (*K. pneumoniae* stabilized MrkA) or an immunogenic fragment thereof. In some embodiments, a fusion protein comprises a polypeptide of SEQ ID NO:24.

In some embodiments, a fusion protein comprises a complementary affinity molecule described herein (e.g., a biotin-binding protein described herein) and a polypeptide comprising an amino acid sequence having at least 80%, 85%, 90%, 95%, 96%, 97%, 98%, 99%, or 100% identity to the sequence of SEQ ID NO:8 (*P. aeruginosa* PcrV) or an immunogenic fragment thereof and a polypeptide comprising an amino acid sequence having at least 80%, 85%, 90%, 95%, 96%, 97%, 98%, 99%, or 100% identity to the sequence of SEQ ID NO:3 (*K. pneumoniae* stabilized MrkA) or an immunogenic fragment thereof.

Backbone Polymers

As described herein, in some embodiments, immune complexes of the disclosure include a backbone polymer comprising a polymer conjugated to one or more antigenic polysaccharides. In some embodiments, the polymer is or comprises a polysaccharide, a polypeptide, or a synthetic dendrimer. In some embodiments, the polymer is or comprises a poly-L-lysine (PLL). In some embodiments, the polymer is or comprises a linear PLL, or a dendrimer of L-lysine. In some embodiments, the polymer is a CPS derived from a gram-negative or gram-positive bacteria. In some embodiments, the CPS is a *K. pneumoniae* CPS, *P. aeruginosa* exopolysaccharide, and/or an *E. coli* CPS. In some embodiments, the polymer is a KP K19 CPS. In some embodiments, the polymer is a dendrimer of a synthetic monosaccharide or oligosaccharide. In some embodiments, the polymer is about 50 KDa to about 2000 KDa in size. In some embodiments, the polymer has antigenic properties. In some embodiments, the polymer is not antigenic. In some embodiments the polymer is or comprises one or more antigenic polysaccharides. In some embodiments, the one or more antigenic polysaccharides may be a *K. pneumoniae* OPS, a *P. aeruginosa* OPS, or a combination thereof.

Backbone Polymer 1 (BP-1)

In some embodiments, an immunogenic complex described herein includes a backbone polymer comprising a polymer conjugated to one or more antigenic polysaccharides. In some embodiments, a backbone polymer includes a first affinity molecule described herein (e.g., biotin) conjugated (e.g., cross-linked or covalently bonded) to the polymer. In some embodiments, the polymer is a polysaccharide. In some embodiments, the antigenic polysaccharide is an O-antigen polysaccharide, core-O-antigen, or core polysaccharide. In some embodiments, the backbone polymer includes at least one polymer (e.g., polysaccharide) that is biotinylated and at least one antigenic polysaccharide (e.g., at least one O-antigen polysaccharide) that is not biotinylated.

In some embodiments, a backbone polymer that includes at least one biotinylated polymer (e.g., biotinylated polysaccharide) and at least one non-biotinylated O-antigen polysaccharide is produced by combining a non-biotinylated O-antigen polysaccharide that contains a primary amine group (natively or with a linker) with a partially oxidized polysaccharide containing an aldehyde group and a biotin containing primary amine to obtain a mixture; and reductively aminating the mixture with a reducing agent to chemically link the O-antigen polysaccharide (i.e., antigenic polysaccharide) with the polysaccharide (i.e., polymer), thereby forming a backbone polymer that includes a biotinylated polysaccharide chemically linked to a non-biotinylated antigenic polysaccharide (i.e., non-biotinylated O-antigen polysaccharide).

In some embodiments, the O-antigen polysaccharide is chemically linked with a partially oxidized polymer (e.g., polysaccharide) by way of a spacer. In some embodiments, the spacer is a short spacer. In some embodiments, the short spacer contains a primary amine at each end of the spacer. In some embodiments, the spacer may be adipic acid dihydrazide. In some embodiments, the polymer (e.g., polysaccharide) is biotinylated, and the chemically linked O-antigen polysaccharide is not biotinylated.

In some embodiments, an O-antigen polysaccharide comprises a primary amino group. In some embodiments, the primary amino group is the L-Alanine α-amino group of the outer core O-polysaccharide of *P. aeruginosa* or an amino group that has been introduced into the reducing end of the O-antigen polysaccharide by chemically linking a spacer molecule containing a primary group at each end by reductive amination with a reducing agent. In some embodiments, an O-antigen polysaccharide comprising a primary amino group is chemically linked by mixing the O-antigen polysaccharide comprising a primary amino group with a partially oxidized polymer (e.g., polysaccharide) containing an aldehyde group and a biotin containing primary amine to obtain a mixture; and reductively aminating the mixture with a reducing agent, thereby forming a backbone polymer, wherein the polymer (e.g., polysaccharide) is biotinylated but the chemically linked O-antigen polysaccharide is not biotinylated.

In some embodiments, the polymer (e.g., polysaccharide) is partially oxidized with an oxidizing agent. In some embodiments, the oxidizing agent comprises sodium periodate. In some embodiments, the reducing agent comprises sodium cyanoborohydride or sodium borohydride.

Backbone Polymer 1.2 (BP-1.2)

In some embodiments, an immunogenic complex described herein includes a backbone polymer comprising a polymer conjugated to one or more antigenic polysaccharides. In some embodiments, a backbone polymer includes a first affinity molecule described herein (e.g., biotin) conjugated (e.g., cross-linked or covalently bonded) to the polymer. In some embodiments, the polymer is a polysaccharide. In some embodiments, the antigenic polysaccharide is an O-antigen polysaccharide, core-O-antigen, or core polysaccharide. In some embodiments, the backbone polymer includes at least one polymer (e.g., polysaccharide) that is biotinylated and at least one antigenic polysaccharide (e.g., at least one O-antigen polysaccharide) that is not biotinylated.

In some embodiments, a backbone polymer that includes at least one biotinylated polymer (e.g., biotinylated polysaccharide) and at least one non-biotinylated O-antigen polysaccharide is produced by combining a non-biotinylated O-antigen polysaccharide that contains a primary amine group (natively or with a linker) with a partially oxidized polysaccharide containing one or more aldehyde groups, and one or more biotin residues introduced at an orthogonal site by reacting with carbodiimide (EDC) and N hydroxysuccinimide (NETS) and using the carboxylates of the uronic acid residues of the polysaccharide, and reductively aminating the mixture with a reducing agent to chemically link the O-antigen polysaccharide (i.e., antigenic polysaccharide) with the polysaccharide (i.e., polymer), thereby forming a backbone polymer that includes a biotinylated polysaccharide chemically linked to a non-biotinylated antigenic polysaccharide (i.e., non-biotinylated O-antigen polysaccharide). In some embodiments, the O-antigen polysaccharide is chemically linked with a partially oxidized polymer (e.g., polysaccharide) by way of a spacer. In some embodiments, the spacer is a short spacer. In some embodiments, the short spacer contains a primary amine at each end of the spacer. In some embodiments, the spacer may be adipic acid dihydrazide. In some embodiments, the polymer (e.g., polysaccharide) is biotinylated, and the chemically linked O-antigen polysaccharide is not biotinylated.

In some embodiments, an O-antigen polysaccharide comprises a primary amino group. In some embodiments, the primary amino group is the L-Alanine α-amino group of the outer core O-polysaccharide of P. aeruginosa or an amino group that has been introduced into the reducing end of the O-antigen polysaccharide by chemically linking a spacer molecule containing a primary group at each end by reductive amination with a reducing agent. In some embodiments, an O-antigen polysaccharide comprising a primary amino group is chemically linked by mixing the O-antigen polysaccharide comprising a primary amino group with a partially oxidized polymer (e.g., polysaccharide) containing an aldehyde group and a biotin containing primary amine to obtain a mixture; and reductively aminating the mixture with a reducing agent, thereby forming a backbone polymer, wherein the polymer (e.g., polysaccharide) is biotinylated but the chemically linked O-antigen polysaccharide is not biotinylated.

In some embodiments, the polymer (e.g., polysaccharide) is partially oxidized with an oxidizing agent. In some embodiments, the oxidizing agent comprises sodium periodate. In some embodiments, the reducing agent comprises sodium cyanoborohydride or sodium borohydride.

In some embodiments, an OPS comprising an aldehyde or ketone is aminated at its reducing terminal end using a short spacer containing a primary amine at each end (e.g., adipic dihydrazide ADH) by reductive amination with sodium cyanoborohydride (NaBH3CN) to produce a hydrazide derivatized OPS. In some embodiments, a KP19 CPS backbone is biotinylated with one or more biotin residues introduced at an orthogonal site by reacting the carboxylates of the uronic acid residues of the polysaccharide with carbodiimide (EDC), N-hydroxysuccinimide (NETS) and a biotin derivative containing primary amine (such as e.g. amine-PEG3-biotin). In some embodiments, the biotinylated KP19 CPS polymer is then partially oxidized with periodate to generate one or more aldehyde groups, mixed with the hydrazide derivatized OPS, and the mixture reductively aminated with a reducing agent such as sodium cyanoborohydride (NaBH3CN) to form a backbone polymer BP-1.2 comprising one or more biotin moeities on the uronic residues of the polymer backbone and no biotin on the O-antigen polysaccharide.

Backbone Polymer 1.3 (BP-1.3)

In some embodiments, an immunogenic complex described herein includes a backbone polymer comprising a polymer conjugated to one or more antigenic polysaccharides. In some embodiments, a backbone polymer includes a first affinity molecule described herein (e.g., biotin) conjugated (e.g., cross-linked or covalently bonded) to the polymer. In some embodiments, the polymer is a polysaccharide. In some embodiments, the antigenic polysaccharide is an O-antigen polysaccharide, core-O-antigen, or core polysaccharide. In some embodiments, the backbone polymer includes at least one polymer (e.g., polysaccharide) that is biotinylated and at least one antigenic polysaccharide (e.g., at least one O-antigen polysaccharide) that is not biotinylated.

In some embodiments, a backbone polymer that includes at least one biotinylated polymer (e.g., biotinylated polysaccharide) and at least one non-biotinylated O-antigen polysaccharide is produced by combining a non-biotinylated O-antigen polysaccharide that contains a primary amine group (natively or with a linker) with a CDAP-activated polysaccharide, and one or more biotin residues introduced at an orthogonal site by reacting with carbodiimide (EDC) and N hydroxysuccinimide (NHS) and using the carboxylates of the uronic acid residues of the polysaccharide, thereby forming a backbone polymer that includes a biotinylated polysaccharide chemically linked to a non-biotinylated antigenic polysaccharide (i.e., non-biotinylated O-antigen polysaccharide). In some embodiments, the O-antigen polysaccharide is chemically linked with a CDAP activated polymer (e.g., polysaccharide) by way of a spacer. In some embodiments, the spacer is a short spacer. In some embodiments, the short spacer contains a primary amine at each end of the spacer. In some embodiments, the spacer may be adipic acid dihydrazide. In some embodiments, the polymer (e.g., polysaccharide) is biotinylated and the chemically linked O-antigen polysaccharide is not biotinylated.

In some embodiments, an OPS comprising an aldehyde or ketone is aminated at its reducing terminal end using a short spacer containing a primary amine at each end (e.g., adipic dihydrazide ADH) by reductive amination with sodium cyanoborohydride (NaBH3CN) to produce a hydrazide derivatized OPS. In some embodiments, a KP19 CPS backbone is biotinylated with one or more biotin residues introduced at an orthogonal site by reacting the carboxylates of the uronic acid residues of the polysaccharide with carbodiimide (EDC), N-hydroxysuccinimide (NETS) and a biotin derivative containing primary amine (such as e.g. amine-PEG3-biotin). In some embodiments, the biotinylated KP 19 CPS polymer is then activated with CDAP, mixed with the hydrazide derivatized OPS, to form a backbone polymer BP-1.3 comprising one or more biotin moeities on the uronic residues of the polymer backbone and no biotin on the O-antigen polysaccharide.

Backbone Polymer 2a (BP-2a)

In some embodiments, an immunogenic complex described herein includes a backbone polymer comprising a polymer conjugated to one or more antigenic polysaccharides. In some embodiments, a backbone polymer includes a first affinity molecule described herein (e.g., biotin) conjugated (e.g., cross-linked or covalently bonded) to the polymer, and includes a first affinity molecule described herein (e.g., biotin) conjugated (e.g., cross-linked or covalently bonded) to one or more antigenic polysaccharides. In some embodiments, the polymer is a polysaccharide. In some embodiments, the antigenic polysaccharide is an O-antigen polysaccharide. In some embodiments, the backbone polymer includes at least one polymer (e.g., polysaccharide) that is biotinylated and at least one O-antigen polysaccharide that is biotinylated.

In some embodiments, a backbone polymer that includes at least one biotinylated polymer (e.g., biotinylated polysaccharide) and at least one biotinylated O-antigen polysaccharide is produced by combining an O-antigen polysaccharide with a partially oxidized polymer (e.g., polysaccharide) containing an aldehyde group to obtain a mixture; and reductively aminating the mixture with a reducing agent to chemically link the O-antigen polysaccharide with the polymer (e.g., polysaccharide), thereby forming a backbone polymer that includes an O-antigen polysaccharide and a polymer (e.g., polysaccharide); and derivatizing the backbone polymer with CDAP or another cyanylating reagent (e.g., CNBr) and a biotin containing primary amine, thereby forming a backbone polymer that includes a biotinylated polymer (e.g., biotinylated polysaccharide) chemically linked to a biotinylated O-antigen and polymer polysaccharide.

In some embodiments, the O-antigen polysaccharide is chemically linked with a partially oxidized polysaccharide backbone by way of a spacer. In some embodiments, the spacer is a short spacer. In some embodiments, the short spacer contains a primary amine at each end of the spacer. In some embodiments, the spacer may be adipic acid dihydrazide.

In some embodiments, an O-antigen polysaccharide comprises a primary amino group. In some embodiments, the primary amino group is the L-Alanine α-amino group of the outer core O-antigen polysaccharide of *P. aeruginosa* or an amino group that has been introduced into the reducing end of the O-antigen polysaccharide by chemically linking a short spacer molecule containing a primary group at each end by reductive amination with a reducing agent.

In some embodiments, the polymer (e.g., polysaccharide) is partially oxidized with an oxidizing agent. In some embodiments, the oxidizing agent comprises sodium periodate. In some embodiments, the reducing agent comprises sodium cyanoborohydride or sodium borohydride.

Backbone Polymer 2b (BP-2b)

In some embodiments, an immunogenic complex described herein includes a backbone polymer comprising a polymer conjugated to one or more antigenic polysaccharides. In some embodiments, a backbone polymer includes a first affinity molecule described herein (e.g., biotin) conjugated (e.g., cross-linked or covalently bonded) to the antigenic polysaccharide. In some embodiments, the polymer is a polysaccharide. In some embodiments, the antigenic polysaccharide is an O-antigen polysaccharide. In some embodiments, the backbone polymer includes at least one polymer (e.g., polysaccharide) that is not biotinylated and at least one biotinylated O-antigen polysaccharide.

In some embodiments, a backbone polymer that includes at least one non-biotinylated polymer (e.g., non-biotinylated polysaccharide) and at least one biotinylated O-antigen polysaccharide is produced by biotinylating an O-antigen polysaccharide comprising the O polysaccharide repeats and one or more core alpha KDOs and/or heptose moieties with CDAP and a biotin containing primary amine to obtain a biotinylated O-antigen polysaccharide mixture; partially oxidizing the biotinylated OPS mixture with sodium periodate to introduce aldehydes into the core KDOs and/or heptose moieties and/or OPS residues; reductively aminating the biotinylated polysaccharide with adipic acid dihydrazide; mixing the biotinylated and aminated OPS with a partially oxidized polymer (e.g., polysaccharide) to form a mixture; and reductively aminating the mixture; thereby forming a backbone polymer that includes a polymer (e.g., polysaccharide) that is not biotinylated and a chemically linked O-antigen polysaccharide that is biotinylated.

In some embodiments, the O-antigen polysaccharide is partially oxidized with an oxidizing agent. In some embodiments, the oxidizing agent comprises sodium periodate. In some embodiments, the reducing agent comprises sodium cyanoborohydride or sodium borohydride.

Backbone Polymer 3 (BP-3)

In some embodiments, an immunogenic complex described herein includes a backbone polymer comprising a polymer conjugated to one or more antigenic polysaccharides. In some embodiments, a backbone polymer includes a first affinity molecule described herein (e.g., biotin) conjugated (e.g., cross-linked or covalently bonded) to the antigenic polysaccharide. In some embodiments, the polymer is a Poly-L-Lysine (PLL) polymer. In some embodiments, the antigenic polysaccharide is an O-antigen polysaccharide. In some embodiments, the backbone polymer includes at least one biotinylated O-antigen polysaccharide and a PLL polymer.

In some embodiments, a backbone polymer that includes at least one non-biotinylated polymer (e.g., non-biotinylated PLL polymer) and at least one biotinylated O-antigen polysaccharide is produced by reductively aminating an O-antigen polysaccharide containing terminal aldehydes or KDOs with the ε-NH2 groups of a PLL polymer to produce an OPS PLL polymer; treating or not treating the mixture with an acylating reagent to cap the unreacted ε-NH2 groups of the PLL polymer; derivatizing the OPS with CDAP to form a derivative mixture; and reacting the derivative mixture with a biotin containing primary amine; thereby making a backbone polymer, wherein the capped N-acetylated-PLL polymer or uncapped PLL is not biotinylated and the chemically linked O-antigen polysaccharide is biotinylated.

In some embodiments, the acylating agent is acetic anhydride or acetyl chloride.

In some embodiments "click chemistry" is used to link the polymer (e.g., polysaccharide) equipped with an alkyne functional group on its carboxylate groups or to oxidized polysaccharide aldehydes to the O-antigen polysaccharide derivatized with azido groups at their terminal end. The click-linking of the 2 polysaccharides are carried out with a catalyst in aqueous media. The click-linking of the O-antigen polysaccharide to the polysaccharide can be used in a reverse way with either the azido group attached to OPS and the alkyne group attached to the polysaccharide or vice versa. Biotinylation can be effected using this chemistry selectively either on the polysaccharide to generate backbone polymer-1 or on the O-antigen polysaccharide to generate backbone polymer-2b.

In some embodiments, the catalyst for the alkyne-azide cycloaddition is copper sulfate. In some embodiments, the alkyne group to derivatize the polysaccharide is selected from the group consisting of 1-Amino-3-butyne, 1-Amino-4-pentyne, DBCO-amine, and Alkyne-PEG4-Amine.

In some embodiments, the azide group to derivatize the O-antigen polysaccharide at its reducing end is selected from the group consisting of Amino-PEG-Azide, Azido-PEG3-Amine, Azido-Propylamine and Azido-Butylamine.

Uses of Immunogenic Complexes

In some embodiments, an immunogenic complex described herein that includes one or more antigenic polysaccharides is characterized in that one or more of the opsonization potential, or immunogenicity of one or more antigenic polysaccharides is increased relative to a predetermined level, as measured by ELISA and or by a functional antibody assay. In some embodiments, one or more of the opsonization potential, or immunogenicity of the one or more antigenic polysaccharides is increased at least 1-fold, 2-fold, 3-fold, 4-fold, or 5-fold relative to a predetermined level, as measured by ELISA and or by a functional antibody assay. In some embodiments, the predetermined level is a preimmune level. In some embodiments, the epitope valency of the one or more antigenic polysaccharides is at least 1-fold, 2-fold, 3-fold, 4-fold, or 5-fold above that of the native polysaccharide. In some embodiments, one or more polypeptide antigens are carrier proteins for one or more antigenic polysaccharides.

In some embodiments, an immunogenic complex described herein, upon administration to a subject, induces antibody production against one or more pathogens in the subject at a level greater than a composition comprising an antigenic polysaccharide alone and not comprising the backbone polymer, as measured by ELISA. In some embodiments, an immunogenic complex described herein, upon administration to a subject, induces antibody production against one or more pathogens in the subject at a level greater than a composition comprising the backbone polymer and not an antigenic polysaccharide alone as measured by ELISA.

In some embodiments, an immunogenic complex described herein, upon administration to a subject, induces an immune response against one or more pathogens in the subject at a level greater than a composition comprising an antigenic polysaccharide alone and not comprising the backbone polymer. In some embodiments, an immunogenic complex described herein, upon administration to a subject, induces an immune response against one or more pathogens in the subject at a level greater than a composition comprising comprising the backbone polymer and not an antigenic polysaccharide alone. In some embodiments, the immune response is an antibody or B cell response. In some embodiments, the immune response is a CD4+ T cell response, including Th1, Th2, or Th17 response, or a CD8+ T cell response, or CD4+/CD8+ T cell response. In some embodiments, the immune response is an antibody or B cell response and a T cell response.

In some embodiments, an immunogenic complex described herein, upon administration to a subject, induces antibody production against one or more pathogens in the subject at level greater than a composition comprising a polypeptide antigen alone and not comprising the backbone polymer, as measured by ELISA. In some embodiments, the one or more pathogens are selected from *K. pneumoniae, P. aeruginosa*, and *E. coli*. In some embodiments, an immunogenic complex described herein, upon administration to a subject, elicits an immune response against one or more of *K. pneumoniae, P. aeruginosa*, and *E. coli*.

In some embodiments, an immunogenic complex described herein, upon administration to a subject, elicits an immune response against gram-negative and/or gram-positive bacteria. In some embodiments, the gram-negative bacteria are selected from *K. pneumoniae, P. aeruginosa, E. coli*. and a combination thereof. In some embodiments, an immunogenic complex described herein, upon administration to a subject, elicits antibodies that recognize native MrkA on *K. pneumoniae* expressing MrkA.

In some embodiments, an immunogenic complex described herein comprises one or more polypeptide antigens. In some embodiments, the one or more polypeptide antigens is a bacterial polypeptide, a fungal polypeptide, and/or a viral polypeptide. In some embodiments, the one or more polypeptide antigens is a polypeptide derived from *Klebsiella, Pseudomonas*, and/or a *E. coli* polypeptide.

In some embodiments, at least one of the antigenic polysaccharides is the *P. aeruginosa* exopolysaccharide PsL. In some embodiments, the PsL comprises at least one epitope that binds to a monoclonal antibody comprising a sequence having at least 80%, 85%, 90%, 95%, 96%, 97%, 98%, 99%, or 100% identity to the sequence of SEQ ID NO:4 and/or a sequence having at least 80%, 85%, 90%, 95%, 96%, 97%, 98%, 99%, or 100% identity to the sequence of SEQ ID NO:5 (Cam-003). In some embodiments, at least one polypeptide antigen comprises an amino acid sequence having at least 80%, 85%, 90%, 95%, 96%, 97%, 98%, 99%, or 100% identity to the sequence of SEQ ID NO:1 (*K. pneumoniae* Type I fimbrial protein). In some embodiments, at least one polypeptide antigen comprises an amino acid sequence having at least 80%, 85%, 90%, 95%, 96%, 97%, 98%, 99%, or 100% identity to the sequence of SEQ ID NO:2 (*K. pneumoniae* conserved Type III fimbrial protein MrkA) or an amino acid sequence having at least 80%, 85%, 90%, 95%, 96%, 97%, 98%, 99%, or 100% identity to the sequence of the monomer stabilized MrkA SEQ ID NO:3 or an immunogenic fragment thereof. In some embodiments, at least one polypeptide antigen is a *P. aeruginosa* FliC flagellin subtype A, *P. aeruginosa* FliC flagellin subtype B, or an immunogenic fragment thereof. In some embodiments, at least one polypeptide antigen comprises an amino acid sequence having at least 80%, 85%, 90%, 95%, 96%, 97%, 98%, 99%, or 100% identity to the sequence of SEQ ID NO:6 (subtype A1), an amino acid sequence having at least 80%, 85%, 90%, 95%, 96%, 97%, 98%, 99%, or 100% identity to the sequence of SEQ ID NO:9 (subtype A2), or an immunogenic fragment thereof.

Manufacture of Immunogenic Complexes

The present disclosure includes methods for manufacturing immunogenic complexes described herein. In some embodiments, a method of manufacturing immunogenic complexes comprises complexing at least one biotinylated backbone polymer with at least one biotin-binding fusion protein. In some embodiments, the fusion protein comprises an amino acid sequence having at least 80%, 85%, 90%, 95%, 96%, 97%, 98%, 99%, or 100% identity to any one of SEQ ID NOs:16-26.

Diseases, Disorders, and Conditions

In some embodiments, upon administration to a subject, an immunogenic complex disclosed herein (e.g., a composition comprising an immunogenic complex described herein) induces antibody production against one or more pathogens in the subject at level greater than a composition comprising an antigenic polysaccharide and not comprising the backbone polymer, as measured by ELISA. In some embodiments, the one or more pathogens are selected from, *Klebsiella, Pseudomonas*, and *E. coli*.

In some embodiments, upon administration to a subject, an immunogenic complex disclosed herein (e.g., a composition comprising an immunogenic complex described herein) elicits an immune response against one or more pathogens in the subject. In some embodiments, upon administration to a subject, an immunogenic complex disclosed herein elicits an immune response against one or more pathogens in the subject at level greater than a composition comprising an antigenic polysaccharide and not comprising the backbone polymer. In some embodiments, the one or more pathogens are selected from, *Klebsiella, Pseudomonas*, and *E. coli*.

In some embodiments, upon administration to a subject, an immunogenic complex disclosed herein (e.g., a composition comprising an immunogenic complex described herein) is used to treat or prevent infection. In some embodiments, the infection is burn wound infection, GI infection, surgical site infection, urinary tract infection, corneal infection, skin and/or soft tissue infection, diabetic wound infection, device associated infection (e.g., catheter, surgical implant, prosthesis). In some embodiments, upon administration to a subject, an immunogenic composition disclosed herein is used to treat or prevent pneumonia, sepsis, and/or colonization.

Immunogenic Compositions and Formulations

The specification also provides compositions that include one or more immunogenic complexes described herein. For example, an immunogenic composition, e.g., vaccine composition, can include one or more immunogenic complexes described herein. In some embodiments, such compositions can include a plurality of one type of immunogenic complex described herein. Additionally or alternatively, such compositions can include a plurality of more than one type of immunogenic complex described herein. In some embodiments immunogenic complexes described herein are formulated into a pharmaceutical composition. In some embodiments a pharmaceutical composition may be a vaccine. In some embodiments a pharmaceutical composition comprises a pharmaceutically acceptable carrier.

In some embodiments, a vaccine composition is a polyvalent or multivalent vaccine. In some embodiments, the valency of a vaccine composition refers to the number of types of immunogenic complexes present in the vaccine composition. The valency of a vaccine described herein is not limiting with respect to the total antigens present in said pharmaceutical composition, immunogenic complex, or vaccine, or to the number of pathogen strains for which administration of said pharmaceutical composition, immunogenic complex, immunogenic composition, or vaccine composition may induce an immune-protective response. In a non-limiting example, a 12-valent vaccine composition may comprise more than 12 antigenic components (e.g., peptide and/or polysaccharide components) and may induce an immuno-protective response against more than 12 pathogens or pathogenic strains.

In some embodiments, a vaccine composition comprises between 1-50 types of immunogenic complexes. In some embodiments, a vaccine composition comprises between 1-25 types of immunogenic complexes. In some embodiments, a vaccine composition comprises between 1-15 types of immunogenic complexes. In some embodiments, a vaccine composition comprises between 1-10 types of immunogenic complexes. In some embodiments, a vaccine composition comprises between 1-5 types of immunogenic complexes. In some embodiments, a vaccine is a polyvalent vaccine.

In some embodiments, a vaccine composition comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 types of immunogenic complexes. In some embodiments, a vaccine composition comprises 1 type of immunogenic complex. In some embodiments, a vaccine composition comprises 2 types of immunogenic complexes. In some embodiments, a vaccine composition comprises 4 types of immunogenic complexes. In some embodiments, a vaccine composition comprises 6 types of immunogenic complexes. In some embodiments, a vaccine composition comprises 8 types of immunogenic complexes. In some embodiments, a vaccine composition comprises 10 types of immunogenic complexes. In some embodiments, a vaccine composition comprises 12 types of immunogenic complexes. In some embodiments, a vaccine composition comprises two or more types of immunogenic complexes in amounts such that the weight of OPS in the vaccine composition from each immunogenic composition is different, e.g., present in a w/w ratio that is not about 1:1. In some embodiments, a vaccine composition comprises two or more types of immunogenic complexes in amounts such that the weight of OPS in the vaccine composition from each immunogenic composition is about the same, e.g., present in a w/w ratio of about 1:1. In some embodiments, the weight of OPS in the vaccine from each immunogenic composition is about 1 µg. In some embodiments, the weight of OPS in the vaccine from each immunogenic composition is about 2 µg. In some embodiments, the weight of OPS in the vaccine from each immunogenic composition is about 3 µg. In some embodiments, the weight of OPS in the vaccine from each immunogenic composition is about 4 µg. In some embodiments, the weight of OPS in the vaccine from each immunogenic composition is about 5 µg.

In some embodiments, a vaccine composition comprises two or more types of immunogenic complexes in amounts such that the combined weight of OPS and CPS in the vaccine composition from each immunogenic composition is different, e.g., present in a w/w ratio that is not about 1:1. In some embodiments, a vaccine composition comprises two or more types of immunogenic complexes in amounts such that the combined weight of OPS and CPS in the vaccine composition from each immunogenic composition is different, e.g., present in a w/w ratio that is not about 1:1. In some embodiments, a vaccine composition comprises two or more types of immunogenic complexes in amounts such that the combined weight of OPS and CPS in the vaccine composition from each immunogenic composition is about the same, e.g., present in a w/w ratio of about 1:1. In some embodiments, the combined weight of OPS and CPS in the vaccine from each immunogenic composition is about 1 µg. In some embodiments, the combined weight of OPS and CPS in the vaccine from each immunogenic composition is about 2 µg. In some embodiments, the weight of OPS in the vaccine from each immunogenic composition is about 3 µg. In some embodiments, the combined weight of OPS and CPS in the vaccine from each immunogenic composition is about 4 µg. In some embodiments, the combined weight of OPS and CPS in the vaccine from each immunogenic composition is about 5 µg.

In some embodiments, a vaccine composition comprises two or more types of immunogenic compositions selected from (a) an immunogenic composition comprising a backbone polymer comprising a polymer comprising a biotinylated *Klebsiella* spp. K19 capsular polysaccharide, a KP O1 OPS conjugated to the *Klebsiella* spp. K19 capsular polysaccharide, and a Rhavi-FlaBD2-MrkA fusion protein non-covalently complexed to the biotinylated backbone polymer;

(b) an immunogenic composition comprising a backbone polymer comprising a polymer comprising a biotinylated *Klebsiella* spp. K19 capsular polysaccharide, a KP O2 OPS conjugated to the *Klebsiella* spp. K19 capsular polysaccharide, and a Rhavi-FlaBD2-MrkA fusion protein non-covalently complexed to the biotinylated backbone polymer;

(b') an immunogenic composition comprising a backbone polymer comprising a polymer comprising a biotinylated *Klebsiella* spp. K19 capsular polysaccharide, a KP O2 OPS conjugated to the *Klebsiella* spp. K19 capsular polysaccharide, and a Rhavi-FlaBD2-PcrV fusion protein non-covalently complexed to the biotinylated backbone polymer;

(c) an immunogenic composition comprising a backbone polymer comprising a polymer comprising a biotinylated *Klebsiella* spp. K19 capsular polysaccharide, a KP O3 OPS conjugated to the *Klebsiella* spp. K19 capsular polysaccharide, and a Rhavi-FlaBD2-MrkA fusion protein non-covalently complexed to the biotinylated backbone polymer;

(d) an immunogenic composition comprising a backbone polymer comprising a polymer comprising a biotinylated *Klebsiella* spp. K19 capsular polysaccharide, a KP O5 OPS conjugated to the *Klebsiella* spp. K19 capsular polysaccharide, and a Rhavi-FlaBD2-MrkA fusion protein non-covalently complexed to the biotinylated backbone polymer;

(d') an immunogenic composition comprising a backbone polymer comprising a polymer comprising a biotinylated *Klebsiella* spp. K19 capsular polysaccharide, a KP O5 OPS conjugated to the *Klebsiella* spp. K19 capsular polysaccharide, and a Rhavi-FlaBD2-PcrV fusion protein non-covalently complexed to the biotinylated backbone polymer;

(e) an immunogenic composition comprising a backbone polymer comprising a polymer comprising a biotinylated *Klebsiella* spp. K19 capsular polysaccharide, a PA O1 OPS conjugated to the *Klebsiella* spp. K19 capsular polysaccharide, and a Rhavi-FlaBD2-MrkA fusion protein non-covalently complexed to the biotinylated backbone polymer;

(e') an immunogenic composition comprising a backbone polymer comprising a polymer comprising a biotinylated *Klebsiella* spp. K19 capsular polysaccharide, a PA O1 OPS conjugated to the *Klebsiella* spp. K19 capsular polysaccharide, and a Rhavi-FlaBD2-PcrV fusion protein non-covalently complexed to the biotinylated backbone polymer;

(f) an immunogenic composition comprising a backbone polymer comprising a polymer comprising a biotinylated *Klebsiella* spp. K19 capsular polysaccharide, a PA O2 OPS conjugated to the *Klebsiella* spp. K19 capsular polysaccharide, and a Rhavi-FlaBD2-MrkA fusion protein non-covalently complexed to the biotinylated backbone polymer;

(f') an immunogenic composition comprising a backbone polymer comprising a polymer comprising a biotinylated *Klebsiella* spp. K19 capsular polysaccharide, a PA O2 OPS conjugated to the *Klebsiella* spp. K19 capsular polysaccharide, and a Rhavi-FlaBD2-PcrV fusion protein non-covalently complexed to the biotinylated backbone polymer;

(g) an immunogenic composition comprising a backbone polymer comprising a polymer comprising a biotinylated *Klebsiella* spp. K19 capsular polysaccharide, a PA O3 OPS conjugated to the *Klebsiella* spp. K19 capsular polysaccharide, and a Rhavi-FlaBD2-MrkA fusion protein non-covalently complexed to the biotinylated backbone polymer;

(g') an immunogenic composition comprising a backbone polymer comprising a polymer comprising a biotinylated *Klebsiella* spp. K19 capsular polysaccharide, a PA O3 OPS conjugated to the *Klebsiella* spp. K19 capsular polysaccharide, and a Rhavi-FlaBD2-PcrV fusion protein non-covalently complexed to the biotinylated backbone polymer;

(h) an immunogenic composition comprising a backbone polymer comprising a polymer comprising a biotinylated *Klebsiella* spp. K19 capsular polysaccharide, a PA O4 OPS conjugated to the *Klebsiella* spp. K19 capsular polysaccharide, and a Rhavi-FlaBD2-MrkA fusion protein non-covalently complexed to the biotinylated backbone polymer;

(h') an immunogenic composition comprising a backbone polymer comprising a polymer comprising a biotinylated *Klebsiella* spp. K19 capsular polysaccharide, a PA O4 OPS conjugated to the *Klebsiella* spp. K19 capsular polysaccharide, and a Rhavi-FlaBD2-PcrV fusion protein non-covalently complexed to the biotinylated backbone polymer;

(i) an immunogenic composition comprising a backbone polymer comprising a polymer comprising a biotinylated *Klebsiella* spp. K19 capsular polysaccharide, a PA O5 OPS conjugated to the *Klebsiella* spp. K19 capsular polysaccharide, and a Rhavi-FlaBD2-MrkA fusion protein non-covalently complexed to the biotinylated backbone polymer;

(j) an immunogenic composition comprising a backbone polymer comprising a polymer comprising a biotinylated *Klebsiella* spp. K19 capsular polysaccharide, a PA O6 OPS conjugated to the *Klebsiella* spp. K19 capsular polysaccharide, and a Rhavi-FlaBD2-MrkA fusion protein non-covalently complexed to the biotinylated backbone polymer;

(k) an immunogenic composition comprising a backbone polymer comprising a polymer comprising a biotinylated *Klebsiella* spp. K19 capsular polysaccharide, a PA O10 OPS conjugated to the *Klebsiella* spp. K19 capsular polysaccharide, and a Rhavi-FlaBD2-MrkA fusion protein non-covalently complexed to the biotinylated backbone polymer; and (l) an immunogenic composition comprising a backbone polymer comprising a polymer comprising a biotinylated *Klebsiella* spp. K19 capsular polysaccharide, a PA O11 OPS conjugated to the *Klebsiella* spp. K19 capsular polysaccharide, and a Rhavi-FlaBD2-MrkA fusion protein non-covalently complexed to the biotinylated backbone polymer.

In some embodiments, a vaccine composition comprises two or more types of immunogenic compositions selected from (a) an immunogenic composition comprising a backbone polymer comprising a polymer comprising a biotinylated *Klebsiella* spp. K19 capsular polysaccharide, a KP O1 OPS conjugated to the *Klebsiella* spp. K19 capsular polysaccharide, and a Rhavi-FlaBD2-MrkA fusion protein non-covalently complexed to the biotinylated backbone polymer;

(a') an immunogenic composition comprising a backbone polymer comprising a polymer comprising a biotinylated *Klebsiella* spp. K19 capsular polysaccharide, a KP O1 OPS conjugated to the *Klebsiella* spp. K19 capsular polysaccharide, and a Rhavi-FlaBD2-PcrV fusion protein non-covalently complexed to the biotinylated backbone polymer;

(b) an immunogenic composition comprising a backbone polymer comprising a polymer comprising a biotinylated *Klebsiella* spp. K19 capsular polysaccharide, a KP O2 OPS conjugated to the *Klebsiella* spp. K19 capsular polysaccharide, and a Rhavi-FlaBD2-MrkA fusion protein non-covalently complexed to the biotinylated backbone polymer;

(b') an immunogenic composition comprising a backbone polymer comprising a polymer comprising a biotinylated

*Klebsiella* spp. K19 capsular polysaccharide, a KP O2 OPS conjugated to the *Klebsiella* spp. K19 capsular polysaccharide, and a Rhavi-FlaBD2-PcrV fusion protein non-covalently complexed to the biotinylated backbone polymer;

(c) an immunogenic composition comprising a backbone polymer comprising a polymer comprising a biotinylated *Klebsiella* spp. K19 capsular polysaccharide, a KP O3 OPS conjugated to the *Klebsiella* spp. K19 capsular polysaccharide, and a Rhavi-FlaBD2-MrkA fusion protein non-covalently complexed to the biotinylated backbone polymer;

(c') an immunogenic composition comprising a backbone polymer comprising a polymer comprising a biotinylated *Klebsiella* spp. K19 capsular polysaccharide, a KP O3 OPS conjugated to the *Klebsiella* spp. K19 capsular polysaccharide, and a Rhavi-FlaBD2-PcrV fusion protein non-covalently complexed to the biotinylated backbone polymer;

(d) an immunogenic composition comprising a backbone polymer comprising a polymer comprising a biotinylated *Klebsiella* spp. K19 capsular polysaccharide, a KP O5 OPS conjugated to the *Klebsiella* spp. K19 capsular polysaccharide, and a Rhavi-FlaBD2-MrkA fusion protein non-covalently complexed to the biotinylated backbone polymer;

(d') an immunogenic composition comprising a backbone polymer comprising a polymer comprising a biotinylated *Klebsiella* spp. K19 capsular polysaccharide, a KP O5 OPS conjugated to the *Klebsiella* spp. K19 capsular polysaccharide, and a Rhavi-FlaBD2-PcrV fusion protein non-covalently complexed to the biotinylated backbone polymer;

(e) an immunogenic composition comprising a backbone polymer comprising a polymer comprising a biotinylated *Klebsiella* spp. K19 capsular polysaccharide, a PA O1 OPS conjugated to the *Klebsiella* spp. K19 capsular polysaccharide, and a Rhavi-FlaBD2-MrkA fusion protein non-covalently complexed to the biotinylated backbone polymer;

(e') an immunogenic composition comprising a backbone polymer comprising a polymer comprising a biotinylated *Klebsiella* spp. K19 capsular polysaccharide, a PA O1 OPS conjugated to the *Klebsiella* spp. K19 capsular polysaccharide, and a Rhavi-FlaBD2-PcrV fusion protein non-covalently complexed to the biotinylated backbone polymer;

(f) an immunogenic composition comprising a backbone polymer comprising a polymer comprising a biotinylated *Klebsiella* spp. K19 capsular polysaccharide, a PA O2 OPS conjugated to the *Klebsiella* spp. K19 capsular polysaccharide, and a Rhavi-FlaBD2-MrkA fusion protein non-covalently complexed to the biotinylated backbone polymer;

(f') an immunogenic composition comprising a backbone polymer comprising a polymer comprising a biotinylated *Klebsiella* spp. K19 capsular polysaccharide, a PA O2 OPS conjugated to the *Klebsiella* spp. K19 capsular polysaccharide, and a Rhavi-FlaBD2-PcrV fusion protein non-covalently complexed to the biotinylated backbone polymer;

(g) an immunogenic composition comprising a backbone polymer comprising a polymer comprising a biotinylated *Klebsiella* spp. K19 capsular polysaccharide, a PA O3 OPS conjugated to the *Klebsiella* spp. K19 capsular polysaccharide, and a Rhavi-FlaBD2-MrkA fusion protein non-covalently complexed to the biotinylated backbone polymer;

(g') an immunogenic composition comprising a backbone polymer comprising a polymer comprising a biotinylated *Klebsiella* spp. K19 capsular polysaccharide, a PA O3 OPS conjugated to the *Klebsiella* spp. K19 capsular polysaccharide, and a Rhavi-FlaBD2-PcrV fusion protein non-covalently complexed to the biotinylated backbone polymer;

(h) an immunogenic composition comprising a backbone polymer comprising a polymer comprising a biotinylated *Klebsiella* spp. K19 capsular polysaccharide, a PA O4 OPS conjugated to the *Klebsiella* spp. K19 capsular polysaccharide, and a Rhavi-FlaBD2-MrkA fusion protein non-covalently complexed to the biotinylated backbone polymer;

(h') an immunogenic composition comprising a backbone polymer comprising a polymer comprising a biotinylated *Klebsiella* spp. K19 capsular polysaccharide, a PA O4 OPS conjugated to the *Klebsiella* spp. K19 capsular polysaccharide, and a Rhavi-FlaBD2-PcrV fusion protein non-covalently complexed to the biotinylated backbone polymer;

(i) an immunogenic composition comprising a backbone polymer comprising a polymer comprising a biotinylated *Klebsiella* spp. K19 capsular polysaccharide, a PA O5 OPS conjugated to the *Klebsiella* spp. K19 capsular polysaccharide, and a Rhavi-FlaBD2-MrkA fusion protein non-covalently complexed to the biotinylated backbone polymer;

(i') an immunogenic composition comprising a backbone polymer comprising a polymer comprising a biotinylated *Klebsiella* spp. K19 capsular polysaccharide, a PA O5 OPS conjugated to the *Klebsiella* spp. K19 capsular polysaccharide, and a Rhavi-FlaBD2-PcrV fusion protein non-covalently complexed to the biotinylated backbone polymer;

(j) an immunogenic composition comprising a backbone polymer comprising a polymer comprising a biotinylated *Klebsiella* spp. K19 capsular polysaccharide, a PA O6 OPS conjugated to the *Klebsiella* spp. K19 capsular polysaccharide, and a Rhavi-FlaBD2-MrkA fusion protein non-covalently complexed to the biotinylated backbone polymer;

(j') an immunogenic composition comprising a backbone polymer comprising a polymer comprising a biotinylated *Klebsiella* spp. K19 capsular polysaccharide, a PA O6 OPS conjugated to the *Klebsiella* spp. K19 capsular polysaccharide, and a Rhavi-FlaBD2-PcrV fusion protein non-covalently complexed to the biotinylated backbone polymer;

(k) an immunogenic composition comprising a backbone polymer comprising a polymer comprising a biotinylated *Klebsiella* spp. K19 capsular polysaccharide, a PA O10 OPS conjugated to the *Klebsiella* spp. K19 capsular polysaccharide, and a Rhavi-FlaBD2-MrkA fusion protein non-covalently complexed to the biotinylated backbone polymer;

(k') an immunogenic composition comprising a backbone polymer comprising a polymer comprising a biotinylated *Klebsiella* spp. K19 capsular polysaccharide, a PA O10 OPS conjugated to the *Klebsiella* spp. K19 capsular polysaccharide, and a Rhavi-FlaBD2-PcrV fusion protein non-covalently complexed to the biotinylated backbone polymer;

(l) an immunogenic composition comprising a backbone polymer comprising a polymer comprising a biotinylated *Klebsiella* spp. K19 capsular polysaccharide, a PA O11 OPS conjugated to the *Klebsiella* spp. K19 capsular polysaccharide, and a Rhavi-FlaBD2-MrkA fusion protein non-covalently complexed to the biotinylated backbone polymer;

(l') an immunogenic composition comprising a backbone polymer comprising a polymer comprising a biotinylated *Klebsiella* spp. K19 capsular polysaccharide, a PA O11 OPS conjugated to the *Klebsiella* spp. K19 capsular polysaccharide, and a Rhavi-FlaBD2-PcrV fusion protein non-covalently complexed to the biotinylated backbone polymer.

In some embodiments, a vaccine composition comprises (a) an immunogenic composition comprising a backbone polymer comprising a polymer comprising a biotinylated *Klebsiella* spp. K19 capsular polysaccharide, a KP O1 OPS conjugated to the *Klebsiella* spp. K19 capsular polysaccharide, and a Rhavi-FlaBD2-MrkA fusion protein non-covalently complexed to the biotinylated backbone polymer;

(b) an immunogenic composition comprising a backbone polymer comprising a polymer comprising a biotinylated *Klebsiella* spp. K19 capsular polysaccharide, a KP O2 OPS conjugated to the *Klebsiella* spp. K19 capsular polysaccharide, and a Rhavi-FlaBD2-MrkA fusion protein non-covalently complexed to the biotinylated backbone polymer;

(c) an immunogenic composition comprising a backbone polymer comprising a polymer comprising a biotinylated *Klebsiella* spp. K19 capsular polysaccharide, a KP O3 OPS conjugated to the *Klebsiella* spp. K19 capsular polysaccharide, and a Rhavi-FlaBD2-MrkA fusion protein non-covalently complexed to the biotinylated backbone polymer;

(d) an immunogenic composition comprising a backbone polymer comprising a polymer comprising a biotinylated *Klebsiella* spp. K19 capsular polysaccharide, a KP O5 OPS conjugated to the *Klebsiella* spp. K19 capsular polysaccharide, and a Rhavi-FlaBD2-MrkA fusion protein non-covalently complexed to the biotinylated backbone polymer;

(e) an immunogenic composition comprising a backbone polymer comprising a polymer comprising a biotinylated *Klebsiella* spp. K19 capsular polysaccharide, a PA O1 OPS conjugated to the *Klebsiella* spp. K19 capsular polysaccharide, and a Rhavi-FlaBD2-MrkA fusion protein non-covalently complexed to the biotinylated backbone polymer;

(f) an immunogenic composition comprising a backbone polymer comprising a polymer comprising a biotinylated *Klebsiella* spp. K19 capsular polysaccharide, a PA O2 OPS conjugated to the *Klebsiella* spp. K19 capsular polysaccharide, and a Rhavi-FlaBD2-MrkA fusion protein non-covalently complexed to the biotinylated backbone polymer;

(g) an immunogenic composition comprising a backbone polymer comprising a polymer comprising a biotinylated *Klebsiella* spp. K19 capsular polysaccharide, a PA O3 OPS conjugated to the *Klebsiella* spp. K19 capsular polysaccharide, and a Rhavi-FlaBD2-MrkA fusion protein non-covalently complexed to the biotinylated backbone polymer;

(h) an immunogenic composition comprising a backbone polymer comprising a polymer comprising a biotinylated *Klebsiella* spp. K19 capsular polysaccharide, a PA O4 OPS conjugated to the *Klebsiella* spp. K19 capsular polysaccharide, and a Rhavi-FlaBD2-MrkA fusion protein non-covalently complexed to the biotinylated backbone polymer.

(i) an immunogenic composition comprising a backbone polymer comprising a polymer comprising a biotinylated *Klebsiella* spp. K19 capsular polysaccharide, a PA O5 OPS conjugated to the *Klebsiella* spp. K19 capsular polysaccharide, and a Rhavi-FlaBD2-MrkA fusion protein non-covalently complexed to the biotinylated backbone polymer;

(j) an immunogenic composition comprising a backbone polymer comprising a polymer comprising a biotinylated *Klebsiella* spp. K19 capsular polysaccharide, a PA O6 OPS conjugated to the *Klebsiella* spp. K19 capsular polysaccharide, and a Rhavi-FlaBD2-MrkA fusion protein non-covalently complexed to the biotinylated backbone polymer;

(k) an immunogenic composition comprising a backbone polymer comprising a polymer comprising a biotinylated *Klebsiella* spp. K19 capsular polysaccharide, a PA O10 OPS conjugated to the *Klebsiella* spp. K19 capsular polysaccharide, and a Rhavi-FlaBD2-MrkA fusion protein non-covalently complexed to the biotinylated backbone polymer; and (l) an immunogenic composition comprising a backbone polymer comprising a polymer comprising a biotinylated *Klebsiella* spp. K19 capsular polysaccharide, a PA O11 OPS conjugated to the *Klebsiella* spp. K19 capsular polysaccharide, and a Rhavi-FlaBD2-MrkA fusion protein non-covalently complexed to the biotinylated backbone polymer.

In some embodiments, a vaccine composition comprises (a) an immunogenic composition comprising a backbone polymer comprising a polymer comprising a biotinylated *Klebsiella* spp. K19 capsular polysaccharide, a KP O1 OPS conjugated to the *Klebsiella* spp. K19 capsular polysaccharide, and a Rhavi-FlaBD2-MrkA fusion protein non-covalently complexed to the biotinylated backbone polymer;

(b) an immunogenic composition comprising a backbone polymer comprising a polymer comprising a biotinylated *Klebsiella* spp. K19 capsular polysaccharide, a KP O2 OPS conjugated to the *Klebsiella* spp. K19 capsular polysaccharide, and a Rhavi-FlaBD2-PcrV fusion protein non-covalently complexed to the biotinylated backbone polymer;

(c) an immunogenic composition comprising a backbone polymer comprising a polymer comprising a biotinylated *Klebsiella* spp. K19 capsular polysaccharide, a KP O3 OPS conjugated to the *Klebsiella* spp. K19 capsular polysaccharide, and a Rhavi-FlaBD2-MrkA fusion protein non-covalently complexed to the biotinylated backbone polymer;

(d) an immunogenic composition comprising a backbone polymer comprising a polymer comprising a biotinylated *Klebsiella* spp. K19 capsular polysaccharide, a KP O5 OPS conjugated to the *Klebsiella* spp. K19 capsular polysaccharide, and a Rhavi-FlaBD2-PcrV fusion protein non-covalently complexed to the biotinylated backbone polymer;

(e) an immunogenic composition comprising a backbone polymer comprising a polymer comprising a biotinylated *Klebsiella* spp. K19 capsular polysaccharide, a PA O1 OPS conjugated to the *Klebsiella* spp. K19 capsular polysaccharide, and a Rhavi-FlaBD2-PcrV fusion protein non-covalently complexed to the biotinylated backbone polymer;

(f) an immunogenic composition comprising a backbone polymer comprising a polymer comprising a biotinylated *Klebsiella* spp. K19 capsular polysaccharide, a PA O2 OPS conjugated to the *Klebsiella* spp. K19 capsular polysaccharide, and a Rhavi-FlaBD2-PcrV fusion protein non-covalently complexed to the biotinylated backbone polymer;

(g) an immunogenic composition comprising a backbone polymer comprising a polymer comprising a biotinylated *Klebsiella* spp. K19 capsular polysaccharide, a PA O3 OPS conjugated to the *Klebsiella* spp. K19 capsular polysaccharide, and a Rhavi-FlaBD2-PcrV fusion protein non-covalently complexed to the biotinylated backbone polymer;

(h) an immunogenic composition comprising a backbone polymer comprising a polymer comprising a biotinylated *Klebsiella* spp. K19 capsular polysaccharide, a PA O4 OPS conjugated to the *Klebsiella* spp. K19 capsular polysaccharide, and a Rhavi-FlaBD2-PcrV fusion protein non-covalently complexed to the biotinylated backbone polymer;

(i) an immunogenic composition comprising a backbone polymer comprising a polymer comprising a biotinylated *Klebsiella* spp. K19 capsular polysaccharide, a PA O5 OPS conjugated to the *Klebsiella* spp. K19 capsular polysaccharide, and a Rhavi-FlaBD2-MrkA fusion protein non-covalently complexed to the biotinylated backbone polymer;

(j) an immunogenic composition comprising a backbone polymer comprising a polymer comprising a biotinylated *Klebsiella* spp. K19 capsular polysaccharide, a PA O6 OPS conjugated to the *Klebsiella* spp. K19 capsular polysaccharide, and a Rhavi-FlaBD2-MrkA fusion protein non-covalently complexed to the biotinylated backbone polymer;

(k) an immunogenic composition comprising a backbone polymer comprising a polymer comprising a biotinylated *Klebsiella* spp. K19 capsular polysaccharide, a PA O10 OPS conjugated to the *Klebsiella* spp. K19 capsular polysaccharide, and a Rhavi-FlaBD2-MrkA fusion protein non-covalently complexed to the biotinylated backbone polymer; and (l) an immunogenic composition comprising a backbone polymer comprising a polymer comprising a biotinylated *Klebsiella* spp. K19 capsular polysaccharide, a PA O11 OPS conjugated to the *Klebsiella* spp. K19 capsular polysaccharide, and a Rhavi-FlaBD2-MrkA fusion protein non-covalently complexed to the biotinylated backbone polymer.

In some embodiments, a vaccine composition comprises two or more types of immunogenic compositions selected from
(a) an immunogenic composition comprising a KP O1 OPS and a FlaBD2-MrkA fusion protein;
(a') an immunogenic composition comprising a KP O1 OPS and a FlaBD2-PcrV fusion protein;
(b) an immunogenic composition comprising a KP O2 OPS and a FlaBD2-MrkA fusion protein;
(b') an immunogenic composition comprising a KP O2 OPS and a FlaBD2-PcrV fusion protein;
(c) an immunogenic composition comprising a KP O3 OPS and a FlaBD2-MrkA fusion protein;
(c') an immunogenic composition comprising a KP O3 OPS and a FlaBD2-PcrV fusion protein;
(d) an immunogenic composition comprising a KP O5 OPS and a FlaBD2-MrkA fusion protein;
(d') an immunogenic composition comprising a KP O5 OPS and a FlaBD2-PcrV fusion protein;
(e) an immunogenic composition comprising a PA O1 OPS and a FlaBD2-MrkA fusion protein;
(e') an immunogenic composition comprising a PA O1 OPS and a FlaBD2-PcrV fusion protein;
(f) an immunogenic composition comprising a PA O2 OPS and a FlaBD2-MrkA fusion;
(f') an immunogenic composition comprising a PA O2 OPS and a FlaBD2-PcrV fusion protein;
(g) an immunogenic composition comprising a PA O3 OPS and a FlaBD2-MrkA fusion protein;
(g') an immunogenic composition comprising a PA O3 OPS and a FlaBD2-PcrV fusion protein;
(h) an immunogenic composition comprising a PA O4 OPS and a FlaBD2-MrkA fusion protein;
(h') an immunogenic composition comprising a PA O4 OPS and a FlaBD2-PcrV fusion protein;
(i) an immunogenic composition comprising a PA O5 OPS and a FlaBD2-MrkA fusion protein;
(i') an immunogenic composition comprising a PA O5 OPS and a FlaBD2-PcrV fusion protein;
(j) an immunogenic composition comprising a PA O6 OPS and a FlaBD2-MrkA fusion protein;
(j') an immunogenic composition comprising a PA O6 OPS and a FlaBD2-PcrV fusion protein;
(k) an immunogenic composition comprising a PA O10 OPS and a FlaBD2-MrkA fusion protein;
(k') an immunogenic composition comprising a PA O10 OPS and a FlaBD2-PcrV fusion protein;
(l) an immunogenic composition comprising a PA O11 OPS and a FlaBD2-MrkA fusion protein; and
(l') an immunogenic composition comprising a PA O11 OPS and a FlaBD2-PcrV fusion protein.

In some embodiments, one or more of the types of immunogenic compositions further comprises one or more polymers. In some embodiments, an OPS is conjugated to the one or more polymers. In some embodiments the FlaBD2-MrkA fusion protein is conjugated to the one or more polymers. In some embodiments the FlaBD2-PcrV fusion protein is conjugated to the one or more polymers. In some embodiments an OPS and the FlaBD2-MrkA fusion protein are conjugated to the one or more polymers. In some embodiments an OPS and the FlaBD2-PcrV fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the one or more polymers comprise PLL.

In some embodiments, a vaccine composition comprises an immunogenic composition selected from
(a) an immunogenic composition comprising a combination of *K. pneumoniae* OPS of type O1, O2, O3, O5, and a FlaBD2-MrkA fusion protein; and
(b) an immunogenic composition comprising a combination of a *P. aeruginosa* OPS of type O1, O2, O3, O4, O5, O6, O10, O11, and a FlaBD2-MrkA fusion protein.

In some embodiments, one or more of the types of immunogenic compositions further comprises one or more polymers. In some embodiments, a *K. pneumoniae* OPS is conjugated to the one or more polymers. In some embodiments the FlaBD2-MrkA fusion protein is conjugated to the one or more polymers. In some embodiments an OPS and the FlaBD2-MrkA fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the one or more polymers comprise PLL.

In some embodiments, a vaccine composition comprises
(a) an immunogenic composition comprising
(i) one or more of *K. pneumoniae* OPS of type O1, O2, O3, O5, and any combination thereof; and
(ii) a FlaBD2-MrkA fusion protein; and/or
(b) an immunogenic composition comprising
(i) one or more of a *P. aeruginosa* OPS of type O1, O2, O3, O4, O5, O6, O10, O11, and any combination thereof; and
(ii) a FlaBD2-MrkA fusion protein.

In some embodiments, one or more of the types of immunogenic compositions further comprises one or more polymers. In some embodiments, an OPS is conjugated to the one or more polymers. In some embodiments the FlaBD2-MrkA fusion protein is conjugated to the one or more polymers. In some embodiments an OPS and the FlaBD2-MrkA fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the one or more polymers comprise PLL.

In some embodiments, a vaccine composition comprises an immunogenic composition selected from
(a) an immunogenic composition comprising a combination of *K. pneumoniae* OPS of type O1, O2, O3, O5, a FlaBD2-PcrV fusion protein, and a FlaBD2-MrkA fusion protein; and
(b) an immunogenic composition comprising a combination of a *P. aeruginosa* OPS of type O1, O2, O3, O4, O5, O6, O10, O11, a FlaBD2-PcrV fusion protein, and a FlaBD2-MrkA fusion protein.

In some embodiments, the vaccine further comprises one or more polymers. In some embodiments, an OPS is conjugated to the one or more polymers. In some embodiments the FlaBD2-MrkA fusion protein is conjugated to the one or more polymers. In some embodiments the FlaBD2-PcrV fusion protein is conjugated to the one or more polymers. In some embodiments an OPS and the FlaBD2-MrkA fusion protein are conjugated to the polymer. In some embodiments an OPS and the FlaBD2-PcrV fusion protein are conjugated to the polymer. In some embodiments, the polymer comprises a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5; and
(b) one or more polypeptides comprising an amino acid sequence having at least 80%, 85%, 90%, 95%, 96%, 97%, 98%, 99%, or 100% identity to the sequence of one or more of SEQ ID NOs: 1-3, 6-12, or 16-26.

In some embodiments, the vaccine composition further comprises one or more polymers. In some embodiments, the one or more OPS are conjugated to the one or more polymers. In some embodiments the one or more polypeptides are conjugated to the one or more polymers. In some embodiments an OPS and the one or more polypeptides are conjugated to the one or more polymers. In some embodiments, the polymer comprises a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *P. aeruginosa* OPS of type O1, O2, O3, O4, O5, O6, O10, O11; and
(b) one or more polypeptides comprising an amino acid sequence having at least 80%, 85%, 90%, 95%, 96%, 97%, 98%, 99%, or 100% identity to the sequence of one or more of SEQ ID NOs: 1-3, 6-12, or 16-26.

In some embodiments, the vaccine composition further comprises one or more polymers. In some embodiments, an OPS is conjugated to the one or more polymers. In some embodiments the one or more polypeptides are conjugated to the one or more polymers. In some embodiments an OPS and one or more polypeptides are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5;
(b) one or more of *P. aeruginosa* OPS of type O1, O2, O3, O4, O5, O6, O10, O11; and
(c) one or more polypeptides comprising an amino acid sequence having at least 80%, 85%, 90%, 95%, 96%, 97%, 98%, 99%, or 100% identity to the sequence of one or more of SEQ ID NOs: 1-3, 6-12, or 16-26.

In some embodiments, the vaccine composition further comprises one or more polymers. In some embodiments, an OPS is conjugated to the one or more polymers. In some embodiments the one or more polypeptides are conjugated to the one or more polymers. In some embodiments an OPS and the one or more polypeptides are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5; and
(b) a FlaBD2-MrkA fusion protein.

In some embodiments, the vaccine composition further comprises one or more polymers. In some embodiments, an OPS is conjugated to the one or more polymers. In some embodiments the FlaBD2-MrkA fusion protein is conjugated to the one or more polymers. In some embodiments an OPS and the FlaBD2-MrkA fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *P. aeruginosa* OPS of type O1, O2, O3, O4, O5, O6, O10, O11; and
(b) a FlaBD2-MrkA fusion protein.

In some embodiments, the vaccine composition further comprises one or more polymers. In some embodiments, an OPS is conjugated to the one or more polymers. In some embodiments the FlaBD2-MrkA fusion protein is conjugated to the one or more polymers. In some embodiments an OPS and the FlaBD2-MrkA fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5;
(b) one or more of *P. aeruginosa* OPS of type O1, O2, O3, O4, O5, O6, O10, O11; and
(c) a FlaBD2-MrkA fusion protein.

In some embodiments, the vaccine composition further comprises one or more polymers. In some embodiments, an OPS is conjugated to the one or more polymers. In some embodiments the FlaBD2-MrkA fusion protein is conjugated to the one or more polymers. In some embodiments an OPS and the FlaBD2-MrkA fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5; and
(b) a FlaBD2-PcrV fusion protein.

In some embodiments, the vaccine composition further comprises one or more polymers. In some embodiments, an OPS is conjugated to the one or more polymers. In some embodiments the FlaBD2-PcrV fusion protein is conjugated to the one or more polymers. In some embodiments an OPS and the FlaBD2-PcrV fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *P. aeruginosa* OPS of type O1, O2, O3, O4, O5, O6, O10, O11; and
(b) a FlaBD2-PcrV fusion protein.

In some embodiments, the vaccine composition further comprises one or more polymers. In some embodiments, an OPS is conjugated to the one or more polymers. In some embodiments the FlaBD2-PcrV fusion protein is conjugated to the one or more polymers. In some embodiments an OPS and the FlaBD2-PcrV fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5;
(b) one or more of *P. aeruginosa* OPS of type O1, O2, O3, O4, O5, O6, O10, O11; and
(c) a FlaBD2-PcrV fusion protein.

In some embodiments, the vaccine composition further comprises one or more polymers. In some embodiments, an OPS is conjugated to the one or more polymers. In some embodiments the FlaBD2-PcrV fusion protein is conjugated to the one or more polymers. In some embodiments an OPS and the FlaBD2-PcrV fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5;
(b) a FlaBD2-MrkA fusion protein; and
(c) a FlaBD2-PcrV fusion protein In some embodiments, the vaccine composition further comprises one or more polymers. In some embodiments, an OPS is conjugated to the one or more polymers. In some embodiments the FlaBD2-MrkA fusion protein is conjugated to the one or more polymers. In some embodiments the FlaBD2-PcrV fusion protein is conjugated to the one or more polymers. In some embodiments an OPS and the FlaBD2-MrkA fusion protein are conjugated to the one or more polymers. In some embodiments an OPS and the FlaBD2-PcrV fusion protein are conjugated to the one or more polymers. In some embodiments the FlaBD2-MrkA fusion protein and the FlaBD2-PcrV fusion protein are conjugated to the one or more polymers. In some embodiments an OPS, the FlaBD2-MrkA fusion protein, and the FlaBD2-PcrV fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *P. aeruginosa* OPS of type O1, O2, O3, O4, O5, O6, O10, O11; and
(b) a FlaBD2-MrkA fusion protein; and
(c) a FlaBD2-PcrV fusion protein.

In some embodiments, the vaccine composition further comprises one or more polymers. In some embodiments, an OPS is conjugated to the one or more polymers. In some embodiments the FlaBD2-MrkA fusion protein is conjugated to the one or more polymers. In some embodiments the FlaBD2-PcrV fusion protein is conjugated to the one or more polymers. In some embodiments an OPS and the FlaBD2-MrkA fusion protein are conjugated to the one or more polymers. In some embodiments an OPS and the FlaBD2-PcrV fusion protein are conjugated to the one or more polymers. In some embodiments the FlaBD2-MrkA fusion protein and the FlaBD2-PcrV fusion protein are conjugated to the one or more polymers. In some embodiments an OPS, the FlaBD2-MrkA fusion protein, and the FlaBD2-PcrV fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5;
(b) one or more of *P. aeruginosa* OPS of type O1, O2, O3, O4, O5, O6, O10, O11; and
(c) a FlaBD2-MrkA fusion protein; and
(d) a FlaBD2-PcrV fusion protein.

In some embodiments, the vaccine composition further comprises one or more polymers. In some embodiments, an OPS is conjugated to the one or more polymers. In some embodiments the FlaBD2-MrkA fusion protein is conjugated to the one or more polymers. In some embodiments the FlaBD2-PcrV fusion protein is conjugated to the one or more polymers. In some embodiments an OPS and the FlaBD2-MrkA fusion protein are conjugated to the one or more polymers. In some embodiments an OPS and the FlaBD2-PcrV fusion protein are conjugated to the one or more polymers. In some embodiments the FlaBD2-MrkA fusion protein and the FlaBD2-PcrV fusion protein are conjugated to the one or more polymers. In some embodiments an OPS, the FlaBD2-MrkA fusion protein, and the FlaBD2-PcrV fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5, wherein the *K. pneumoniae* OPS is conjugated to one or more polymers; and
(b) one or more polypeptides comprising an amino acid sequence having at least 80%, 85%, 90%, 95%, 96%, 97%, 98%, 99%, or 100% identity to the sequence of one or more of SEQ ID NOs: 1-3, 6-12, or 16-26.

In some embodiments the one or more polypeptides are conjugated to the one or more polymers. In some embodiments an OPS and the one or more polypeptides are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *P. aeruginosa* OPS of type O1, O2, O3, O4, O5, O6, O10, O11, wherein the *P. aeruginosa* OPS is conjugated to one or more polymers; and
(b) one or more polypeptides comprising an amino acid sequence having at least 80%, 85%, 90%, 95%, 96%, 97%, 98%, 99%, or 100% identity to the sequence of one or more of SEQ ID NOs: 1-3, 6-12, or 16-26.

In some embodiments the one or more polypeptides are conjugated to the one or more polymers. In some embodiments an OPS and the one or more polypeptides are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5, wherein the *K. pneumoniae* OPS is conjugated to one or more first polymers;
(b) one or more of *P. aeruginosa* OPS of type O1, O2, O3, O4, O5, O6, O10, O11, wherein the *P. aeruginosa* OPS is conjugated to one or more second polymers; and (c) one or more polypeptides comprising an amino acid sequence having at least 80%, 85%, 90%, 95%, 96%, 97%, 98%, 99%, or 100% identity to the sequence of one or more of SEQ ID NOs: 1-3, 6-12, or 16-26.

In some embodiments the one or more polypeptides are conjugated to the one or more first polymers. In some embodiments the one or more polypeptides are conjugated to the one or more second polymers. In some embodiments the one or more polypeptides are conjugated to the one or more first polymers and the one or more second polymers. In some embodiments, the one or more first polymers and the one or more second polymers are the same. In some embodiments, the one or more first polymers and the one or more second polymers are different. In some embodiments, the one or more first polymers comprise a capsular polysaccharide from a first pathogen. In some embodiments, the one or more second polymers comprise a capsular polysaccharide from a second pathogen. In some embodiments the first pathogen and the second pathogen are different bacteria. In some embodiments the first pathogen and the second pathogen are the same bacteria of the same serotype. In some embodiments the first pathogen and the second pathogen are the same bacteria of different serotypes. In some embodiments, the one or more first polymers comprise PLL. In some embodiments, the one or more second polymers comprise PLL.

In some embodiments, a vaccine composition comprises
(a) one or more of *K. pneumoniae* OPS of type O1, O2, O3, O5, wherein the *K. pneumoniae* OPS is conjugated to one or more polymers; and
(b) a FlaBD2-MrkA fusion protein.

In some embodiments the FlaBD2-MrkA fusion protein is conjugated to the one or more polymers. In some embodiments an OPS and the FlaBD2-MrkA fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *P. aeruginosa* OPS of type O1, O2, O3, O4, O5, O6, O10, O11, wherein the *P. aeruginosa* OPS is conjugated to one or more polymers; and
(b) a FlaBD2-MrkA fusion protein.

In some embodiments the FlaBD2-MrkA fusion protein is conjugated to the one or more polymers. In some embodiments an OPS and the FlaBD2-MrkA fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5, wherein the *K. pneumoniae* OPS is conjugated to one or more polymers;
(b) one or more of *P. aeruginosa* OPS of type O1, O2, O3, O4, O5, O6, O10, O11, wherein the *P. aeruginosa* OPS is conjugated to one or more second polymers; and
(c) a FlaBD2-MrkA fusion protein.

In some embodiments the FlaBD2-MrkA fusion protein is conjugated to the one or more first polymers. In some embodiments the FlaBD2-MrkA fusion protein is conjugated to the one or more second polymers. In some embodiments the FlaBD2-MrkA fusion protein is conjugated to the one or more first polymers and the one or more second polymers. In some embodiments, the one or more first polymers and the one or more second polymers are the same. In some embodiments, the one or more first polymers and the one or more second polymers are different. In some embodiments, the one or more first polymers comprise a capsular polysaccharide from a first pathogen. In some embodiments, the one or more second polymers comprise a capsular polysaccharide from a second pathogen. In some embodiments the first pathogen and the second pathogen are different bacteria. In some embodiments the first pathogen and the second pathogen are the same bacteria of the same serotype. In some embodiments the first pathogen and the second pathogen are the same bacteria of different serotypes. In some embodiments, the one or more first polymers comprise PLL. In some embodiments, the one or more second polymers comprise PLL.

In some embodiments, a vaccine composition comprises
(a) one or more of *P. aeruginosa* OPS of type O1, O2, O3, O4, O5, O6, O10, O11, wherein the *P. aeruginosa* OPS is conjugated to one or more polymers; and
(b) a FlaBD2-PcrV fusion protein.

In some embodiments the FlaBD2-PcrV fusion protein is conjugated to the one or more polymers. In some embodiments an OPS and the FlaBD2-PcrV fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5, wherein the *K. pneumoniae* OPS is conjugated to one or more first polymers;
(b) one or more of *P. aeruginosa* OPS of type O1, O2, O3, O4, O5, O6, O10, O11, wherein the *P. aeruginosa* OPS is conjugated to one or more second polymers; and
(c) a FlaBD2-PcrV fusion protein.

In some embodiments the FlaBD2-PcrV fusion protein is conjugated to the one or more first polymers. In some embodiments the FlaBD2-PcrV fusion protein is conjugated to the one or more second polymers. In some embodiments the FlaBD2-PcrV fusion protein is conjugated to the one or more first polymers and the one or more second polymers. In some embodiments, the one or more first polymers and the one or more second polymers are the same. In some embodiments, the one or more first polymers and the one or more second polymers are different. In some embodiments, the one or more first polymers comprise a capsular polysaccharide from a first pathogen. In some embodiments, the one or more second polymers comprise a capsular polysaccharide from a second pathogen. In some embodiments the first pathogen and the second pathogen are different bacteria. In some embodiments the first pathogen and the second pathogen are the same bacteria of the same serotype. In some embodiments the first pathogen and the second pathogen are the same bacteria of different serotypes. In some embodiments, the one or more first polymers comprise PLL. In some embodiments, the one or more second polymers comprise PLL.

In some embodiments, a vaccine composition comprises
(a) one or more of *K. pneumoniae* OPS of type O1, O2, O3, O5, wherein the *K. pneumoniae* OPS is conjugated to one or more polymers;
(b) a FlaBD2-MrkA fusion protein; and
(c) a FlaBD2-PcrV fusion protein.

In some embodiments the FlaBD2-MrkA fusion protein is conjugated to the one or more polymers. In some embodiments the FlaBD2-PcrV fusion protein is conjugated to the one or more polymers. In some embodiments an OPS and the FlaBD2-MrkA fusion protein are conjugated to the one or more polymers. In some embodiments an OPS and the FlaBD2-PcrV fusion protein are conjugated to the one or more polymers. In some embodiments the FlaBD2-MrkA fusion protein and the FlaBD2-PcrV fusion protein are conjugated to the one or more polymers. In some embodiments an OPS, the FlaBD2-MrkA fusion protein, and the FlaBD2-PcrV fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *P. aeruginosa* OPS of type O1, O2, O3, O4, O5, O6, O10, O11, wherein the *P. aeruginosa* OPS is conjugated to one or more polymers;
(b) a FlaBD2-MrkA fusion protein; and
(c) a FlaBD2-PcrV fusion protein.

In some embodiments the FlaBD2-MrkA fusion protein is conjugated to the one or more polymers. In some embodiments the FlaBD2-PcrV fusion protein is conjugated to the one or more polymers. In some embodiments an OPS and the FlaBD2-MrkA fusion protein are conjugated to the one or more polymers. In some embodiments an OPS and the FlaBD2-PcrV fusion protein are conjugated to the one or more polymers. In some embodiments the FlaBD2-MrkA fusion protein and the FlaBD2-PcrV fusion protein are conjugated to the one or more polymers. In some embodiments an OPS, the FlaBD2-MrkA fusion protein, and the FlaBD2-PcrV fusion protein are conjugated to the one or more polymers. In some embodiments, the one or more polymers comprise a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises
(a) one or more of *K. pneumoniae* OPS of type O1, O2, O3, O5, wherein the *K. pneumoniae* OPS is conjugated to one or more first polymers;
(b) one or more of *P. aeruginosa* OPS of type O1, O2, O3, O4, O5, O6, O10, O11, wherein the *P. aeruginosa* OPS is conjugated to one or more second polymers;
(c) a FlaBD2-MrkA fusion protein; and
(d) a FlaBD2-PcrV fusion protein.

In some embodiments, the one or more first polymers and the one or more second polymers are the same. In some embodiments, the one or more first polymers and the one or more second polymers are different. In some embodiments, the one or more first polymers comprise a capsular polysaccharide from a first pathogen. In some embodiments, the one or more second polymers comprise a capsular polysaccharide from a second pathogen. In some embodiments the first pathogen and the second pathogen are different bacteria. In some embodiments the first pathogen and the second pathogen are the same bacteria of the same serotype. In some embodiments the first pathogen and the second pathogen are the same bacteria of different serotypes. In some embodiments, the one or more first polymers comprise PLL. In some embodiments, the one or more second polymers comprise PLL. In some embodiments the FlaBD2-MrkA fusion protein is conjugated to the one or more first polymers. In some embodiments the FlaBD2-PcrV fusion protein is conjugated to the one or more first polymers. In some embodiments the FlaBD2-MrkA fusion protein is conjugated to the one or more second polymers. In some embodiments the FlaBD2-PcrV fusion protein is conjugated to the one or more second polymers. In some embodiments the FlaBD2-MrkA fusion protein is conjugated to the one or more first polymers and the FlaBD2-PcrV fusion protein is conjugated to the one or more second polymers. In some embodiments the FlaBD2-PcrV fusion protein is conjugated to the one or more first polymers and the FlaBD2-MrkA fusion protein is conjugated to the one or more second polymers. In some embodiments the FlaBD2-MrkA fusion protein is conjugated to the one or more first polymers and the one or more second polymers. In some embodiments the FlaBD2-PcrV fusion protein is conjugated to the one or more first polymers and the one or more second polymers.

In some embodiments, a vaccine composition comprises two or more types of immunogenic compositions selected from
(a) an immunogenic composition comprising a KP O1 OPS covalently linked to a FlaBD2-MrkA fusion protein;
(a') an immunogenic composition comprising a KP O1 OPS covalently linked to a FlaBD2-PcrV fusion protein;
(b) an immunogenic composition comprising a KP O2 OPS covalently linked to a FlaBD2-MrkA fusion protein;
(b') an immunogenic composition comprising a KP O2 OPS covalently linked to a FlaBD2-PcrV fusion protein;
(c) an immunogenic composition comprising a KP O3 OPS covalently linked to a FlaBD2-MrkA fusion protein;
(c') an immunogenic composition comprising a KP O3 OPS covalently linked to a FlaBD2-PcrV fusion protein;
(d) an immunogenic composition comprising a KP O5 OPS covalently linked to a FlaBD2-MrkA fusion protein;
(d') an immunogenic composition comprising a KP O5 OPS covalently linked to a FlaBD2-PcrV fusion protein;
(e) an immunogenic composition comprising a PA O1 OPS covalently linked to a FlaBD2-MrkA fusion protein;
(e') an immunogenic composition comprising a PA O1 OPS covalently linked to a FlaBD2-PcrV fusion protein;
(f) an immunogenic composition comprising a PA O2 OPS covalently linked to a FlaBD2-MrkA fusion;
(f) an immunogenic composition comprising a PA O2 OPS covalently linked to a FlaBD2-PcrV fusion protein;
(g) an immunogenic composition comprising a PA O3 OPS covalently linked to a FlaBD2-MrkA fusion protein;
(g') an immunogenic composition comprising a PA O3 OPS covalently linked to a FlaBD2-PcrV fusion protein;
(h) an immunogenic composition comprising a PA O4 OPS covalently linked to a FlaBD2-MrkA fusion protein;
(h') an immunogenic composition comprising a PA O4 OPS covalently linked to a FlaBD2-PcrV fusion protein;
(i) an immunogenic composition comprising a PA O5 OPS covalently linked to a FlaBD2-MrkA fusion protein;
(i') an immunogenic composition comprising a PA O5 OPS covalently linked to a FlaBD2-PcrV fusion protein;
(j) an immunogenic composition comprising a PA O6 OPS covalently linked to a FlaBD2-MrkA fusion protein;
(j') an immunogenic composition comprising a PA O6 OPS covalently linked to a FlaBD2-PcrV fusion protein;
(k) an immunogenic composition comprising a PA O10 OPS covalently linked to a FlaBD2-MrkA fusion protein;
(k') an immunogenic composition comprising a PA O10 OPS covalently linked to a FlaBD2-PcrV fusion protein;
(l) an immunogenic composition comprising a PA O11 OPS covalently linked to a FlaBD2-MrkA fusion protein; and
(l') an immunogenic composition comprising a PA O11 OPS covalently linked to a FlaBD2-PcrV fusion protein.

In some embodiments, a vaccine composition comprises two or more types of immunogenic compositions selected from (a) an immunogenic composition comprising a polymer, a KP O1 OPS, and a FlaBD2-MrkA fusion protein, wherein the fusion protein is covalently linked to the polymer and/or the KP O1 OPS;

(a') an immunogenic composition comprising a polymer, a KP O1 OPS, and a FlaBD2-PcrV fusion protein, wherein the fusion protein is covalently linked to the polymer and/or the KP O1 OPS;

(b) an immunogenic composition comprising a polymer, a KP O2 OPS, and a FlaBD2-MrkA fusion protein, wherein the fusion protein is covalently linked to the polymer and/or the KP O2 OPS;

(b') an immunogenic composition comprising a polymer, a KP O2 OPS, and a FlaBD2-PcrV fusion protein, wherein the fusion protein is covalently linked to the polymer and/or the KP O2 OPS;

(c) an immunogenic composition comprising a polymer, a KP O3 OPS, and a FlaBD2-MrkA fusion protein, wherein the fusion protein is covalently linked to the polymer and/or the KP O3 OPS;

(c') an immunogenic composition comprising a polymer, a KP O3 OPS, and a FlaBD2-PcrV fusion protein, wherein the fusion protein is covalently linked to the polymer and/or the KP O3 OPS;

(d) an immunogenic composition comprising a polymer, a KP O5 OPS, and a FlaBD2-MrkA fusion protein, wherein the fusion protein is covalently linked to the polymer and/or the KP O5 OPS;

(d') an immunogenic composition comprising a polymer, a KP O5 OPS, and a FlaBD2-PcrV fusion protein, wherein the fusion protein is covalently linked to the polymer and/or the KP O5 OPS;

(e) an immunogenic composition comprising a polymer, a PA O1 OPS, and a FlaBD2-MrkA fusion protein, wherein the fusion protein is covalently linked to the polymer and/or the PA O1 OPS;

(e') an immunogenic composition comprising a polymer, a PA O1 OPS, and a FlaBD2-PcrV fusion protein, wherein the fusion protein is covalently linked to the polymer and/or the PA O1 OPS;

(f) an immunogenic composition comprising a polymer, a PA O2 OPS, and a FlaBD2-MrkA fusion, wherein the fusion protein is covalently linked to the polymer and/or the PA O2 OPS;

(f') an immunogenic composition comprising a polymer, a PA O2 OPS, and a FlaBD2-PcrV fusion protein, wherein the fusion protein is covalently linked to the polymer and/or the PA O2 OPS;

(g) an immunogenic composition comprising a polymer, a PA O3 OPS, and aFlaBD2-MrkA fusion protein, wherein the fusion protein is covalently linked to the polymer and/or the PA O3 OPS;

(g') an immunogenic composition comprising a polymer, a PA O3 OPS, and a FlaBD2-PcrV fusion protein, wherein the fusion protein is covalently linked to the polymer and/or the PA O3 OPS;

(h) an immunogenic composition comprising a polymer, a PA O4 OPS, and a FlaBD2-MrkA fusion protein, wherein the fusion protein is covalently linked to the polymer and/or the PA O4 OPS;

(h') an immunogenic composition comprising a polymer, a PA O4 OPS, and a FlaBD2-PcrV fusion protein, wherein the fusion protein is covalently linked to the polymer and/or the PA O4 OPS;

(i) an immunogenic composition comprising a polymer, a PA O5 OPS, and a FlaBD2-MrkA fusion protein, wherein the fusion protein is covalently linked to the polymer and/or the PA O5 OPS;

(i') an immunogenic composition comprising a polymer, a PA O5 OPS, and a FlaBD2-PcrV fusion protein, wherein the fusion protein is covalently linked to the polymer and/or the PA O5 OPS;

(j) an immunogenic composition comprising a polymer, a PA O6 OPS, and a FlaBD2-MrkA fusion protein, wherein the fusion protein is covalently linked to the polymer and/or the PA O6 OPS;

(j') an immunogenic composition comprising a polymer, a PA O6 OPS, and a FlaBD2-PcrV fusion protein, wherein the fusion protein is covalently linked to the polymer and/or the PA O6 OPS;

(k) an immunogenic composition comprising a polymer, a PA O10 OPS, and a FlaBD2-MrkA fusion protein, wherein the fusion protein is covalently linked to the polymer and/or the PA O10 OPS;

(k') an immunogenic composition comprising a polymer, a PA O10 OPS, and a FlaBD2-PcrV fusion protein, wherein the fusion protein is covalently linked to the polymer and/or the PA O10 OPS;

(l) an immunogenic composition comprising a polymer, a PA O11 OPS, and a FlaBD2-MrkA fusion protein, wherein the fusion protein is covalently linked to the polymer and/or the PA O11 OPS; and (l') an immunogenic composition comprising a polymer, a PA O11 OPS, and a FlaBD2-PcrV fusion protein, wherein the fusion protein is covalently linked to the polymer and/or the PA O11 OPS.

In some embodiments, at least one polymer comprises a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises an immunogenic composition selected from (a) an immunogenic composition comprising a polymer, a combination of *K. pneumoniae* OPS of type O1, O2, O3, O5, and a FlaBD2-MrkA fusion protein, wherein the fusion protein is covalently linked to the polymer and/or at least one of the types of OPS; and (b) an immunogenic composition comprising a polymer, a combination of a *P. aeruginosa* OPS of type O1, O2, O3, O4, O5, O6, O10, O11, and a FlaBD2-MrkA fusion protein, wherein the fusion protein is covalently linked to the polymer and/or at least one of the types of OPS.

In some embodiments, at least one polymer comprises a capsular polysaccharide. In some embodiments the capsular polysaccharide is a *Klebsiella* spp. K19 capsular polysaccharide. In some embodiments, the polymer comprises a PLL.

In some embodiments, a vaccine composition comprises an immunogenic composition selected from (a) an immunogenic composition comprising one or more first polymers, a combination of *K. pneumoniae* OPS of type O1, O2, O3, O5, a FlaBD2-PcrV fusion protein, wherein the FlaBD2-PcrV fusion protein is covalently linked to at least a portion of the one or more first polymers and/or the at least one of the types of OPS, and a FlaBD2-MrkA fusion protein, wherein the FlaBD2-MrkA fusion protein is covalently linked to at least a portion of the one or more first polymers and/or the at least one of the types of OPS; and (b) an immunogenic composition comprising one or more second polymers, a combination of a *P. aeruginosa* OPS of type O1, O2, O3, O4, O5, O6, O10, O11, a FlaBD2-PcrV fusion protein, wherein the FlaBD2-PcrV fusion protein is covalently linked to at least a portion of the one or more second polymers and/or the at least one of the types of OPS, and a FlaBD2-MrkA fusion protein, wherein the FlaBD2-MrkA fusion protein is covalently linked to at least a portion of the one or more second polymers and/or the at least one of the types of OPS.

In some embodiments the FlaBD2-MrkA fusion protein is conjugated to the one or more first polymers. In some embodiments the FlaBD2-PcrV fusion protein is conjugated to the one or more first polymers. In some embodiments the FlaBD2-MrkA fusion protein is conjugated to the one or more second polymers. In some embodiments the FlaBD2-PcrV fusion protein is conjugated to the one or more second polymers. In some embodiments the FlaBD2-MrkA fusion protein is conjugated to the one or more first polymers and the FlaBD2-PcrV fusion protein is conjugated to the one or more second polymers. In some embodiments the FlaBD2-PcrV fusion protein is conjugated to the one or more first polymers and the FlaBD2-MrkA fusion protein is conjugated to the one or more second polymers. In some embodiments the FlaBD2-MrkA fusion protein is conjugated to the one or more first polymers and the one or more second polymers. In some embodiments the FlaBD2-PcrV fusion protein is conjugated to the one or more first polymers and the one or more second polymers. In some embodiments, the one or more first polymers and the one or more second polymers are the same. In some embodiments, the one or more first polymers and the one or more second polymers are different. In some embodiments, the one or more first polymers comprise a capsular polysaccharide from a first pathogen. In some embodiments, the one or more second polymers comprise a capsular polysaccharide from a second pathogen. In some embodiments the first pathogen and the second pathogen are different bacteria. In some embodiments the first pathogen and the second pathogen are the same bacteria of the same serotype. In some embodiments the first pathogen and the second pathogen are the same bacteria of different serotypes. In some embodiments, the one or more first polymers comprise PLL. In some embodiments, the one or more second polymers comprise PLL.

In some embodiments, a vaccine composition comprises
(a) one or more polymers;
(b) one or more of *K. pneumoniae* OPS of type O1, O2, O3, O5; and
(c) a polypeptide comprising an amino acid sequence having at least 80%, 85%, 90%, 95%, 96%, 97%, 98%, 99%, or 100% identity to the sequence of one or more of SEQ ID NOs: 1-3, 6-12, or 16-26, wherein the polypeptide is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *P. aeruginosa* OPS of type O1, O2, O3, O4, O5, O6, O10, O11; and
(c) a polypeptide comprising an amino acid sequence having at least 80%, 85%, 90%, 95%, 96%, 97%, 98%, 99%, or 100% identity to the sequence of one or more of SEQ ID NOs: 1-3, 6-12, or 16-26, wherein the polypeptide is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *K. pneumoniae* OPS of type O1, O2, O3, O5;
(c) one or more of *P. aeruginosa* OPS of type O1, O2, O3, O4, O5, O6, O10, O11; and
(d) a polypeptide comprising an amino acid sequence having at least 80%, 85%, 90%, 95%, 96%, 97%, 98%, 99%, or 100% identity to the sequence of one or more of SEQ ID NOs: 1-3, 6-12, or 16-26, wherein the polypeptide is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *K. pneumoniae* OPS of type O1, O2, O3, O5; and
(c) a FlaBD2-MrkA fusion protein, wherein the FlaBD2-MrkA fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *P. aeruginosa* OPS of type O1, O2, O3, O4, O5, O6, O10, O11; and
(c) a FlaBD2-MrkA fusion protein, wherein the FlaBD2-MrkA fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *K. pneumoniae* OPS of type O1, O2, O3, O5;
(c) one or more of *P. aeruginosa* OPS of type O1, O2, O3, O4, O5, O6, O10, O11; and
(d) a FlaBD2-MrkA fusion protein, wherein the FlaBD2-MrkA fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *K. pneumoniae* OPS of type O1, O2, O3, O5; and (c) a FlaBD2-PcrV fusion, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *P. aeruginosa* OPS of type O1, O2, O3, O4, O5, O6, O10, O11; and
(c) a FlaBD2-PcrV fusion, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *K. pneumoniae* OPS of type O1, O2, O3, O5;
(c) one or more of *P. aeruginosa* OPS of type O1, O2, O3, O4, O5, O6, O10, O11; and
(d) a FlaBD2-PcrV fusion, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *K. pneumoniae* OPS of type O1, O2, O3, O5;
(c) a FlaBD2-MrkA fusion protein, wherein the FlaBD2-MrkA fusion protein is covalently linked to at least a portion of the one or more polymers and/or the at least one of the types of OPS; and
(d) a FlaBD2-PcrV fusion, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *P. aeruginosa* OPS of type O1, O2, O3, O4, O5, O6, O10, O11; and
(c) a FlaBD2-MrkA fusion protein, wherein the FlaBD2-MrkA fusion protein is covalently linked to at least a portion of the one or more polymers and/or the at least one of the types of OPS; and
(d) a FlaBD2-PcrV fusion, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *K. pneumoniae* OPS of type O1, O2, O3, O5;
(c) one or more of *P. aeruginosa* OPS of type O1, O2, O3, O4, O5, O6, O10, O11; and
(d) a FlaBD2-MrkA fusion protein, wherein the FlaBD2-MrkA fusion protein is covalently linked to at least a portion of the one or more polymers and/or the at least one of the types of OPS; and
(e) a FlaBD2-PcrV fusion, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more of *K. pneumoniae* OPS of type O1, O2, O3, O5, wherein the *K. pneumoniae* OPS is covalently linked to one or more polymers; and
(b) a polypeptide comprising an amino acid sequence having at least 80%, 85%, 90%, 95%, 96%, 97%, 98%, 99%, or 100% identity to the sequence of one or more of SEQ ID NOs: 1-3, 6-12, or 16-26, wherein the polypeptide is covalently linked to at least a portion of the polymer and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more of *P. aeruginosa* OPS of type O1, O2, O3, O4, O5, O6, O10, O11, wherein the *P. aeruginosa* OPS is covalently linked to one or more polymers; and
(b) a polypeptide comprising an amino acid sequence having at least 80%, 85%, 90%, 95%, 96%, 97%, 98%, 99%, or 100% identity to the sequence of one or more of SEQ ID NOs: 1-3, 6-12, or 16-26, wherein the polypeptide is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more of *K. pneumoniae* OPS of type O1, O2, O3, O5, wherein the *K. pneumoniae* OPS is covalently linked to one or more polymers;
(b) one or more of *P. aeruginosa* OPS of type O1, O2, O3, O4, O5, O6, O10, O11, wherein the *P. aeruginosa* OPS is covalently linked to one or more polymers; and (c) a polypeptide comprising an amino acid sequence having at least 80%, 85%, 90%, 95%, 96%, 97%, 98%, 99%, or 100% identity to the sequence of one or more of SEQ ID NOs: 1-3, 6-12, or 16-26, wherein the polypeptide is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more of *K. pneumoniae* OPS of type O1, O2, O3, O5, wherein the *K. pneumoniae* OPS is covalently linked to one or more polymers; and
(b) a FlaBD2-MrkA fusion, wherein the FlaBD2-MrkA fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more of *P. aeruginosa* OPS of type O1, O2, O3, O4, O5, O6, O10, O11, wherein the *P. aeruginosa* OPS is covalently linked to one or more polymers; and
(b) a FlaBD2-MrkA fusion, wherein the FlaBD2-MrkA fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more of *K. pneumoniae* OPS of type O1, O2, O3, O5, wherein the *K. pneumoniae* OPS is covalently linked to one or more polymers;
(b) one or more of *P. aeruginosa* OPS of type O1, O2, O3, O4, O5, O6, O10, O11, wherein the *P. aeruginosa* OPS is covalently linked to one or more polymers; and
(c) a FlaBD2-MrkA fusion, wherein the FlaBD2-MrkA fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more polymers,
(b) one or more of *K. pneumoniae* OPS of type O1, O2, O3, O5; and
(c) a FlaBD2-PcrV fusion, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more of *P. aeruginosa* OPS of type O1, O2, O3, O4, O5, O6, O10, O11, wherein the *P. aeruginosa* OPS is covalently linked to one or more polymers; and
(b) a FlaBD2-PcrV fusion, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more of *K. pneumoniae* OPS of type O1, O2, O3, O5, wherein the *K. pneumoniae* OPS is covalently linked to one or more polymers;
(b) one or more of *P. aeruginosa* OPS of type O1, O2, O3, O4, O5, O6, O10, O11, wherein the *P. aeruginosa* OPS is covalently linked to one or more polymers; and
(c) a FlaBD2-PcrV fusion, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more of *K. pneumoniae* OPS of type O1, O2, O3, O5, wherein the *K. pneumoniae* OPS is covalently linked to one or more polymers;
(b) a FlaBD2-MrkA fusion protein, wherein the FlaBD2-MrkA fusion protein is covalently linked to at least a portion of the one or more polymers and/or the at least one of the types of OPS; and
(c) a FlaBD2-PcrV fusion, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more of *P. aeruginosa* OPS of type O1, O2, O3, O4, O5, O6, O10, O11, wherein the *P. aeruginosa* OPS is covalently linked to one or more polymers;
(b) a FlaBD2-MrkA fusion protein, wherein the FlaBD2-MrkA fusion protein is covalently linked to at least a portion of the one or more polymers and/or the at least one of the types of OPS; and
(c) a FlaBD2-PcrV fusion, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises
(a) one or more of *K. pneumoniae* OPS of type O1, O2, O3, O5, wherein the *K. pneumoniae* OPS is covalently linked to one or more polymers;
(b) one or more of *P. aeruginosa* OPS of type O1, O2, O3, O4, O5, O6, O10, O11, wherein the *P. aeruginosa* OPS is covalently linked to one or more polymers;

(c) a FlaBD2-MrkA fusion protein, wherein the FlaBD2-MrkA fusion protein is covalently linked to at least a portion of the one or more polymers and/or the at least one of the types of OPS; and (d) a FlaBD2-PcrV fusion protein, wherein the FlaBD2-PcrV fusion protein is covalently linked to at least a portion of the one or more polymers and/or the at least one of the types of OPS.

In some embodiments, the one or more polymers comprise a capsular polysaccharide. In some embodiments the capsular polysaccharide is a *Klebsiella* spp. K19 capsular polysaccharide. In some embodiments, the one or more polymers comprises PLL.

In some embodiments, a vaccine composition comprises:

(a) a first immunogenic composition comprising a polymer, a KP O1 OPS conjugated to the polymer, and a FlaBD2-MrkA fusion protein covalently linked to the polymer;

(b) a second immunogenic composition comprising a polymer, a KP O2 OPS conjugated to the polymer, and a FlaBD2-PcrV fusion protein covalently linked to the polymer;

(c) a third immunogenic composition comprising a polymer, a KP O3 OPS conjugated to the polymer, and a FlaBD2-MrkA fusion protein covalently linked to the polymer;

(d) a fourth immunogenic composition comprising a polymer, a KP O5 OPS conjugated to the polymer, and a FlaBD2-PcrV fusion protein covalently linked to the polymer;

(e) a fifth immunogenic composition comprising a polymer, a PA O1 OPS conjugated to the polymer, and a FlaBD2-PcrV fusion protein covalently linked to the polymer;

(f) a sixth immunogenic composition comprising a polymer, a PA O2 OPS conjugated to the polymer, and a FlaBD2-PcrV fusion protein covalently linked to the polymer;

(g) a seventh immunogenic composition comprising a polymer, a PA O3 OPS conjugated to the polymer, and a FlaBD2-PcrV fusion protein covalently linked to the polymer;

(h) an eighth immunogenic composition comprising a polymer, a PA O4 OPS conjugated to the polymer, and a FlaBD2-PcrV fusion protein covalently linked to the polymer;

(i) a ninth immunogenic composition comprising a polymer, a PA O5 OPS conjugated to the polymer, and a FlaBD2-MrkA fusion protein covalently linked to the polymer;

(j) a tenth immunogenic composition comprising a polymer, a PA O6 OPS conjugated to the polymer, and a FlaBD2-MrkA fusion protein covalently linked to the polymer;

(k) an eleventh immunogenic composition comprising a polymer, a PA O10 OPS conjugated to the polymer, and a FlaBD2-MrkA fusion protein covalently linked to the polymer; and (l) a twelfth immunogenic composition comprising a polymer, a PA O11 OPS conjugated to the polymer, and a FlaBD2-MrkA fusion protein covalently linked to the polymer.

In some embodiments, at least one of the polymers comprise a capsular polysaccharide. In some embodiments the capsular polysaccharide is a *Klebsiella* spp. K19 capsular polysaccharide. In some embodiments, the one or more polymers comprises PLL.

Optimal amounts of components for a particular vaccine can be ascertained by standard studies involving observation of appropriate immune responses in subjects. Following an initial vaccination, subjects can receive one or several booster immunizations adequately spaced in time.

The immunogenic complexes described herein, and/or preparations thereof may be formulated in a unit dosage form for ease of administration and uniformity of dosage. The specific therapeutically effective dose level for any particular patient or organism may depend upon a variety of factors including the severity or degree of risk of infection; the activity of the specific vaccine or vaccine composition employed; other characteristics of the specific vaccine or vaccine composition employed; the age, body weight, general health, sex of the subject, diet of the subject, pharmacokinetic condition of the subject, the time of administration (e.g., with regard to other activities of the subject such as eating, sleeping, receiving other medicines including other vaccine doses, etc.), route of administration, rate of excretion of the specific vaccine or vaccine composition employed; vaccines used in combination or coincidental with the vaccine composition employed; and like factors well known in the medical arts.

Immunogenic complexes for use in accordance with the present disclosure may be formulated into compositions (e.g., pharmaceutical compositions) according to known techniques. Vaccine preparation is generally described in Vaccine Design (Powell and Newman, 1995). For example, an immunogenic amount of a vaccine product can be formulated together with one or more organic or inorganic, liquid or solid, pharmaceutically suitable carrier materials. Preparation of pneumococcal polysaccharide and conjugate vaccines is described, for example, in U.S. Ser. No. 11/395,593, filed Mar. 31, 2006, the contents of which are incorporated herein by reference.

In general, pharmaceutically acceptable carrier(s) include solvents, dispersion media, and the like, which are compatible with pharmaceutical administration. For example, materials that can serve as pharmaceutically acceptable carriers include, but are not limited to sugars such as lactose, glucose, dextrose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; polyols such as glycerol, propylene glycol, and liquid polyethylene glycol; esters such as ethyl oleate and ethyl laurate; agar; buffering agents such as magnesium hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as preservatives, and antioxidants can also be present in the composition, according to the judgment of the formulator (Martin, 1975).

Vaccines may be formulated by combining one or more of the immunogenic complexes disclosed herein with carriers and/or other optional components by any available means including, for example, conventional mixing, granulating, dissolving, lyophilizing, or similar processes.

Vaccine compositions useful in the provided methods may be lyophilized up until they are about to be used, at which point they are extemporaneously reconstituted with diluent. In some embodiments, vaccine components or compositions are lyophilized in the presence of one or more other components (e.g., adjuvants), and are extemporaneously reconstituted with saline solution. Alternatively, individual components, or sets of components may be separately lyophilized and/or stored (e.g., in a vaccination kit), the components being reconstituted and either mixed prior to use or administered separately to the subject.

Lyophilization can produce a more stable composition (for instance by preventing or reducing breakdown of polysaccharide antigens). Lyophilizing of vaccines or vaccine components is well known in the art. Typically, a liquid vaccine or vaccine component is freeze dried, often in the presence of an anti-caking agent (such as, for example, sugars such as sucrose or lactose). In some embodiments, the anti-caking agent is present, for example, at an initial concentration of 10-200 mg/ml. Lyophilization typically occurs over a series of steps, for instance a cycle starting at −69° C., gradually adjusting to −24° C. over 3 h, then retaining this temperature for 18 h, then gradually adjusting to −16° C. over 1 h, then retaining this temperature for 6 h, then gradually adjusting to +34° C. over 3 h, and finally retaining this temperature over 9 h.

Vaccines or vaccine components for use in accordance with the present invention may be incorporated into liposomes, cochleates, biodegradable polymers such as polylactide, poly-glycolide and poly-lactide-co-glycolides, or immunostimulating complexes (ISCOMS).

In certain situations, it may be desirable to prolong the effect of a vaccine or for use in accordance with the present invention, for example by slowing the absorption of one or more vaccine components. Such delay of absorption may be accomplished, for example, by the use of a liquid suspension of crystalline or amorphous material with poor water solubility. The rate of absorption of the product then depends upon its rate of dissolution, which in turn, may depend upon size and form. Alternatively, or additionally, delayed absorption may be accomplished by dissolving or suspending one or more vaccine components in an oil vehicle. Injectable depot forms can also be employed to delay absorption. Such depot forms can be prepared by forming microcapsule matrices of one or more vaccine components a biodegradable polymers network. Depending upon the ratio of polymer to vaccine component, and the nature of the particular polymer(s) employed, the rate of release can be controlled.

Examples of biodegradable polymers that can be employed in accordance with the present invention include, for example, poly(orthoesters) and poly(anhydrides). One particular exemplary polymer is polylactide-polyglycolide.

Depot injectable formulations may also be prepared by entrapping the product in liposomes or microemulsions, which are compatible with body tissues.

Polymeric delivery systems can also be employed in non-depot formulations including, for example, oral formulations. For example, biodegradable, biocompatible polymers such as ethylene vinyl acetate, polyanhydrides, polyglycolic acid, collagen, polyorthoesters, and polylactic acid, etc., can be used in oral formulations. Polysaccharide antigens or conjugates may be formulated with such polymers, for example to prepare particles, microparticles, extrudates, solid dispersions, admixtures, or other combinations in order to facilitate preparation of useful formulations (e.g., oral).

Vaccines for use in accordance with the present invention include immunogenic compositions, and may additionally include one or more additional active agents (i.e., agents that exert a biological effect—not inert ingredients). It will be appreciated that such additional agents may be formulated together with one or more other vaccine components, or may be maintained separately and combined at or near the time of administration. In some embodiments, such additional components may be administered separately from some or all of the other vaccine components, within an appropriate time window for the relevant effect to be achieved.

For example, it is common in vaccine preparation to include one or more adjuvants. Adjuvants, generally, are agents that enhance the immune response to an antigen. In some embodiments, adjuvants that enhance a Th1-type immune response are utilized.

In some embodiments, adjuvants that enhance a Th17-type immune response are utilized.

Adjuvants

In some embodiments, immunogenic complexes described herein are formulated and/or administered in combination with an adjuvant. In some embodiments, the adjuvant is selected from the group of aluminum hydroxide, phosphate aluminum hydroxide, aluminum phosphate, a TLR agonist, a TLR2 agonist (e.g., a saponin (e.g., QS21, etc.), a porin, etc.), a TLR3 agonist (e.g., dsRNA, polyI:polyC, poly-ICLC, Hiltonol®, etc.), a TLR4 agonist (e.g., monophosphoryl lipid A (MPL A)), a TLR5 agonist (e.g., a flagellin); a TLR 7, 8, or 9 agonist (e.g., CpG-oligonucleotide, etc.).

In some embodiments, adjuvants suitable for use in accordance with the present invention include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (defined below) or bacterial cell wall components, such as, for example,
    (a) MF59 (PCT Publ. No. WO 90/14837), containing 5% Squalene, 0.5% Tween 80, and 0.5% Span 85 (optionally containing various amounts of MTP-PE (see below, although not required)) formulated into submicron particles using a microfluidizer such as Model 110Y microfluidizer (Microfluidics, Newton, Mass.),
    (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and
    (c) Ribi™ adjuvant system (RAS), (Corixa, Hamilton, Mont.) containing 2% Squalene, 0.2% Tween 80, and one or more bacterial cell wall components from the group consisting of 3-O-deaylated monophosphorylipid A (MPL™) described in U.S. Pat. No. 4,912,094 (Corixa), trehalose dimycolate (TDM), and cell wall skeleton (CWS), preferably MPL+CWS (Detox™);

(3) saponin adjuvants, such as Quil A or STIMULON™ QS-21 (Antigenics, Framingham, Mass.) (U.S. Pat. No. 5,057,540) may be used or particles generated therefrom such as ISCOMs (immunostimulating complexes);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-Tetradecanoyloxytetradecanoylamino]ethyl 2-Deoxy-4-O-phosphono-3-O—[(R)-3-tetradecanoyloxytetradecanoyl]-2-[(R)-3-tetradecanoyloxytetradecanoylamino]-b-D-glucopyranoside, which is also known as 529 (formerly known as RC529), which is formulated as an aqueous form or as a stable emulsion, synthetic polynucleotides such as oligonucleotides containing CpG motif(s) (U.S. Pat. No. 6,207,646);

TLR3 agonists (synthetic dsRNA, polyI:polyC, Hiltonol® which are available from InvivoGen);

(5) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc.;

(6) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with published international patent application number WO 00/18434 (see also WO 02/098368 and WO 02/098369), a pertussis toxin (PT), or an E. coli heat-labile toxin (LT), particularly LT-K63, LT-R72, and a novel mutant of LT, designated LT(R192G/L211A), or dmLT can elicit Th17 responses to vaccine antigens (Andreasen, 2009; Norton, 2011; Norton, 2012; Leach, 2012; Toprani, 2017), CT-5109, PT-K9/G129 (see, e.g., WO 93/13302 and WO 92/19265); and (7) other substances that act as immunostimulating agents to enhance the effectiveness of the composition, e.g., delta inulin (Advax®), Matrix M.

Muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

Vaccines for use in accordance with the present invention may include, or be administered concurrently with, other antimicrobial therapy. For example, such vaccines may include or be administered with one or more agents that kills or retards growth of a pathogen. Such agents include, for example, penicillin, vancomycin, erythromycin, azithromycin, and clarithromycin, cefotaxime, ceftriaxone, levoflaxin, gatifloxacin.

Alternatively or additionally, vaccines for use in accordance with the present invention may include, or be administered with, one or more other vaccines or therapies. For example, one or more non-pneumococcal antigens may be included in or administered with the vaccines.

Administration

In some embodiments, immunogenic complexes are administered to a subject at risk of disease, e.g., hospitalized patients. It will be appreciated that an individual can be considered at risk for developing a disease without having been diagnosed with any symptoms of the disease. For example, if the individual is known to have been, or to be intended to be, in situations with relatively high risk of exposure to infection, that individual will be considered at risk for developing the disease (e.g., hospitalized patient, an elderly subject living in long term care facility, etc.).

Any effective route of administration may be utilized such as, for example, orally, nasally, enterally, parenterally, intramuscularly or intravenously, subcutaneously, intradermally, rectally, vaginally, topically, ocularly, pulmonarily, or by contact application. In some embodiments, vaccine compositions may be injected (e.g., via intramuscular, intraperitoneal, intradermal and/or subcutaneous routes); or delivered via the mucosa (e.g., to the oral/alimentary, respiratory, and/or genitourinary tracts). Intranasal administration of vaccines may be particularly useful in some contexts, for example for treatment of pneumonia or otitis media (as nasopharyngeal carriage of pneumococci can be more effectively prevented, thus attenuating infection at its earliest stage). In some embodiments of the invention, it may be desirable to administer different doses of a vaccine by different routes; in some embodiments, it may be desirable to administer different components of one dose via different routes.

In some embodiments of the present invention, pharmaceutical compositions (e.g., vaccines) are administered intradermally. Conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced while providing a slight pressure to elevate it under the skin. The liquid is then injected very slowly thereby forming a bleb or bump on the skin surface, followed by slow withdrawal of the needle.

Devices that are specifically designed to administer liquid agents into or across the skin have been described, for example the devices described in WO 99/34850 and EP 1092444, also the jet injection devices described for example in WO 01/13977; U.S. Pat. Nos. 5,480,381, 5,599, 302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Other methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

As described above, pharmaceutical compositions (e.g., vaccines) may be administered as a single dose or as multiple doses. It will be appreciated that an administration is a single "dose" so long as all relevant components are administered to a subject within a window of time; it is not necessary that every component be present in a single composition. For example, administration of two different immunogenic compositions, within a period of less than 24 h, is considered a single dose. To give but one example, immunogenic compositions having different antigenic components may be administered in separate compositions, but as part of a single dose. As noted above, such separate compositions may be administered via different routes or via the same route. Alternatively or additionally, in embodiments wherein a vaccine comprises combination of immunogenic compositions and additional types of active agents, immunogenic compositions may be administered via one route, and a second active agent may be administered by a the same route or by a different route.

Pharmaceutical compositions (e.g., vaccines) are administered in such amounts and for such time as is necessary to achieve a desired result. In certain embodiments of the present invention, a vaccine composition comprises a therapeutically effective amount of at least immunogenic composition. The exact amount required to achieve a therapeutically effective amount may vary, depending on the immunogenic composition, and from subject to subject, depending on the species, age, and general condition of the subject, the stage of the disease, the particular pharmaceutical mixture, its mode of administration, and the like.

The amount of polysaccharide(s) antigen or conjugate(s) in each pharmaceutical composition (e.g., vaccine) dose is selected to allow the vaccine, when administered as described herein, to induce an appropriate immunoprotective response without significant, adverse side effects. A "immuno-protective" or "protective immune" response as used herein is an immune response sufficient to protect an immunized subject from productive infection by a particular pathogen or pathogens to which a vaccine is directed (e.g., *K. pneumoniae* infection). Such amounts may vary depending upon which specific immunogenic composition or compositions are employed and how it is presented.

In some embodiments, a pharmaceutical composition comprising an immunogenic complex disclosed herein elicits a Th1 and/or Th17 cell response upon administration to a subject. In some embodiments, a pharmaceutical composition comprising an immunogenic complex disclosed herein elicits an opsonic/bactericidal response against one or more of *K. pneumoniae, P. aeruginosa*, and *E. coli* upon administration to a subject. In some embodiments, a pharmaceutical composition comprising an immunogenic complex disclosed herein reduces rate of transmission and/or colonization of the mucosal surfaces by one or more of *K. pneumoniae, P. aeruginosa*, and *E. coli* upon administration to a subject.

In some embodiments, a pharmaceutical composition comprising an immunogenic complex disclosed herein reduces rate of transmission and/or colonization of the GI tract by one or more of *K. pneumoniae, P. aeruginosa*, and *E. coli* upon transmission.

Some embodiments provide for a method of immunizing a subject against *K. pneumoniae* infection comprising administering to the subject an effective amount of an immunogenic complex described herein. Some embodiments provide for a method of immunizing a subject against *K. pneumoniae* infection comprising administering to the subject an effective amount of a pharmaceutical composition described herein.

Some embodiments provide for a method of immunizing a subject against *P. aeruginosa* infection comprising administering to the subject an effective amount of an immunogenic complex described herein. Some embodiments provide for a method of immunizing a subject against *P. aeruginosa* infection comprising administering to the subject an effective amount of a pharmaceutical composition.

Some embodiments provide for a method of immunizing a subject against *E. coli* infection comprising administering to the subject an effective amount of an immunogenic complex described herein. Some embodiments provide for a method of immunizing a subject against *E. coli* infection comprising administering to the subject an effective amount of a pharmaceutical composition.

Dosing

According to the present disclosure, pharmaceutical composition (e.g., vaccine) administration may involve delivery of only a single dose, or alternatively may involve an initial dose followed by one or several additional immunization doses, adequately spaced. An immunization schedule is a program for the administration of one or more specified doses of one or more specified pneumococcal vaccines, by one or more specified routes of administration, at one or more specified ages of a subject.

The present disclosure provides immunization methods that involve administering at least one dose of a vaccine to a juvenile subject. In some embodiments, the juvenile subject is 18 years old or younger. In some embodiments, the juvenile subject has previously received one or more doses of a conjugated pneumococcal polysaccharide vaccine; in other embodiments, the juvenile subject is naïve to pneumococcal vaccines. In some embodiments, the juvenile subject has previously been infected with, or exposed to infection by *Klebsiella, Pseudomonas*, and/or *E. coli*.

The present disclosure provides immunization methods that involve administering at least one dose of a vaccine to an adult subject. In some embodiments, the adult subject is older than about 50 years of age. In some embodiments, the adult subject is older than about 65 years of age. In some embodiments, the adult subject has previously received one or more doses of a conjugated pneumococcal polysaccharide vaccine; in other embodiments, the adult subject is naïve to pneumococcal vaccines. In some embodiments, the adult subject has previously been infected with, or exposed to infection by *Klebsiella, Pseudomonas*, and/or *E. coli*.

Immunization schedules of the present disclosure are provided to elicit or induce an immune response (e.g., an immuno-protective response) in a subject sufficient to reduce at least one measure selected from the group consisting of incidence, prevalence, frequency, and/or severity of at least one infection, disease, or disorder, and/or at least one surrogate marker of the infection, disease, or disorder, in a population and/or subpopulation of the subject(s). A supplemental immunization schedule is one which has this effect relative to the standard schedule which it supplements. A supplemental schedule may call for additional administrations and/or supraimmunogenic doses of the immunogenic compositions disclosed herein, found in the standard schedule, or for the administration of vaccines not part of the standard schedule. A full immunization schedule of the present invention may comprise both a standard schedule and a supplemental schedule. Exemplary sample vaccination schedules are provided for illustrative purposes. Detailed descriptions of methods to assess immunogenic response discussed herein allow one to develop alterations to the sample immunization schedules without undue experimentation.

In one embodiment of the present disclosure, a first administration of a pneumococcal vaccine usually occurs when a subject is more than about 50 years old, more than about 55 years old, more than about 60 years old, more than about 65 years old, or more than about 70 years old.

In some embodiments of the disclosure, a single administration of vaccine is employed. It is possible that the purposes of the present invention can be served with a single administration, especially when one or more utilized vaccine polysaccharide(s) and/or conjugate(s) or combinations thereof is/are strong, and in such a situation a single dose schedule is sufficient to induce a lasting immunoprotective response.

In certain embodiments, it is desirable to administer two or more doses of vaccine, for greater immunoprotective efficacy and coverage. Thus, in some embodiments, a number of doses is at least two, at least three or more doses. There is no set maximum number of doses, however it is good clinical practice not to immunize more often than necessary to achieve the desired effect.

Without being bound by theory, a first dose of vaccine administered according to the disclosure may be considered a "priming" dose. In certain embodiments, more than one dose is included in an immunization schedule. In such a scenario, a subsequent dose may be considered a "boosting" dose.

A priming dose may be administered to a naïve subject (a subject who has never previously received a polysaccharide vaccine). In some embodiments, a priming dose may be administered to a subject who has previously received polysaccharide vaccine at least five or more years previous to administration of an initial vaccine dose according to the invention. In other embodiments, a priming dose may be administered to a subject who has previously received conjugate vaccine at least twenty or more years previous to administration of a priming vaccine according to the invention.

When an immunization schedule calls for two or more separate doses, the interval between doses is considered. The interval between two successive doses may be the same throughout an immunization schedule, or it may change as the subject ages. In immunization schedules of the present invention, once a first vaccine dose has been administered, there is a first interval before administration of a subsequent dose. A first interval is generally at least about 2 weeks, 1 month, 6 weeks, 2 months, 3 months, 6 months, 9 months, 12 months, or longer. Where more than one subsequent dose(s) are administered, second (or higher) intervals may be provided between such subsequent doses. In some embodiments, all intervals between subsequent doses are of the same length; in other embodiments, second intervals may vary in length. In some embodiments, the interval between subsequent doses may be at least about 12 months, at least about 15 months, at least about 18 months, at least about 21 months or at least about 2 years. In certain embodiments, the interval between doses may be up to 3 years, up to about 4 years, or up to about 5 years or 10 years or more. In certain embodiments, intervals between subsequent doses may decrease as the subject ages.

It will be appreciated by those skilled in the art that a variety of possible combinations and subcombinations of the various conditions of timing of the first administration, shortest interval, largest interval and total number of administrations (in absolute terms, or within a stated period) exist, and all of these combinations and subcombinations should be considered to be within the inventor's contemplation though not explicitly enumerated here.

Assays for Determination of Immunogenic Response

In some embodiments, a method of assessing the immunogenicity and/or potency of an immunogenic complex (and/or composition comprising an immunogenic complex) comprises evaluating an immune response to the immunogenic composition. In some embodiments, the evaluation is done by performing one or more of a series of in vitro assays. In some embodiments, the immune response evaluated is a B cell or T cell response.

In some embodiments, the in vitro assay is selected from one or more of ELISA, flow cytometry, Th1/Th17 cell response, cytokine level measurement and functional antibody levels as measured by OPK, serum bactericidal killing (SBA), agglutination, motility, cytotoxicity, adherence, agglutination.

In some embodiments, the evaluation is done by performing one or more of a series of in vivo assays. In some embodiments, an in vivo assay utilizes an animal model of nosocomial disease. In some embodiments, the animal model is a model for one or more of pneumonia, sepsis, burn wounds, GI infection, or surgical site infections. In some embodiments, an in vivo assay measures one or more of bacterial clearance, colonization, or mortality with passive protection following challenge with one or more target pathogens, or active protection following challenge with one or more target pathogens. In some embodiments, the target pathogen is a nosocomial pathogen.

Generally speaking, it may be desirable to assess humoral responses, cellular responses, and/or interactions between the two. Where humoral responses are being assessed, antibody titers and/or types (e.g., total IgG, IgG1, IgG2, IgM, IgA, etc.) to specific pathogen serotypes may be determined, for example before and/or after administration of an initial or a boosting dose of vaccine (and/or as compared with antibody levels in the absence of antigenic stimulation). Cellular responses may be assessed by monitoring reactions such as delayed type hypersensitivity responses, etc. to the carrier protein. Cellular responses can also be measured directly by evaluating the response of peripheral blood mononuclear cells (PBMCs) monocytes to stimulation with the antigens of interest. Precursor and memory B cell populations may be assessed in enzyme linked immunospot (ELISpot) assays directed against specific pathogen CPS and/or OPS.

Any of a variety of assays may be employed to detect levels and/or activity of antibodies in subject sera. Suitable assays include, for example, ligand binding assays, such as radioimmunoassay (RIAs), ELISAs, and multiplex assays (Luminex, Bioplex); functional assays, such as opsonophagocytic assays (OPA); and in vivo protection assays (infant rat protection and adult mouse lung and rodent GI colonization and mortality models).

The RIA method detects type specific antibodies through incubation of sera with radio-labeled type-specific polysaccharides in suspension (e.g., Schiffman et al., 1980). The antigen-antibody complexes are then precipitated with ammonium sulfate and the radiolabeled pellets assayed for counts per minute (cpm).

In the ELISA detection method, serotype-specific antibodies from the sera of vaccinated subjects are quantitated by incubation with serotype-specific polysaccharides which have been adsorbed to a solid support (e.g., Koskela and Leinonen (1981); Kojima et al., 1990; Concepcion and Frasch, 2001). The bound antibody is detected using enzyme-conjugated secondary detection antibodies. The ELISA also allows isotyping and subclassing of the immune response (i.e., IgM vs. IgG or IgG1 vs. IgG2) by using isotype- or subclass-specific secondary antibodies and can be adapted to evaluate the avidity of the serotype-specific antibodies (Anttila, et al, 1998; Romero-Steiner, et al., 2005). Multiplex assays (e.g., Luminex, Bioplex) enable the simultaneous detection of antibodies to multiple serotypes. Serotype-specific CPS and/or OPS are conjugated to spectrally distinct microspheres, which are mixed together and incubated with diluted serum. Bound antibody is detected with a phycoerythrin-conjugated secondary antibody and is quantitated in a specialized flow cytometer that uses one laser to identify the bead type (serotype) and a second laser to quantitate the bound secondary antibody (Pickering, et al, 2002; Lal, et al. 2005).

An approach for assessing functional antibody in serum is the OPA which quantitates only the antibodies that can opsonize the bacteria, leading to ingestion and killing of the bacteria. The standard assay utilizes a human phagocytic effector cell, a source of complement, bacteria, and diluted sera. The assay readout is the serum endpoint titer at which there is >50% killing compared to bacteria incubated with complement and human cells alone (Romero-Steiner, et al, 1997). This killing OPA can also be multiplexed by utilizing target strains of pathogen that carry different antibiotic resistance markers (Kim, et al, 2003). An endpoint titer of 1:8 or greater is considered a positive result in these killing type OPA. Another type of multiplex opsonic assay is a nonkilling assay in which the uptake by phagocytic effector cells of fluorescent stained encapsulated pathogen or fluorescent microspheres conjugated with antigenic CPS and/or OPS from a target pathogen in the presence of diluted sera plus a complement source is evaluated by FC (Martinez, et al, 1999). Opsonic activity of serum antibody plus complement can also be evaluated by measuring the oxidative response of phagocytic human effector cells to ingested pathogen (Munro, et al. 1985; Ojo-Amaize, et al. 1995).

Certain in vivo model systems can be used to evaluate the protection afforded by serum antibodies elicited by vaccines of the present invention. In such passive protection systems, mice or rats are challenged with the pathogen plus diluted sera, and the endpoint titer of the sera which provides protection against bacteremia, colonization of organs or tissues, or mortality is determined (Stack, et al. 1998; Saeland, et al. 2000).

Antibody Compositions

Some embodiments provide for an antibody composition comprising antibodies raised in a mammal immunized with an immunogenic complex of the invention. In some embodiments, an antibody comprises at least one antibody selected from the group consisting of mAbs and anti-idiotype antibodies. In some embodiments, an antibody composition comprises an isolated gamma globulin fraction.

Kits

The present disclosure also provides for kits for producing an immunogenic complex as disclosed herein which is useful for an investigator to tailor an immunogenic complex with their preferred antigens, e.g., for research purposes to assess the effect of an antigen, or a combination of antigens on immune response. Such kits can be prepared from readily available materials and reagents. For example, such kits can comprise any one or more of the following materials: a container comprising a backbone polymer cross-linked with a plurality of first affinity molecules; and a container comprising a complementary affinity molecule which associates with the first affinity molecule, wherein the complementary affinity molecule associates with an antigen.

In another embodiment, the kit can comprise a container comprising a polymer, e.g., a polysaccharide, a container comprising a plurality of first affinity molecules, and a container comprising a cross-linking reagent for cross-linking the first affinity molecules to the backbone polymer.

In some embodiments, the kit further comprises a means to attach the complementary affinity molecule to the antigen, where the means can be by a cross-linking reagent or by some intermediary fusion protein. In some embodiments, the kit can comprise at least one co-stimulation factor which can be added to the polymer. In some embodiments, the kit comprises a cross-linking reagent, for example, but not limited to, CDAP (1-cyano-4-dimethylaminopyridinium tetrafluoroborate), EDC (1-Ethyl-3-[3-dimethylaminopropyl] carbodiimide hydrochloride), sodium cyanoborohydride; cyanogen bromide; ammonium bicarbonate/iodoacetic acid for linking the co-factor to the polymer.

A variety of kits and components can be prepared for use in the methods described herein, depending upon the intended use of the kit, the particular target antigen and the needs of the user.

EXEMPLIFICATION

In order that the invention described herein may be more fully understood, the following examples are set forth. The representative examples contain information, exemplification and guidance, which can be adapted to the practice of this invention in its various embodiments and the equivalents thereof. It should be understood that these examples are for illustrative purposes only and are not to be construed as limiting this invention in any manner.

Example 1: Bacterial Strains

Reagent strains were passaged three times on animal product-free media to remove any possible animal product contaminants. Characteristics of strains were compared pre-passage, during passage and post-passage. For *Pseudomonas*: Gram stain, colony morphology, API, oxidase test, growth on MacConkey agar, IATS serotyping, growth kinetics. For *Klebsiella*: Gram stain, colony morphology, API, molecular serotyping by polymerase chain reaction (PCR), confirmation of mutations by PCR and sequencing (as necessary), K typing (by PCR), growth kinetics.

TABLE 2

*Klebsiella* strains and reagent strains used in the study

| Species | Strains | O-type | K-type | Reagent strain[a] |
|---|---|---|---|---|
| K. pneumoniae | B5055 | 1 | 2 | ΔguaBA Δwzabc |
| K. pneumoniae | 7380 | 2 | No capsule | Wild-type |
| K. pneumoniae | 390 | 3 | 11 | Wild-type |
| K. pneumoniae | 4425/51 | 5 | 57 | Nwzabc |
| K. oxytoca | 160011 | 1 | 19 | Wild-type[b] |

[a]ΔguaBA = guanine biosynthesis mutant (attenuated); Δwzabc = capsule mutant
[b]*Klebsiella oxytoca*

The guaBA and wzabc genes were deleted using lambda red recombination. Briefly, DNA upstream and downstream of the guaBA and wzabc genes were fused to a kanamycin resistance cassette and the linear DNA was transformed into the *K. pneumoniae* strains which also contained a helper plasmid that can express lambda recombinase genes. Upon induction, these genes promoted homologous recombination which enabled the guaBA and wzabc genes to be replaced with the kanamycin resistance cassette. The kanamycin resistance cassette was subsequently removed using a flippase enzyme which promotes recombination between FRT sites which flank the cassette. The mutants were confirmed to be kanamycin-sensitive and the deletion was confirmed by PCR and sequencing of the deletion.

TABLE 3

*Pseudomonas aeruginosa* (PA) strains used in the study

| Reagent | Strains | Final reagent strain |
|---|---|---|
| O1 | IATS-O1 | Wild-type |
| O2 | IATS-O2 | Wild-type |
| O3 | IATS-O3 | Wild-type |
| O4 | IATS-O4 | Wild-type |
| O5 | IATS-O5 | Wild-type |
| O6 | IATS-O6 | Wild-type |
| O10 | IATS-O10 | Wild-type |
| O11 | IATS-O11 | Wild-type |

Creation of PA Strain Overproducing the Exopolysaccharide PsL

Figure 9A:
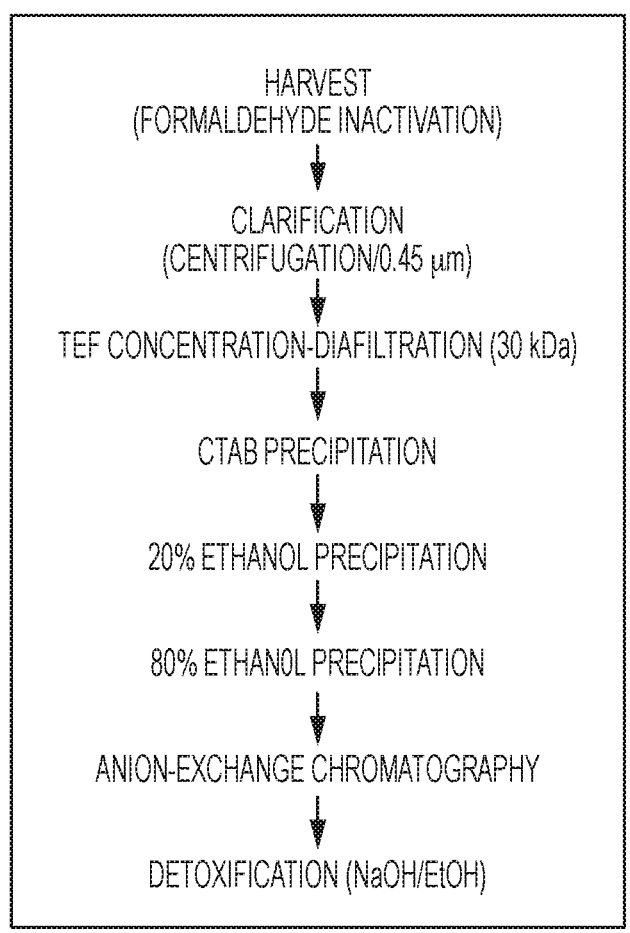
FIG. 9A depicts an exemplary flow diagram of a downstream purification process of KO CPS K19.
Figure 9B:
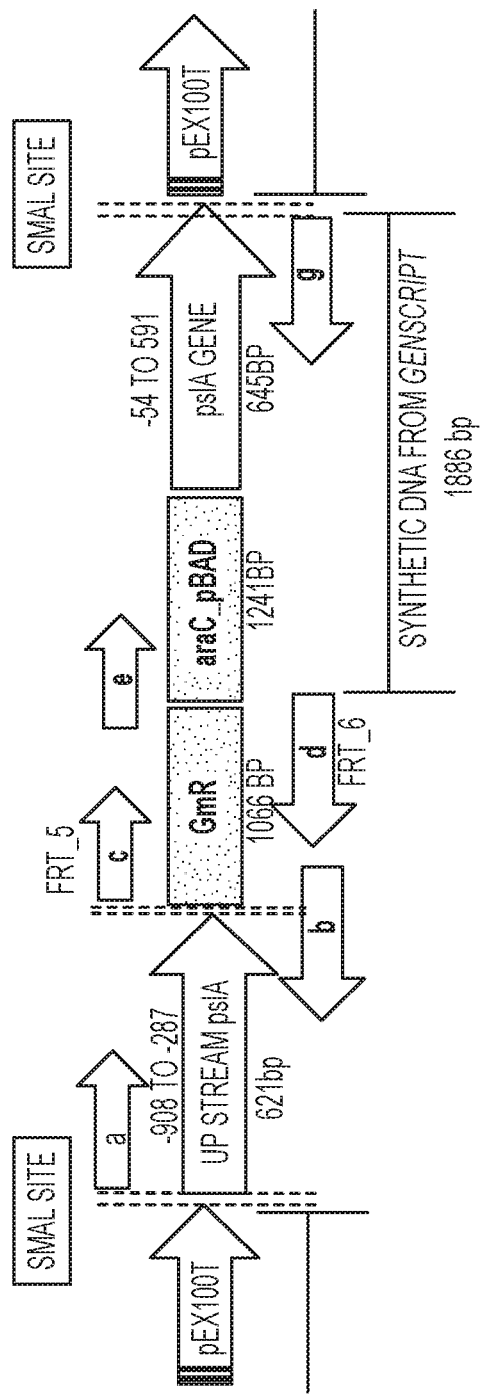
FIG. 9B depicts a construction of a gene for an exopolysaccharide PsL-overproducing *Pseudomonas* reagent strain.

Exemplary genetic approaches to reconstruct *P. aeruginosa* PsL-inducible strain PAO1 Δpsl/pBAD-psl using a 1886 bp synthetic DNA from Genscript, Piscataway, N.J. are shown in FIG. 9B.

The araC-pBAD promoter was inserted upstream of the *P. aeruginosa* PAO1 pslA gene by homologous recombination. Essentially, DNA upstream of pslA was amplified from *P. aeruginosa* PAO1 and fused upstream of a gentamicin resistance cassette. A construct consisting of synthetic DNA containing the araC-pBAD promoter and the pslA gene was fused downstream of the gentamicin-resistance cassette. This entire construct was inserted into the pEX100T *Pseudomonas* mutagenesis plasmid. Mutagenesis was performed as previously described (Schweizer et al., 1992). The gentamicin-resistance gene was subsequently removed and insertion of the araC-pBAD promoter confirmed by PCR and sequencing.

Example 2: Production of O- and K-Polysaccharide Antigens

Growth of *Klebsiella* Spp. and *P. aeruginosa* Strains

All reagent *Klebsiella* and PA strains were passaged three times on animal product-free media to remove any possible animal product contaminants. Research cell banks (RCBs) were grown in shake flasks in Hy-Soy Broth and transferred into aseptically aliquoted vials in 15% glycerol final concentration. Bacteria were grown in an 8 L BioFlo 415 Fermentor in a chemically defined media (CDM) containing potassium phosphate monobasic, ammonium phosphate, citric acid monohydrate, magnesium sulfate ($MgSO_4$) polypropylene glycol (PPG) (antifoam), 3% glycerol as carbon source, trace vitamins and elements, and select amino acids as needed. Dissolved oxygen was maintained at 30% with cascade mode set with a minimum stir rate of 200 RPM, and pH was corrected to 7 with ammonium hydroxide. During the fermentation, the media was supplemented in a batch mode when required, with 50% glycerol, $MgSO_4$, trace vitamins and trace vitamins and elements. Bacteria were grown for 12-18 h to stationary phase at which point cultures were harvested to obtain the polysaccharide.

Purification of KP O-Polysaccharide and PA Core-O-Polysaccharide

Figure 8A:
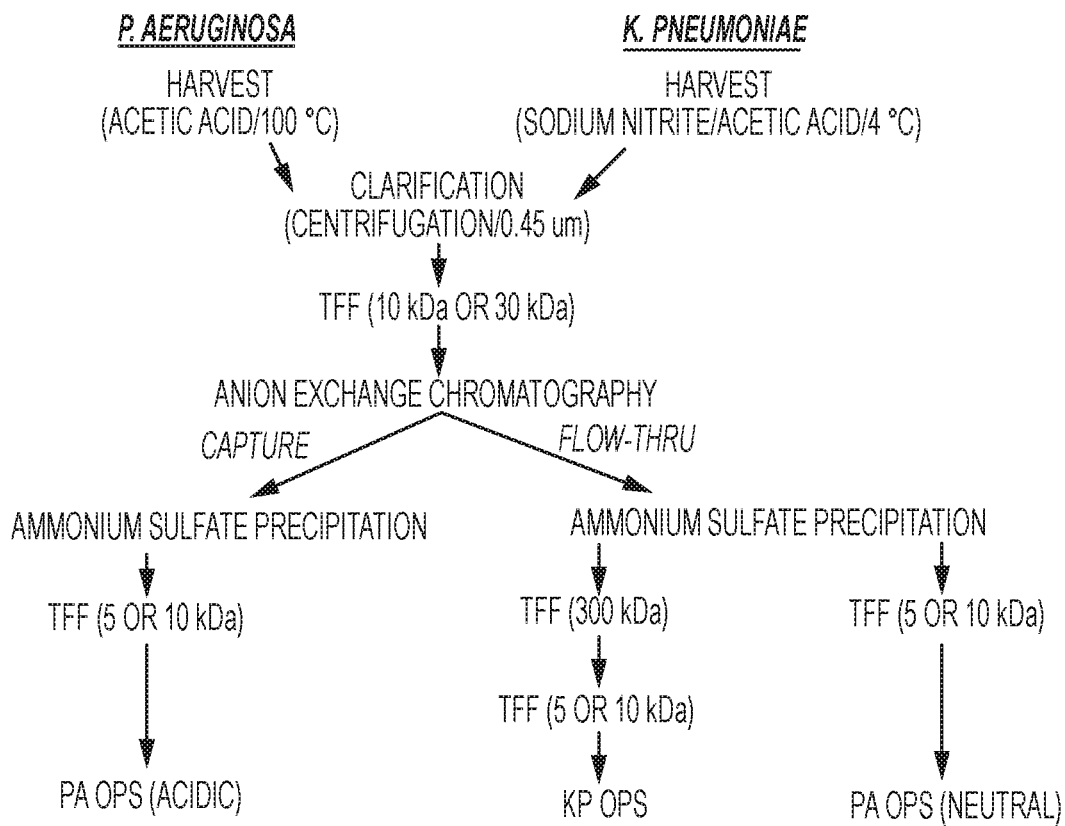
FIG. 8A depicts an exemplary flow diagram of a downstream purification process of OPS from KP and OPS from PA.

A flow diagram of the downstream purification process of the KP and PA OPSs is shown in FIG. 8A. In brief, at the end of the fermentation the whole fermentation culture was treated with either 1% acetic acid at 100° C. for 4 h for *P. aeruginosa* cell culture or with sodium nitrite in acetic acid at 4° C. for *K. pneumoniae* cell culture for 12 h. After clarification by centrifugation and depth filtration (0.45 μm) the clear solution containing the hydrolysed and released OPS was subjected to tangential flow filtration (TFF) UF-DF with a 10 kDa or 30 kDa NMWCO membrane with diafiltration against 1M NaCl and then Tris buffer. The retentate was then passed through a strong anion exchange membrane for the ion exchange chromatography (IEC) in Tris buffer. The negatively charged PA OPSs were captured by the membrane (FIG. 8A) and then eluted with sodium chloride. The neutral KP and neutral or weakly acidic PA OPSs were obtained in the flow thru (FT) of the IEC membrane. The IEC flow through or eluate was then subjected to ammonium sulfate precipitation in order to remove residual protein. The KP OPSs in the ammonium sulfate supernatant were then subjected to two successive TFF filtrations starting with a 300 kDa NMWCO membrane, for which the FT was then concentrated and diafiltered with a 5 or 10 kDa NMWCO membrane. The retentate of this later TFF FT contained the purified KP neutral OPSs (FIG. 8A). The purified neutral and acidic PA OPSs in the ammonium sulfate ($NH_4SO_4$) supernatant were subjected to by 5-10 kDa TFF (FIG. 8A) where they were recovered in the retentate. The average MW of the final OPS product as measured by SEC-multiangle laser light scattering (SEC-MALLS) ranged from 10-30 kDa depending on the 0-type and had low endotoxin, protein, and nucleic acid contents.

Purification of *Klebsiella oxytoca* K19 Capsular Polysaccharide (KP K19 CPS)

A flow diagram of the downstream purification process of the KP K19 CPS is shown in FIG. 9A. In brief, following formaldehyde inactivation, and clarification by discontinued centrifugation and surface filtration (0.45 μm) the clear solution containing the CPS was concentrated and diafiltrated using TFF with a 30 kDa NMWCO membrane. The 30 kDa retentate was precipitated by CTAB. The precipitate was resolubilized with calcium chloride and precipitated with 20% ethanol to remove nucleic acids and protein contaminants. Following centrifugation, the collected supernatant was precipitated with 80% ethanol. The CPS containing precipitate was resolubilized in Tris buffer and captured on a weak anion exchange resin. The K19 CPS eluting from the resin was further treated (detoxified) with 0.1 M NaOH in 90% ethanol to remove any residual terminal lipid contributing to its aggregation and endotoxin (as measured by Limulus amoebocyte lysate (LAL) activity) (FIG. 9A). The final K19 polysaccharide product had an average MW of 220 kDa as measured using SEC-MALLS and had low endotoxin, protein, and nucleic acid contents.

Purification of the PA Exopolysaccharide PsL

Figure 9C:
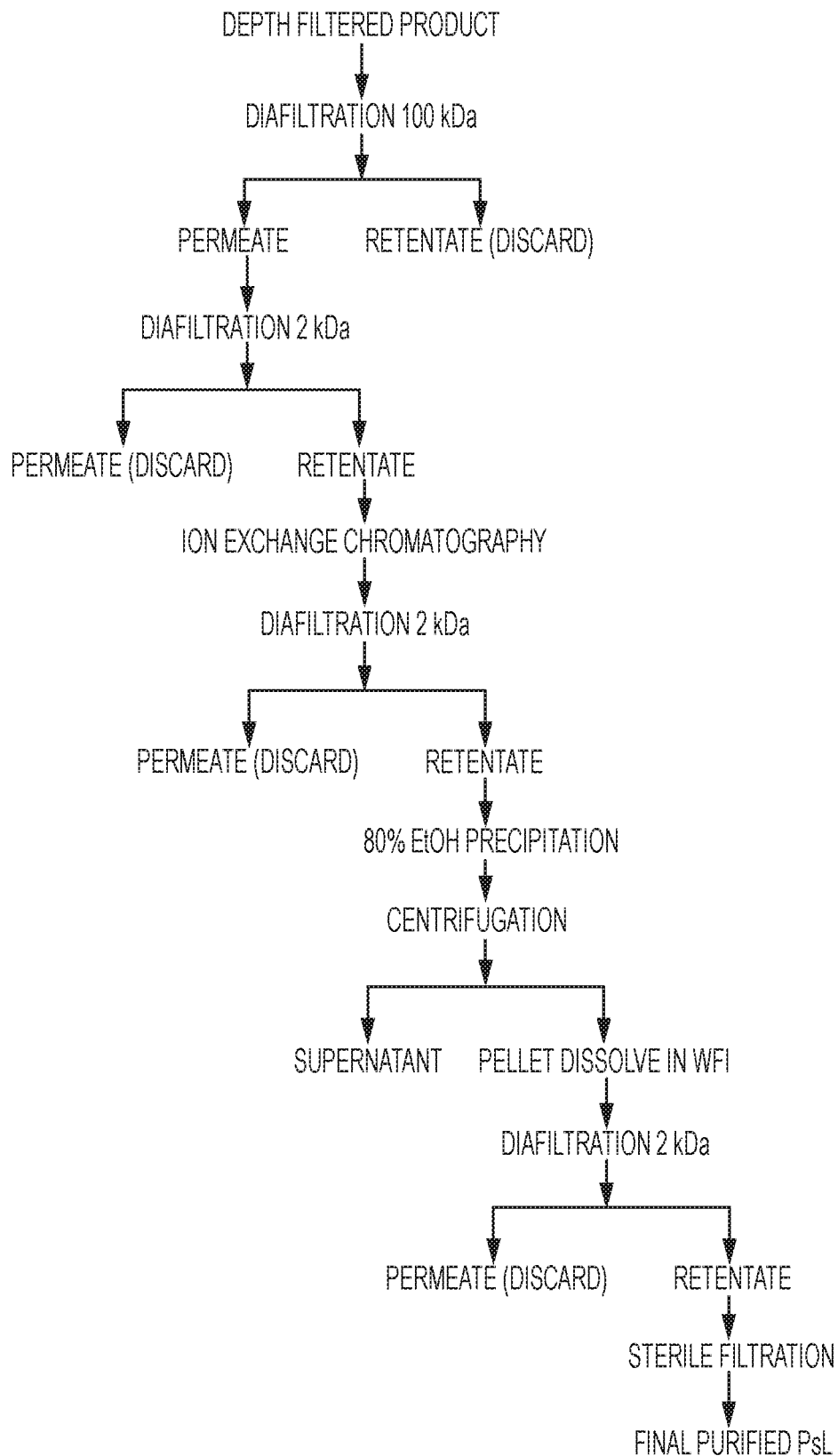
FIG. 9C depicts a flow diagram of a downstream purification process of the PA exopolysaccharide PsL.

A flow diagram of an exemplary purification process of the exoPS PsL is shown in FIG. 9C. Briefly, a PA bacterial culture was clarified by centrifugation at 10,000× g for 40 minutes at RT, and the supernatant filtered through a 0.5-0.3 um depth filter. The filtered supernatant was diafiltered by a TFF using a 100 kDa MWCO PES membrane with 10 diavolumes water for injection (WFI), and the permeate collected and concentrated using a 2 kDa Hydrosart membrane by 10-20× UF, diafiltrated with 10 diavolumes of 50 mM Tris HCl, 50 mM NaCl, pH 7.5. The concentrated eluate was then applied through a strong anion exchange resin (IEX) chromatography on a GE Q-Sepharose Fast Flow and the flow-through was collected with one more column volume wash of eluent. The eluate was concentrated and diafiltrated with WFI using a 2 kDa Hydrosart membrane and then precipitated with 80% ethanol at RT for 18 h. After centrifugation at 4000×g for 30 min the pellet was dissolved in WFI, sterile-filtered through a 0.2 μm filter, and lyophilized. The final purified polysaccharide material was analysed by HPAEC/PAD (high-performance anion-exchange chromatography with pulsed electrochemical detection) using a Dionex ICS-4000 capillary instrument and CarboPac PA10 column and commercially available monosaccharide standards for monosaccharide composition, for residual protein with the Bradford assay, residual nucleic acids with the Q-bit Life Technologies quant-IT kit, endotoxin by the LAL assay, and for total carbohydrate by the anthrone assay. The final material was also analysed by high resolution H-NMR to confirm its structure and by SEC-HPLC for molecular weight estimation.

Analytical Methods for the Characterization of the O- and the K-Antigens

Figure 8B:
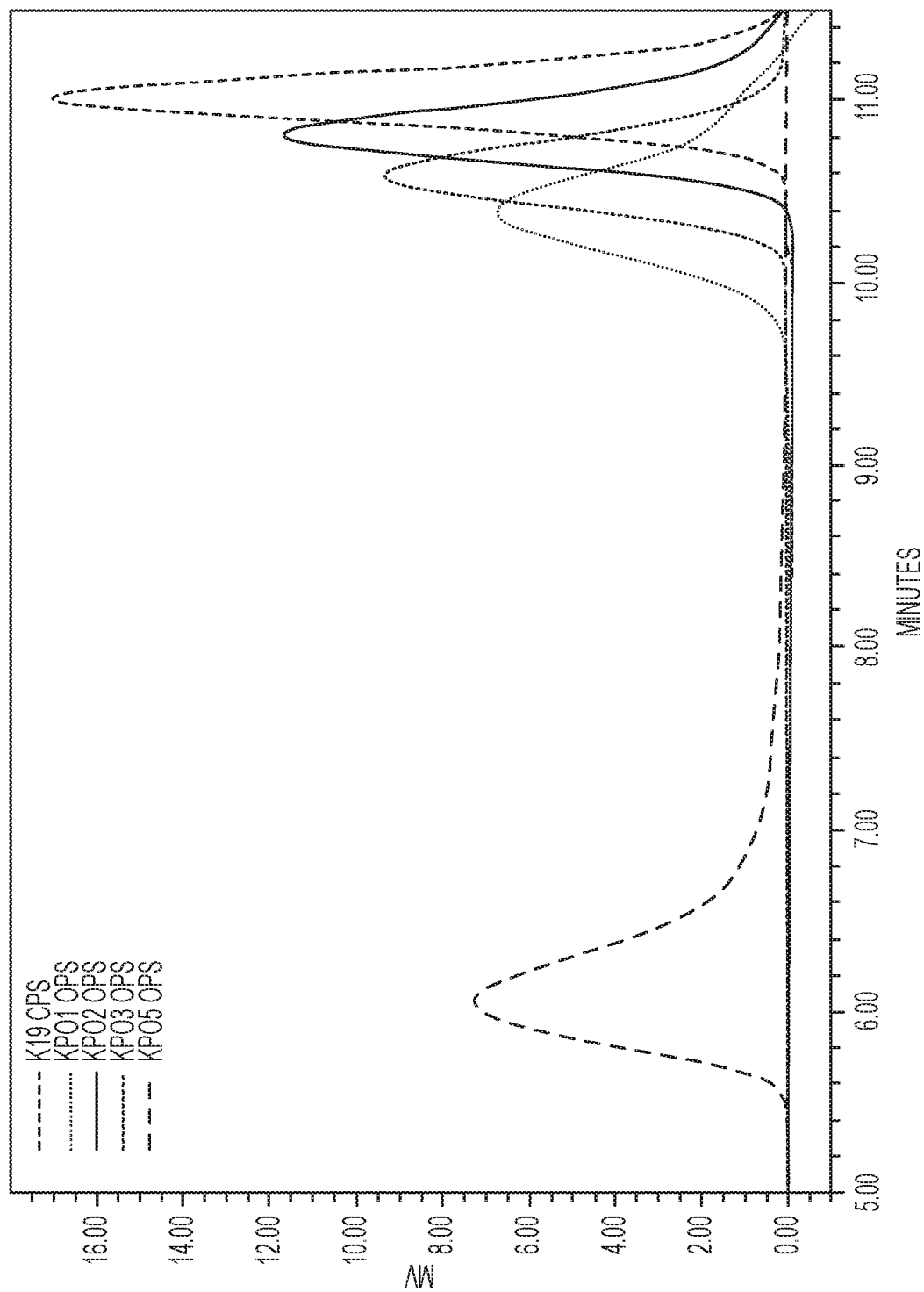
FIG. 8B depicts an exemplary SEC-HPLC (Waters BioAlliance with a phenomenex BioSep SEC-4000 column was used at a flow rate of 1 mL/min in PBS pH 7.4 containing sodium azide (0.02%) profile of purified KP OPS and K19 CPS overlay of refractive index (RI) traces from left to right: K19 CPS, O1, O3, O2, and O5.
Figure 8C:
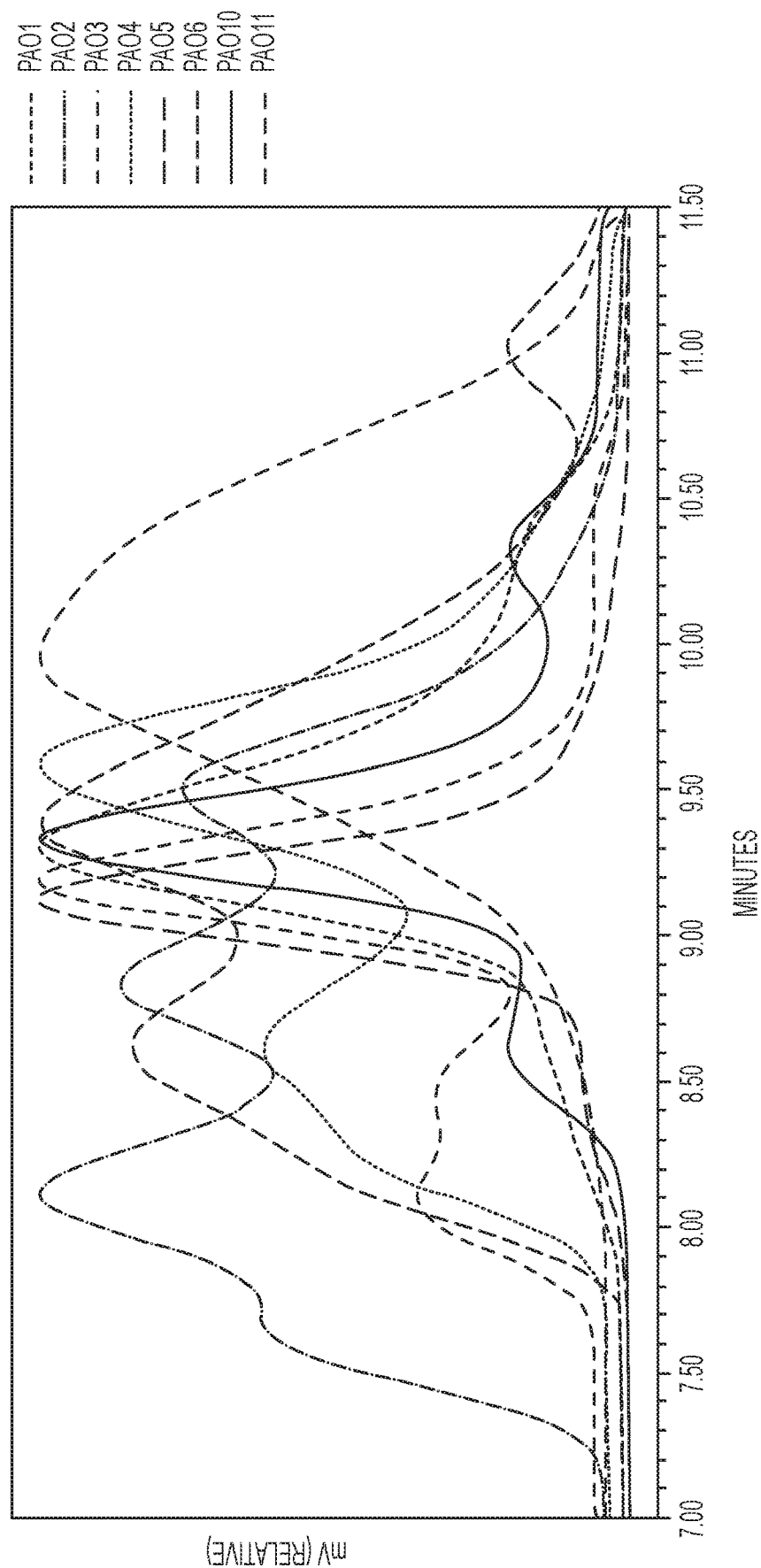
FIG. 8C depicts an exemplary SEC-HPLC (Waters BioAlliance with a phenomenex BioSep SEC-4000 column was used at a flow rate of 1 mL/min in PBS pH 7.4 containing sodium azide (0.02%) profile of purified PA OPS overlay of RI traces from left to right: O2, O6, O3, O4, O5, O1, O10, and O11.

The purity and identity of the OPS and CPS obtained from the processes described above was determined as follows. Residual protein concentration was determined by the Bradford and/or BCA assays; nucleic acid concentration was determined using the pico green assay or absorbance at 260 nm; endotoxin levels were measured using the LAL assay; and the sugar composition of the polysaccharides was determined by acid hydrolysis followed by separation of the individual monosaccharides by HPAEC-PAD (Dionex) as described above. The physical integrity of the polysaccharides was determined by high resolution 1H-NMR at 500, 800 or 950 MHz using a Bruker spectrometer to record the spectra and comparing the obtained spectra with those published in the literature. The identity of the polysaccharide and integrity of the epitopes on the purified native and chemically derivatized polysaccharides, in-process and as final products, were confirmed by ELISA using specific OPS and CPS monoclonal antibodies and polyclonal rabbit antisera raised against heat-killed type-specific bacteria. The presence of O-acetyl groups on the polysaccharides was determined by the Hestrin colorimetric assay and by 1H-NMR. The size of the polysaccharides was determined by SEC-HPLC (FIGS. 8B and 8C) and SEC-MALLS using appropriate sizing columns. Polysaccharide concentration was determined by the anthrone assay.

Example 3: General Method of Biotinylation of OPS and CPS

Biotinylation of polysaccharides (PSs) containing hydroxyl groups was done using CDAP as an activation reagent. The polysaccharides were dissolved in LPS-free water (cell culture grade; HyClone) for a final concentration of 1-5 mg/mL. At time 0, a volume of CDAP (freshly made at a concentration of 100 mg/mL in acetonitrile) was added to a final ratio of 1 mg of CDAP per 1 mg of PS during vortexing. At 30 s, a volume of 0.2 M triethylamine (TEA; Sigma-Aldrich) was added to raise the pH to 8 (For neutral PS, the volume of TEA is equal to the volume of CDAP; for acidic PS, the volume of TEA is doubled). At 2.5 min, a volume of biotin derivative (Pierce EZ-Link Amine-PEG3-Biotin, 20 mg/mL in water) was added to a final ratio of 1 mg of biotin to 1 mg of PS followed by incubation at room temperature for 1-4 h. For more diluted samples (<1 mg/mL), overnight incubation was used. The reaction was terminated by adding 25 mM glycine, and the excess biotin was removed by extensive dialysis against PBS.

For the backbone polymer BP-1.2 the biotinylation of the polymer K19 CPS proceeded by activation of the carboxylate groups of the uronic acid residues with 1-ethyl-3-[3-dimethylaminopropyl]carbodiimide hydrochloride (EDC, Pierce) and N-hydroxysuccinimide (NETS) to improve efficiency or create dry-stable (amine-reactive) intermediates. EDC couples NETS to carboxyls, forming an NETS ester that is considerably more stable than the O-acylisourea intermediate while allowing for efficient conjugation to primary amines at physiologic pH. The biotin amine derivative (Pierce EZ-Link Amine-PEG3-Biotin) is then used for the biotinylation of the NETS ester intermediates of the K19 CPS.

The total sugar concentrations were determined by either the anthrone assay for the *Klebsiella* OPS/CPS or the resorcinol assay for the PA OPS.

Example 4: Construction of Recombinant Rhizavidin and Rhizavidin-Fusion Protein Antigens Design and Engineering of Expression Constructs of Rhizavidin Fusion Proteins Derived From *K. pneumoniae* and *P. aeruginosa*

Figure 12A:
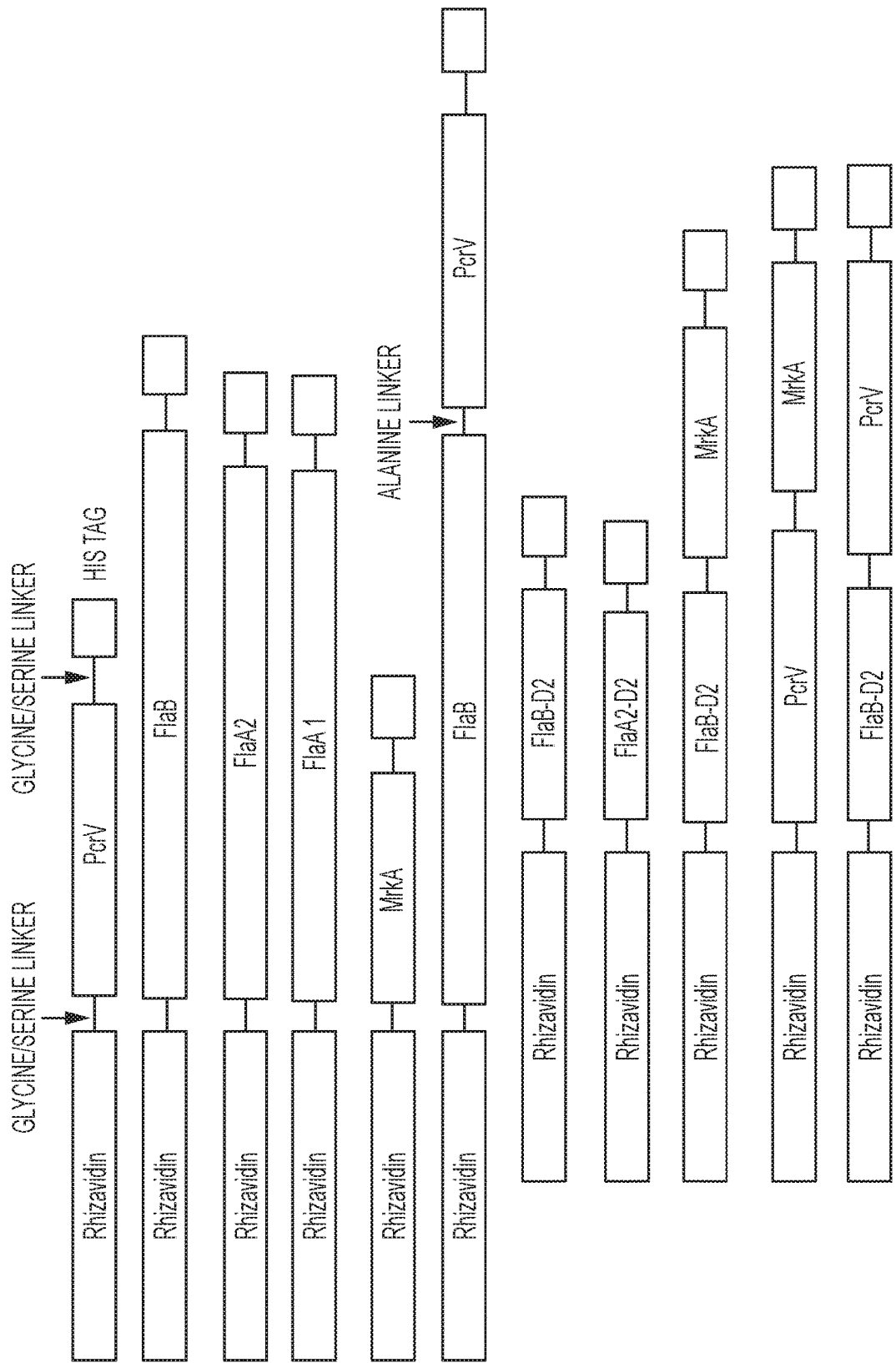
FIG. 12A shows a schematic of rhizavidin-antigen fusion proteins produced that are derived from *Pseudomonas* (PcrV; FlaB; FlaA2; FlaA1; FlaB-PcrV; FlaB-D2; FlaA2-D2) or *Klebsiella* (MrkA) or hybrid proteins derived from both *Klebsiella* and *Pseudomonas* (FlaB-D2-MrkA; PcrV-MrkA).

For the *Pseudomonas* flagellins (FliC) A (FlaA) and B (FlaB) an in silico construction of a flagellar filament based on the packing of *Pseudomonas* FliC in the crystal suggests that the Domain 2 (D2) would be exposed to solution and could play an important role in immunogenicity (Song, 2014). In addition, *Pseudomonas* FliC activates innate immune responses via its recognition by TLR5, possibly leading to reactogenicity, therefore we generated and evaluated some of the *Pseudomonas* flagellins with the TLR5 binding domain and adjacent regions removed leaving only Domain 2. The resulting sequences FlaA2-Domain2 and FlaB-Domain2 lacking the TLR5 domain were either expressed as a fusion with rhizavidin alone or with rhizavidin and *Klebsiella* MrkA or PcrV. A schematic of the rhizavidin-antigen fusion protein variants generated and expressed derived from *Pseudomonas* (FlaB; FlaA1; FlaA2; PcrV; FlaB-PcrV; FlaB-D2; FlaA2-D2; FlaB-D2-PcrV) and for the hybrid rhizavidin fusion proteins derived from both *Klebsiella* and *Pseudomonas* (FlaB-D2-MrkA; PcrV-MrkA) is shown in FIG. 12A.

For *P. aeruginosa*, flagellin was chosen as a likely carrier protein and protective antigen as it is the major component of the flagella and it is known that antibodies to flagellin inhibit motility required for disseminated infections and have been demonstrated as protective in an animal infection model. For flagellin, serotype A2 is highly conserved, but varies slightly from A1 and significantly in domain 2 from serotype B. To evaluate the activity of these variations, serotype A1 (FlaA1), A2 (FlaA2) and B (FlaB) flagellin were cloned and expressed as full-length proteins. Domain 2 only from the flagellins A2 and B was also cloned and expressed as this domain decorates the exterior of the assembled flagella and is a likely target for neutralizing antibodies. This allowed a separate evaluation of the contribution of the TLR5 binding domain to the adaptive immune response. The selected sequences were synthesized and cloned into plasmids to direct expression in *E. coli* with an amino-terminal rhizavidin fusion and a six histidine tag for initial affinity purification (FIG. 12A).

For *P. aeruginosa*, PcrV was also chosen as it encodes the tip protein of the Type III secretion apparatus. It is also known as a protective antigen as antibodies specific for PcrV can protect against invasive infection. The sequence is highly conserved with only 4 positions with amino acid alterations from 294 amino acids across 18 different *P. aeruginosa* strains. The sequence was synthesized and cloned into a plasmid to direct expression in *E. coli* with an amino-terminal rhizavidin fusion and a six histidine tag for initial affinity purification (FIG. 12A).

For *K. pneumoniae*, MrkA was chosen as it encodes the major fimbrial subunit of type 3 pili and immunologically dominant part of fimbriae. Type 3 fimbriae are required to mediate biofilm formation and MrkA plays a major role in the biofilm formation and adherence suggesting that this antigen could provide protection in a vaccine formulation. MrkA was found to be highly conserved with 9 different genotypes of *K. pneumoniae*, providing only 1 position with an amino acid alteration across the 180 amino acids. One additional genotype provided slightly higher alterations with 9 positions with changes across the 180 amino acids (Table 4). For other type 3 pili fimbriae subunits, a strategy to stabilize the monomer during expression was developed called donor strand complementation method (Walczak, 2014). This strategy takes the amino terminal sequence and repeats it at the carboxyl terminus so that it can fold back and bind in the orientation of the beta strand usually provided from the next subunit in the structure. We attempted to extend this strategy to *K. pneumoniae* type 3 pilus subunit MrkA by first removing the secretion signal sequence as we planned to focus on cytoplasmic expression for our Rhizavidin fusions. The putative secretion signal is modeled in Chan et al. 2012, Langmuir based on alignment with *E. coli* FimA amino acids 1-24. We then added a six glycine linker to the carboxyl terminus followed by a repeat of the first 20 amino acids from the N-terminus of MrkA (without the signal sequence) to provide donor strand complementation. The sequence was synthesized and cloned into a plasmid to direct expression in *E. coli* with an amino-terminal rhizavidin fusion and a six histidine tag for initial affinity purification (FIG. 12A).

TABLE 4

K. pneumoniae MrkA Clustal O (1.2.1) multiple sequence alignment
K. pneumoniae MrkA
CLUSTAL O(1.2.1) multiple sequence alignment

| | | |
|---|---|---|
| gi\|149236\|gb\|AAA25093.1\| | --MKKVLLSAAMATAFFGMAAANAADTNVGGGQVNFFGKVTDVSCTVSVNGQGSDANVYL | 58 |
| gi\|660551770\|gb\|AIE00215.1\| | --MKKVLLSAAMATAFFGMTAANAADTNVGGGQVNFFGKVTDVSCTVSVNGQGSDANVYL | 58 |
| gi\|446679613\|ref\|WP_000756959.1\| | --MKKVLLSAAMATAFFGMTAANAADTNVGGGQVNFFGKVTDVSCTVSVNGQGSDANVYL | 58 |
| gi\|197110110\|gb\|ACH42749.1\| | MAMKKVLLSAAMATAFFGMTAANAADTNVGGGQVNFFGKVTDVSCTVSVNGQGSDANVYL | 60 |
| gi\|346425863\|gb\|AEO27492.1\| | --MKKVLLSAAMATAFFGMTAANAADTTVGGGQVNFFGKVTDVSCTVSVNGQGSDANVYL | 58 |
| gi\|283520840\|gb\|ADB25182.1\| | ----------------------------------------KVTDVSCTVSVNGQGSDANVYL | 22 |
| gi\|283520838\|gb\|ADB25181.1\| | ----------------------------------------KVTDVSCTVSVNGQGSDANVYL | 22 |
| gi\|150956647\|gb\|ABR78677.1\| | -----------MATAFFGMTAANAADTTVGGGQVNFFGKVTDVSCTVSVNGQGSDANVYL | 49 |
| gi\|407806110\|gb\|EKF77361.1\| | MAMKKVLLSAAMATAFFGMTAANAADTTVGGGQVNFFGKVTDVSCTVSVNGQGSDANVYL | 60 |
| |                                       \*\*\*\*\*\*\*\*\*\*\*\*\*\*\*\*\*\*\*\*\*\*\* | |
| gi\|149236\|gb\|AAA25093.1\| | SPVTLTEVKAAAADTYLKPKSFTIDVSDCQAADGTKQDDVSKLGVNWTGGNLLAGATAKQ | 118 |
| gi\|660551770\|gb\|AIE00215.1\| | SPVTLTEVKAAAADTYLKPKSFTIDVSNCQAADGTKQDDVTKLGVNWTGGNLLAGATSKQ | 118 |
| gi\|446679613\|ref\|WP_000756959.1\| | SPVTLTEVKAAAADTYLKPKSFTIDVSNCQAADGTKQDDVSKLGVNWTGGNLLAGATSKQ | 118 |
| gi\|197110110\|gb\|ACH42749.1\| | SPVTLTEVKAAAADTYLKPKSFTIDVSNCQAADGTKQDDVSKLGVNWTGGNLLAGATSKQ | 120 |
| gi\|346425863\|gb\|AEO27492.1\| | SPVTLTEVKAAAADTYLKPKSFTIDVSNCQAADGTKQDDVSKLGVNWTGGNLLAGATSKQ | 118 |
| gi\|283520840\|gb\|ADB25182.1\| | SPVTLTEVKAAAADTYLKPKSFTIDVSNCQAADGTKQDDVSKLGVNWTGGNLLAGATSKQ | 82 |
| gi\|283520838\|gb\|ADB25181.1\| | SPVTLTEVKAAAADTYLKPKSFTIDVSNCQAADGTKQDDVSKLGVNWTGGNLLAGATSKQ | 82 |
| gi\|150956647\|gb\|ABR78677.1\| | SPVTLTEVKAAAADTYLKPKSFTIDVSNCQAADGTKQDDVSKLGVNWTGGNLLAGATSKQ | 109 |
| gi\|407806110\|gb\|EKF77361.1\| | SPVTLTEVKAAAADTYLKPKSFTIDVSNCQAADGTKQDDVSKLGVNWTGGNLLAGATSKQ | 120 |
| | \*\*\*\*\*\*\*\*\*\*\*\*\*\*\*\*\*\*\*\*\*\*\*\*\*\*\*\*\*:\*\*\*\*\*\*\*\*\*\*\*\*:\*\*\*\*\*\*\*\*\*\*\*\*\*\*\*\*:\*\* | |
| gi\|149236\|gb\|AAA25093.1\| | QGYLANTEAAGAQNIQLVLSTDNATALTNKIIPGDSTQPKAAGDASAVQDGARFTYYVGY | 178 |
| gi\|660551770\|gb\|AIE00215.1\| | QGYLANTEASGAQNIQLVLSTDNATALTNKIIPGDSTQPKAKGDAAAVADGARFTYYVGY | 178 |
| gi\|446679613\|ref\|WP_000756959.1\| | QGYLANTEASGAQNIQLVLSTDNATALTNKIIPGDSTQPKAKGDASAVADGARFTYYVGY | 178 |
| gi\|197110110\|gb\|ACH42749.1\| | QGYLANTEASGAQNIQLVLSTDNATALTNKIIPGDSTQPKAKGDASAVADGARFTYYVGY | 180 |
| gi\|346425863\|gb\|AEO27492.1\| | QGYLANTEASGAQNIQLVLSTDNATALTNKIIPGDSTQPKAKGDASAVADGARFTYYVGY | 178 |
| gi\|283520840\|gb\|ADB25182.1\| | QGYLANTEASGAQNIQLVLSTDNATALTNKIIPGDSTQPKAKGDASAVADGARFTY---- | 138 |
| gi\|283520838\|gb\|ADB25181.1\| | QGYLANTEASGAQNIQLVLSTDNATALTNKIIPGDSTQPKAKGDASAVADGARFTY---- | 138 |
| gi\|150956647\|gb\|ABR78677.1\| | QGYLANTEASGAQNIQLVLSTDNATALTNKIIPGDSTQPKAKGDASAVADGARFTYYVGY | 169 |
| gi\|407806110\|gb\|EKF77361.1\| | QGYLANTEASGAQNIQLVLSTDNATALTNKIIPGDSTQPKAKGDASAVADGARFTYYVGY | 180 |
| | \*\*\*\*\*\*\*\*\*:\*\*\*\*\*\*\*\*\*\*\*\*\*\*\*\*\*\*\*\*\*\*\*\*\*\*\*\*\* \*\*\*:\*\* \*\*\*\*\*\*\* | |
| gi\|149236\|gb\|AAA25093.1\| | ATSTPITVTTGVVNSYATYEITYQ | 202 |
| gi\|660551770\|gb\|AIE00215.1\| | ATSAPITVTTGVVNSYATYEITYQ | 202 |
| gi\|446679613\|ref\|WP_000756959.1\| | ATSAPITVTTGVVNSYATYEITYQ | 202 |
| gi\|197110110\|gb\|ACH42749.1\| | ATSAPITVTTGVVNSYATYEITYQ | 204 |
| gi\|346425863\|gb\|AEO27492.1\| | ATSAPITVTTGVVNSYATYEITYQ | 202 |
| gi\|283520840\|gb\|ADB25182.1\| | ------------------------ | 138 |
| gi\|283520838\|gb\|ADB25181.1\| | ------------------------ | 138 |
| gi\|150956647\|gb\|ABR78677.1\| | ATSAPITVTTGVVNSYATYEITYQ | 193 |
| gi\|407806110\|gb\|EKF77361.1\| | ATSAPITVTTGVVNSYAIYEITYQ | 204 |

For the *K. pneumoniae* MrkA protein which is highly conserved, the AEO27492 sequence (bold) in Table 4 was used as the source sequence to generate the synthetic gene.

The recombinant Rhizavidin (rRhavi) used in these studies spans amino acids 45 to 179 of the protein encoded from the genome as the predicted signal sequences (amino acids 1-44) were not incorporated. To optimize the expression level of rRhavi in *E. coli*, the gene sequence that encodes Rhizavidin polypeptide (45-179; SEQ ID NO:14) was redesigned using *E. coli*-preferred expression codons and synthesized. The codon-optimized gene was cloned into the pET21b vector to direct protein expression. To facilitate the correct folding and disulfide bond formation in Rhizavidin, an *E. coli* strain was selected for expression that facilitated disulfide bond formation in the cytoplasm, T7 shuffle express (NEB).

To construct Rhizavidin-antigen fusion proteins, a DNA sequence encoding a flexible linker region consisting of seven amino acids (GGGGSSS; SEQ ID NO:15) was directly inserted into the 3' end of the synthetic rRhavi gene to provide separation from rRhavi and promote proper folding of the subsequent fusion protein. The genes encoding candidate antigens (full length or desired fragment) were synthesized and inserted into the rRhavi expression vector just beyond the linker region. To facilitate purification, a six histidine tag was added to the end of the construct.

The plasmids containing DNA to direct rRhavi fusion proteins expression were transformed into T7 shuffle express *E. coli* following the manufacturer's protocol. A culture was initiated from a single colony and inoculated into 30 ml Luria-Bertani (LB) medium containing ampicillin (Amp+) for an overnight culture at 30° C. On day 2, 5 ml of starting culture was inoculated into 1 liter of LB medium/Amp+ and grown at 30° C. until $OD_{600}$~1.2 to 1.6 was reached. After cooling the culture to 16° C., IPTG was added to a final concentration of 0.1 mM. The induced culture was incubated at 16° C. with shaking for 16 to 20 h. Bacteria were collected by centrifugation at 5000×g for 20 min and the pellet was frozen at −20° C.

Exemplary Fusion Proteins

Exemplary rhizavidin fusion proteins of the present invention are set forth in the following sequence listing. For easy reference, the one letter amino acid sequences of the fusion proteins are provided in the following:

Rhavi-PcrV-His SEQ ID NO: 16
MFDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDGGGGSSSMEVRNLNAARELFLDELLAASAAPASA -continued EQEELLALLRSERIVLAHAGQPLSEAQVLKALAWLLAANPSAPPGQGLEVLREVLQA
RRQPGAQWDLREFLVSAYFSLHGRLDEDVIGVYKDVLQTQDGKRKALLDELKALTA
ELKVYSVIQSQINAALSAKQGIRIDAGGIDLVDPTLYGYAVGDPRWKDSPEYALLSNL
DTFSGKLSIKDFLSGSPKQSGELKGLSDEYPFEKDNNPVGNFATTVSDRSRPLNDKVN
EKTTLLNDTSSRYNSAVEALNRFIQKYDSVLRDILSAIGSGHHHHHH Rhavi-MrkA-donor-strand-complementation-His SEQ ID NO: 17
MFDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDGGGGSSSMADTTVGGGQVNFFGKVTDVSCTVSV
NGQGSDANVYLSPVTLTEVKAAAADTYLKPKSFTIDVSNCQAADGTKQDDVSKLGV
NWTGGNLLAGATSKQQGYLANTEASGAQNIQLVLSTDNATALTNKIIPGDSTQPKA
KGDASAVADGARFTYYVGYATSAPTTVTTGVVNSYATYEITYQGGGGGGADTTVG
GGQVNFFGKVTDVSGSGHHHHHH Rhavi-FlaA1-His SEQ ID NO: 18
MFDASNFKDFSSIASASSSWQNQSGSTMHIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDGGGGSSSMALTVNTNIASLNTQRNLNNSSASLNT
SLQRLSTGSRINSAKDDAAGLQIANRLTSQVNGLNVATKNANDGISLAQTAEGALQQ
STNILQRMRDLSLQSANGSNSDSERTALNGEVKQLQKELDRISNTTTFGGRKLLDGSF
GVASFQVGSAANEIISVGIDEMSAESLNGTYFKADGGGAVTAATASGTVDIAIGITGG
SAVNVKVDMKGNETAEQAAAKIAAAVNDANVGIGAFSDGDTISYVSKAGKDGSGAI
TSAVSGVVIADTGSTGVGTAAGVTPSATAFAKTNDTVAKIDISTAKGAQSAVLVIDE
AIKQIDAQRADLGAVQNRFDNTINNLKNIGENVSAARGRIEDTDFAAETANLTKNQV
LQQAGTAILAQANQLPQSVLSLLRGSGHHHHHH Rhavi-FlaA2-His SEQ ID NO: 19
MFDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDGGGGSSSMALTVNTNIASLNTQRNLNNSSASLNT
SLQRLSTGSRINSAKDDAAGLQIANRLTSQVNGLNVATKNANDGISLAQTAEGALQQ
STNILQRMRDLSLQSANGSNSDSERTALNGEVKQLQKELDRISNTTTFGGRKLLDGSF
GVASFQVGSAANEIISVGIDEMSAESLNGTYFTATGGGAVTAATASGTVDIAIGITGG
SAVNVKVDMKGNETAEQAAAKIAAAVNDANVGIGAFTDGAQISYVSKASADGTTS
AVSGVAITDTGSTGAGTAAGTTTFTEANDTVAKIDISTAKGAQSAVLVIDEAIKQIDA
QRADLGAVQNRFDNTINNLKNIGENVSAARGRIEDTDFAAETANLTKNQVLQQAGT
AILAQANQLPQSVLSLLRGSGHHHHHH Rhavi-FlaB-His SEQ ID NO: 20
MFDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDGGGGSSSMALTVNTNIASLNTQRNLNASSNDLNT
SLQRLTTGYRINSAKDDAAGLQISNRLSNQISGLNVATRNANDGISLAQTAEGALQQS
TNILQRIRDLALQSANGSNSDADRAALQKEVAAQQAELTRISDTTTFGGRKLLDGSF
GTTSFQVGSNAYETIDISLQNASASAIGSYQVGSNGAGTVASVAGTATASGIASGTVN
LVGGGQVKNIAIAAGDSAKAIAEKMDGAIPNLSARARTVFTADVSGVTGGSLNFDVT
VGSNTVSLAGVTSTQDLADQLNSNSSKLGITASINDKGVLTITSATGENVKFGAQTGT
ATAGQVAVKVQGSDGKFEAAAKNVVAAGTAATTTIVTGYVQLNSPTAYSVSGTGT
QASQVFGNASAAQKSSVASVDISTADGAQNAIAVVDNALAAIDAQRADLGAVQNRF
KNTIDNLTNISENATNARSRIKDTDFAAETAALSKNQVLQQAGTAILAQANQLPQAV
LSLLRGSGHHHHHH Rhavi-FlaB-Domain2-His SEQ ID NO: 21
MFDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDGGGGSSSMGSYQVGSNGAGTVASVAGTATASGI
ASGTVNLVGGGQVKNIAIAAGDSAKAIAEKMDGAIPNLSARARTVFTADVSGVTGG
SLNFDVTVGSNTVSLAGVTSTQDLADQLNSNSSKLGITASINDKGVLTITSATGENVK
FGAQTGTATAGQVAVKVQGSDGKFEAAAKNVVAAGTAATTTIVTGYVQLNSPTAY
SVSGTGTQASQVFGNASAAQKSSGSGHHHHHH Rhavi-FlaA2-Domain2-His SEQ ID NO: 22
MFDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDGGGGSSSMNGTYFTATGGGAVTAATASGTVDIAI
GITGGSAVNVKVDMKGNETAEQAAAKIAAAVNDANVGIGAFTDGAQISYVSKASA
DGTTSAVSGVAITDTGSTGAGTAAGTTTFTEANDTGSGHHHHHH Rhavi-FlaB-PcrV-His SEQ ID NO: 23
MFDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDGGGGSSSMALTVNTNIASLNTQRNLNASSNDLNT
SLQRLTTGYRINSAKDDAAGLQISNRLSNQISGLNVATRNANDGISLAQTAEGALQQS
TNILQRIRDLALQSANGSNSDADRAALQKEVAAQQAELTRISDTTTFGGRKLLDGSF
GTTSFQVGSNAYETIDISLQNASASAIGSYQVGSNGAGTVASVAGTATASGIASGTVN
LVGGGQVKNIAIAAGDSAKAIAEKMDGAIPNLSARARTVFTADVSGVTGGSLNFDVT
VGSNTVSLAGVTSTQDLADQLNSNSSKLGITASINDKGVLTITSATGENVKFGAQTGT
ATAGQVAVKVQGSDGKFEAAAKNVVAAGTAATTTIVTGYVQLNSPTAYSVSGTGT
QASQVFGNASAAQKSSVASVDISTADGAQNAIAVVDNALAAIDAQRADLGAVQNRF
KNTIDNLTNISENATNARSRIKDTDFAAETAALSKNQVLQQAGTAILAQANQLPQAV -continued LSLLRAAAAMEVRNLNAARELFLDELLAASAAPASAEQEELLALLRSERIVLAHAGQ
PLSEAQVLKALAWLLAANPSAPPGQGLEVLREVLQARRQPGAQWDLREFLVSAYFS
LHGRLDEDVIGVYKDVLQTQDGKRKALLDELKALTAELKVYSVIQSQINAALSAKQ
GIRIDAGGIDLVDPTLYGYAVGDPRWKDSPEYALLSNLDTFSGKLSIKDFLSGSPKQS
GELKGLSDEYPFEKDNNPVGNFATTVSDRSRPLNDKVNEKTTLLNDTSSRYNSAVEA
LNRFIQKYDSVLRDILSAIGSGHHHHHH Rhavi-FlaB-Domain2-MrkA-donor-strand-complementation-His
SEQ ID NO:24
MFDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDGGGGSSSMGSYQVGSNGAGTVASVAGTATASGI
ASGTVNLVGGGQVKNIAIAAGDSAKAIAEKMDGAIPNLSARARTVFTADVSGVTGG
SLNFDVTVGSNTVSLAGVTSTQDLADQLNSNSSKLGITASINDKGVLTITSATGENVK
FGAQTGTATAGQVAVKVQGSDGKFEAAAKNVVAAGTAATTTIVTGYVQLNSPTAY
SVSGTGTQASQVFGNASAAQKSSAAAAMADTTVGGGQVNFFGKVTDVSCTVSVNG
QGSDANVYLSPVTLTEVKAAAADTYLKPKSFTIDVSNCQAADGTKQDDVSKLGVN
WTGGNLLAGATSKQQGYLANTEASGAQNIQLVLSTDNATALTNKIIPGDSTQPKAK
GDASAVADGARFTYYVGYATSAPTTVTTGVVNSYATYEITYQGGGGGGADTTVGG
GQVNFFGKVTDVSGSGHHHHHH Rhavi-MrkA-donor-strand-complementation-PcrV-His SEQ ID
NO: 25
MFDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDGGGGSSSMADTTVGGGQVNFFGKVTDVSCTVSV
NGQGSDANVYLSPVTLTEVKAAAADTYLKPKSFTIDVSNCQAADGTKQDDVSKLGV
NWTGGNLLAGATSKQQGYLANTEASGAQNIQLVLSTDNATALTNKIIPGDSTQPKA
KGDASAVADGARFTYYVGYATSAPTTVTTGVVNSYATYEITYQGGGGGGADTTVG
GGQVNFFGKVTDVSAAAAMEVRNLNAARELFLDELLAASAAPASAEQEELLALLRS
ERIVLAHAGQPLSEAQVLKALAWLLAANPSAPPGQGLEVLREVLQARRQPGAQWDL
REFLVSAYFSLHGRLDEDVIGVYKDVLQTQDGKRKALLDELKALTAELKVYSVIQSQ
INAALSAKQGIRIDAGGIDLVDPTLYGYAVGDPRWKDSPEYALLSNLDTFSGKLSIKD
FLSGSPKQSGELKGLSDEYPFEKDNNPVGNFATTVSDRSRPLNDKVNEKTTLLNDTSS
RYNSAVEALNRFIQKYDSVLRDILSAIGSGHHHHHH Rhavi-FlaB-Domain2-PcrV-His SEQ ID NO: 26
MFDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDGGGGSSSMGSYQVGSNGAGTVASVAGTATASGI
ASGTVNLVGGGQVKNIAIAAGDSAKAIAEKMDGAIPNLSARARTVFTADVSGVTGG
SLNFDVTVGSNTVSLAGVTSTQDLADQLNSNSSKLGITASINDKGVLTITSATGENVK
FGAQTGTATAGQVAVKVQGSDGKFEAAAKNVVAAGTAATTTIVTGYVQLNSPTAY
SVSGTGTQASQVFGNASAAQKSSAAAAMEVRNLNAARELFLDELLAASAAPASAEQ
EELLALLRSERIVLAHAGQPLSEAQVLKALAWLLAANPSAPPGQGLEVLREVLQARR
QPGAQWDLREFLVSAYFSLHGRLDEDVIGVYKDVLQTQDGKRKALLDELKALTAEL
KVYSVIQSQINAALSAKQGIRIDAGGIDLVDPTLYGYAVGDPRWKDSPEYALLSNLD
TFSGKLSIKDFLSGSPKQSGELKGLSDEYPFEKDNNPVGNFATTVSDRSRPLNDKVNE
KTTLLNDTSSRYNSAVEALNRFIQKYDSVLRDILSAIGSGHHHHHH Purification of Fusion Proteins To initiate purification, bacterial pellets were resuspended in 4 ml of chilled 20 mM Tris pH 8.0, 500 mM NaCl, 20 mM imidazole, 10 mM $MgCl_2$, and 2λ Halt Protease Inhibitor (Thermo Fisher) per gram of cell pellet. The bacteria were disrupted with sonication followed by the addition of DNase I to a final concentration of 25 µg/ml. Insoluble debris was removed by centrifugation at 5000×g for 20 min. The cleared lysate was diluted with an equivalent volume of 20 mM Tris pH 8.0 with 500 mM NaCl to bring the final buffer concentration to 20 mM Tris, 500 mM NaCl, 10 mM imidazole, 5 mM $MgCl_2$, and 1× Halt Protease Inhibitor. Proteins were purified by binding to nickel affinity resin, washing with 20 mM Tris, 500 mM NaCl, 20 mM imidazole and eluting bound protein with 20 mM Tris, 500 mM NaCl, 500 mM imidazole. The peak fractions at the expected elution for a dimer of the target protein were pooled and concentrated. The proteins eluted from these columns were further purified by gel filtration and/or SEC. These proteins were then analyzed by SDS-PAGE, Western blotting, and SEC. All fusion proteins migrated in SDS-PAGE at the predicted MW. The protein concentration of each sample was measured using a BCA protein assay kit (BioRad). Purified proteins were aliquoted, flash-frozen in liquid nitrogen, and stored at −80° C. for future use.

A summary of the physical attributes of exemplary rhizavidin fusion proteins and variants of the invention are shown in Table 5. All rhizavidin fusion proteins of the invention were expressed and determined to be dimeric protein as demonstrated by size exclusion chromatography (SEC) (Table 5).

TABLE 5

Physical attributes of the E. coli expressed rhizavidin fusion proteins of the invention

| Protein | Bacteria | Monomer MW (kDa) | Dimer present by SEC | TLR5 domain present |
|---|---|---|---|---|
| Rhavi-PerV-his | P. aeruginosa | 48 | Yes | NA |
| Rhavi-FlaB-his | P. aeruginosa | 65 | Yes | Yes |
| Rhavi-FlaA1-his | P. aeruginosa | 56 | Yes | Yes |
| Rhavi-FlaA2-his | P. aeruginosa | 55 | Yes | Yes |
| Rhavi-MrkA-his | K. pneumoniae | 37 | Yes | NA |
| Rhavi-FlaBD2-his | P. aeruginosa | 37 | Yes | No |
| Rhavi-FlaA2D2-his | P. aeruginosa | 27 | Yes | No |
| Rhavi-FlaBD2-MrkA-his | K. pneumoniae | 58 | Yes | No |
| Rhavi-FlaB-PcrV-his | P. aeruginosa | 97 | Yes | Yes |
| Rhavi-PcrV-MrkA-his | P. aeruginosa K. pneumoniae | 69 | Yes | NA |

TABLE 5-continued

Physical attributes of the E. coli expressed rhizavidin fusion proteins of the invention

| Protein | Bacteria | Monomer MW (kDa) | Dimer present by SEC | TLR5 domain present |
|---|---|---|---|---|
| Rhavi-FlaBD2-PcrV-his | P. aeruginosa | 70 | Yes | No |

Assessment of TLR5 Activity in Flagellin Fusion Proteins

Figure 12B:
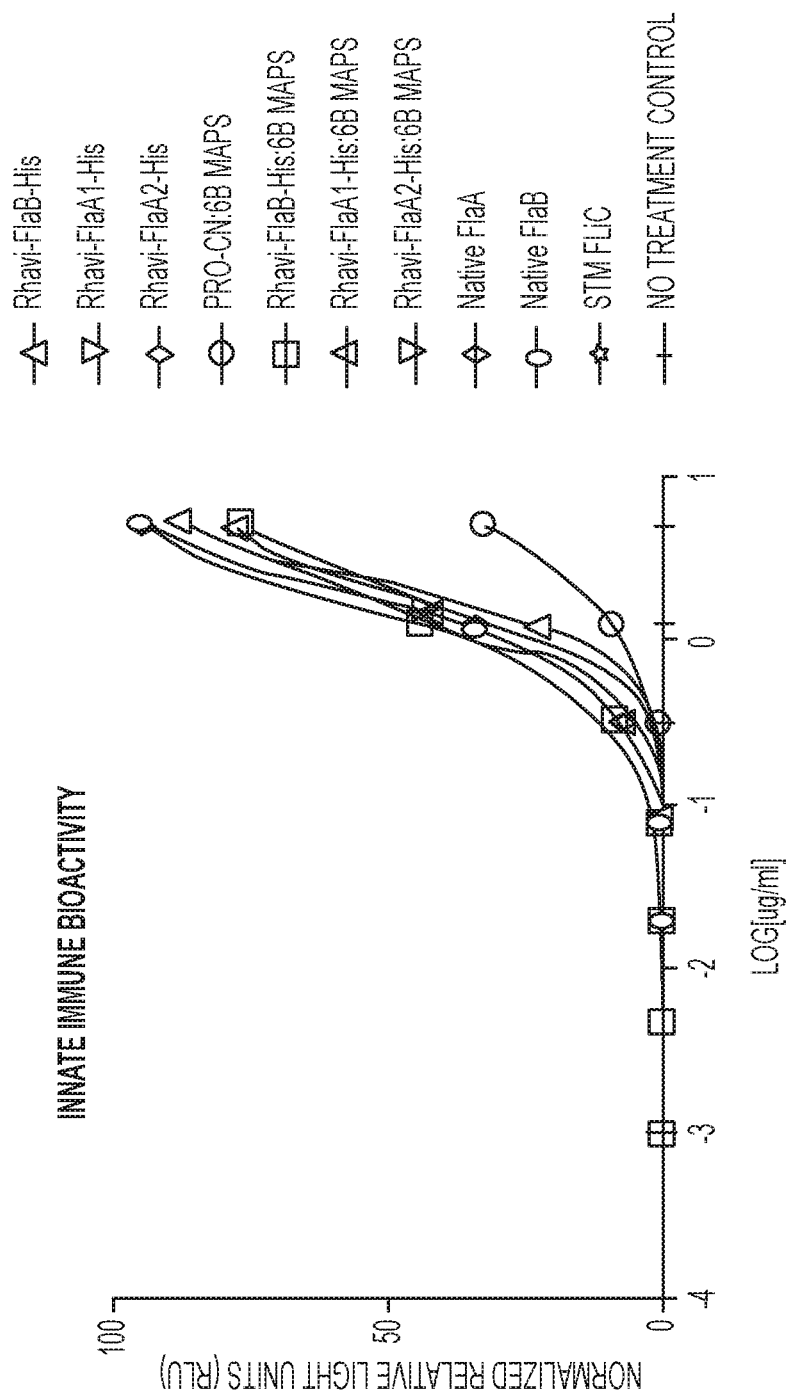
FIG. 12B shows the toll-like receptor (TLR) 5 bioactivity for native *Pseudomonas* flagellins and Rhavi fusion proteins, alone or as a variant MAPS complex with pneumococcal polysaccharides (PnPS) 6B, in this assay HEK293-NFkB:Luc cells responded to flagellin but not media alone. These results indicate that the rhizavidin flagellin constructs (FlaB, FlaA1, FlaA2) alone or in a MAPS complex with the PnPS 6B promoted TLR5 activity, hence were properly folded.

To assess whether the fusion proteins are properly folded, HEK293-NFkB: Luc cells were stimulated by incubation for 4 hours with a titration of each test protein or complex as shown in FIG. 12B. HEK293-NFkB: Luc cells had been previously documented to respond to flagellin but not LPS or non-flagellated Salmonella (Simon and Samuel, 2007). After the cells were lysed, luciferase activity was determined with Promega Firefly Luciferase. The assay measures activation of NF-kB. (Simon and Samuel, 2007).

The TLR5 bioactivity in an assay using HEK293-NFkB: Luc cells and native Pseudomonas flagellins and Rhavi fusion proteins, alone or as a MAPS complex with PnPS 6B, is shown in FIG. 12B. These results clearly indicate that the rhizavidin flagellin constructs FlaB, FlaA1, FlaA2 promoted TLR5 activity on their own or as a MAPS complex with the PnPS 6B, and hence were properly folded.

Immunogenicity of Exemplary Fusion Proteins

Figure 14:
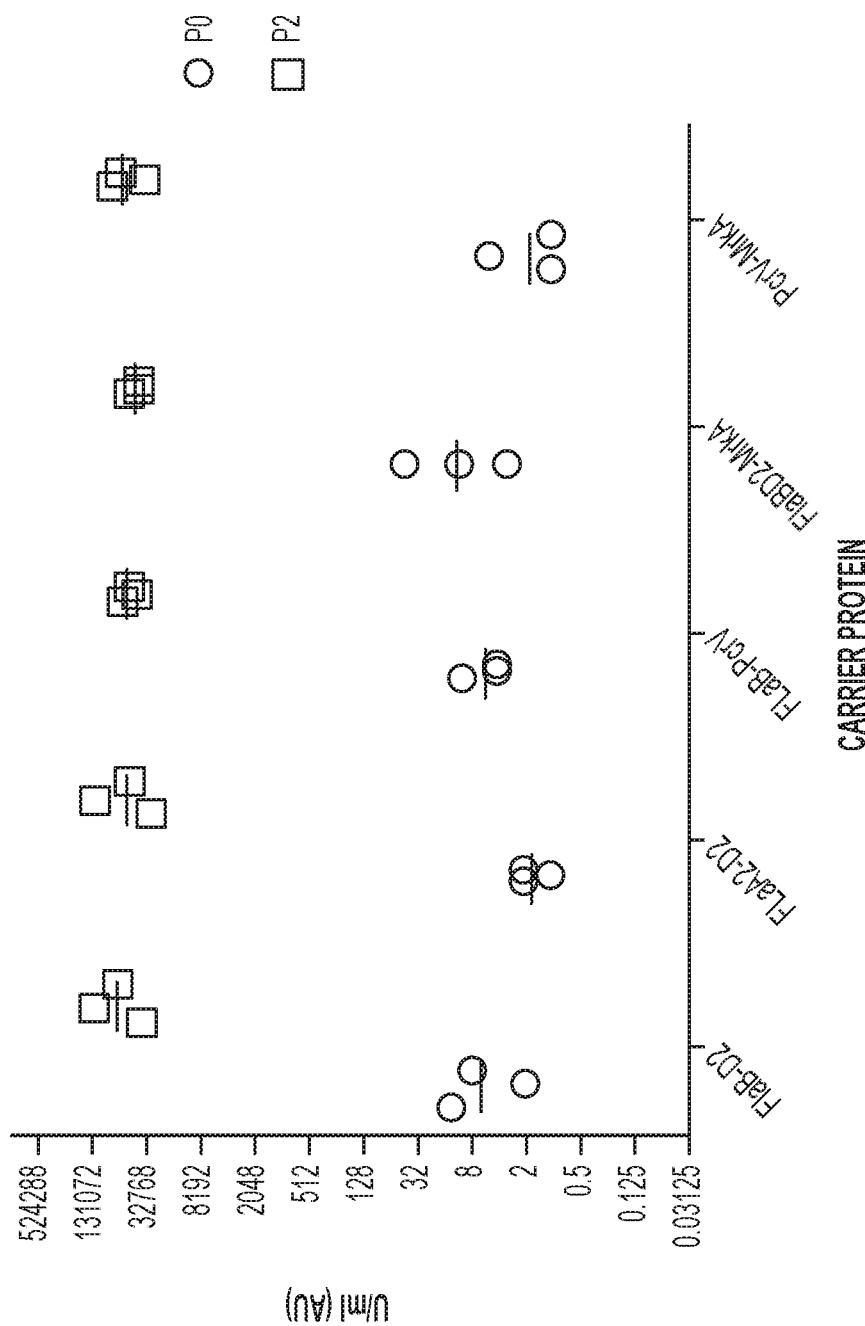
FIG. 14 shows the immune response of rabbits immunized with rhizavidin-antigen fusion proteins (100 μg of protein in Freund's adjuvant). Rabbit IgG was measured by ELISA to the immunizing antigen with sera samples prior to immunization (P0) and two weeks after the second immunization (P2). The measured IgG response was assigned an AU from a standard curve assigned as AU per ml of 12,500. The geometric mean is indicated as a horizontal black line. Titers are shown in AUs for the proteins Rhavi-FlaB-D2 (FlaB-D2); Rhavi-FlaA2-D2 (FlaA2-D2); Rhavi-FlaB-PcrV (FlaB-PcrV); Rhavi-FlaB-D2-MrkA (FlaB-D2-MrkA); and Rhavi-PcrV-MrkA (PcrV-MrkA).

High titer sera to the fusion protein variants were generated to evaluate the in vitro activity of protein specific antibodies. The ELISA IgG titers to the corresponding immunogen for each of the following fusion proteins (FP): Rhavi-FlaB-D2; Rhavi-FlaA2-D2; Rhavi-FlaB-PcrV; Rhavi-FlaB-D2-MrkA and Rhavi-PcrV-MrkA are shown in FIG. 14. All FPs are very immunogenic and elicit high-titer of FP-specific IgG antibody.

FlaB and FlaA1 cross-reactivity with rabbit sera raised against FlaB containing rhizavidin fusion proteins is summarized in Table 6.

TABLE 6

Cross-reactivity of sera from rabbits immunized with FlaB containing rhizavidin fusion proteins to native FlaB purified from PA PAO1 or FlaA1 purified from PA PAK

| | | FlaA1 ELISA | | | FlaB ELISA | | |
|---|---|---|---|---|---|---|---|
| | Rabbit # | P0 | P2 | P3 | P0 | P2 | P3 |
| Rhavi-FlaB-D2-His | AFV791 | 121 | 356 | 744 | 22 | 344,903 | 279,209 |
| | AFV792 | 397 | 442 | 627 | 309 | 126,159 | 154,104 |
| | AFV793 | 162 | 379 | 763 | 155 | 434,194 | 423,514 |
| Rhavi-FlaB-PcrV-His | AFV797 | 263 | 23,995 | 31,497 | 278 | 317,789 | 318,117 |
| | AFV798 | 126 | 38,872 | 40,911 | 128 | 250,535 | 230,702 |
| | AFV799 | 178 | 27,108 | 41,566 | 139 | 299,454 | 499,941 |
| Rhavi-FlaB-D2-MrkA-His | AFV800 | 213 | 217 | 1916 | 45 | 17,602 | 35,651 |
| | AFV801 | 54 | 165 | 944 | 48 | 21,320 | 53,477 |
| | AFV802 | 440 | 161 | 291 | 298 | 24,500 | 34,790 |

Both anti-Rhavi-FlaB-D2 and -Rhavi-FlaB-PcrV rabbit sera have high titers of FlaB-specific antibody but the anti-Rhavi-FlaB-D2-MrkA sera have low titers of FlaB-specific antibody by comparison. Anti-Rhavi-FlaB-PcrV sera had significant cross-reactive FlaA1-specific antibody, thus suggesting that the FlaB component of the fusion protein is properly folded and that the cross-reactive FlaA1 epitopes presumably reside outside the flagellin domain 2, in the common conserved D0 and D1 domains (Song and Yoon, 2014) that are not expressed in either Rhavi-FlaB-D2 or FlaB-D2-MrkA. Hence, because of its significant cross-reactivity with FlaA1, Rhavi-FlaB-PcrV is an excellent candidate fusion protein that may provide broad-based flagellin immunity against Pseudomonas infections.

Example 5: Preparation of Immunogenic Complexes

Preparation of Native OPS Backbone Polymers
Native OPSs

Figure 1C:
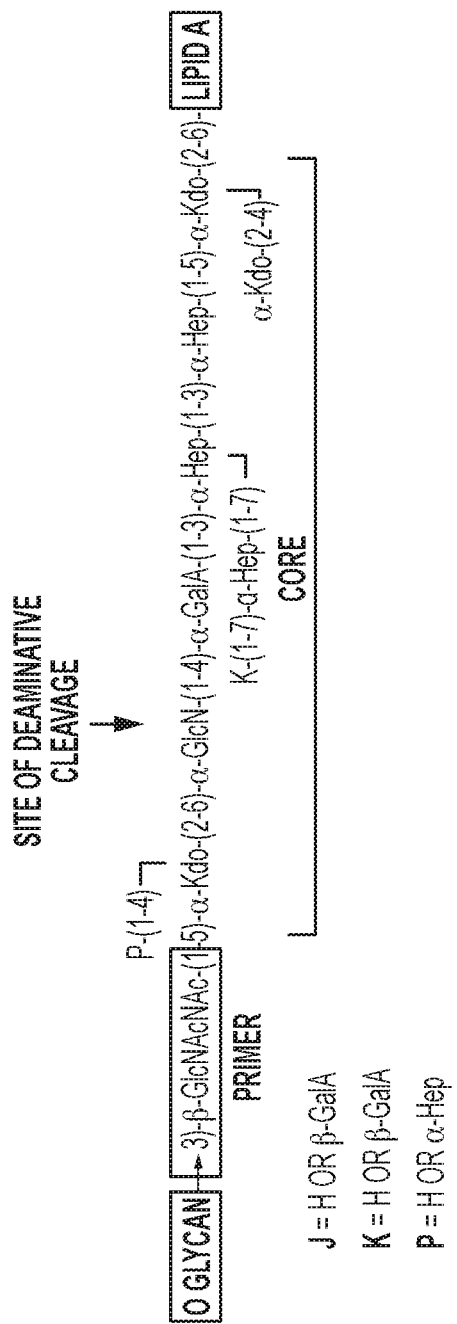
FIG. 1C shows the structure of part of the core polysaccharide of *K. pneumoniae* lipopolysaccharide (LPS) with the site of deaminative cleavage between the glucosamine and the galacturonic residues of the core when the LPS is treated with sodium nitrite and acetic acid (nitrous acid), which results in the formation of a 2,5 anhydromannose with an aldehyde group at C-1 at the reducing end of the common part (CP) of the OPS.
Figure 6A:
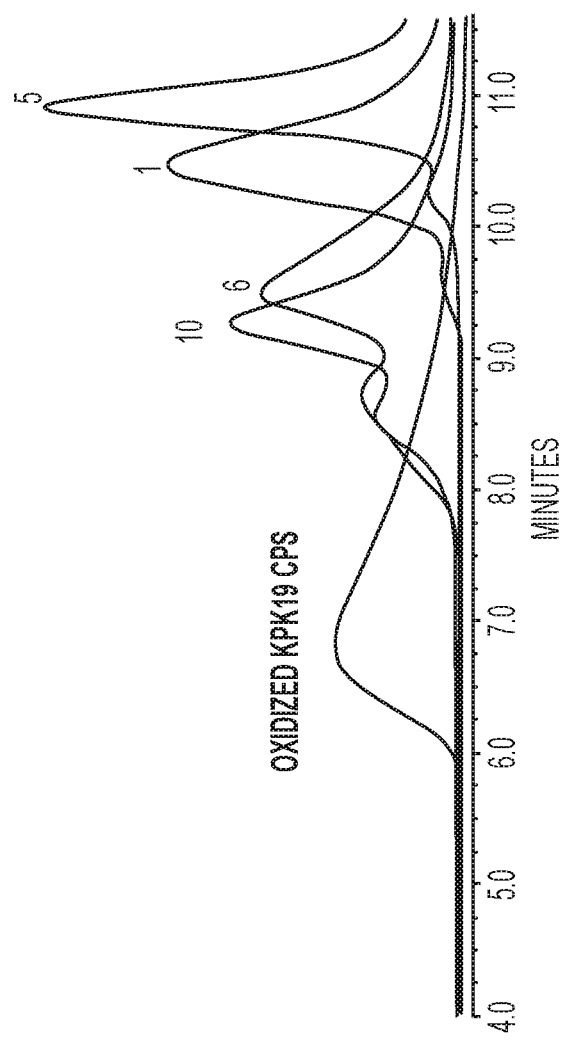
FIG. 6A depicts exemplary size exclusion chromatography (SEC) high performance liquid chromatography (HPLC) (Waters BioAlliance with a Phenomenex BioSep SEC-4000 column and a flow rate of 1 mL/min in PBS pH 7.4 containing sodium azide (0.02%) elution profiles of KP K19 oxidized CPS, OPS-ADH derivatized KPO1 (trace 1), KPO5 (trace 5), PAO6 (trace 6), PAO10 (trace 10).
Figure 6B:
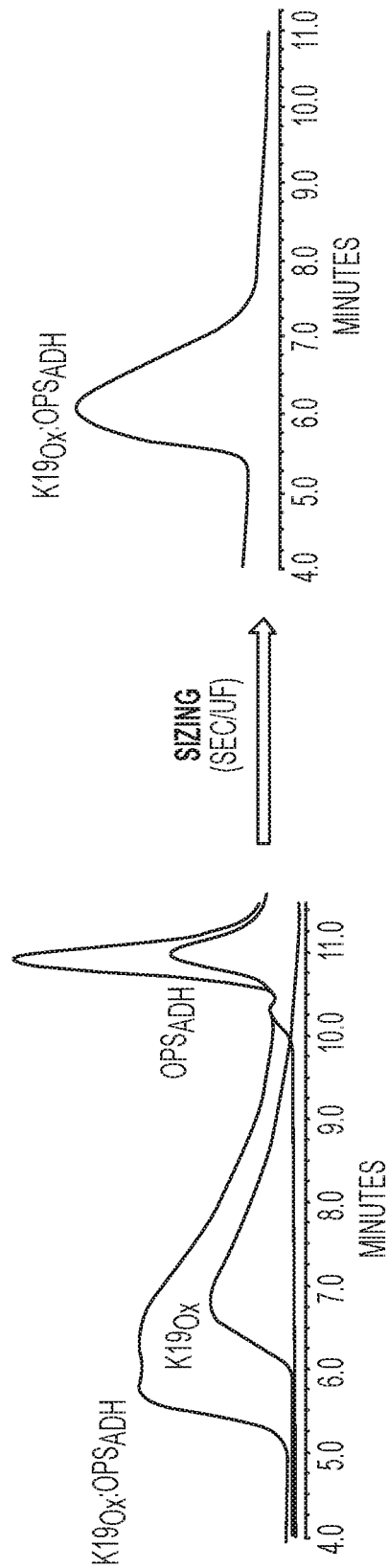
FIG. 6B depicts SEC HPLC (Waters BioAlliance with a Phenomenex BioSep SEC-4000 column and a flow rate of 1 mL/min in PBS pH 7.4 containing sodium azide (0.02%) elution profiles of (left): an $OPS_{ADH}$; oxidized KP K19 CPSox (indicated in figure as K19ox); and a K19 CPSox: $OPS_{ADH}$ backbone polymer and (right): a K19 CPSox: $OPS_{ADH}$ backbone polymer after molecular sizing by using either SEC or ultrafiltration (UF) using a 100 kDa nominal molecular weight cut-off (NMWCO) membrane.
Figure 6C:
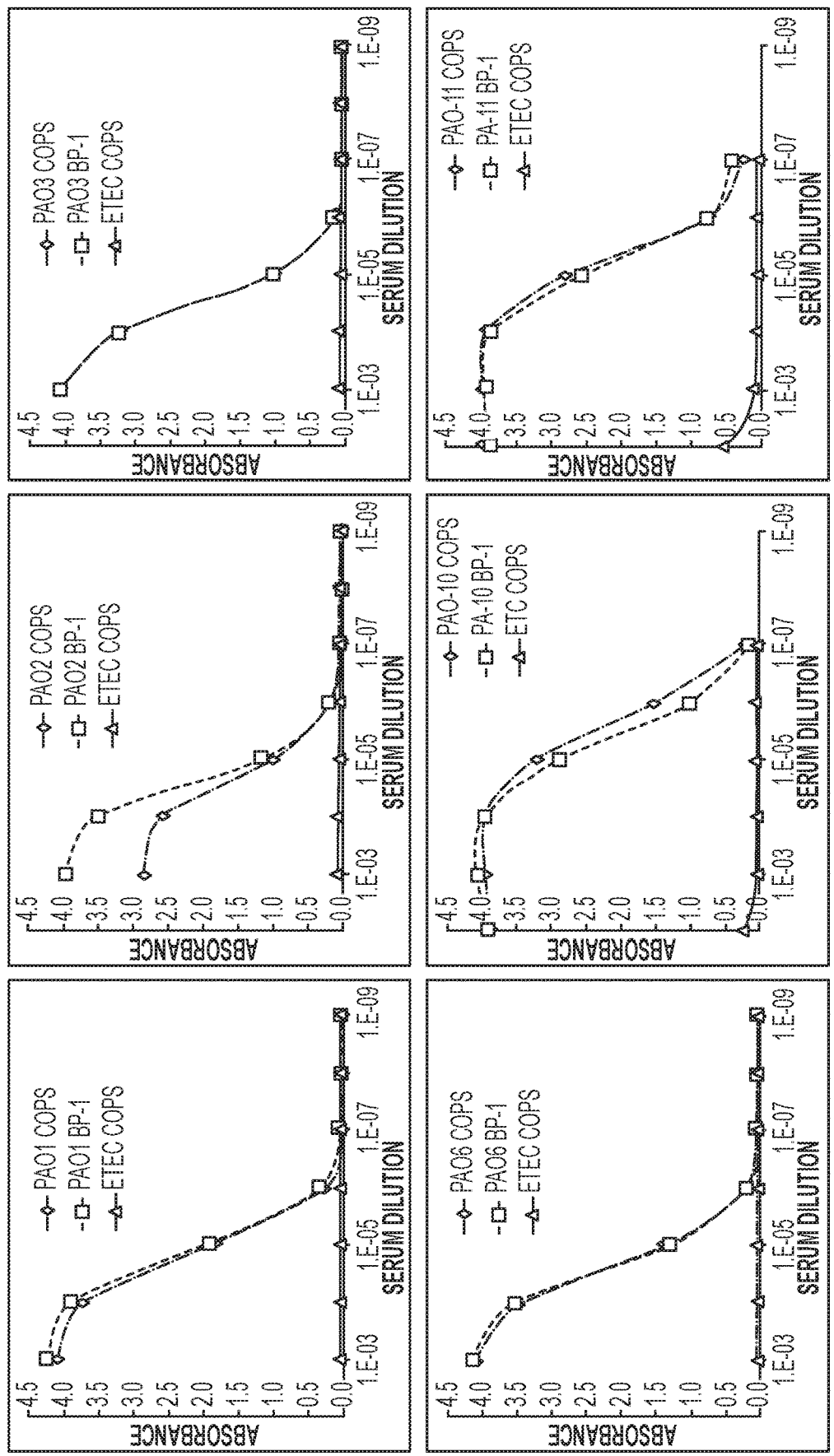
FIG. 6C depicts antigenicity analyses by enzyme linked immunosorbent assay (ELISA) with PA COPS or PA COPS: K19 BP-1 constructs, using rabbit hyper-immune sera from heat-killed (HK)-*Pseudomonas aeruginosa* immunization (post fourth immunization). An enterotoxic *E. coli* (ETEC) COPS is used as a negative control in the ELISA. The strong reactivity of the PA COPS K19 BP-1 with the *Pseudomonas aeruginosa* specific OPS antisera indicates that the OPS epitopes in the backbone polymer are preserved.
Figure 7A:
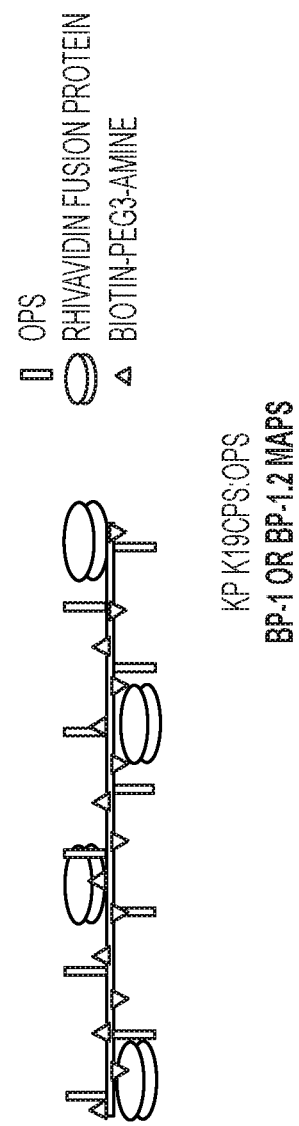
FIG. 7A depicts an exemplary schematic of a BP-1 MAPS complex with a rhizavidin fusion protein and an OPS BP-1 or BP-1.2.
Figure 7B:
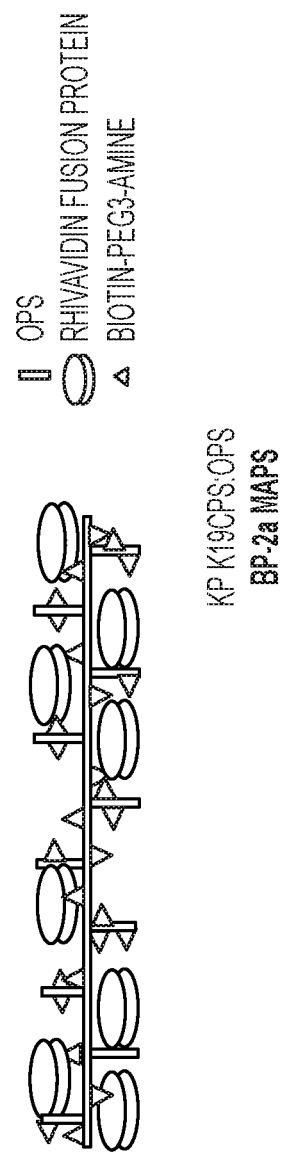
Figure 7C:
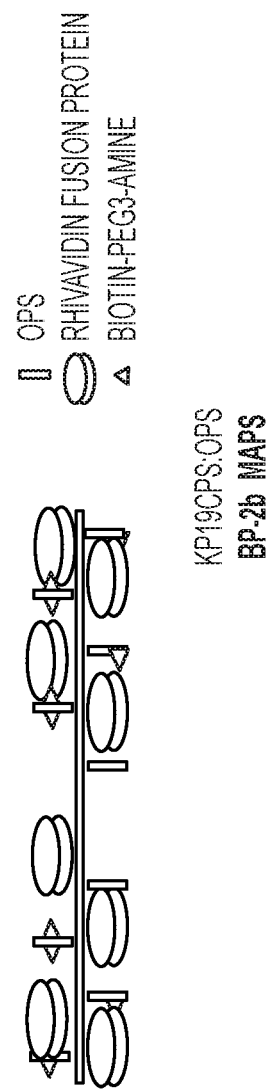
FIG. 7C depicts an exemplary schematic of a BP-2b MAPS complex with a rhizavidin fusion protein and an OPS BP-2b.
Figure 7D:
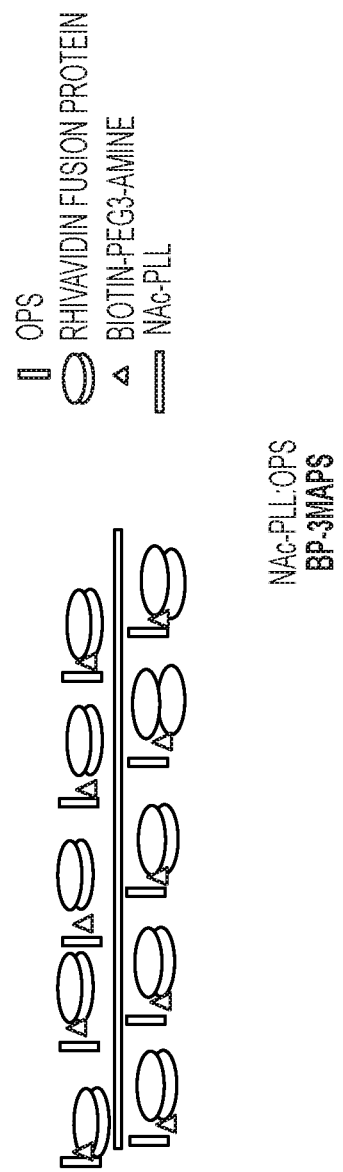
FIG. 7D depicts a schematic of a BP-3 MAPS complex with a rhizavidin fusion protein and an OPS BP-3.
Figure 7E:
FIG. 7E depicts a schematic of a MAPS complex with a rhizavidin fusion protein and a native OPS.

The O-polysaccharides (OPS) of K. pneumoniae (KP OPS) serotypes O1, O2, O3 and O5 and P. aeruginosa core OPS (PA OPS) serotypes O1, O2, O3, O4, O5, O6, O10, O11 were isolated from the biomass of the fermentation of the organisms grown in CDM after treatment with either boiling at 100° C. in one percent acetic acid for the PA OPS or with acetic acid and sodium nitrite ($NaNO_2$) for the KP OPS. For PA LPS the acetic acid treatment cleaved the KDO bond of the inner core of the LPS and the lipid A (FIG. 1A) and generated a KDO moiety at the reducing end of the COPS. For the KP LPS the nitrous acid deamination cleaved the bond between the inner core glucosamine residue and the rest of the inner core lipid A portion of the LPS and generated a reducing 2,5-anhydromannose residue with an aldehyde on Carbon-1 (FIG. 1C). The structures of the PA OPS (Knirel et al., 2006) and KP OPS (Vinogradov et al., 2002) are shown in FIGS. 1B and 1D respectively. The downstream purification process of the PA and KP OPS is shown in FIG. 8A. These purification processes yielded high amounts (>50-100 mg/L of purified material) of highly pure OPS with low levels of residual protein, nucleic acids and endotoxin. The chemical and immunochemical identity of the OPS was ascertained by TFA depolymerization and Dionex HPAEC-PAD, high resolution 1H-NMR comparing NMR spectral data (chemical shifts and coupling constants) with published literature, and by ELISA immunoreactivity with KP OPS and PA OPS type specific monoclonal antibodies or antisera raised with heat-killed whole bacteria (FIG. 6C). The average MW of the OPS as measured by SEC and SEC-MALLS ranged from approximately 10 kDa to 30 kDa, depending on the type, with the PA OPS being typically larger than the KP OPS. A summary of HPAEC-PAD (Dionex) monosaccharide composition analyses of purified KP OPS and PA OPS is shown in Table 7.

TABLE 7

HPAEC-PAD monosaccharide composition analyses of purified KP OPS and PA COPS

| Bacteria | O-polysaccharide | HPAEC-PAD monosaccharide analysis[a] | Expected composition of OPS repeat[b] |
|---|---|---|---|
| K. pneumoniae | O1 | Galactose | Galactose |
| K. pneumoniae | O2a | Galactose | Galactose |
| K. pneumoniae | O3 | Mannose | Mannose |

TABLE 7-continued

HPAEC-PAD monosaccharide composition analyses of purified KP OPS and PA COPS

| Bacteria | O-polysaccharide | HPAEC-PAD monosaccharide analysis[a] | Expected composition of OPS repeat[b] |
|---|---|---|---|
| K. pneumoniae | O5 | Mannose | Mannose |
| P. aeruginosa | IATS O1 | Fucosamine, Quinovosamine, Galactosamine | NAc-fucosamine, NAc-galactosamine, NAc-quinovosamine, 2,3-diamino-2,3 dideoxy-NAc-glucuronic acid |
| P. aeruginosa | IATS O2 | Fucosamine | 2,3-diamino-2,3 dideoxy-NAc-mannuronic acid, 2,3-diamino-2,3-dideoxy-NAc-guluronic acid, NAc-fucosamine |
| P. aeruginosa | IATS O3 | Rhamnose, Glucosamine | Rhamnose, NAc-glucosamine, NAc-galacturonic acid, |
| P. aeruginosa | IATS O4 | Fucosamine, Quinovosamine, Rhamnose | NAc-fucosamine, Rhamnose, NAc-quinovosamine |
| P. aeruginosa | IATS O5 | Fucosamine | NAc-NAc-Mannuronic acid, NAc-NAm-Mannuronic acid, NAc-fucosamine |
| P. aeruginosa | IATS O6 | Quinovosamine, Rhamnose[c] | Rhamnose, NAc-Ac-galacturonic acid, Nfo-galacturonic acid, NAc-quinovosamine |
| P. aeruginosa | IATS O10 | Quinovosamine, Rhamnose | Ac-Rhamnose, NAc-Galacturonic acid, NAc-quinovosamine |
| P. aeruginosa | IATS O11 | Fucosamine, Glucose | NAc-fucosamine, Glucose |

Figure 1E:
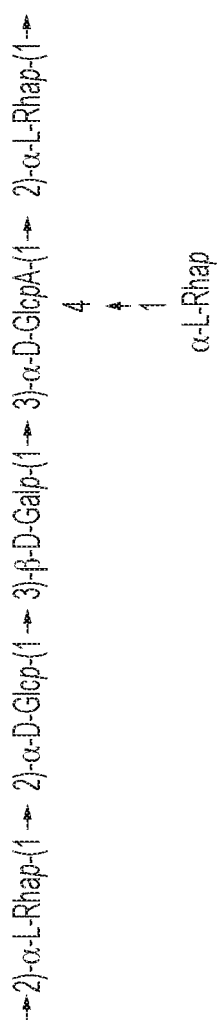
FIG. 1E shows the chemical structure of the repeating unit of the *K. oxytoca* (KO) capsular polysaccharide (CPS) K19 which is identical to the *K. pneumoniae* K19 CPS (Brisse et al., 2013), hence the two are interchangeably referred to herein as KP K19 CPS.
Figure 1F:
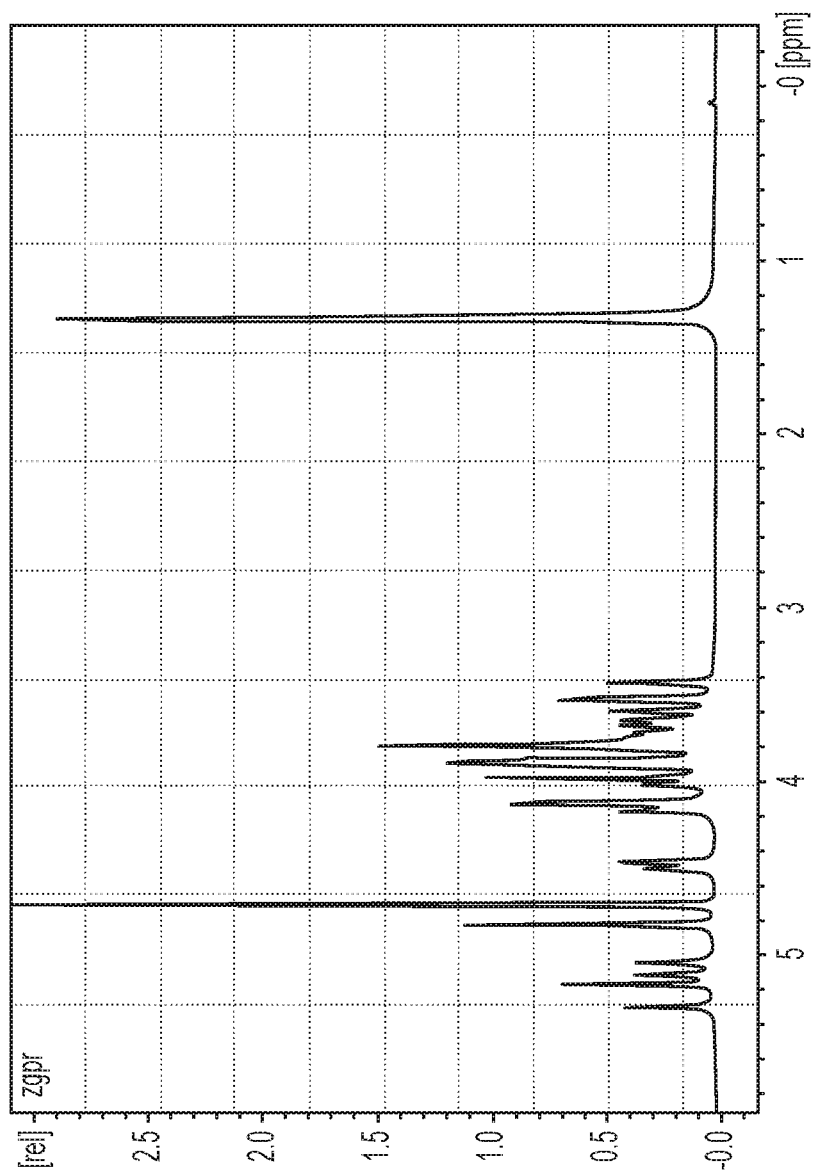
FIG. 1F is a H-Nuclear Magnetic Resonance (H-NMR) spectrum at 950 MHz of purified KP K19 CPS.

[a]Instrument only detects neutral saccharides, not uronic acid; polysaccharides depolymerized in 2M TFA/100 C./4 hours unless stated otherwise
[b]Knirel et al. 2006
[c]determined after 4M TFA/100 C./18 hours Backbone Polymer OPS FIG. 1E depicts the chemical structure of the repeating unit of the K. oxytoca (KO) capsular polysaccharide (CPS) K19 which is identical to the K. pneumoniae K19 CPS. FIG. 1F depicts an H-NMR spectrum at 950 MHz of purified KP K19 CPS. The native KP OPSs and PA OPSs of average MW 10-30 kDa were covalently linked onto the larger K19 CPS (avMW 218 kDa) to increase both their effective MW size and their epitope valency. The backbone polymer OPS were biotinylated subsequently or during the enlarging process either selectively on the K19 CPS backbone polymer to produce BP-1, BP-1.2, or BP-1.3 (FIGS. 2A-2C), or randomly on both the OPS and the CPS to produce BP-2a (FIG. 3) or selectively on the OPS to produce BP-2b (FIG. 4).

The backbone polymers elute noticeably earlier on a size exclusion column than the K19 CPS or OPSs alone suggesting they are increased significantly in size from the components alone, and demonstrated reduction of the free OPS level relative to the amount in the starting material indicating incorporation into the backbone polymer.

This enlarging process using a CPS such as the K19 CPS as a backbone polymer is a universal process that can be applicable to any CPS/OPS or small MW bacterial polysaccharides, can lead to a well defined and consistent product and generates minimal to no alterations of the OPS/CPS epitopes. As is shown in FIG. 6C this was clearly demonstrated following antigenicity analyses by ELISA with native PA OPS O1, O2, O3, O6, O10 and O11 and the corresponding PA OPS: K19 BP-1 constructs, using rabbit hyper-immune sera from HK-PA immunization (FIG. 6C). In these experiments no difference in antigenicity was observed between the native PA OPS and the corresponding backbone polymer OPS indicating that the OPS epitopes were retained during the enlarging process.

Biotinylation of Backbone Polymers (BP)

BP-1

Figure 2A:
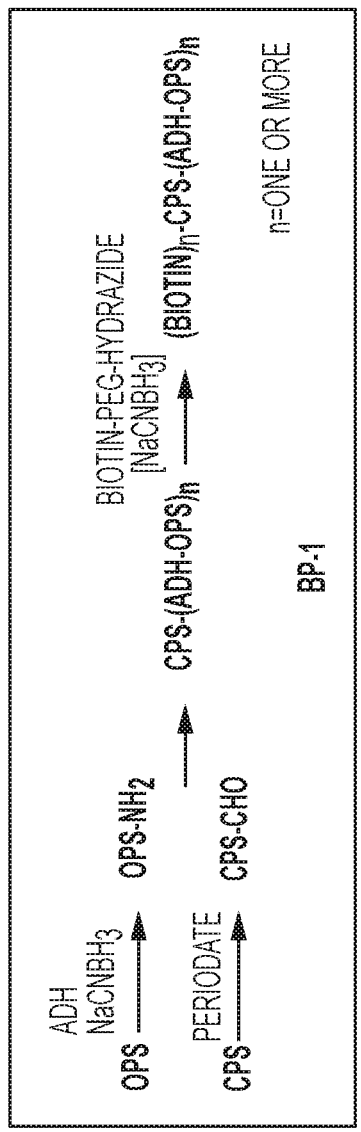
FIG. 2A is a schematic of an exemplary chemical process for the production of a KP/PA OPS labeled with adipic acid dihydrazide (ADH) and linked by reductive amination to an oxidized CPS that is selectively biotinylated on the CPS (BP-1).

The OPS was first equipped at its reducing end with a short spacer containing a primary amine at each end (e.g., ADH) by reductive amination with NaBH$_3$CN. The reactive aldehydes on KP OPS were located on the terminal 2,5-anhydromannose (2,5-anMan) residues generated during the extraction procedure by treatment of the whole LPS with sodium nitrite (FIG. 8A), while the reactive ketones on PA OPS were located on the reducing terminal KDO residues of the innercore of the PA OPS generated by treatment of the LPS with acetic acid as depicted in FIG. 8A. The ADH derivatized OPS were subsequently mixed with the partially periodate oxidized KP 19 CPS backbone (exemplary SEC-HPLC traces of these derivatives depicted in FIGS. 6A and 6B) and a biotin containing primary amine (such as amine-PEG3-biotin), and the mixture reductively aminated to form an OPS backbone polymer uniquely biotinylated on the polysaccharide backbone that we termed backbone polymer-1 (BP-1) (FIG. 2A).

BP-1.2

Figure 2B:
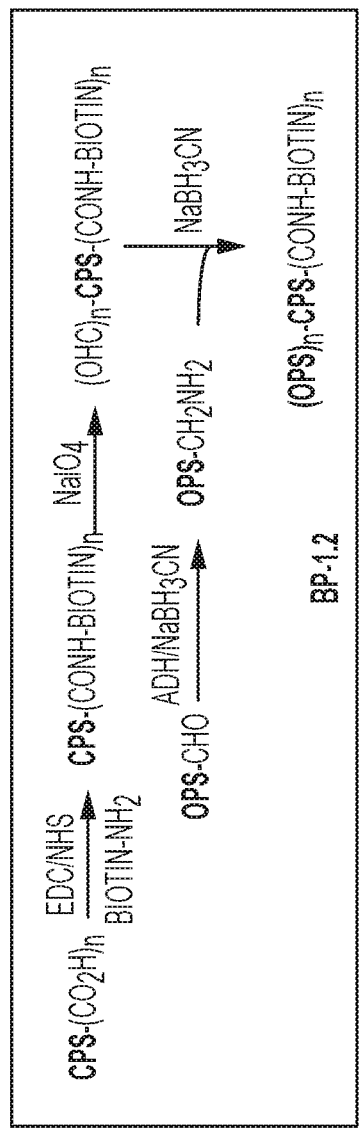
FIG. 2B shows a schematic of an exemplary chemical process for the production of a KP/PA CPS/OPS BP-1.2 where biotin residues are linked on the carboxylate groups of the CPS of the backbone polymer via 1-Ethyl-3-(3-dimethylaminopropyl)-carbodiimide N-hydroxysuccinimide (EDC-NHS) reaction and ADH-labeled OPS are linked to the biotinylated CPS backbone polymer by reductive amination with periodate oxidized and biotinylated CPS.
Figure 2C:
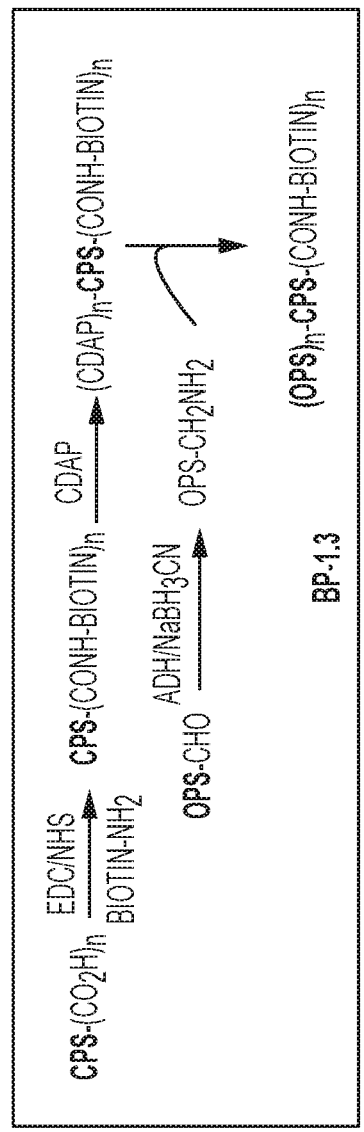
FIG. 2C shows a schematic of an exemplary chemical process for the production of a KP/PA CPS/OPS BP-1.3 where biotin residues are linked on the carboxylate groups of the CPS of the backbone polymer via 1-Ethyl-3-(3-dimethylaminopropyl)-carbodiimide N-hydroxysuccinimide (EDC-NHS) reaction and subsequently the ADH-labeled OPS are linked to the biotinylated and CDAP-activated CPS backbone polymer.

Alternatively, the KP 19 CPS backbone reactive carboxylate groups can be first biotinylated with 1-Ethyl-3-(3-dimethylaminopropyl)-carbodiimide N-hydroxysuccinimide (EDC) and N-Hydroxysuccinimide (NETS) and a biotin containing primary amine (such as amine PEG biotin), then periodate oxidized, mixed with the ADH derivatized OPS, and the mixture reductively aminated to form an OPS backbone polymer uniquely biotinylated on the polysaccharide backbone that we termed BP-1.2 (FIG. 2B). Alternatively, the ADH step can be eliminated for the PA OPS since they contain an amino acid alanine substituent with a free α-amino group on the carbon-2 of their outercore galactosamine residues (FIG. 1A). Hence, these available amino groups can be readily used for direct coupling by reductive amination to the periodate oxidized K19 CPS polymer together with the biotin containing amine to form biotinylated BP-1 (FIG. 2A) or BP-1.2 (FIG. 2B).

Figure 5A:
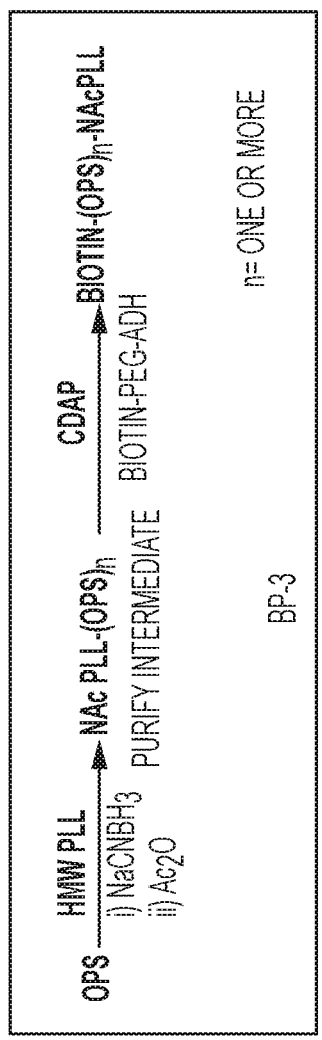
FIG. 5A shows an exemplary schematic of a chemical process for the production of an OPS backbone polymer with a poly-L-Lysine (PLL) polymer in which the biotin residues are selectively introduced into the OPS and the unreacted ε-free amino groups of the PLL are capped to generate a biotinylated OPS N-Acetylated PLL (NAPLL) backbone polymer (BP-3).
Figure 5B:
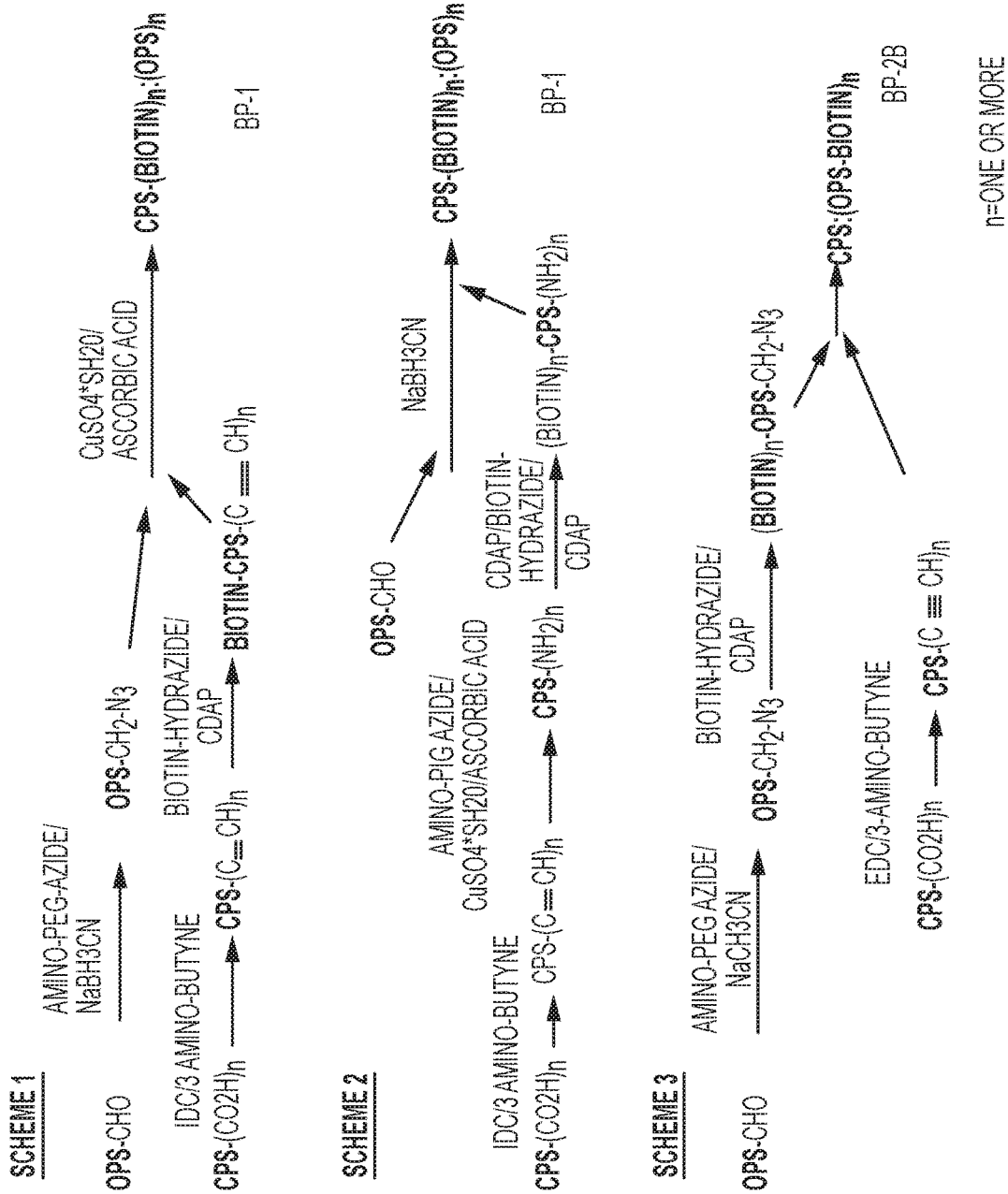
FIG. 5B depicts three schemes for making exemplary backbone polymers. Scheme 1 and scheme 2 show two ways for the schematic of the chemical process for the production of a CPS/OPS backbone 1 (BP-1) using click chemistry; scheme 3 shows the schematic of the chemical process using click chemistry for the production of a CPS/OPS backbone-2b (BP-2b).

Alternatively, the OPS containing aldehyde or ketone at their reducing end are derivatized with an azide amino compound in presence of a reducing agent to produce an OPS with an azido group at their terminal end. A polysaccharide backbone is then equipped with alkyne groups via the polysaccharide carboxylate groups and EDC. The backbone polysaccharide is further biotinylated with CDAP and a biotin-hydrazide compound to generate a biotinylated and alkynylated containing polysaccharide. The derivatized azido-OPS and the biotinylated alkyne-CPS are then click-linked with a copper catalyst to form the (OPS)$_n$-CPS BP-1 in which the backbone polymer is biotinylated and the OPS are not biotinylated (FIG. 5B; scheme 1). Using this click-linking chemistry OPS BP-1 can also be obtained by first introducing the alkyne groups into the CPS using the carboxylate groups and EDC followed by amination using amino-PEG-azide and a copper sulfate catalyst, biotinylation of the CPS with CDAP and biotin hydrazide; the biotinylated CPS containing primary amino groups is mixed with the native OPS (containing aldehyde or ketone groups at their terminal reducing ends) and reductively aminated with a reducing agent to produce an OPS/CPS BP-1 (FIG. 5B; scheme 2). BP-2b can be obtained by this click chemistry by first introducing selectively biotin residues into the OPS derivatized with azido groups at their terminal end and then biotinylated using CDAP chemistry and biotin hydrazide; and second click-linking the biotinylated OPS azido derivatized with the alkynylated CPS as shown in FIG. 5B; scheme 3).

BP-2a

Figure 3:
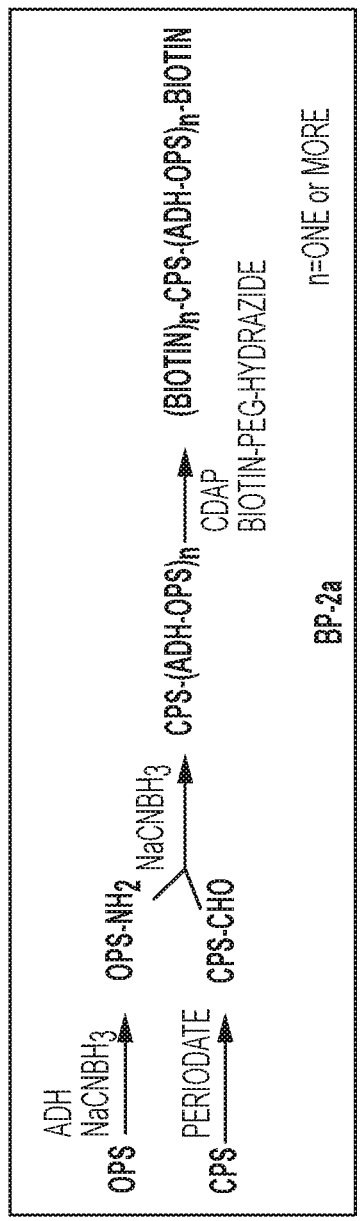
FIG. 3 shows a schematic of an exemplary chemical process for the production of an ADH-labeled OPS linked to an oxidized CPS followed by addition of biotin residues on the CPS and the OPS (BP-2a).
Figure 4:
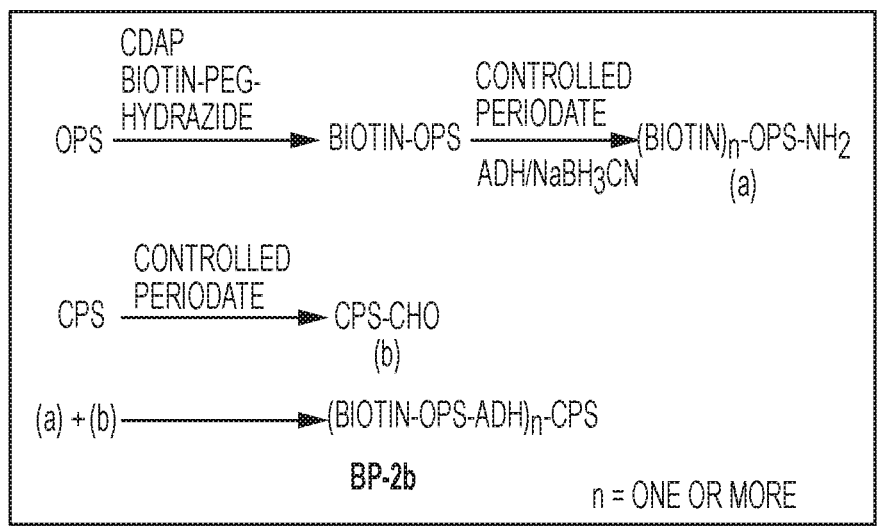
FIG. 4 shows an exemplary schematic of a chemical process for the production of an OPS linked to an oxidized CPS in which the biotin residues are selectively linked to the OPS (BP-2b).

Alternatively, the ADH derivatized OPS or underivatized OPS are mixed with the partially periodate oxidized KP strain 19 CPS backbone and reductively aminated to form an OPS backbone polymer; the backbone polymer is further derivatized with CDAP and biotin PEG amine to obtain a backbone polymer randomly biotinylated with biotin on both the backbone polysaccharide and the OPS that we termed BP-2a (BP-2a) (FIG. 3).

BP-2b

Alternatively, the OPS is first biotinylated with CDAP and amine PEG biotin; the resulting biotinylated OPS is partially oxidized with periodate to introduce aldehydes into its innercore KDOs or heptose moieties and reductively aminated with ADH; the biotinylated and aminated OPS is then mixed with the partially periodate oxidized KP 19 CPS backbone and reductively aminated to form an OPS backbone polymer selectively biotinylated on its OPS; we termed it BP-2b (FIG. 4 and FIG. 5B, scheme 3).

BP-3

Alternatively, the ADH derivatized OPS is first reductively aminated with the ε-NH2 groups of a PLL backbone to produce an OPS-PLL backbone polymer. The resulting OPS-PLL is treated with an acylating reagent such as acetic anhydride to cap the unreacted amino (ε-NH2) groups of the PLL backbone to form an OPS-Poly-N-acetyl-Lysine (OPS-PNAcLL) backbone polymer. This OPS-PNAcLL backbone polymer is then biotinylated on its OPS by first treatment with CDAP, and then with amine PEG biotin. This backbone polymer selectively biotinylated on its OPS is termed BP-3 (FIG. 5A).

Unreacted OPS, biotin, CPS, and residual conjugation chemicals were removed by FPLC-SEC with Superdex 200 or by 50-300 kDa TFF UF-DF.

Generation and Purification of Exemplary Immunogenic Complexes

MAPS complexes or variant MAPS complexes were generated by adding the candidate rRhavi-antigen fusion protein to the biotinylated polysaccharide in 20 mM Tris pH 8.0, 150 mM NaCl at the selected ratio (typically 3:1, protein:PS w:w) with 0.01% thimerosal added to inhibit microbial growth. The sample was incubated with end-over-end rotation at 25° C. overnight followed by centrifugation at 10,000×g for 5 min to remove any insoluble material (Zhang et al., 2013). The soluble material was collected and MAPS complexes or variant MAPS complexes were purified with size exclusion chromatography on a Superdex 75 column (native OPS PS MAPS) or Superdex 200 column (CPS MAPS and backbone polymer PS variant MAPS) with 2 mM Tris, pH 8.0, 150 mM NaCl (Zhang et al., 2013). The peak fractions were analyzed for protein content with SDS-PAGE of reduced samples without heating and visualized with total protein stain. The fractions containing MAPS or variant MAPS complexes were identified from observation of the gel by the stained protein retention in large molecular weight complexes in the gel rather than the expected migration at the size of the protein dimer (Zhang et al., 2013). The fractions containing the MAPS complexes were pooled and the protein/polysaccharide ratio of the MAPS or variant MAPS was determined using the BCA protein assay kit and the anthrone assay for polysaccharide (Zhang et al., 2013). The integrity of the MAPS or variant MAPS complexes was evaluated with SDS-PAGE of reduced samples without heating visualized with total protein stain (Zhang et al., 2013). The free protein content of the MAPS or variant MAPS complexes was quantitated by densitometry of the protein dimer content on the SDS-PAGE MAPS or variant MAPS complex without heating compared to a standard amount of control protein dimer (Zhang et al., 2013). The molecular weight of the protein incorporated into the MAPS or variant MAPS complexes was analyzed with SDS-PAGE of reduced, boiled samples visualized with total protein stain and a molecular weight protein standard.

KP/PA OPS were produced as various OPS backbone polymer forms (1, 2a, 2b) using K19 CPS as the backbone polymer and were complexed into variant MAPS with the following recombinant E. coli rhizavidin fusion proteins derived from KP and PA genome: Rhavi-PcrV; Rhavi-MrkA; Rhavi-FlaA1; Rhavi-FlaA2; Rhavi-FlaB; Rhavi-FlaB-Domain2; Rhavi-FlaA2-Domain2; Rhavi-FlaB-PcrV; Rhavi-FlaB-Domain2-MrkA; Rhavi-MrkA-PcrV; Rhavi-FlaB-Domain2-PcrV with each of SEQ ID NOs: 16-26 and using PRO-CN as a control protein.

Figure 10:
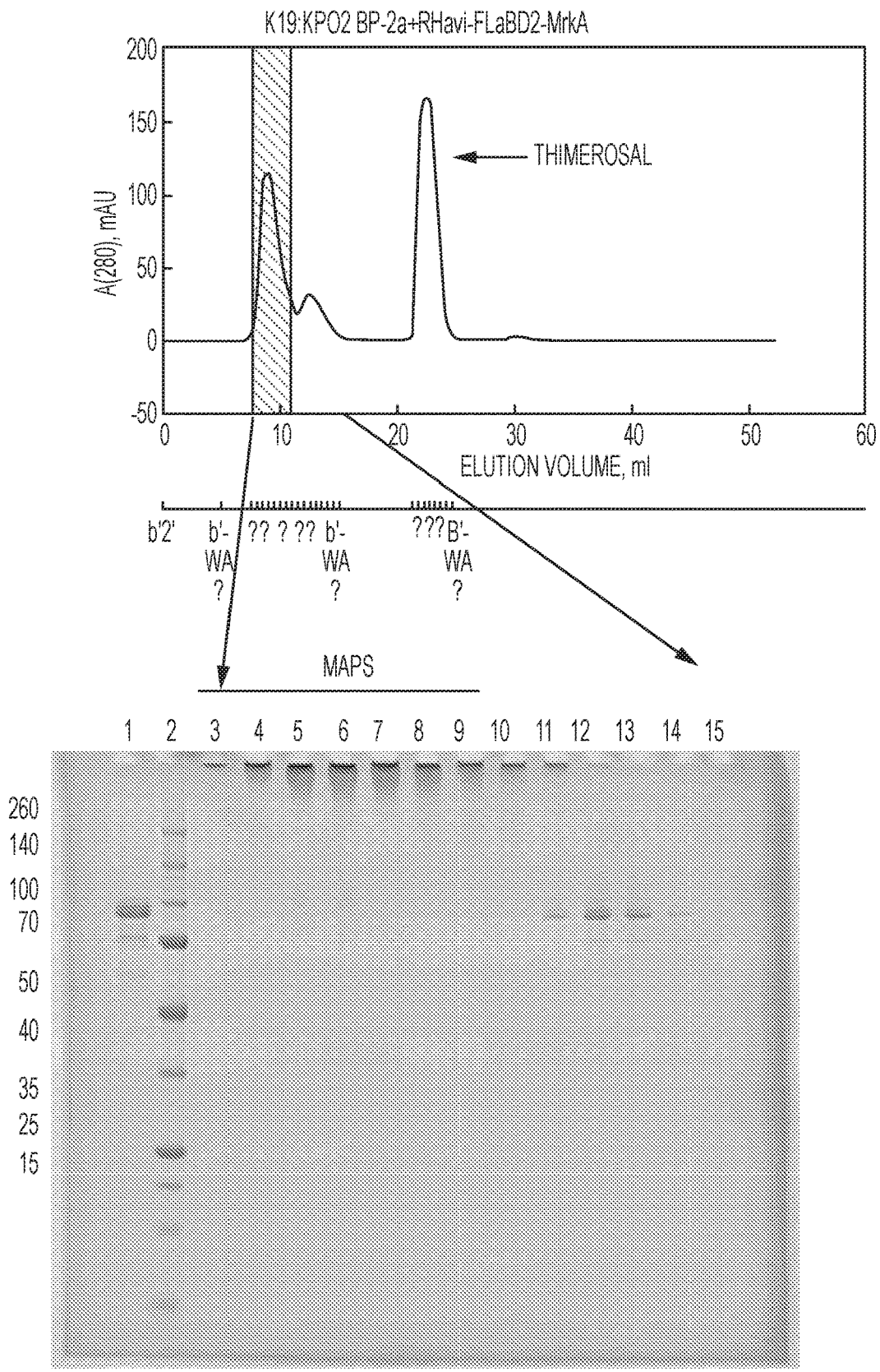
Figure 11A:
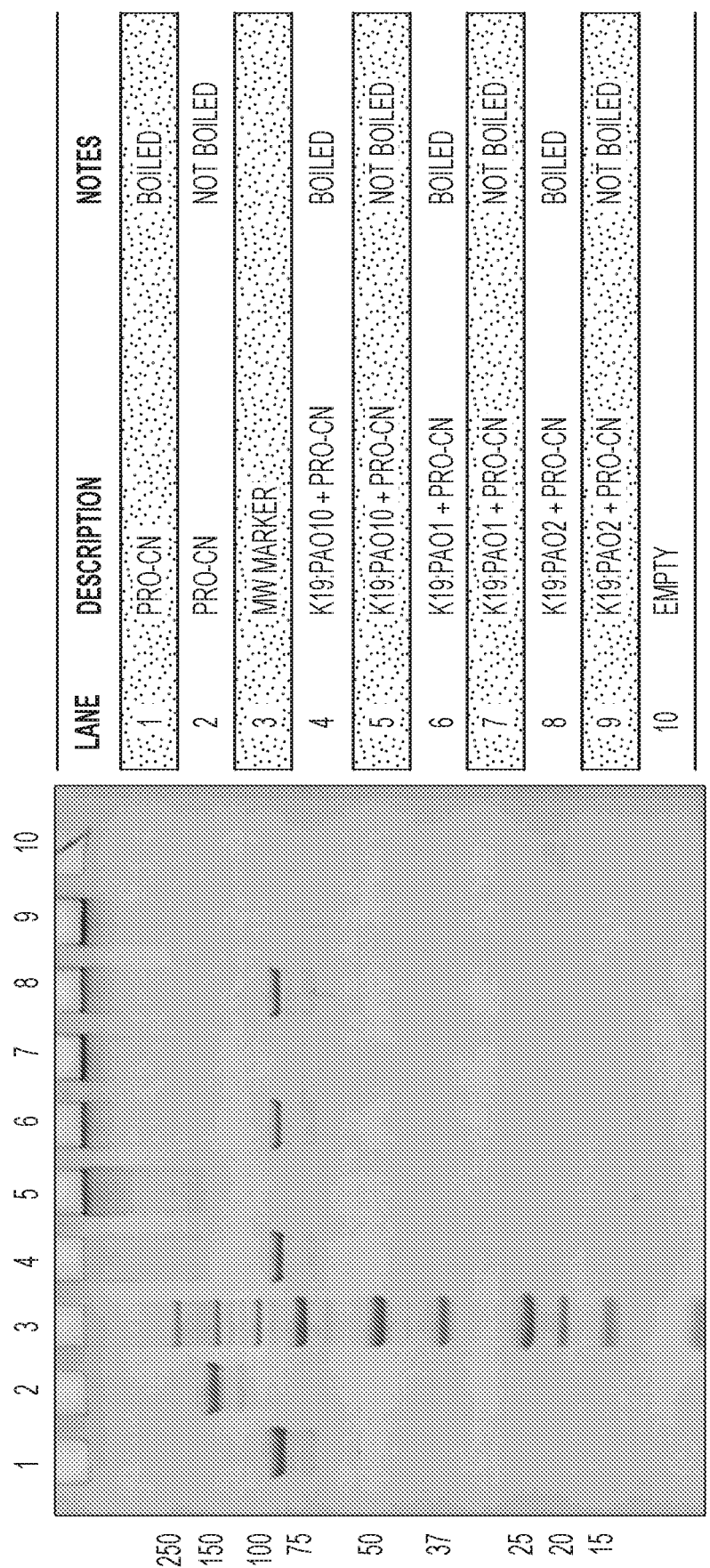
FIGS. 11A-11C depict examples of SDS-PAGE analysis and total protein staining for exemplary BP-1 variant MAPS complexes prepared using different fusion proteins.
Figure 11B:
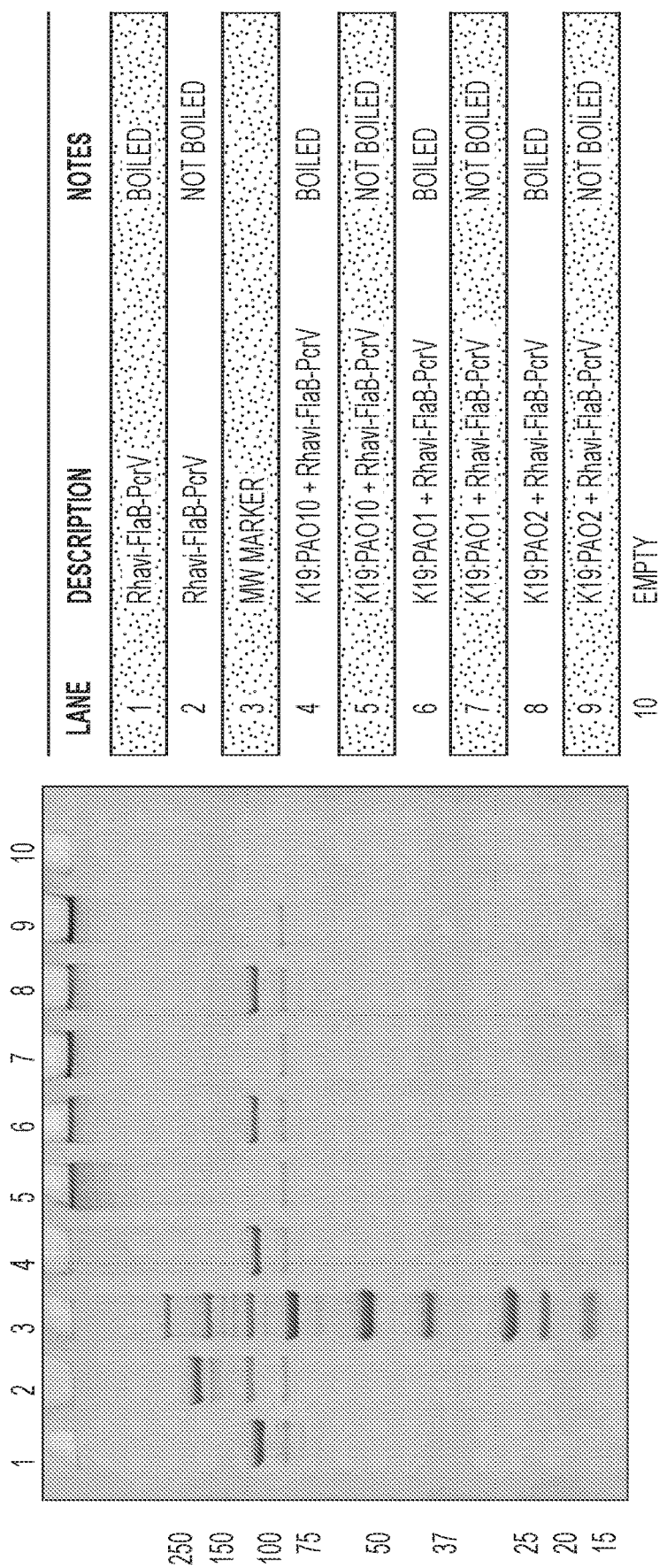
Figure 11C:
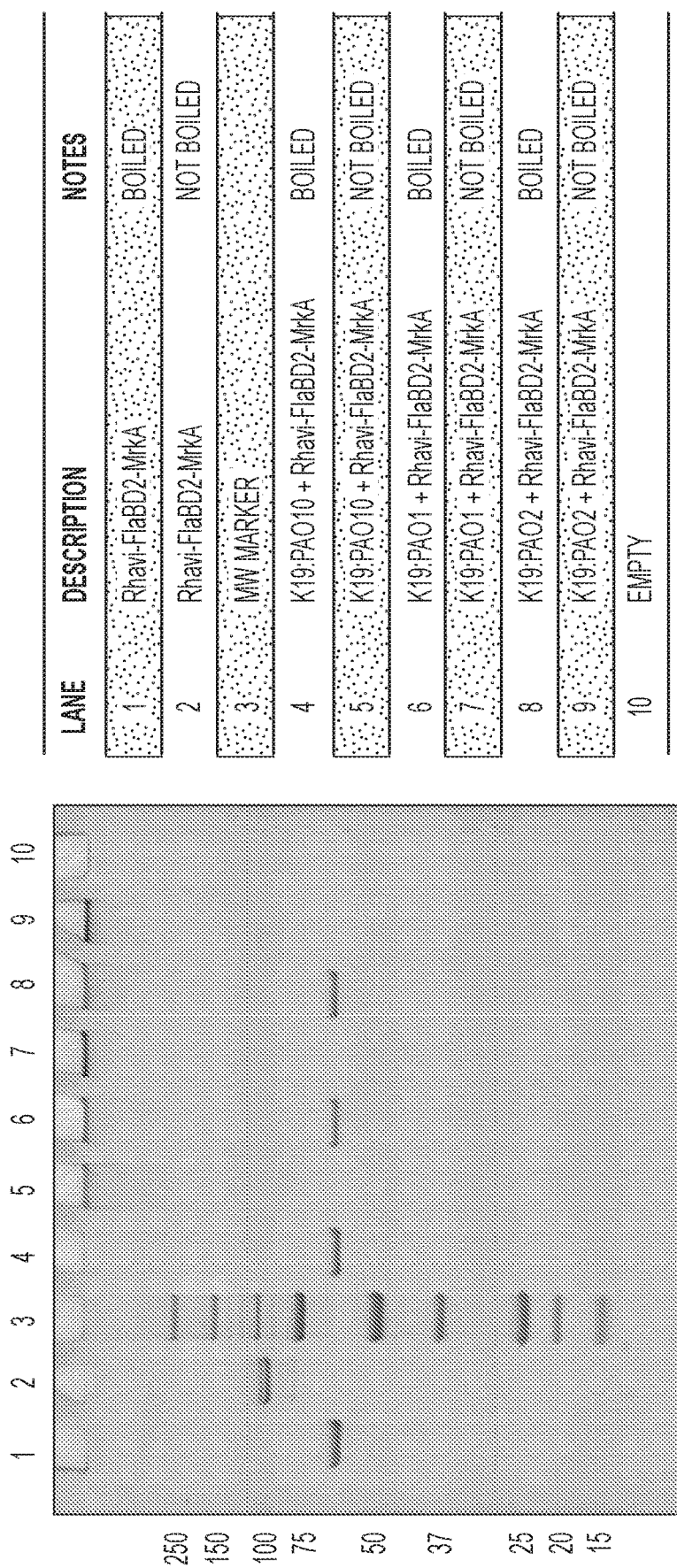

Exemplary attributes of some MAPS lots generated with rhizavidin fusion protein of the invention and complexed with biotinylated pneumococcal PS types 6B, 7F and 19A polysaccharides are shown in Table 8. Exemplary purifications for variant MAPS complexes are shown in FIGS. 10 and 11. Variant MAPS complexes were purified from unreacted protein by SEC and the eluting fractions from the gel analysed by SDS-PAGE, a typical analysis is shown in FIG. 10 where free protein was shown eluting in the late fractions of the gel and can be separated from the variant MAPS as originally noted for MAPS complexes in Zhang et al., 2013. FIGS. 11A-11C depict SDS-PAGE analyses of purified K19-PA O1 OPS BP-1 MAPS complexes, K19-PA O2 OPS BP-1 MAPS complexes, and K19-PA O10 OPS BP-1 MAPS complexes with PRO-CN (FIG. 11A); Rhavi-FlaB-PcrV (FIG. 11B); Rhavi-FlaB-D2-MrkA (FIG. 11C). Each of the purified variant MAPS samples were separately processed with boiling and without heat. The variant MAPS complexes were not disrupted without heat, and the protein in the variant MAPS complexes was retained at the very top of the gel (Zhang et al., 2013). With boiling, variant MAPS complexes were disrupted, the protein was released and the protein dimer formed through rhizavidin inter-molecular interaction was also disassociated (Zhang et al., 2013). The protein content of variant MAPS was then determined with BCA assay and the polysaccharide content was determined with anthrone assay. The protein to polysaccharide ratio was calculated as a weight to weight ratio and as a molar ratio.

All final purified MAPS and variant MAPS were amenable to sterile-filtration with a 0.22 μm filter (Table 8 and data not shown).

immunization respectively. Each carrier protein (0.1 mg) was separately mixed with Freund's adjuvant for a final volume of 1 ml with 0.2 ml injected subcutaneously at 4 different sites and 0.2 ml injected IM per rabbit per immunization. Immunizations were administered to 4 month old

TABLE 8

Rhizavidin fusion proteins purified MAPS attributes

| PS | PS MW (kDa) | Protein | Protein MW (kDa) | [PS], mg/mL (anthrone) | [Protein], mg/mL (BCA) | protein: PS ratio (w:w) | protein:PS molar ratio | HMW complexes present in SDS-PAGE (not boiled) | Appropriate size protein present in SDS-PAGE (boiled) | % free protein (densitometry, SDS/PAGE, boiled vs. not) | filtered with PES 0.22 micron |
|---|---|---|---|---|---|---|---|---|---|---|---|
| 6B | 1092 | PRO-CN | 82 | 0.16 | 0.37 | 2.2:1 | 33:1 | yes | yes | 4 | yes |
| 6B | 1092 | Rhavi-PcrV-his | 48 | 0.13 | 0.21 | 1.7:1 | 38:1 | yes | yes | 7 | yes |
| 6B | 1092 | Rhavi-FlaB-his | 65 | 0.14 | 0.37 | 2.6:1 | 44:1 | yes | yes | <1 | yes |
| 6B | 1092 | Rhavi-FlaA1-his | 56 | 0.13 | 0.21 | 1.6:1 | 31:1 | yes | yes | 5 | yes |
| 6B | 1092 | Rhavi-FlaA2-his | 56 | 0.12 | 0.12 | 1.0:1 | 20:1 | yes | yes | <1 | yes |
| 6B | 1092 | Rhavi-MrkA-his | 37 | 0.14 | 0.20 | 1.4:1 | 42:1 | yes | yes | <1 | yes |
| 7F | 901 | PRO-CN | 82 | 0.18 | 0.68 | 3.8:1 | 41:1 | yes | yes | <1 | yes |
| 7F | 901 | Rhavi-PcrV-his | 48 | 0.14 | 0.19 | 1.4:1 | 25:1 | yes | yes | <1 | yes |
| 7F | 901 | Rhavi-FlaB-his | 65 | 0.13 | 0.29 | 2.2:1 | 31:1 | yes | yes | 3 | yes |
| 7F | 901 | Rhavi-FlaA1-his | 56 | 0.12 | 0.14 | 1.2:1 | 19:1 | yes | yes | <1 | yes |
| 7F | 901 | Rhavi-FlaA2-his | 56 | 0.13 | 0.11 | 0.8:1 | 14:1 | yes | yes | <1 | yes |
| 7F | 901 | Rhavi-MrkA-his | 37 | 0.16 | 0.17 | 1.1:1 | 26:1 | yes | yes | <1 | yes |
| 19A | 157 | PRO-CN | 82 | 0.23 | 0.89 | 3.9:1 | 7:1 | yes | yes | <1 | yes |
| 19A | 157 | Rhavi-PcrV-his | 48 | 0.09 | 0.19 | 2.1:1 | 7:1 | yes | yes | 4 | yes |
| 19A | 157 | Rhavi-FlaB-his | 65 | 0.14 | 0.39 | 2.8:1 | 7:1 | yes | yes | <1 | yes |
| 19A | 157 | Rhavi-FlaA1-his | 56 | 0.10 | 0.26 | 2.6:1 | 7:1 | yes | yes | 6 | yes |
| 19A | 157 | Rhavi-FlaA2-his | 56 | 0.11 | 0.15 | 1.4:1 | 4:1 | yes | yes | <1 | yes |
| 19A | 157 | Rhavi-MrkA-his | 37 | 0.08 | 0.19 | 2.4:1 | 10:1 | yes | yes | <1 | yes |

Example 6: Immunization Studies

Immunization of Animals

Prior to immunization of rabbits, the MAPS or variant MAPS complexes or PS alone were formulated with adjuvant approximately 48 h prior to injection. MAPS or variant MAPS were adsorbed to adjuvant at a final concentration of 10 μg/ml of each serotype PS as either single or a multivalent mixture with 40 mM histidine, pH 5.5, 150 mM NaCl, and 0.25 mg/ml aluminum phosphate gel with end-over-end mixing overnight at 4° C. This formulated mixture was used directly for immunizations at a volume of 0.5 ml for a 5 μg dose of PS. For lower PS doses, the appropriate dilution was made with 40 mM histidine, pH 5.5, 150 mM NaCl. Two IM immunizations (0.5 ml) were administered at a 2- or 4-week interval to 4 month old New Zealand White rabbits (Cocalico Biologicals, n=8 to 10 per group). Blood samples were obtained 2 weeks after the first and second immunization with a 2-week dose interval. Samples were collected at 2- and 4-weeks after the first immunization and 2-weeks after the second immunization for the 4-week dose interval.

To obtain high titer antibody against the carrier fusion protein candidates, Freund's complete adjuvant was used for the first and Freund's incomplete for the second and third New Zealand White rabbits (Cocalico Biologicals), (n=3 per group) at day 0, day 14 and day 21 and blood samples were collected 2 weeks after the second and third immunization.

Antibody Measurement

Assays for rabbit antibodies to capsular polysaccharides (CPS) or OPS or different protein antigens were done in Immulon 2 HB or Greiner Bio-one medium binding 96 microwell plates (Thermo Scientific Waltham Mass) coated with (1 μg CPS or OPS or PS conjugated to HSA/ml PBS) or with protein antigens (1 μg of protein/ml PBS). Plates were blocked with 1% BSA in PBS. Antibody diluted in PBS-T was added and incubated at room temperature for 2 h. Plates were washed with PBS-T and secondary HRP conjugated antibody to rabbit immunoglobulin G (from Sigma) was added and incubated at room temperature for 1 h. The plates were washed and developed with SureBlue TMB Microwell Peroxidase Substrate (KPL, Gaithersburg, Md.).

The titer of rabbit IgG in sera samples specific for different protein antigens was determined with ELISA and a standard curve from polyclonal sera assigned arbitrary units. Protein antigens were coated overnight at room temperature in Immulon 2 HB 96 microwell plates (Thermo Scientific) at 0.5-1 μg of protein/ml PBS with 100 μl per well. Protein solution was removed and plates were blocked PBS+1.0% BSA for 1 h at room temperature and washed with Dulbeco's phosphate buffered saline with 0.05% Tween-20 (PBS-T). Rabbit sera was diluted in PBS-T, added to the plate and incubated at room temperature for 2 h. Plates were washed with PBS-T and secondary donkey anti-rabbit IgG conjugated to HRP (Santa Cruz Biotechnology) diluted 1 to 20,000 in PBS-T was added 100 µl per well and incubated at room temperature for 1 h. The plates were washed and developed with SureBlue TMB Microwell Peroxidase Substrate (KPL, Gaithersburg, Md.). The reaction was stopped with an equal volume of 1 N HCl and the absorbance as read at 450 nm in a Spectramax plate reader (Molecular Devices). An AU value of 12,500 AU/ml was assigned to the polyclonal sera standard included on every plate and an equation from a 4 parameter curve fit was used to assign AU for each diluted sera sample based on absorbance at 450 nm and corrected for the dilution factor. The polyclonal sera (AFV160, specific to PRO-CN, rhizavidin, and 6 histidine tag) standard curve acceptance criteria was an $R^2$ for the 4 parameter curve fit of 0.99 or greater and less than 10% CV between duplicates. An internal control sera (AFV151, specific for PRO-CN, rhizavidin, and 6 histidine tag) was also included on every plate and the CV for the assigned value had to be equal or less than 20% between plates for acceptance of the data.

Evaluation of Carrier Function

The carrier function capacity of the rhizavidin fusion proteins to generate an increased immune response to polysaccharides in the MAPS complexes was assessed and compared to rhizavidin alone and a control carrier protein (PRO-CN) that has previously generated robust immune responses to complexed polysaccharides. The various fusion proteins generated were complexed with polysaccharides of known immunogenicity (S. pneumoniae 6B, 7F, and 19A) (Zhang et al., 2013) and compared to a carrier protein control of robust function (PRO-CN). All fusion proteins were able to complex with biotinylated PS and form high molecular weight complexes that were amenable to purification and subsequent use for rabbit immunization and evaluation of carrier function.

Figure 13A:
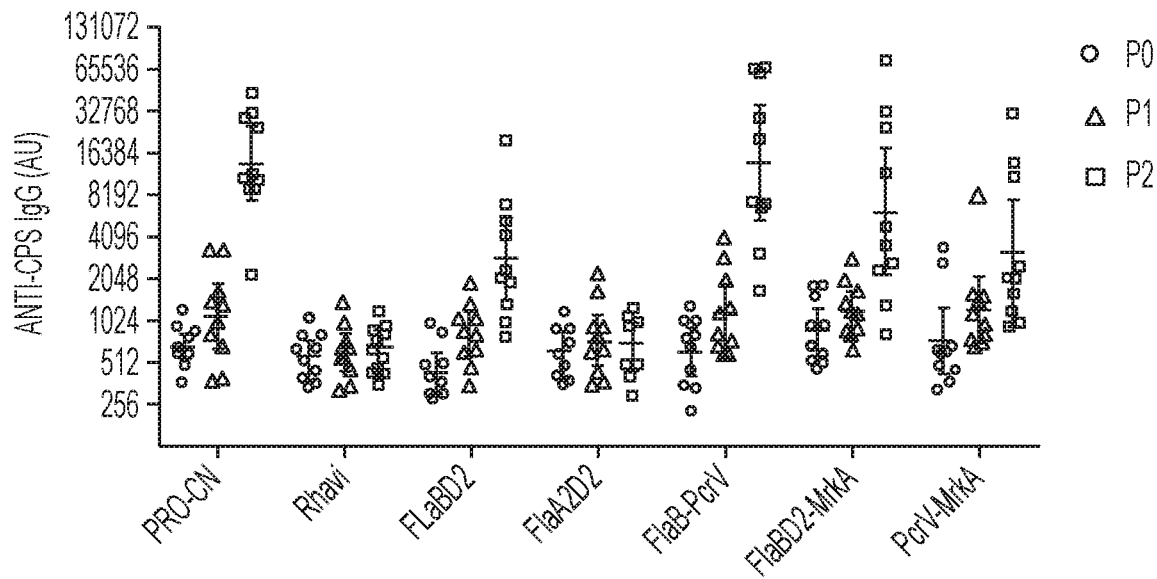
FIGS. 13A-13B compare the capacity of MAPS complexes generated with various rhizavidin-antigen fusion proteins and pneumococcal capsular polysaccharides (PnCPS) to elicit an anti-CPS 19A antibody (FIG. 13A) or anti-CPS-6B antibody (FIG. 13B) response in rabbits as measured by ELISA. Sera samples were evaluated from prior to immunization (P0), two weeks after the first immunization (P1) and two weeks after the second immunization (P2). The measured IgG response was assigned an arbitrary unit (AU) from a standard curve assigned an AU per ml of 12,500. The geometric mean is indicated as a horizontal black line with error bars for 95% confidence interval.
Figure 13A:
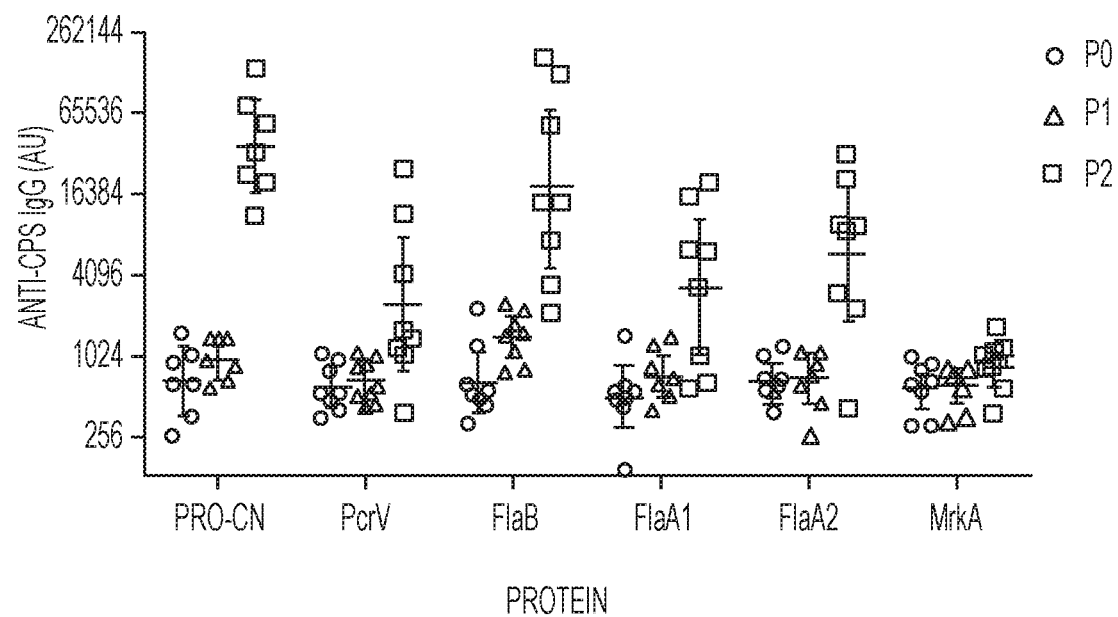
Figure 13B:
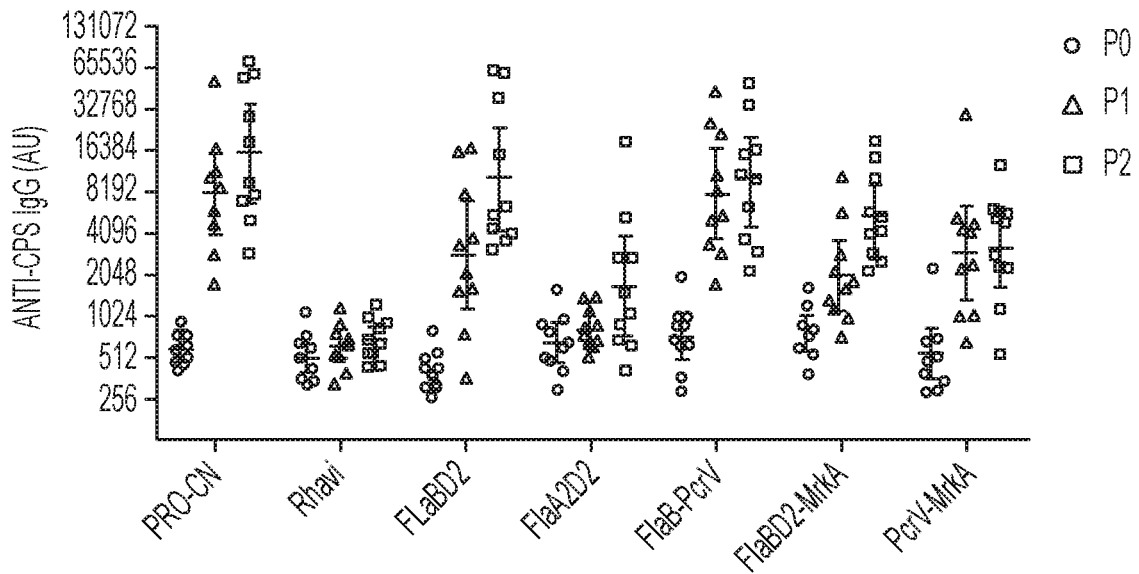
Figure 13B:
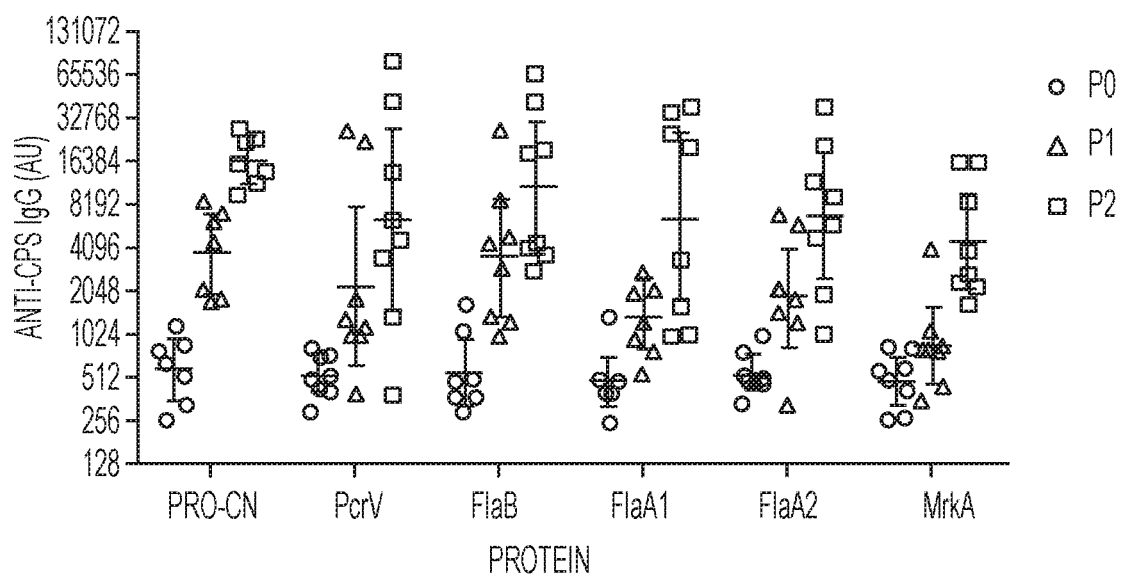

Rabbits were immunized with MAPS complexes generated with pneumococcal polysaccharides (PnPS) 6B and 19A generated with various rhizavidin fusion proteins. Sera was collected 2 weeks after the first immunization (P1) and the second immunization (P2). The rabbit IgG levels to the PnPS 19A and 6B for each sample were measured by ELISA and reported as AU that were determined from a standard curve with polyclonal sera assigned an AU of 12,500 AU/ml. As shown in FIGS. 13A and 13B, Pseudomonas Flagellin B (FlaB) as a rhizavidin fusion protein (Rhavi-FlaB) and Pseudomonas FlaB fused to Pseudomonas PcrV as a rhizavidin fusion protein (Rhavi-FlaB-PcrV) was able to generate IgG titers to pneumococcal polysaccharides (PnPS) 6B and 19A similar to the previously identified carrier protein, PRO-CN. Pseudomonas FlaA1 and FlaA2 as rhizavidin fusion proteins (Rhavi-FlaA1 and Rhavi-FlaA2) and Pseudomonas FlaB Domain 2 fused to Klebsiella MrkA as a rhizavidin fusion protein (Rhavi-FlaBD2-MrkA) demonstrate titers that were similar or within 2-fold of Rhavi-FlaB and PRO-CN titers. Klebsiella MrkA and Pseudomonas PcrV demonstrated very low to not detectable IgG titers to the challenging 19A PS and low titers for 6B and 7F at the 0.044 µg dose. To overcome the poor carrier function of MrkA while at the same time generating antibodies directed to MrkA it was fused with the strong carrier FlaB-Domain2 protein to retain carrier function (Rhavi-FlaBD2-MrkA).

Table 9 summarizes the carrier attributes of exemplary rhizavidin fusion proteins of the invention. The carrier function of each fusion protein is expressed as a percent of that demonstrated with carrier protein, PRO-CN, and compared to the rhizavidin protein alone which had only 4% of the immune response to 6B and 5% of the immune response to 19A when compared to that of PRO-CN. Rhavi-FlaB-PcrV, a doubly pathogen-specific protein (a chimeric protein with FlaB and PcrV two Pseudomonas derived antigens fused with rhizavidin), emerged as a strong carrier in terms of raising a robust PnPS specific rabbit immune response to type 6B (62%) and 19A (102%) relative to PRO-CN (100%). Rhavi-FlaB also demonstrated strong carrier function with robust responses to both 6B (66%) and 19A (49%) relative to PRO-CN. Rhavi-MrkA had lower carrier protein function for 6B (27%) and 19A (2%) relative to PRO-CN respectively. Rhavi-FlaBD2 had a robust carrier function for 6B (66%) and lower carrier function for 19A (20%). The chimeric Rhavi-FlaBD2-MrkA containing both Pseudomonas (FlaBD2) and Klebsiella (MrkA) antigens provided carrier function for both 6B (34%) and 19A (45%), that is approximately 2-fold lower than the carrier protein, PRO-CN, and increased over rhizavidin alone. Because an immune response was generated to both PnPS that were greater than 30% of PRO-CN and because a greater number of pathogen specific proteins was represented, both Rhavi-FlaB-PcrV and Rhavi-FlaBD2-MrkA variants were selected as carrier protein candidates to complex in variant MAPS with the OPS backbone polymer of the invention. In addition to the demonstrated carrier function, a carrier protein IgG-specific to the highly conserved Pseudomonas PcrV, and to some extent FlaB (i.e. ca. 45 percent Pseudomonas strains expressed FlaB) and to the conserved Klebsiella MrkA generated against these FPs can bring significant additional broad protective coverage against disease cause by these 2 pathogens.

TABLE 9

Carrier protein attributes of exemplary rhizavidin fusion proteins and variants

| Protein | Bacteria | TLR5 domain present | Carrier Function* | % of PRO-CN geometric mean 6B | % of PRO-CN geometric mean 19A |
| --- | --- | --- | --- | --- | --- |
| PRO-CN | S. pneumoniae | NA | ++++ | 100 | 100 |
| Rhavi-PcrV-his | P. aeruginosa | NA | ++ | 38 | 7 |
| Rhavi-FlaB-his | P. aeruginosa | Yes | ++++ | 66 | 49 |
| Rhavi-FlaA1-his | P. aeruginosa | Yes | +++ | 40 | 9 |
| Rhavi-FlaA2-his | P. aeruginosa | Yes | +++ | 42 | 16 |
| Rhavi-MrkA-his | K. pneumoniae | NA | + | 27 | 2 |
| Rhavi-his | S. pneumoniae | NA | + | 4 | 5 |
| Rhavi-FlaBD2-his | P. aeruginosa | No | +++ | 66 | 20 |
| Rhavi-FlaA2D2-his | P. aeruginosa | No | + | 11 | 5 |

TABLE 9-continued

Carrier protein attributes of exemplary rhizavidin fusion proteins and variants

| Protein | Bacteria | TLR5 domain present | Carrier Function* | % of PRO-CN geometric mean 6B | % of PRO-CN geometric mean 19A |
|---|---|---|---|---|---|
| Rhavi-FlaBD2-MrkA-his | P. aeruginosa K. pneumoniae | No | +++ | 34 | 45 |
| Rhavi-FlaB-PcrV-his | P. aeruginosa | Yes | ++++ | 62 | 102 |
| Rhavi-PcrV-MrkA-his | P. aeruginosa K. pneumoniae | NA | ++ | 30 | 23 |

*Ability of the fusion protein to raise an antibody response to type 19A and 6B pneumococcal PS (PnPS), relative to PRO-CN fusion protein taken as the 100 percent reference (++++).

Evaluation of Immunogenicity

Figure 15:
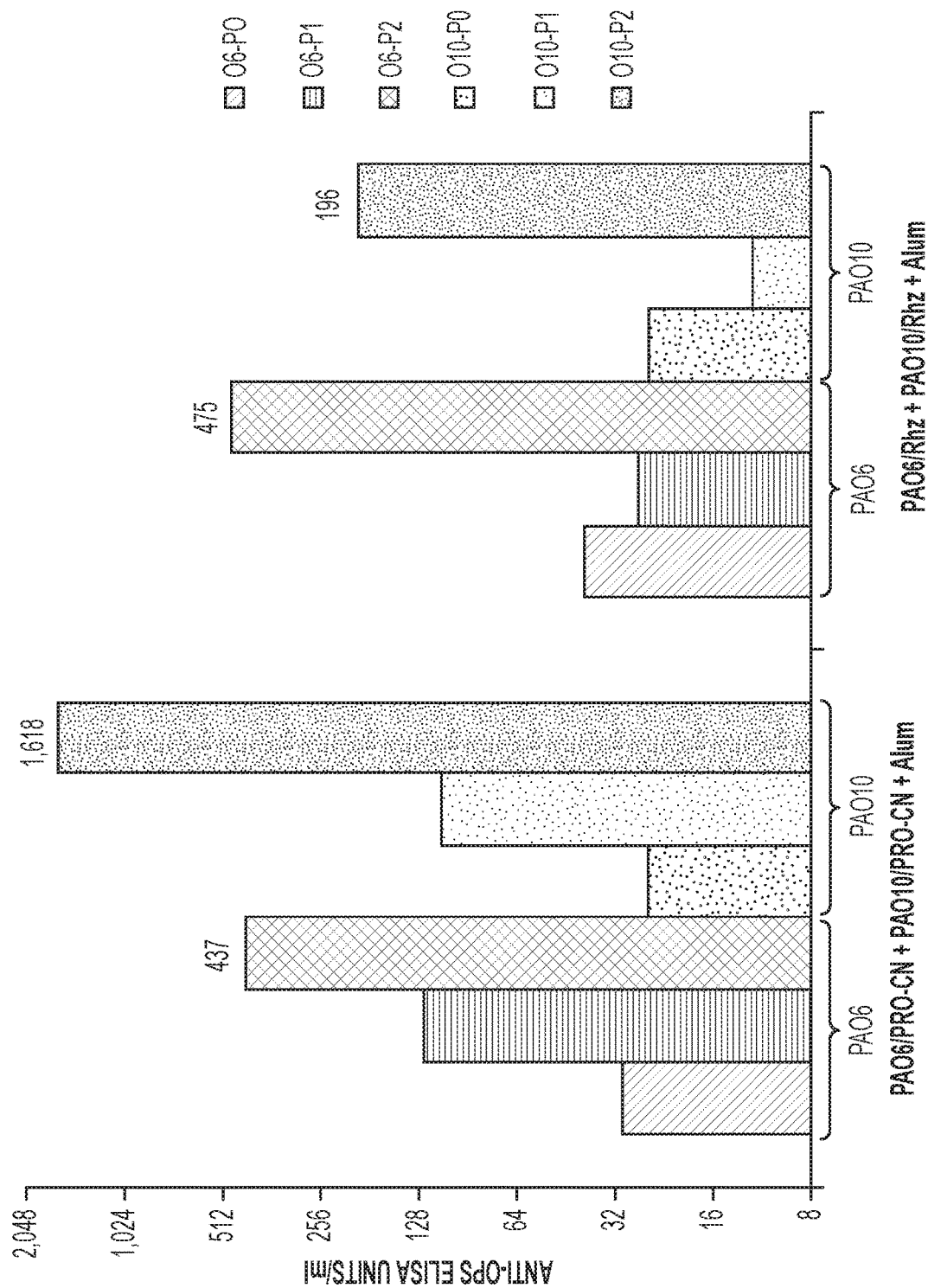
FIG. 15 compares the immunogenicity in rabbits of bivalent formulations of PA O6 and O10 native OPS in MAPS complexes with the rhizavidin fusion protein PRO-CN, or rhizavidin (Rhz). Anti O6 or O10 OPS IgG titers are shown in ELISA units before (P0), after one (P1) or two injections (P2).

A comparative immunogenicity study in rabbits of various formulations of native PA O6 and O10 OPS as MAPS complexes with the rhizavidin fusion protein PRO-CN, or rhizavidin is shown in FIG. 15. OPS-specific IgG ELISA titers are reported in ELISA units. Titers of OPS-specific IgG antibody greater than 100-fold over P0 could not be generated with either of these formulations after 2 immunizations (P2). This suggests that the molecular size of the native PA OPSs (10-30 kDa) was too small, the epitope valency was too low, or the molecular structure was not appropriate to induce a response even as a MAPS complex with the carrier protein, PRO-CN.

Figure 16:
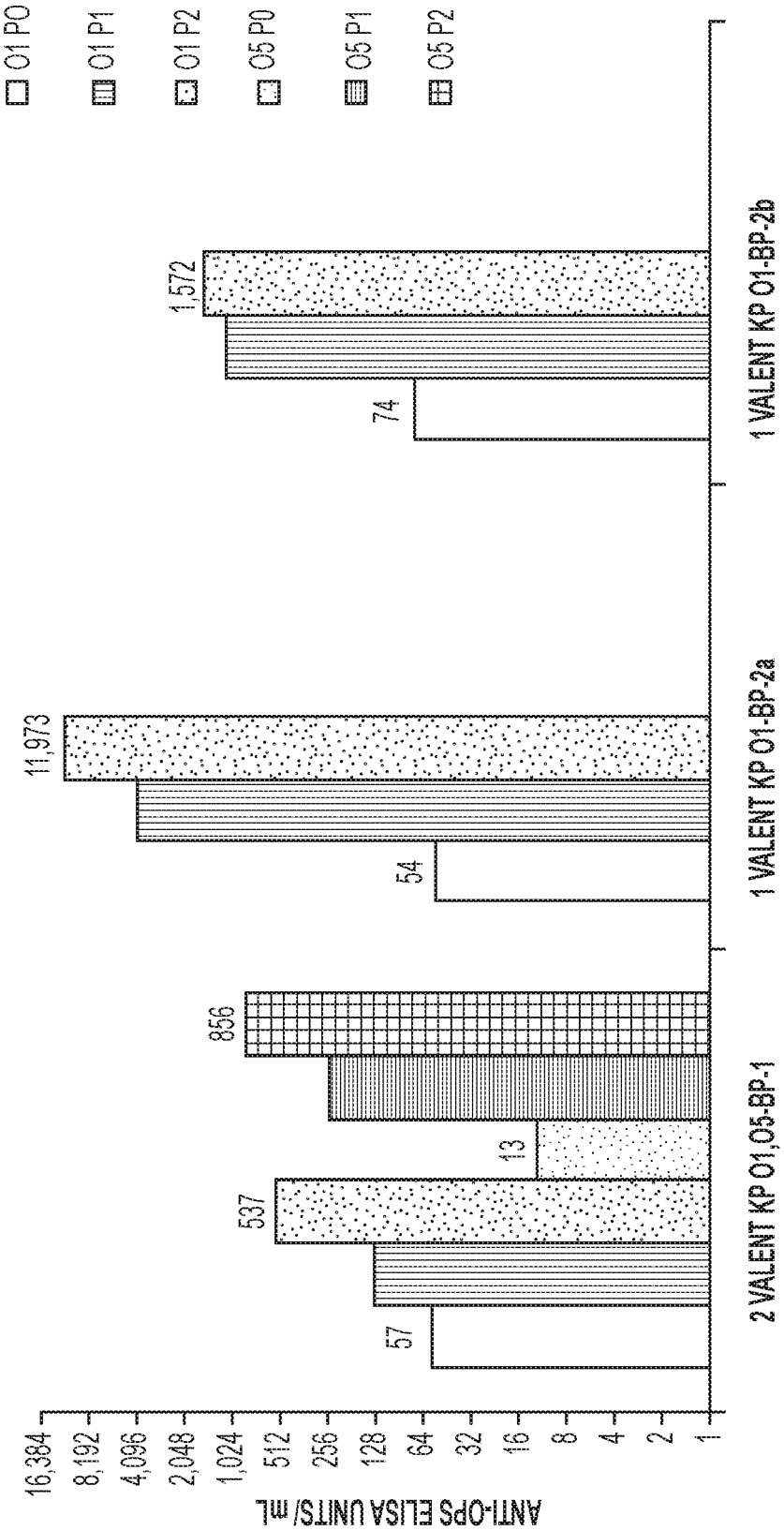
FIG. 16 compares the immunogenicity in rabbits of formulations of 2-valent KP O1 and KP O5 OPS BP-1; monovalent KP O1 BP-2a; and KP O1 BP-2b all in variant MAPS complexes with the rhizavidin fusion protein PRO-CN and with aluminum phosphate. Anti KP O1 or KP O5 OPS IgG titers are shown in ELISA units before (P0), after one (P1) or two injections (P2).

An immunogenicity study comparing various backbone polymer variants of KP-O1 OPS complexed into variant MAPS was carried out in rabbits. BP-1, BP-2a and BP-2b variants of KP O1 OPS linked to the Klebsiella capsular polysaccharide (CPS) K19 were evaluated for immunogenicity. A BP-1 variant of KP O5 linked to K19 was also evaluated. Four mixtures of variant MAPS complexes were compared for their immunogenicity; a 2-valent KP-O1 and -O5 OPS BP-1 (a schematic of which is shown in FIG. 2A); a KP-O1 BP-2a (FIG. 3); and a KP-O1 BP-2b (FIG. 4). These polysaccharides were all complexed in variant MAPS with the carrier protein PRO-CN and formulated with alum prior to injection. Anti KP-O1 OPS IgG titers are shown in ELISA units for the preimmune (P0), after one (P1) or 2 immunizations (P2) sera and are shown in FIG. 16. BP-2a OPS (12,000 EIA units) displayed O1 OPS-specific IgG titers greater than 100-fold over P0. O1 OPS BP-1 and O5 OPS BP-1 displayed titers that were 10-fold greater than P0.

Figure 17:
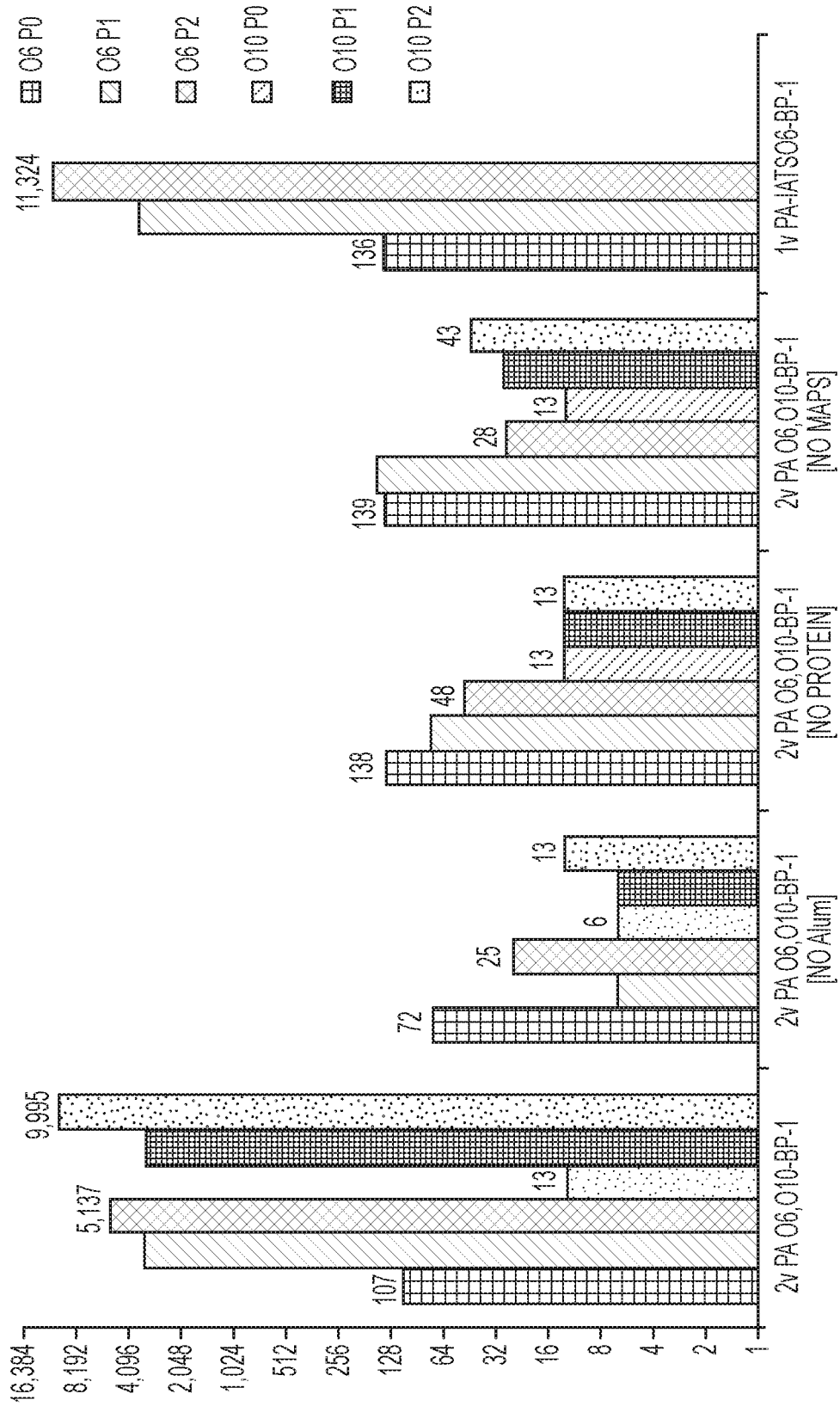
FIG. 17 compares the immunogenicity in rabbits of formulations of: 2-valent PA O6, O10 OPS BP-1 complexed with PRO-CN; PA O6, O10 OPS BP-1 complexed with PRO-CN (no alum); PA O6, O10-BP-1 (no protein, e.g., no PRO-CN); PA O6, O10 OPS BP-1 (no MAPS; e.g., no biotinylation but component backbone polymer and PRO-CN included); and monovalent PA-O6 OPS BP-1 in BP-1 MAPS complexes with the rhizavidin fusion protein PRO-CN with aluminum phosphate unless otherwise indicated. Anti-PA O6 and anti-PA O10 OPS IgG titers are shown in ELISA units before (P0), after one (P1) or two injections (P2).

Similarly an immunogenicity study in rabbits compared various formulations of PA-O6 and -O10 OPS BP-1: a 2-valent PA-O6, -O10 OPS BP-1 PRO-CN MAPS with alum; a 2-valent PA-O6, -O10 OPS BP-1 PRO-CN MAPS with no adjuvant (no alum); a 2-valent PA-O6, -O10 OPS BP-1 polysaccharide only (alum, no protein); a 2-valent PA-O6, -O10 OPS BP-1 mixture with PRO-CN not complexed (unbiotinylated; alum; no variant MAPS formation); and a monovalent PA-IATS O6 OPS BP-1 PRO-CN MAPS with alum (additional PA O6 strain source of OPS). Anti PA-O6 and PA-O10 OPS IgG titers are given in ELISA units for the preimmune (P0), after one (P1) or 2 immunizations (P2) sera and are shown in FIG. 17. PA-O6 and PA-O10 OPS-specific IgG titers greater than 100-fold over P0 could be achieved (5,000-11,000 range in ELISA units) only when the OPS backbone polymer was present in a variant MAPS complex with alum.

The size of the KP OPS produced using the laboratory standardized growth conditions with a chemically defined media is in the range of 10-15 kDa, comparatively smaller than that of the PA OPS (20-30 kDa) obtained under similar conditions, these size differences might explain in part why in this comparative immunogenicity studies PA OPS BP-1 were more immunogenic than KP OPS BP-1. KP OPS BP-2b constructs on the other hand were significantly immunogenic (FIG. 16). Other structural differences in the OPS repeating unit might have been a factor too, such as the charges, both repeating units of PA-O6 and -O10 are negatively charged whereas KP-O1 OPS is neutral.

Example 7: Functional Antibody Assays

Opsonophagocytic Killing Assay

Opsonophagocytic killing (OPK) assays with HL-60: Assays were performed as previously described, with modifications (Ramachandran et al., 2016). In brief, assays were performed in 96-well round bottom plates using P. aeruginosa and K. pneumoniae strains from log-phase cultures diluted to $3 \times 10^5$ cells/ml; Baby Rabbit Complement (BRC); PMA-differentiated HL-60 cells ($2 \times 10^7$ cells/ml) as the polymorphonuclear leukocyte source; and rabbit preimmune/immune serum at several dilutions. Following a 45 min incubation at 37° C., an aliquot was removed from the well and plated onto bacteriological agar plates (5% Hy-Yeast extract [Kerry Bio-Science], 10% Animal-Free Soytone [Teknova], 5% NaCl [Americanbio] and 1.4% Agar [Americanbio] referred to hereafter as HySoy Agar or HSA). After overnight incubation on HSA the CFU were counted. A positive OPK response is obtained when the CFU for bacteria treated with immune serum is reduced from that of a similar dilution of preimmune serum.

Figure 18A:
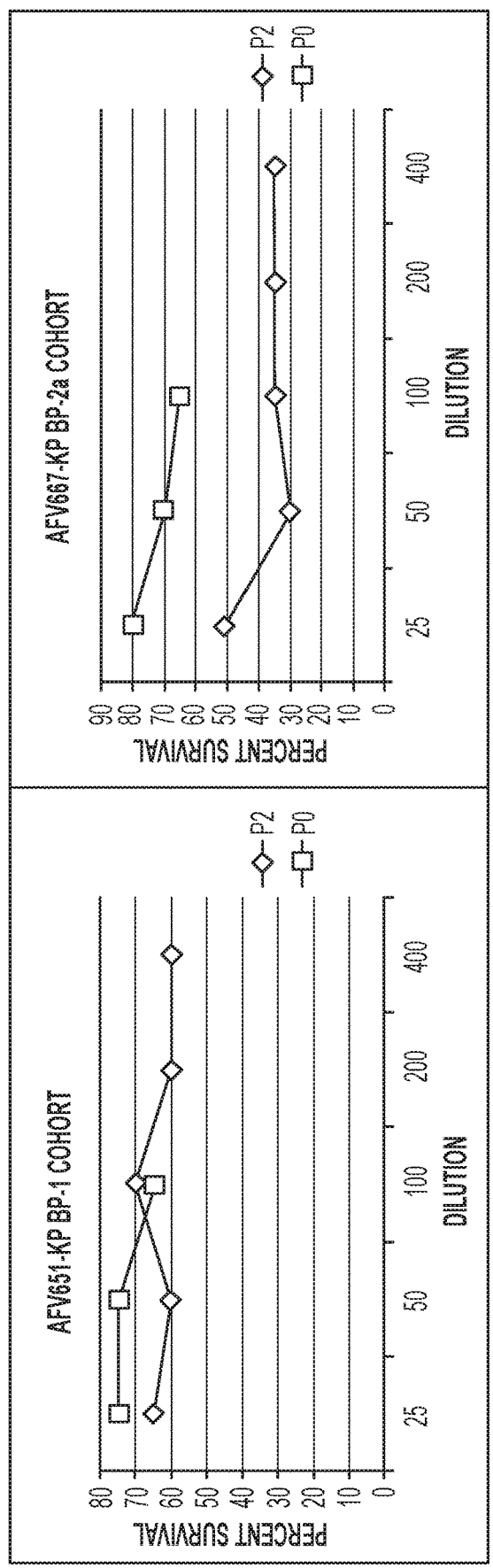
FIG. 18A compares opsonophagocytic killing (OPK) with human promyelocytic leukemia cells (HL-60) cells of *Klebsiella* strain 12-0581 (O1: K62) of rabbit antisera (from rabbits AFV651 and AFV667) to: a KP O1 OPS BP-1 PRO-CN MAPS pre and post second immunization (left); a KP O1 OPS BP-2a/Rhizavidin PRO-CN MAPS pre and post second immunization (right) panel. Increased killing was observed for BP-2a sera for immune serum compared with preimmune serum from the same rabbit.

FIG. 18A compares the OPK of Klebsiella strain KP 12-0581 (O1: K62) with HL-60 cells and rabbit antisera to: a KP-O1 OPS BP-1 PRO-CN MAPS pre and post second immunization (left) and a KP-O1 OPS BP-2a/Rhizavidin PRO-CN MAPS pre and post second immunization (right). Significant KP killing was observed for BP-2a immune sera (P2) when compared with preimmune sera (P0) from the same rabbit. No significant killing was observed with BP-1 immune sera, in agreement with the O1-OPS-specific IgG titers obtained with these constructs i.e. BP-2a>BP-1 in terms of relative titers.

Figure 18B:
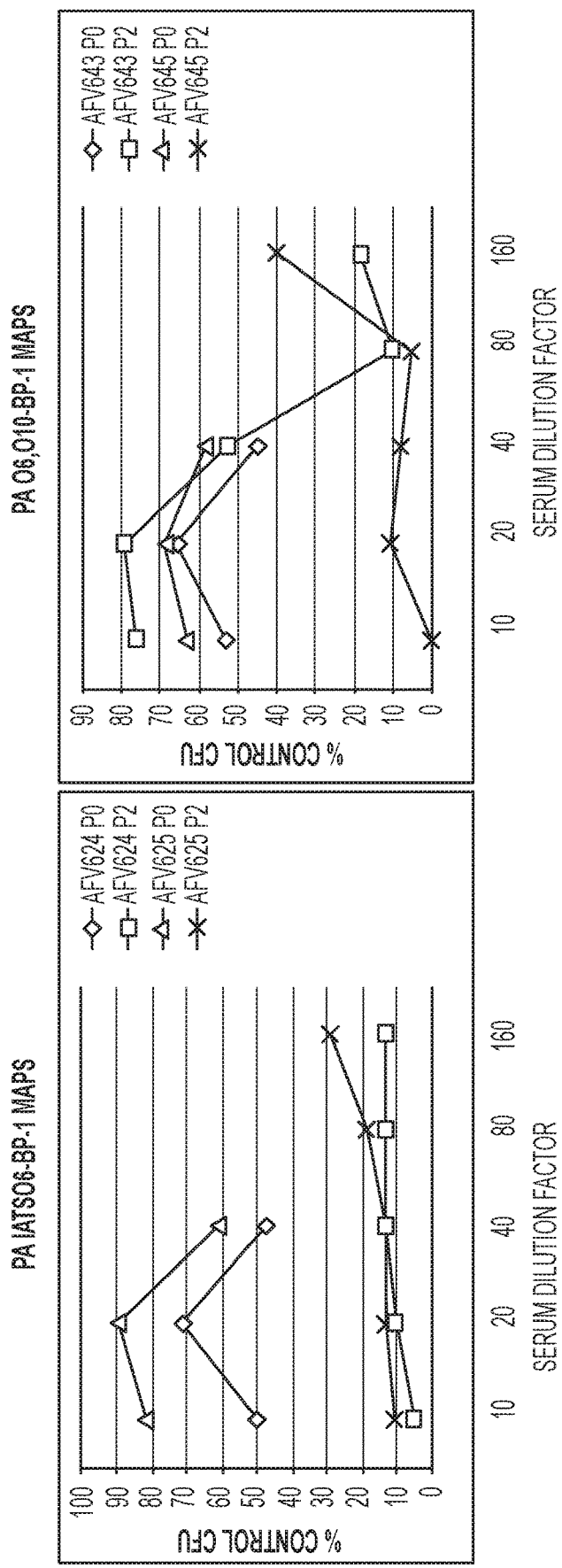
FIG. 18B compares the OPK with HL-60 cells of *Pseudomonas* strain PA IATSO6 with rabbit antisera to bivalent PA O6, O10-OPS BP-1 PRO-CN MAPS and monovalent PA IATSO6-OPS BP-1 PRO-CN MAPS. The individual rabbit sera tested produced OPK of PA IATSO6, rabbit serum AFV643 produced a prozone effect which is suggestive of a strong OPS antibody titer.

The OPK of Pseudomonas strain PA IATS O6 with HL-60 cells and rabbit antisera to bivalent PA O6, O10-OPS BP-1 PRO-CN MAPS and monovalent PA IATSO6-OPS BP-1 PRO-CN MAPS is shown in FIG. 18B. The individual 2 rabbit P2 sera (AFV 624; AFV 625) to PA O6, O10-BP-1 MAPS generated significant OPK of PA IATSO6 (left panel), rabbit post immune sera (P2) against PA IATSO6-BP-1 MAPS produced significant OPK of PA IATS O6 as well although serum AFV643 (P2) produced a prozone effect suggestive of a strong OPS antibody titer.

Figure 18C:
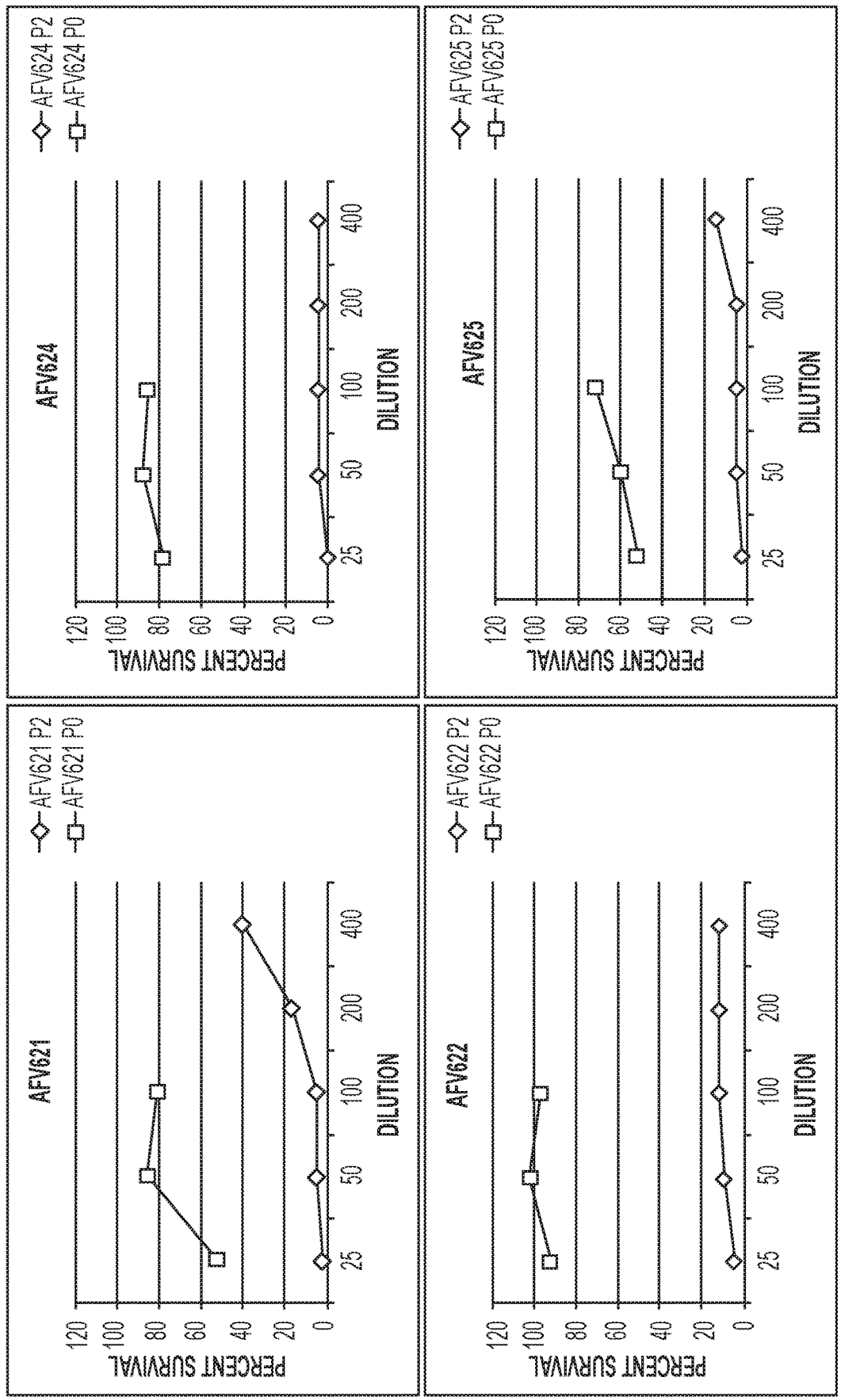
FIG. 18C shows that four individual rabbits immune sera (P2) generated with a 2-valent PA O6, PA O10 OPS BP-1-PRO-CN-MAPS vaccine induced robust OPK of PA O10 bacteria with HL-60 cells.

Four individual rabbit immune sera (P2) generated with a 2-valent PA-O6, -O10 OPS BP-1-PRO-CN-MAPS vaccine induced robust OPK of Pseudomonas O10 bacteria with HL-60 cells (FIG. 18C).

Figure 22:
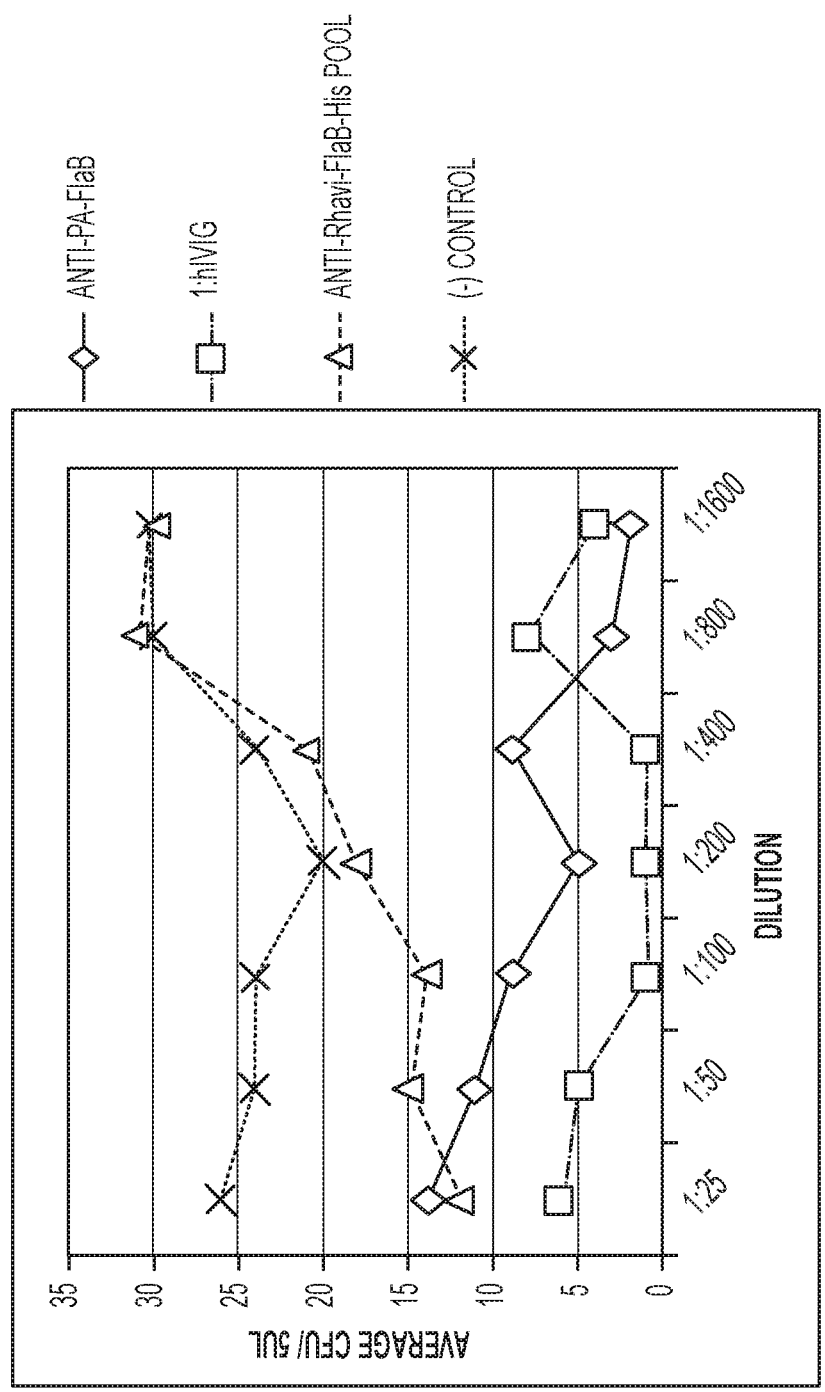
FIG. 22 depicts OPK with HL-60 cells of target strain *Pseudomonas* strain PAO1 (O5: expressing FlaB) with pooled rabbit anti-Rhavi-FlaB-His antiserum compared to positive controls anti-PA-FlaB antibody raised against PAO1 FlaB, and polyclonal human intravenous immunoglobulin (IVIG) antibody and negative control (no antibody).

An OPK of target strain *P. aeruginosa* strain PAO1 (O5: expressing FlaB) with a pool rabbit anti-Rhavi-FlaB-His antiserum and HL-60 cells is shown in FIG. 22. In this experiment, there was some OPK (up to 1/100 dilution) elicited by the anti-Rhavi-FlaB-His antiserum. Strong OPKs were registered with a human IVIG raised with a *Pseudomonas* vaccine and an anti-*Pseudomonas* FlaB serum. The (−) control serum did not induce any OPK.

OPK Assays with Human PMNs

Assays were performed as previously described with modifications (Cross et al., 1986). In brief, assays were performed in 96-well plates using polymorphonuclear leukocytes (PMN) freshly isolated from healthy human donors by dextran sedimentation and Ficoll-Hypaque density gradient centrifugation. The stock PMN solution was adjusted to $23\times10^6$ cells/ml in HBSS with calcium/magnesium. Sixty µl of PMN stock is added to the microtiter well along with 10-20 µl of either baby rabbit complement or fresh normal human serum (NETS), 10 µl of bacteria (~$10^6$ CFUs for MOI ~1:1) in the presence or absence of 10 µl of heat-inactivated pre- or post-immune serum at various dilutions. A time 0 sample is obtained, diluted and plated onto HySoy plates and the 96-well plate is then incubated for 2 h at 37° C. with shaking. At 2 h, samples are again obtained, diluted and plated. After overnight incubation at 37° C., the plates are counted. The 2 h counts for each well are divided by the 0 time counts and % kill is calculated by $1.0-T_{2h}$ CFU/$T_0$ CFU. Alternatively, we will convert the CFUs for each well to log CFU and subtract the log CFU count from the 2 h sample from the log CFU count from the 0 time count and express the killing difference as "delta log CFU". We then compare the killing of the wells with pre- and post-immune sera to the no-antibody control.

Flow Cytometry Based Binding Assays

Mid-log phase *P. aeruginosa* and *K. pneumoniae* strains were concentrated in PBS to an $OD_{600}$ of 0.8. For polysaccharide antigens the bacteria were fixed with 1% formaldehyde before adding antibody. For protein antigens, the bacteria were not formaldehyde fixed before adding antibody in order to preserve the cell surface antigens. Bacteria were incubated with various dilutions of rabbit preimmune/immune serum for 1 h room temperature. Unbound antibody was removed by pelleting the bacteria through centrifugation and washing with PBS, washed cells were incubated with an Alexa Fluor 488 goat anti-rabbit IgG antibody (Invitrogen) for 1 h at room temperature. Unbound secondary antibody was removed by pelleting the bacteria and washing with PBS. Immunostained bacteria were fixed in 1% formaldehyde to kill any viable organisms. Samples were injected into an LSR II flow cytometer (BD) and analyzed using FACS Diva (v. 6.1.3; BD) and FlowJo (v. 9.2; Tree Star).

Figure 19A:
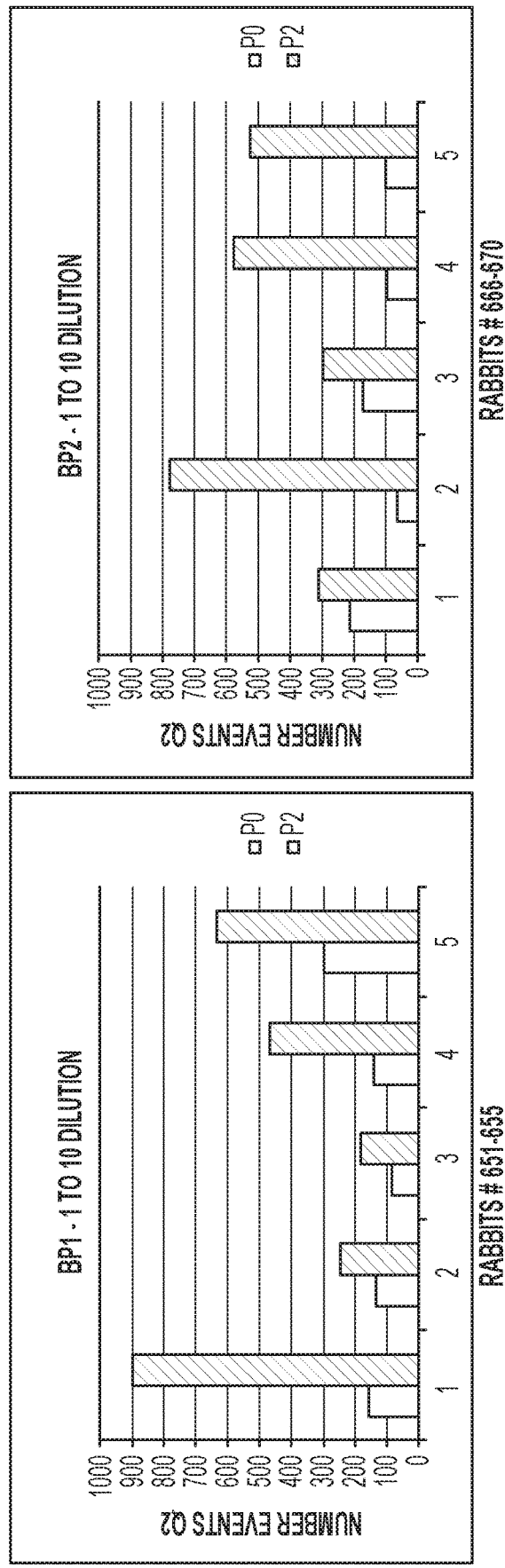
FIG. 19A compares Flow Cytometry (FC) binding to whole *Klebsiella* strain B5055 (O1: K2) with individual rabbit sera to PRO-CN variant MAPS of KPO1, O5 OPS BP-1 (left) and KPO1 OPS BP-2a (right). These FC binding results with whole bacteria have similar trends with the ELISA titer to purified KPO1 OPS, i.e., low titer, low FC binding. Small number of double-positive events indicated weak binding of antibody or limited OPS exposure on *Klebsiella* strain B5055 surface.

FC binding to *Klebsiella* strain B5055 (O1: K2) with rabbit antisera to K-19: O1- and O5-OPS BP-1, and BP-2a PRO-CN MAPS are shown in FIG. 19A. FC binding to whole *Klebsiella* bacteria strain B5055 with individual rabbit sera to 2-valent KP O1, O5 OPS BP-1 (#651-655) (left) and KP O1 OPS BP-2a (#666-670) (right).

These FC binding results with whole bacteria correlate well with the corresponding IgG ELISA titers to purified KP O1 OPS as shown in Table 10. i.e. low titer corresponds to low FC binding, a small number of double-positive events indicates weak binding of antibody or limited OPS antibody access on KP B5055 surface.

TABLE 10

KP O1-OPS IgG ELISA titers to O1-OPS backbone polymer BP-1 MAPS and BP-2a MAPS constructs

| Rabbit antisera | EIA Titers | | |
|---|---|---|---|
| | P0 | P1 | P2 |
| KP 2v-O1, O5 BP-1 #651-655 | 57.29 | 130.25 | 537.31 |
| KP O1 BP-2a #666-670 | 54.28 | 4,114.96 | 11,973.1 |

Figure 19B:
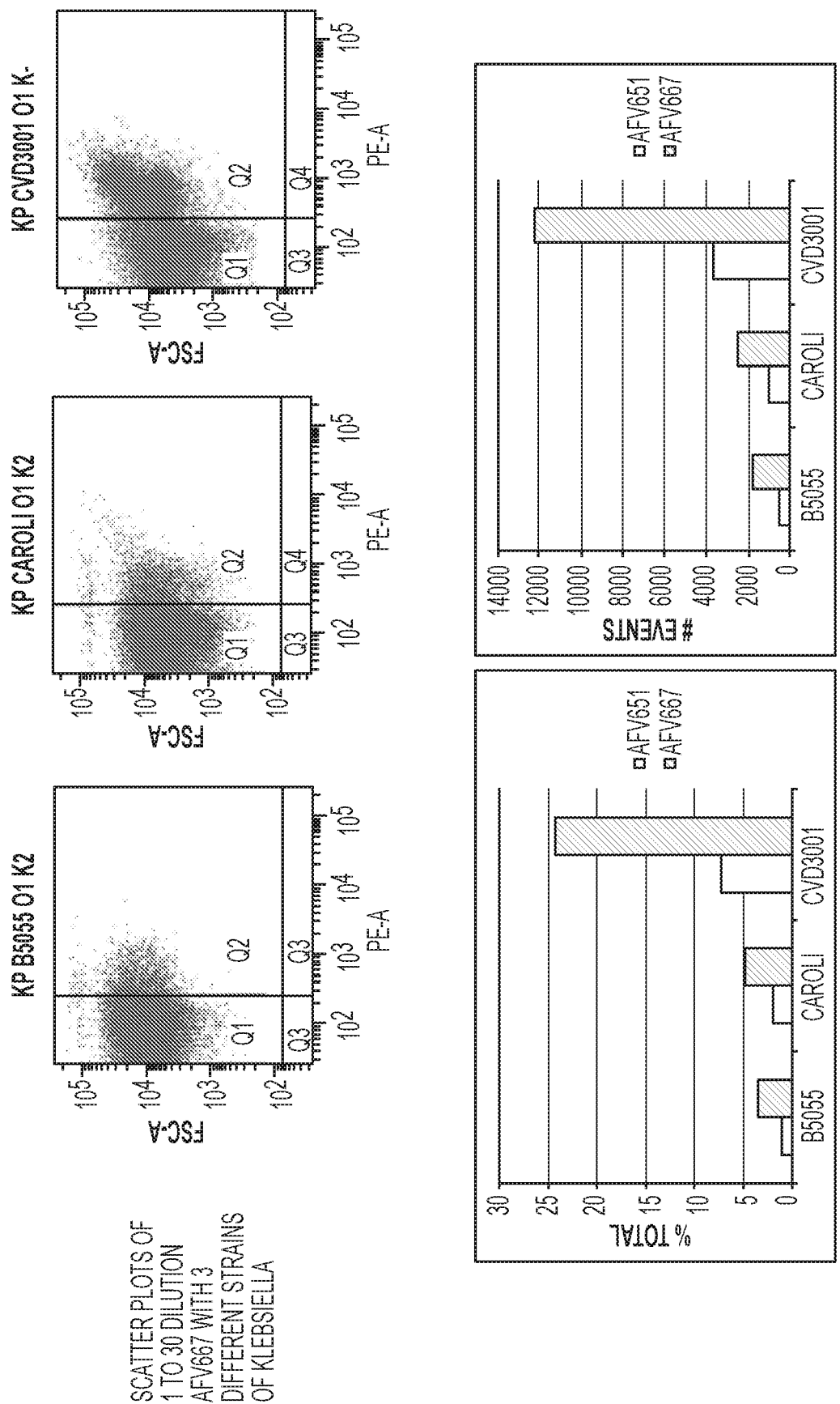
FIG. 19B (top panel) shows FC scatter plots of an individual rabbit serum (AFV667) to a PRO-CN BP-2a MAPS complex with KPO1 OPS BP-2a comparing weakly binding to (B5055), and (*K. pneumoniae*, strain *Caroli*, O1: K2) and strong binding to non-encapsulated *Klebsiella* (CVD 3001) O1 strains.

FIG. 19B compares FC binding scatter plots to three *Klebsiella* O1 strains with a rabbit antiserum (AFV667) raised with a KP O1 OPS BP-2a PRO-CN MAPS complex; observed in the top panels are a weak FC binding to KP B5055 (left), a weak binding to *K. caroli* (middle) and a strong binding to non-encapsulated KP CVD 3001 (right). In the bottom panel (FIG. 19B) a comparison of the FC total binding events to the same 3 *Klebsiella* O1 strains between a serum from a rabbit vaccinated with a 2-valent KP O1, O5 OPS BP-1 (AFV651) PRO-CN MAPS and a rabbit serum (AFV667) raised with a monovalent KP O1 OPS BP-2a PRO-CN MAPS. Of note, there is significantly more FC antibody binding with the O1 OPS BP-2a construct than with the corresponding BP-1 OPS and these data seem to correlate with the IgG titers to O1 OPS i.e. KP O1 OPS BP-2a are more immunogenic than their equivalent BP-1. These binding data also suggest that the amount of CPS affects antibody OPS exposure possibly influenced by growth conditions.

Figure 20:
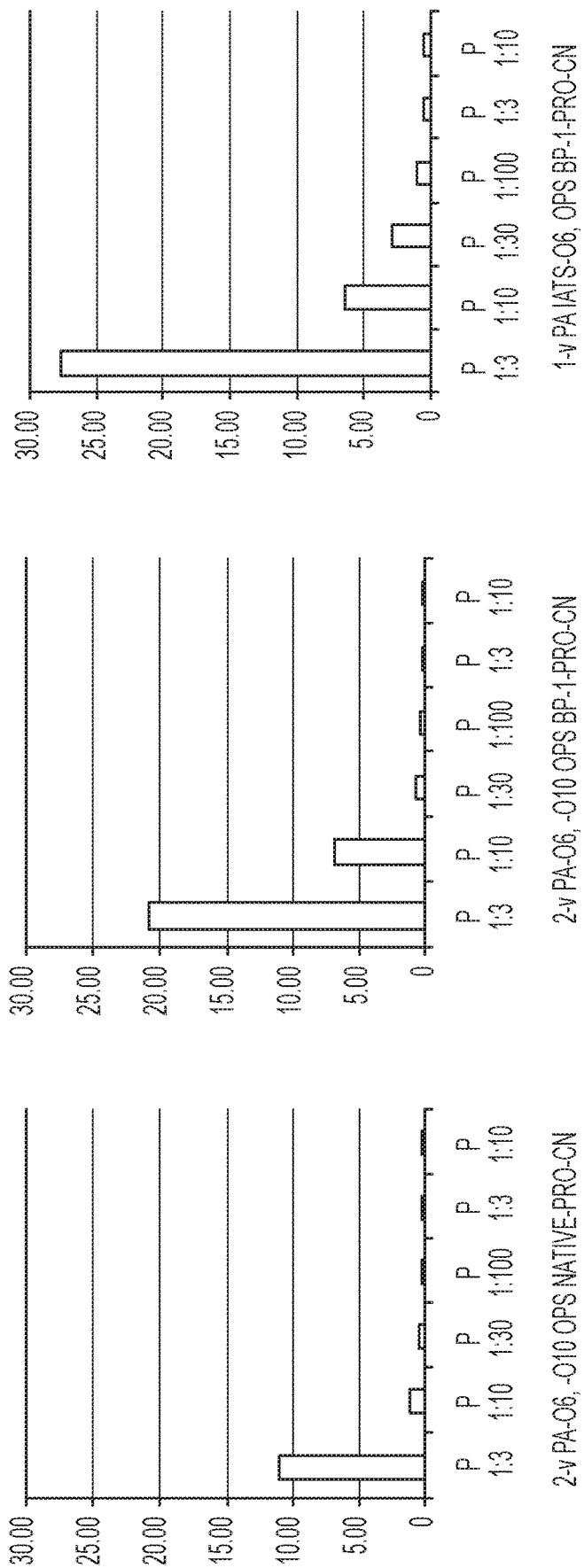
FIG. 20 compares the FC binding to whole *Pseudomonas* bacteria strain PAK (O6:FlaA1) with (left) rabbit sera of 2-valent PAO6-PAO10 native OPS-PRO-CN (pool sera of 3 rabbits, post second immunization); (middle) rabbit sera to a of 2-valent PAO6-PAO10 OPS BP-1-PRO-CN MAPS (pool sera of 3 rabbits, post second immunization); (right) rabbit sera to a of monovalent PAO6-IATSO6-OPS BP-1-PRO-CN MAPS (pool sera of 3 rabbits, post second immunization); stronger FC binding is observed for the PAO6 OPS BP-1 MAPS compared to the native form of the OPS MAPS.

A comparison of the FC antibody binding to whole *Pseudomonas* bacteria strain PAK (O6:FlaA1) is shown in FIG. 20: with rabbit sera (pool sera of 3 rabbits, post second immunization) to 2-valent PA-O6, -O10 native OPS-PRO-CN-MAPS (left); rabbit sera (pool sera of 3 rabbits, post second immunization) to 2-valent PA O6, O10-OPS BP-1-PRO-CN MAPS (middle); rabbit sera (pool sera of 3 rabbits, post second immunization) to monovalent PAO6-IATS-OPS BP-1-PRO-CN MAPS; stronger FC antibody binding to PAK strain is observed for PAO6 OPS BP-1 PRO-CN MAPS when compared with the native form of PA O6 OPS MAPS indicating that there is a minimum size for the OPS critical for its immunogenicity i.e. native PA OPS size is too small and needs to be enlarged by chemical linking to a backbone polysaccharide to increase its epitope valency as well as its size.

The binding to *Pseudomonas* strain PAO1 (O5 expressing FlaB) of individual rabbit anti-FlaB antibodies raised with various rhizavidin FPs variants containing the FlaB epitopes was examined by FC and is summarized in Table 11. The percentage binding above threshold and high binding of preimmune sera (P0) versus post third immunization (P3) sera are indicated for 3 individual rabbit sera to the fusion protein antigens. These binding data demonstrate that rhizavidin FlaB-D2 and FlaB-PcrV fusion proteins can induce strong antibody binding and recognize the whole *Pseudomonas* strain PAO1 expressing FlaB flagella, suggesting that these 2 proteins were produced with correct folding and were able to induce FlaB antibodies with specificity for the native flagella B epitopes on the whole *Pseudomonas* bacteria. The anti-RhaviFlaB-D2-MrkA fusion protein serum didn't significantly (or poorly at best) recognize flagella on whole *Pseudomonas* strain PAO1 indicating that the FlaB portion of the rhizavidin construct was either not properly folded or not sufficiently immunogenic in the context of the fusion protein with MrkA when evaluated as a protein alone immunization with Freund's adjuvant.

Figure 21A:
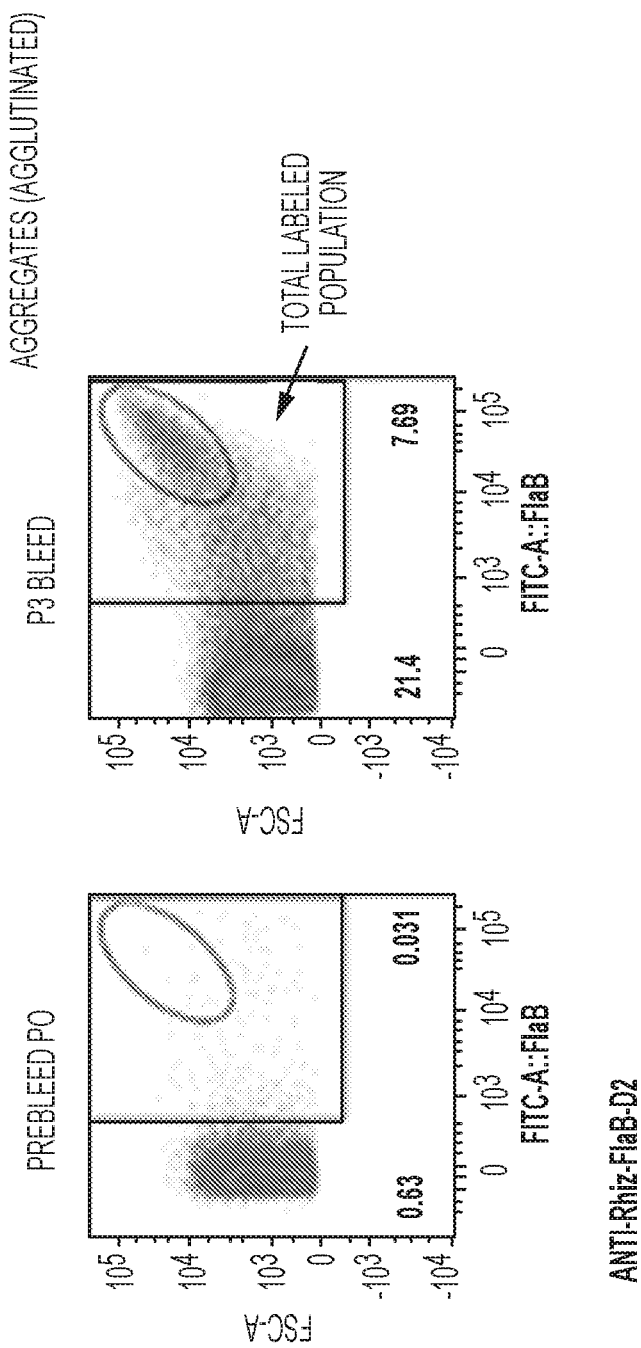
FIG. 21A depicts FC binding data for rabbit anti-FlaB binding to PAO1 strain O5: expressing FlaB: right panel demonstrates a scatter plot with high percentage of labeled PAO1 population in the post third bleed (P3 bleed; pool serum 10 rabbits) of rabbits vaccinated with a rhizavidin FlaB-D2 (lacking TLR5 binding region) when compared to prebleed (P0) serum (left panel).
Figure 21B:
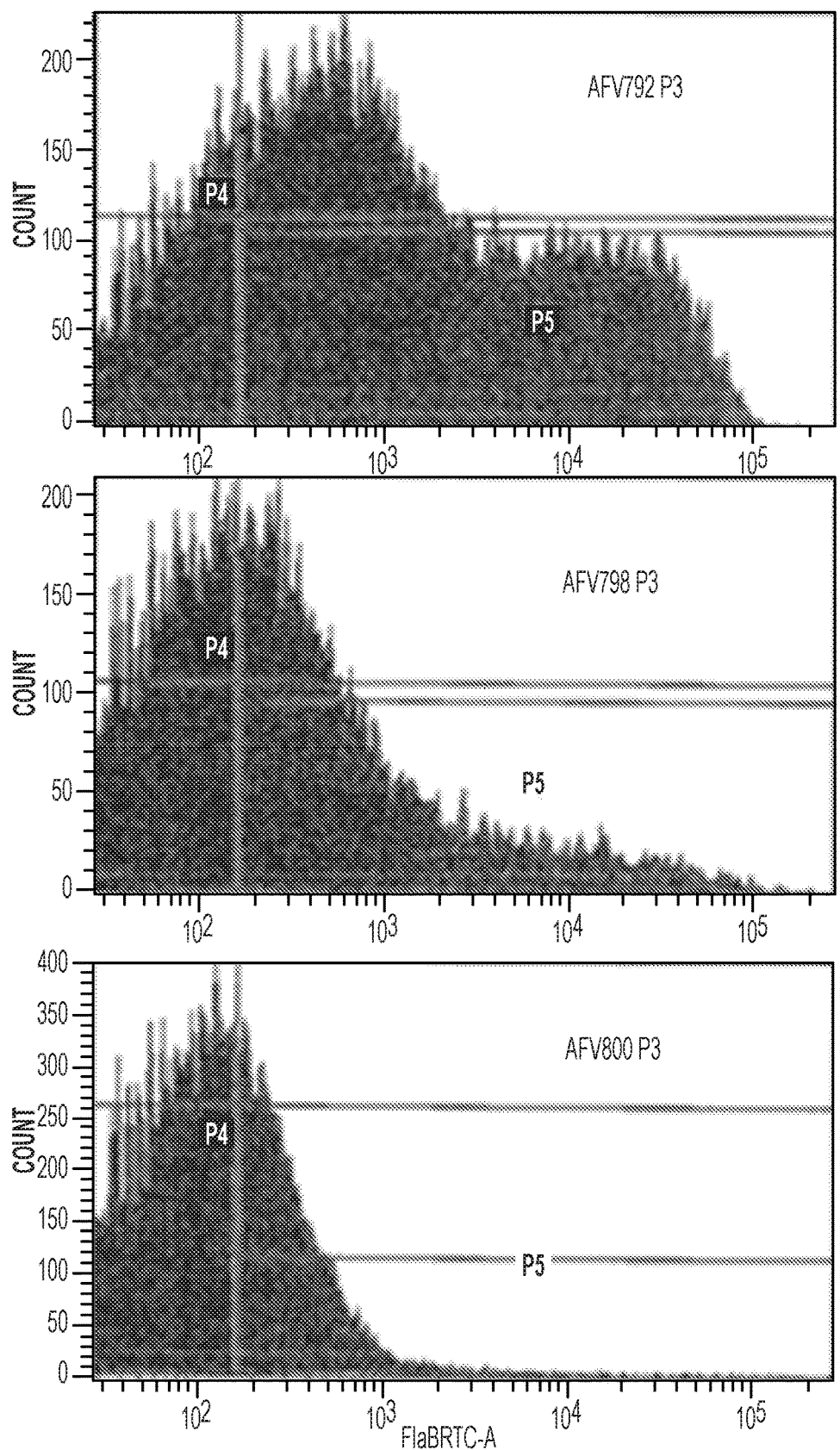
FIG. 21B upper panel shows FC for an individual rabbit P3 bleed serum against rhizavidin FlaB-D2; middle panel for an individual rabbit P3 bleed serum against rhizavidin FlaB-PcrV; bottom for an individual rabbit P3 bleed serum against rhizavidin FlaB-D2-MrkA.

FC scatter plots for some of the individual rabbit sera (#792, #798 and #800) listed in Table 11 are also shown in FIG. 21B (upper panel) shows strong FC binding for individual rabbit #792 (P3 bleed) serum to rhizavidin FlaB-D2; (middle panel) intermediate FC binding of rabbit serum #798 (P3 bleed) to rhizavidin FlaB-PcrV; and (bottom) poor FC binding for individual rabbit serum #800 (P3 bleed) to rhizavidin FlaB-D2-MrkA. In FIG. 21A a pool of rabbit serum from rabbits immunized with rhizavidin FlaB-Domain2 fusion protein (lacking TL5 binding region) (P3) shows a high percentage of labeled *Pseudomonas* strain PAO1 population (scatter plot right panel) compared to the preimmune (P0).

TABLE 11

FC binding of rabbit anti-FlaB antibodies to *Pseudomonas* strain PAO1 strain (O5 expressing FlaB)

| Rhiz-Fusion Proteins | Rabbit # | Percent Above Threshold | | Percent High Binding | |
|---|---|---|---|---|---|
| | | P0 | P3 | P0 | P3 |
| FlaB-D2 | 791 | 2.3 | 2.1 | 0 | 0.1 |
| | 792 | 2.3 | 44.2 | 0.1 | 14.8 |
| | 793 | 1 | 31.8 | 0 | 11.4 |
| FlaB-PcrV | 797 | 3.3 | 28.5 | 0.1 | 7.7 |
| | 798 | 3.6 | 13 | 0 | 2.2 |
| | 799 | 2 | 11.7 | 0.1 | 2.2 |
| FlaB-D2-MrkA | 800 | 0.3 | 3.7 | 0 | 0.1 |
| | 801 | 0.3 | 2.2 | 0 | 0.1 |
| | 802 | 1.9 | 3 | 0 | 0 |

These ELISA and FC binding data support the notion that rhizavidin fusion proteins containing FlaB such as Rhizavidin FlaB-Domain2 and Rhizavidin FlaB-PcrV can be produced with the proper folding to induce functional antibodies able to recognize native flagella B on whole *Pseudomonas* organisms.

Motility and Motility Inhibition Assays

*P. aeruginosa* strain PAO1 (O5: expressing FlaB) was grown to mid-log phase in HySoy broth. Bacteria were pelleted by centrifugation and suspended in PBS to and $OD_{600}$ reading of 0.3, then diluted 100-fold in PBS. Soft agar was poured into 24-well plates in the presence or absence of various dilutions of antisera raised to flagellin. Antisera dilutions were performed in triplicate wells. A flamed needle was dipped into the bacterial suspension then used to inoculate the center of the agar plug. Plates were incubated at 30° C. for 14 h or longer until the bacteria had spread from the site of inoculation across the surface of the agar. Images of the plates were captured by digital camera to record the diameter of the bacterial colony. A positive motility inhibition test results when the size of the colony on agar with anti-flagellin serum is significantly reduced relative to preimmune sera.

The ELISA and corresponding motility inhibition titers of sera from rabbits vaccinated with Rhizavidin FlaB constructs: Rhavi-FlaB-D2; Rhavi-FlaB-PcrV; and Rhavi-FlaB-D2-MrkA are summarized in Table 12. In this table, ELISA titers to FlaA1 and FlaB are shown for post third immunizations (P3) antisera and motility inhibition titers for the respective P3 antisera using *P. aeruginosa* strain PAO1 (O5: expressing FlaB) are also shown. There is a good correlation between the levels of anti-FlaB antibody (ELISA titers) and the corresponding motility inhibition titers i.e., both Rhavi-FlaB-D2 and Rhavi-FlaB-PcrV antisera with high titers of FlaB specific antibody induced high levels of motility inhibition of PAO1 whereas the Rhavi-FlaB-D2-MrkA fusion protein construct did not, presumably due to low levels of FlaB antibody likely from either improper folding of the FlaB protein component in the construct or lack of an immune response in the context of the fusion protein with MrkA when evaluated as a protein alone immunization with Freund's adjuvant.

TABLE 12

ELISA and motility inhibition titers for various rhizavidin FlaB containing constructs

| | | Post third vaccination sera | | |
|---|---|---|---|---|
| Rhizxavidin Fusion Protein Construct | Rabbit # | FlaA1 ELISA | FlaB ELISA | Motility Inhibition titer |
| FlaB-D2 | AFV791 | 744 | 279,209 | 1250 |
| | AFV791 | 627 | 154,104 | 1250 |
| | AFV793 | 763 | 423,514 | 250 |
| FlaB-PcrV | AFV797 | 31,497 | 318,117 | 1250 |
| | AFV798 | 40,911 | 230,702 | 1250 |
| | AFV799 | 41,566 | 499,941 | 1250 |
| FlaB-D2 MrkA | AFV800 | 1916 | 35,651 | 10 |
| | AFV801 | 944 | 53,477 | 50 |
| | AFV802 | 291 | 34,790 | 10 |

Cytotoxicity Assays (for *Pseudomonas* PcrV Protein Constructs)

Assays were performed as follows. Briefly, rabbit antisera raised against the bacterial secretion system protein PcrV were added to A549 cells seeded in flat bottom 96-well plates (Corning Costar). All antiserum and bacterial dilutions were performed in RPMI medium without antibiotic. Log-phase *P. aeruginosa* strain PAK capable of expressing ExoU were added at an approximate MOI of 10 and incubated for 2 h at 37°/5% $CO_2$ during which time A549 cells become intoxicated and are no longer viable. The number of viable cells in each well is estimated by the cell uptake of the vital dye Neutral Red (*Pseudomonas* also metabolizes Alamar Blue and cannot be used). The percentage of viable cells in each well is estimated by measuring Neutral Red absorbance and comparing these values to cells that had not been exposed to bacteria. A positive test for this assay results when PcrV antiserum increases the number of viable cells (i.e. cells able to take up the Neutral Red) compared with an equivalent dilution of preimmune serum.

Figure 24A:
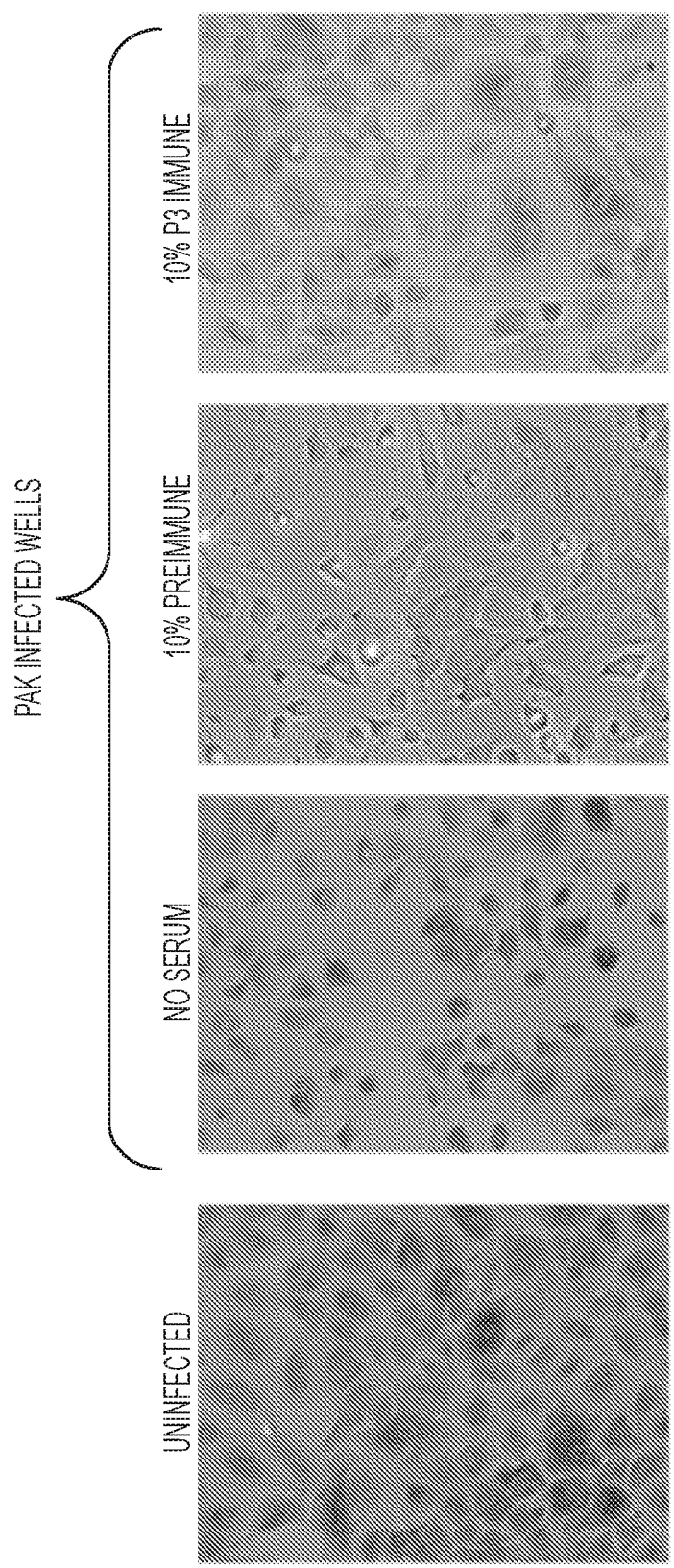
FIG. 24A shows anti-PcrV antibody protection of A549 cells from cytotoxic intoxication by *Pseudomonas* strain PAK (O6:FlaA1). A549 monolayers were infected with *Pseudomonas* strain PAK (O6:FlaA1) for 4 hours in the presence of 10% serum from rabbits (pool of 3) vaccinated with a Rhavi-FlaB-PcrV fusion protein. Anti-Rhavi-FlaB-PcrV (P3, post third immunization) sera protected cells from *Pseudomonas* strain PAK intoxication compared to preimmune serum as seen by fewer rounded and detached cells.
Figure 24B:
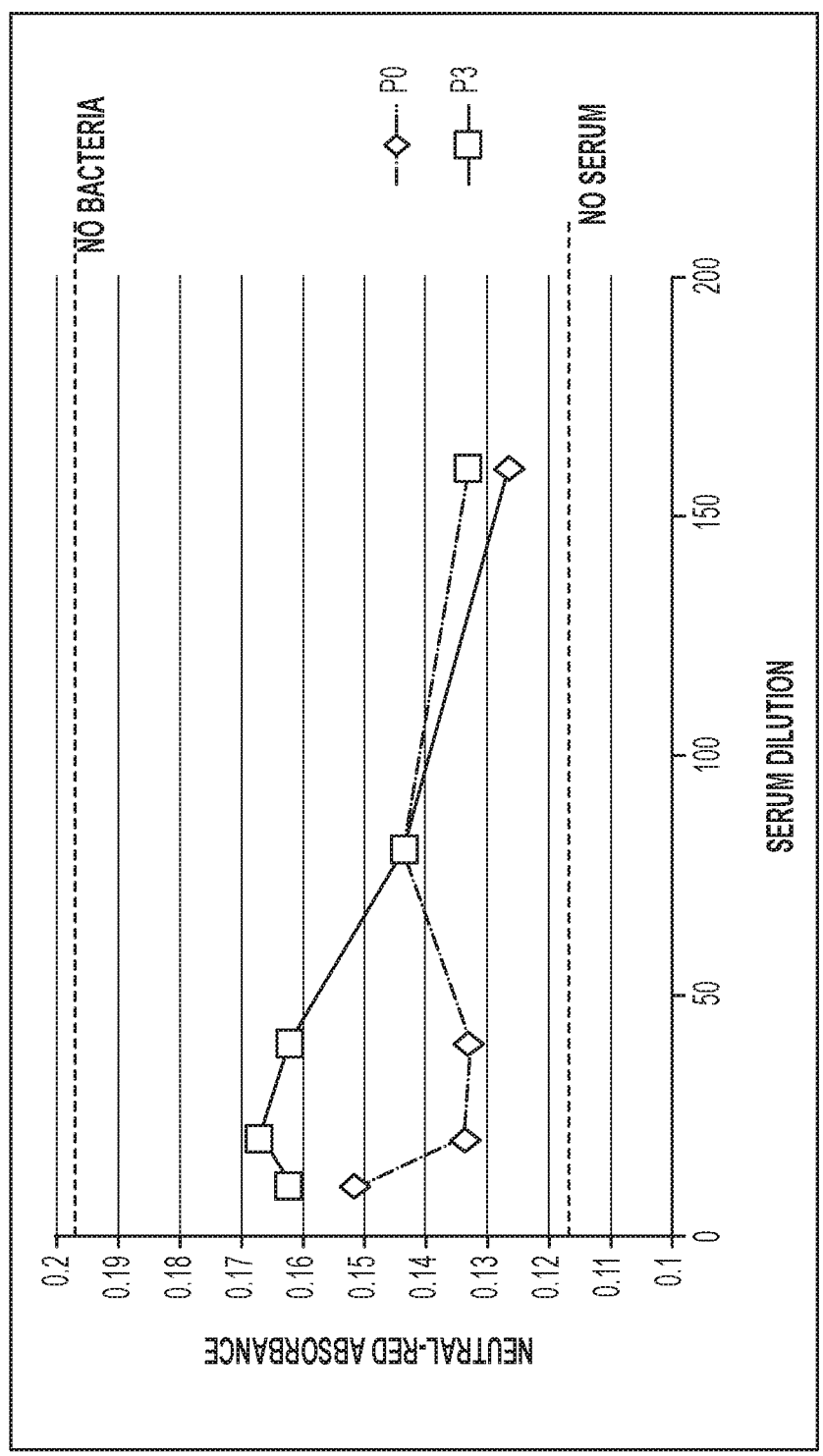
FIG. 24B A549 monolayer cells were infected with *Pseudomonas* strain PAK for 4 hours in the presence of serum from NCB006 Rhavi-FlaB-PcrV (pool 3) at various dilutions. Cells were washed with PBS and incubated for 1 hour with Neutral-Red. Cells were lysed and the dye absorbance in each well was recorded. Anti-Rhavi-FlaB-PcrV (P3) sera protected cells from *Pseudomonas* strain PAK cytotoxic intoxication compared to preimmune serum out to a dilution of 1 to 40.

A model of prevention of cell cytotoxicity by *Pseudomonas* bacteria (Warrener et al., 2014) was used to test the potency of an anti-Rhavi-FlaB-PcrV FT rabbit antibody and is shown in FIG. 24A. Anti-PcrV antibody protection of A549 (Lung Carcinoma) cells from intoxication by *Pseudomonas* strain PAK (O6:FlaA1) was obtained as follows. A549 monolayers were infected with *Pseudomonas* strain PAK (O6:FlaA1) for 4 h in the presence of a 10% serum from rabbits (pool of 3, post third immunization, P3) vaccinated with a Rhavi-FlaB-PcrV fusion protein. Anti-Rhavi-FlaB-PcrV sera protected cells from intoxication with *Pseudomonas* strain PAK compared to preimmune serum as seen by fewer rounded and detached cells. In a following experiment (FIG. 24B), A549 monolayer cells were infected with *Pseudomonas* strain PAK for 4 h in the presence of serum anti Rhavi-FlaB-PcrV (pool 3, P3) at various dilutions. Cells were washed with PBS and incubated for 1 h with Neutral-Red. Cells were lysed and the dye absorbance in each well was recorded. Anti-Rhavi-FlaB-PcrV (P3) sera protected cells from PAK intoxication compared to preimmune serum out to a dilution of 1 to 40.

Figure 25:
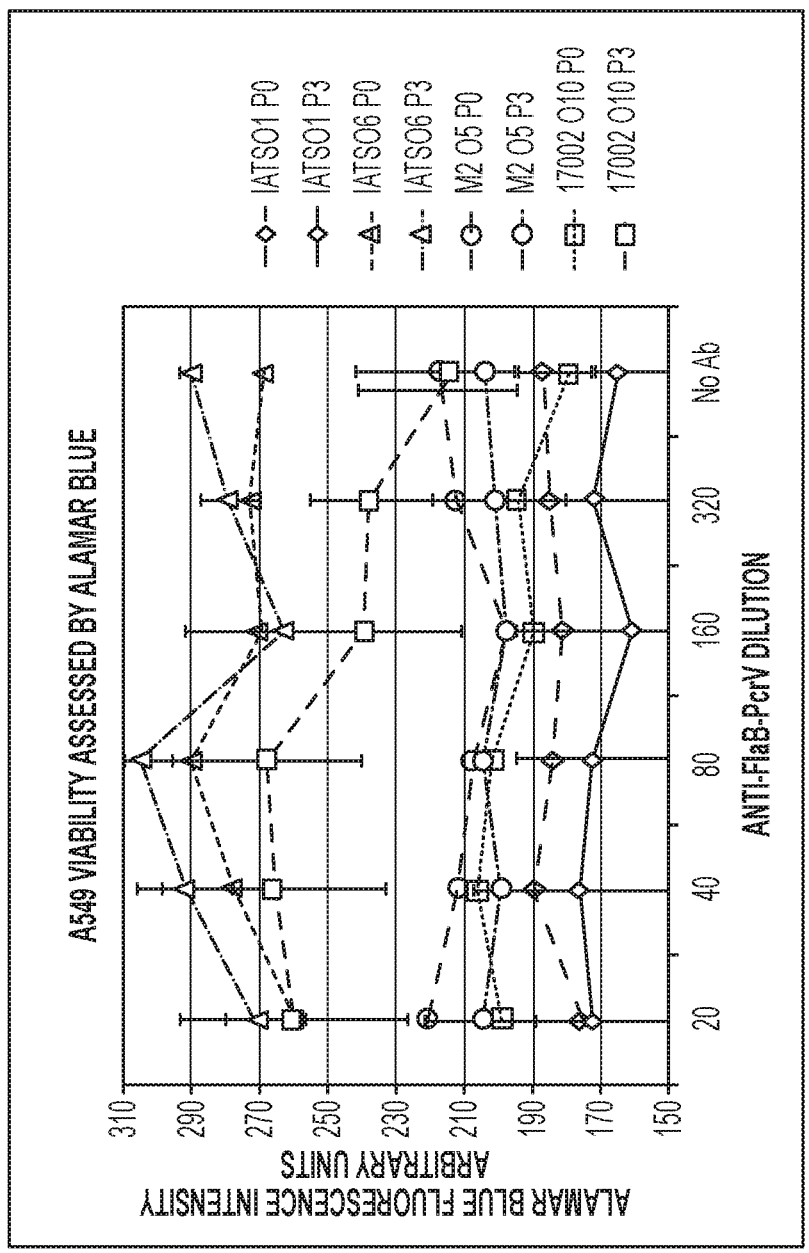
FIG. 25 depicts a cytotoxicity assay using A549 cells and an anti-FlaB-PcrV rabbit serum (post third immunization; P3) with various *Pseudomonas* strains: with highly toxic PA IATS O1 (closed diamond), no serum protection from cytotoxicity; with cytotoxic PA M2 O5 (closed circle), no serum protection; with cytotoxic PA 17002 O10 (closed rectangle), there is clear serum protection; with non-cytotoxic PA IATS O6 (closed triangle), no toxicity detected.

Without wishing to be bound by any theory, the polyclonal nature of the response to Rhavi-FlaB-PcrV as well as its configuration within the fusion protein may be the reason for the increase in the affinity of the antibody to the PcrV component of the fusion protein. Several *Pseudomonas* strains were tested in this cytotoxic assay using A549 cells and an anti-FlaB-PcrV rabbit serum (post third immunization; P3) (FIG. 25): with the highly toxic PA IATS O1 (closed diamond), no serum protection from cytotoxicity was observed; with the cytotoxic PA M-2 O5 strain (closed circle) no serum protection as well; with non-cytotoxic PA IATS O6 (closed triangle) no toxicity was found; with the cytotoxic PA 17002 (O10) (closed rectangle) there was clear serum protection; These variations in serum protection depending on the strain might reflect the expression and the level of the PcrV target on the *Pseudomonas* strains.

Cell-Attachment Assay

*Klebsiella* attachment to A549 cells was assayed as described (Clements et al., 2008) with some modifications. Rabbit antiserum raised against fimbrial protein MrkA were diluted into RPMI buffer (without supplements) and added to A549 cells seeded in 96-well plates. An equal volume of *K. pneumoniae* O5 strain 6997 ($10^4$ CFU/ml) was mixed with the antiserum dilutions. The infected cells were incubated for 1 h at 37° C. and 5% $CO_2$ after which time the wells were washed 6 times with sterile PBS to remove unbound bacteria. Cells were lysed with 0.1% Triton X-100 in PBS and an aliquot of the solution was plated onto HSA. Plates were incubated overnight and the number of CFU enumerated. A positive assay results when the number of adherent *Klebsiella* are reduced with MrkA antiserum compared to an equal dilution of preimmune serum.

Figure 23:
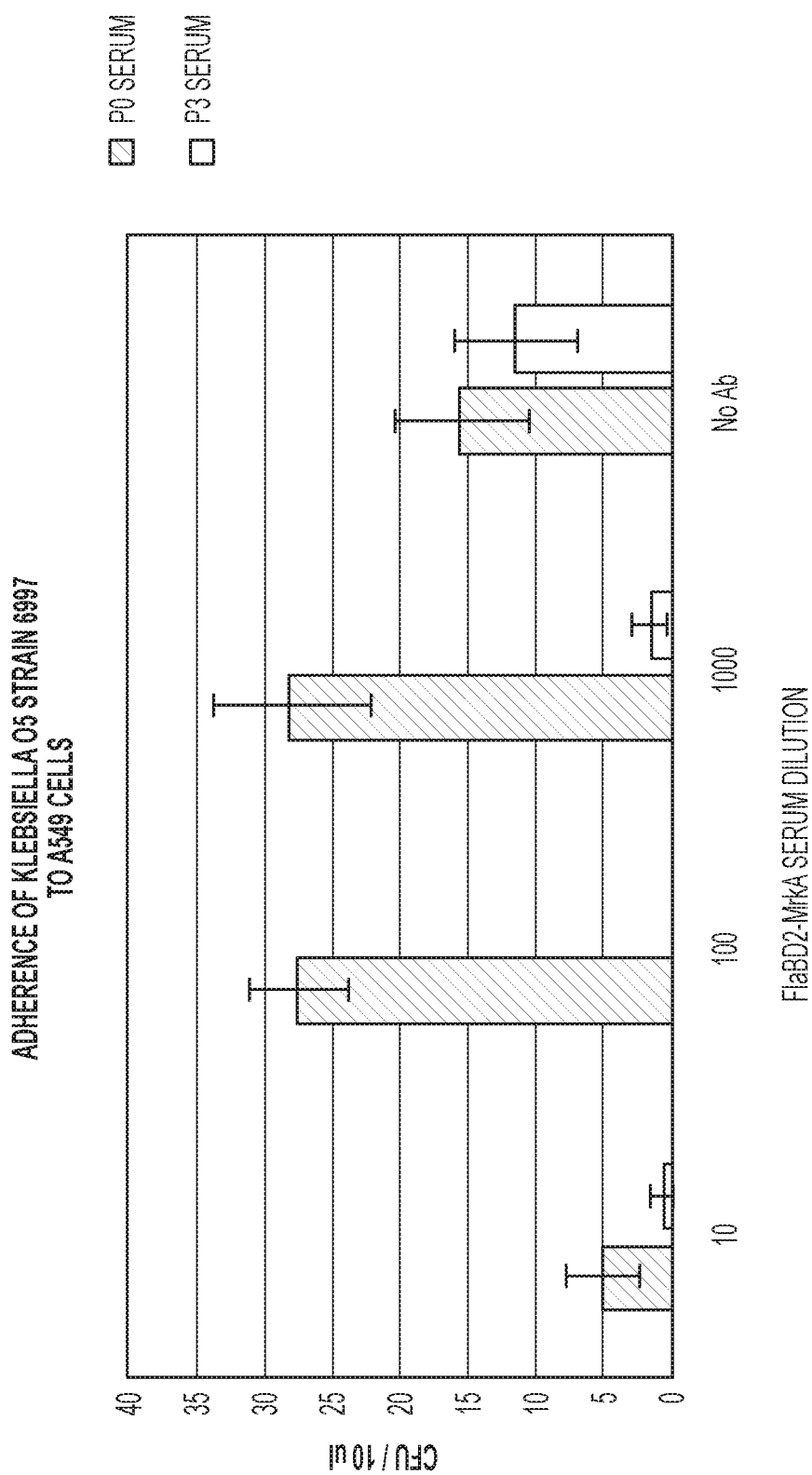
FIG. 23 shows the blocking of adherence of KP O5 6997 (origin South Africa) to A549 (lung carcinoma) cells by different dilutions of anti-FlaBD2-MrkA rabbit serum. FlaBD2-MrkA (post third immunization, P3) serum inhibited binding of *Klebsiella* strain 6997 to A549 cells while preimmune serum did not. This indicates that the MrkA protein component of the FlaBD2-MrkA FP was properly folded and elicited functional antibodies.

The blocking of adherence of *Klebsiella* KP O5 6997 (origin South Africa) to A549 Cells by an anti-Rhavi-FlaBD2-MrkA rabbit serum is shown in FIG. 23. High titer Rhavi-FlaBD2-MrkA (post third immunization, P3) specific serum significantly inhibited binding of KP Strain 6997 to A549 cells up to a dilution of 1/1000 while a preimmune serum (P0) did not. This indicated that the MrkA protein component of the Rhavi-FlaBD2-MrkA FP was properly folded and capable of eliciting functional blocking antibodies specific for the native MrkA on the surface of KP bacteria. A second experiment was carried out using individual anti-MrkA rabbit antisera obtained by immunization with the two MrkA rhizavidin fusion proteins Rhavi-FlaB-D2-MrkA and Rhavi-PcrV-MrkA, the results of which are summarized in Table 13. All MrkA FPs rabbit sera (except for one #804) were able to reduce adherence of *Klebsiella* O5 strain 6997 to A549 Cells indicating that these 2 rhizavidin FPs have the potential to elicit functional MrkA-specific antibodies.

TABLE 13

Anti-MrkA serum inhibition of *Klebsiella* O5 strain 6997 binding To A549 Cells

| Rabbit Serum | Dilution To Which P3 Reduced Adherence |
|---|---|
| # 800 - Rhavi FlaBD2 MrkA | 1 to 150 |
| # 801 - Rhavi FlaBD2 MrkA | 1 to 2400 |
| # 802 - Rhavi FlaBD2 MrkA | 1 to 75 |
| # 803 - Rhavi PcrV MrkA | 1 to 300 |
| # 804 - Rhavi PcrV MrkA | 0 Decrease |
| # 805 - Rhavi PcrV MrkA | 1 to 75 |

MrkA Antibody Response Assay

*Klebsiella* that express MrkA/type-3 fimbriae are agglutinated by anti-MrkA antibody, causing the bacteria to cluster and fall out of solution. Preimmune or immune sera were evaluated from rabbits that had been inoculated with Rhavi-MrkA-his, Rhavi-FlaB-D2-MrkA-his, or Rhavi-PcrV-MrkA-his carrier proteins. *Klebsiella* strain 4425 (O5:K57) was incubated with serum dilutions in PBS at 25° C. for 1 h in 96-well round-bottom microtiter plates. Plates were gently shaken to suspend non-agglutinated bacteria. The supernatant from each well was carefully removed and transferred to a fresh microtiter plate and the light scattering at 600 nm was measured to assess solution turbidity. A positive result is obtained when the absorbance is reduced from that of a control well without antibody indicating decreased number of bacteria in the supernatant due to antibody induced agglutination. The result of the assay is recorded as the highest antibody dilution (lowest concentration) at which *K. pneumoniae* was agglutinated by immune serum more than preimmune serum as measured by the difference in absorbance at 600 nm.

Assessment of the agglutination of *Klebsiella pneumoniae* strains O5K57, strain 4425 and O1 K22, strain 170381, with rabbit antisera to various MrkA rhizavidin fusion protein constructs: Rhavi-FlaB-D2-MrkA and Rhavi-PcrV-MrkA are summarized in Table 14. The titers for 3 individual rabbits antisera specific for each construct post second (P2) and third (P3) immunizations are the highest serum dilution with detectable agglutination. In this experiment, agglutinated clumps are allowed to settle, and the remaining (non-agglutinated) amounts of bacteria were measured at optical density (OD) 600 nm. MrkA-specific antibodies induced by the 2 constructs Rhavi-FlaB-D2-MrkA and Rhavi-PcrV-MrkA recognized MrkA expressed on both *Klebsiella* strains indicating that the MrkA component on these 2 fusion proteins is properly folded and generates a functional antibody response.

TABLE 14

Agglutination of *Klebsiella* bacteria by rhizavidin FP MrkA-specific antibodies

| | | Highest serum solution with detectable agglutination | | | |
|---|---|---|---|---|---|
| | | KP 4425 O5 K57 | | KP 170381 O1 K22 | |
| Protein Construct | Rabbit # | P2 | P3 | P2 | P3 |
| Rhavi-FlaB-D2-MrkA-His | AFV800 | $10^3$ | $10^5$ | $10^2$ | $10^3$ |
| | AFV801 | $10^4$ | $10^5$ | $10^3$ | $10^5$ |
| | AFV802 | $10^4$ | $10^4$ | $10^2$ | $10^4$ |
| Rhavi-PcrV-MrkA-His | AFV803 | $10^3$ | $10^4$ | $10^2$ | $10^4$ |
| | AFV804 | $10^4$ | $10^5$ | $10^2$ | $10^5$ |
| | AFV805 | $10^4$ | $10^4$ | $10^2$ | $10^4$ |

Example 8: *P. aeruginosa* Thermal Injury and Bacteremia Mouse Models

The thermal injury and bacteremia models were performed as described with modifications (Neely et al., 2002). For thermal injury, 11-week-old CD-1 outbred mice were shaved dorsally and anesthetized with ketamine and xylazine before exposure to a heat-resistant polymer card template with a 1 by 1.5 inch opening. This platform was designed to induce a 12-15% total body surface area thermal injury. Ethanol (0.5 ml 100%) is evenly spread over the area of back outlined by the window, ignited and allowed to burn for precisely 10 seconds and then blown out. Immediately after the burn, the mice are given 0.5 ml of sterile normal saline for hydration. *P. aeruginosa* is then injected SC under the thermal wound. The wound is left uncovered. Animals are monitored closely for 14 days after infection for mortality and organ burden (i.e. distant dissemination).

Figure 26:
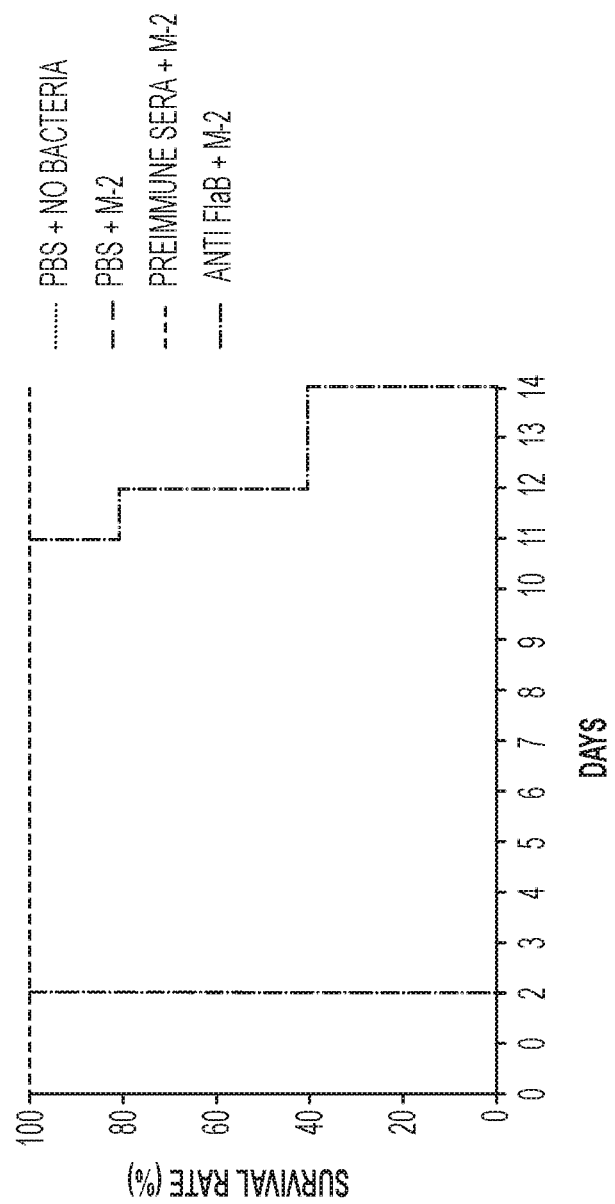
FIG. 26 depicts a Kaplan-Meier survival plot of mice that were burned and then infected with 28 colony forming units (CFU) of the FlaB expressing *Pseudomonas* strain M-2 (O5) administered into the burn wound. In this model, CD-1 mice were passively transferred preimmune rabbit sera or an anti-FlaB rabbit sera and either mock-infected with phosphate-buffered solution (PBS) or with *Pseudomonas* strain M-2 in PBS. Mice administered anti-FlaB antisera were protected (5/5 or 100% survival) for 10 days or more from wound challenge with *Pseudomonas* strain M-2, whereas all the mice from the other groups other than mock-infected mice died from the wound challenge.

In order to evaluate the potency of anti-*Pseudomonas* FlaB rabbit antibodies a burn wound sepsis mouse model was used (Cryz et al., 1984). In this model CD1 mice were burned as described above, and 28 CFU of *P. aeruginosa* strain M2 (O5:FlaB) (Burn-wound infection $LD_{50}<1\times10^2$) was injected into the burn wound. CD-1 mice were injected IP with PBS, preimmune, or anti-FlaB serum prior to the burn wound challenge. As shown in Kaplan-Meier survival plots in FIG. 26 mice were protected by anti-FlaB for 10 days or more from wound challenge with the FlaB expressing *Pseudomonas* strain M-2 whereas all the mice from the other groups died from the wound challenge.

In the bacteremia model, 7-week-old BALB/c mice are treated with control IgG or with vaccine-induced antibody by IP administration 24 h before IV challenge with *K. pneumoniae* or *P. aeruginosa*. Depending on the organism, animals are bled at intervals over 1-4 h to monitor clearance from the blood, and follow this by euthanizing the mouse and harvesting liver and spleen at 1-24 h after infection.

Example 9: Mouse Protection Assays

Clearance and Organ Burden Mouse Model

Figure 27:
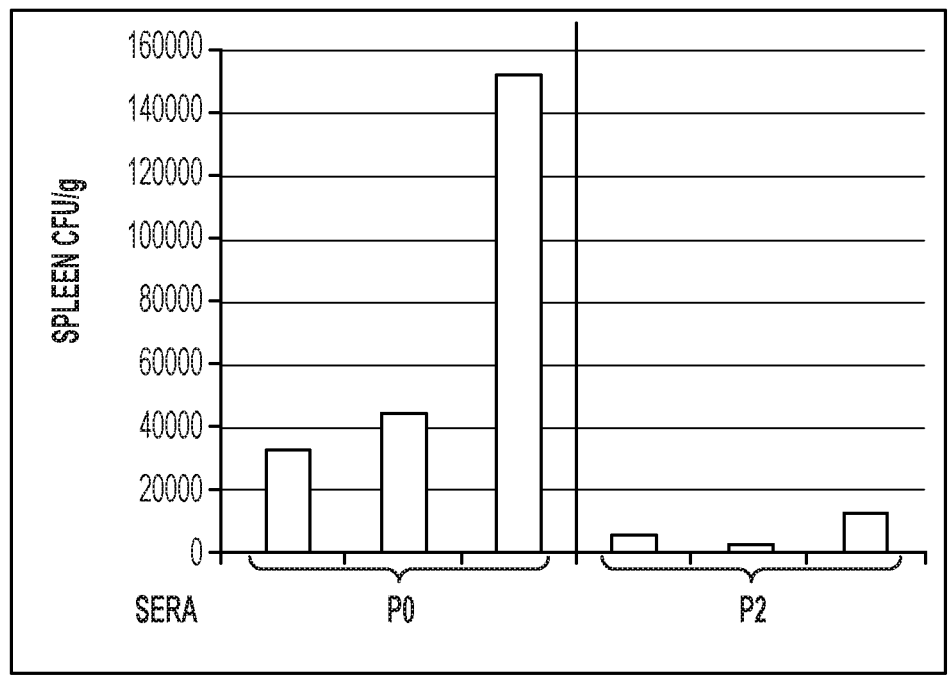
FIG. 27 shows clearance and organ burden in the mouse model of KP infection. Mice (CD1; groups of 3) were passively administered intraperitoneal (IP) rabbit serum against KPO1 BP-2a OPS-PRO-CN MAPS and then challenged intravenously (IV) with *Klebsiella* strain KP B5055 O1: K2 ($9 \times 10^4$ CFU). Spleen KP viable counts were measured 14 h post challenge. There is a clear reduction of viable counts of KP in the spleens of mice that received the immune serum (P2) compared to the spleens of mice that received the preimmune serum (P0). These data indicate that OPS 01 antibody generated by the backbone polymer in the variant MAPS vaccine was able to clear organisms from the mouse tissue, and hence had functional in vivo protective activity.

The ability of KP OPS-specific antibody to prevent *Klebsiella* infection was tested in a clearance and organ burden mice model. CD1 mice (groups of 3) were administered IP with a rabbit serum against KPO1 BP-2a OPS-PRO-CN MAPS and then challenged (IV) with *Klebsiella* KP B5055 O1 ($9\times10^4$ CFU). Spleen KP viable counts were measured 14 h post challenge. A significant reduction in KP viable counts in the spleen of mice that received the immune serum (P2) compared to the spleen of mice that received preimmune serum (P0) was observed (FIG. 27). This data indicate that O1 OPS-specific antibody induced by the OPS BP-2a MAPS vaccine has the ability to clear organisms from the spleen of the mice, hence is protective against *Klebsiella* infection.

KP (O1: K2) Grown in Sodium Salicylate

*Klebsiella pneumoniae* strain B5055 (O1: K2) was grown overnight in HySoy broth containing 2.5 mM sodium salicylate (Sigma) to decrease expression of CPS (Domenico, 1989). 12 ml of HySoy broth with 2.5 mM sodium salicylate was inoculated with 5% overnight culture then grown to mid-log phase (37° C. with shaking). Bacteria were pelleted by centrifugation then resuspended in sterile PBS to a concentration of approximately $1\times10^8$ CFU/ml. Concentrated bacteria were diluted in PBS to $2\times10^5$ CFU/ml. 1 h after IP administration of 0.1 ml rabbit serum, female mice CD-1, 8-12 week-old mice were infected IP with $2\times10^4$ CFU B5055 in 0.1 ml. Mice were monitored for mortality over a period of 7 days.

In experiment 1, CD1 mice were given 0.1 ml of KP O1 OPS BP-1; BP-2a PRO-CN MAPS rabbit or HK KP O1: K2 rabbit antisera (diluted 1/10) IP 1 h before being challenged IP with $2\times10^4$ of KP O1 B5055 organisms. The results of the experiment are summarized in Table 15.

TABLE 15

Mouse passive protection with KP O1: K2 organisms grown in sodium salicylate

| Serum | Mice surviving | | ELISA Titer |
|---|---|---|---|
| | Experiment 1 | Experiment 2 | |
| PBS | 0 of 5 | 0 of 5 | 0 |
| P0 BP-1 | 1 of 4 | 0 of 5 | 57 |
| P2 BP-1 | 0 of 5 | 2 of 5 | 537 |
| P0 BP-2a | 0 of 5 | 2 of 5 | 54 |
| P2 BP-2a | 5 of 5 | 4 of 5 | 11,973 |
| HK control* | 5 of 5 | 3 of 5 | 27,343 |

*HK KP O1 organisms rabbit antiserum positive control given at 1/10 dilution

In experiment 1, the positive control HK KP O1 bacteria and KP O1 OPS BP-2 PRO-CN MAPS antisera provided complete protection against KP O1: K2 (B5055) challenge whereas the PBS control and KP O1 OPS BP-1 PRO-CN MAPS antisera did not protect the mice.

In experiment 2, CD1 mice (5/group) were given IP 0.1 mL of a pool rabbit immune or preimmune serum prior to IP bacterial challenge with $2\times10^4$ of KP O1 B5055 bacteria. Mice received PBS and a KPO1 HK serum (1/10 diluted) as negative and positive control respectively. All KP O1 OPS PRO-CN MAPS sera were able to afford protection in the model although mice that received BP-2a (4 out of 5) survive significantly better the challenge. KP O1 OPS BP-1 PRO-CN MAPS sera afforded some protection with 2 out 5 mice surviving. None of the mice receiving PBS survived the challenge. These survival results are in good agreement and correlate quite well with the levels of anti-KP O1 OPS-specific IgG ELISA titers (i.e., better levels of protection were observed with higher levels of antibody).

Passive Protection Against *Pseudomonas* Organisms in a Mouse Model

The ability of PA OPS-specific antibody to prevent *Pseudomonas* infection was tested in a passive protection survival mice model using CD1-mice challenged IP by PA Strain 17002 (O10) along with D-galactosamine to sensitize the animals to the lethal effects of endotoxin (Galanos et al., 1979) and to render them more susceptible to infection. Mice received rabbit anti-2-valent PA O6/O10 BP-1 PRO-CN MAPS (rabbit AFV624 or AFV629, given IP) 1 h prior to being challenged with ($1\times10^6$ CFU) and D-galactosamine. The results are summarized in Table 16. In this protection study PA O6/O10 2v BP-1 PRO-CN MAPS immune serum (AFV624; P2) protected 40% more mice against PA O10 strain 17002 compared with preimmune serum (AFV624 P0). Similarly, PA O6/O10 2v BP-1 PRO-CN MAPS immune serum (AFV629; P2) protected 40% more mice against PA O10 strain 17002 compared with preimmune serum (AFV629 P0). A high titer rabbit antiserum positive control raised with heat-killed PA O10 bacteria gave significant protection versus the PBS control. The preimmune serum from some rabbits may have provided some protection compared with PBS (AFV624 P0). There seems to be some correlation between the levels of protection (survival) and the levels of vaccine-induced PA O10 OPS-specific IgG antibody as measured by ELISA (Table 16).

TABLE 16

Passive protection in mice challenged with
PA O10 Strain 17002 and D-galactosamine from
2-valent PA O6/O10 BP-1 PRO-CN MAPS group.

| Group | Survival | ELISA TITER PA O10 OPS (EU/ml) |
|---|---|---|
| PBS Control | 0/5 | |
| Anti-heat killed O10 | 4/5 | |
| Rabbit AFV624 P0 | 2/5 | 7,745,537 |
| | | 12.5 |
| Rabbit AFV624 P2 | 4/5 | 15,246 |
| Rabbit AFV629 P0 | 0/5 | 12.5 |
| Rabbit AFV629 P2 | 2/5 | 3,955 |

Figure 28:
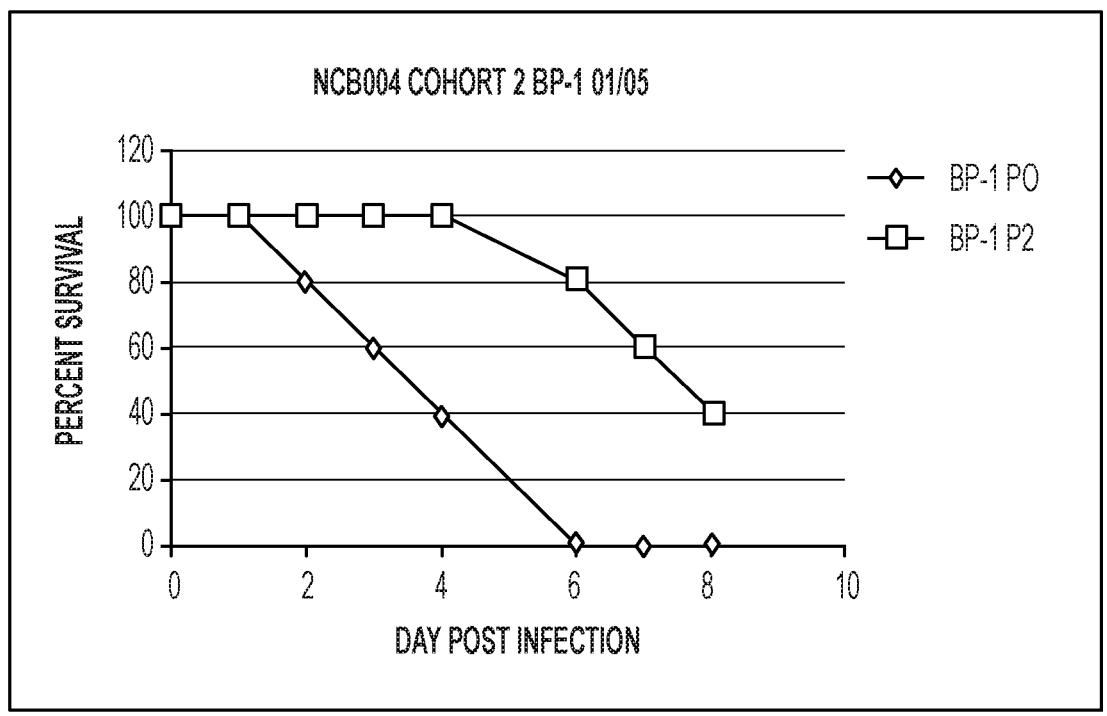
FIG. 28 depicts Kaplan-Meier survival for passive protection of mice administered rabbit sera against KPO1 BP-1 OPS-PRO-CN MAPS prior to infection with *Klebsiella* strain B5055 (O1: K2) grown in salicylate to reduce capsule expression. CD1 mice (5/group) were given IP 0.1 mL of a pool of rabbit immune (P2) or preimmune (P0) serum prior to IP bacterial challenge with $2 \times 10^4$ CFU *Klebsiella* strain B5055 (O1: K2). Kaplan-Meier survival plots for mice that received P0 or P2 KPO1 BP-1 OPS-PRO-CN MAPS sera are shown. The P2 sera protected in the model with a higher proportion of mice that had received KPO1 BP-1 OPS-PRO-CN MAPS antisera surviving and for an extended period of time relative to mice administered P0 sera.

FIG. 28 depicts Kaplan-Meier survival for passive protection of mice administered rabbit sera against KPO1 BP-1 OPS-PRO-CN MAPS prior to infection with *Klebsiella* strain B5055 (O1: K2) grown in salicylate to reduce capsule expression. CD1 mice (5/group) were given IP 0.1 mL of a pool of rabbit immune (P2) or preimmune (P0) serum prior to IP bacterial challenge with $2\times10^4$ CFU *Klebsiella* strain B5055 (O1: K2). Kaplan-Meier survival plots for mice that received P0 or P2 KPO1 BP-1 OPS-PRO-CN MAPS sera are shown. The P2 sera protected in the model with a higher proportion of mice that had received KPO1 BP-1 OPS-PRO-CN MAPS antisera surviving and for an extended period of time relative to mice administered P0 sera.

Example 10: Exemplary Multi-Valent Immunogenic Compositions

Exemplary 4-Valent KP Vaccine 4 different immunogenic complexes were separately prepared and then formulated together to prepare an exemplary 4-valent KP vaccine.

Each complex included a BP-1 polymer, prepared by conjugation of OPS from a KP single bacterial serotype to the oxidized K19 polysaccharide with subsequent biotinylation of the K19 polysaccharide. These were then complexed with a rhizavidin fusion carrier protein. The components of each of these complexes are detailed in Table 17.

TABLE 17

Components of complexes included in
exemplary 4-valent KP vaccine.

| Complex | BP-1 CPS | Pathogen | Serotype | Carrier Protein |
|---|---|---|---|---|
| 1 | KP K19 | *Klebsiella* | O1 | Rhavi-FlaBD2-MrkA |
| 2 | KP K19 | *Klebsiella* | O2 | Rhavi-FlaBD2-MrkA |
| 3 | KP K19 | *Klebsiella* | O3 | Rhavi-FlaBD2-MrkA |
| 4 | KP K19 | *Klebsiella* | O5 | Rhavi-FlaBD2-MrkA |

These four complexes were formulated together with an adjuvant as detailed below in Table 21.

Exemplary 8-Valent PA Vaccine 8 different immunogenic complexes were separately prepared and then formulated together to prepare an exemplary 8-valent PA vaccine.

Each complex included a BP-1 polymer, prepared by conjugation of OPS from a single PA bacterial serotype to the oxidized K19 polysaccharide with subsequent biotinylation of the K19 polysaccharide. These were then complexed with a rhizavidin fusion carrier protein. The components of each of these complexes are detailed in Table 18.

TABLE 18

Components of complexes included in
exemplary 8-valent PA vaccine.

| Complex | BP-1 CPS | OPS | Rhizavidin Fusion Carrier Protein |
|---|---|---|---|
| 1 | KP K19 | PAO1 | Rhavi-FlaBD2-MrkA |
| 2 | KP K19 | PAO2 | Rhavi-FlaBD2-MrkA |
| 3 | KP K19 | PAO3 | Rhavi-FlaBD2-MrkA |
| 4 | KP K19 | PAO4 | Rhavi-FlaBD2-MrkA |
| 5 | KP K19 | PAO5 | Rhavi-FlaBD2-MrkA |
| 6 | KP K19 | PAO6 | Rhavi-FlaBD2-MrkA |
| 7 | KP K19 | PAO10 | Rhavi-FlaBD2-MrkA |
| 8 | KP K19 | PAO11 | Rhavi-FlaBD2-MrkA |

These eight complexes were formulated together with an adjuvant as detailed below in Table 21.

Exemplary 12-valent KP/PA Vaccine 1

12 different immunogenic complexes were separately prepared and then formulated together to prepare exemplary 12-valent KP/PA vaccine 1.

Each complex included a BP-1 polymer, prepared by conjugation of an OPS to the oxidized K19 polysaccharide with subsequent biotinylation of the K19 polysaccharide. These were then complexed with a rhizavidin fusion carrier protein. The components of each of these complexes are detailed in Table 19.

TABLE 19

Components of complexes included in exemplary
12-valent KP/PA vaccine 1.

| Complex | BP-1 CPS | OPS | Rhizavidin Fusion Carrier Protein |
|---|---|---|---|
| 1 | KPK19 | KPO1 | Rhavi-FlaBD2-MrkA |
| 2 | KPK19 | KPO2 | Rhavi-FlaBD2-PcrV |
| 3 | KPK19 | KPO3 | Rhavi-FlaBD2-PcrV |
| 4 | KPK19 | KP05 | Rhavi-FlaBD2-PcrV |
| 5 | KPK19 | PAO1 | Rhavi-FlaBD2-PcrV |
| 6 | KPK19 | PAO2 | Rhavi-FlaBD2-PcrV |
| 7 | KPK19 | PAO3 | Rhavi-FlaBD2-PcrV |
| 8 | KPK19 | PAO4 | Rhavi-FlaBD2-PcrV |
| 9 | KPK19 | PAO5 | Rhavi-FlaBD2-MrkA |
| 10 | KPK19 | PAO6 | Rhavi-FlaBD2-MrkA |
| 11 | KPK19 | PAO10 | Rhavi-FlaBD2-MrkA |
| 12 | KPK19 | PAO11 | Rhavi-FlaBD2-MrkA |

These twelve complexes were formulated together with an adjuvant as detailed below in Table 21.

Exemplary 12-valent KP/PA Vaccine 2

12 different immunogenic complexes were separately prepared and then formulated together to prepare exemplary 12-valent KP/PA vaccine 2.

Each complex included a BP-1 polymer, prepared by conjugation of an OPS to the oxidized K19 polysaccharide with subsequent biotinylation of the K19 polysaccharide. These were then complexed with a rhizavidin fusion carrier protein. The components of each of these complexes are detailed in Table 20.

TABLE 20

Components of complexes included in exemplary
12-valent KP/PA vaccine 2.

| Complex | BP-1 CPS | OPS | Rhizavidin Fusion Carrier Protein |
|---|---|---|---|
| 1 | KPK19 | KPO1 | Rhavi-FlaBD2-MrkA |
| 2 | KPK19 | KPO2 | Rhavi-FlaBD2-MrkA |
| 3 | KPK19 | KPO3 | Rhavi-FlaBD2-MrkA |
| 4 | KPK19 | KPO5 | Rhavi-FlaBD2-MrkA |

TABLE 20-continued

Components of complexes included in exemplary 12-valent KP/PA vaccine 2.

| Complex | BP-1 CPS | OPS | Rhizavidin Fusion Carrier Protein |
|---|---|---|---|
| 5 | KPK19 | PAO1 | Rhavi-FlaBD2-MrkA |
| 6 | KPK19 | PAO2 | Rhavi-FlaBD2-MrkA |
| 7 | KPK19 | PAO3 | Rhavi-FlaBD2-MrkA |
| 8 | KPK19 | PAO4 | Rhavi-FlaBD2-MrkA |
| 9 | KPK19 | PAO5 | Rhavi-FlaBD2-MrkA |
| 10 | KPK19 | PAO6 | Rhavi-FlaBD2-MrkA |
| 11 | KPK19 | PAO10 | Rhavi-FlaBD2-MrkA |
| 12 | KPK19 | PAO11 | Rhavi-FlaBD2-MrkA |

These twelve complexes were formulated together with an adjuvant as detailed below in Table 21.

Example 11: Rabbit Immunization Study of *P. aeruginosa/K. Pneumoniae* 12-Valent Vaccine Immunization of Animals Prior to immunization of rabbits, exemplary 4-valent KP vaccine, exemplary 8-valent PA vaccine, exemplary 12-valent KP/PA vaccine 1, and exemplary 12-valent KP/PA vaccine 2 were formulated with adjuvant approximately 48 h prior to injection. The complexes were adsorbed to adjuvant at a final concentration of 10 µg/ml for the 5 µg PS dose and 2 µg/ml for the 1 µg PS dose of each serotype BP-1 as either single or a multivalent mixture with 40 mM histidine, pH 5.5, 150 mM NaCl, and 1.25 mg/ml aluminum phosphate gel with end-over-end mixing overnight at 4° C. These formulated mixtures were used directly for immunizations at a volume of 0.5 ml per dose. A summary of the compositions of exemplary 4-valent KP vaccine, exemplary 8-valent PA vaccine, exemplary 12-valent KP/PA vaccine 1, and exemplary 12-valent KP/PA vaccine 2 is provided in Table 21.

TABLE 21

Summary of vaccine formulations used in rabbit study NCB012.

| Group | Vaccine | Pathogen | Carrier protein | Serotypes | Dose PS (total) | Protein:PS ratio (total protein) | Adjuvant | Rabbits |
|---|---|---|---|---|---|---|---|---|
| 1 | 12-valent KP/PA vaccine 2 5 µg PS per BP | *Pseudomonas* | Rhavi-FlaBD2-MrkA-his | O1, O2, O3, O4, O5, O6, O10, O11 | 5 µg (60 µg) | 3:1 (180 µg) | 625 µg AlPO4 | 10 |
|  |  | *Klebsiella* | Rhavi-FlaBD2-MrkA-his | O1, O2, O3, O5 |  |  |  |  |
| 2 | 12-valent KP/PA vaccine 2 1 µg PS per BP | *Pseudomonas* | Rhavi-FlaBD2-MrkA-his | O1, O2, O3, O4, O5, O6, O10, O11 | 1 µg (12 µg) | 3:1 (36 µg) | 625 µg AlPO4 | 10 |
|  |  | *Klebsiella* | Rhavi-FlaBD2-MrkA-his | O1, O2, O3, O5 |  |  |  |  |
| 3 | 8-valent PA | *Pseudomonas* | Rhavi-FlaBD2-MrkA-his | O1, O2, O3, O4, O5, O6, O10, O11 | 5 µg (40 µg) | 3:1 (120 µg) | 625 µg AlPO4 | 10 |
| 4 | 4-valent KP | *Klebsiella* | Rhavi-FlaBD2-MrkA-his | O1, O2, O3, O5 | 5 µg (20 µg) | 3:1 (60 µg) | 625 µg AlPO4 | 10 |
| 5 | 12-valent KP/PA vaccine 1 5 µg PS per BP | *Pseudomonas* | Rhavi-FlaBD2-MrkA-his | O5, O6, O10, O11 | 5 µg (60 µg) | 3:1 (180 µg) | 625 µg AlPO4 | 10 |
|  |  | *Klebsiella* | Rhavi-FlaBD2-MrkA-his | O1, O3 |  |  |  |  |
|  |  | *Pseudomonas* | Rhavi-FlaBD2-PerV-his | O1, O2, O3, O4 |  |  |  |  |
|  |  | *Klebsiella* | Rhavi-FlaBD2-PerV-his | O2, O5 |  |  |  |  |
| 6 | 12-valent KP/PA vaccine 1 1 µg PS per BP | *Pseudomonas* | Rhavi-FlaBD2-MrkA-his | O5, O6, O10, O11 | 1 µg (12 µg) | 3:1 (36 µg) | 625 µg AlPO4 | 10 |
|  |  | *Klebsiella* | Rhavi-FlaBD2-MrkA-his | O1, O3 |  |  |  |  |
|  |  | *Pseudomonas* | Rhavi-FlaBD2-PerV-his | O1, O2, O3, O4 |  |  |  |  |
|  |  | *Klebsiella* | Rhavi-FlaBD2-PerV-his | O2, O5 |  |  |  |  |

12-valent KP/PA vaccine 1 was administered to treatment group 5 and 6 (with FlaBD2-MrkA and FlaBD2-PcrV as carrier proteins) and 12-valent KP/PA vaccine 2 was administered to treatment group 1 and 2 (with FlaBD2-MrkA as carrier protein). For comparison, two additional treatment groups that received an 8-valent PA vaccine or a 4-valent KP vaccine were included in this study. Treatment group 3 received an 8-valent PA vaccine and treatment group 4 received a 4-valent KP vaccine. Groups 1, 3, 4, and 5 received 5 µg of each polysaccharide (PS) in the vaccine and treatment groups 2 and 6 received a lower dose of 1 µg of each PS in the vaccine. All vaccines contained the same amount of aluminum phosphate as adjuvant (625 µg).

Two IM immunizations (0.5 ml) were administered at a 4 week interval to 4 month old New Zealand White rabbits (Cocalico Biologicals, n=10 per group). Blood samples were collected at 4 weeks after the first immunization and 2 weeks after the second immunization.

Immune Responses to OPS

Figure 29:
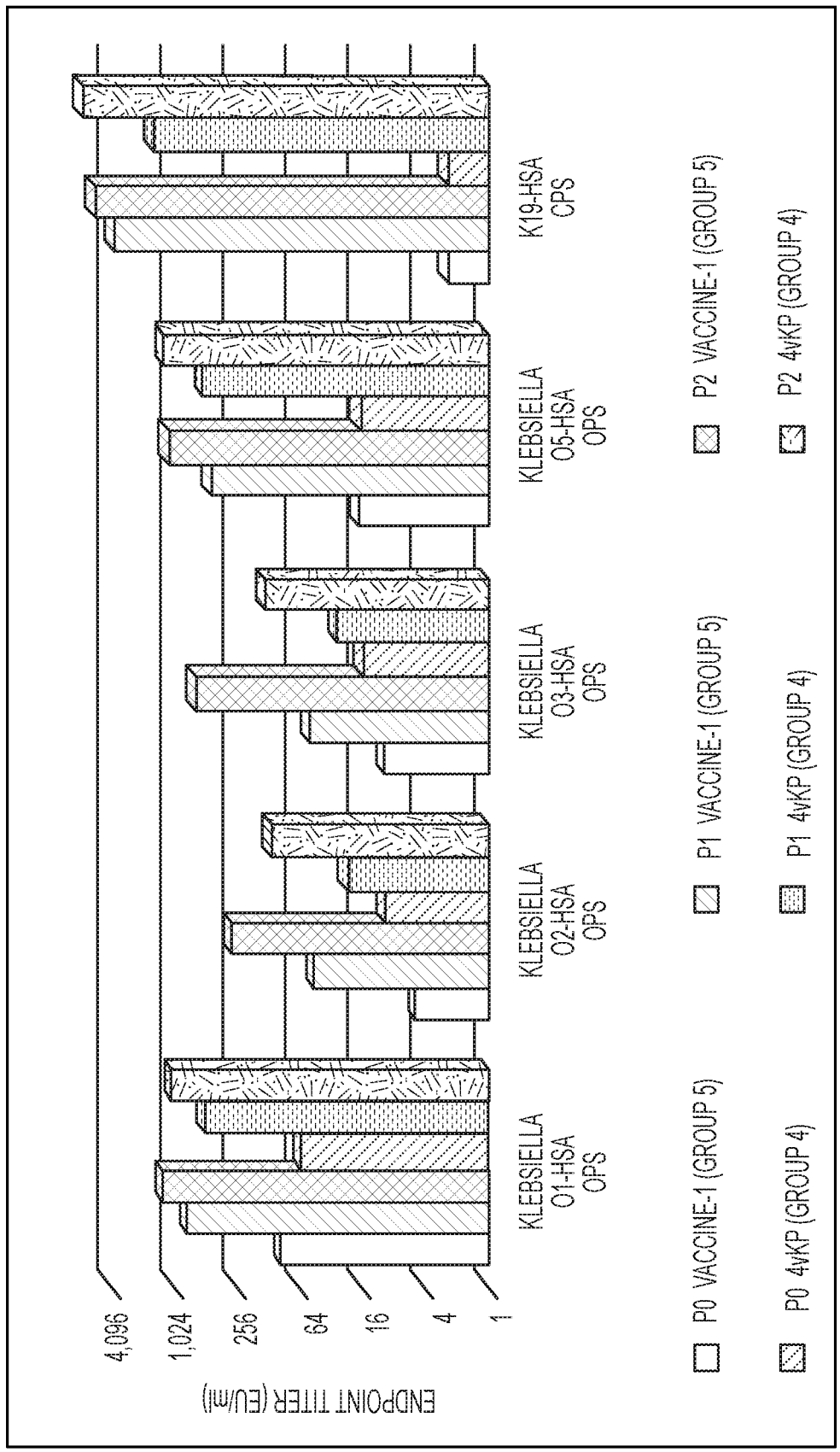
FIG. 29 depicts the results of the KP OPS IgG endpoint ELISA titers for pooled sera from rabbits immunized with 12-valent KP/PA vaccine 1 (5 μg PS contributed by each type of BP in the vaccine, treatment group 5) compared with a 4-valent KP vaccine (5 μg PS contributed by each type of BP in the vaccine, treatment group 4).

Immune Responses to KP OPS in 12-Valent KP/PA Vaccine 1 Compared to a 4-Valent KP Vaccine FIG. 29 depicts the results of the KP OPS IgG endpoint ELISA titers for pooled sera from rabbits immunized with 12-valent KP/PA vaccine 1 (5 µg dose, treatment group 5) compared with a 4-valent KP vaccine (5 µg dose, treatment group 4).

A robust IgG response to all KP OPS vaccine serotypes (as well as to KP19 CPS) was demonstrated with no significant differences in titers between each KP OPS type in the 4-valent KP vaccine and each of the corresponding KP OPS IgG titer of 12-valent KP/PA vaccine 1. There is a trend towards a slightly better KP OPS response induced with the 12-valent KP/PA vaccine 1. These results also indicate that there is no negative interference in the immune response to each of the KP OPS of the 4-valent KP vaccine when it is combined with the additional 8 PA OPS that are included in the 12-valent KP/PA vaccine 1 (all prepared as BP-1 MAPS).

Figure 30:
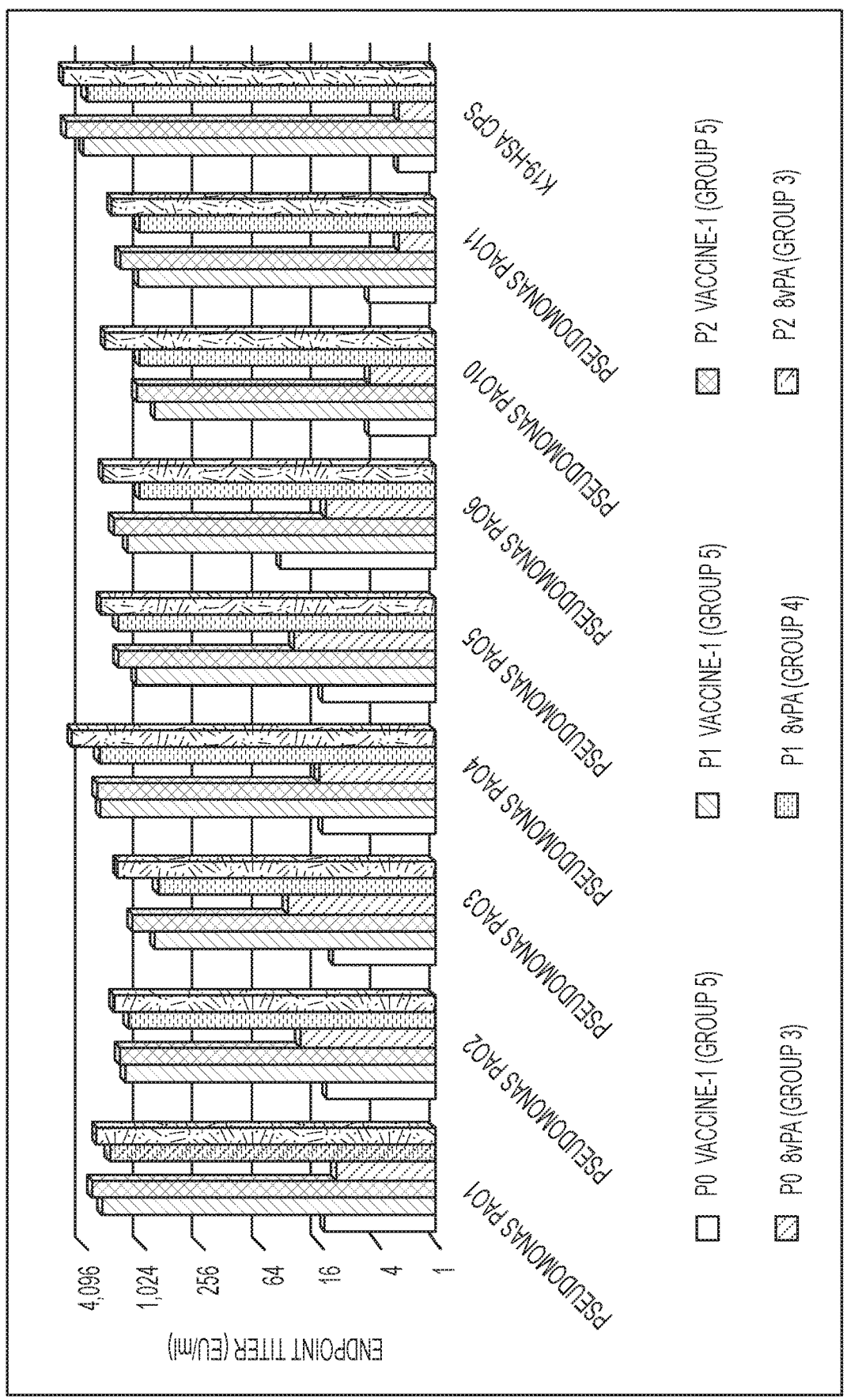
FIG. 30 depicts the results of the PA OPS IgG endpoint ELISA titers for pooled sera from rabbits immunized with 12-valent KP/PA vaccine 1 (5 μg PS contributed by each type of BP in the vaccine, treatment group 5) compared with an 8-valent PA vaccine (5 μg PS contributed by each type of BP in the vaccine, treatment group 4).

Immune Responses to PA OPS in 12-Valent KP/PA Vaccine 1 Compared to an 8-Valent PA Vaccine FIG. 30 depicts the results of the PA OPS IgG endpoint ELISA titers for pooled sera from rabbits immunized with 12-valent KP/PA vaccine 1 (5 µg dose, treatment group 5) compared with an 8-valent PA vaccine (5 µg dose, treatment group 3).

As observed for the KP OPS response, robust IgG responses to all PA OPS vaccine serotypes were demonstrated with no significant differences in titers between each PA OPS type in the 8-valent PA MAPS vaccine and each of the corresponding PA OPS IgG titer of 12-valent KP/PA vaccine 1. These results indicate that there is no negative interference in the immune response to each of the PA OPS of the 8-valent vaccine when it is combined with the additional 4 KP OPS in 12-valent KP/PA vaccine 1 (all prepared as BP-1 MAPS). Robust IgG responses are also demonstrated to each of the PA OPS after one immunization (P1) with no significant increases after the second immunization (P2).

Immune Responses to 12-Valent KP/PA Vaccine 1 at Two Different Dose Levels

Figure 31:
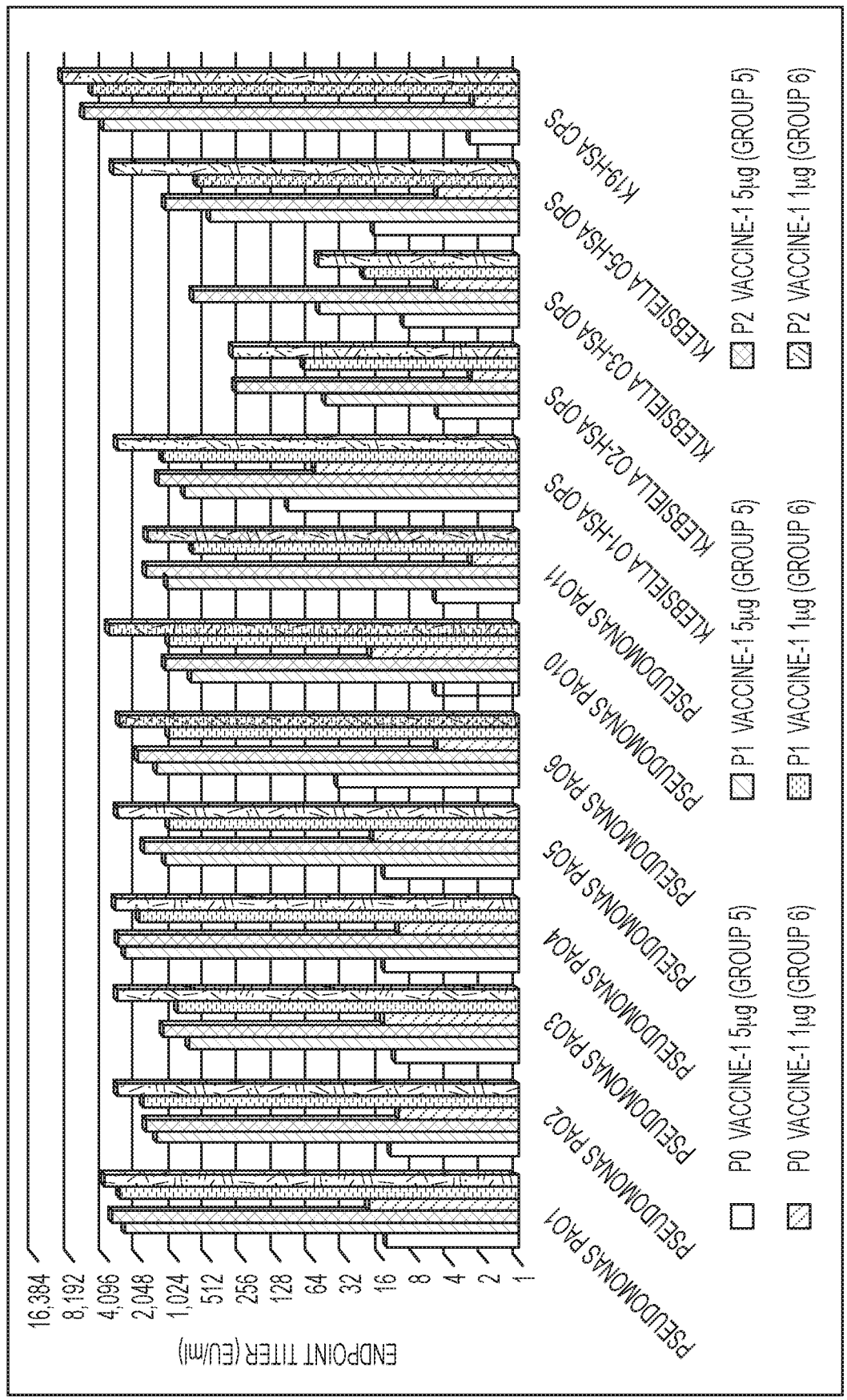
FIG. 31 depicts the results of the PA OPS IgG endpoint ELISA titers for pooled sera from rabbits immunized with 12-valent KP/PA vaccine 1 (e.g., 60 μg total PS in vaccine; 5 μg PS contributed by each type of BP in the vaccine) compared with 12-valent KP/PA vaccine 1 at (1 μg PS contributed by each type of BP in the vaccine, treatment group 6).

FIG. 31 depicts the results of the PA OPS IgG endpoint ELISA titers for pooled sera from rabbits immunized with 12-valent KP/PA vaccine 1 at 5 µg PS contributed by each type of BP in the vaccine dose (treatment group 5) compared with 12-valent KP/PA vaccine 1 at 1 µg PS contributed by each type of BP in the vaccine (treatment group 6)

No significant differences in IgG titers to PA and KP OPS were observed for 12-valent KP/PA vaccine 1 when the 5 µg dose and the 1 µg dose treatment groups were compared after one (P1) or after two immunizations (P2), except for KP O3 where the second immunization showed an improved IgG response.

Figure 32:
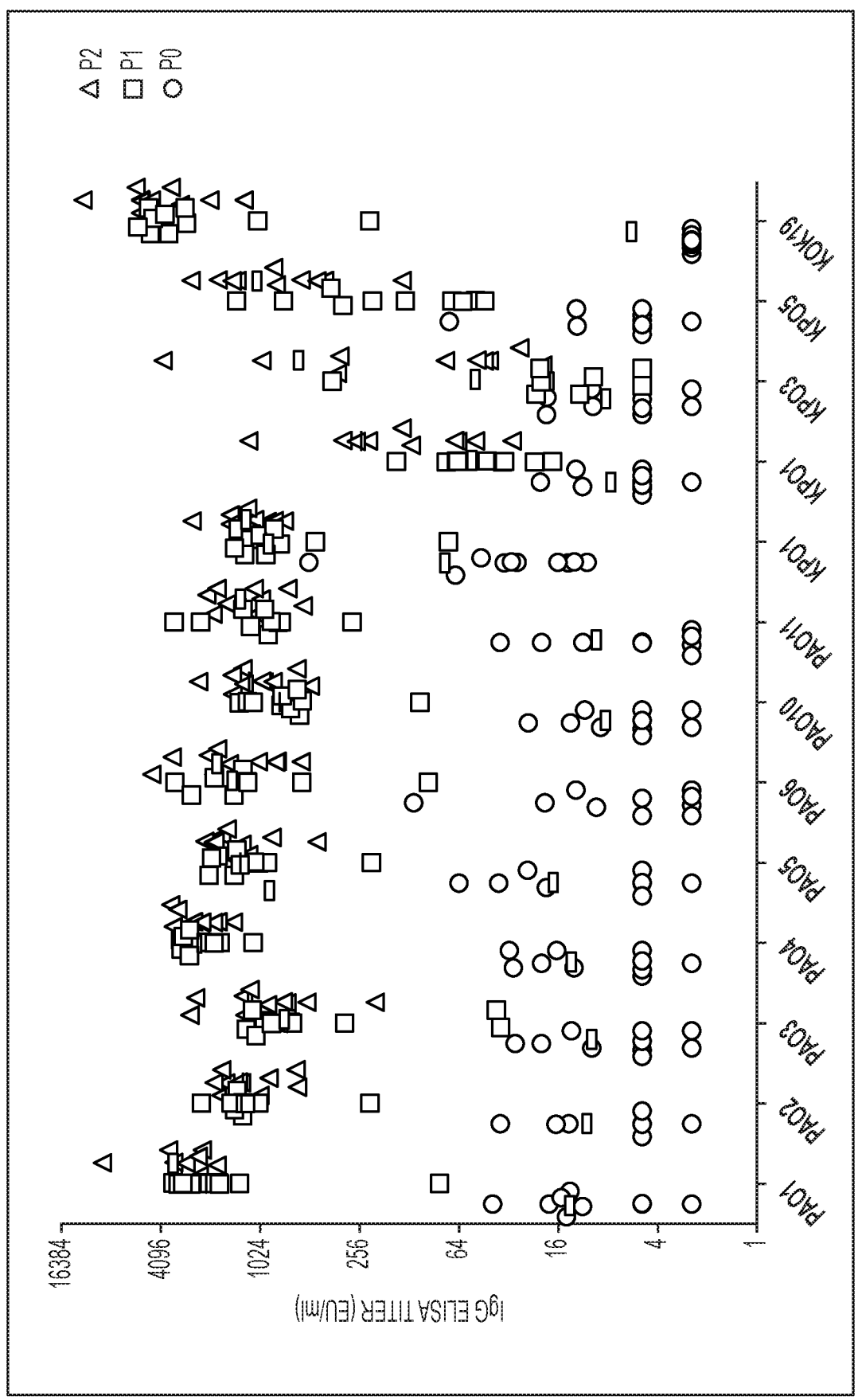
FIG. 32 depicts individual IgG titers against each PS in 12-valent KP/PA vaccine 1 at 5 μg dose (e.g., 60 μg total PS in vaccine; 5 μg PS contributed by each type of BP in the vaccine).
Figure 33:
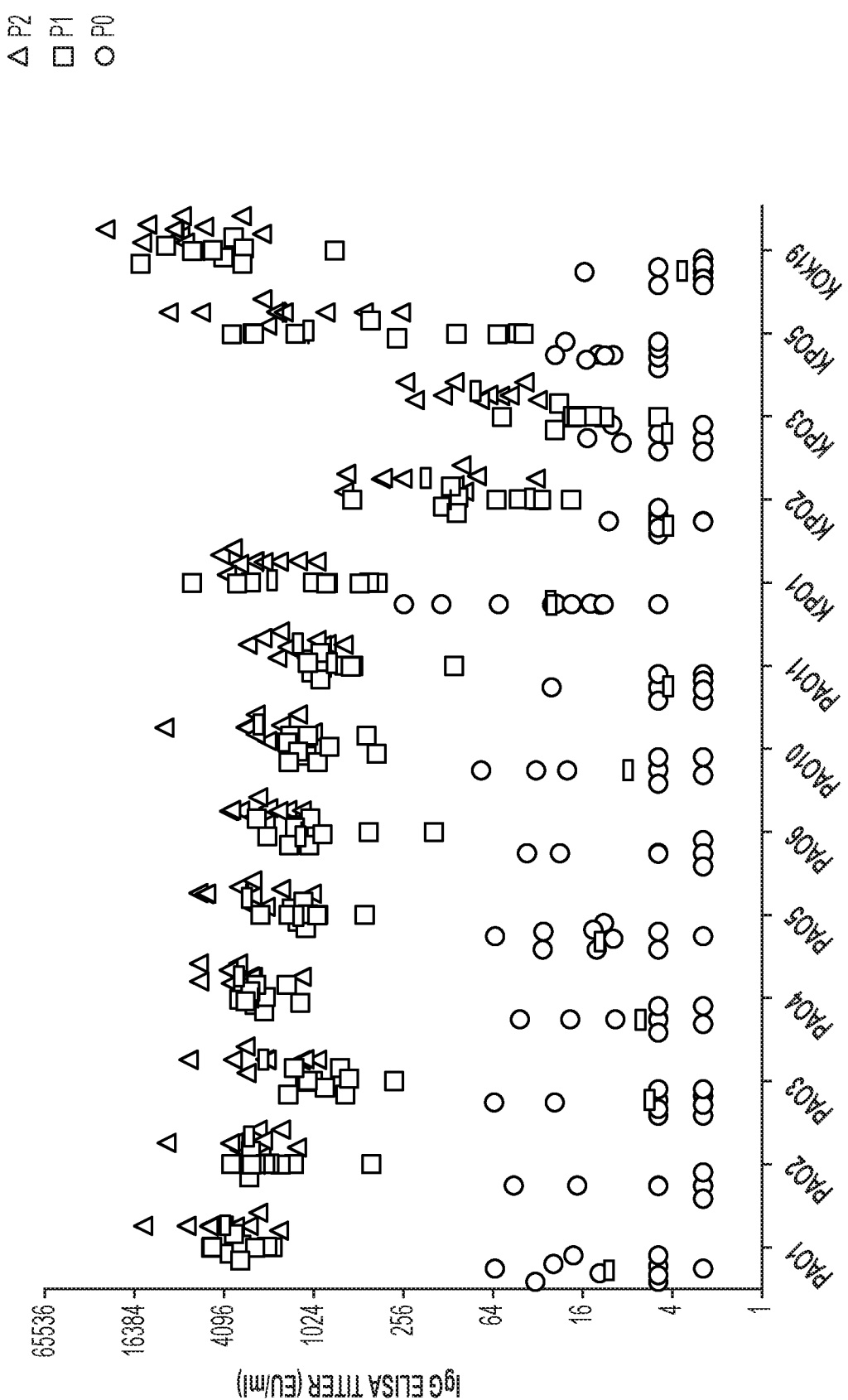
FIG. 33 depicts individual IgG titers against each PS in 12-valent KP/PA vaccine 1 at 1 μg dose (e.g., 12 μg total PS in vaccine; 1 μg PS contributed by each type of BP in the vaccine).

The individual IgG OPS-specific ELISA titers for 12-valent KP/PA vaccine 1 28 days post first immunization (P1) and 14 days post second immunization (P2) are shown in FIG. 32 and FIG. 33. Robust IgG responses to all 12 OPS vaccine serotypes as well as to the KP K19 CPS are demonstrated for 12-valent KP/PA vaccine 1 at 5 µg dose (FIG. 32) and at 1 µg dose (FIG. 33). However, although robust, the magnitude of the IgG response to OPS KPO2 and KPO3 is not as large as the response to KPO1 and KPO5, particularly after the first immunization. The highest response was observed for KO K19.

Figure 34:
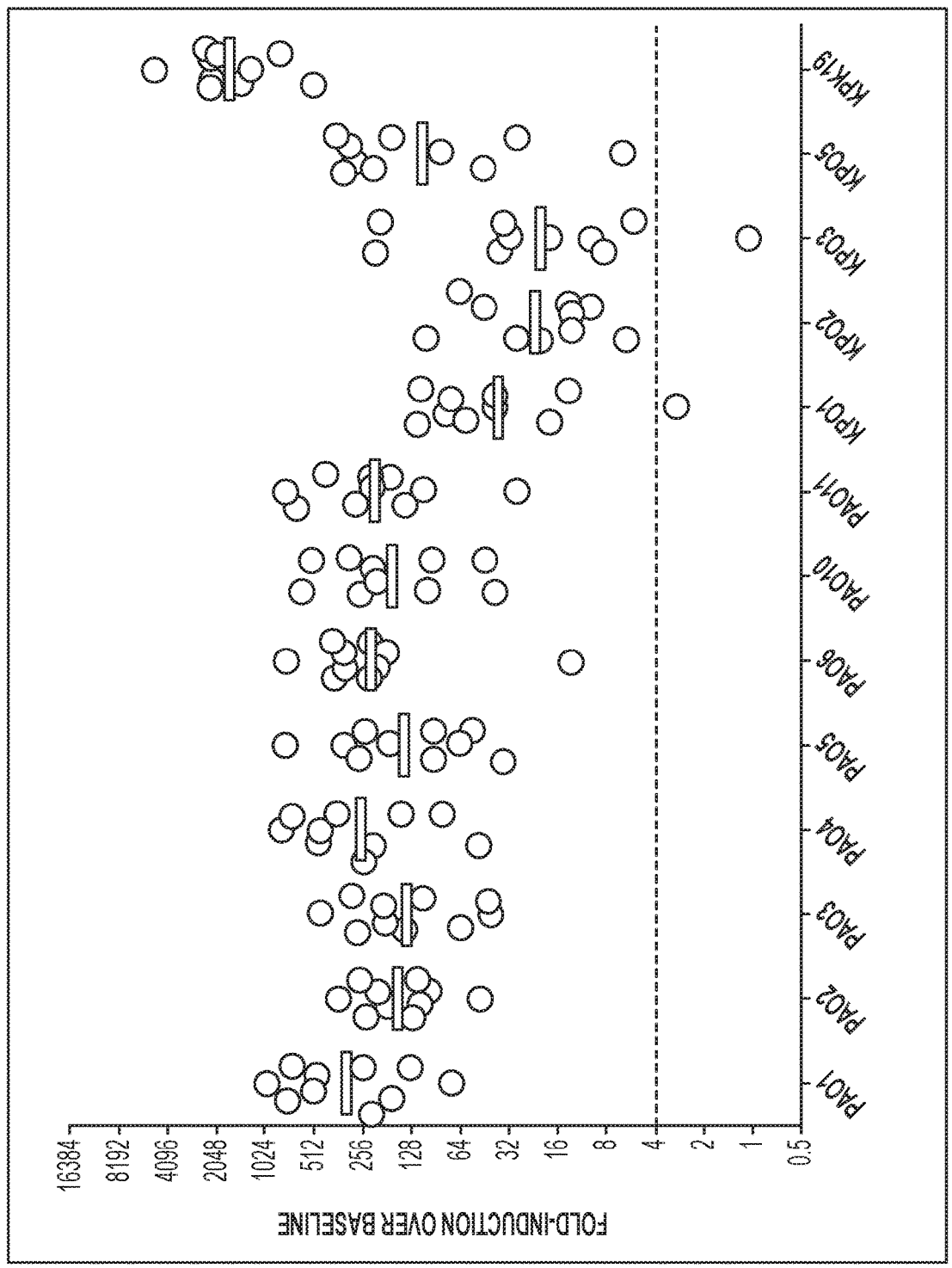
FIG. 34 depicts the increase in induction of individual anti-OPS IgG for the 12-valent KP/PA vaccine 1 at 5 µg dose.

A comparison of the individual x-fold induction of anti-OPS IgG for the 12-valent KP/PA vaccine 1 was performed for the 5 µg dose treatment group. The results are shown in FIG. 34. Except for two outliers, all animals showed at least a 4-fold induction of the ELISA titers over baseline (P2/P0) for each of the OPS serotypes. As a mean, a 20-fold induction was exceeded for all OPS serotypes for the 12-valent KP/PA vaccine 1. The highest induction was observed for KO 19.

Figure 35:
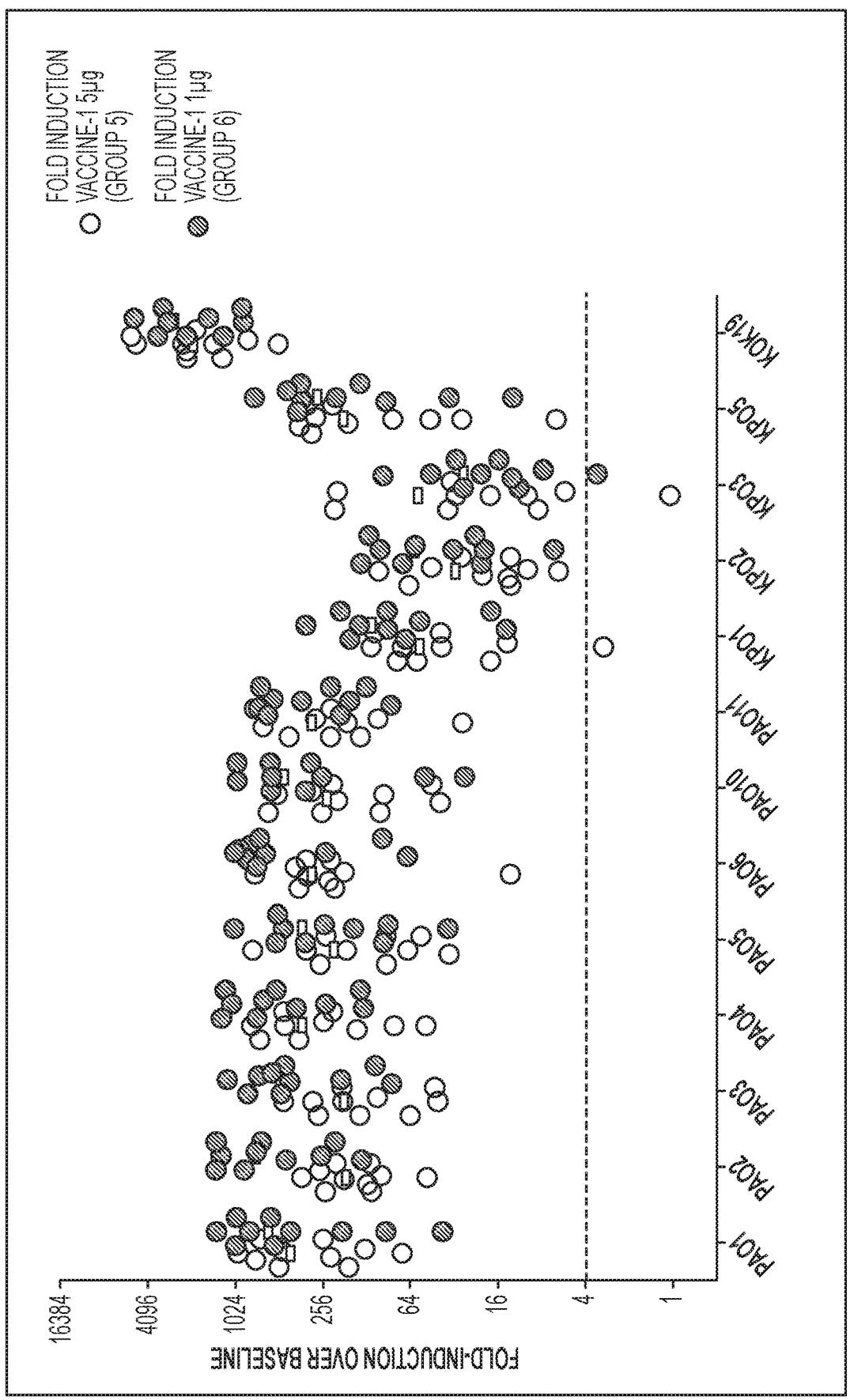
FIG. 35 depicts the comparison of the increase in induction of individual anti-OPS IgG for the 12-valent KP/PA vaccine 1 at 5 µg PS per BP dose and 1 µg PS per BP dose.

FIG. 35 provides results for the comparison of the individual x-fold induction of anti-OPS IgG ELISA titers over baseline (P2/P0) for the 12-valent KP/PA vaccine 1 at 5 µg and 1 µg dose. Interestingly, all animals from the 1 µg dose treatment group showed at least a 4-fold increase over baseline as already described for the 5 µg dose treatment group. The mean x-fold increase in IgG titers for all OPS serotypes included in the 12-valent KP/PA vaccine 1 exceeds a 20-fold increase over baseline for all OPS serotypes at 5 µg as well as at the 1 µg administered to the animals. The highest x-fold induction was observed for KO K19 at both dose levels and the lowest x-fold inductions were observed for KP O2 and KP O3.

Immune Responses to the 12-Valent KP/PA Vaccine 2 at Two Different Dose Levels

Figure 36:
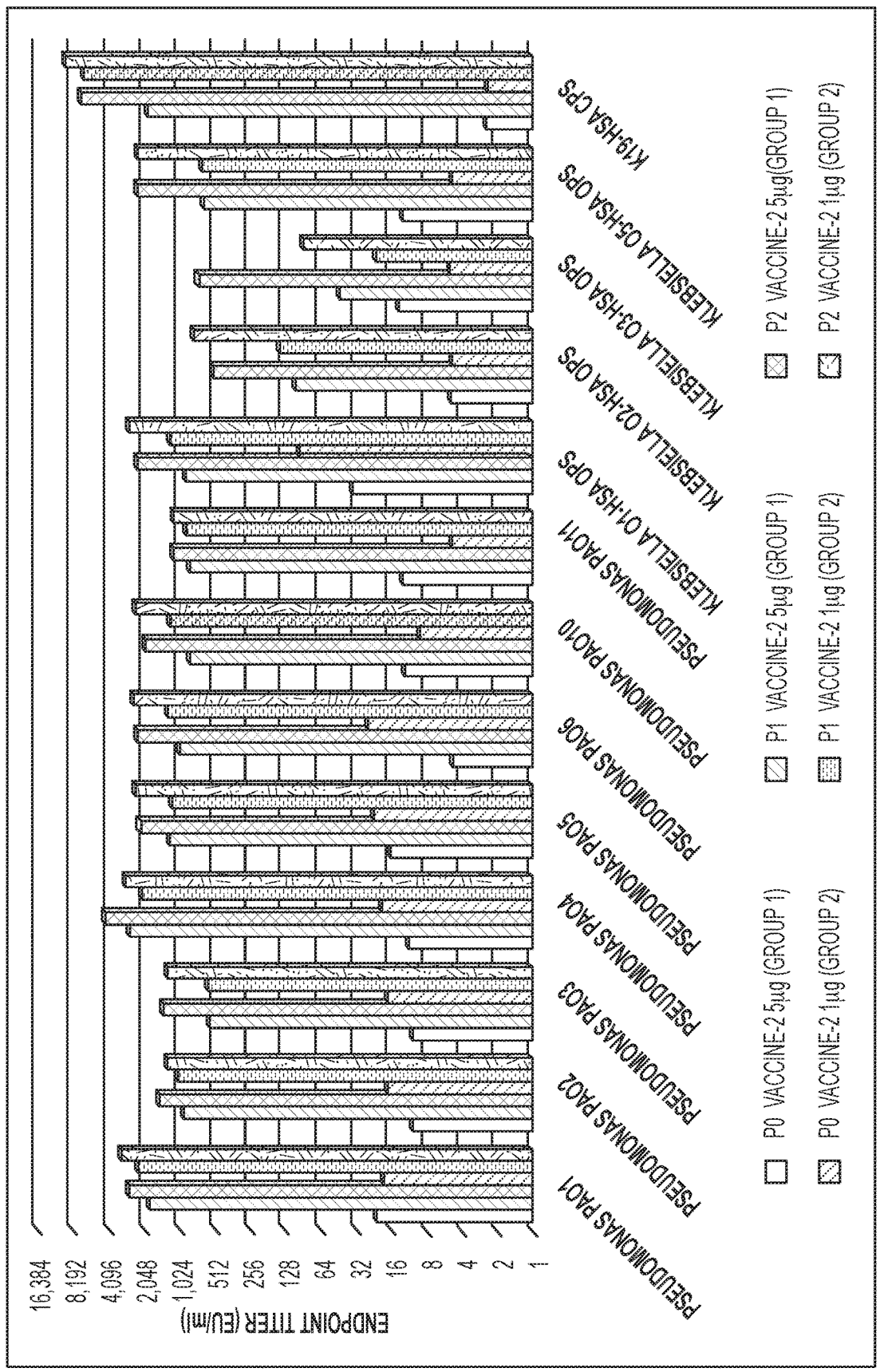
FIG. 36 depicts the results of the PA and KP OPS IgG endpoint ELISA titers for pooled sera from rabbits immunized with 12-valent KP/PA vaccine 2 at a dose of 60 µg, 5 µg PS contributed by each type of BP in the vaccine dose (treatment group 1) compared with 12-valent KP/PA vaccine 2 at a dose of 12 µg, 1 µg PS contributed by each type of BP in the vaccine (treatment group 2).

FIG. 36 shows the results for the comparison of the KP/PA OPS responses in pooled sera 28 days post first vaccination (P1) and 14 days post second vaccination (P2) from rabbits immunized with the 12-valent KP/PA vaccine 2. Remarkably, in the 5 µg dose treatment group, the vaccine induced a robust IgG response to all OPS serotypes after the first immunization with no significant increase in titers following the second immunization, except for KP O2 and KP O3 OPS. For those OPS serotypes, the second immunization produced a significant increase of the titers. The OPS IgG responses are equivalent for the 5 µg and the 1 µg dose treatment groups, except for KP O3 OPS showing a less immunogenic response at the lower dose.

Figure 37:
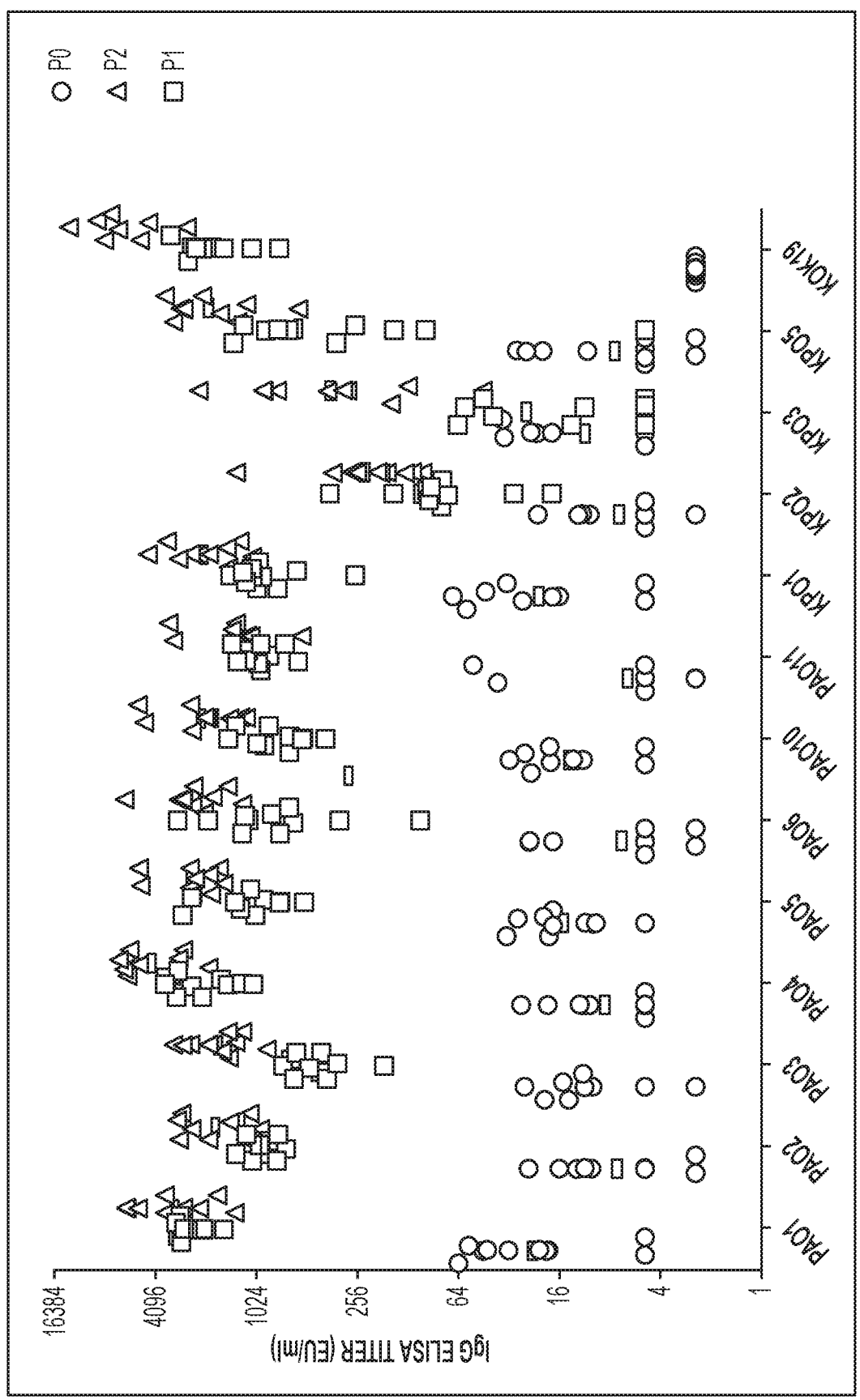
FIG. 37 depicts individual IgG titers against each PS in 12-valent KP/PA vaccine 2 at 5 µg dose.
Figure 38:
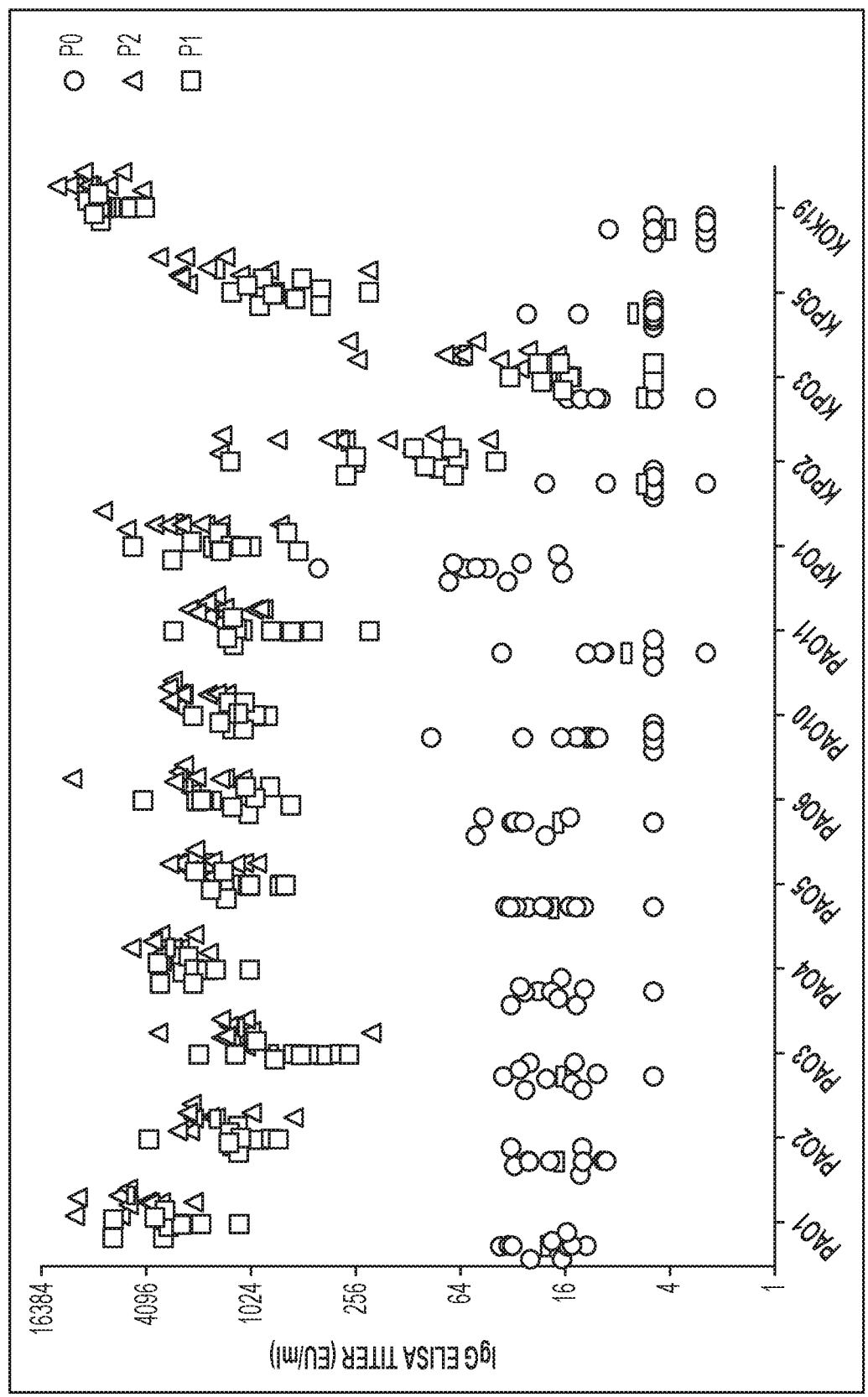
FIG. 38 depicts the increase in induction of individual anti-OPS IgG for the 12-valent KP/PA vaccine 2 at 5 µg dose.

The individual IgG OPS-specific ELISA titers for 12-valent KP/PA vaccine 2 28 days post first immunization (P1) and 14 days post second immunization (P2) are shown in FIG. 37 and FIG. 38. Robust IgG responses to all 12 OPS vaccine serotypes as well as to the KP K19 CPS are demonstrated for 12-valent KP/PA vaccine 2 at 5 µg dose (FIG. 37) and at 1 µg dose (FIG. 38). The titers for each of the OPS serotypes further increased 14 days post second vaccination. However, the magnitude of this increase was not remarkable, except for KP O3. As observed for 12-valent KP/PA vaccine 1, the difference in the immune response between the 5 µg and the 1 µg dose treatment groups was minor. The highest titers were observed for OPS serotype KO K19 and the lowest responses were observed for KP O2 and KP O3.

Summary of OPS Immune Response Results for the 12-Valent KP/PA Vaccine 1 and the 12-Valent KP/PA Vaccine 2

The anti-OPS immune responses to all PA OPS in the 12-valent KP/PA vaccine 1 in pooled rabbit sera were equivalent to those for the 8-valent PA MAPS vaccine.

The anti-OPS immune response to all KP OPS in the 12-valent KP/PA vaccine 1 in pooled rabbit sera were similar or slightly better than those for the 4-valent KP MAPS vaccine.

Approximately 200-fold increases over baseline were observed for PA OPS antibodies and approximately 50-fold increases over baseline were observed for KP OPS antibodies.

The antibodies for the 5 µg PS per BP dose and 1 µg PS per BP dose treatment groups in pooled sera are similar among the 12-valent KP/PA vaccine 1 and the 12-valent KP/PA vaccine 2, except for KP O3.

The analyses of individual sera for the 5 µg PS per BP dose and 1 µg PS per BP dose treatment groups for the 12-valent KP/PA vaccine 1 demonstrate a robust response to all KP and PA OPS after a single immunization with very little increase after the second immunization, except for the response to KP O2 and KP O3 OPS, where the second immunization produced a significant increase in IgG antibody titers.

The analyses of individual sera for the 5 µg PS per BP dose and 1 µg PS per BP dose treatment groups for the 12-valent KP/PA vaccine 2 also demonstrated a robust response to all KP and PA OPS after a single immunization with very little increase after the second immunization, except for the response to KP O3 OPS, where the second immunization produced a significant increase in IgG titers.

Carrier Protein Performance

Antibody Response to Carrier Proteins

Carrier protein antibody responses induced by the 12-valent KP/PA vaccine 1 with FlaBD2-MrkA and FlaBD2-PcrV as carrier proteins and to the 12-valent KP/PA vaccine 2 with FlaBD2-MrkA only as carrier proteins were evaluated. The responses to the carrier proteins for individual rabbits are expressed as ELISA IgG units for the preimmune (P0) levels and obtained after one (P1) and two immunizations (P2). The ELISA analysis of individual rabbit IgG for the carrier proteins were determined using the corresponding individual recombinant protein components as coating antigens (i.e. FlaBD2, MrkA and PcrV). For each analysis the responses to the carrier proteins components were compared for vaccine 1 and 2 with the responses to the 8-valent PA FlaBD2-MrkA vaccine and the 4-valent KP FlaBD2-MrkA vaccine. Details on the vaccine doses and treatment groups are provided in Table 21.

(a) ELISA Results for the Different Carrier Proteins

Figure 39:
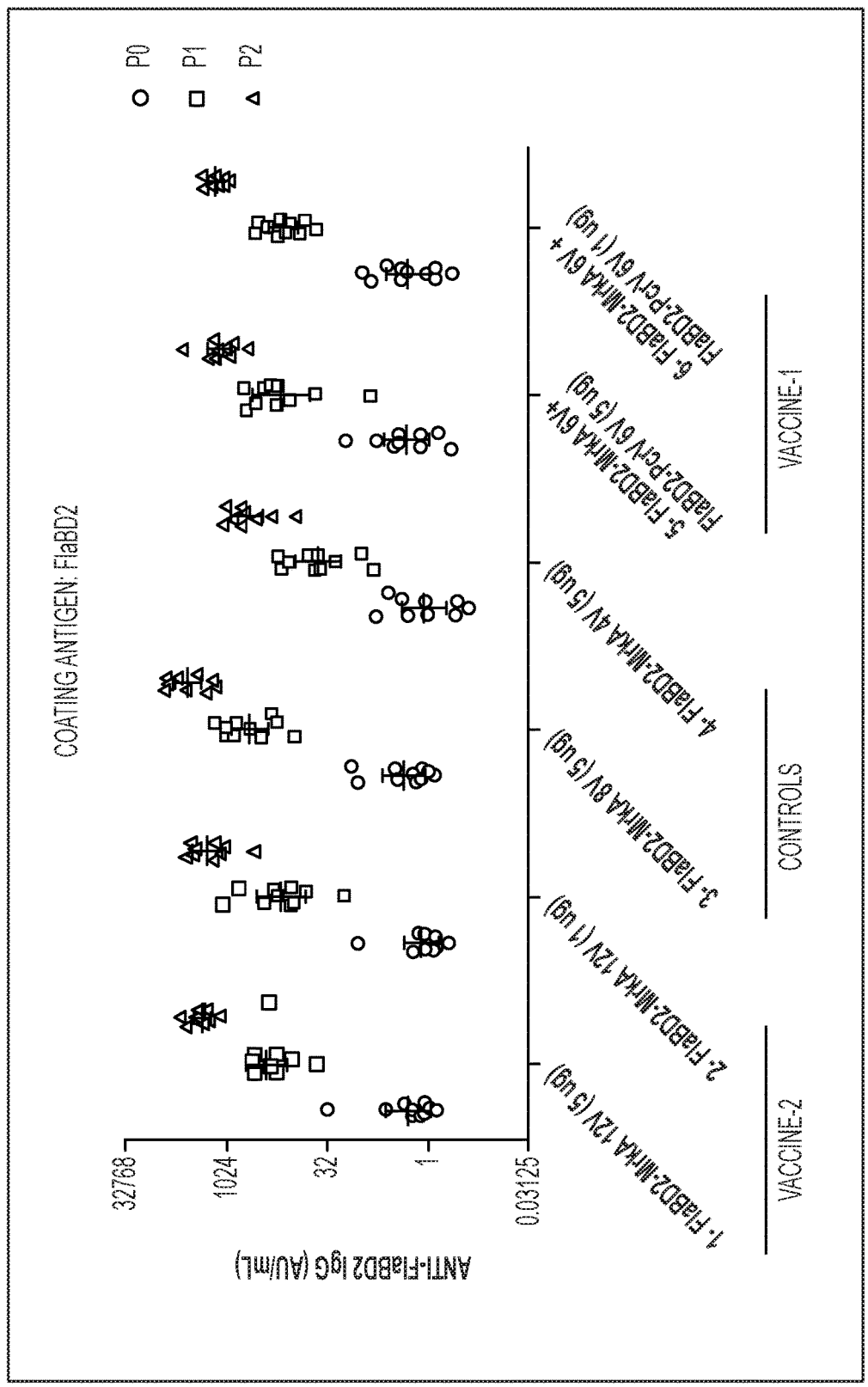
FIG. 39 depicts an ELISA analysis of rabbit IgG against FlaBD2 induced by administration of 12-valent KP/PA vaccine 1, 12-valent KP/PA vaccine 2, 8-valent PA vaccine, and 4-valent KP vaccine.

The results of the ELISA IgG titers for FlaB-D2 are provided in FIG. 39. A robust increase of the IgG titers was observed after the first immunization, followed by a second increase of the titers after the second immunization in all groups that were compared. The level of antibodies after each vaccination was similar between all groups, the two different dose groups (1 µg or 5 µg total PS contributed by each type of complex present in the vaccine composition, e.g., total of 12 µg or 60 µg PS present in the 12-valent KP/PA vaccine 1 and vaccine 2 compositions) of the 12-valent KP/PA vaccine 1 and 12-valent KP/PA vaccine 2 and the 8-valent PA vaccine and the 4-valent KP vaccine (both at 5 µg of each PS in the vaccine, e.g., total of 40 µg or 20 µg PS present in the vaccine, respectively).

Figure 40:
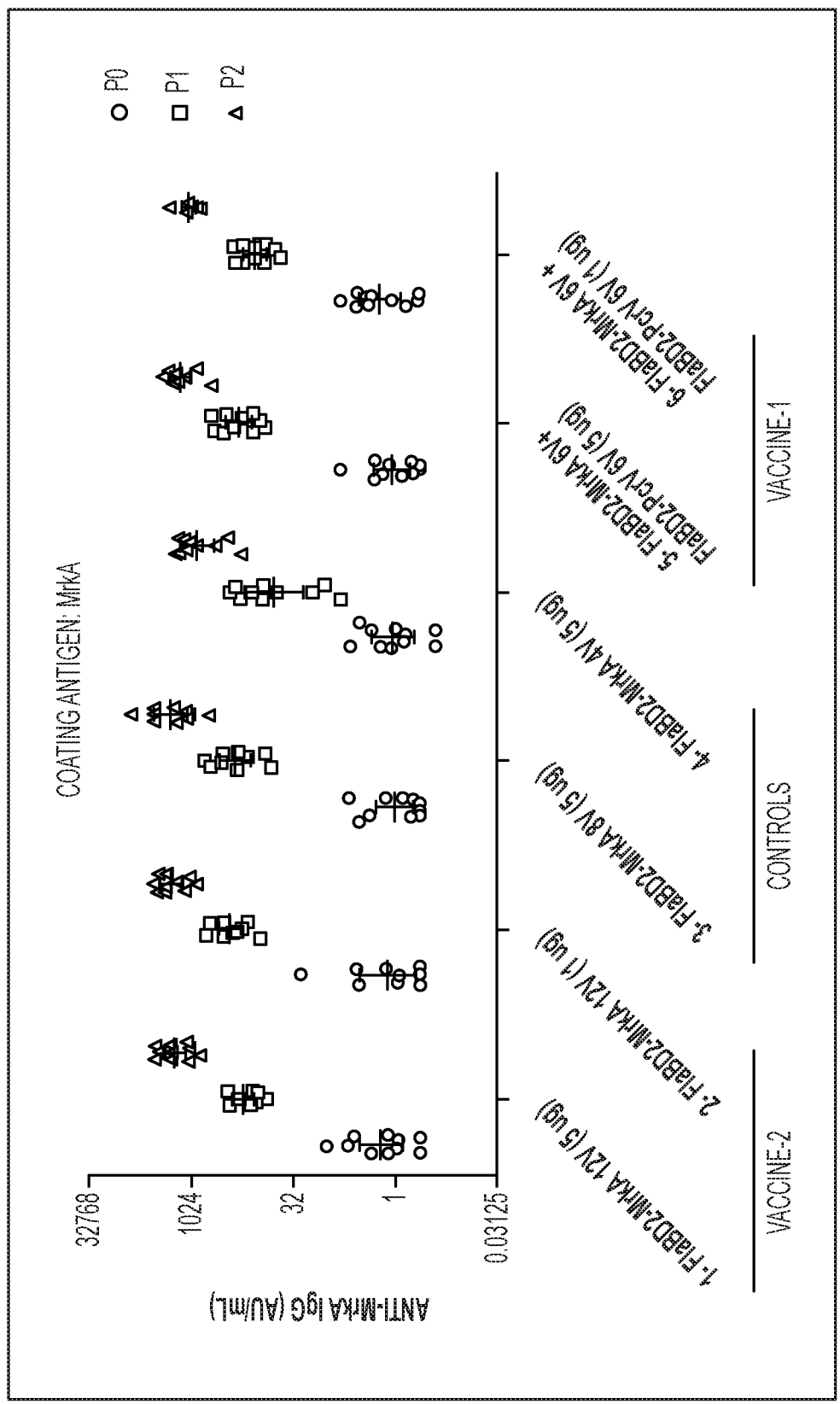
FIG. 40 depicts an ELISA analysis of rabbit IgG against MrkA induced by administration of 12-valent KP/PA vaccine 1, 12-valent KP/PA vaccine 2, 8-valent PA vaccine, and 4-valent KP vaccine.

The results of the ELISA IgG titers for MrkA are provided in FIG. 40. As observed for FlaBD2, a robust increase of the IgG titers was observed after the first immunization with an additional elevation after the second immunization in all groups with similar increases for each group, the two different dose groups (1 µg or 5 µg of PS contributed by each type of complex in the vaccine) of the 12-valent KP/PA vaccine 1 and 12-valent KP/PA vaccine 2 and the 8-valent PA vaccine and the 4-valent KP vaccine (both at 5 µg PS contributed by each type of complex in the vaccine).

Figure 41:
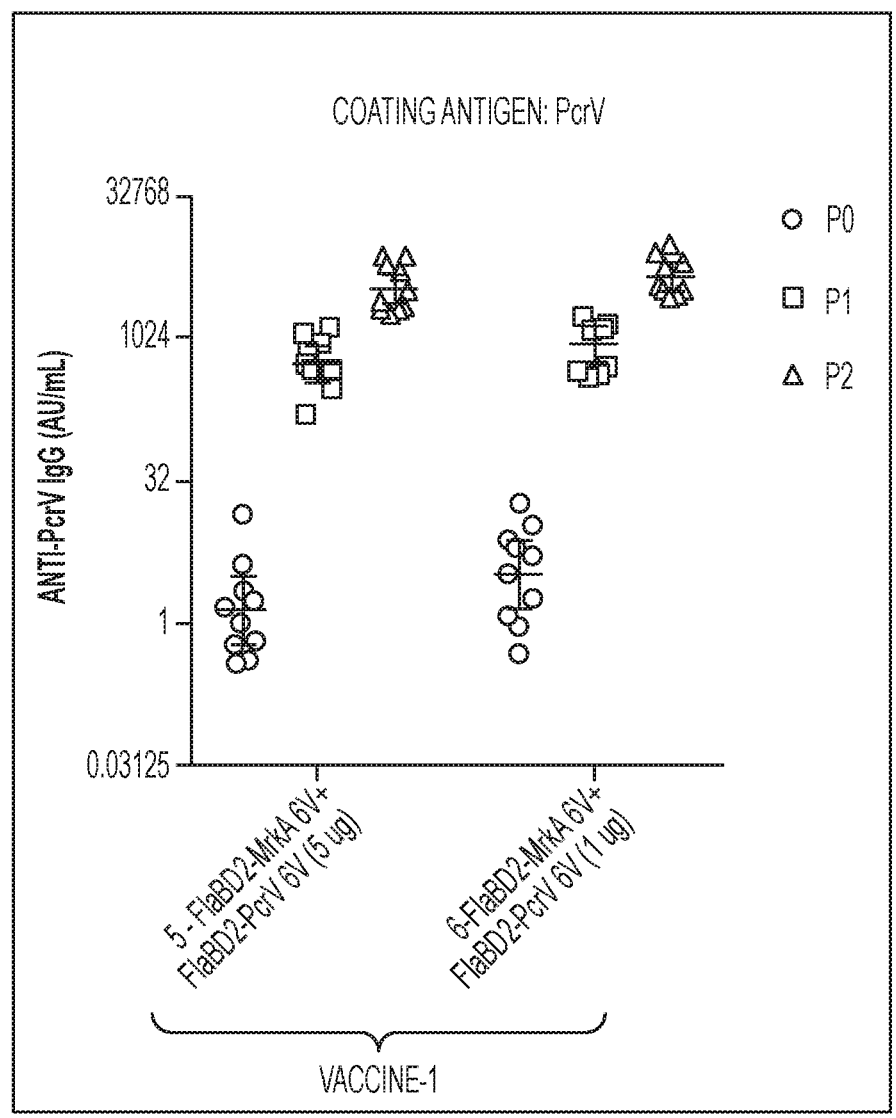
FIG. 41 depicts an ELISA analysis of rabbit IgG against PcrV induced by administration of 12-valent KP/PA vaccine 1.

FIG. 41 shows the results for the antibody response against PcrV after immunization with the 12-valent KP/PA vaccine 1 at 1 µg and at 5 µg of each PS in the vaccine. The IgG response was robust after the first immunization with a further increase of the titers after the second vaccination. However, the responses were similar between the two dose groups.

Figure 42:
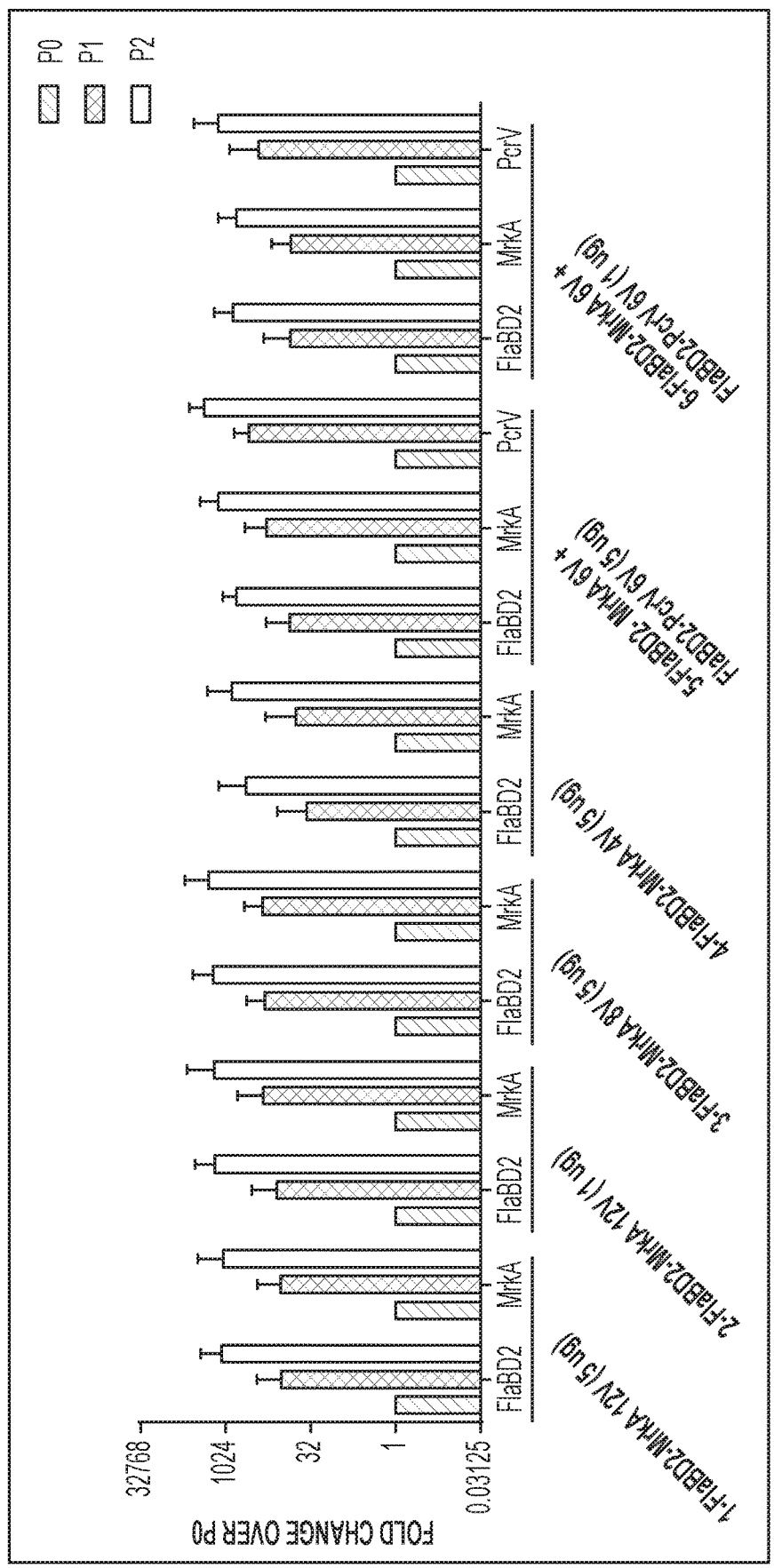
FIG. 42 depicts the increase in induction of individual anti-carrier protein IgG induced by administration of 12-valent KP/PA vaccine 1, 12-valent KP/PA vaccine 2, 8-valent PA vaccine, and 4-valent KP vaccine.

The carrier protein responses induced to the 12-valent KP/PA vaccine 1 with FlaBD2-MrkA and FlaBD2-PcrV as carrier proteins, to the 12-valent KP/PA vaccine 2 with FlaBD2-MrkA as carrier protein, the 8-valent PA vaccine (FlaBD2-MrkA) and the 4-valent KP vaccine (FlaBD2-MrkA) expressed as ELISA x-fold changes in titers over the preimmune (P0) levels after one (P1) and two immunizations (P2) are shown in FIG. 42.

Robust responses were demonstrated against each of the three carrier proteins FlaBD2, MrkA and PcrV in the 12-valent KP/PA vaccine 1 with over 30-fold changes after the first immunization and 500-fold changes after the second immunization. No significant differences in immunogenicity to the three proteins were observed between the 5 µg and the 1 µg dose groups.

A robust IgG response to each of the two protein components was observed already after one immunization with an increase exceeding 30-fold for the two fusion protein components FlaBD2, and MrkA in the 12-valent KP/PA vaccine 2. Additional significant increases were observed post second immunization reaching over 1000-fold increases. No significant differences were observed in the x-fold changes for FlaBD2 and MrkA between the 5 µg and the 1 µg dose groups.

No significant differences in immunogenicity to the two components FlaBD2 and MrkA between the groups that received the 8-valent PA vaccine or the 4-valent KP vaccine were observed. However, these responses were slightly lower in the 4-valent vaccine group compared to those of the 12-valent KP/PA vaccine 2 group and the 8-valent PA vaccine group.

(b) Comparison of x-Fold Changes of the IgG Responses to the Different Carrier Proteins Across Three Studies The x-fold change comparison of the IgG response to FlaB was examined across three rabbit immunogenicity studies: NCB007, NCB008 and NCB012. In NCB007, the 5 µg dose of the 6-valent PA FlaBD2-MrkA (containing PA O1, O2, O3, O6, O10 and O11 OPS) was compared with the equivalent 6-valent PA FlaB-PcrV, in NCB008 the 5 µg dose of the 4-valent (O1, O2, O3, O5) KP FlaBD2-MrkA was compared with the 4-valent KP FlaB-PcrV, and in NCB012 the 5 µg dose of the 12-valent KP/PA vaccine 2 with FlaBD2-MrkA was compared with the 12-valent KP/PA vaccine 1 FlaBD2-MrkA and FlaBD2-PcrV. All vaccines were of the BP-1 scaffold type. The results as x-fold changes are provided in FIG. 43, FIG. 44, and FIG. 45.

Figure 43:
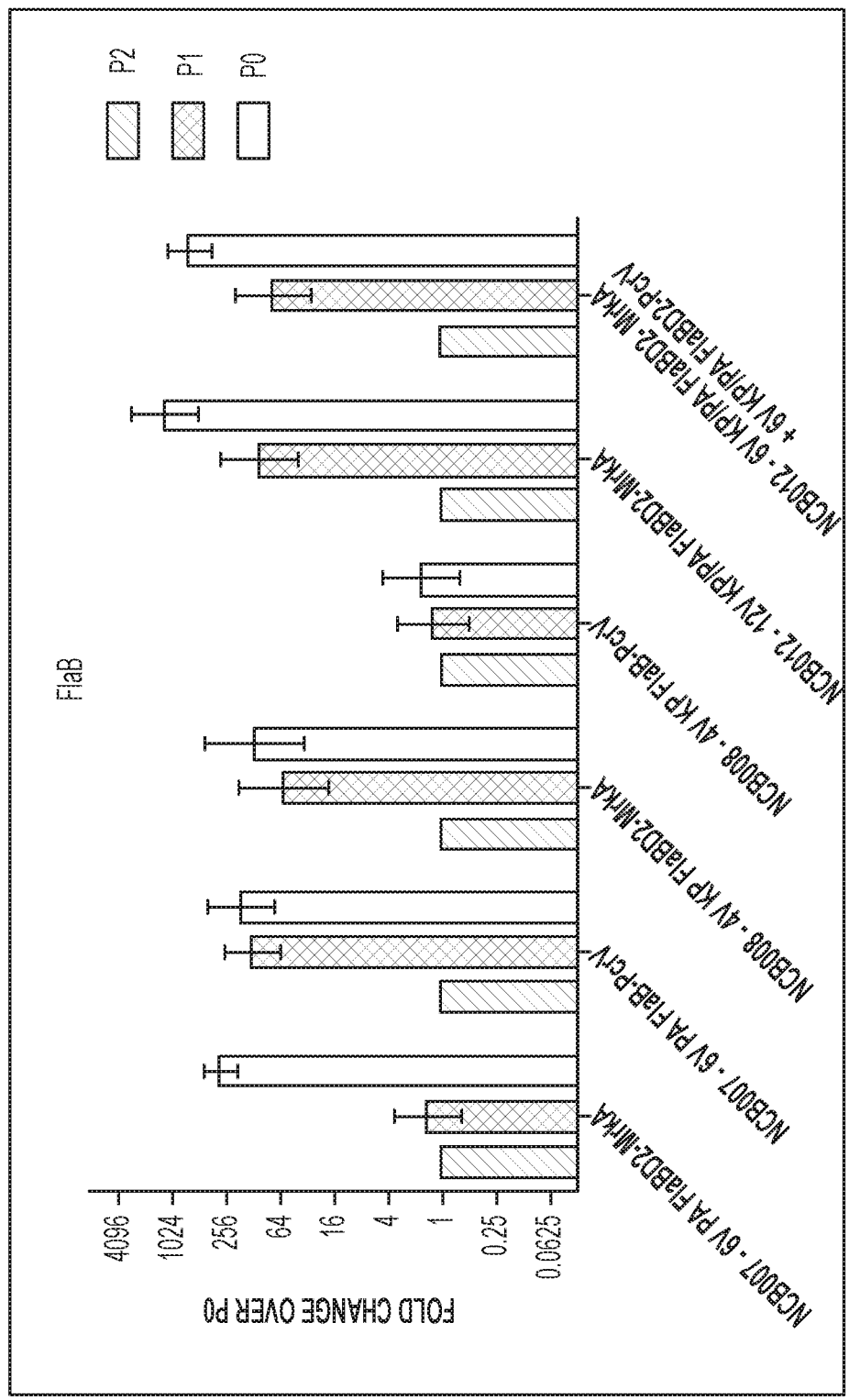
FIG. 43 depicts the increase in induction of FlaB response induced by administration of various vaccine formulations in three rabbit immunogenicity studies: NCB007, NCB008 and NCB012.

FIG. 43 shows the x-fold changes of the IgG responses to FlaB with the highest increase in response to the 12-valent KP/PA vaccine 1 and 12-valent KP/PA vaccine 2. A good response was already observed after the first immunization with further increase after the second immunization. The responses to the 4-valent KP FlaBD2-MrkA and the 4-valent FlaB-PcrV complexes in NCB008 showed a good response after the first immunization with little additional increase after the second immunization for FlaBD-2-MrkA and basically no response after either immunization for FlaB-PcrV. A poor response to FlaB was also observed for the 6-valent PA FlaBD2-MrkA in NCB007 after the first immunization, but a significant increase was elicited after the second vaccination. The response to FlaB-PcrV in NCB007 was robust after the first immunization with no additional increase after the second immunization.

Figure 44:
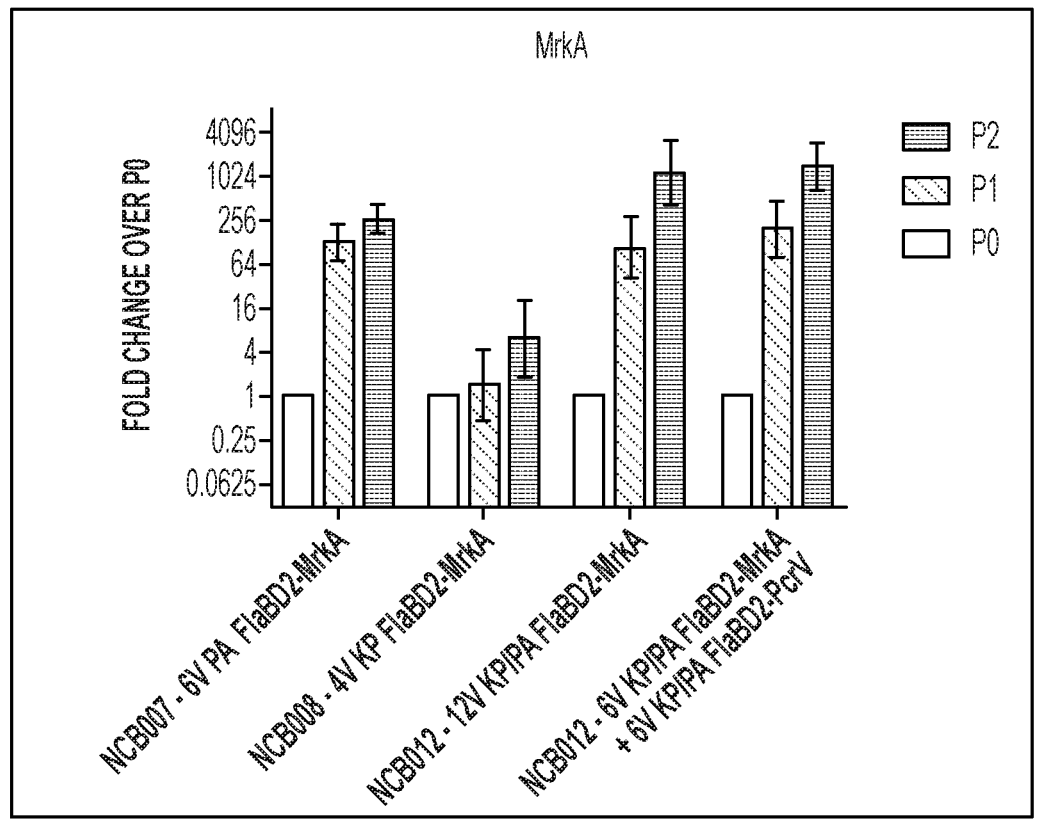
FIG. 44 depicts the increase in induction of MrkA response induced by administration of various vaccine formulations in three rabbit immunogenicity studies: NCB007, NCB008 and NCB012.

FIG. 44 shows the responses to MrkA with the highest responses in changes from baseline for the 12-valent KP/PA vaccine 2 and 12-valent KP/PA vaccine 1 in NCB012 when compared with the responses to the 4-valent KP FlaBD2-MrkA in NCB008 and the 6-valent PA FlaBD2-MrkA in NCB007. There was almost no response observed for MrkA in NCB008 after the first and second vaccination, while a robust response to MrkA was observed with the 6-valent PA FlaBD2-MrkA after the first immunization and further increase after the second immunization.

Figure 45:
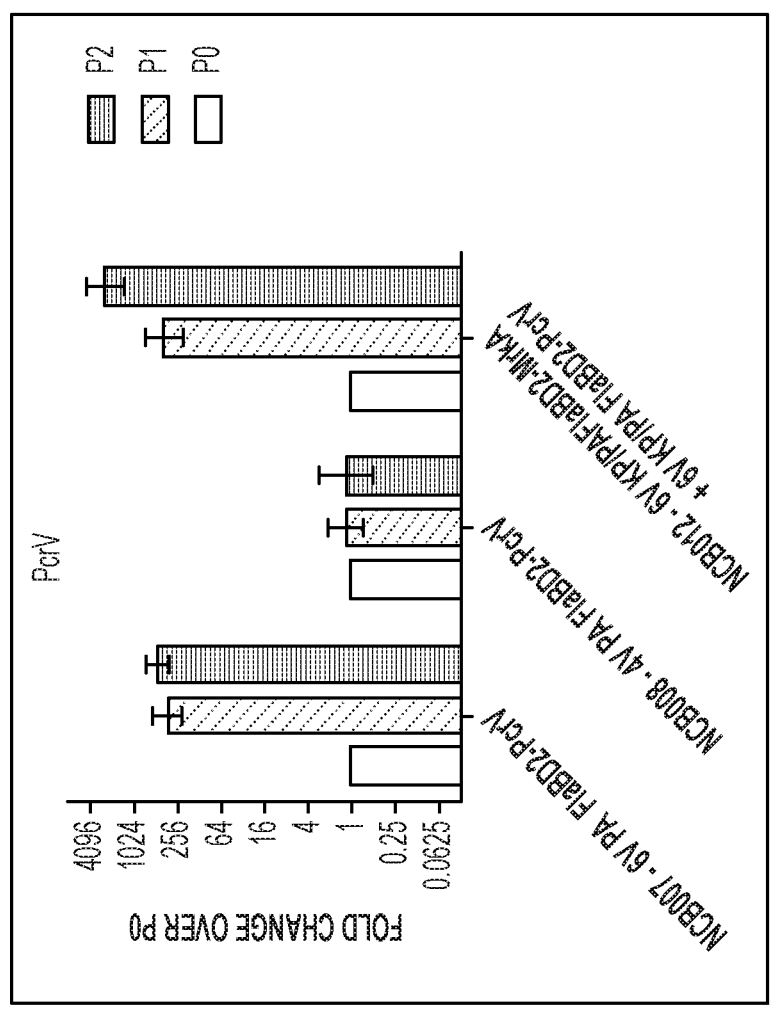
FIG. 45 depicts the increase in induction of PcrV response induced by administration of various vaccine formulations in three rabbit immunogenicity studies: NCB007, NCB008 and NCB012.

FIG. 45 shows the x-fold changes in the IgG response to PcrV with the highest increase for the 12-valent KP/PA vaccine 1 in study NCB012 after first and second immunization. Almost no response to PcrV was observed in the 4-valent KP FlaB-PcrV study in NCB008. A robust response to PcrV was observed after the first and second immunization in study NCB007.

(c) Summary of Results

A robust IgG antibody response to all three carrier proteins was demonstrated for the 12-valent KP/PA vaccine 1 and 12-valent KP/PA vaccine 2.

The responses to the carrier proteins were similar for the 1 µg and 5 µg dose groups.

The x-fold increase generated to each of the three carrier proteins was approximately 500- to 1000-fold for the 12-valent KP/PA vaccine 1.

There was consistent boosting between the first and the second dose in naïve animals. Without wishing to be bound by any theory, in adults who are not naïve, near maximal responses are expected after one dose and within 7-10 days.

The previous issue encountered with lower responses to MrkA and PcrV in animals immunized with the 4-valent KP vaccine was not observed in animals immunized with 12-valent KP/PA vaccine 1 or 12-valent KP/PA vaccine 2.

Lack of TLR5 Agonist Bioactivity in the Carrier Proteins Containing Only FlaB2

FIG. 12B describes the TLR5 bioactivity of fusion proteins and MAPS complexes containing FlaA and FlaB proteins using HEK293 cells expressing NF-kB driven luciferase reporter. Flagellin TLR5 activation causes upregulation of reporter expression.

Figure 46:
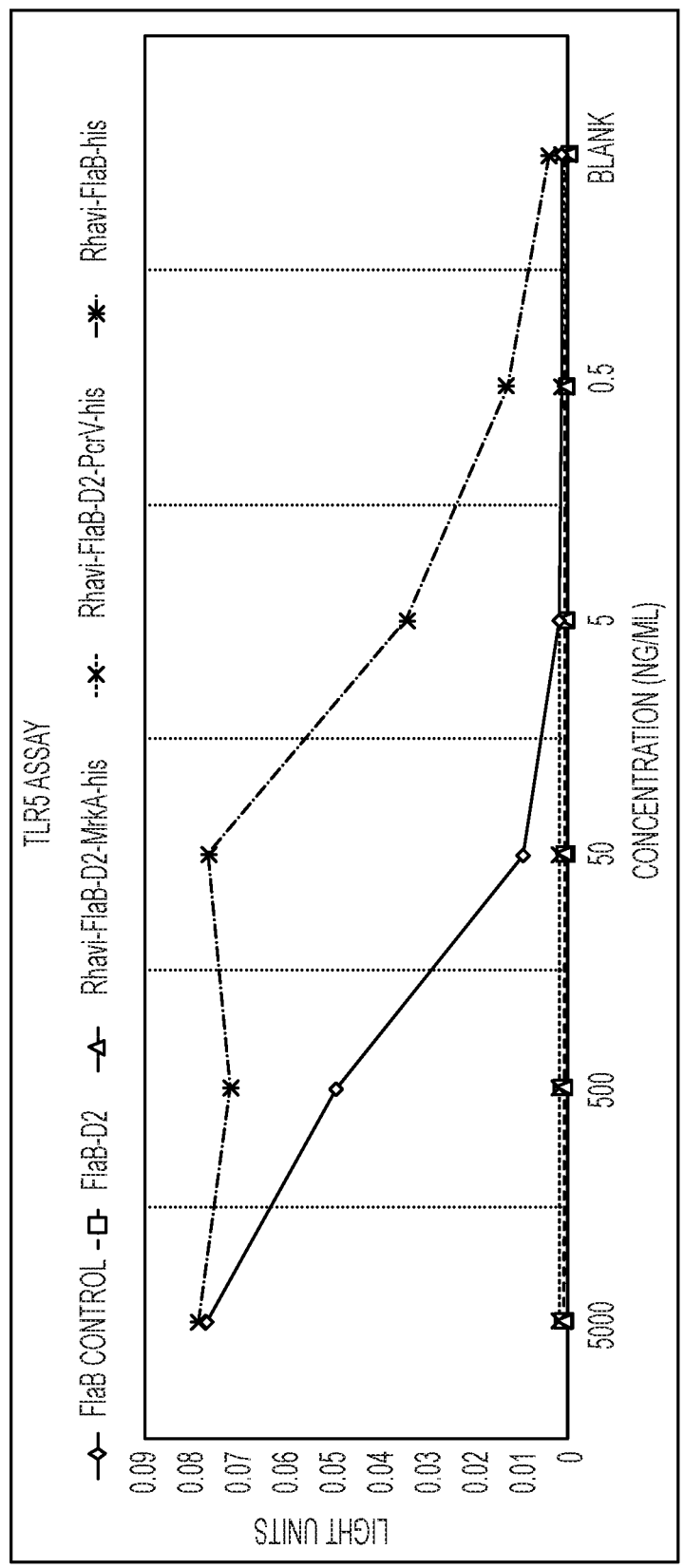
FIG. 46 depicts the lack of TLR5 agonist bioactivity exhibited by carrier proteins containing only FlaB domain 2.

KP/PA MAPS carrier proteins containing only FlaB domain 2 (FlaBD2) were found to lack TLR5 agonist bioactivity as is demonstrated by the data from the luciferase assay for FlaBD2-MrkA and FlaBD2-PcrV, shown in FIG. 46. FlaBD2-MrkA and FlaBD2-PcrV are the two carrier proteins in the 12-valent KP/PA vaccine 1.

The FlaB control and the fusion protein Rhavi-FlaB-his showed a strong TLR5 agonist bioactivity while FlaBD2, FlaBD2-MrkA and FlaBD2-PcrV, all containing only FlaB domain 2 (FlaBD2), showed no activity in this assay.

Breadth of Binding by FACS and Agglutination for Non-OPS Vaccine Strains

KP and PA strains that are not OPS vaccine serotypes were tested by flow cytometry and in agglutination assays to study the breadth of coverage by antibodies to the 12-valent KP/PA vaccine 1.

Table 22 shows the results of FACS binding and bacterial agglutination of non-OPS KP strains obtained with pooled sera (AFV1502-1511) from rabbits that were immunized with the 12-valent KP/PA vaccine 1 at a 5 µg dose of each BP-1. Twelve of 14 strains tested showed an obvious difference in recognition by P0 and P2 sera in agglutination and an increase in bacterial binding measured by flow cytometry at a serum dilution of 1:100.

TABLE 22

Response to the 12-valent KP/PA vaccine 1 - binding and agglutination of non-OPS KP vaccine strains

| Strain ID | Country of origin | O type | Bacterial agglutination | Bacterial binding flow cytometry | MrkA gene presence (PCR) |
|---|---|---|---|---|---|
| 70721 | USA | NOT (O1, O2, O3, O5) | No | No | No |
| GN05275 | USA | NOT (O1, O2, O3, O5) | Yes | Yes | Yes |
| NUH5575 | Japan | NOT (O1, O2, O3, O5) | Yes | Yes | Yes |
| 170241 | USA | NOT (O1, O2, O3, O5) | Yes | Yes | Yes |
| 60111 | USA | NOT (O1, O2, O3, O5) | Yes | Yes | Yes |
| 5205 | South Africa | NOT (O1, O2, O3, O5) | Yes | Yes | Yes |
| 7075 | South Africa | NOT (O1, O2, O3, O5) | Yes | Yes | Yes |
| 7069 | South Africa | NOT (O1, O2, O3, O5) | Yes | Yes | Yes |
| 11818/3 | Mali | NOT (O1, O2, O3, O5) | No | No | No |
| 9536/15 | Mali | NOT (O1, O2, O3, O5) | Yes | Yes | Yes |
| 12287/3 | Mali | NOT (O1, O2, O3, O5) | Yes | Yes | Yes |
| KP1015 | Denmark | O4 | Yes | Yes | Yes |
| NUH5218 | Japan | O4 | Yes | Yes | Yes |
| EC 1793 | Singapore | O4 | Yes | Yes | Yes |

Table 23 shows the results of FACS binding and bacterial agglutination of non-OPS PA strains with pooled sera (AFV1502-1511) from rabbits immunized with the 12-valent KP/PA vaccine 1 at a 5 µg dose of each serotype BP-1. For flagellin B, 6 of 7 strains agglutinated, and 7 of 7 showed antibody binding by flow cytometry. For flagellin A1, 3 of 4 strains showed antibody binding by flow cytometry. For flagellin A2, no evidence of antibody recognition in 4 strains was observed.

TABLE 23

Response to the 12-valent KP/PA vaccine 1 - binding and agglutination of non-OPS PA vaccine strains

| Strain ID | Country of origin | O serotype (Medimabs) | Flagellin type | Bacterial agglutination | Bacterial binding flow cytometry |
|---|---|---|---|---|---|
| 12-01831 | USA | O8 | A2 | No | No |
| 379/2014 | Greece | O8 | B | Yes | Yes |
| 12-03320 | USA | O9 | A1 | No | Maybe |
| 425/2015 | Greece | O9 | A2 | No | No |

TABLE 23-continued

Response to the 12-valent KP/PA vaccine 1 - binding and agglutination of non-OPS PA vaccine strains

| Strain ID | Country of origin | O serotype (Medimabs) | Flagellin type | Bacterial agglutination | Bacterial binding flow cytometry |
|---|---|---|---|---|---|
| PA0814 | Denmark | O9 | A1 | No | Yes |
| NUH6346 | Japan | O9 | A2 | No | No |
| CJLSG533 | Japan | O9 | B | Yes | Yes |
| 197/2012 | Greece | O12 | B | Yes | Yes |
| 12-04889 | USA | O14 | B | No | Yes |
| 12-01852 | USA | O15 | B | Yes | Yes |
| 12-00232 | USA | O16 | B | Yes | Yes |
| 10024 | South Africa | O16 | A1 | No | No |
| 10-04727 | USA | O17 | B | Yes | Yes |
| 11-04251 | USA | O17 | A1 | No | Yes |
| PA0002 | Singapore | Nontypable | A2 | No | No |

Fourteen KP and 15 PA strains that are non-OPS vaccine serotypes were tested to determine the breadth of coverage by antibodies generated in rabbits to the 12-valent KP/PA vaccine 1. In summary:

The elicited antibodies bind and agglutinate 12 of 14 non-OPS KP serotypes strains:
The serotypes that do not contain the MrkA gene did not bind antibodies
The binding to these strains is likely due to MrkA directed antibodies
The elicited antibodies bind 10 out of 15 non-OPS PA vaccine serotypes:
The binding occurred for strains with FlaB and some with FlaA1
The binding is most likely due to FlaB directed antibodies and due to cross reactivity to FlaA1
The antibodies directed to the carrier proteins (FlaBD2 and MrkA) expand the breadth of coverage for non-OPS vaccine serotypes.

Passive Protection in Animals Induced by Antibodies to Carrier Proteins

The potential of carrier proteins to induce passive protection in mice was evaluated in a burn-wound infection model with *Klebsiella* KP B5055 (O1: K2) using anti-O1 sera and anti-MrkA sera as detailed in Table 24.

The results indicate that there is a trend for a protective role of MrkA (FlaBD2-MrkA) in preventing the death of animals infected with an encapsulated KP strain. On day 6 post challenge, 60% (3/5) of the animals were still alive. The OPS O1 antibodies did not protect against infection in this experiment.

TABLE 24

Protection against burn-wound infection with KP B5055 (O1: K2) using anti-O1 and anti-MrkA sera

| Group | Infection* | Treatment | Survival (D6) |
|---|---|---|---|
| 1 | B5055 | PBS | 33% (1/3) |
| 2 | (12 CFU/mice) | Anti-KP O1 P0 sera | 50% (2/4) |
| 3 | | Anti-KP O1 P2 sera | 20% (1/5) |
| 4 | | Anti-MrkA P0 sera | 25% (1/4) |
| 5 | | Anti-MrkA P2 sera | 60% (3/5) |
| 6 | | Anti-KP O1 + MrkA P0 sera | 25% (1/4) |
| 7 | | Anti-KP O1 + MrkA P2 sera | 40% (2/5) |

*Mice passively transferred twice with 200 µl sera, infected SC after burn wound with 12 CFU B5055.
KPO1 antibody: Pool of 3 highest titer sera from NCB008 FlaB-PcrV 4-valent KP MAPS
MrkA antibody: Pool of 10 sera NCB010 FlaBD2-MrkA 1v PA MAPS Summary of performance of two carrier proteins in a vaccine formulation The carrier proteins FlaBD2-MrkA, and FlaBD2-PcrV in the 12-valent KP/PA vaccine 1 and 12-valent KP/PA vaccine 2 were demonstrated to be robust carriers of the KP/PA OPS.
A strong anti-protein response was seen for FlaBD2-MrkA and FlaBD2-PcrV in the 12-valent KP/PA vaccine 1 as well as for the FlaBD2-MrkA in the 12-valent KP/PA vaccine 2.
The antibodies directed to the carrier proteins in the 12-valent KP/PA vaccine 1 expand the breadth of coverage for non-OPS vaccine serotypes.
Consistent with the experimental design for FlaB containing only the FlaB domain 2 (FlaBD2), a complete ablation of TLR5 agonist activity was demonstrated for the FlaBD2 fusion carrier proteins.
First challenge results in a burn-wound model of *Klebsiella* infection in mice show a trend of protection for antibodies against MrkA.

Figure 47:
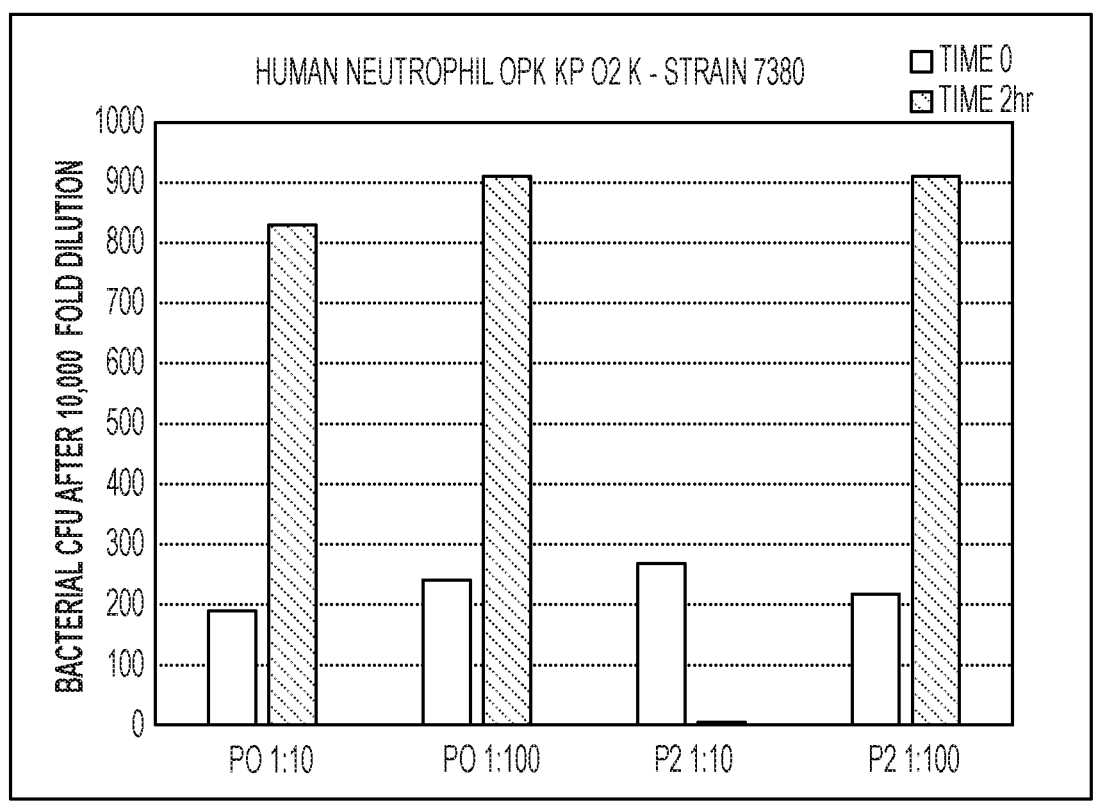
FIG. 47 depicts the results of a human neutrophil OPK assay with KP O2 K-Strain 7380.

Example 12: Functional Assays of *P. aeruginosa*/*K. Pneumoniae* 12-Valent Vaccine Opsonophagocytic Killing (OPK) Assays
Human Neutrophil OPK Assays A human neutrophil opsonophagocytic killing (OPK) assay was used to assess the functional response of pooled rabbit sera (P2) raised with the 12-valent KP/PA vaccine 1 at 5 µg dose (NCB012, Table 21) using the a capsular KP serotype O2 (KP O2 K-) strain 7380. The results of the OPK assay are shown in FIG. 47.

The immune sera provided 100% killing of the KP O2 bacteria at 1/10 dilution after 24 hours incubation, while the 1/100 dilution did not have killing activity of the bacteria. The killing activity of the sera could be attributed to either the KP O2 OPS or MrkA, or the combination of the two vaccine components.

J774 Macrophage Cell Line OPK Assays

This OPK assay uses the J774 macrophage cell line in the presence or absence of the antibiotic gentamicin to assess functional activity. Several antibiotics cannot penetrate eukaryotic cells. Therefore, these antibiotics cannot hurt bacteria that are already internalized. Using such antibiotics allows to differentiate between bacteria that succeed in penetrating eukaryotic cells and those that do not. Applying such an antibiotic to a culture of eukaryotic cells infected with bacteria would kill the bacteria that remain outside the cells while sparing the ones that penetrated. The antibiotic of choice for this assay is the aminoglycoside gentamicin.

Pooled rabbit sera from rabbits in treatment group 5, who received the 5 µg dose of the 12-valent KP/PA vaccine 1 in NCB012 and showed the highest OPS titers (1502, 1506, 1508, 1511) were used in a J774 macrophage cell line OPK assay to assess the effect of the sera on phagocyotic uptake of *Klebsiella* strains KP O1, KP O2, KP O3, and KP O5.

J774 macrophage cells were seeded in 96 well plates 24 hours before the experiment. *Klebsiella* strains of various O-type were grown to mid-log phase in broth and pooled sera were used in the killing assay. Approximately $1 \times 10^5$ CFU bacteria were incubated with pooled preimmune (P0) or immune (P2) sera for 30 min. Opsonized bacteria were incubated with J774 cells for 15 minutes at room temperature, a time sufficient to allow antibody-mediated phagocytosis. Unbound bacteria were removed from cells and fresh buffer ±50 µg/ml gentamicin added for an additional 20 minutes. Cells were washed two times with PBS, then lysed by the addition of pure water. Ten ml were plated in duplicate from each well and colony forming units (CFU) were counted the following day.

Figure 48:
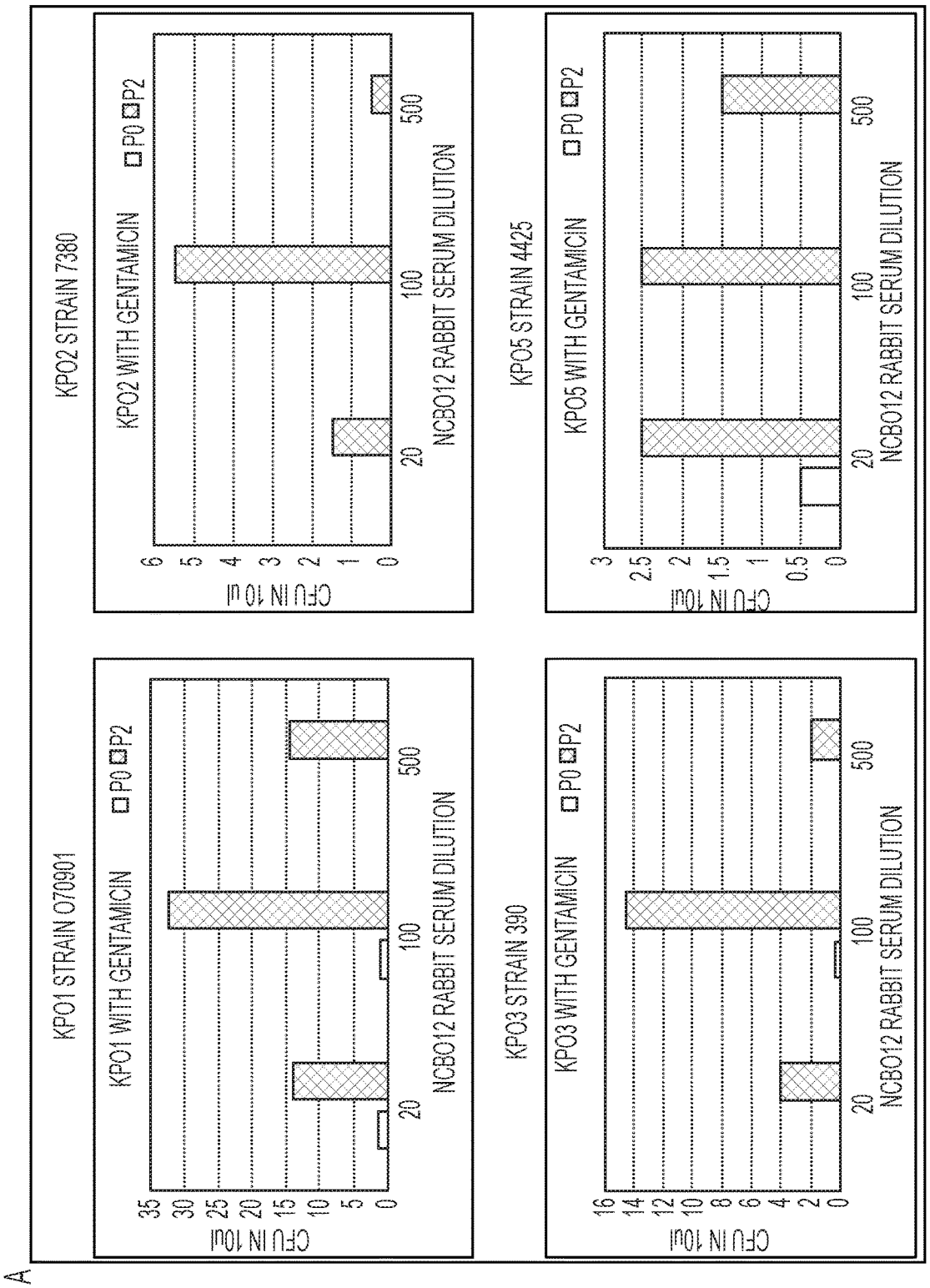
FIG. 48A depicts the results of an OPK uptake assay with J774 macrophage cell line in the presence of gentamicin.
FIG. 48B depicts the results of an OPK uptake assay with J774 macrophage cell line in the absence of gentamicin.
Figure 48:
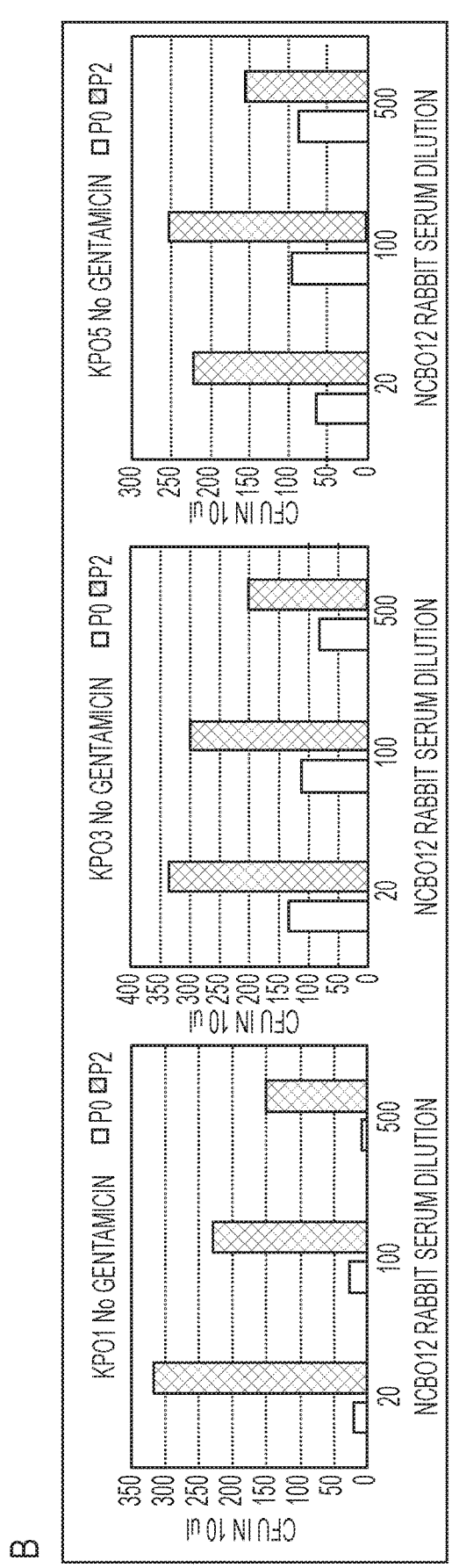

The results for this assay are shown in FIGS. 48A and 48B. The J774 cell phagocytic uptake of *Klebsiella* opsonized with immune or preimmune sera at 1/20, 1/100 and 1/500 dilution demonstrate an increased uptake of KP O1, KP O2, KP O3, and KP O5 in presence of immune sera and presence of gentamicin (FIG. 48A). Highest uptake was observed at the 1/100 dilution for KP O1, KP O2 and KP O3. For KP O5, the uptake was similar at a dilution of 1/20 and 1/100.

In the absence of gentamicin, significant uptakes by the J774 cells of KP O1, KP O3 and KP O5 was also observed with P2 sera when compared to preimmune where there is less bacterial uptake. For KP O2 no results are presented because the CFU counts were too high to count (FIG. 48B). For KP O1 and KP O3 the uptake decreased with higher dilution and for KP O5 the highest uptake was observed for the 1/100 dilution, a slightly lower uptake for the 1/20 dilution and the lowest uptake for the 1/500 dilution.

Pooled sera from rabbits who received the 5 µg dose of the 12-valent KP/PA vaccine 1 in NCB012 and showed the highest OPS titers (1502, 1506, 1508, 1511) were also used in a J774 macrophage cell line OPK assay to assess the effect of the sera on phagocytic uptake of both *Pseudomonas* PA (O5:FlaB and 06:FlaA1) and *Klebsiella* strain KP O5 (strain 6997). The assay was performed as described above with respect to the J774 OPK testing of *Klebsiella* strains KP O1, KP O2, KP O3, and KP O5.

Figure 49:
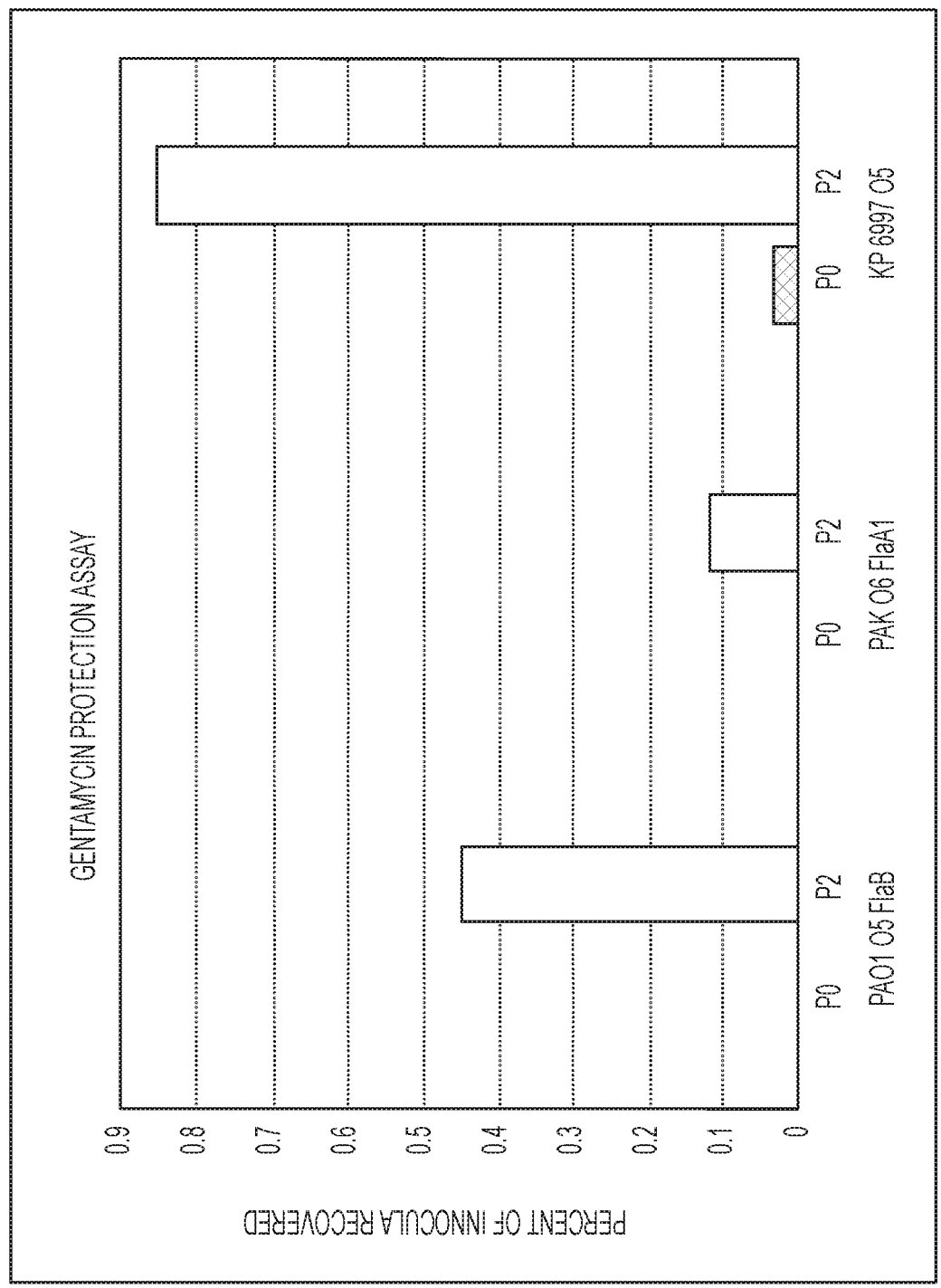
FIG. 49 depicts the results of a gentamicin protection assay of PA and KP opsonised with pooled sera from rabbits immunized with the 12-valent vaccine-1. Immune sera (P2) mediates uptake of bacteria by macrophage-like J774 cells while preimmune sera (P0) does not.
Figure 50:
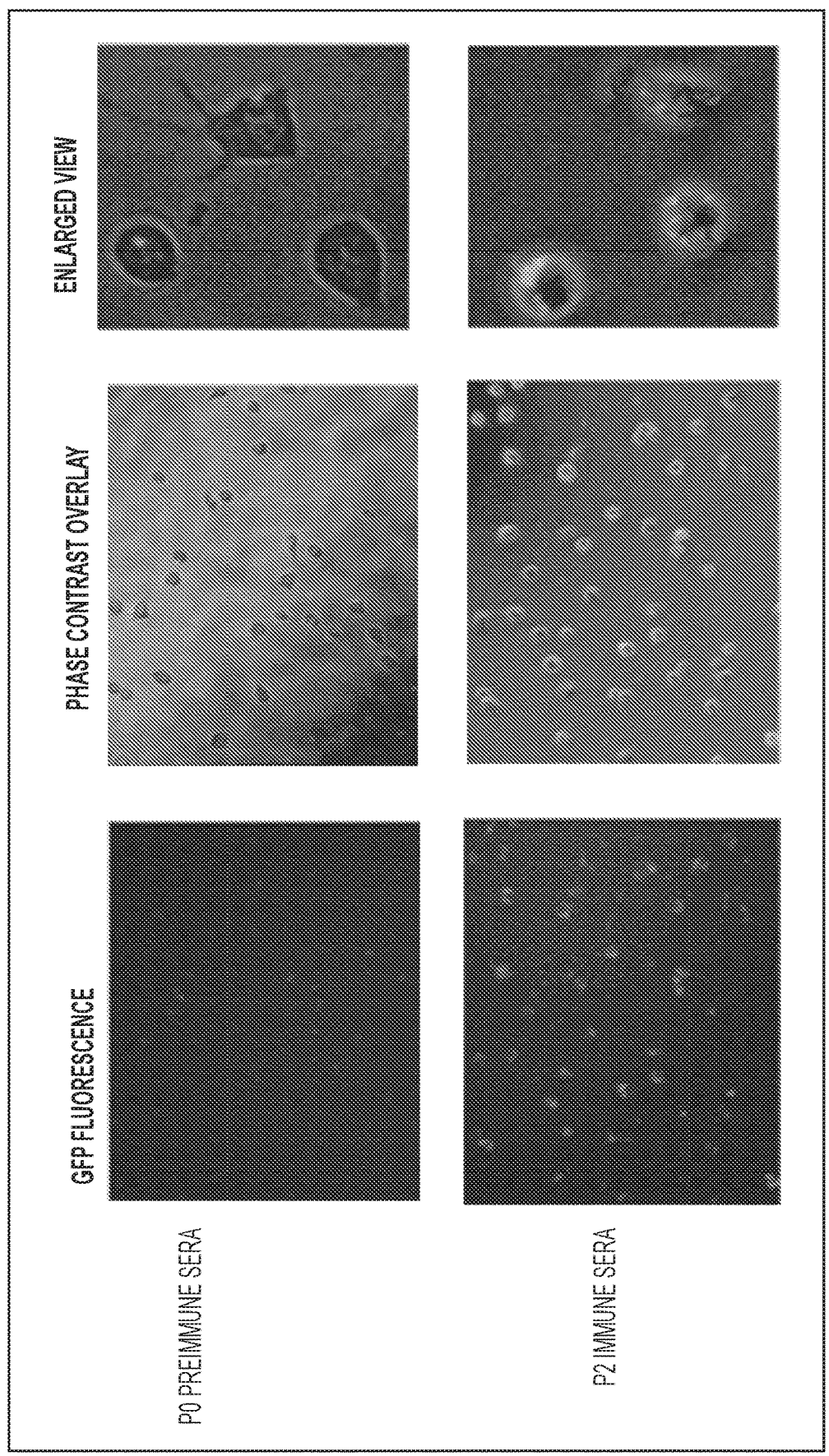
FIG. 50 depicts microscopy analysis of the uptake of bacteria by the macrophage-like J774 cells using a GFP-labeled PA. PA is avidly taken up after exposure to immune sera.
Figure 51:
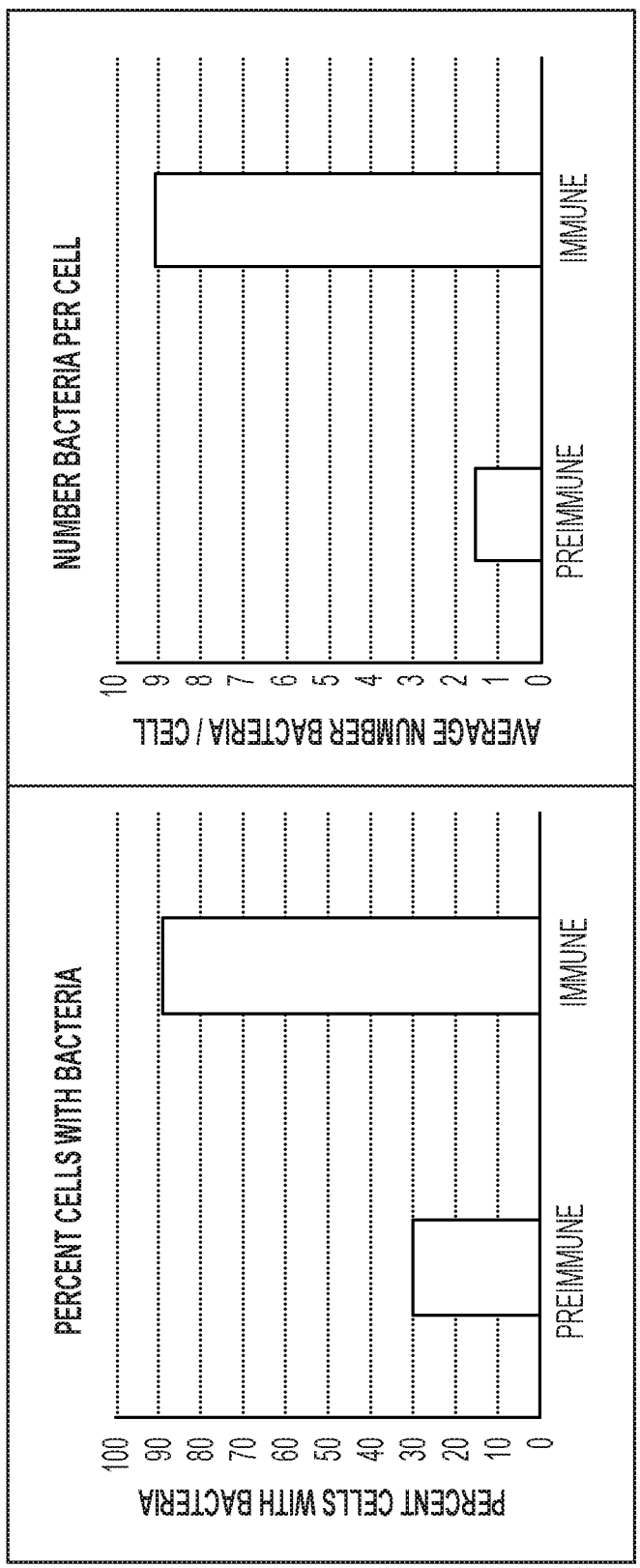
FIG. 51 shows that pooled sera from rabbits who received a 5 µg dose of the 12-valent KP/PA vaccine 1 (60 µg PS total) promotes bacterial uptake by phagocytic cells.

The results for this assay are shown in FIGS. 49, 50, and 51. Immune sera (P0) mediated the uptake of each of these bacterial strains by the phagocytes as demonstrated in FIG. 49. The uptake of bacteria by the macrophage-like J774 cells is further shown by microscopy using a GFP-labeled PA (PA O1, PA O5 FlaB) as illustrated in FIG. 50. PA exposed to the immune sera were avidly taken up by the cells. Multiple P2-treated PA isolates in each J774 cell is shown in the enlarged view in FIG. 50. FIG. 51 shows that a higher proportion of cells (left panel) and higher number of bacteria per cell (right panel) was observed for those cells treated with immune sera compared to those treated with preimmune sera.

HL-60 OPK Assays

In this type of assay, KP O2 strain 7380 bacteria were first opsonized with serum and then differentiated HL-60 cells were added to the mixture. After incubation of the mixture for 45 minutes, viable bacteria were counted. The OPK titer was defined as the titer at which less than 50% of bacteria survive in relation to the negative control (bacteria+HL-60 cells only).

Figure 52:
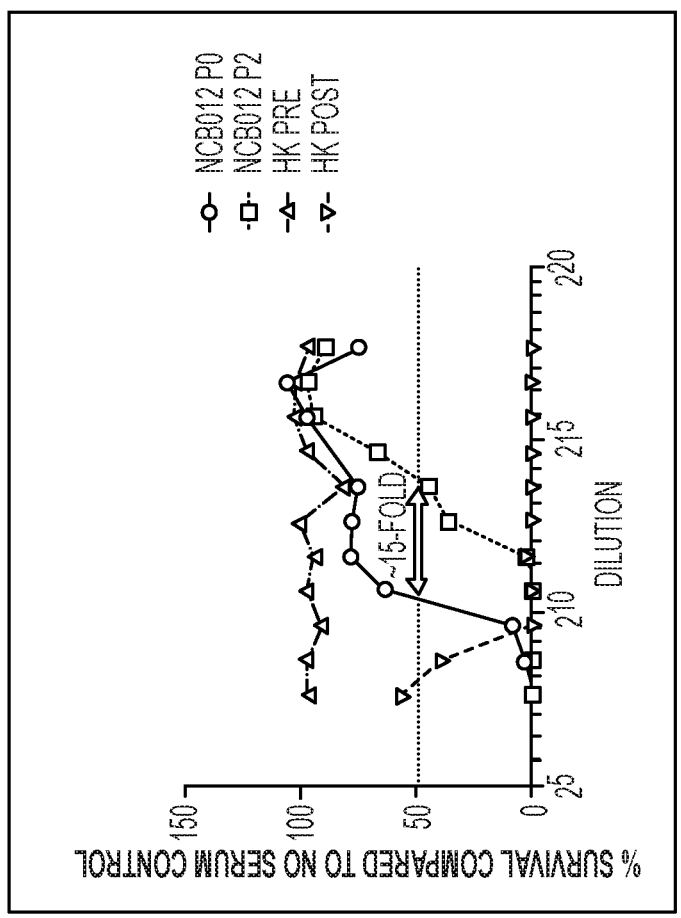
FIG. 52 depicts the percent survival of cells in an HL60 OPK assay with KP O2 strain 7380.

FIG. 52 and Table 25 show the results of the HL60 OPK assay with KP O2 strain 7380 and pooled sera from rabbits immunized with the 5 µg dose of the 12-valent KP/PA vaccine 1. Anti KP O2 heat-killed (HK) rabbit sera pre- and post-immunization served as positive controls. The assay was performed using 1/200 to 1/204,800 dilutions of the sera.

Sera from rabbits immunized with the 12-valent KP/PA vaccine 1 show a significant OPK activity against KP O2 strain 7380 whereas the corresponding preimmune sera showed a much lower effect at killing the bacteria. The killing activity could be attributed to either the KP O2 OPS antibodies or MrkA or to both. Details on the OPK titers for the pre- and post-immunization sera as well as for the positive controls are provided in Table 25. There was a significant difference (>15-fold increase) in killing activity between the pre- (1/800) and the post-immune sera (1/12,800).

TABLE 25

OPK titer for KP O2 strain 7380 in HL-60 assay

| Serum | Time Point | Titer |
|---|---|---|
| NCB012 (pooled) | P0 | 1/800 |
|  | P2 | 1/12,800 |
| Heat-killed bacteria (pooled) | Pre | <1/200 |
|  | Post | >1/204,800 |

A similar assay was performed using strain KP O5 strain 6997. The bacteria were mixed with either preimmune (P0) or immune serum (P2) pools from NCB012 and added to HL-60 cells in the presence of complement (Table 26). A 50 percent reduced survival was observed with immune sera out to a titer of 1:1,280 while the preimmune serum pool exhibited modest reduction at a 1:40 serum dilution

TABLE 26

Percent survival of KP O5 strain 6997 in HL-60 cells using pooled sera

| | Dilution | | | |
|---|---|---|---|---|
| | 1:40 | 1:160 | 1:320 | 1:1280 |
| NCB012 P0 | 83 | >100 | >100 | >100 |
| NCB012 P2 | 23 | 50 | 48 | 50 |

Conclusions for the different OPK assays

Three different OPK assays were used to evaluate the efficacy of the antibodies induced in rabbits after two administrations of the 12-valent KP/PA vaccine 1. Significant OPK activity could be demonstrated against KP types O1, O2, O3 and O5 serotypes in the assays using either human PMNs, J774 macrophage cells, or differentiated HL60 cells. The OPK activity could be attributed to either the OPS-specific antibodies and/or the antibodies to the carrier protein MrkA. The uptake of KP and PA by phagocytic cells promoted by the 12-valent immune serum is likely due to OPS antibody.

Protection from Cell Toxicity

Figure 53:
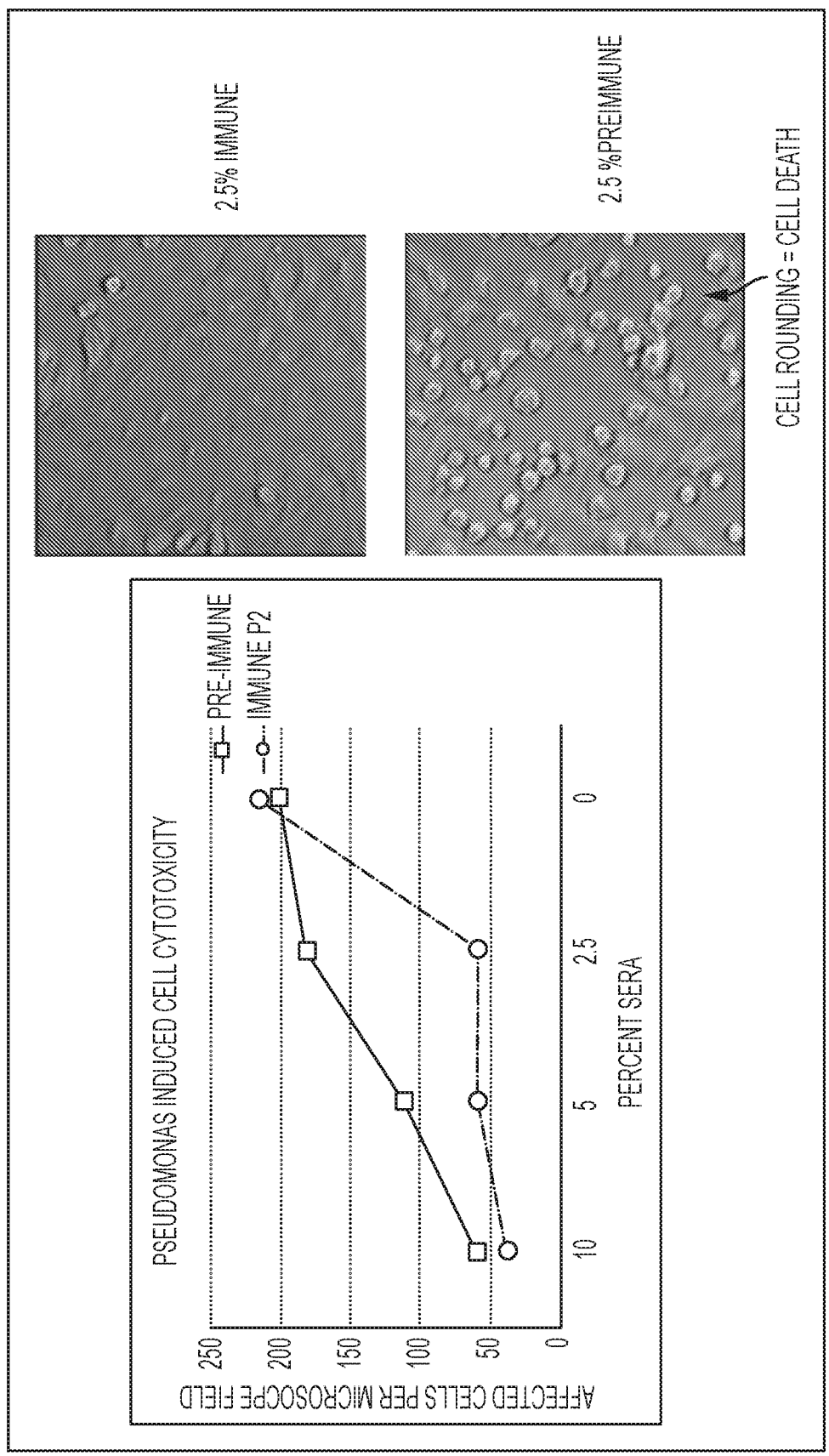
FIG. 53 depicts the results of assays demonstrating that antibodies to PcrV protect cells from cytotoxicity. PA strain (without FlaB) mixed with 12-valent immune serum (pool 10, vaccine-1 high dose) shows decreased cell cytotoxicity compared with preimmune serum from the same rabbits.

Per the protocol described in Example 7, (Cytotoxicity assays for *Pseudomonas* PcrV protein constructs), *Pseudomonas* strain PAK (O6 FlaA1) was grown overnight and used to infect monolayers of human lung epithelial derived A549 cells in the presence of various concentrations (10%, 5%, 2.5%, or nil) of serum from 12-valent KP/PA vaccine-1 immunized rabbits that contain anti-PcrV antibody generated from immune response against MAPS carrier protein or with preimmune serum from these same rabbits at the same range of serum concentrations. *Pseudomonas* induced A549 cytotoxicity is characterized by cell rounding as cells become apoptotic and detach from the surface of the tissue culture plate. Anti-PcrV antibody mediated protection from cytotoxicity is indicated by reduction in the number of rounded (apoptotic) cells in a given microscope field compared to a cells treated with a similar concentration of preimmune serum. The maximum difference in rounded (apoptotic) cells between immune and preimmune serum treatment was observed at a serum concentration of 2.5% (FIG. 53, left graph). Photomicrographs of representative PAK infected A549 cells treated with 2.5% serum demonstrate this difference as a decrease in the number of highly refractive rounded cells in the immune serum treated sample (FIG. 53, right panel). Similar images were used to estimate the number of affected cells at each serum concentration (FIG. 53, left graph).

Reduction of Motility of *P. aeruginosa* Through Antibodies to FlaB

Figure 54:
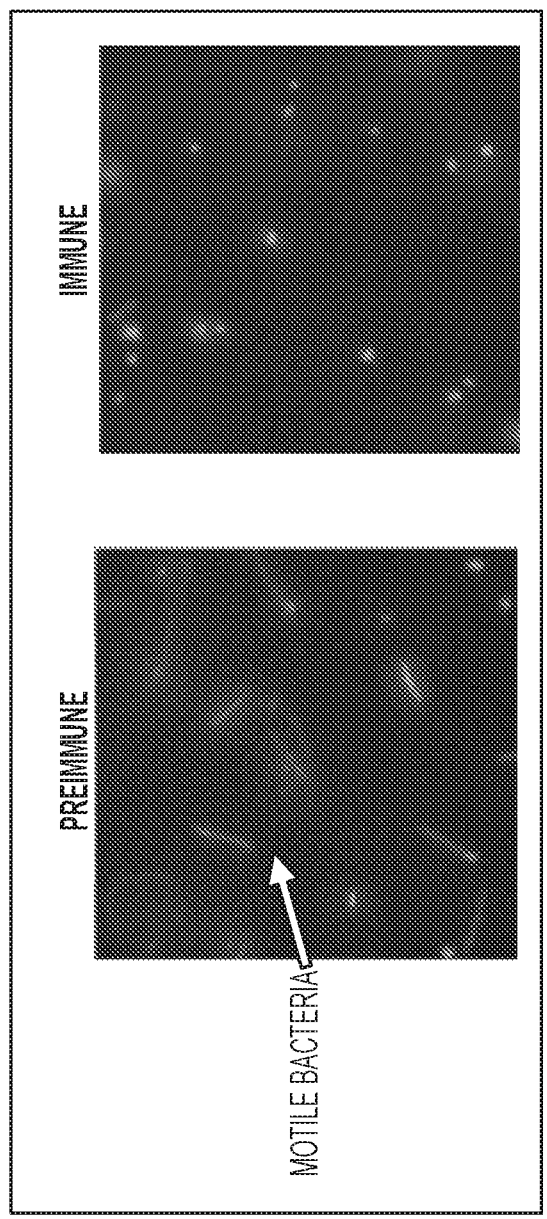
FIG. 54 demonstrates that cells treated with pooled sera from rabbits immunized with a dose of 5 (e.g., 60 µg total PS in vaccine; 5 µg PS contributed by each type of BP in the vaccine) of the 12-valent KP/PA vaccine-1 shows reduced motility of PA O5 FlaB strain through antibody to FlaB compared to treatment with preimmune sera.

As shown in FIG. 54, cells treated with pooled sera from rabbits immunized with a dose of 5 μg per PS (e.g., 60 μg total PS in vaccine; 5 μg PS contributed by each type of BP in the vaccine) of the 12-valent KP/PA vaccine 1 showed reduced motility of PA O5 FlaB strain through antibody to FlaB compared to treatment with preimmune sera.

Aggregation of *P. aeruginosa* Via FlaB Antibodies

Figure 55:
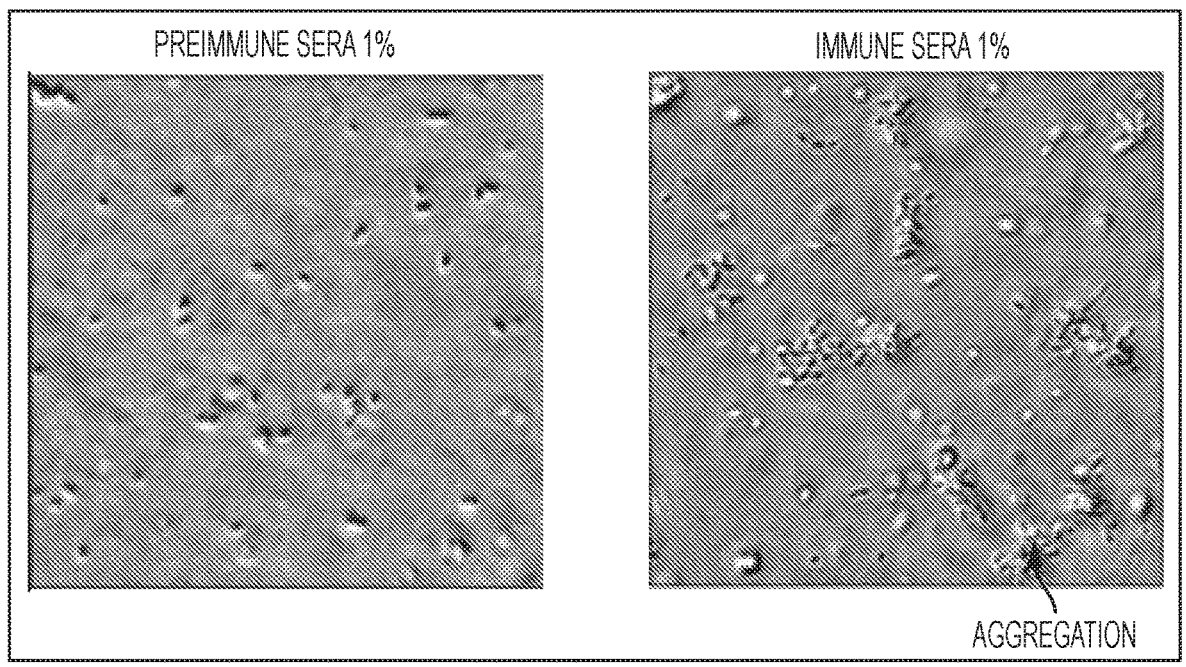
FIG. 55 shows that pooled sera from rabbits immunized with a 4-valent KP vaccine (5 µg dose, treatment group 4), which contains no PA OPS, increased aggregation of FlaB-expressing PA, demonstrating that antibody generated to the FlaB-containing carrier protein is functional.

*P. aeruginosa* strain PAO1 (O5 FlaB) was grown overnight and suspended in PBS to a concentration of $10^7$ CFU/ml then incubated with 1% serum from rabbits vaccinated with 4-valent KP vaccine or with preimmune serum from the same rabbits for 1 hour at room temperature. Anti-FlaB antibody in the serum generated from immune response to the Rhavi-FlaBD2-MrkA-His carrier protein was able to agglutinate FlaB expressing *Pseudomonas* as demonstrated by the clusters of bacteria seen in photomicrographs as black rods (FIG. 55, right panel) and labeled aggregation while no such aggregates were observed with bacteria treated with the preimmune serum (FIG. 55, left panel). FlaBD2 was the only *Pseudomonas* antigen in this vaccine preparation and observation of cross-linked bacteria indicates that the carrier protein induces production of functional antibody capable of recognizing the native epitope produced in bacterial flagellin. Serum from rabbits immunized with 12-valent KP/PA MAPS vaccine-1 was able to agglutinate FlaB expressing *Pseudomonas* with O-type not in the vaccine (data not shown) which strongly suggests that the FlaBD2 containing carrier protein elicited functional anti-FlaB antibody in the 12-valent formulation, although cross-reactivity between the *Pseudomonas* O-types as contributing to the observed agglutination cannot be ruled out.

Adherence Inhibition Assays

Figure 56:
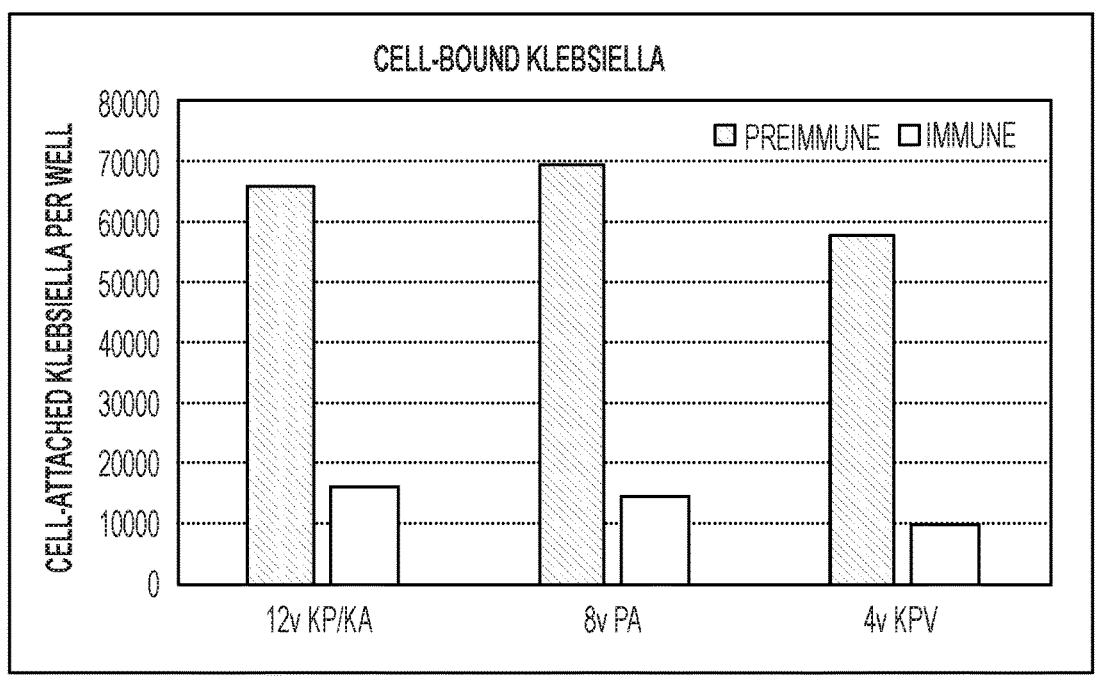
FIG. 56 shows that the pooled sera of rabbits immunized with the 12-valent KP/PA vaccine 1, pooled sera of rabbits immunized with 8-valent PA vaccine (MrkA is the only KP antigen in the 8-valent PA vaccine), pooled sera of rabbits immunized with the 4-valent KP vaccine block the adherence of KP O5 strain 6997 to A549 cells. Data suggest that the MrkA antibody induced by the carrier protein FlaBD2-MrkA is responsible.

In this assay, pooled sera from NCB012 were used to assess the adherence inhibition of the antibody response generated to different exemplary vaccines. Type 3 fimbria-expressing KP O5 strain 6997 bacterial cells were mixed with preimmune and immune sera (10%) and incubated with A549 epithelial cell line cells. Non-adherent bacteria were washed from the cells before lysis of cells and determination of the number of adherent bacteria. Adherence inhibition results in fewer CFU on the plate. FIG. 56 shows that the pooled sera of rabbits immunized with the 12-valent KP/PA vaccine 1, pooled sera of rabbits immunized with 8-valent PA vaccine (MrkA is the only KP antigen in the 8-valent PA vaccine), pooled sera of rabbits immunized with the 4-valent KP vaccine blocked the adherence of KP O5 strain 6997 to A549 cells. Without wishing to be bound by any theory, since the pooled sera of rabbits immunized with the 8-valent PA OPS only vaccine also inhibited adherence, it suggests that the MrkA antibody induced by the carrier protein offers protection.

Example 13: Mouse Protection Assays

Passive immunization studies were performed in mice with antisera obtained from rabbits immunized with the KP/PA vaccines. Table 21 provides information on the vaccine formulations that were used for the immunization of rabbits. Sera from pre- and post immunization of the rabbits (as pooled sera) were used for passive immunization of the mice as described for the different models. Details on the different challenge strains are also described per study.

Passive Protection Study in Mice Against Lethal PA Infection Using Sera from Rabbits Immunized with 12-Valent KP/PA Vaccine 1

A passive protection study in mice was performed using pooled sera from rabbits immunized with a dose of 5 μg per PS (e.g., 60 μg total PS in vaccine; 5 μg PS contributed by each type of BP in the vaccine) of the 12-valent KP/PA vaccine 1 (Table 21, group 5) in study NCB012. Mice were pretreated with either preimmune or immune sera (pooled rabbit sera) and challenged IP with the different PA strains.

At lethal PA challenge doses, the immune sera protected mice from infection with PA O5 and PA O6. There was a trend towards protection with PA O10 and O11 challenges, but the marked difference in survival of mice treated with preimmune serum and challenged with $1 \times 10^8$ CFU and only a 3-fold lower dose illustrates how steep the dose-response curve is for many Gram-negative bacteria. This often presents challenges in performing these assays. Details on the survival rates are presented in Table 27.

TABLE 27

Survival rates of mice in a lethal challenge study with PA

| Bacteria | Dose | Survival Preimmune | Survival Immune |
|---|---|---|---|
| Pseudomonas O5 FlaB Strain M2 | $1.3 \times 10^7$ CFU | 1/5 | 4/5 |
| Pseudomonas O5 FlaB Strain M2 | $1.1 \times 10^8$ CFU | 0/5 | 4/5 |
| Pseudomonas O6 FlaA2 Strain SBI-N | $1 \times 10^8$ CFU | 0/5 | 5/5 |
| Pseudomonas O10 FlaB Strain 17002 | $1 \times 10^7$ CFU | 2/5 | 5/5 |
| Pseudomonas O11 FlaB Strain 1071 | $1 \times 10^8$ CFU | 0/5 | 3/5 |
| Pseudomonas O11 FlaB Strain 1071 | $3 \times 10^7$ CFU | 4/5 | 5/5 |

Passive Protection Study in Mice Against *Klebsiella* KP O3 Using Sera from Rabbits Immunized with the 12-Valent KP/PA Vaccine 1

Sera from the four highest anti-KP-O3 responders (rabbits 1502, 1506, 1508 and 1511; Table 28) immunized with the 12-valent KP/PA vaccine 1 at a dose of 5 μg per PS (e.g., 60 μg total PS in vaccine; 5 μg PS contributed by each type of BP in the vaccine) (group 5) in NCB012 were pooled and injected (preimmune or immune sera) IP 20 hours and 2 hours before IV challenge with KP O3 strain 700603 at 50,000 CFU in 0.1 ml.

TABLE 28

Preimmune and immune titers for rabbit sera included in the pooled samples

| Rabbit Number/ Serum Sample | Preimmune O3 Titer | Immune O3 Titer |
|---|---|---|
| 1502 | 5 | 1,017 |
| 1506 | 10 | 2,306 |
| 1508 | 19 | 4,024 |
| 1511 | 5 | 704 |

Four hours after challenge mice were euthanized and blood, liver and spleen were harvested, and colony counts determined. Results are provided in Table 29. Mice given pooled immune sera showed blood clearance and reduced numbers of viable bacteria in the liver and spleen compared to mice treated with preimmune sera from the same rabbits. These results were similar for bacterial clearance using sera of equivalent titer from rabbits immunized with the 4-valent KP MAPS in study NCB008.

TABLE 29

Geometric mean CFU for blood clearance and viable bacteria in organs after challenge with *Klebsiella* KP O3

| Sera Sample | Blood | Liver | Spleen |
|---|---|---|---|
| NCB008 Preimmune | 5,235 | 12,590 | 7,353,290 |
| NCB008 Immune | No bacteria | 3,302 | 89,159 |
| NCB012 Preimmune | 10,020 | 27,180 | 2,635,845 |
| NCB012 Immune | No bacteria | 2,952 | 195,421 |

Passive Protection Study in Mice Against *Klebsiella* KP O1 Strain B5055 Using Sera from Rabbits Immunized with the 12-Valent KP/PA Vaccine 1

Figure 57:
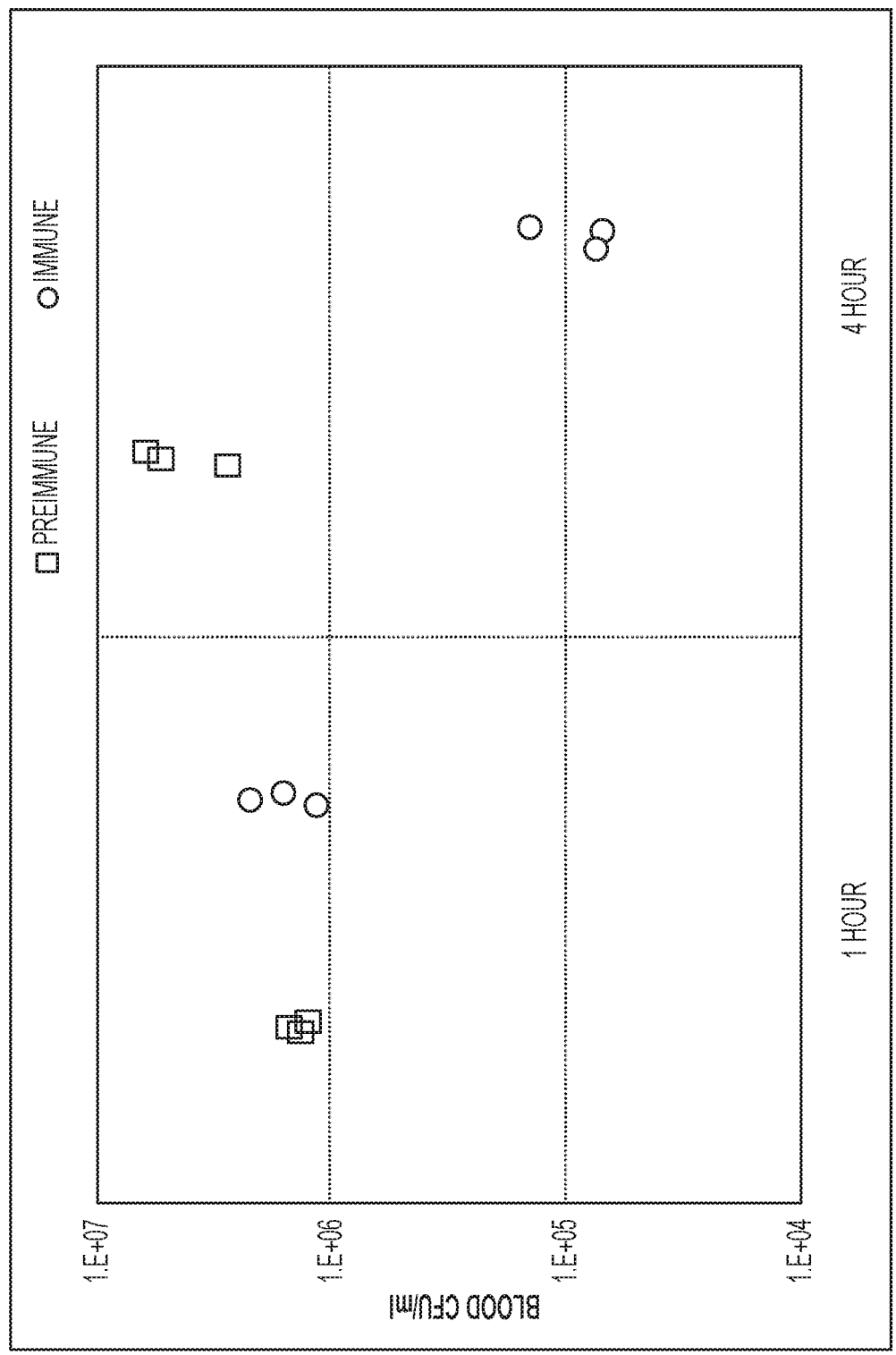
FIG. 57 depicts blood clearance assay results for 3 mice challenged with KP O1 strain B5055 1 hour and 4 hours post challenge.

In this study three mice per group were injected with pooled sera from rabbits that were immunized with the 12-valent KP/PA vaccine 1 at a dose of 5 µg per PS (e.g., 60 µg total PS in vaccine; 5 µg PS contributed by each type of BP in the vaccine) (Table 21, group 5) in study NCB012 (preimmune and immune sera) followed by an intravenous (IV) challenge with KP O1 strain B5055 at $5 \times 10^6$. Results for the blood clearance assay at 1 and 4 hours post challenge are listed in Table 30 as geometric mean CFU/ml blood and illustrated in FIG. 57 for individual mice.

At four hours post challenge, blood from mice in the immune sera group had a significant reduction in CFU/ml while the CFU/ml in mice that received the preimmune sera stayed elevated.

TABLE 30

Blood clearance assay results as geometric mean CFU/ml in mice afte rchallenge with KP O1 strain B5055

| | | Blood | |
|---|---|---|---|
| Serum Sample | Dose | 1 hour | 4 hours |
| Preimmune | $5 \times 10^6$ CFU | 1,362,840 | 4,449,118 |
| Immune | $5 \times 10^6$ CFU | 1,593,725 | 91,308 |

Figure 58:
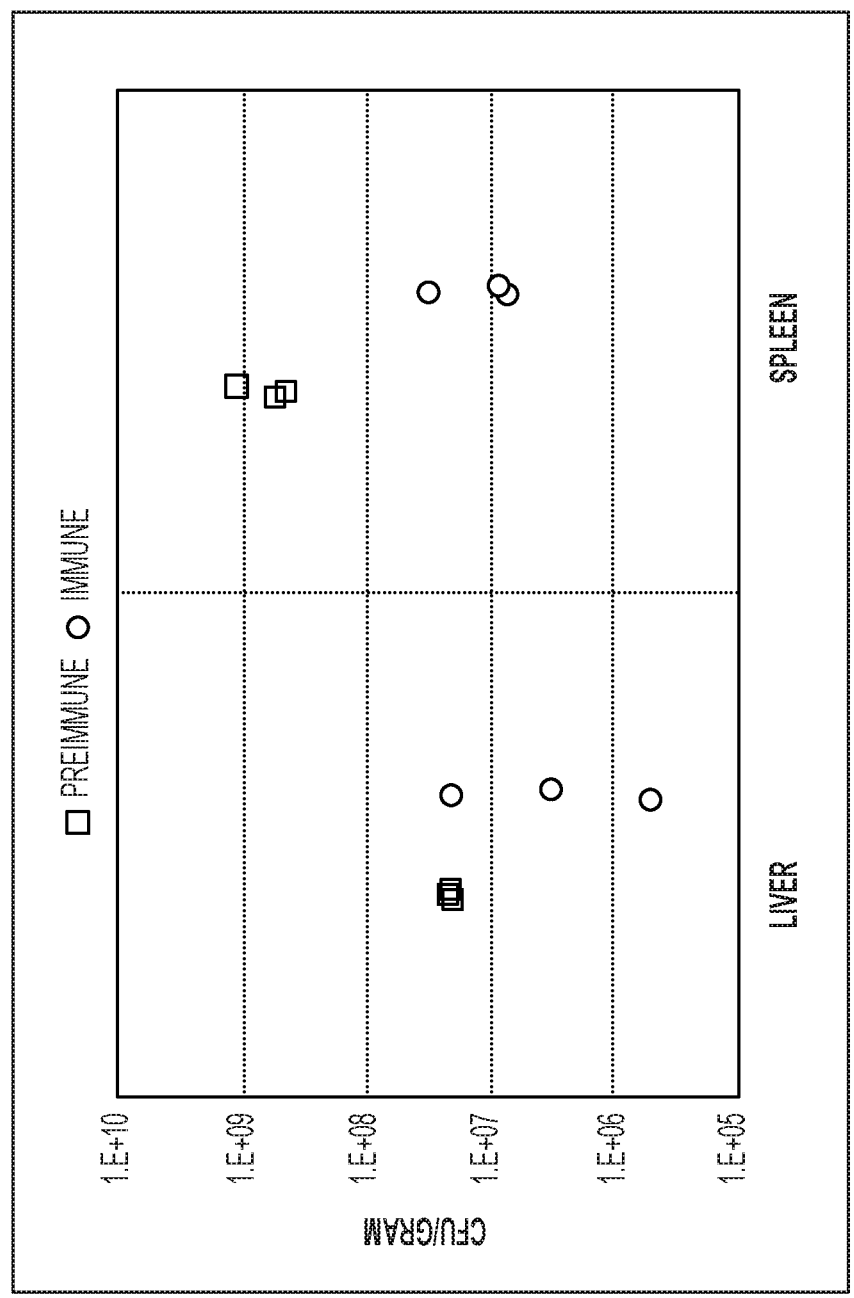
FIG. 58 depicts organ burden in liver and spleen of mice after challenge with KP O1 strain B5055.

The results for the organ burden of spleen and liver in these mice are listed in Table 31 as geometric mean CFU/g tissue for the three mice. FIG. 58 shows the results of the organ burden for spleen and liver of the three mice 20 hours post challenge.

Two of three mice that received the immune sera showed decreased geometric mean CFU counts in the liver compared to the mice that received the preimmune sera. The results for the spleen show a similar pattern for mice pretreated with the immune sera showing significant decrease 20 hours post challenge compared to the mice that received the preimmune sera who had a significantly higher bacteria count.

TABLE 31

Organ burden in mice as geometric mean CFU/g tissue after challenge with KP O1 strain B5055

| | Dose | Spleen | Liver |
|---|---|---|---|
| Preimmune | $5 \times 10^6$ CFU | 672,204,849 | 21,447,778 |
| Immune | $5 \times 10^6$ CFU | 12,867,923 | 3,308,911 |

Passive Protection Study in Mice Against *Klebsiella* KP O5 Strain 6997 Using Sera from Rabbits Immunized with the 12-Valent KP/PA Vaccine 1

Figure 59:
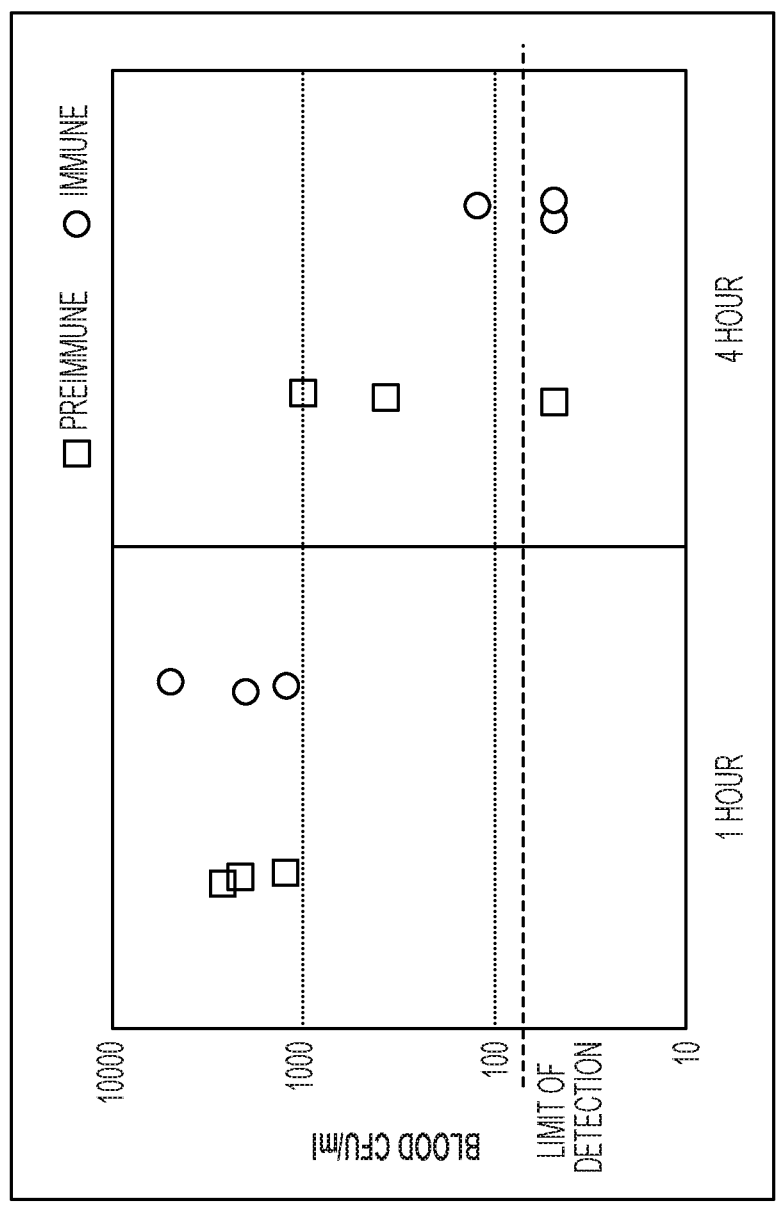
FIG. 59 depicts blood clearance assay results for 3 mice challenged with KP O5 strain 6997 1 hour and 4 hours post challenge.

In this study three mice per group were injected with pooled sera from rabbits that were immunized with the 12-valent KP/PA vaccine 1 at a dose of 5 µg per PS (e.g., 60 µg total PS in vaccine; 5 µg PS contributed by each type of BP in the vaccine) in study NCB012 (Table 21, group 5 preimmune and immune sera) followed by an IV challenge with KP O5 strain 6997 at $5 \times 10^6$. Results for the blood clearance assay at 1 and 4 hours post challenge are listed in Table 32 as mean CFU/ml blood and illustrated in FIG. 59 for individual mice.

At four hours post challenge, blood from 2 of the 3 mice in the immune sera group had cleared the bacteria with a significant decrease in CFU burden in the third mouse, while the CFU in mice that received the preimmune sera stayed elevated (2 out of 3 mice) at four hours post challenge.

TABLE 32

Blood clearance assay results as geometric mean CFU/ml in mice after challenge with KP O5 strain 6997

| | | Blood | |
|---|---|---|---|
| | Dose | 1 hour | 4 hours |
| Preimmune | $5 \times 10^6$ CFU | 1910 | 458 |
| Immune | $5 \times 10^6$ CFU | 2340 | 42 |

Figure 60:
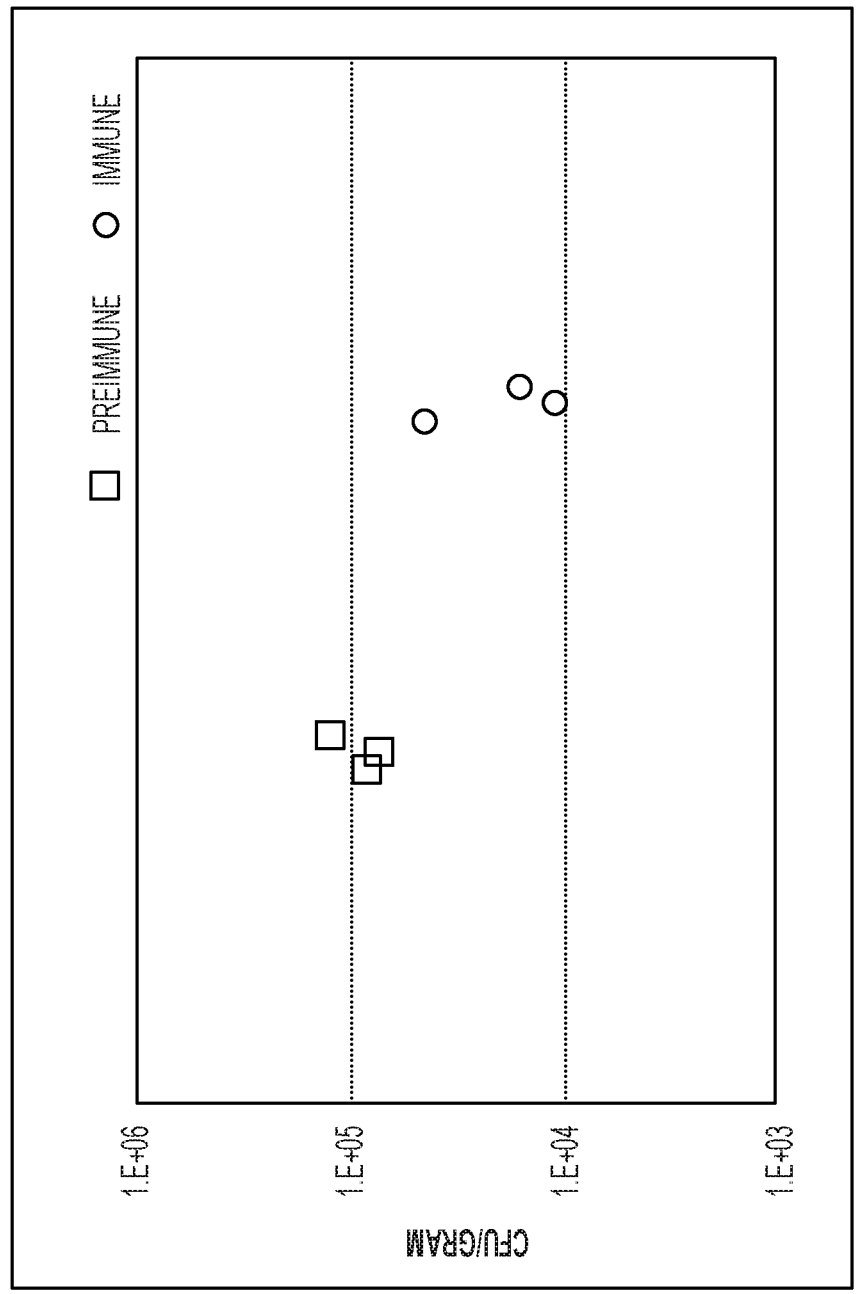
FIG. 60 depicts organ burden in spleen of mice after challenge with KP O5 (strain 6997).

The results for the organ burden of spleen in these mice are listed in Table 33 as geometric mean CFU/g tissue for the three mice and FIG. 60 shows the results of the organ burden for spleen of the three mice 20 hours post challenge.

For the spleen, it was observed that the mice that received the immune sera had much lower bacteria counts 20 hours post challenge than those mice that received the preimmune sera.

TABLE 33

Organ burden in mice as geometric mean CFU/g tissue after challenge with KP O5 strain 6997

| | Dose | Spleen |
|---|---|---|
| Preimmune | $5 \times 10^6$ CFU | 93,750 |
| Immune | $5 \times 10^6$ CFU | 20,432 |

Passive Protection Study in Mice Against *Klebsiella* KP O2 (Strain KPN 12) from Rabbits Immunized with the 12-Valent KP/PA Vaccine 1

Figure 61:
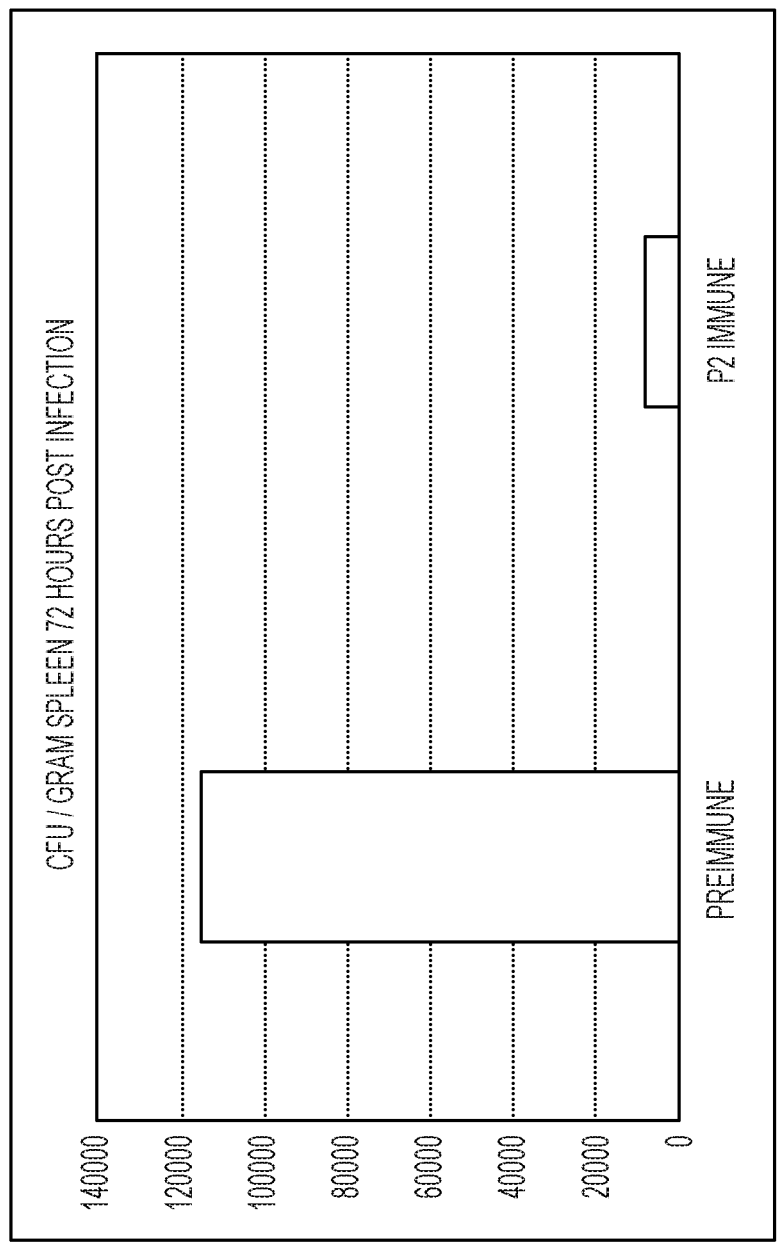
FIG. 61 depicts passive protection analysis of organ burden in spleen of mice, demonstrating clearance of KP O2 (strain KPN-12) from circulation in mice treated with sera from rabbits immunized with the 12-valent KP/PA vaccine 1.

In this study, CD-1 mice (3/group) were given 0.2 ml of pre- or immune serum pools (10 rabbits per pool, study NCB012) 24 hrs and 2 hrs prior to IV administration of $2 \times 10^5$ CFU KP O2 strain KPN-12. The spleens were harvested 72 hours after infection and the bacterial burden per gram of tissue was determined. Mice that received the immune sera showed reduced numbers of viable bacteria compared with mice treated with preimmune sera (7,978 versus 114,687 mean CFU; FIG. 61). The pooled immune sera promoted the clearance of KP O2 (strain KPN-12) from the circulation.

Figure 62:
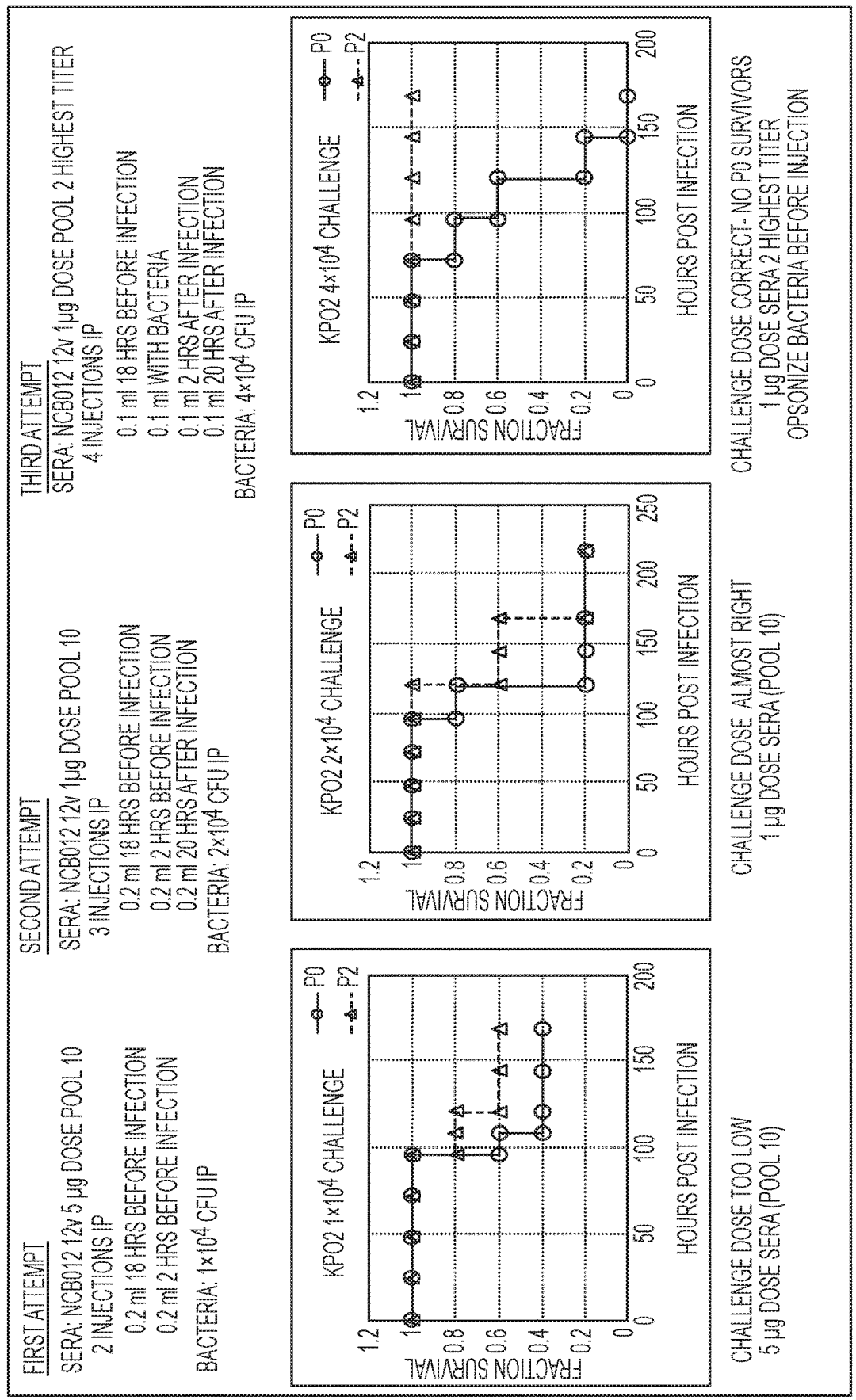
FIG. 62 depicts various exemplary optimizing protocols and results of CD-1 mouse passive protection experiments with NCB012 preimmune and immune sera against *Klebsiella* O2 K2.

Several experiments with NCB012 preimmune and immune sera were done to develop and optimize a passive protection protocol in a lethal challenge model with *Klebsiella* KP O2. Similar experiments may be done to develop and optimize a passive protection protocol for other organisms, other vaccines or immunogenic compositions, and/or other pathogens/strains. Variables such as the challenge dose of bacteria, the delivery of the inoculum (e.g. opsonizing the bacteria before injection) and the number, timing and strength of the sera for passive protection (e.g. sera generated with either the 5 µg or 1 µg polysaccharide dose) were examined. Exemplary parameters tested and results are depicted in FIG. 62.

Th17 Response and Colonization of CD-1 Mice—with Challenge

This experiment was designed to determine the ability of three doses of the KP O1 MAPS vaccine with FlaBD2 and MrkA administered to mice, each dose administered fourteen days after the previous dose, to reduce bacterial colonization after bacterial challenge two weeks after the last immunization. Two groups of CD-1 mice were to undergo bacterial challenge; one group was immunized with KPO1/FlaBD2-MrkA MAPS vaccine and the other group was immunized with buffer (PBS) alone.

Five mice per group were challenged with $3-5 \times 10^3$ CFU KP B5055 (O1:K2) intratracheally (IT). At 48 hours after bacterial challenge the lungs were harvested and weighed, homogenates plated for bacterial counts and then centrifuged. The supernatants were assessed for IL-17a levels. Concurrently, the spleens were co-cultured with PBS, FlaBD2 and MrkA as described above, and after three days supernatants were assessed for IL-17a levels.

Figure 63:
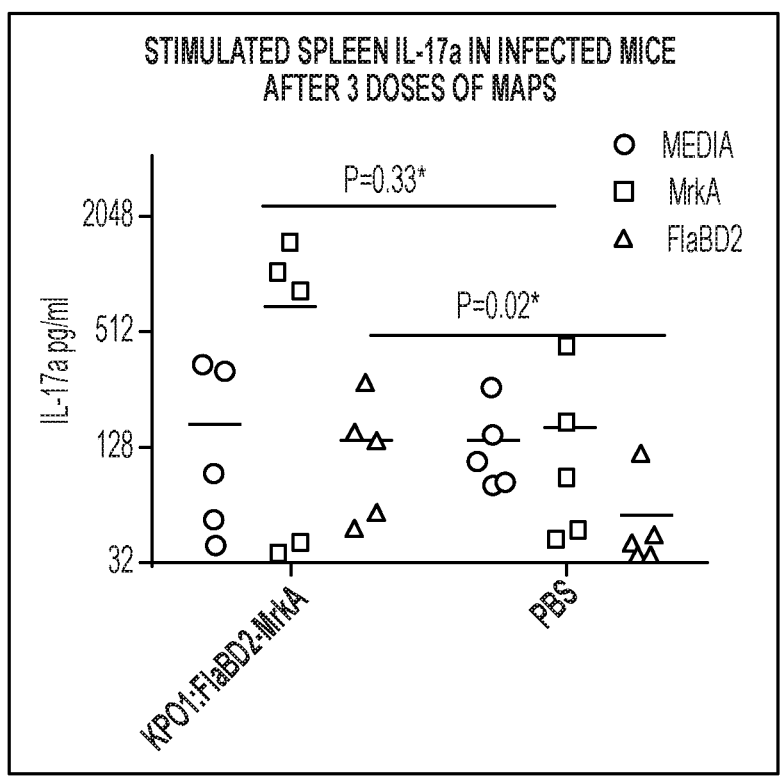
FIG. 63 depicts IL-17a induction in stimulated spleen cells from mice immunized with KP O1 MAPS vaccine followed by bacterial challenge with KP O1:K2 strain B5055.

FIG. 63 shows the IL-17a induction for stimulated spleen cells after bacterial challenge. A significant induction was observed for FlaBD2 stimulated spleen cells (p=0.02).

Effect of Immunization on GI Tract Colonization with *P. aeruginosa*

The following experimental protocol was designed to examine the effect of immunization with a monovalent PA O6 MAPS vaccine on gastrointestinal (GI) colonization with *P. aeruginosa*.

Eight Sprague-Dawley rats were immunized two times with 0.5 ml SC at two-week intervals with a monovalent MAPS vaccine, MA6-93-PAO6 (*Klebsiella pneumoniae* K19: *Pseudomonas aeruginosa* 06/Rhavi-FlaBD2-MrkA-his BP-1). Seven rats were immunized with buffer alone. Fourteen days after the second immunization rats were treated with ceftriaxone (50 mg/kg IM) and continued to receive once daily doses of the antibiotic for nine days. Rats were given antibiotics to overcome the colonization resistance in the GI tract to opportunistic bacteria, such as PA, and to mimic the clinical situation. After four days of antibiotic alone the rats were administered *P. aeruginosa* (PA, IATS O6) at $10^8$ CFU by gavage for a total of five days. After five daily doses of PA and nine daily doses of ceftriaxone, rats were euthanized, and the cecum was removed, weighed and then cultured. Blood was obtained for antibody levels before antibiotics and bacteria were administered, and stool samples were obtained for PA culture the day before and two days after the first dose of PA. Details can also be found in the upper half of FIG. 64.

Figure 64:
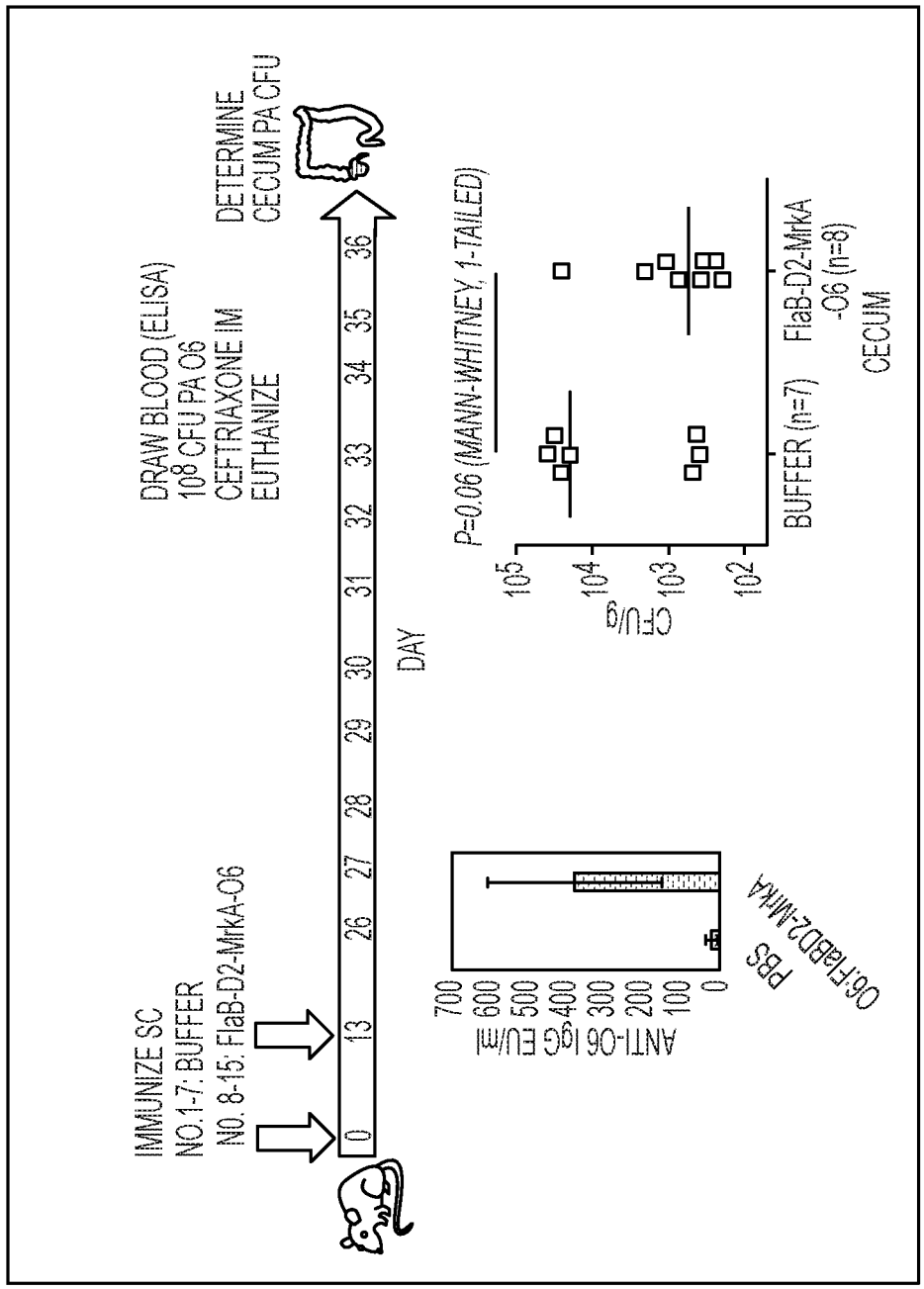
FIG. 64 depicts treatment protocol and results of a GI tract colonization study with PA O6 in rats immunized with two doses of a PA O6 MAPS vaccine followed by bacterial challenge.

The results of the colonization study in rats with the two dose PA O6 FlaBD2-MrkA MAPS vaccine are shown in the bottom of FIG. 64. Rats that received the PA O6 vaccine had an elevated ELISA IgG titer over the rats that received PBS (bottom left of the figure). The vaccinated rats also showed a median of less than $10^3$ CFU/g bacteria compared with the control rats who had a median of $>10^4$ CFU/g (bottom right of the figure). The study results indicate a reduction of cecum colonization of PA O6 after two immunizations with a monovalent PA O6 MAPS vaccine.

Example 14: Anti-OPS Antibody to Carbapenem-Resistant KP (CRKP) Strains Expressing the Gal-III Epitope In contrast to other classes of bacterial carbapenemase (e.g. oxa-48 or metallo-beta-lactamases), the spread of KPC (*K. pneumoniae* carbapenemase) appears to be at least partially a clonal phenomenon. A specific lineage termed sequence type (ST) 258 has been shown to be responsible for the majority of KPC-producing *Klebsiella* infections that are endemic in several geographical regions. Currently, in the Northeast states of the USA >30% of all nosocomial *K. pneumoniae* infections are caused by CRKP, and about 70% of these belong to the KPC-producing ST258 clone. Similarly, this clone (including single locus ST variants) is epidemic in other parts of the world, including Israel, Poland, Italy, Greece, South America, and China. Recently, an investigation of the molecular evolution of ST258 identified two clades that are associated with the expression of different capsular polysaccharides (Chen 2014a, Chen 2014b, DeLeo 2014). *Klebsiella pneumoniae* ST258 is a globally disseminated, extremely drug resistant, nosocomial clone with limited treatment options.

Figure 65:
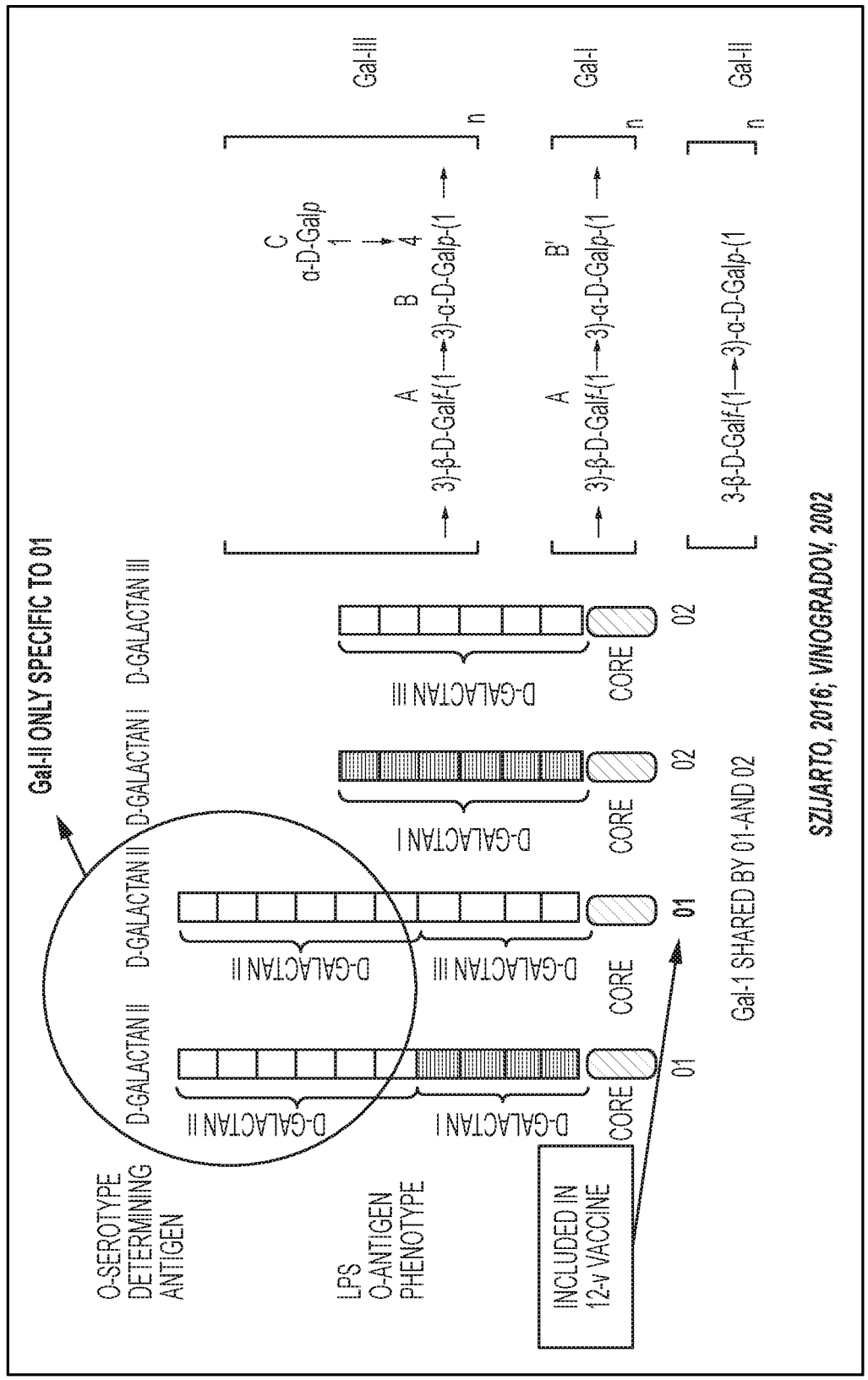
FIG. 65 depicts a schematic of the structure of the KP OPS Gal-I, Gal-II and Gal-III epitopes.

KP O1 and KP O2 antigens are built of homopolymers of galactose, i.e. galactans. The KP O2 antigen termed d-galactan-I (gal-I) is composed of galactose disaccharide repeating units. In the case of KP O1, gal-I is capped by repeats of an antigenically different galactose disaccharide termed d-galactan-II (gal-II), which determines serotype specificity. The rare serotype KP O2ac has an analogous structure, i.e. repeats of gal-I subunits are capped by a polymer of a distinct, in this case, non-galactan repeating unit. Accordingly, KP O1, KP O2, and KP O2ac strains all share the gal-I antigen, however, while in KP O2 this is the sole O-antigen determinant, in the case of KP O1 and KP O2ac, gal-I is shielded by the outer repeating units. Moreover, the gal-I disaccharide repeating units can be decorated by stoichiometric and non-stoichiometric addition of O-acetyl- or galactosyl groups generating subtypes within the KP O2 serogroup (FIG. 65). The clear majority of ST258 isolates express modified d-galactan-I lipopolysaccharide O-antigen, with the galactosyl groups decorated Gal-I termed hereinafter as d-galactan-III (Szijártó V. et al., 2016).

The KP O1 OPS is comprised by a short "primer" stretch of D-Gal-I or D-Gal-III followed by a long stretch of D-Gal-II. KP O2 OPS is comprised by only D-Gal-I or D-Gal-III (FIG. 65). The Gal-II epitope is only specific to the KP O1 serotype.

B5055 OPS which is the source of the KP O1 antigen in the MAPS vaccine has the short stretch of D-Gal-III followed by long D-Gal-II polymer. KP 7380 (source of the KP O2 vaccine antigen) has only D-Gal-I.

Figure 66:
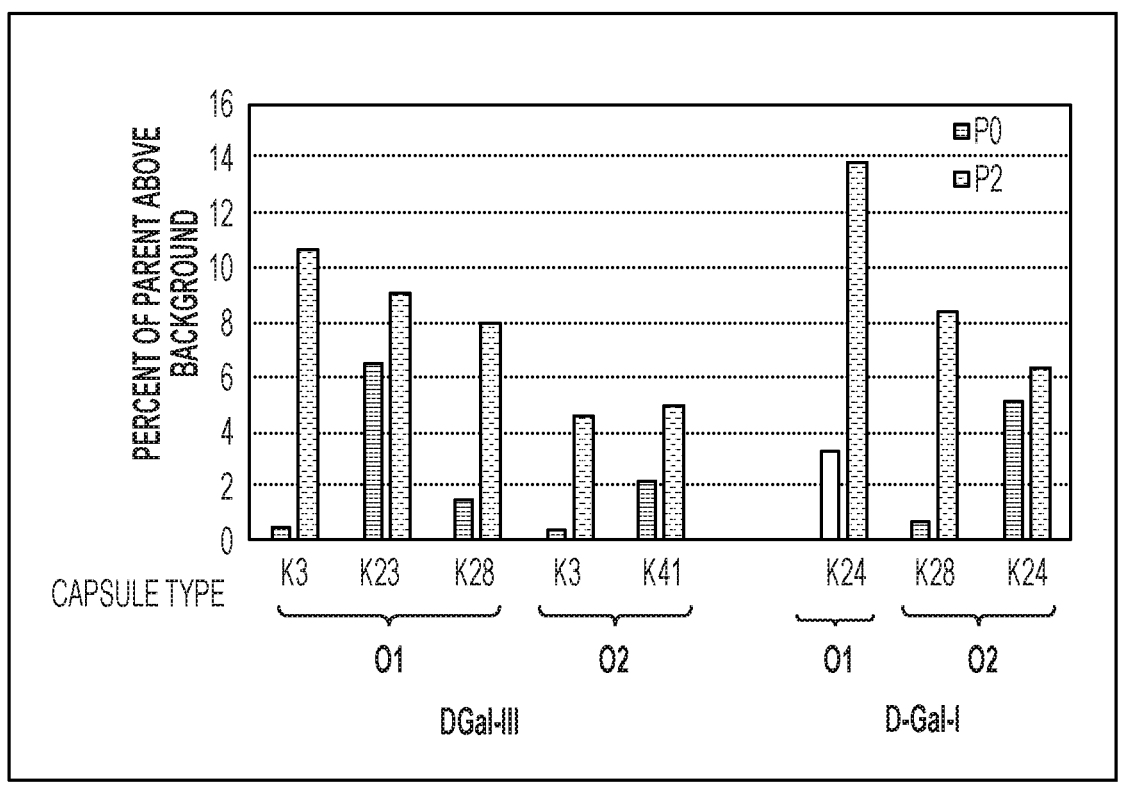
FIG. 66 depicts the binding to KP D-Gal-III and KP D-Gal-I expressing epitopes by flow cytometry in antisera from animals immunized with a 4-valent KP PRO-CN MAPS vaccine.

To investigate if the KP/PA MAPS vaccine has the potential to generate antibodies to the Gal-III epitope and thus would have the potential to prevent infections due to the KPCR ST 258 clonal strains was investigated. Pooled sera (P2) from rabbits immunized with the 4-valent KP PRO-CN MAPS vaccine at 5 µg dose were used in a flow cytometry assay to demonstrate the binding capacity to KP D-Gal-III and KP D-Gal-I expressing epitopes. In this case the only relevant response would be to OPS recognized D-Gal-I O2 and D-Gal-III O2 OPS, D-Gal-II O1 OPS. The results demonstrated an increase in binding over the corresponding preimmune sera (P0) for both KP O1 and KP O2 of D-Gal III and D-Gal I OPS (FIG. 66). It is therefore likely that antibodies were generated against all three KP D-Gal types.

Figure 67:
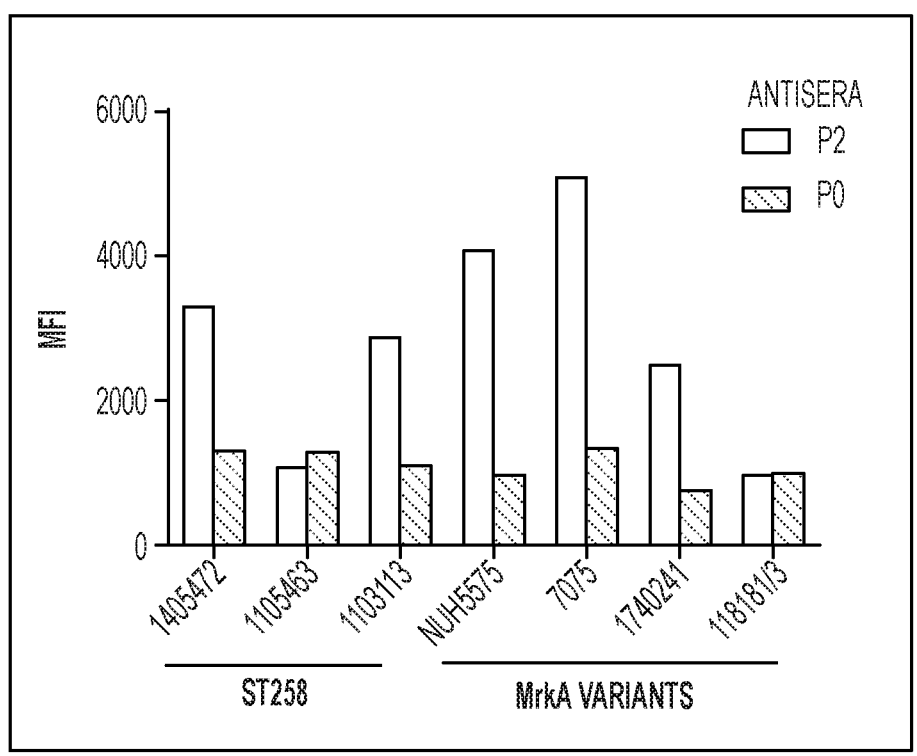
FIG. 67 depicts results of flow cytometry analysis demonstrating that antibodies in sera pooled from rabbits immunized with the 12-valent KP/PA vaccine 1 bound to two of three ST258 strains from bacteremia isolates and also bound three of four strains of serotypes not in the vaccine with mutant alleles of MrkA.

Flow cytometry analysis as provided in Table 34 and FIG. 67 show that antibodies in sera pooled from rabbits immunized with the 12-valent KP/PA vaccine 1 bound to two of three ST258 strains from bacteremia isolates. 12-valent KP/PA vaccine 1 antisera bound to three of four strains of serotypes not included in the vaccine, including strains with MrkA alleles with minor sequence variants (FIG. 67). Without wishing to be bound by any theory, these data suggest that the majority of KP strains, not just those having the serotypes of the OPS components of the 12-valent KP/PA vaccine 1, will be recognized by antibodies raised by the vaccine via the MrkA fusion protein component.

TABLE 34

Flow cytometry results of 12-valent sera vaccine-1 to *Klebsiella* strains of serotypes not included in the vaccine and which possess mutant alleles of MrkA

| Strain | Country | Serotype | ST | KType | Mr kA Alleles | Binding by Flow |
|---|---|---|---|---|---|---|
| 1405472 | USA | O1 | 258 | Wzi 154 | Unknown | Yes |
| 1105463 | USA | O2 | 258 | Wzi 154 | Unknown | No |
| 1103113 | USA | O2 | 258 | Wzi 154 | Conserved | Yes |
| NUH5575 | Japan | Not O1, O2, O3 or O5 | Unknown | Wzi 41 | T23N | Yes |
| 7075 | South Africa | Not O1, O2, O3 or O5 | Unknown | Wzi 212 | A9V, T12S | Yes |
| 170241 | USA | Not O1, O2, O3 or O5 | Unknown | K24 | Conserved | Yes |
| 118181/3 | DRC | Not O1, O2, O3 or O5 | Unknown | Wzi 52 | No MrkA | No |

The results for the binding capacity of the 4-valent KP MAPS vaccine to the KP D-Gal-I and D-Gal-III expressing epitopes indicate that a 12-valent KP/PA vaccine has the potential to generate antibodies to the Gal-III epitope and to prevent infections due to the KPCR ST 258 clonal strains.

Example 15: Preparation of BP-1.2

BP-1 benefits from having biotin residues located solely on the CPS aspect of the BP which can be advantageous in terms of product characterization and minimal disturbance of OPS epitopes. A variant of this process for making such a backbone was developed, which relies on linking the biotin residues to the CPS at an orthogonal site, using the carboxylates of the uronic acid residues of the polysaccharide as opposed to an aldehyde. This reaction, which involves the use of the carbodiimide (EDC) and N-hydroxysuccinimide (NETS) is highly controllable and allows for a consistent level of biotinylation in the CPS and the resulting BP. The BP prepared by such a method is referred to as BP-1.2. A schematic of an exemplary process for preparing BP-1.2 is depicted in FIG. 2B.

Some advantages of this process include providing a consistent biotinylation process with better control over the level of biotin derivatization, and better product consistency as all BPs derive from the same biotinylated CPS batch, providing a stable biotinylated intermediate that can be stored in large batches, and the potential for achieving a higher OPS/CPS ratio in the BP because more aldehyde groups are available on the CPS leading to less competition for the same binding sites.

Example 16: Immunization Studies of BP-1 and BP-1.2 Immunogenic Complexes 4-valent vaccines were prepared as either a BP-1 MAPS or a BP-1.2 MAPS and formulated according to Table 35. These compositions were administered to rabbits using the protocols described above, e.g., Examples 6 and 11.

TABLE 35

Summary of vaccine formulations used in BP-1 and BP-1.2 comparison study.

| Group | Vaccine | Pathogen | Carrier protein | Serotypes | Dose per PS (total) | Protein:PS ratio (total protein) | Adjuvant | Rabbits |
|---|---|---|---|---|---|---|---|---|
| 1 | 4-valent KP/PA vaccine BP-1 5 µg per PS dose | *Pseudomonas* | Rhavi-FlaBD2-MrkA-his | O6, O11 | 5 µg (20 µg) | 3:1 (60 µg) | 625 µg ALPO4 | 10 |
|   |   | *Klebsiella* | Rhavi-FlaBD2-MrkA-his | O3, O5 |   |   |   |   |
| 2 | 4-valent KP/PA vaccine BP-1.2 5 µg per PS dose | *Pseudomonas* | Rhavi-FlaBD2-MrkA-his | O6, O11 | 5 µg (20 µg) | 3:1 (60 µg) | 625 µg AlPO4 | 10 |
|   |   | *Klebsiella* | Rhavi-FlaBD2-MrkA-his | O3, O5 |   |   |   |   |

Figure 68:
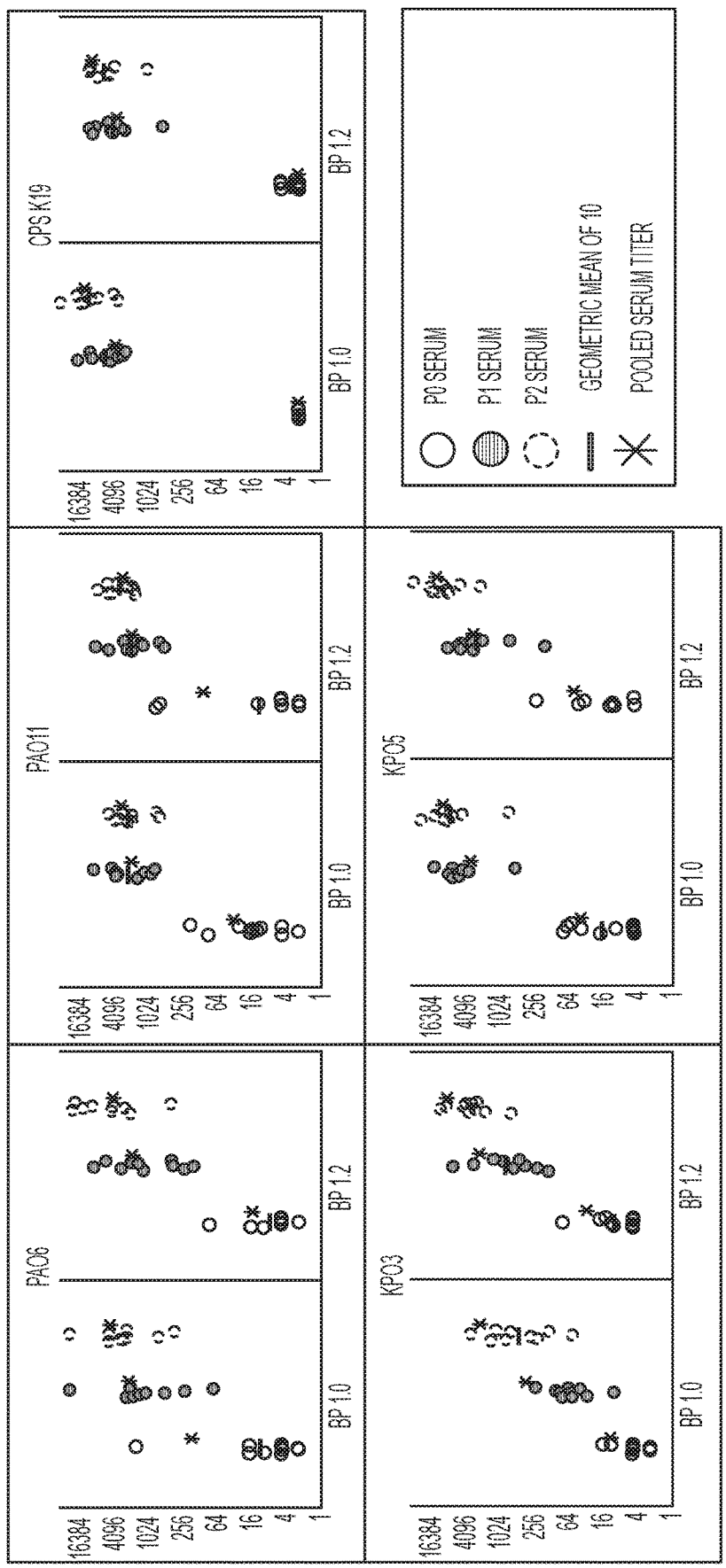
FIG. 68 depicts individual anti-OPS IgG titers following immunization with BP-1 (group 1) and BP-1.2 (group 2) KP/PA 4-valent MAPS vaccine.
Figure 69:
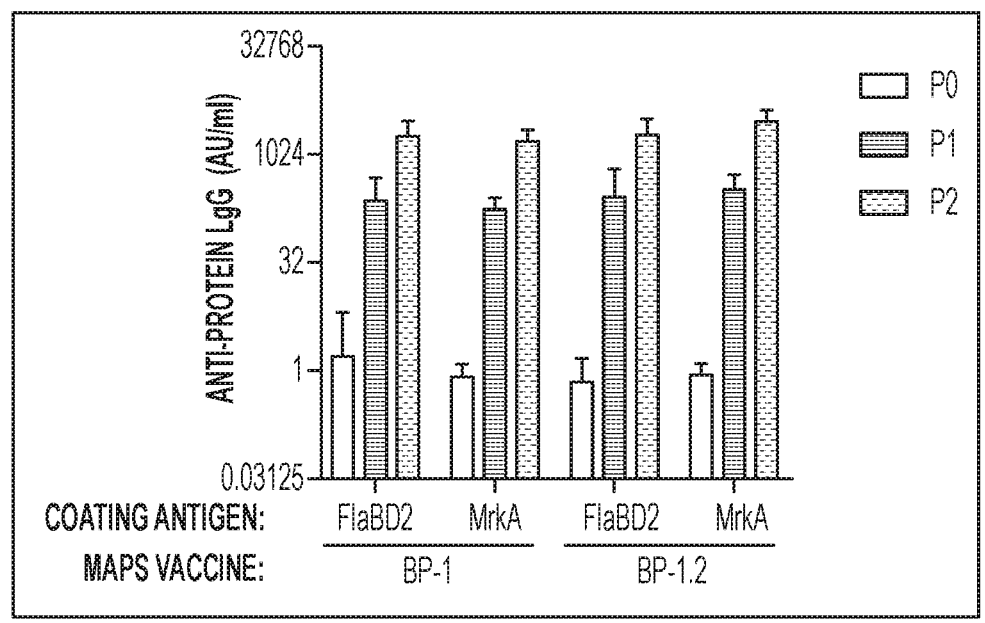
FIG. 69 depicts the carrier protein IgG response observed from a comparison of BP-1 MAPS (Group 1) to BP-1.2 MAPS (Group 2) pooled sera.

A robust IgG antibody response to both KP and PA OPS was observed for both BP-1 and BP-1.2 groups. The individual OPS and CPS K19 IgG titers for group 1 and group 2 are shown in FIG. 68. The anti-OPS immune responses to both PA O6 and PA O11 OPS were equivalent for BP-1 and BP-1.2 MAPS constructs. Similarly, equivalent responses were observed for the KP O3 and KP O5 OPS albeit significantly better titers for KP O3 with BP-1.2 MAPS construct (approximately 5 to 6 fold higher in geometric mean titer). IgG titers to the K19 CPS were equivalent for both BP-1 and BP-1.2 MAPS constructs. A robust IgG antibody response to both FlaB-D2 and MrkA carrier proteins was also for both BP-1 and 1.2 groups. The antibody response (pooled sera) to both carrier proteins was comparable for both BP-1 and BP-1.2 groups (FIG. 69). A summary of the results is shown in Table 36.

TABLE 36

Immunogenicity Comparison of BP-I MAPS (Group 1) to BP-1.2 MAPS (Group 2): OPS IgG Response

| Group | P0 | P1 | P2 |
|---|---|---|---|
| PAO6 COPS | | | |
| 1 | 181.28 | 2,300.15 | 5,085.86 |
| 2 | 16.65 | 2,042.22 | 4,406.58 |
| PAO11 COPS | | | |
| 1 | 33.36 | 2,203.98 | 2,945.89 |
| 2 | 114.82 | 2,067.88 | 3,040.69 |
| KPO3-HSA | | | |
| 1 | 12.29 | 372.45 | 2,532.76 |
| 2 | 32.57 | 2,597.55 | 8,993.09 |
| KPO5-HSA | | | |
| 1 | 40.98 | 3,434.84 | 10,532.81 |
| 2 | 53.82 | 3,191.94 | 14,063.62 |
| KPK19-HSA | | | |
| 1 | 2.50 | 4,082.60 | 14,138.69 |
| 2 | 2.50 | 3,983.78 | 10,201.15 |

The individual OPS and CPS K19 IgG titers for group 1 and group 2 are shown in FIG. 68. The anti-OPS immune responses to both PA O6 and PA O11 OPS were equivalent for BP-1 and BP-1.2 MAPS constructs. Similarly, equivalent responses were observed for the KP O3 and KP O5 OPS albeit significantly better titers for KP O3 with BP-1.2 MAPS construct (approximately 5 to 6 fold higher in geometric mean titer). IgG titers to the K19 CPS were equivalent for both BP-1 and BP-1.2 MAPS constructs.

Figure 70:
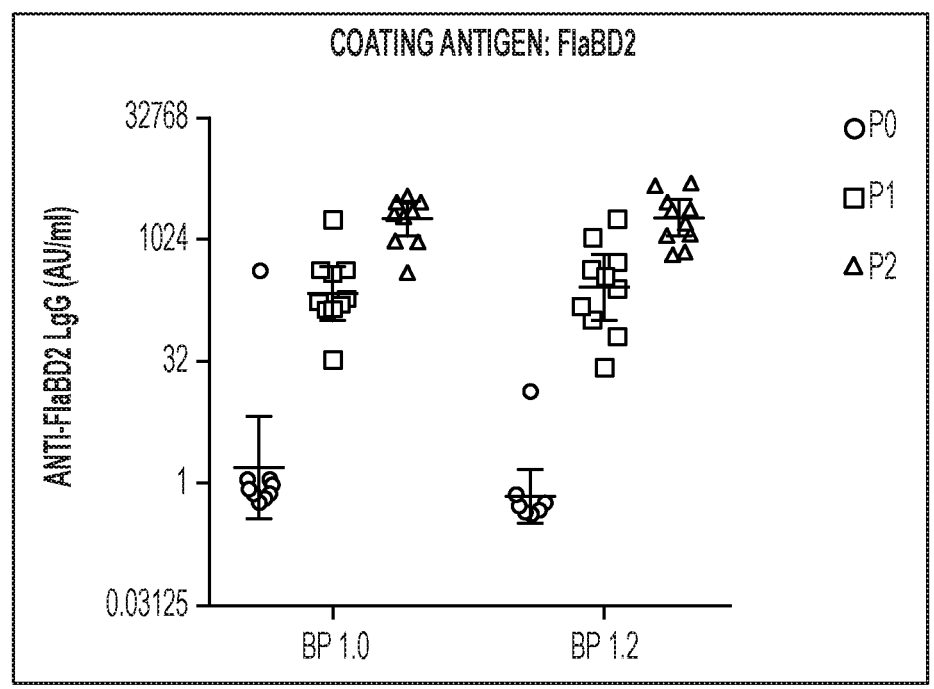
FIG. 70 depicts antibody responses in individual sera to carrier protein FlaBD2 for BP-1 and BP-1.2 (KP/PA 4-valent) respectively
Figure 71:
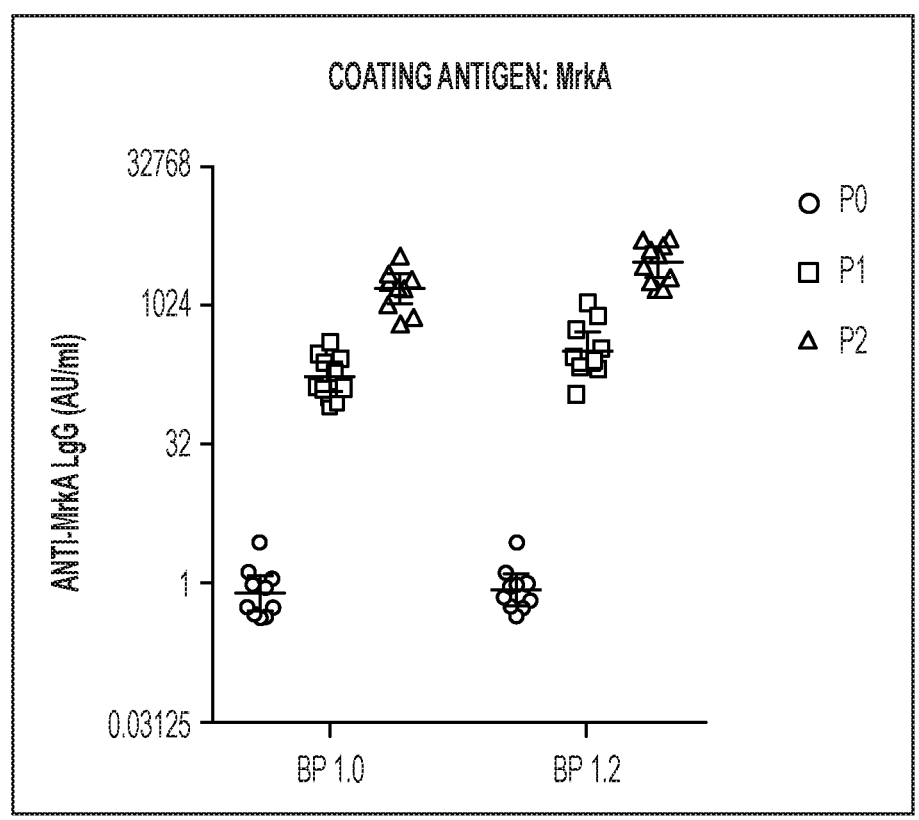
FIG. 71 depicts antibody responses in individual sera to carrier protein MrkA for BP-1 and BP-1.2 (KP/PA 4-valent) respectively.

In study NCB013 a comparison of BP-1 (scaffold-1) and BP-1.2 (scaffold-1.2) 2-valent KP/PA vaccines was performed in rabbits (see also Table 35 for description of vaccine formulations). FIG. 70 and FIG. 71 demonstrate the individual antibody responses to the two carrier proteins FlaBD2 and MrkA for BP-1 and BP-1.2 (KP/PA 4-valent) respectively. A significant increase of antibody titers was observed after the first immunization for both carrier proteins for both scaffolds. Antibodies titers increased further after the second immunization. A robust antibody response to both FlaBD2 and MrkA for both BP-1 and BP-1.2 groups was observed and the antibody response to both proteins was comparable for the BP-1 and BP-1.2 groups.

Sequences

| SEQ ID | Description | Sequence |
|---|---|---|
| SEQ ID NO: 1 | K. pneumoniae Type I fimbrial protein | MKIKTLAMIVVSALSLSSTAALADTTTVNGGTVHFKGE VVNAACAVDAGSIDQTVQLGQVRSAKLATAGSTSSAV GFNIQLDDCDTTVATKASVAFAGTAIDSSNTTVLALQNS AAGSATNVGVQILDNTGTPLALDGATFSAATTLNDGPNI IPFQARYYATGAATAGIANADATFKVQYE |
| SEQ ID NO: 2 | K. pneumoniae conserved Type III fimbrial protein MrkA | MKKVLLSAAMATAFFGMTAAHAADTTVGGGQVNFFG KVTDVSCTVSVNGQGSDANVYLSPVTLTEVKAAAADT YLKPKSFTIDVSNCQAADGTKQDDVSKLGVNWTGGNL LAGATSKQQGYLANTEASGAQNIQLVLSTDNATALTNK IIPGDSTQPKAKGDASAVADGARFTYYVGYATSAPTTVT TGVVNSYATYEITYQ |
| SEQ ID NO: 3 | K. pneumoniae stabilized Type III fimbrial protein MrkA | ADTTVGGGQVNFFGKVTDVSCTVSVNGQGSDANVYLS PVTLTEVKAAAADTYLKPKSFTIDVSNCQAADGTKQDD VSKLGVNWTGGNLLAGATSKQQGYLANTEASGAQNIQ LVLSTDNATALTNKIIPGDSTQPKAKGDASAVADGARFT YYVGYATSAPTTVTTGVVNSYATYEITYQGGGGGGAD TTVGGGQVNFFGKVTDVS |
| SEQ ID NO: 4 | Sequence in PsL binding Cam-003 mAb | QVRLQQSGPGLVKPSETLSLTCTVSGGSTSPYFWSWLRQ PPGKGLEWIGYIHSNGGTNYNPSLKSRLTISGDTSKNQFS LNLSFVTAADTALYYCARTDYDVYGPAFDIWGQGTMV TV |
| SEQ ID NO: 5 | Sequence in PsL binding Cam-003 mAb | SSELTQDPAVSVALGQTVRITCQGDSLRSYYASWYQQK PGQAPVLVIYGKNNRPSGIPDRFSGSSSGNTASLTITGAQ AEDEADYYCNSRDSSGNHVVFGGGTKLTVL |

| SEQ ID | Description | Sequence |
|---|---|---|
| SEQ ID NO: 6 | P. aeruginosa FliC flagellin subtype A1 | MALTVNTNIASLNTQRNLNNSSASLNTSLQRLSTGSRIN SAKDDAAGLQIANRLTSQVNGLNVATKNANDGISLAQT AEGALQQSTNILQRMRDLSLQSANGSNSDSERTALNGE VKQLQKELDRISNTTTFGGRKLLDGSFGVASFQVGSAA NEIISVGIDEMSAESLNGTYFKADGGGAVTAATASGTVD IAIGITGGSAVNVKVDMKGNETAEQAAAKIAAAVNDAN VGIGAFSDGDTISYVSKAGKDGSGAITSAVSGVVIADTG STGVGTAAGVTPSATAFAKTNDTVAKIDISTAKGAQSA VLVIDEAIKQIDAQRADLGAVQNRFDNTINNLKNIGENV SAARGRIEDTDFAAETANLTKNQVLQQAGTAILAQANQ LPQSVLSLLR |
| SEQ ID NO: 7 | P. aeruginosa FliC flagellin subtype B | MALTVNTNIASLNTQRNLNASSNDLNTSLQRLTTGYRIN SAKDDAAGLQISNRLSNQISGLNVATRNANDGISLAQTA EGALQQSTNILQRIRDLALQSANGSNSDADRAALQKEV AAQQAELTRISDTTTFGGRKLLDGSFGTTSFQVGSNAYE TIDISLQNASASAIGSYQVGSNGAGTVASVAGTATASGI ASGTVNLVGGGQVKNIAIAAGDSAKAIAEKMDGAIPNL SARARTVFTADVSGVTGGSLNFDVTVGSNTVSLAGVTS TQDLADQLNSNSSKLGITASINDKGVLTITSATGENVKF GAQTGTATAGQVAVKVQGSDGKFEAAAKNVVAAGTA ATTTIVTGYVQLNSPTAYSVSGTGTQASQVFGNASAAQ KSSVASVDISTADGAQNAIAVVDNALAAIDAQRADLGA VQNRFKNTIDNLTNISENATNARSRIKDTDFAAETAALS KNQVLQQAGTAILAQANQLPQAVLSLLR |
| SEQ ID NO: 8 | P. aeruginosa type three secretion system (TTSS) Virulence Factor PcrV | MEVRNLNAARELFLDELLAASAAPASAEQEELLALLRS ERIVLAHAGQPLSEAQVLKALAWLLAANPSAPPGQGLE VLREVLQARRQPGAQWDLREFLVSAYFSLHGRLDEDVI GVYKDVLQTQDGKRKALLDELKALTAELKVYSVIQSQI NAALSAKQGIRIDAGGIDLVDPTLYGYAVGDPRWKDSP EYALLSNLDTFSGKLSIKDFLSGSPKQSGELKGLSDEYPF EKDNNPVGNFATTVSDRSRPLNDKVNEKTTLLNDTSSR YNSAVEALNRFIQKYDSVLRDILSAI |
| SEQ ID NO: 9 | P. aeruginosa FlaA2 flagellin | MALTVNTNIASLNTQRNLNNSSASLNTSLQRLSTGSRIN SAKDDAAGLQIANRLTSQVNGLNVATKNANDGISLAQT AEGALQQSTNILQRMRDLSLQSANGSNSDSERTALNGE VKQLQKELDRISNTTTFGGRKLLDGSFGVASFQVGSAA NEIISVGIDEMSAESLNGTYFTATGGGAVTAATASGTVD 1AIGITGGSAVNVKVDMKGNETAEQAAAKIAAAVNDAN VGIGAFTDGAQISYVSKASADGTTSAVSGVAITDTGSTG AGTAAGTTTFTEANDTVAKIDISTAKGAQSAVLVIDEAI KQIDAQRADLGAVQNRFDNTINNLKNIGENVSAARGRIE DTDFAAETANLTKNQVLQQAGTAILAQANQLPQSVLSL LR |
| SEQ ID NO: 10 | P. aeruginosa FlaB flagellin D2 domain lacking the TLR5 binding motif | GSYQVGSNGAGTVASVAGTATASGIASGTVNLVGGGQ VKNIAIAAGDSAKAIAEKMDGAIPNLSARARTVFTADVS GVTGGSLNFDVTVGSNTVSLAGVTSTQDLADQLNSNSS KLGITASINDKGVLTITSATGENVKFGAQTGTATAGQVA VKVQGSDGKFEAAAKNVVAAGTAATTTIVTGYVQLNS PTAYSVSGTGTQASQVFGNASAAQKSS |
| SEQ ID NO: 11 | P. aeruginosa FlaA1 flagellin D2 domain lacking the TLR5 binding motif | NGTYFKADGGGAVTAATASGTVDIAIGITGGSAVNVKV DMKGNETAEQAAAKIAAAVNDANVGIGAFSDGDTISYV SKAGKDGSGAITSAVSGVVIADTGSTGVGTAAGVTPSA TAFAKTNDT |
| SEQ ID NO: 12 | P. aeruginosa FlaA2 flagellin D2 domain lacking the TLR5 binding motif | NGTYFTATGGGAVTAATASGTVDIAIGITGGSAVNVKV DMKGNETAEQAAAKIAAAVNDANVGIGAFTDGAQISY VSKASADGTTSAVSGVAITDTGSTGAGTAAGTTTFTEA NDT |
| SEQ ID NO: 13 | rhizavidin | MIITSLYATFGTIADGRRTSGGKTMIRTNAVAALVFAVA TSALAFDASNFKDFSSIASASSSWQNQSGSTMIIQVDSFG NVSGQYVNRAQGTGCQNSPYPLTGRVNGTFIAFSVGWN NSTENCNSATGWTGYAQVNGNNTEIVTSWNLAYEGGS GPAIEQGQDTFQYVPTTENKSLLKD |

| SEQ ID | Description | Sequence |
|---|---|---|
| SEQ ID NO: 14 | rhizavidin lacking signal sequences | FDASNFKDFSSIASASSSWQNQSGSTMIIQVDSFGNVSGQ YVNRAQGTGCQNSPYPLTGRVNGTFIAFSVGWNNSTEN CNSATGWTGYAQVNGNNTEIVTSWNLAYEGGSGPAIEQ GQDTFQYVPTTENKSLLKD |
| SEQ ID NO: 15 | GGGGSSS linker | GGGGSSS |
| SEQ ID NO: 16 | Rhavi-PerV-his | MFDASNFKDFSSIASASSSWQNQSGSTMIIQVDSFGNVS GQYVNRAQGTGCQNSPYPLTGRVNGTFIAFSVGWNNST ENCNSATGWTGYAQVNGNNTEIVTSWNLAYEGGSGPAI EQGQDTFQYVPTTENKSLLKDGGGGSSSMEVRNLNAAR ELFLDELLAASAAPASAEQEELLALLRSERIVLAHAGQP LSEAQVLKALAWLLAANPSAPPGQGLEVLREVLQARRQ PGAQWDLREFLVSAYFSLHGRLDEDVIGVYKDVLQTQD GKRKALLDELKALTAELKVYSVIQSQINAALSAKQGIRI DAGGIDLVDPTLYGYAVGDPRWKDSPEYALLSNLDTFS GKLSIKDFLSGSPKQSGELKGLSDEYPFEKDNNPVGNFA TTVSDRSRPLNDKVNEKTTLLNDTSSRYNSAVEALNRFI QKYDSVLRDILSAIGSGHHHHHH |
| SEQ ID NO: 17 | Rhavi-MrkA-donor-strand-complementation-his | MFDASNFKDFSSIASASSSWQNQSGSTMIIQVDSFGNVS GQYVNRAQGTGCQNSPYPLTGRVNGTFIAFSVGWNNST ENCNSATGWTGYAQVNGNNTEIVTSWNLAYEGGSGPAI EQGQDTFQYVPTTENKSLLKDGGGGSSSMADTTVGGG QVNFFGKVTDVSCTVSVNGQGSDANVYLSPVTLTEVKA AAADTYLKPKSFTIDVSNCQAADGTKQDDVSKLGVNW TGGNLLAGATSKQQGYLANTEASGAQNIQLVLSTDNAT ALTNKIIPGDSTQPKAKGDASAVADGARFTYYVGYATS apttvttgvvnsyatyeityqgggggadttvgggqv NFFGKVTDVSGSGHHHHHH |
| SEQ ID NO: 18 | Rhavi-FlaA1-his | MFDASNFKDFSSIASASSSWQNQSGSTMIIQVDSFGNVS GQYVNRAQGTGCQNSPYPLTGRVNGTFIAFSVGWNNST ENCNSATGWTGYAQVNGNNTEIVTSWNLAYEGGSGPAI EQGQDTFQYVPTTENKSLLKDGGGGSSSMALTVNTNIA SLNTQRNLNNSSASLNTSLQRLSTGSRINSAKDDAAGLQ IANRLTSQVNGLNVATKNANDGISLAQTAEGALQQSTNI LQRMRDLSLQSANGSNSDSERTALNGEVKQLQKELDRI SNTTTFGGRKLLDGSFGVASFQVGSAANEIISVGIDEMS AESLNGTYFKADGGGAVTAATASGTVDIAIGITGGSAV NVKVDMKGNETAEQAAAKIAAAVNDANVGIGAFSDGD TISYVSKAGKDGSGAITSAVSGVVIADTGSTGVTAAGV TPSATAFAKTNDTVAKIDISTAKGAQSAVLVIDEAIKQID AQRADLGAVQNRFDNTINNLKNIGENVSAARGRIEDTD FAAETANLTKNQVLQQAGTAILAQANQLPQSVLSLLRG SGHHHHHH |
| SEQ ID NO: 19 | Rhavi-FlaA2-his | MFDASNFKDFSSIASASSSWQNQSGSTMIIQVDSFGNVS GQYVNRAQGTGCQNSPYPLTGRVNGTFIAFSVGWNNST ENCNSATGWTGYAQVNGNNTEIVTSWNLAYEGGSGPAI EQGQDTFQYVPTTENKSLLKDGGGGSSSMALTVNTNIA SLNTQRNLNNSSASLNTSLQRLSTGSRINSAKDDAAGLQ IANRLTSQVNGLNVATKNANDGISLAQTAEGALQQSTNI LQRMRDLSLQSANGSNSDSERTALNGEVKQLQKELDRI SNTTTFGGRKLLDGSFGVASFQVGSAANEIISVGIDEMS AESLNGTYFTATGGGAVTAATASGTVDIAIGITGGSAVN VKVDMKGNETAEQAAAKIAAAVNDANVGIGAFTDGAQ ISYVSKASADGTTSAVSGVAITDTGSTGAGTAAGTTTFT EANDTVAKIDISTAKGAQSAVLVIDEAIKQIDAQRADLG AVQNRFDNTINNLKNIGENVSAARGRIEDTDFAAETANL TKNQVLQQAGTAILAQANQLPQSVLSLLRGSGHHHHHH |
| SEQ ID NO: 20 | Rhavi-FlaB-his | MFDASNFKDFSSIASASSSWQNQSGSTMIIQVDSFGNVS GQYVNRAQGTGCQNSPYPLTGRVNGTFIAFSVGWNNST ENCNSATGWTGYAQVNGNNTEIVTSWNLAYEGGSGPAI EQGQDTFQYVPTTENKSLLKDGGGGSSSMALTVNTNIA SLNTQRNLNASSNDLNTSLQRLTTGYRINSAKDDAAGL QISNRLSNQISGLNVATRNANDGISLAQTAEGALQQSTNI LQRIRDLALQSANGSNSDADRAALQKEVAAQQAELTRI SDTTTFGGRKLLDGSFGTTSFQVGSNAYETIDISLQNASA SAIGSYQVGSNGAGTVASVAGTATASGIASGTVNLVGG GQVKNIAIAAGDSAKAIAEKMDGAIPNLSARARTVFTA DVSGVTGGSLNFDVTVGSNTVSLAGVTSTQDLADQLNS |

| SEQ ID | Description | Sequence |
|---|---|---|
| | | NSSKLGITASINDKGVLTITSATGENVKFGAQTGTATAG<br>QVAVKVQGSDGKFEAAAKNVVAAGTAATTTIVTGYVQ<br>LNSPTAYSVSGTGTQASQVFGNASAAQKSSVASVDISTA<br>DGAQNAIAVVDNALAAIDAQRADLGAVQNRFKNTIDN<br>LTNISENATNARSRIKDTDFAAETAALSKNQVLQQAGTA<br>ILAQANQLPQAVLSLLRGSGHHHHHH |
| SEQ ID NO: 21 | Rhavi-FlaB-Domain2-his | MFDASNFKDFSSIASASSSWQNQSGSTMIIQVDSFGNVS<br>GQYVNRAQGTGCQNSPYPLTGRVNGTFIAFSVGWNNST<br>ENCNSATGWTGYAQVNGNNTEIVTSWNLAYEGGSGPAI<br>EQGQDTFQYVPTTENKSLLKDGGGGSSSMGSYQVGSNG<br>AGTVASVAGTATASGIASGTVNLVGGGQVKNIAIAAGD<br>SAKAIAEKMDGAIPNLSARARTVFTADVSGVTGGSLNF<br>DVTVGSNTVSLAGVTSTQDLADQLNSNSSKLGITASIND<br>KGVLTITSATGENVKFGAQTGTATAGQVAVKVQGSDG<br>KFEAAAKNVVAAGTAATTTIVTGYVQLNSPTAYSVSGT<br>GTQASQVFGNASAAQKSSGSGHHHHHH |
| SEQ ID NO: 22 | Rhavi-FlaA2-Domain2-his | MFDASNFKDFSSIASASSSWQNQSGSTMIIQVDSFGNVS<br>GQYVNRAQGTGCQNSPYPLTGRVNGTFIAFSVGWNNST<br>ENCNSATGWTGYAQVNGNNTEIVTSWNLAYEGGSGPAI<br>EQGQDTFQYVPTTENKSLLKDGGGGSSSMNGTYFTATG<br>GGAVTAATASGTVDIAIGITGGSAVNVKVDMKGNETAE<br>QAAAKIAAAVNDANVGIGAFTDGAQISYVSKASADGTT<br>SAVSGVAITDTGSTGAGTAAGTTTFTEANDTGSGHHHH<br>HH |
| SEQ ID NO: 23 | Rhavi-FlaB-PcrV-his | MFDASNFKDFSSIASASSSWQNQSGSTMIIQVDSFGNVS<br>GQYVNRAQGTGCQNSPYPLTGRVNGTFIAFSVGWNNST<br>ENCNSATGWTGYAQVNGNNTEIVTSWNLAYEGGSGPAI<br>EQGQDTFQYVPTTENKSLLKDGGGGSSSMALTVNTNIA<br>SLNTQRNLNASSNDLNTSLQRLTTGYRINSAKDDAAGL<br>QISNRLSNQISGLNVATRNANDGISLAQTAEGALQQSTNI<br>LQRIRDLALQSANGSNSDADRAALQKEVAAQQAELTRI<br>SDTTTFGGRKLLDGSFGTTSFQVGSNAYETIDISLQNASA<br>SAIGSYQVGSNGAGTVASVAGTATASGIASGTVNLVGG<br>GQVKNIAIAAGDSAKAIAEKMDGAIPNLSARARTVFTA<br>DVSGVTGGSLNFDVTVGSNTVSLAGVTSTQDLADQLNS<br>NSSKLGITASINDKGVLTITSATGENVKFGAQTGTATAG<br>QVAVKVQGSDGKFEAAAKNVVAAGTAATTTIVTGYVQ<br>LNSPTAYSVSGTGTQASQVFGNASAAQKSSVASVDISTA<br>DGAQNAIAVVDNALAAIDAQRADLGAVQNRFKNTIDN<br>LTNISENATNARSRIKDTDFAAETAALSKNQVLQQAGTA<br>ILAQANQLPQAVLSLLRAAAAMEVRNLNAARELFLDEL<br>LAASAAPASAEQEELLALLRSERIVLAHAGQPLSEAQVL<br>KALAWLLAANPSAPPGQGLEVLREVLQARRQPGAQWD<br>LREFLVSAYFSLHGRLDEDVIGVYKDVLQTQDGKRKAL<br>LDELKALTAELKVYSVIQSQINAALSAKQGIRIDAGGIDL<br>VDPTLYGYAVGDPRWKDSPEYALLSNLDTFSGKLSIKD<br>FLSGSPKQSGELKGLSDEYPFEKDNNPVGNFATTVSDRS<br>RPLNDKVNEKTTLLNDTSSRYNSAVEALNRFIQKYDSVL<br>RDILSAIGSGHHHHHH |
| SEQ ID NO: 24 | Rhavi-FlaB-Domain2-MrkA-donor-strand-complementation-his | MFDASNFKDFSSIASASSSWQNQSGSTMIIQVDSFGNVS<br>GQYVNRAQGTGCQNSPYPLTGRVNGTFIAFSVGWNNST<br>ENCNSATGWTGYAQVNGNNTEIVTSWNLAYEGGSGPAI<br>EQGQDTFQYVPTTENKSLLKDGGGGSSSMGSYQVGSNG<br>AGTVASVAGTATASGIASGTVNLVGGGQVKNIAIAAGD<br>SAKAIAEKMDGAIPNLSARARTVFTADVSGVTGGSLNF<br>DVTVGSNTVSLAGVTSTQDLADQLNSNSSKLGITASIND<br>KGVLTITSATGENVKFGAQTGTATAGQVAVKVQGSDG<br>KFEAAAKNVVAAGTAATTTIVTGYVQLNSPTAYSVSGT<br>GTQASQVFGNASAAQKSSAAAAMADTTVGGGQVNFFG<br>KVTDVSCTVSVNGQGSDANVYLSPVTLTEVKAAAADT<br>YLKPKSFTIDVSNCQAADGTKQDDVSKLGVNWTGGNL<br>LAGATSKQQGYLANTEASGAQNIQLVLSTDNATALTNK<br>IIPGDSTQPKAKGDASAVADGARFTYYVGYATSAPTTVT<br>TGVVNSYATYEITYQGGGGGGADTTVGGGQVNFFGKV<br>TDVSGSGHHHHHH |
| SEQ ID NO: 25 | Rhavi-MrkA-donor-strand-complementation-PcrV-his | MFDASNFKDFSSIASASSSWQNQSGSTMIIQVDSFGNVS<br>GQYVNRAQGTGCQNSPYPLTGRVNGTFIAFSVGWNNST<br>ENCNSATGWTGYAQVNGNNTEIVTSWNLAYEGGSGPAI<br>EQGQDTFQYVPTTENKSLLKDGGGGSSSMADTTVGGG |

Sequences

| SEQ ID | Description | Sequence |
|---|---|---|
| | | QVNFFGKVTDVSCTVSVNGQGSDANVYLSPVTLTEVKA AAADTYLKPKSFTIDVSNCQAADGTKQDDVSKLGVNW TGGNLLAGATSKQQGYLANTEASGAQNIQLVLSTDNAT ALTNKIIPGDSTQPKAKGDASAVADGARFTYYVGYATS apttvttgvvnsyatyeityqgggggadttvgggqv NFFGKVTDVSAAAAMEVRNLNAARELFLDELLAASAAP ASAEQEELLALLRSERIVLAHAGQPLSEAQVLKALAWL LAANPSAPPGQGLEVLREVLQARRQPGAQWDLREFLVS AYFSLHGRLDEDVIGVYKDVLQTQDGKRKALLDELKAL TAELKVYSVIQSQINAALSAKQGIRIDAGGIDLVDPTLYG YAVGDPRWKDSPEYALLSNLDTFSGKLSIKDFLSGSPKQ SGELKGLSDEYPFEKDNNPVGNFATTVSDRSRPLNDKV NEKTTLLNDTSSRYNSAVEALNRFIQKYDSVLRDILSAIG SGHHHHHH |
| SEQ ID NO: 26 | Rhavi-FlaB-Domain2-PcrV-his | MFDASNFKDFSSIASASSSWQNQSGSTMIIQVDSFGNVS GQYVNRAQGTGCQNSPYPLTGRVNGTFIAFSVGWNNST ENCNSATGWTGYAQVNGNNTEIVTSWNLAYEGGSGPAI EQGQDTFQYVPTTENKSLLKDGGGGSSSMGSYQVGSNG AGTVASVAGTATASGIASGTVNLVGGGQVKNIAIAAGD SAKAIAEKMDGAIPNLSARARTVFTADVSGVTGGSLNF DVTVGSNTVSLAGVTSTQDLADQLNSNSSKLGITASIND KGVLTITSATGENVKFGAQTGTATAGQVAVKVQGSDG KFEAAAKNVVAAGTAATTTIVTGYVQLNSPTAYSVSGT GTQASQVFGNASAAQKSSAAAAMEVRNLNAARELFLD ELLAASAAPASAEQEELLALLRSERIVLAHAGQPLSEAQ VLKALAWLLAANPSAPPGQGLEVLREVLQARRQPGAQ WDLREFLVSAYFSLHGRLDEDVIGVYKDVLQTQDGKR KALLDELKALTAELKVYSVIQSQINAALSAKQGIRIDAG GIDLVDPTLYGYAVGDPRWKDSPEYALLSNLDTFSGKL SIKDFLSGSPKQSGELKGLSDEYPFEKDNNPVGNFATTV SDRSRPLNDKVNEKTTLLNDTSSRYNSAVEALNRFIQKY DSVLRDILSAIGSGHHHHHH |

REFERENCES

Agodi A, Voulgari E, Barchitta M, Politi L, Koumaki V, et al. Containment of an outbreak of KPC-3-producing *Klebsiella pneumoniae* in Italy. J Clin Microbiol. 2011 November; 49(11):3986-9.

Altschul S F, Gish W, Miller W, Myers E W, Lipman D J. Basic local alignment search tool. J Mol Biol. 1990 Oct. 5; 215(3):403-10.

Altschul S F, Madden T L, Schäffer A A, Zhang J, Zhang Z, et al. Gapped BLAST and PSI-BLAST: a new generation of protein database search programs. Nucleic Acids Res. 1997 Sep. 1; 25(17):3389-402.

Andreasen C., Powell D A., Carbonetti N. Pertussis Toxin Stimulates IL-17 Production in Response to *Bordetella pertussis* Infection in Mice. PloS One 2009 4:Issue 9 e7079.

Anttila M, Eskola J, Ahman H, Käyhty H. Avidity of IgG for *Streptococcus pneumoniae* type 6B and 23F polysaccharides in infants primed with pneumococcal conjugates and boosted with polysaccharide or conjugate vaccines. J Infect Dis. 1998 June; 177(6):1614-21.

Baer M, Sawa T, Flynn P, Luehrsen K, Martinez D, et al. An engineered human antibody fab fragment specific for *Pseudomonas aeruginosa* PcrV antigen has potent antibacterial activity. Infect Immun. 2009 March; 77(3):1083-90.

Baraniak, A., Grabowska, A., Izdebski, R., Fiett, J., Herda, M., Bojarska, K., Zabicka, D., Kania-Pudlo, M., Mlynarczyk, G., Zak-Pulawska, Z., Hryniewicz, W., Gniadkowski, M., 2011. Molecular characteristics of KPC-producing Enterobacteriaceae at the early stage of their dissemination in Poland, 2008-2009. Antimicrob. Agents Chemother. 55, 5493-5499.

Barnea Y, Carmeli Y, Gur E, Kuzmenko B, Gat A, et al. Efficacy of antibodies against the N-terminal of *Pseudomonas aeruginosa* flagellin for treating infections in a murine burn wound model. Plast Reconstr Surg. 2006 June; 117(7):2284-91.

Barnea Y, Carmeli Y, Neville L F, Kahel-Reifer H, Eren R, et al. Therapy with anti-flagellin A monoclonal antibody limits *Pseudomonas aeruginosa* invasiveness in a mouse burn wound sepsis model. Burns. 2009 May; 35(3):390-6.

Baumgartner J D. Monoclonal anti-endotoxin antibodies for the treatment of gram-negative bacteremia and septic shock. Eur J Clin Microbiol Infect Dis. 1990 October; 9(10):711-6.

Baxevanis A D and Ouellette B F, Eds., Bioinformatics: A Practical Guide to the Analysis of Genes and Proteins. New York, N.Y.: Wiley-Interscience, 1998.

Bergogne-Bérézin E. [Nosocomial infections: new agents, incidence, prevention]. Presse Med. 1995 Jan. 14; 24(2):89-97. Review. French.

Brisse S. et al., wzi Gene Sequencing, a Rapid Method for Determination of Capsular Type for *Klebsiella* Strains. J Clin Microbiol. 2013 51(12):4073-4078.

Bryan C S, Reynolds K L, Brenner E R. Analysis of 1,186 episodes of gram-negative bacteremia in non-university hospitals: the effects of antimicrobial therapy. Rev Infect Dis. 1983 July-August; 5(4): 629-38.

Burmølle M, Bahl M I, Jensen L B, Sørensen S J, Hansen L H. Type 3 fimbriae, encoded by the conjugative plasmid pOLA52, enhance biofilm formation and transfer frequencies in Enterobacteriaceae strains. Microbiology. 2008 January; 154(Pt 1):187-95.

Campodónico V L, Llosa N J, Grout M, Döring G, Maira-Litrán T, et al. Evaluation of flagella and flagellin of Pseudomonas aeruginosa as vaccines. Infect Immun. 2010 February; 78(2):746-55.

Campodónico V L, Llosa N J, Bentancor L V, Maira-Litran T, Pier G B. Efficacy of a conjugate vaccine containing polymannuronic acid and flagellin against experimental Pseudomonas aeruginosa lung infection in mice. Infect Immun. 2011 August; 79(8):3455-64.

Centers for Disease Control and Prevention (CDC). Antibiotic Resistance Threats in the United States, 2013. http://www.cdc.gov/drugresistance/pdf/ar-threats-2013-508.pdf. 2013.

Chaloupka I, Schuler A, Marschall M, Meier-Ewert H. Comparative analysis of six European influenza vaccines. Eur J Clin Microbiol Infect Dis. 1996 February; 15(2):121-7.

Chang H H, Cohen T, Grad Y H, Hanage W P, O'Brien T F, et al. Origin and proliferation of multiple-drug resistance in bacterial pathogens. Microbiol Mol Biol Rev. 2015 March; 79(1):101-16.

Chen K, McAleer J P, Lin Y, Paterson D L, Zheng M, et al. Th17 cells mediate Glade-specific, serotype-independent mucosal immunity. Immunity. 2011 Dec. 23; 35(6):997-1009.

Chen, L., Chavda, K. D., Findlay, J., Peirano, G., Hopkins, K., Pitout, J. D., Bonomo, R. A., Woodford, N., DeLeo, F. R., Kreiswirth, B. N., 2014a. Multiplex PCR for identification of two capsular types in epidemic KPC-producing Klebsiella pneumoniae sequence Type 258 strains. Antimicrob. Agents Chemother. 58, 4196-4199.

Chen, L., Mathema, B., Pitout, J. D., DeLeo, F. R., Kreiswirth, B. N., 2014b. Epidemic Klebsiella pneumoniae ST258 is a hybrid strain. mBio 5, e01355-14.

Clegg S, Gerlach G F. Enterobacterial fimbriae. J Bacteriol. 1987; 169:934-938.

Clements A, Gaboriaud F, Duval J F, Farn J L, Jenney A W, et al. The major surface-associated saccharides of Klebsiella pneumoniae contribute to host cell association. PLoS One. 2008; 3(11):e3817.

Collignon P. Resistant Escherichia coli—we are what we eat. Clin Infect Dis. 2009 Jul. 15; 49(2):202-4.

Concepcion N F, Frasch C E. Pneumococcal type 22f polysaccharide absorption improves the specificity of a pneumococcal-polysaccharide enzyme-linked immunosorbent assay. Clin Diagn Lab Immunol. 2001 March; 8(2):266-72.

Cross A S, Zollinger W, Mandrell R, Gemski P, Sadoff J. Evaluation of immunotherapeutic approaches for the potential treatment of infections caused by K1-positive Escherichia coli. J Infect Dis. 1983 January; 147(1):68-76.

Cross A S, Gemski P, Sadoff J C, Orskov F, Orskov I. The importance of the K1 capsule in invasive infections caused by Escherichia coli. J Infect Dis. 1984 February; 149(2):184-93.

Cross A S, Kim K S, Wright D C, Sadoff J C, Gemski P. Role of lipopolysaccharide and capsule in the serum resistance of bacteremic strains of Escherichia coli. J Infect Dis. 1986 September; 154(3):497-503.

Cross A, Artenstein A, Que J, Fredeking T, Furer E, et al. Safety and immunogenicity of a polyvalent Escherichia coli vaccine in human volunteers. J Infect Dis. 1994 October; 170(4):834-40.

Crowe B A, Enzersberger O, Schober-Bendixen S, Mitterer A, Mundt W, et al. The first clinical trial of immuno's experimental Pseudomonas aeruginosa flagellar vaccines. Antibiot Chemother (1971). 1991; 44:143-56.

Cryz S J Jr, Fürer E, Germanier R. Protection against fatal Pseudomonas aeruginosa burn wound sepsis by immunization with lipopolysaccharide and high-molecular-weight polysaccharide. Infect Immun. 1984 March; 43(3):795-9.

Cryz S J, Jr, Fürer E, Germanier R. Safety and immunogenicity of Klebsiella pneumoniae K1 capsular polysaccharide vaccine in humans. J Infect Dis. 1985; 151:665-671.

Cryz S J Jr, Mortimer P, Cross A S, Furer E, Germanier R. Safety and immunogenicity of a polyvalent Klebsiella capsular polysaccharide vaccine in humans. Vaccine. 1986 March; 4(1):15-20.

Cryz S J Jr, Mortimer P M, Mansfield V, Germanier R. Seroepidemiology of Klebsiella bacteremic isolates and implications for vaccine development. J Clin Microbiol. 1986 April; 23(4):687-90.

Cryz S J Jr, Wedgwood J, Lang A B, Ruedeberg A, Que J U, et al. Immunization of noncolonized cystic fibrosis patients against Pseudomonas aeruginosa. J Infect Dis. 1994 May; 169(5):1159-62.

DeLeo, F. R., Chen, L., Porcella, S. F., Martens, C. A., Kobayashi, S. D., Porter, A. R., Chavda, K. D., Jacobs, M. R., Mathema, B., Olsen, R. J., Bonomo, R. A., Musser, J. M., Kreiswirth, B. N., 2014. Molecular dissection of the evolution of carbapenem-resistant multilocus sequence type 258 Klebsiella pneumoniae. Proc. Natl. Acad. Sci. U.S. A 111, 4988-4993.

Deng J C, Moore T A, Newstead M W, Zeng X, Krieg A M, et al. CpG oligodeoxynucleotides stimulate protective innate immunity against pulmonary Klebsiella infection. J Immunol. 2004 Oct. 15; 173(8):5148-55.

DiGiandomenico A, Sellman B R. Antibacterial monoclonal antibodies: the next generation?. Curr Opin Microbiol. 2015 October; 27:78-85.

DiGiandomenico A, Rao J, Goldberg J B. Oral vaccination of BALB/c mice with Salmonella enterica serovar Typhimurium expressing Pseudomonas aeruginosa 0 antigen promotes increased survival in an acute fatal pneumonia model. Infect Immun. 2004 December; 72(12):7012-21.

DiGiandomenico A, Rao J, Harcher K, Zaidi T S, Gardner J, et al. Intranasal immunization with heterologously expressed polysaccharide protects against multiple Pseudomonas aeruginosa infections. Proc Natl Acad Sci USA. 2007 Mar. 13; 104(11):4624-9.

DiGiandomenico A, Warrener P, Hamilton M, Guillard S, Ravn P, et al. Identification of broadly protective human antibodies to Pseudomonas aeruginosa exopolysaccharide Psl by phenotypic screening. J Exp Med. 2012 Jul. 2; 209(7):1273-87.

DiGiandomenico A, Keller A E, Gao C, Rainey G J, Warrener P, et al. A multifunctional bispecific antibody protects against Pseudomonas aeruginosa. Sci Transl Med. 2014 Nov. 12; 6(262):262ra155.

Domenico P, Schwartz S, Cunha B A. Reduction of capsular polysaccharide production in Klebsiella pneumoniae by sodium salicylate. Infect Immun. 1989 December; 57(12):3778-82.

Döring G, Dorner F. A multicenter vaccine trial using the Pseudomonas aeruginosa flagella vaccine IMMUNO in patients with cystic fibrosis. Behring Inst Mitt. 1997 February;

Döring G, Pier G B. Vaccines and immunotherapy against *Pseudomonas aeruginosa*. Vaccine. 2008 Feb. 20; 26(8): 1011-24.

Döring G, Pfeiffer C, Weber U, Mohr-Pennert A, Dorner F. Parenteral application of a *Pseudomonas aeruginosa* flagella vaccine elicits specific anti-flagella antibodies in the airways of healthy individuals. Am J Respir Crit Care Med. 1995 April; 151(4):983-5.

Döring G, Meisner C, Stern M. A double-blind randomized placebo-controlled phase III study of a *Pseudomonas aeruginosa* flagella vaccine in cystic fibrosis patients. Proc Natl Acad Sci USA. 2007 Jun. 26; 104(26):11020-5.

Du H, Chen L, Tang Y W, Kreiswirth B N. Emergence of the mcr-1 colistin resistance gene in carbapenem-resistant Enterobacteriaceae. Lancet Infect Dis. 2016 March; 16(3):287-8.

Edelman R, Taylor D N, Wasserman S S, McClain J B, Cross A S, et al. Phase 1 trial of a 24-valent *Klebsiella* capsular polysaccharide vaccine and an eight-valent *Pseudomonas* O-polysaccharide conjugate vaccine administered simultaneously. Vaccine. 1994 November; 12(14):1288-94.

Faezi S, Sattari M, Mandavi M, Roudkenar M H. Passive immunisation against *Pseudomonas aeruginosa* recombinant flagellin in an experimental model of burn wound sepsis. Burns. 2011 August; 37(5):865-72.

Faezi S, Safarloo M, Amirmozafari N, Nikokar I, Siadat S D, et al. Protective efficacy of *Pseudomonas aeruginosa* type-A flagellin in the murine burn wound model of infection. APMIS. 2014 February; 122(2):115-27.

Feldman M F, Wacker M, Hernandez M, Hitchen P G, Marolda C L, et al. Engineering N-linked protein glycosylation with diverse O antigen lipopolysaccharide structures in *Escherichia coli*. Proc Natl Acad Sci USA. 2005 Feb. 22; 102(8):3016-21.

Fine P E. Herd immunity: history, theory, practice. Epidemiol Rev. 1993; 15(2):265-302.

Foglia G, Shah S, Luxemburger C, Pietrobon P J. *Clostridium difficile*: development of a novel candidate vaccine. Vaccine. 2012 Jun. 19; 30(29):4307-9.

Fowler V G Jr, Proctor R A. Where does a *Staphylococcus aureus* vaccine stand?. Clin Microbiol Infect. 2014 May; 20 Suppl 5:66-75.

François B, Luyt C E, Dugard A, Wolff M, Diehl J L, et al. Safety and pharmacokinetics of an anti-PcrV PEGylated monoclonal antibody fragment in mechanically ventilated patients colonized with *Pseudomonas aeruginosa*: a randomized, double-blind, placebo-controlled trial. Crit Care Med. 2012 August; 40(8):2320-6.

Frank D W, Vallis A, Wiener-Kronish J P, Roy-Burman A, Spack E G, et al. Generation and characterization of a protective monoclonal antibody to *Pseudomonas aeruginosa* PcrV. J Infect Dis. 2002 Jul. 1; 186(1):64-73.

Galanos C, Freudenberg M A, Reutter W. Galactosamine-induced sensitization to the lethal effects of endotoxin. Proc Natl Acad Sci USA. 1979 November; 76(11):5939-43.

Gerding D N, Meyer T, Lee C, Cohen S H, Murthy U K, et al. Administration of spores of nontoxigenic *Clostridium difficile* strain M3 for prevention of recurrent *C. difficile* infection: a randomized clinical trial. JAMA. 2015 May 5; 313(17):1719-27.

Gerlach G F, Clegg S, Allen B L. Identification and characterization of the genes encoding the type 3 and type 1 fimbrial adhesins of *Klebsiella pneumoniae*. J Bacteriol. 1989 March; 171(3):1262-70.

Giakkoupi, P., Papagiannitsis, C. C., Miriagou, V., Pappa, O., Polemis, M., Tryfinopoulou, K., Tzouvelekis, L. S., Vatopoulos, A. C., 2011. An update of the evolving epidemic of blaKPC-2-carrying *Klebsiella pneumoniae* in Greece (2009-10). J. Antimicrob. Chemother. 66, 1510-1513.

Giani, T., Pini, B., Arena, F., Conte, V., Bracco, S., Migliavacca, R., Pantosti, A., Pagani, L., Luzzaro, F., Rossolini, G. M., 2013. Epidemic diffusion of KPC carbapenemase-producing *Klebsiella pneumoniae* in Italy: results of the first countrywide survey, 15 May to 30 Jun. 2011. Eurosurveillance, 18.

Gransden W R, Eykyn S J, Phillips I, Rowe B. Bacteremia due to *Escherichia coli*: a study of 861 episodes. Rev Infect Dis. 1990 November-December; 12(6):1008-18.

Greenberger M J, Kunkel S L, Strieter R M, Lukacs N W, Bramson J, et al. IL-12 gene therapy protects mice in lethal *Klebsiella pneumonia*. J Immunol. 1996 Oct. 1; 157(7):3006-12.

Hansen D S, Mestre F, Alberti S, Hernandez-Allés S, Alvarez D, et al. *Klebsiella pneumoniae* lipopolysaccharide O typing: revision of prototype strains and O-group distribution among clinical isolates from different sources and countries. J Clin Microbiol. 1999 January; 37(1):56-62.

Henriques-Normark B, Normark S. Bacterial vaccines and antibiotic resistance. Ups J Med Sci. 2014 May; 119(2): 205-8.

Holder I A, Naglich J G. Experimental studies of the pathogenesis of infections due to *Pseudomonas aeruginosa*: immunization using divalent flagella preparations. J Trauma. 1986 February; 26(2): 118-22.

Holder I A, Wheeler R, Montie T C. Flagellar preparations from *Pseudomonas aeruginosa*: animal protection studies. Infect Immun. 1982 January; 35(1):276-80.

Holder I A, Neely A N, Frank D W. PcrV immunization enhances survival of burned *Pseudomonas aeruginosa*-infected mice. Infect Immun. 2001 September; 69(9): 5908-10.

Holliger P, Prospero T, Winter G. "Diabodies": small bivalent and bispecific antibody fragments. Proc Natl Acad Sci USA. 1993 Jul. 15; 90(14):6444-8.

Horan T, Culver D, Jarvis W, Emori G, Banerjee S, Martone W, Thornsberry C. Pathogens Causing Nosocomial Infections. Antimicrobic Newsl. 1988 September; 5(9):65-68.

Hornick D B, Allen B L, Horn M A, Clegg S. Adherence to respiratory epithelia by recombinant *Escherichia coli* expressing *Klebsiella pneumoniae* type 3 fimbrial gene products. Infect Immun. 1992 April; 60(4):1577-88.

Hu R. et al., Outer Membrane Protein A (OmpA) Conferred Immunoprotection against Enterobacteriaceae Infection in Mice. Israel Journal of Veterinary Medicine. 2103. Vol. 68 (1):48-55.

Jansen K U, Girgenti D Q, Scully I L, Anderson A S. Vaccine review: "*Staphylococcus aureus* vaccines: problems and prospects". Vaccine. 2013 Jun. 7; 31(25):2723-30.

Jones R J, Roe E A, Lowbury E J, Miler J J, Spilsbury J F. A new *Pseudomonas* vaccine: preliminary trial on human volunteers. J Hyg (Lond). 1976 June; 76(3):429-39.

Jones R J, Roe E A, Gupta J L. Low mortality in burned patients in a *Pseudomonas* vaccine trial. Lancet. 1978 Aug. 19; 2(8086):401-3.

Jones R J, Roe E A, Gupta J L. Controlled trials of a polyvalent *Pseudomonas* vaccine in burns. Lancet. 1979 Nov. 10; 2(8150):977-82.

Jones R J, Roe E A, Gupta J L. Controlled trial of *Pseudomonas* immunoglobulin and vaccine in burn patients. Lancet. 1980 Dec. 13; 2(8207):1263-5.

Kaijser B, Ahlstedt S. Protective capacity of antibodies against *Escherichia coli* and K antigens. Infect Immun. 1977 August; 17(2):286-9.

Kelly, R F et al., 1995. Structures of the O-antigens of *Klebsiella* serotypes O2 (2a,2e), O2 (2a,2e,2h), and O2 (2a,2f,2g), members of a family of related D-galactan O-antigens in *Klebsiella* spp. J. Endotoxin Res. 2:131-140.

Kim K H, Yu J, Nahm M H. Efficiency of a pneumococcal opsonophagocytic killing assay improved by multiplexing and by coloring colonies. Clin Diagn Lab Immunol. 2003 July; 10(4):616-21.

Knirel Y A, Bystrova O V, Kocharova N A, Zähringer U, Pier G B. Conserved and variable structural features in the lipopolysaccharide of *Pseudomonas aeruginosa*. J Endotoxin Res. 2006; 12(6):324-36.

Kojima K, Ishizaka A, Oshika E, Taguchi Y, Tomizawa K, et al. Quantitation of IgG subclass antibodies to pneumococcal capsular polysaccharides by ELISA, using Pneumovax-specific antibodies as a reference. Tohoku J Exp Med. 1990 July; 161(3):209-15.

Kol, O., Wieruszeski, J. M., Strecker, G., Fournet, B., Zalisz, R., Smets, P., 1992. Structure of the O-specific polysaccharide chain of *Klebsiella pneumoniae* O1K2 (NCTC 5055) lipopolysaccharide. A complementary elucidation. Carbohydr. Res. 236, 339-344.

Koskela M, Leinonen M. Comparison of ELISA and RIA for measurement of pneumococcal antibodies before and after vaccination with 14-valent pneumococcal capsular polysaccharide vaccine. J Clin Pathol. 1981 January; 34(1):93-8.

Kreger B E, Craven D E, Carling P C, McCabe W R. Gram-negative bacteremia III Reassessment of etiology, epidemiology and ecology in 612 patients. Am J Med. 1980 March; 68(3):332-43.

Lal G, Balmer P, Stanford E, Martin S, Warrington R, et al. Development and validation of a nonaplex assay for the simultaneous quantitation of antibodies to nine *Streptococcus pneumoniae* serotypes. J Immunol Methods. 2005 January; 296(1-2):135-47.

Landman, D., Babu, E., Shah, N., Kelly, P., Olawole, O., Backer, M., Bratu, S., Quale, J., 2012. Transmission of carbapenem-resistant pathogens in New York City hospitals: progress and frustration. J. Antimicrob. Chemother. 67, 1427-1431.

Lang A B, Schaad U B, Rüdeberg A, Wedgwood J, Que J U, et al. Effect of high-affinity anti-*Pseudomonas aeruginosa* lipopolysaccharide antibodies induced by immunization on the rate of *Pseudomonas aeruginosa* infection in patients with cystic fibrosis. J Pediatr. 1995 November; 127(5):711-7.

Langford D T, Hiller J. Prospective, controlled study of a polyvalent *Pseudomonas* vaccine in cystic fibrosis—three year results. Arch Dis Child. 1984 December; 59(12): 1131-4.

Langstraat J, Bohse M, Clegg S. Type 3 fimbrial shaft (MrkA) of *Klebsiella pneumoniae*, but not the fimbrial adhesin (MrkD), facilitates biofilm formation. Infect Immun. 2001 September; 69(9):5805-12.

Leach S, Clements J D, Kaim J, Lundgren A. The adjuvant double mutant *Escherichia coli* heat labile toxin enhances IL-17A production in human T cells specific for bacterial vaccine antigens. PLoS One. 2012; 7(12):e51718. doi: 10.1371.

Levin B R, Cornejo O E. The population and evolutionary dynamics of homologous gene recombination in bacterial populations. PLoS Genet. 2009 August; 5(8):e1000601.

Levin B R, Stewart F M, Rice V A. The kinetics of conjugative plasmid transmission: fit of a simple mass action model. Plasmid. 1979 April; 2(2):247-60.

Lipsitch M, Siber G R. How Can Vaccines Contribute to Solving the Antimicrobial Resistance Problem?. MBio. 2016 Jun. 7; 7(3)

Liu Y, Filler S G. *Candida albicans* Als3, a multifunctional adhesin and invasin. Eukaryot Cell. 2011 February; 10(2): 168-73.

Liu Y Y, Wang Y, Walsh T R, Yi L X, Zhang R, et al. Emergence of plasmid-mediated colistin resistance mechanism MCR-1 in animals and human beings in China: a microbiological and molecular biological study. Lancet Infect Dis. 2016 February; 16(2):161-8.

Ma L, Jackson K D, Landry R M, Parsek M R, Wozniak D J. Analysis of *Pseudomonas aeruginosa* conditional psl variants reveals roles for the psl polysaccharide in adhesion and maintaining biofilm structure post attachment. J Bacteriol. 2006 December; 188(23):8213-21.

Magill S S, Edwards J R, Bamberg W, Beldays Z G, Dumyati G, et al. Multistate point-prevalence survey of health care-associated infections. N Engl J Med. 2014 Mar. 27; 370(13):1198-208.

Mandine E, Salles M F, Zalisz R, Guenounou M, Smets P. Murine monoclonal antibodies to *Klebsiella pneumoniae* protect against lethal endotoxemia and experimental infection with capsulated *K. pneumoniae*. Infect Immun. 1990 September; 58(9):2828-33.

Martin, E W, Ed. Remington's Pharmaceutical Sciences. 15th ed. Easton, Pa.: Mack Publishing Company, 1975.

Martinez J E, Romero-Steiner S, Pilishvili T, Barnard S, Schinsky J, et al. A flow cytometric opsonophagocytic assay for measurement of functional antibodies elicited after vaccination with the 23-valent pneumococcal polysaccharide vaccine. Clin Diagn Lab Immunol. 1999 July; 6(4):581-6.

McCabe W R, Kaij ser B, Olling S, Uwaydah M, Hanson L A. *Escherichia coli* in bacteremia: K and O antigens and serum sensitivity of strains from adults and neonates. J Infect Dis. 1978 July; 138(1): 33-41.

McGann P, Chahine S, Okafor D, Ong A C, Maybank R, et al. Detecting 16S rRNA Methyltransferases in Enterobacteriaceae by Use of Arbekacin. J Clin Microbiol. 2016 January; 54(1):208-11.

Meir A, Helppolainen S H, Podoly E, Nordlund H R, Hytonen V P, et al. Crystal structure of rhizavidin: insights into the enigmatic high-affinity interaction of an innate biotin-binding protein dimer. J Mol Biol. 2009 Feb. 20; 386(2):379-90.

Milla C E, Chmiel J F, Accurso F J, VanDevanter D R, Konstan M W, et al. Anti-PcrV antibody in cystic fibrosis: a novel approach targeting *Pseudomonas aeruginosa* airway infection. Pediatr Pulmonol. 2014 July; 49(7):650-8.

Misener S and Krawetz S A, Eds., Bioinformatics: Methods and Protocols (Methods in Molecular Biology, Volume 132). Totowa, N. J.: Humana Press, 1999.

Montie T C, Drake D, Sellin H, Slater O, Edmonds S. Motility, virulence, and protection with a flagella vaccine against *Pseudomonas aeruginosa* infection. Antibiot Chemother (1971). 1987; 39:233-48.

Moore T A, Perry M L, Getsoian A G, Newstead M W, Standiford T J. Divergent role of gamma interferon in a murine model of pulmonary versus systemic *Klebsiella pneumoniae* infection. Infect Immun. 2002 November; 70(11):6310-8.

Moriel D G, Bertoldi I, Spagnuolo A, Marchi S, Rosini R, et al. Identification of protective and broadly conserved vaccine antigens from the genome of extraintestinal pathogenic *Escherichia coli*. Proc Natl Acad Sci USA. 2010 May 18; 107(20):9072-7.

Munro C S, Stanley P J, Cole P J. Assessment of biological activity of immunoglobulin preparations by using opsonized micro-organisms to stimulate neutrophil chemiluminescence. Clin Exp Immunol. 1985 July; 61(1): 183-8.

Murphy C N, Clegg S. *Klebsiella pneumoniae* and type 3 fimbriae: nosocomial infection, regulation and biofilm formation. Future Microbiol. 2012 August; 7(8):991-1002.

Navon-Venezia, S., Leavitt, A., Schwaber, M. J., Rasheed, J. K., Srinivasan, A., Patel, J. B., Carmeli, Y., 2009. First report on a hyperepidemic clone of KPC-3-producing *Klebsiella pneumoniae* in Israel genetically related to a strain causing outbreaks in the United States. Antimicrob. Agents Chemother. 53, 818-820.

Neely A N, Bhattacharjee A K, Babcock G F, Holder I A, Cross A S. Differential effects of two different routes of immunization on protection against gram-negative sepsis by a detoxified *Escherichia coli* J5 lipopolysaccharide group B meningococcal outer membrane protein complex vaccine in a burned mouse model. J Burn Care Rehabil. 2002 September-October; 23(5):333-40.

Nesta B, Spraggon G, Alteri C, Moriel D G, Rosini R, et al. FdeC, a novel broadly conserved *Escherichia coli* adhesin eliciting protection against urinary tract infections. MBio. 2012; 3(2)

Norton E B et al., Characterization of a Mutant *Escherichia coli* Heat-Labile Toxin, L T(R192G/L211A), as a Safe and Effective Oral Adjuvant. Clin Vaccine Immunol. 2011 18:546-551.

Norton E B et al., The A Subunit of *Escherichia coli* Heat-Labile Enterotoxin Functions as a Mucosal Adjuvant and Promotes IgG2a, IgA, and Th17 Responses to Vaccine Antigens. Infection and Immunity 2012, 80:2426-2435.

Ojo-Amaize E A, Church J A, Barka N E, Agopian M S, Peter J B. A rapid and sensitive chemiluminescence assay for evaluation of functional opsonic activity of *Haemophilus influenzae* type b-specific antibodies. Clin Diagn Lab Immunol. 1995 May; 2(3):286-90.

Old D C, Adegbola R A. Antigenic relationships among type-3 fimbriae of Enterobacteriaceae revealed by immunoelectronmicroscopy. J Med Microbiol. 1985 August; 20(1):113-21.

Pereira, P. S., de Araujo, C. F., Seki, L. M., Zahner, V., Carvalho-Assef, A. P., Asensi, M. D., 2013. Update of the molecular epidemiology of KPC-2-producing *Klebsiella pneumoniae* in Brazil: spread of clonal complex 11 (ST11 ST437 and ST340). J. Antimicrob. Chemother. 68, 312-316.

Pickering J W, Martins T B, Greer R W, Schroder M C, Astill M E, et al. A multiplexed fluorescent microsphere immunoassay for antibodies to pneumococcal capsular polysaccharides. Am J Clin Pathol. 2002 April; 117(4):589-96.

Podschun R, Ullmann U. *Klebsiella* spp as nosocomial pathogens: epidemiology, taxonomy, typing methods, and pathogenicity factors. Clin Microbiol Rev. 1998 October; 11(4):589-603.

Poljak R J. Production and structure of diabodies. Structure. 1994 Dec. 15; 2(12):1121-3.

Poolman J T, Wacker M. Extraintestinal Pathogenic *Escherichia coli*, a Common Human Pathogen: Challenges for Vaccine Development and Progress in the Field. J Infect Dis. 2016 Jan. 1; 213(1):6-13.

Powell M F and Newman M J, Eds. Vaccine Design: The Subunit and Adjuvant Approach. New York, N. Y.: Plenum Press, 1995.

Priebe G P, Walsh R L, Cederroth T A, Kamei A, Coutinho-Sledge Y S, et al. IL-17 is a critical component of vaccine-induced protection against lung infection by lipopolysaccharide-heterologous strains of *Pseudomonas aeruginosa*. J Immunol. 2008 Oct. 1; 181(7):4965-75.

Qi, Y., Wei, Z., Ji, S., Du, X., Shen, P., Yu, Y., 2011. ST11, the dominant clone of KPC-producing *Klebsiella pneumoniae* in China. J. Antimicrob. Chemother. 66, 307-312.

Ramachandran G, Boyd M A, MacSwords J, Higginson E E, Simon R, et al. Opsonophagocytic Assay To Evaluate Immunogenicity of Nontyphoidal *Salmonella* Vaccines. Clin Vaccine Immunol. 2016 June; 23(6):520-3.

Rappuoli R. Reverse vaccinology. Curr Opin Microbiol. 2000 October; 3(5):445-50.

Rayner B L, Willcox P A. Community-acquired bacteraemia; a prospective survey of 239 cases. Q J Med. 1988 November; 69(259):907-19.

Robbins J B, McCracken G H Jr, Gotschlich E C, Orskov F, Orskov I, et al. *Escherichia coli* K1 capsular polysaccharide associated with neonatal meningitis. N Engl J Med. 1974 May 30; 290(22): 1216-20.

Romero-Steiner S, Libutti D, Pais L B, Dykes J, Anderson P, et al. Standardization of an opsonophagocytic assay for the measurement of functional antibody activity against *Streptococcus pneumoniae* using differentiated HL-60 cells. Clin Diagn Lab Immunol. 1997 July; 4(4):415-22.

Romero-Steiner S, Holder P F, Gomez de Leon P, Spear W, Hennessy T W, et al. Avidity determinations for *Haemophilus influenzae* Type b anti-polyribosylribitol phosphate antibodies. Clin Diagn Lab Immunol. 2005 September; 12(9):1029-35.

Ross P J, Sutton C E, Higgins S, Allen A C, Walsh K, et al. Relative contribution of Th1 and Th17 cells in adaptive immunity to *Bordetella pertussis*: towards the rational design of an improved acellular pertussis vaccine. PLoS Pathog. 2013; 9(4):e1003264.

Saeland E, Vidarsson G, Jonsdottir I. Pneumococcal pneumonia and bacteremia model in mice for the analysis of protective antibodies. Microb Pathog. 2000 August; 29(2):81-91.

Saha S, Takeshita F, Matsuda T, Jounai N, Kobiyama K, et al. Blocking of the TLR5 activation domain hampers protective potential of flagellin DNA vaccine. J Immunol. 2007 Jul. 15; 179(2):1147-54.

Sambrook J, Maniatis T and Fritsch E F. Molecular Cloning: A Laboratory Manual. 2nd ed. Cold Spring Harbor, N. Y.: Cold Spring Harbor Laboratory Press, 1989.

Sawa T, Yahr T L, Ohara M, Kurahashi K, Gropper M A, et al. Active and passive immunization with the *Pseudomonas* V antigen protects against type III intoxication and lung injury. Nat Med. 1999 April; 5(4):392-8.

Schaad U B, Lang A B, Wedgwood J, Ruedeberg A, Que J U, et al. Safety and immunogenicity of *Pseudomonas aeruginosa* conjugate A vaccine in cystic fibrosis. Lancet. 1991 Nov. 16; 338(8777): 1236-7.

Schaberg D R, Culver D H, Gaynes R P. Major trends in the microbial etiology of nosocomial infection. Am J Med. 1991 Sep. 16; 91(3B):72S-75S.

Schmidt A C, McAuliffe J M, Murphy B R, Collins P L. Recombinant bovine/human parainfluenza virus type 3 (B/HPIV3) expressing the respiratory syncytial virus (RSV) G and F proteins can be used to achieve simultaneous mucosal immunization against RSV and HPIV3. J Virol. 2001 May; 75(10):4594-603.

Schmidt C S, White C J, Ibrahim A S, Filler S G, Fu Y, et al. NDV-3, a recombinant alum-adjuvanted vaccine for *Candida* and *Staphylococcus aureus*, is safe and immunogenic in healthy adults. Vaccine. 2012 Dec. 14; 30(52):7594-600.

Schweizer H P. Allelic exchange in *Pseudomonas aeruginosa* using novel ColEl-type vectors and a family of cassettes containing a portable oriT and the counterselectable *Bacillus subtilis* sacB marker. Mol Microbiol. 1992 May; 6(9):1195-204.

Scully I L, Liberator P A, Jansen K U, Anderson A S. Covering all the Bases: Preclinical Development of an Effective *Staphylococcus aureus* Vaccine. Front Immunol. 2014 Mar. 24; 5:109.

Shime N, Sawa T, Fujimoto J, Faure K, Allmond L R, et al. Therapeutic administration of anti-PcrV F(ab')(2) in sepsis associated with *Pseudomonas aeruginosa*. J Immunol. 2001 Nov. 15; 167(10):5880-6.

Simon R, Samuel C E. Activation of N F-kappaB-dependent gene expression by *Salmonella* flagellins FliC and FljB. Biochem Biophys Res Commun. 2007 Mar. 30; 355(1):280-5.

Song W S, Yoon S I. Crystal structure of FliC flagellin from *Pseudomonas aeruginosa* and its implication in TLR5 binding and formation of the flagellar filament. Biochem Biophys Res Commun. 2014 Feb. 7; 444(2):109-15.

Stack A M, Malley R, Thompson C M, Kobzik L, Siber G R, et al. Minimum protective serum concentrations of pneumococcal anti-capsular antibodies in infant rats. J Infect Dis. 1998 April; 177(4):986-90.

Szijártó V. et al., 2016. Both clades of the epidemic KPC-producing *Klebsiella pneumoniae* clone ST258 share a modified galactan O-antigen type. International Journal of Medical Microbiology 306:89-98.

Tarkkanen A M, Virkola R, Clegg S, Korhonen T K. Binding of the type 3 fimbriae of *Klebsiella pneumoniae* to human endothelial and urinary bladder cells. Infect Immun. 1997 April; 65(4): 1546-9.

Tarkkanen A M, Allen B L, Westerlund B, Holthöfer H, Kuusela P, et al. Type V collagen as the target for type-3 fimbriae, enterobacterial adherence organelles. Mol Microbiol. 1990 August; 4(8):1353-61.

Thammavongsa V, Kim H K, Missiakas D, Schneewind O. Staphylococcal manipulation of host immune responses. Nat Rev Microbiol. 2015 September; 13(9):529-43.

Therasse P, Arbuck S G, Eisenhauer E A, Wanders J, Kaplan R S, et al. New Guidelines to Evaluate the Response to Treatment in Solid Tumors. J Natl Cancer Inst. 2000 Feb. 2; 92(3):205-216.

Tomas J M, Camprubi S, Williams P. Surface exposure of the O-antigen in *Klebsiella pneumoniae* 01:K1 serotype strains. Microb Pathog. 1988 August; 5(2):141-7.

Toprani V S. et al., Development of a candidate stabilizing formulation for bulk storage of a double mutant heat labile toxin (dmLT) protein based adjuvant. Vaccine. 2017. 35:5471-548.

Trautmann, M., et al., 1997. O-Antigen Seroepidemiology of *Klebsiella* Clinical Isolates and Implications for Immunoprophylaxis of *Klebsiella* Infections. Clinical and Diagnostic Laboratory Immnuology 4:550-555.

Westritschnig K, Hochreiter R, Wallner G, Firbas C, Schwameis M, Jilma B. 2014. A randomized, placebo-controlled phase I study assessing the safety and immunogenicity of a *Pseudomonas aeruginosa* hybrid outer membrane protein OprF/I vaccine (IC43) in healthy volunteers. Hum Vaccin Immunother 10:170-183.

Ullmann U. [Bacterial infection agents in hospitalized patients]. Zentralbl Bakteriol Mikrobiol Hyg B. 1986 December; 183(2-3):103-13.

Vaudaux P and Waldvogel F A (1979). Gentamicin antibacterial activity in the presence of human polymorphonuclear leukocytes. Antimicrob Agents Chemother. 16 (6): 743-749.

Vinogradov E, Frirdich E, MacLean L L, Perry M B, Petersen B O, et al. Structures of lipopolysaccharides from *Klebsiella pneumoniae* Eluicidation of the structure of the linkage region between core and polysaccharide 0 chain and identification of the residues at the non-reducing termini of the 0 chains. J Biol Chem. 2002 Jul. 12; 277(28):25070-81.

Wang Q, Chang C S, Pennini M, Pelletier M, Raj an S, et al. Target-Agnostic Identification of Functional Monoclonal Antibodies Against *Klebsiella pneumoniae* Multimeric MrkA Fimbrial Subunit. J Infect Dis. 2016 Jun. 1; 213 (11):1800-8.

Walczak M J, Puorger C, Glockshuber R, Wider G. Intramolecular donor strand complementation in the *E. coli* type 1 pilus subunit FimA explains the existence of FimA monomers as off-pathway products of pilus assembly that inhibit host cell apoptosis. J Mol Biol. 2014 February 6; 426(3):542-9.

Warfel J M, Zimmerman L I, Merkel T J. Acellular pertussis vaccines protect against disease but fail to prevent infection and transmission in a nonhuman primate model. Proc Natl Acad Sci USA. 2014 January 14; 111(2):787-92.

Warrener P, Varkey R, Bonnell J C, DiGiandomenico A, Camara M, et al. A novel anti-PcrV antibody providing enhanced protection against *Pseudomonas aeruginosa* in multiple animal infection models. Antimicrob Agents Chemother. 2014 August; 58(8):4384-91.

Welch W D, Martin W J, Stevens P, Young L S. Relative opsonic and protective activities of antibodies against K1, O and lipid A antigens of *Escherichia coli*. Scand J Infect Dis. 1979; 11(4):291-301.

Whitfield, C., Perry, M. B., MacLean, L. L., Yu, S. H., 1992. Structural analysis of the O-antigen side chain polysaccharides in the lipopolysaccharides of *Klebsiella* serotypes O2(2a) O2(2a, 2b), and O2(2a, 2c). J. Bacteriol. 174, 4913-4919.

Whitfield, C., Richards, J. C., Perry, M. B., Clarke, B. R., MacLean, L. L., 1991. Expression of two structurally distinct d-galactan O antigens in the lipopolysaccharide of *Klebsiella pneumoniae* serotype 01. J. Bacteriol. 173, 1420-1431.

Woodford N, Turton J F, Livermore D M. Multiresistant Gram-negative bacteria: the role of high-risk clones in the dissemination of antibiotic resistance. FEMS Microbiol Rev. 2011 S ep; 35(5): 736-55.

World Health Organization (WHO). Antimicrobial Resistance—Global Report on Surveillance. 2014.

Wu W, Huang J, Duan B, Traficante D C, Hong H, et al. Th17-stimulating protein vaccines confer protection against *Pseudomonas aeruginosa* pneumonia. Am J Respir Crit Care Med. 2012 September 1; 186(5):420-7.

Wiirker M, Beuth J, Ko H L, Przondo-Mordarska A, Pulverer G. Type of fimbriation determines adherence of *Klebsiella* bacteria to human epithelial cells. Zentralbl Bakteriol. 1990 November; 274(2):239-45

Zhang F, Lu Y J, Malley R. Multiple antigen-presenting system (MAPS) to induce comprehensive B- and T-cell immunity. Proc Natl Acad Sci USA. 2013 August 13; 110(33):13564-9.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

---

We claim:

1. A vaccine composition comprising:
   (a) a first immunogenic composition comprising a backbone polymer comprising a polymer comprising a biotinylated *Klebsiella* spp. K19 capsular polysaccharide, a *P. aeruginosa* (PA) O1 OPS conjugated to the *Klebsiella* spp. K19 capsular polysaccharide, and a Rhavi-FlaBD2-PcrV fusion protein non-covalently complexed to the biotinylated backbone polymer;
   (b) a second immunogenic composition comprising a backbone polymer comprising a polymer comprising a biotinylated *Klebsiella* spp. K19 capsular polysaccharide, a PA O2 OPS conjugated to the *Klebsiella* spp. K19 capsular polysaccharide, and a Rhavi-FlaBD2-PcrV fusion protein non-covalently complexed to the biotinylated backbone polymer;
   (c) a third immunogenic composition comprising a backbone polymer comprising a polymer comprising a biotinylated *Klebsiella* spp. K19 capsular polysaccharide, a PA O3 OPS conjugated to the *Klebsiella* spp. K19 capsular polysaccharide, and a Rhavi-FlaBD2-PcrV fusion protein non-covalently complexed to the biotinylated backbone polymer;
   (d) a fourth immunogenic composition comprising a backbone polymer comprising a polymer comprising a biotinylated *Klebsiella* spp. K19 capsular polysaccharide, a PA O4 OPS conjugated to the *Klebsiella* spp. K19 capsular polysaccharide, and a Rhavi-FlaBD2-PcrV fusion protein non-covalently complexed to the biotinylated backbone polymer;
   (e) a fifth immunogenic composition comprising a backbone polymer comprising a polymer comprising a biotinylated *Klebsiella* spp. K19 capsular polysaccharide, a PA O5 OPS conjugated to the *Klebsiella* spp. K19 capsular polysaccharide, and a Rhavi-FlaBD2-MrkA fusion protein non-covalently complexed to the biotinylated backbone polymer;
   (f) a sixth immunogenic composition comprising a backbone polymer comprising a polymer comprising a biotinylated *Klebsiella* spp. K19 capsular polysaccharide, a PA O6 OPS conjugated to the *Klebsiella* spp. K19 capsular polysaccharide, and a Rhavi-FlaBD2-MrkA fusion protein non-covalently complexed to the biotinylated backbone polymer;
   (g) a seventh immunogenic composition comprising a backbone polymer comprising a polymer comprising a biotinylated *Klebsiella* spp. K19 capsular polysaccharide, a PA O10 OPS conjugated to the *Klebsiella* spp. K19 capsular polysaccharide, and a Rhavi-FlaBD2-MrkA fusion protein non-covalently complexed to the biotinylated backbone polymer; and
   (h) an eighth immunogenic composition comprising a backbone polymer comprising a polymer comprising a biotinylated *Klebsiella* spp. K19 capsular polysaccharide, a PA O11 OPS conjugated to the *Klebsiella* spp. K19 capsular polysaccharide, and a Rhavi-FlaBD2-MrkA fusion protein non-covalently complexed to the biotinylated backbone polymer.

2. A pharmaceutical composition comprising the vaccine composition of claim 1 and a pharmaceutically acceptable carrier.

3. A method of immunizing a subject against *Klebsiella* infection and/or *P. aeruginosa* infection comprising administering to the subject an effective amount of the vaccine composition of claim 1.

4. The vaccine composition of claim 1, wherein the OPS in at least one of the immunogenic compositions is conjugated with a linker to the *Klebsiella* spp. K19 capsular polysaccharide.

5. The vaccine composition of claim 1, wherein the Rhavi-FlaBD2-MrkA fusion protein comprises (i) a biotin-binding protein or biotin-binding domain thereof comprising an amino acid sequence having at least 80%, 85%, 90%, 95%, 96%, 97%, 98%, 99%, or 100% identity to the sequence of SEQ ID NO: 14 (rhizavidin lacking signal sequences), (ii) a polypeptide comprising an amino acid sequence having at least 80%, 85%, 90%, 95%, 96%, 97%, 98%, 99%, or 100% identity to the sequence of SEQ ID NO:10 (*P. aeruginosa* flagellin subtype B D2 domain (FlaBD2) lacking the TLR5 binding motif) or an immunogenic fragment thereof, and (iii) a polypeptide comprising an amino acid sequence having at least 80%, 85%, 90%, 95%, 96%, 97%, 98%, 99%, or 100% identity to the sequence of SEQ ID NO:2 or SEQ ID NO:3 (*K. pneumoniae* MrkA) or an immunogenic fragment thereof.

6. The vaccine composition of claim 1, wherein the Rhavi-FlaBD2-PcrV fusion protein comprises (i) a biotin-binding protein or biotin-binding domain thereof comprising an amino acid sequence having at least 80%, 85%, 90%, 95%, 96%, 97%, 98%, 99%, or 100% identity to the sequence of SEQ ID NO: 14 (rhizavidin lacking signal sequences), (ii) a polypeptide comprising an amino acid sequence having at least 80%, 85%, 90%, 95%, 96%, 97%, 98%, 99%, or 100% identity to the sequence of SEQ ID NO:10 (*P. aeruginosa* flagellin subtype B D2 domain (FlaBD2) lacking the TLR5 binding motif) or an immunogenic fragment thereof, and (iii) a polypeptide comprising an amino acid sequence having at least 80%, 85%, 90%, 95%, 96%, 97%, 98%, 99%, or 100% identity to the sequence of SEQ ID NO:8 (*P. aeruginosa* PcrV) or an immunogenic fragment thereof.

7. The vaccine composition of claim 5, wherein the Rhavi-FlaBD2-MrkA fusion protein is or comprises an amino acid sequence having at least 80%, 85%, 90%, 95%, 96%, 97%, 98%, 99%, or 100% identity to SEQ ID NO: 24.

8. The vaccine composition of claim 6, wherein the Rhavi-FlaBD2-PcrV fusion protein is or comprises an amino acid sequence having at least 80%, 85%, 90%, 95%, 96%, 97%, 98%, 99%, or 100% identity to SEQ ID NO: 26.

9. The vaccine composition of claim 1, further comprising at least one additional immunogenic composition that comprises: (i) a backbone polymer comprising a polymer and one or more antigenic polysaccharides conjugated to the polymer; and (ii) one or more polypeptide antigens non-covalently complexed with the polymer and/or the antigenic polysaccharide.

10. The vaccine composition of claim 9, wherein the polymer of at least one of the additional immunogenic composition(s) is a capsular polysaccharide derived from a gram-negative or gram-positive bacteria.

11. The vaccine composition of claim 9, wherein the polymer of at least one of the additional immunogenic composition(s) is a *Klebsiella* capsular polysaccharide, *Pseudomonas* exopolysaccharide, and/or *Escherichia* capsular polysaccharide.

12. The vaccine composition of claim 9, wherein the polymer of at least one of the additional immunogenic composition(s) is a *Klebsiella* spp. K19 capsular polysaccharide.

13. The vaccine composition of claim 9, wherein the polymer of at least one of the additional immunogenic composition(s) is a linear poly-L-lysine, or a dendrimer of L-lysine.

14. The vaccine composition of claim 9, wherein the at least one additional immunogenic composition comprises:
   (a) a backbone polymer comprising a polymer and one or more antigenic polysaccharides conjugated to the polymer;
   (b) one or more polypeptide antigens; and
   (c) at least one affinity-molecule pair comprising a first affinity molecule and a second affinity molecule complementary to the first affinity molecule;
   wherein the backbone polymer is associated with the first affinity molecule;
   wherein at least one of the polypeptide antigen(s) is associated with the second affinity molecule; and
   wherein the first affinity molecule non-covalently complexes with the second affinity molecule to link the backbone polymer and the one or more polypeptide antigens.

15. The vaccine composition of claim 14, wherein the affinity-molecule pair is selected from the group consisting of: biotin/biotin-binding protein, antibody/antigen, enzyme/substrate, receptor/ligand, metal/metal-binding protein, carbohydrate/carbohydrate binding protein, lipid/lipid-binding protein, and His tag/His tag-binding molecule.

16. The vaccine composition of claim 14, wherein the first affinity molecule is or comprises biotin or a derivative thereof.

17. The vaccine composition of claim 14, wherein the second affinity molecule is or comprises a biotin-binding protein or biotin-binding domain thereof.

18. The vaccine composition of claim 17, wherein the biotin-binding protein is or comprises rhizavidin or a biotin-binding domain thereof.

19. The vaccine composition of claim 17, wherein the biotin-binding protein or biotin-binding domain thereof is or comprises an amino acid sequence having at least 80%, 85%, 90%, 95%, 96%, 97%, 98%, 99%, or 100% identity to the sequence of SEQ ID NO: 14 (rhizavidin lacking signal sequences).

20. The vaccine composition of claim 14, wherein the first affinity molecule is cross-linked or covalently bonded to the polymer and/or the one or more antigenic polysaccharides, of the additional immunogenic composition.

21. The vaccine composition of claim 14, wherein the second affinity molecule is associated with the one or more polypeptide antigens of the additional immunogenic composition to form a fusion protein.

22. The vaccine composition of claim 21, wherein the fusion protein comprises (i) a biotin-binding protein or biotin-binding domain thereof, and (ii) the one or more polypeptide antigens.

23. The vaccine composition of claim 22, wherein the one or more polypeptide antigens are each independently selected from the group consisting of: *P. aeruginosa* flagellin subtype B D2 domain (FlaBD2) lacking the TLR5 binding motif, *P. aeruginosa* PcrV, *K. pneumoniae* MrkA, and immunogenic fragments thereof.

24. The vaccine composition of claim 22, wherein the one or more polypeptide antigens are each independently selected from the group consisting of: a *P. aeruginosa* flagellin subtype A, *P. aeruginosa* flagellin subtype B, and immunogenic fragments thereof.

25. The vaccine composition of claim 21, wherein the fusion protein comprises (i) a biotin-binding protein or biotin-binding domain thereof, (ii) a polypeptide comprising an amino acid sequence having at least 80%, 85%, 90%, 95%, 96%, 97%, 98%, 99%, or 100% identity to the sequence of SEQ ID NO:10 (*P. aeruginosa* flagellin subtype B D2 domain (FlaBD2) lacking the TLR5 binding motif) or an immunogenic fragment thereof, and (iii) a polypeptide comprising an amino acid sequence having at least 80%, 85%, 90%, 95%, 96%, 97%, 98%, 99%, or 100% identity to the sequence of SEQ ID NO:2 or SEQ ID NO:3 (*K. pneumoniae* MrkA) or an immunogenic fragment thereof.

26. The vaccine composition of claim 21, wherein the fusion protein comprises (i) a biotin-binding protein or biotin-binding domain thereof, (ii) a polypeptide comprising an amino acid sequence having at least 80%, 85%, 90%, 95%, 96%, 97%, 98%, 99%, or 100% identity to the sequence of SEQ ID NO:10 (*P. aeruginosa* flagellin subtype B D2 domain (FlaBD2) lacking the TLR5 binding motif) or an immunogenic fragment thereof, and (iii) a polypeptide comprising an amino acid sequence having at least 80%, 85%, 90%, 95%, 96%, 97%, 98%, 99%, or 100% identity to the sequence of SEQ ID NO:8 (*P. aeruginosa* PcrV) or an immunogenic fragment thereof.

27. The vaccine composition of claim 25, wherein the fusion protein is or comprises an amino acid sequence having at least 80%, 85%, 90%, 95%, 96%, 97%, 98%, 99%, or 100% identity to SEQ ID NO: 24.

28. The vaccine composition of claim 26, wherein the fusion protein is or comprises an amino acid sequence having at least 80%, 85%, 90%, 95%, 96%, 97%, 98%, 99%, or 100% identity to SEQ ID NO: 26.

29. The vaccine composition of claim 9, wherein the one or more antigenic polysaccharides of at least one of the additional immunogenic composition(s) comprise a polysaccharide of one or more of *Klebsiella, Pseudomonas*, and *E. coli*.

30. The vaccine composition of claim 9, wherein the one or more antigenic polysaccharides of at least one of the additional immunogenic composition(s) comprise a *K. pneumoniae* OPS of type O1, O2, O3, O5, or a combination thereof.

31. The vaccine composition of claim 9, wherein the one or more antigenic polysaccharides of at least one of the additional immunogenic composition(s) comprise a *P. aeruginosa* OPS of type O1, O2, O3, O4, O5, O6, O10, O11, O12, or a combination thereof.

32. The vaccine composition of claim 9, wherein the at least one additional immunogenic composition comprises:
    (a) a backbone polymer comprising:
        (i) a polymer comprising a *Klebsiella* spp. K19 capsular polysaccharide; and
        (ii) one or more antigenic polysaccharides comprising a polysaccharide of *Klebsiella* or *Pseudomonas* conjugated to the *Klebsiella* spp. K19 capsular polysaccharide;
    (b) one or more polypeptide antigens; and
    (c) at least one affinity-molecule pair comprising a first affinity molecule and a second affinity molecule complementary to the first affinity molecule;
    wherein the polymer is associated with the first affinity molecule;
    wherein at least one of the polypeptide antigen(s) is associated with the second affinity molecule; and
    wherein the first affinity molecule non-covalently complexes with the second affinity molecule to link the polymer and the one or more polypeptide antigens.

33. The vaccine composition of claim 32, further comprising:
    (a) a ninth immunogenic composition comprising a backbone polymer comprising a polymer comprising a biotinylated *Klebsiella* spp. K19 capsular polysaccharide, a KP O1 OPS conjugated to the *Klebsiella* spp. K19 capsular polysaccharide, and a Rhavi-FlaBD2-MrkA fusion protein non-covalently complexed to the biotinylated backbone polymer;
    (b) a tenth immunogenic composition comprising a backbone polymer comprising a polymer comprising a biotinylated *Klebsiella* spp. K19 capsular polysaccharide, a KP O2 OPS conjugated to the *Klebsiella* spp. K19 capsular polysaccharide, and a Rhavi-FlaBD2-PcrV fusion protein non-covalently complexed to the biotinylated backbone polymer;
    (c) an eleventh immunogenic composition comprising a backbone polymer comprising a polymer comprising a biotinylated *Klebsiella* spp. K19 capsular polysaccharide, a KP O3 OPS conjugated to the *Klebsiella* spp. K19 capsular polysaccharide, and a Rhavi-FlaBD2-MrkA fusion protein non-covalently complexed to the biotinylated backbone polymer; and
    (d) a twelfth immunogenic composition comprising a backbone polymer comprising a polymer comprising a biotinylated *Klebsiella* spp. K19 capsular polysaccharide, a KP O5 OPS conjugated to the *Klebsiella* spp. K19 capsular polysaccharide, and a Rhavi-FlaBD2-PcrV fusion protein non-covalently complexed to the biotinylated backbone polymer.

34. The pharmaceutical composition of claim 2, further comprising one or more adjuvants.

35. The pharmaceutical composition of claim 34, wherein at least one of the adjuvant(s) is selected from the group consisting of: aluminum phosphate, aluminum hydroxide, phosphate aluminum hydroxide, a TLR agonist, and combinations thereof.

36. The pharmaceutical composition of claim 2, wherein the composition is formulated for injection.

37. The pharmaceutical composition of claim 2, wherein the pharmaceutical composition is characterized in that upon administration to a subject, the pharmaceutical composition elicits (i) a Th1 and/or Th17 cell response; and/or (ii) an opsonic/bactericidal response against *Klebsiella* and/or *Pseudomonas*.

38. The pharmaceutical composition of claim 2, wherein the pharmaceutical composition is characterized in that upon administration to a subject, the pharmaceutical composition reduces rate of transmission and/or colonization of the mucosal surfaces and/or the GI tract by *Klebsiella* and/or *Pseudomonas*.

39. The method of claim 3, wherein upon administration to the subject, the vaccine composition elicits (i) a Th1 and/or Th17 cell response; and/or (ii) an opsonic/bactericidal response against *Klebsiella* and/or *Pseudomonas*.

40. The method of claim 3, wherein upon administration to the subject, the vaccine composition reduces rate of transmission and/or colonization of the mucosal surfaces and/or the GI tract by *Klebsiella* and/or *Pseudomonas*.

* * * * *